(12) United States Patent
Doroski et al.

(10) Patent No.: US 8,828,401 B2
(45) Date of Patent: Sep. 9, 2014

(54) CYTOTOXIC PEPTIDES AND ANTIBODY DRUG CONJUGATES THEREOF

(71) Applicant: Pfizer Inc., New York, NY (US)

(72) Inventors: Matthew David Doroski, Mystic, CT (US); Andreas Maderna, Stony Point, NY (US); Christopher John O'Donnell, Mystic, CT (US); Chakrapani Subramanyam, South Glastonburty, CT (US); Beth Vetelino, North Stonington, CT (US); Russell George Dushin, Old Lyme, CT (US); Pavel Strop, San Mateo, CA (US); Edmund Idris Graziani, Chestnut Ridge, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/670,612

(22) Filed: Nov. 7, 2012

(65) Prior Publication Data
US 2013/0129753 A1    May 23, 2013

Related U.S. Application Data

(60) Provisional application No. 61/561,255, filed on Nov. 17, 2011, provisional application No. 61/676,423, filed on Jul. 27, 2012.

(51) Int. Cl.
*C07K 7/02* (2006.01)
*C07K 5/02* (2006.01)
*C07K 16/00* (2006.01)
*A61K 47/48* (2006.01)

(52) U.S. Cl.
CPC ............. *C07K 7/02* (2013.01); *A61K 47/48584* (2013.01); *A61K 47/48569* (2013.01); *C07K 16/00* (2013.01); *A61K 47/48715* (2013.01); *A61K 47/48384* (2013.01); *C07K 5/0205* (2013.01); *A61K 47/48615* (2013.01)
USPC ..................... 424/179.1; 530/331; 530/391.9; 530/323

(58) Field of Classification Search
None
See application file for complete search history.

(56) References Cited

U.S. PATENT DOCUMENTS

| | | | |
|---|---|---|---|
| 4,816,397 A | 3/1989 | Boss et al. |
| 4,816,567 A | 3/1989 | Cabilly et al. |
| 5,225,539 A | 7/1993 | Winter |
| 5,545,806 A | 8/1996 | Lonberg et al. |
| 5,569,825 A | 10/1996 | Lonberg et al. |
| 5,585,089 A | 12/1996 | Queen et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,840,699 A | 11/1998 | Sakakibara et al. |
| 5,985,837 A | 11/1999 | Ritter et al. |
| 6,124,431 A | 9/2000 | Sakakibara et al. |
| 6,884,869 B2 | 4/2005 | Senter et al. |
| 7,521,425 B2 | 4/2009 | Bradshaw et al. |
| 7,750,116 B1 | 7/2010 | Doronina et al. |

FOREIGN PATENT DOCUMENTS

| | | |
|---|---|---|
| EP | 012 023 | 6/1980 |
| EP | 0 171 496 | 2/1986 |
| EP | 0 173 494 | 3/1986 |
| EP | 0 184 187 | 6/1986 |
| EP | 0 404 097 | 12/1990 |
| EP | 0 695 758 | 2/1996 |
| WO | WO 86/01533 | 3/1986 |
| WO | WO 87/02671 | 5/1987 |
| WO | WO 93/11161 | 6/1993 |
| WO | WO 95/09864 | 4/1995 |
| WO | WO 96/33212 | 10/1996 |
| WO | WO 97/34631 | 9/1997 |
| WO | WO 01/18032 | 3/2001 |
| WO | WO 2005/081711 | 9/2005 |
| WO | WO 2007/008848 | 1/2007 |
| WO | WO 2008/052187 | 5/2008 |
| WO | WO 2009/048967 | 4/2009 |
| WO | WO 2009/117531 | 9/2009 |
| WO | WO 2012/007896 | 1/2012 |
| WO | WO 2012/059882 | 5/2012 |

OTHER PUBLICATIONS

Miyazaki et al. Chem Pharm Bull. 43(10;1706-1718:1995.*
Beidler, C., et al., "Cloning and High Level Expression of a Chimeric Antibody With Specificity for Human Carcinoembryonic Antigen," Journal of Immunology, 1988, vol. 141:4053-4060.
Better, M., et al., "*Escherichia coli* Secretion of an Active Chimeric Antibody Fragment," Science, 1988, vol. 240:1041-1043.
Chothia , C. et al. "Canonical Structures for the Hypervariable Regions of Immunoglobulins," Journal of Molecular Biology, 1987, vol. 196:901-917.
Doronina, S., et. al., "Enhanced Activity of Monomethylauristatin F through Monoclonal Antibody Delivery: Effects of Linker Technology on Efficacy and Toxicity," Bioconjugate Chemistry, 2006, vol. 17:114-124.
Doronina, S., et al., "Novel Peptide Linkers for Highly Potent Antibody—Auristatin Conjugate," Bioconjugate Chemistry, 2008, vol. 19:1960-1963.
Garner M., et. al., "Effect of Z-DNA on Nucleosome Placement", Journal of Molecular Biology, 1987, vol. 196:581-590.
Goodson, J., "Dental Applications," Medical Applications of Controlled Release, supra, 1984, vol. 2:115-138.
Holliger, P., et al., ""Diabodies": Small bivalent and bispecific antibody fragments," Proc. Natl. Acad. Sci., 1993, vol. 90:6444-6448.
Hoogenboom, H., et. al., "By-passing Immunisation Human Antibodies from Synthetic Repertoires of Germline VH Gene Segments Rearranged in Vitro," Journal of Molecular Biology, 1991, vol. 227:381-388.

(Continued)

*Primary Examiner* — Karlheinz R Skowronek
*Assistant Examiner* — Schuyler Milton
(74) *Attorney, Agent, or Firm* — David Rubin

(57) ABSTRACT

The present invention is directed to cytotoxic pentapeptides, to antibody drug conjugates thereof, and to methods for using the same to treat cancer.

36 Claims, 16 Drawing Sheets

(56) References Cited

OTHER PUBLICATIONS

International Search Report for PCT/IB2012/056224, issued Apr. 26, 2013.
Jespers, L., et al., "Guiding the Selection of Human Antibodies from Phage Display Repertoires to a Single Epitope of an Antigen," Bio/technology. 1994, vol. 12:899-903.
Jones, P., et al., "Replacing the complementarity-determining regions in a human antibody with those from a mouse," Letters to Nature, 1986, vol. 321:522-525.
Kabat E., "Origins of Antibody Complementarity and Specificity-Hypervariable Regions and the Minigen Hypothesis 1,2," The Journal of Immunology, 1980, vol. 125(3):961-969.
Kozbor, D., et al., "The production of monocolonal antibodies from human lymphocytes," Immunology Today, 1983, vol. 4:72-79.
Laguzza, B. et al., "New Antitumor Monoclonal Antibody-Vinca Conjugates LY203725 and Related Compounds: Design, Preparation, and Representative in Vivo Activity," J. Med. Chem., 1989, vol. 32 (3):548-55.
Langer, R., "New Methods of Drug Delivery," Science, 1990, vol. 249:1527-1533.
Lehmann, B., et. al., "Identification of human triple-negative breast cancer subtypes and preclinical models for selection of targeted therapies," The Journal of Clinical Investigation, 2011, vp;/121(7):2750-2767.
Liu A., et. al., "Chimeric mouse-human IgG1 antibody that can mediate lysis of cancer cells," Proc. Natl. Acad. Sci., 1987, vol. 84:3439-3443.
Liu A., et. al., "Production of a Mouse-Human Chimeric Monoclonal Antibody to CD20 With Potent Fc-Dependent Biologic Activity," The Journal of Immunology, 1987, vol. 139:3521-3526.
Lonberg, N., et. al., "Human Antibodies from Transgenic Mice," Intern. Rev. Immunol., 1995, vol. 13:65-93.
Morrison, S., "Transfectomas Provide Novel Chimeric Antibodies," Science, 1985, vol. 229:1202-1207.
Nishimura, Y., et. al., "Recombinant Human-Mouse Chimeric Monoclonal Antibody Specific for Common Acute Lymphocytic Leukemia Antigen," Cancer Research, 1987, vol. 47:999-1005.
Oi, V.T., et. al., "Chimeric Antibodies," BioTechniques, 1986, vol. 4:214-221.

Olsson, L., et. al., "Human-Human Monoclonal Antibody-Producing Hybridomas: Technical Aspects," et al., Methods in Enzymology, 1983, vol. 92:3-16.
Palanki, M., et. al., "Development of Novel linkers to conjugate pharmacophores to a carrier antibody," Bioorganic and Medicinal Chemistry Letters, 2012, vol. 22(13) 4249-4253.
Pettit, G., et. al., "The Absolute Configuration and Synthesis of Natural (−)-Dolastatin 101," J. Am. Chem. Soc., 1989, vol, 111:5463-5465.
Pettit, G., et. al., "Antineoplastic agents 365. Dolastatin 10 SAR probes," Anti-Cancer Drug Design, 1998, vol. 13:243-277.
Pettit, G., et. al., "Antineoplastic Agents. 592. Highly Effective Cancer Cell Growth Inhibitory Structural Modifications of Dolastatin 10," Journal of Natural Products, 2011, vol. 74:962-968.
Plückthun, A., "Antibodies from *Escherichia coli*," The Pharmacology of Monoclonal Antibodies, 1994, vol. 113:269-315.
Presta, L., "Antibody engineering," Current Opinion in Structural Biology, 1992, vol. 2:593-596.
Quan , M. et. al., "The Rise of Antibodies as Therapeutics," n Anti-IgE and Allergic Disease, 2002, Chapter 20, pp. 427-469.
Riechmann, L. et. al., "Reshaping human antibodies for therapy," Nature, 1988, vol. 332:323-329.
Shaw, D., et. al., "Mouse/Human Chimeric Antibodies to a Tumopr-Associated Antigen: Biologic Activity of the Four Human IgG Subclasses," J. Natl. Cancer Inst. , 1988, vol. 80:1553-1559.
Siedlecki, J., et. al., "Array Synthesis of Novel Lipodepsipeptide," Bioorganic & Medicinal Chemistry Letters, 2003, vol. 13:4245-4249.
Sun, L., et. al. "Chimeric antibody with human constant regions and mouse variable regions directed against carcinoma-associated antigen 17-1A," Proc. Natl. Acad. Sci., 1987, vol. 84:214-218.
Teng, N., et. al., "Construction and testing of mouse-human heteromyelomas for human monoclonal antibody production," Proc. Natl. Acad. Sci., 1983, vol. 80:7308-7312.
Verhoeyen, M., et. al., "Reshaping Human Antibodies: Grafting an Antilysozyme Activity," Science, 1988, vol. 239:1534-1536.
Wood, C., et. al., "The synthesis and in vivo assembly of functional antibodies in yeast," Letters to Nature, 1985, vol. 314:446-449.

\* cited by examiner

[A]

[B]

[C]

[D]

[E]

[F]

Figure 8A. Efficacy of rat-human chimeric anti-Notch ADCs dosed at 5mg/kg in HCC2429 lung xenografts HCC2429 Lung xenografts, tumor volume (mm³ +/- SEM)

| Day | PBS | ch28-me0101 | ch28-mc3377 | ch28-me0131 | ch28-MALPEG6 C2-0131 | ch75-me0131 | ch28-vc0101 | ch28-vc6780 | ch75-vc0101 | ch75-vc6780 | huNeg8.8-me0131 | huNeg8.8-mc3377 | huNeg8.8-me0131 | huNeg8.8-vc0101 | huNeg8.8-vc6780 |
|---|---|---|---|---|---|---|---|---|---|---|---|---|---|---|---|
| -2 | 198 ±144 | 195 ±137 | 195 ±139 | 196 ±139 | 196 ±147 | 195 ±35 | 195 ±126 | 195 ±133 | 195 ±125 | 205 ±35 | 195 ±143 | 195 ±145 | 195 ±142 | 209 ±145 | 195 ±143 |
| 2 | 503 ±106 | 457 ±73 | 525 ±101 | 458 ±90 | 505 ±128 | 483 ±96 | 395 ±54 | 378 ±77 | 450 ±48 | 420 ±66 | 603 ±119 | 500 ±127 | 543 ±115 | 650 ±136 | 516 ±117 |
| 4 | 838 ±187 | 506 ±96 | 654 ±136 | 504 ±112 | 638 ±192 | 522 ±125 | 298 ±46 | 329 ±73 | 366 ±47 | 430 ±92 | 845 ±149 | 637 ±175 | 746 ±168 | 845 ±201 | 759 ±177 |
| 6 | 1008 ±229 | 562 ±126 | 789 ±156 | 600 ±152 | 750 ±207 | 634 ±158 | 259 ±33 | 319 ±79 | 318 ±48 | 474 ±108 | 1117 ±171 | 939 ±243 | 1016 ±225 | 1118 ±270 | 988 ±229 |
| 9 | 1618 ±265 | 652 ±133 | 1186 ±253 | 787 ±177 | 1020 ±213 | 620 ±129 | 177 ±24 | 280 ±72 | 217 ±30 | 502 ±125 | 1773 ±264 | 1346 ±284 | 1506 ±367 | 1549 ±394 | 1449 ±304 |
| 11 | 1605± 228 | 761 ±166 | 1458 ±314 | 941 ±199 | 1302 ±257 | 737 ±162 | 169 ±22 | 290 ±77 | 196 ±30 | 601 ±155 | 1986 ±170 | 1608 ±259 | 1475 ±283 | 1532 ±407 | 1582 ±316 |
| 13 | 2033± 293 | 865 ±176 | 1534 ±339 | 1096 ±264 | 1599 ±274 | 802 ±184 | 122 ±15 | 293 ±88 | 166 ±33 | 735 ±186 | 2535 ±228 | 2257 ±350 | 1831 ±400 | - | - |
| 16 | - | 917 ±207 | - | 949 ±190 | 1556 ±300 | 878 ±200 | 97 ±13 | 266 ±105 | 120 ±26 | 781 ±210 | - | - | - | - | - |
| 19 | - | 1222 ±275 | - | 1322 ±276 | 1966 ±414 | 1051 ±247 | 88 ±14 | 484 ±171 | 102 ±28 | 770 ±153 | - | - | - | - | - |
| 23 | - | 1694 ±401 | - | - | - | 1354 ±340 | 79 ±25 | 496 ±238 | 72 ±25 | 855 ±156 | - | - | - | - | - |
| 26 | - | - | - | - | - | - | 77 ±47 | 658 ±329 | 64 ±28 | 1159 ±253 | - | - | - | - | - |
| 30 | - | - | - | - | - | - | 109 ±86 | 533 ±290 | 36 ±20 | 1270 ±205 | - | - | - | - | - |
| 33 | - | - | - | - | - | - | 138 ±128 | 775 ±411 | 36 ±34 | 1628 ±30 9 | - | - | - | - | - |
| 37 | - | - | - | - | - | - | 210 ±199 | - | 46 ±45 | - | - | - | - | - | - |
| 40 | - | - | - | - | - | - | 323 ±311 | - | 58 ±57 | - | - | - | - | - | - |
| 44 | - | - | - | - | - | - | 17 ±17 | - | 108 ±107 | - | - | - | - | - | - |
| 51 | - | - | - | - | - | - | 43 ±43 | - | 201 ±200 | - | - | - | - | - | - |
| 58 | - | - | - | - | - | - | 82 ±82 | - | 0±0 | - | - | - | - | - | - |
| 65 | - | - | - | - | - | - | 138 ±138 | - | 0±0 | - | - | - | - | - | - |
| 73 | - | - | - | - | - | - | 301 ±301 | - | 0±0 | - | - | - | - | - | - |
| 79 | - | - | - | - | - | - | - | - | 0±0 | - | - | - | - | - | - |
| 89 | - | - | - | - | - | - | - | - | 0±0 | - | - | - | - | - | - |
| 96 | - | - | - | - | - | - | - | - | 0±0 | - | - | - | - | - | - |

Figure 8B. Efficacy of rat-human chimeric anti-Notch ADCs dosed at 5mg/kg in MDA-MB-468 breast xenografts

| | MDA-MB-468 Breast xenografts, tumor volume (mm³ ± SEM) | | | | | | | |
|---|---|---|---|---|---|---|---|---|
| Day | PBS | ch75-mc3377 | ch75-mc0131 | ch75-MALPEG6 C2-0131 | ch75-mc0131 | huNeg8.8-mc0131 | huNeg8.8-mc3377 | huNeg8.8-mc0131 |
| -1 | 303 ±10 | 304 ±19 | 303 ±18 | 308 ±22 | 305 ±14 | 306 -14 | 302 ±15 | 306 ±21 |
| 2 | 344 ±14 | 315 ±26 | 348 ±21 | 375 ±16 | 354 -7 | 340 -16 | 363 ±25 | 343 ±26 |
| 5 | 360 ±17 | 339 ±25 | 339 ±16 | 325 ±23 | 346 ±14 | 349 -19 | 366 ±19 | 349 ±31 |
| 8 | 439 ±28 | 340 ±20 | 352 ±21 | 346 ±27 | 368 ±15 | 437 -35 | 431 ±25 | 421 ±36 |
| 12 | 533 ±41 | 337 ±22 | 311 ±26 | 312 ±31 | 350 ±18 | 492 -27 | 449 ±30 | 486 ±41 |
| 15 | 542 ±40 | 304 ±23 | 291 ±22 | 271 ±18 | 322 ±22 | 543 -42 | 484 ±48 | 523 ±35 |
| 19 | 608 ±46 | 234 ±20 | 228 ±25 | 204 ±20 | 283 ±19 | 552 -37 | 516 ±26 | 542 ±45 |
| 22 | 644 ±34 | 240 ±20 | 210 ±26 | 156 ±21 | 261 ±22 | 602 -38 | 561 ±38 | 586 ±47 |
| 26 | 707 ±58 | 256 ±22 | 169 ±14 | 127 ±14 | 252 ±25 | 616 -65 | 604 ±34 | 664 ±52 |
| 29 | 785 ±72 | 278 ±33 | 191 ±18 | 119 ±16 | 285 ±27 | 701 -58 | 641 ±42 | 695 ±57 |
| 33 | 822 ±78 | 320 ±45 | 205 ±23 | 133 ±22 | 315 ±31 | 755 -80 | 737 ±57 | 759 ±66 |
| 36 | 840 ±87 | 308 ±53 | 220 ±18 | 119 ±20 | 320 ±30 | 798 -55 | 865 ±54 | 788 ±81 |
| 40 | 894 ±80 | 346 ±51 | 276 ±39 | 143 ±20 | 367 ±41 | 882 -90 | 946 ±69 | 853 ±77 |
| 44 | 1040 ±104 | 373 ±49 | 312 ±34 | 162 ±29 | 421 ±29 | 1050 ±109 | 1055 ±54 | 1002 ±82 |
| 48 | 1174 ±146 | 459 ±69 | 362 ±58 | 193 ±31 | 455 ±42 | 1138 ±131 | 1148 ±36 | 1066 ±92 |
| 51 | 1266 ±144 | 539 ±83 | 418 ±49 | 237 ±31 | 563 ±48 | 1301 ±127 | 1368 ±57 | 1164 ±98 |
| 54 | 1244 ±155 | 543 ±80 | 422 ±45 | 220 ±37 | 592 ±52 | 1288 ±134 | 1321 ±56 | 1206 ±139 |
| 57 | 1366 ±161 | 594 ±97 | 474 ±85 | 260 ±36 | 665 ±56 | 1380 ±151 | 1530 ±23 | 1132 ±102 |
| 61 | 1492 ±129 | 659 ±100 | 497 ±80 | 275 ±36 | 690 ±52 | 1380 ±149 | 1607 ±39 | - |
| 64 | - | 718 ±117 | 519 ±93 | 363 ±45 | 758 ±64 | 1420 ±160 | 1580 ±47 | - |
| 68 | - | 872 ±152 | 636 ±117 | 369 ±48 | - | 1552 -198 | 1550 -71 | - |
| 71 | - | 897 ±151 | 706 ±102 | 377 ±65 | - | - | - | - |
| 78 | - | - | 906 ±137 | 511 ±74 | - | - | - | - |

Figure 8C. Efficacy of rat-human chimeric anti-Notch ADCs dosed at 5mg/kg in MDA-MB-468 breast xenograft MDA-MB-468 Breast xenografts, tumor volume (mm³ ± SEM)

| Day | PBS | ch28-mc0131 | ch28-mc3377 | ch28-me0131 | ch28-MAI.PEG 6C2-0131 | ch75-mc0131 | ch28-vc0101 | ch28-vc6780 | ch75-vc0101 | ch75-vc6780 | huNeg8.8-mc0131 | huNeg8.8-mc3377 | huNeg8.8-me0131 | huNeg8.8-vc0101 | huNeg8.8-vc6780 |
|---|---|---|---|---|---|---|---|---|---|---|---|---|---|---|---|
| -1 | 309 ±11 | 314 ±12 | 313 ±20 | 314 ±15 | 311 ±22 | 307 ±19 | 313 ±22 | 309 ±23 | 312 ±7 | 308 ±8 | 313 ±21 | 310 ±15 | 308 ±22 | 312 ±18 | 314 ±21 |
| 4 | 396 ±20 | 358 ±19 | 321 ±20 | 329 ±19 | 331 ±26 | 337 ±16 | 303 ±21 | 323 ±20 | 328 ±21 | 341 ±17 | 353 ±27 | 333 ±19 | 358 ±27 | 333 ±27 | 379 ±18 |
| 8 | 414 ±25 | 315 ±18 | 297 ±17 | 306 ±14 | 295 ±25 | 315 ±14 | 241 ±24 | 293 ±21 | 297 ±23 | 323 ±21 | 384 ±33 | 391 ±26 | 398 ±32 | 349 ±22 | 387 ±18 |
| 11 | 452 ±31 | 262 ±15 | 237 ±15 | 256 ±12 | 238 ±22 | 324 ±22 | 149 ±17 | 237 ±25 | 219 ±16 | 306 ±25 | 422 ±33 | 408 ±31 | 422 ±40 | 350 ±35 | 426 ±21 |
| 18 | 578 ±48 | 143 ±11 | 121 ±10 | 173 ±21 | 115 ±9 | 257 ±28 | 38 ±8 | 136 ±19 | 108 ±12 | 257 ±35 | 496 ±45 | 479 ±40 | 537 ±56 | 310 ±61 | 485 ±22 |
| 21 | 615 ±46 | 107 ±9 | 119 ±10 | 145 ±19 | 68 ±6 | 214 ±27 | 24 ±7 | 138 ±23 | 70 ±10 | 232 ±43 | 499 ±47 | 569 ±49 | 572 ±55 | 275 ±66 | 546 ±43 |
| 28 | 691 ±89 | 113 ±16 | 132 ±15 | 95 ±18 | 26 ±10 | 171 ±24 | 14 ±7 | 163 ±28 | 37 ±11 | 258 ±50 | 584 ±51 | 638 ±72 | 638 ±61 | 251 ±66 | 614 ±31 |
| 35 | 835 ±87 | 131 ±25 | 191 ±20 | 127 ±19 | 15 ±8 | 206 ±29 | 7 ±5 | 176 ±33 | 26 ±9 | 340 ±58 | 662 ±64 | 758 ±101 | 772 ±86 | 279 ±72 | 737 ±64 |
| 39 | 968 ±103 | 179 ±37 | 234 ±19 | 148 ±33 | 32 ±12 | 267 ±36 | 0 ±0 | 229 ±41 | 13 ±9 | 400 ±74 | 702 ±56 | 882 ±110 | 881 ±114 | 361 ±99 | 860 ±65 |
| 42 | 1004 ±112 | 168 ±35 | 256 ±22 | 174 ±37 | 32 ±13 | 240 ±42 | 0 ±0 | 242 ±41 | 10 ±8 | 420 ±72 | 753 ±75 | 945 ±123 | 926 ±115 | 362 ±90 | 888 ±49 |
| 46 | 1140 ±126 | 191 ±43 | 290 ±27 | 188 ±48 | 44 ±16 | 295 ±35 | 0 ±0 | 243 ±41 | 11 ±8 | 442 ±77 | 834 ±77 | 1016 ±148 | 930 ±152 | 377 ±101 | 965 ±102 |
| 49 | 1211 ±192 | 233 ±56 | 333 ±33 | 207 ±45 | 37 ±17 | 334 ±46 | 0 ±0 | 295 ±52 | 7 ±7 | 495 ±86 | 896 ±90 | 1114 ±150 | 1133 ±171 | 439 ±115 | 1038 ±128 |
| 57 | 1402 ±112 | 298 ±67 | 447 ±37 | 272 ±59 | 72 ±28 | 400 ±53 | 0 ±0 | 369 ±65 | 13 ±13 | 652 ±110 | 1093 ±106 | 1356 ±189 | 1329 ±175 | 577 ±155 | 1275 ±143 |
| 60 | - | 328 ±69 | 513 ±42 | 335 ±67 | 69 ±28 | 472 ±59 | 0 ±0 | 373 ±61 | 25 ±16 | 688 ±118 | 1108 ±97 | 1296 ±158 | 1187 ±161 | 483 ±88 | 1161 ±77 |
| 63 | - | 320 ±70 | 516 ±44 | 354 ±67 | 67 ±29 | 498 ±58 | 0 ±0 | 415 ±76 | 21 ±14 | 709 ±114 | 1092 ±113 | 1376 ±137 | 1332 ±160 | 579 ±148 | 1270 ±93 |
| 67 | - | 379 ±85 | 538 ±49 | 371 ±77 | 85 ±37 | 563 ±63 | 0 ±0 | 462 ±94 | 21 ±15 | 798 ±136 | 1203 ±121 | - | - | 655 ±165 | - |
| 74 | - | 434 ±96 | 682 ±57 | 382 ±47 | 114 ±47 | 665 ±74 | 0 ±0 | 499 ±91 | 42 ±27 | 928 ±143 | - | - | - | 715 ±206 | - |
| 77 | - | 470 ±113 | - | 423 ±42 | 122 ±51 | - | 0 ±0 | - | 45 ±26 | - | - | - | - | - | - |
| 84 | - | - | - | - | 177 ±72 | - | 0 ±0 | - | 67 ±37 | - | - | - | - | - | - |
| 98 | - | - | - | - | 162 ±75 | - | 0 ±0 | - | 55 ±37 | - | - | - | - | - | - |
| 104 | - | - | - | - | - | - | 0 ±0 | - | - | - | - | - | - | - | - |
| 112 | - | - | - | - | - | - | 0 ±0 | - | - | - | - | - | - | - | - |
| 117 | - | - | - | - | - | - | 0 ±0 | - | - | - | - | - | - | - | - |
| 126 | - | - | - | - | - | - | 0 ±0 | - | - | - | - | - | - | - | - |

Figure 8D. Efficacy of rat-human chimeric anti-Notch ADCs dosed at 5mg/kg in N87 gastric xenograft

| | | | N87 Gastric xenografts, tumor volume (mm³ ± SEM) | | | | | |
|---|---|---|---|---|---|---|---|---|
| Day | PBS | ch28-mc0131 | ch28-vc0101 | ch28-vc6780 | ch75-vc0101 | ch75-vc6780 | huNeg8.8-vc0101 | huNeg8.8-vc6780 |
| -1 | 388 ±16 | 391 ±11 | 394 ±16 | 388 ±17 | 391 ±8 | 385 ±18 | 394 ±18 | 393 ±16 |
| 3 | 815 ±48 | 669 ±35 | 558 ±20 | 484 ±72 | 596 ±38 | 631 ±31 | 722 ±60 | 711 ±31 |
| 6 | 907 ±56 | 583 ±41 | 488 ±48 | 522 ±41 | 611 ±27 | 672 ±40 | 745 ±76 | 733 ±43 |
| 11 | 1335 ±67 | 623 ±50 | 313 ±26 | 416 ±48 | 437 ±29 | 568 ±74 | 858 ±112 | 1019 ±46 |
| 14 | 1260 ±85 | 452 ±48 | 208 ±21 | 297 ±52 | 275 ±18 | 447 ±87 | 771 ±124 | 988 ±86 |
| 18 | 1393 ±101 | 468 ±55 | 183 ±20 | 285 ±65 | 228 ±17 | 419 ±91 | 727 ±167 | 997 ±88 |
| 21 | 1701 ±117 | 528 ±61 | 189 ±25 | 314 ±80 | 221 ±28 | 462 ±121 | 775 ±180 | 1202 ±156 |
| 25 | - | 531 ±72 | 194 ±30 | 305 ±84 | 224 ±44 | 430 ±131 | 579 ±112 | 1151 ±119 |
| 28 | - | 579 ±78 | 173 ±26 | 291 ±88 | 230 ±56 | 427 ±133 | 570 ±133 | 1247 ±137 |
| 31 | - | 597 ±75 | 176 ±32 | 349 ±110 | 256 ±62 | 458 ±148 | 646 ±148 | 1310 ±160 |
| 35 | - | 671 ±89 | 214 ±45 | 380 ±121 | 326 ±72 | 490 ±177 | 685 ±163 | 1465 ±237 |
| 39 | - | 762 ±98 | 256 ±53 | 406 ±133 | 416 ±109 | 514 ±190 | 791 ±186 | - |
| 46 | - | 873 ±115 | 279 ±58 | 493 ±158 | 549 ±156 | 603 ±225 | 912 ±248 | - |
| 50 | - | 1020 ±149 | 341 ±80 | 573 ±179 | 630 ±187 | 806 ±285 | - | - |
| 55 | - | 1055 ±153 | 374 ±83 | 560 ±174 | 715 ±207 | 600 ±238 | - | - |
| 62 | - | 1193 ±207 | 379 ±85 | 653 ±204 | 806 ±253 | 649 ±254 | - | - |
| 69 | - | - | 490 ±106 | 773 ±254 | - | 788 ±313 | - | - |
| 77 | - | - | 534 ±126 | 720 ±269 | - | - | - | - |
| 83 | - | - | 627 ±156 | - | - | - | - | - |
| 90 | - | - | 813 ±197 | - | - | - | - | - |
| 95 | - | - | 903 ±207 | - | - | - | - | - |
| 101 | - | - | 901 ±213 | - | - | - | - | - |

Figure 8E. Efficacy of rat-human chimeric anti-Notch ADCs dosed at 5mg/kg in N87 gastric xenografts

| | N87 Gastric xenografts, tumor volume (mm³ ± SEM) | | | | |
|---|---|---|---|---|---|
| Day | PBS | ch28-mc0131 | ch28-m(H2O)c-0131 | ch75-mc0131 | ch75-m(H2O)c-0131 |
| -1 | 372 ±8 | 371 ±18 | 371 ±17 | 364 ±12 | 375 ±15 |
| 4 | 589 ±28 | 473 ±41 | 469 ±41 | 461 ±33 | 497 ±34 |
| 7 | 706 ±56 | 479 ±39 | 446 ±34 | 466 ±28 | 484 ±35 |
| 11 | 837 ±71 | 442 ±37 | 391 ±29 | 468 ±33 | 414 ±28 |
| 14 | 959 ±98 | 395 ±43 | 303 ±24 | 430 ±33 | 337 ±20 |
| 18 | 1069 ±106 | 328 ±36 | 231 ±27 | 424 ±41 | 279 ±14 |
| 21 | 1252 ±123 | 337 ±48 | 232 ±29 | 448 ±42 | 268 ±13 |
| 25 | 1230 ±112 | 324 ±55 | 230 ±38 | 422 ±45 | 271 ±11 |
| 28 | 1352 ±132 | 363 ±62 | 256 ±41 | 487 ±52 | 266 ±17 |
| 32 | - | 381 ±66 | 255 ±49 | 530 ±56 | 298 ±22 |
| 35 | - | 419 ±85 | 283 ±52 | 541 ±56 | 307 ±21 |
| 39 | - | 453 ±87 | 315 ±65 | 570 ±55 | 358 ±23 |
| 42 | - | 522 ±108 | 347 ±71 | 619 ±66 | 388 ±34 |
| 46 | - | 559 ±119 | 381 ±87 | 629 ±68 | 432 ±41 |
| 49 | - | 637 ±139 | 418 ±96 | 697 ±87 | 447 ±48 |
| 53 | - | 681 ±149 | 441 ±107 | 755 ±91 | 484 ±52 |
| 56 | - | 713 ±167 | 479 ±113 | 753 ±90 | 512 ±55 |
| 63 | - | 783 ±192 | 542 ±139 | 869 ±112 | 563 ±70 |
| 70 | - | 847 ±219 | 535 ±148 | 827 ±107 | 579 ±86 |
| 77 | - | 1081 ±273 | 726 ±191 | 1041 ±139 | 788 ±110 |
| 84 | - | - | 855 ±230 | 1172 ±165 | 872 ±131 |
| 91 | - | - | 722 ±194 | 1332 ±194 | 1015 ±169 |
| 98 | - | - | 757 ±204 | - | 1125 ±198 |

CYTOTOXIC PEPTIDES AND ANTIBODY DRUG CONJUGATES THEREOF

CROSS-REFERENCE TO RELATED APPLICATIONS

This application claims the benefits of U.S. Provisional Application No. 61/561,255 filed Nov. 17, 2011, and U.S. Provisional Application No. 61/676,423 filed Jul. 27, 2012, which are both hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71886ASequenceListing_ST25.txt" created on Oct. 24, 2012 and having a size of 45 KB. The sequence listing contained in this .txt file is part of the specification and is incorporated herein by reference in its entirety.

FIELD OF THE INVENTION

The present invention is directed to novel peptide-based compounds useful as payloads in antibody-drug-conjugates (ADC's), and payload-linker compounds useful in connection with ADC's. The present invention further relates to compositions including the aforementioned payloads, payload-linkers and ADC's, and methods for using these payloads, payload-linkers and ADC's, to treat pathological conditions including cancer.

BACKGROUND

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

While a number of different drug classes have been tried for delivery via antibodies, only a few drug classes have proved efficacious as antibody drug conjugates, while having a suitable toxicity profile. One such class is the auristatins, derivatives of the natural product dolastatin 10. Representative auristatins include (N-methylvaline-valine-dolaisoleuine-dolaproine-norephedrine) and (N-methylvaline-valine-dolaisoleuine-dolaproine-phenylalanine). However, there remains a need for additional auristatins with improved properties.

SUMMARY

The present invention relates to cytotoxic pentapeptides and antibody drug conjugates thereof represented by formula:

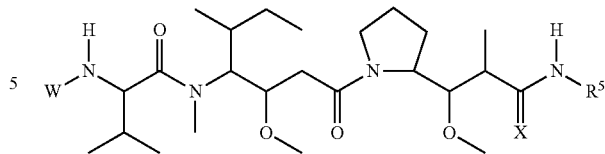

or a pharmaceutically acceptable salt or solvate thereof, wherein, independently for each occurrence, W is

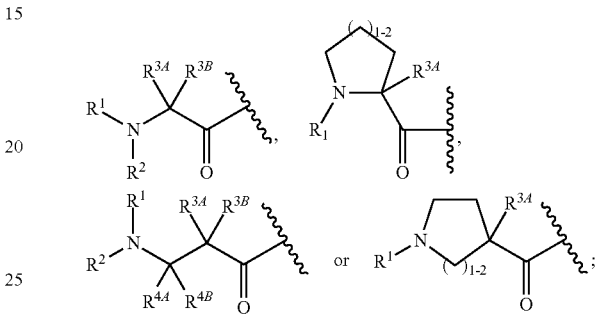

$R^1$ is hydrogen, $C_1$-$C_8$ alkyl, or $C_1$-$C_8$ haloalkyl, or $R^1$ is a linker or a linker-antibody such

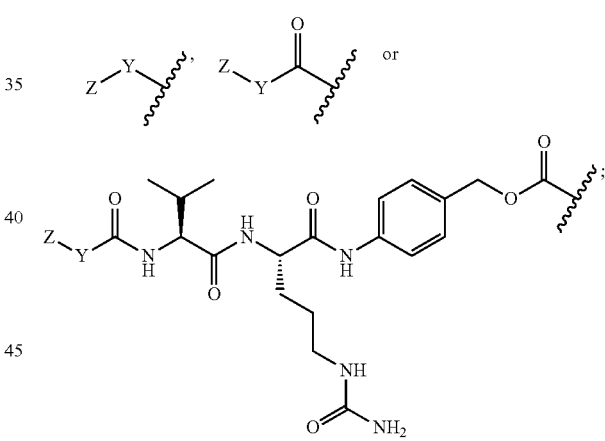

as

Y is —$C_2$-$C_{20}$ alkylene-, —$C_2$-$C_{20}$ heteroalkylene-, $C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)- or —($C_3$-$C_8$ heterocyclo)-$C_1$-$C_{10}$alkylene-;

Z is

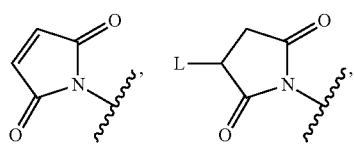

3
-continued

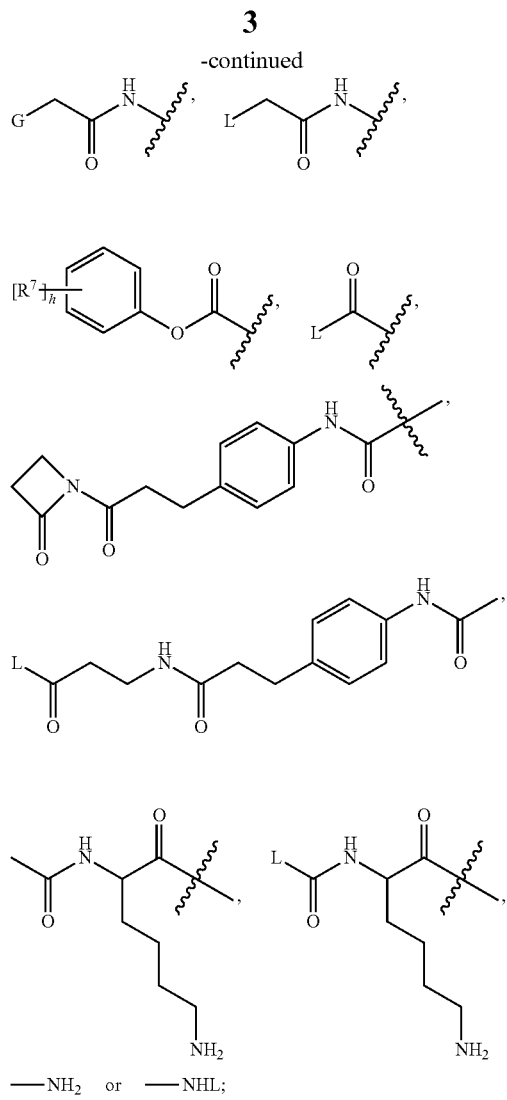

G is halogen, —OH, —SH or —S—$C_1$-$C_6$ alkyl;

L is an antibody;

$R^2$ is hydrogen, $C_1$-$C_8$ alkyl or $C_1$-$C_8$ haloalkyl;

$R^{3A}$ and $R^{3B}$ are defined as either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; or (ii) $R^{3A}$ and $R^{3B}$ taken together are $C_2$-$C_8$ alkylene or $C_1$-$C_8$ heteroalkylene;

$R^{4A}$ and $R^{4B}$ are defined as either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

4

$R^5$ is

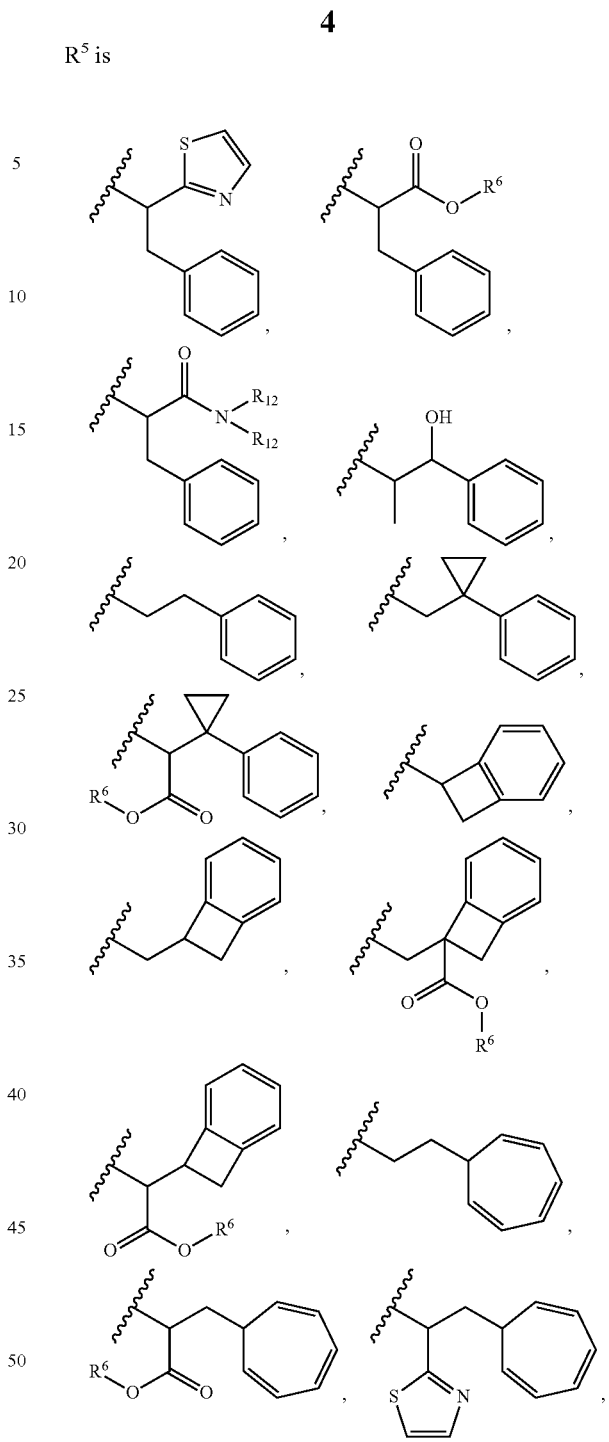

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

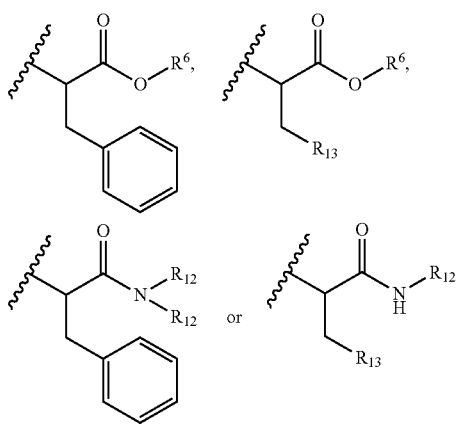

optionally substituted with 1, 2, 3, 4 or 5 groups independently selected from the group consisting of $C_1$-$C_8$ alkyl, —$C_1$-$C_8$ alkyl-$N(R')_2$, —$C_1$-$C_8$ alkyl-$C(O)R'$, —$C_1$-$C_8$ alkyl-$C(O)OR'$, —O—($C_1$-$C_8$ alkyl), —$C(O)R'$, —$OC(O)R'$, —$C(O)OR'$, —$C(O)N(R')_2$, —$NHC(O)R'$, —$S(O)_2R'$, —$S(O)R'$, —OH, halogen, —$N_3$, —$N(R')_2$, —CN, —NHC(=NH)$NH_2$, —$NHCONH_2$, —$S(=O)_2R'$, —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and $R^7$ is F, Cl, I, Br, $NO_2$, CN and $CF_3$;

h is 1, 2, 3, 4 or 5; and

X is O or S;

provided that when $R^{3A}$ is hydrogen X is S.

The present invention relates to cytotoxic pentapeptides and antibody drug conjugates thereof represented by formula:

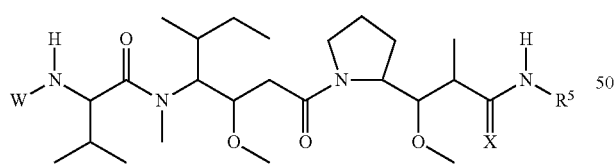

or a pharmaceutically acceptable salt or solvate thereof, wherein, independently for each occurrence, W is

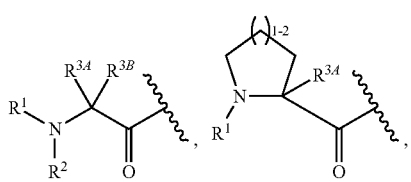

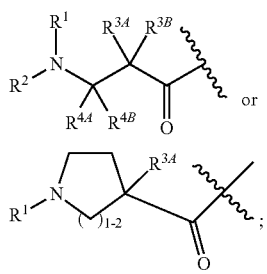

$R^1$ is hydrogen, $C_1$-$C_8$ alkyl or $C_1$-$C_8$ haloalkyl;

$R^2$ is hydrogen, $C_1$-$C_8$ alkyl or $C_1$-$C_8$ haloalkyl;

$R^{3A}$ and $R^{3B}$ are defined as either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl, halogen or hydrogen; or (ii) $R^{3A}$ and $R^{3B}$ taken together are $C_2$-$C_8$ alkylene or $C_1$-$C_8$ heteroalkylene;

$R^{4A}$ and $R^{4B}$ are defined as either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

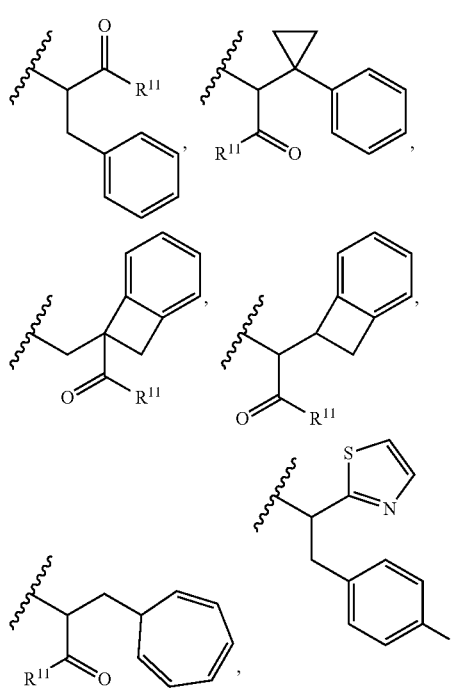

-continued

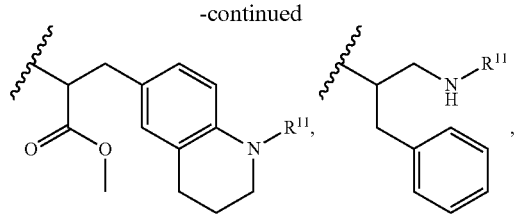

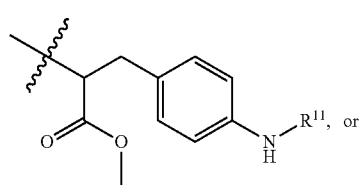

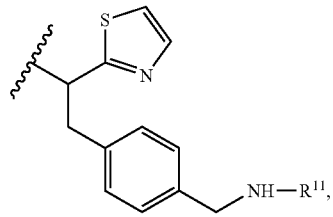

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

$R^{11}$ is hydrogen, $C_1$-$C_8$ alkyl, $C_1$-$C_8$ haloalkyl, or $R^{11}$ is a linker or linker-antibody such as

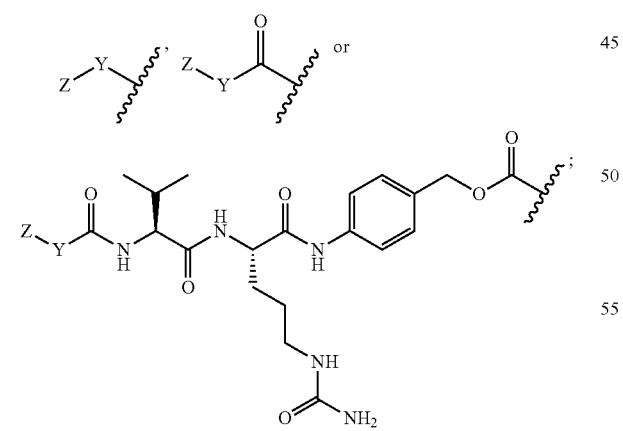

Y is $C_2$-$C_{20}$ alkylene or $C_2$-$C_{20}$ heteroalkylene; $C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z is

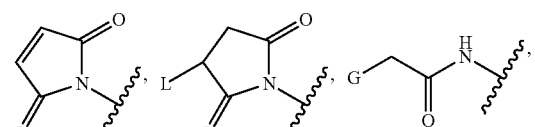

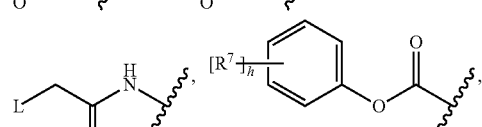

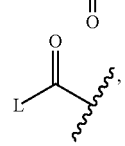

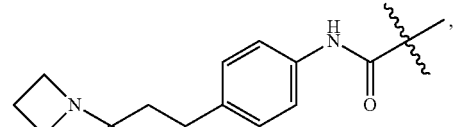

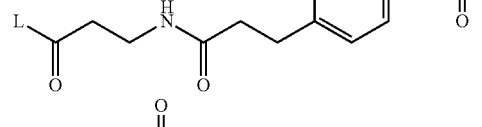

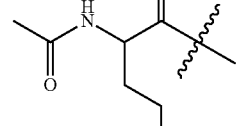

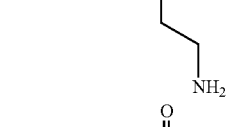

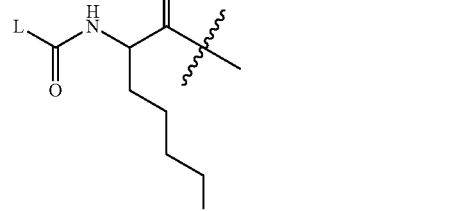

G is halogen, —OH, —SH or —S—$C_1$-$C_6$ alkyl; L is an antibody;

$R^7$ is F, Cl, I, Br, NO$_2$, CN and CF$_3$, h is 1, 2, 3, 4 or 5; and

X is O or S.

Another aspect of the invention relates to pharmaceutical compositions including an effective amount of any one of the aforementioned compounds and/or any one of the aforementioned antibody drug conjugates and a pharmaceutically acceptable carrier or vehicle.

Another aspect of the invention relates to a method of using an effective amount of any one of the aforementioned compounds and/or any one of the aforementioned antibody drug conjugates to treat cancer by administering to a patient in need thereof an effective amount of said compound and/or conjugate.

Another aspect of the invention relates to a method of treating cancer wherein said cancer includes a tumor, metastasis, or other disease or disorder characterized by uncontrolled cell growth wherein said cancer is selected from the group consisting of carcinomas of the bladder, breast, cervix, colon, gliomas, endometrium, kidney, lung, esophagus, ovary, prostate, pancreas, melanoma, stomach, and testes.

BRIEF DESCRIPTION OF THE FIGURES

FIGS. 8A through E show [A] the efficacy of rat-human chimeric anti-Notch ADCs dosed at 5 mg/kg in HCC2429 lung xenografts; [B and C] the efficacy of rat-human chimeric anti-Notch ADCs dosed at 5 mg/kg in MDA-MB-468 breast xenografts; [D and E] the efficacy of rat-human chimeric anti-Notch ADCs dosed at 5 mg/kg in N87 gastric xenograft.

DETAILED DESCRIPTION

Figure 1:
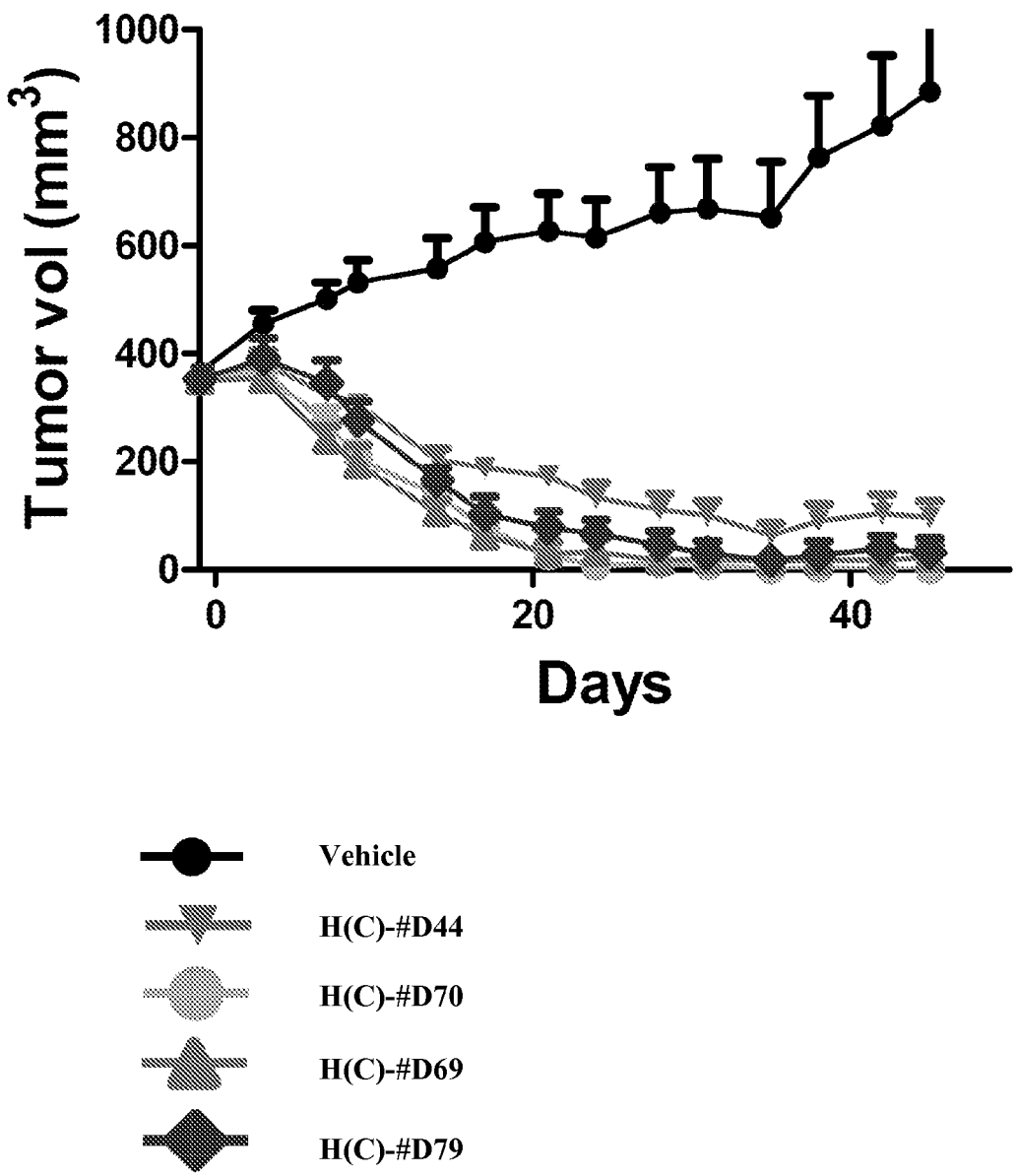
FIG. 1 depicts a graph of anti-tumor activity of four conjugates (each administered at 1 mg/kg, Q4dx4) plotted as tumor volume over time.

The present invention is directed to cytotoxic pentapeptides, to antibody drug conjugates comprising said cytotoxic pentapeptides, and to methods for using the same to treat cancer and other pathological conditions. The invention also relates to methods of using such compounds and/or conjugates in vitro, in situ, and in vivo for the detection, diagnosis or treatment of mammalian cells, or associated pathological conditions.

DEFINITIONS AND ABBREVIATIONS

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab") herein is used in the broadest sense and specifically covers intact monoclonal antibodies, polyclonal antibodies, monospecific antibodies, multi-specific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

As used herein, "H(C)-" refers to trastuzumab (trade name HERCEPTIN®) which is a monoclonal antibody that interferes with the HER2/neu receptor, bound through one of its' cystine to compound of the invention. As used herein, "H(K)-" refers to trastuzumab which is a monoclonal antibody that interferes with the HER2/neu receptor, bound through one of its' lysines to compound of the invention.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the V.sub.H and V.sub.L domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture.

As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). When the number of carbon atoms is not indicated, the alkyl group has from 1 to 8 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene —$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

Unless otherwise indicated, the term "heteroalkylene" by itself or as part of another substituent means a divalent group derived from heteroalkyl (as discussed above). For heteroalkylene groups, heteroatoms can also occupy either or both of the chain termini.

Unless otherwise indicated, "aryl," by itself or an part of another term, means a substituted or unsubstituted monovalent carbocyclic aromatic hydrocarbon radical of 6-20, preferably 6-14, carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted carbocyclic aromatic group (e.g., an aryl group) can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$, —NHC(O)R', —S(O)$_2$R', —S(O)R', —OH, halogen, —$N_3$, —$NH_2$, —NH(R'), —N(R')$_2$ and —CN; wherein each R' is independently selected from —H, $C_1$-$C_8$ alkyl and unsubstituted aryl. In some embodiments, a substituted carbocyclic aromatic group can further include one or more of: —NHC(=NH)$NH_2$, —NHCON$H_2$, —S(=O)$_2$R' and —SR'. "Arylene" is the corresponding divalent moiety.

"Substituted alkyl" means an alkyl in which one or more hydrogen atoms are each independently replaced with a substituent. Typical substituents include, but are not limited to, —X, —R, —O—, —OR, —SR, —S$^-$, —NR$_2$, —NR$_3$, =NR, —CX$_3$, —CN, —OCN, —SCN, —N=C=O, —NCS, —NO, —NO$_2$, =$N_2$, —$N_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, $C_1$-$C_{20}$ alkyl, $C_1$-$C_{20}$ heteroalkyl, $C_6$-$C_{20}$ aryl, $C_1$-$C_{10}$ heterocyclyl, a protecting group or a prodrug moiety. Aryl, alkylene and heteroalkylene groups as described above may also be similarly substituted.

Unless otherwise indicated, "aralkyl" by itself or part of another term, means an alkyl group, as defined above, substituted with an aryl group, as defined above.

Unless otherwise indicated, "$C_1$-$C_{10}$ heterocyclyl" by itself or as part of another term, refers to a monovalent substituted or unsubstituted aromatic or non-aromatic monocyclic, bicyclic or tricyclic ring system having from 1 to 10, preferably 3 to 8, carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Unless otherwise noted, the heterocyclyl is attached to its pendant group at any heteroatom or carbon atom that results in a stable structure. Representative examples of a $C_1$-$C_{10}$ heterocyclyl include, but are not limited to, tetrahyrofuranyl, oxetanyl, pyranyl, pyrrolidinyl, piperidinyl, piperazinyl, benzofuranyl, benzothiophene, benzothiazolyl, indolyl, benzopyrazolyl, pyrrolyl, thiophenyl (thiopene), furanyl, thiazolyl, imidazolyl, pyrazolyl, triazolyl, quinolinyl including moieties such as 1,2,3,4-tetrshyhroquinolinyl, pyrimidinyl, pyridinyl, pyridonyl, pyrazinyl, pyridazinyl, isothiazolyl, isoxazolyl, tetrazolyl, epoxide, oxetane and BODIPY (substituted or unsubstituted). A $C_1$-$C_{10}$ heterocyclyl can be substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)$NH_2$, —C(O)NHR', —C(O)N(R')$_2$, —NHC(O)R', —S(=O)$_2$R', —S(O)R', halogen, —$N_3$, —$NH_2$, —NH(R'), —N(R')$_2$ and —CN; wherein each R' is independently selected from —H, $C_1$-$C_8$ alkyl, $C_1$-$C_8$ heteroalkyl and aryl. In some embodiments, a substituted heterocyclyl can also include one or more of: —NHC(=NH)$NH_2$, —NHCON$H_2$, —S(=O)$_2$R' and —SR'. "Heterocyclo" "$C_1$-$C_{10}$ heterocyclo" is the corresponding divalent moiety.

Unless otherwise indicated, "heteroaralkyl" by itself or part of another term, means an alkyl group, as defined above, substituted with an aromatic heterocyclyl group, as defined above. Heteroaralklo is the corresponding divalent moiety.

Unless otherwise indicated, "$C_3$-$C_8$ carbocyclyl" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.)pentane, and bicyclo(2.2.2.)octane. A $C_3$-$C_8$ carbocyclyl group can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)$NH_2$, —C(O)NHR', —C(O)N(R')$_2$, —NHC(O)R', —S(=O)$_2$R', —S(=O)R', —OH, -halogen, —$N_3$, —$NH_2$, —NH(R'), —N(R')$_2$ and —CN; where each R' is independently selected from —H, $C_1$-$C_8$ alkyl, $C_1$-$C_8$ heteroalkyl and aryl. "$C_3$-$C_8$ carbocyclo" is the corresponding divalent moiety.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

"Protecting group" refers to a moiety that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, malate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound or conjugate of the invention. Examples of solvents that form pharmaceutically acceptable solvates include, but are not limited to, water, isopropanol, ethanol, methanol, DMSO, ethyl acetate, acetic acid, and ethanolamine.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADC's with a distribution of one or more drugs moieties per antibody. The average number of drugs per antibody may be calculated from the mixture by, for example, dual ELISA antibody assay, specific for antibody and specific for the drug. Individual ADC's may be identified in the mixture by mass spectroscopy, and separated by HPLC, e.g., hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1', 1''-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

Compounds and Antibody Drug Conjugates Thereof

One aspect of the invention relates to a compound of formula I:

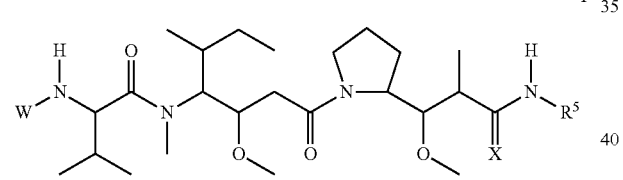

or a pharmaceutically acceptable salt or solvate thereof, wherein, independently for each occurrence, W is

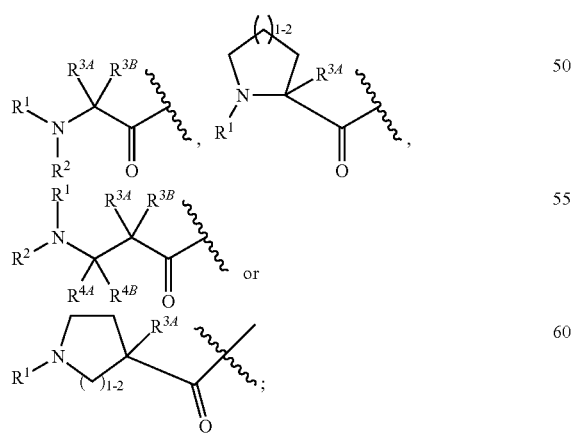

$R^1$ is hydrogen, $C_1$-$C_8$ alkyl or $C_1$-$C_8$ haloalkyl;
$R^2$ is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

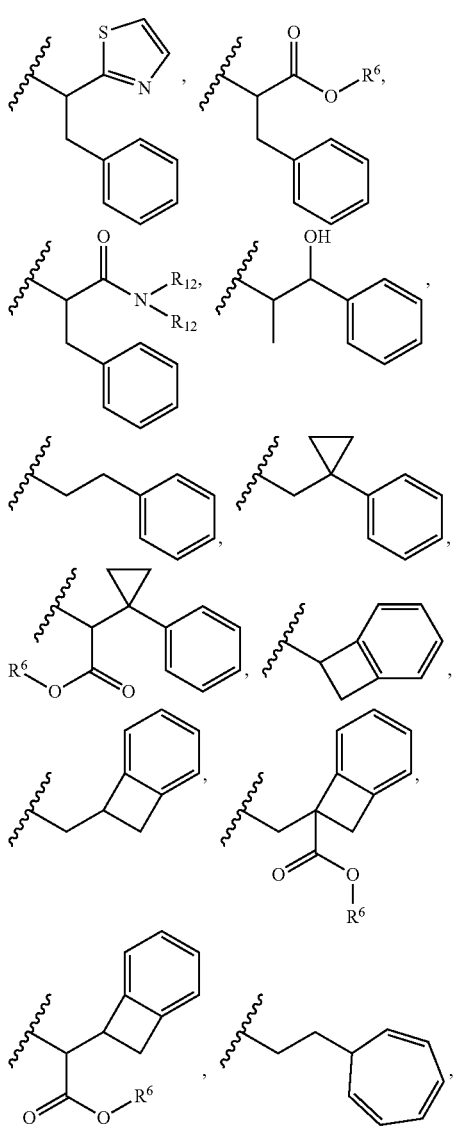

-continued

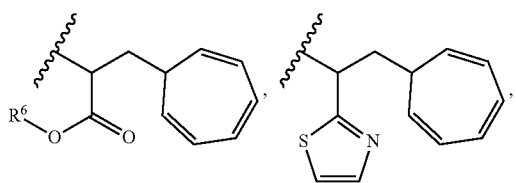

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

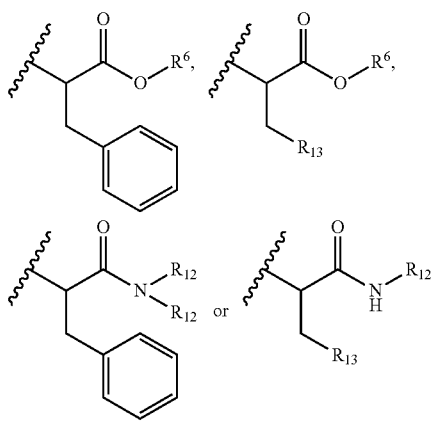

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O or S;

provided that when $R^{3A}$ is hydrogen X is S.

Another aspect of the invention relates to compound of formula IIa:

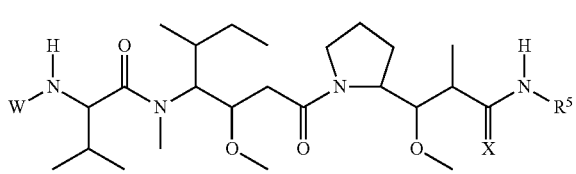

or a pharmaceutically acceptable salt or solvate thereof, wherein, independently for each occurrence, W is

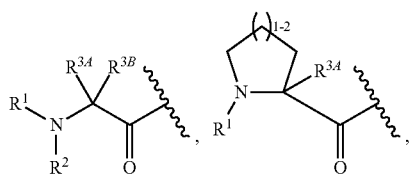

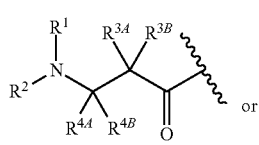

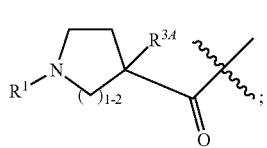

$R^1$ is

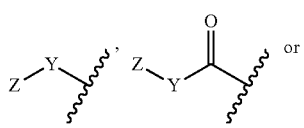

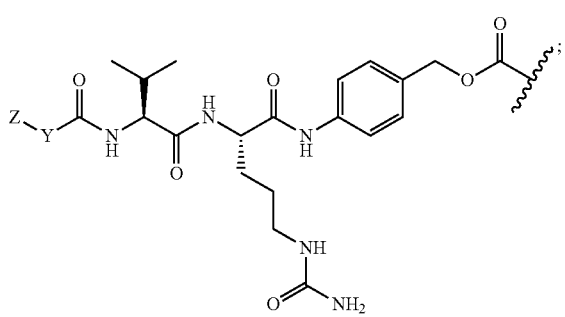

Y is —$C_2$-$C_{20}$ alkylene-, —$C_2$-$C_{20}$ heteroalkylene-; —$C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)- or —($C_3$-$C_8$ heterocyclo)-$C_1$-$C_{10}$alkylene-;

Z is

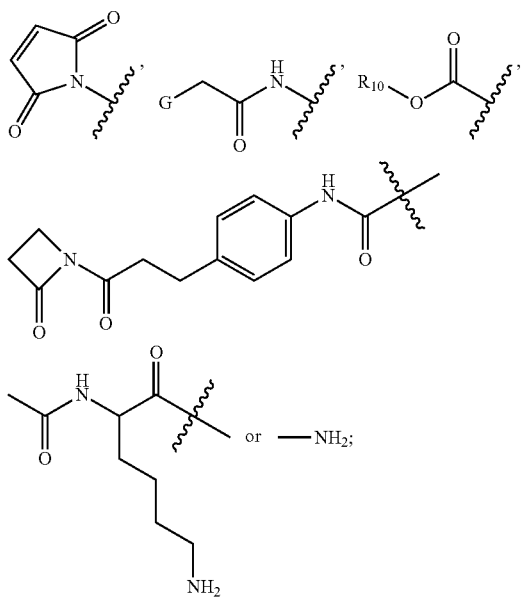
or —NH$_2$;

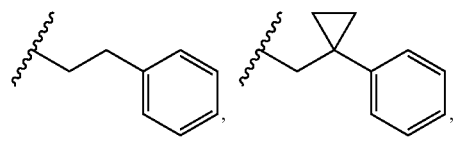

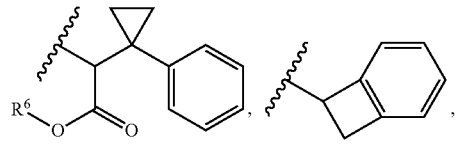

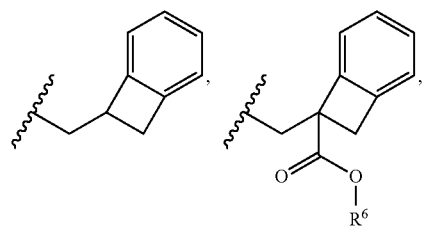

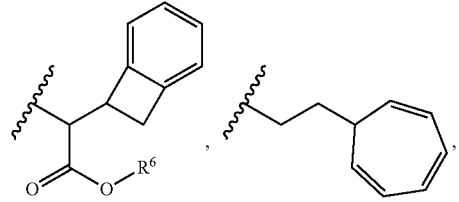

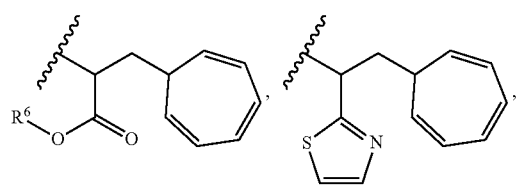

G is halogen, —OH, —SH or —S—C$_1$-C$_6$ alkyl;
R$^2$ is hydrogen, C$_1$-C$_8$ alkyl or C$_1$-C$_8$ haloalkyl;
R$^{3A}$ and R$^{3B}$ are either of the following:
(i) R$^{3A}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, aralkyl or halogen; and
R$^{3B}$ is C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl or halogen; or
(ii) R$^{3A}$ and R$^{3B}$ taken together are C$_2$-C$_8$ alkylene or C$_1$-C$_8$ heteroalkylene;
R$^{4A}$ and R$^{4B}$ are either of the following:
(i) R$^{4A}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; and
R$^{4B}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; or
(ii) R$^{4A}$ and R$^{4B}$ taken together are C$_2$-C$_8$ alkylene or C$_1$-C$_8$ heteroalkylene;
R$^5$ is

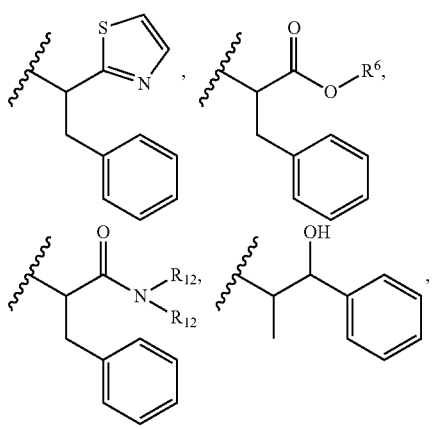

C$_1$-C$_{10}$ heterocyclyl, C$_3$-C$_8$ carbocycly and C$_6$-C$_{14}$ aryl optionally substituted with 1, 2, 3, 4 or 5 groups independently selected from the group consisting of —C$_1$-C$_8$ alkyl, —C$_1$-C$_8$ alkyl-N(R')$_2$, —C$_1$-C$_8$ alkyl-C(O)R', —C$_1$-C$_8$ alkyl-C(O)OR'—O—(C$_1$-C$_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, C$_1$-C$_8$ alkyl and unsubstituted aryl, or two R' can, together with the nitrogen to which they are attached, form a C$_1$-C$_{10}$ heterocyclyl;
or R$^5$ is

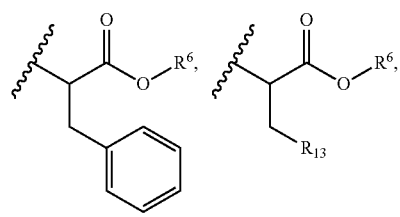

-continued

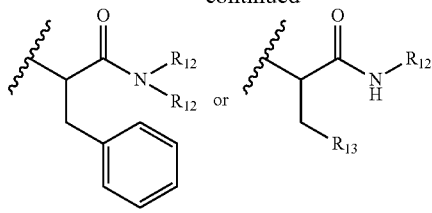

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$aryl;

$R^{13}$ is $C_1$-$C_{10}$ heterocyclyl; and $R^7$ is independently selected for each occurrence from the group consisting of F, Cl, I, Br, NO$_2$, CN and CF$_3$;

$R^{10}$ is hydrogen, —$C_1$-$C_{10}$alkyl, —$C_3$-$C_8$-carbocyclyl, -aryl, —$C_1$-$C_{10}$heteroalkyl, —$C_3$-$C_8$heterocyclo, —$C_1$-$C_{10}$alkylene-aryl, -arylene-$C_1$-$C_{10}$alkyl, —$C_1$-$C_{10}$alkylene-($C_3$-$C_8$-carbocyclo), —($C_3$-$C_8$ carbocyclo)-$C_1$-$C_{10}$alkyl, —$C_1$-$C_{10}$alkylene-($C_3$-$C_8$heterocyclo), and —($C_3$-$C_8$ heterocyclo)-$C_1$-$C_{10}$alkyl, where aryl on $R^{10}$ comprising aryl is optionally substituted with [$R_7$]$_h$;

h is 1, 2, 3, 4 or 5; and

X is O or S;

provided that when $R^{3A}$ is hydrogen X is S.

Another aspect of the invention relates to compound of formula IIIa:

IIIa

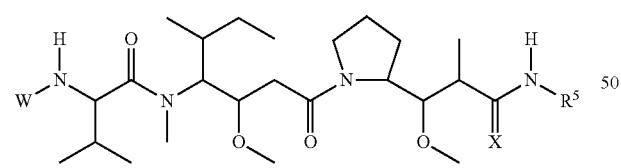

or a pharmaceutically acceptable salt or solvate thereof, wherein, independently for each occurrence, W is

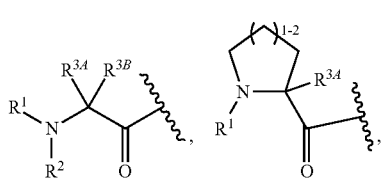

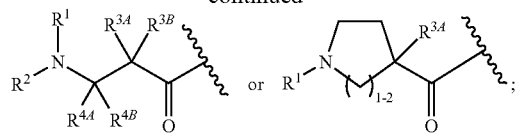

$R^1$ is hydrogen, $C_1$-$C_8$ alkyl or $C_1$-$C_8$ haloalkyl;

$R^2$ is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

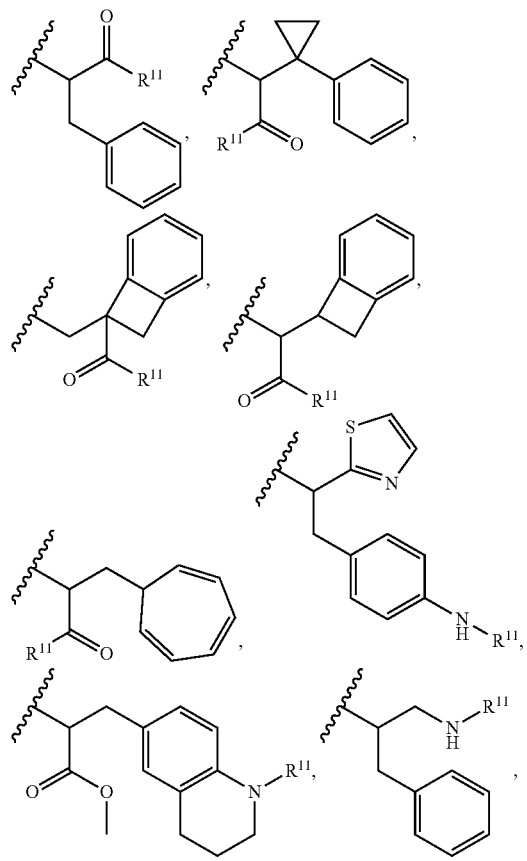

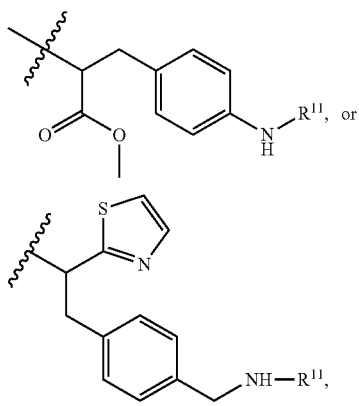

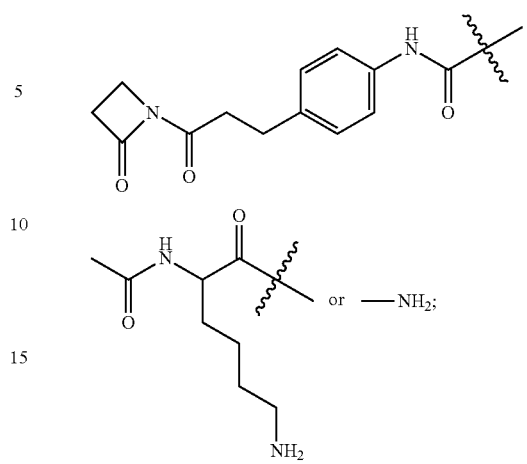

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

$R^{11}$ is

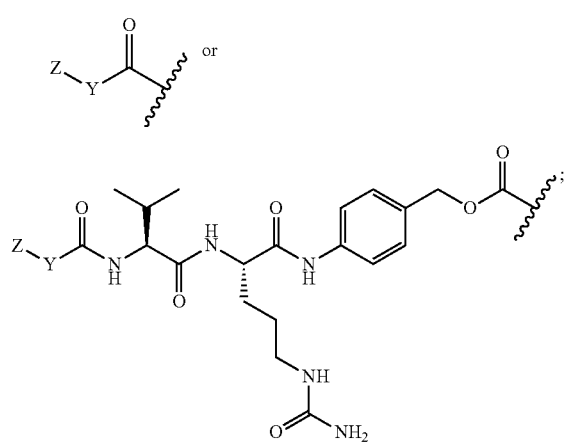

Y is —$C_2$-$C_{20}$ alkylene-, —$C_2$-$C_{20}$ heteroalkylene-, $C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z is

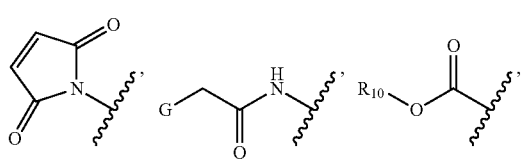

$R^7$ is independently selected for each occurrence from the group consisting of F, Cl, I, Br, NO$_2$, CN and CF$_3$;

$R^{10}$ is hydrogen, —$C_1$-$C_{10}$alkyl, —$C_3$-$C_8$-carbocycle, aryl, —$C_1$-$C_{10}$heteroalkyl, —$C_3$-$C_8$heterocyclo, —$C_1$-$C_{10}$alkylene-aryl, -arylene-$C_1$-$C_{10}$alkyl, —$C_1$-$C_{10}$alkylene-($C_3$-$C_8$-carbocyclo), —($C_3$-$C_8$ carbocyclo)-$C_1$-$C_{10}$alkyl, —$C_1$-$C_{10}$alkylene-($C_3$-$C_8$heterocyclo), and —($C_3$-$C_8$ heterocyclo)-$C_1$-$C_{10}$alkyl, where aryl on $R_{10}$ comprising aryl is optionally substituted with $[R_7]_h$;

h is 1, 2, 3, 4 or 5; and

X is O or S.

$R^6$ is hydrogen, $C_1$-$C_8$ alkyl or $C_1$-$C_8$ haloalkyl; and h is 1, 2, 3, 4 or 5.

Another aspect of the invention relates to compound of formula In:

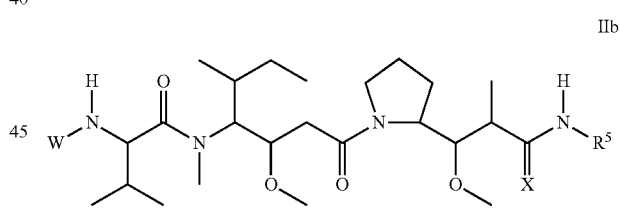

IIb or a pharmaceutically acceptable salt or solvate thereof, wherein, independently for each occurrence, W is

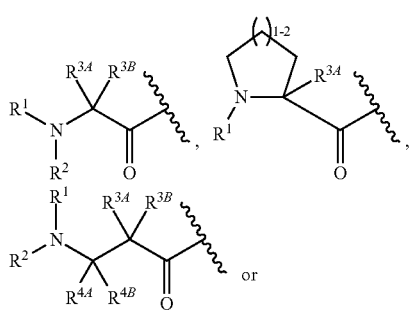

-continued

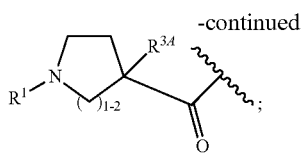

R¹ i,

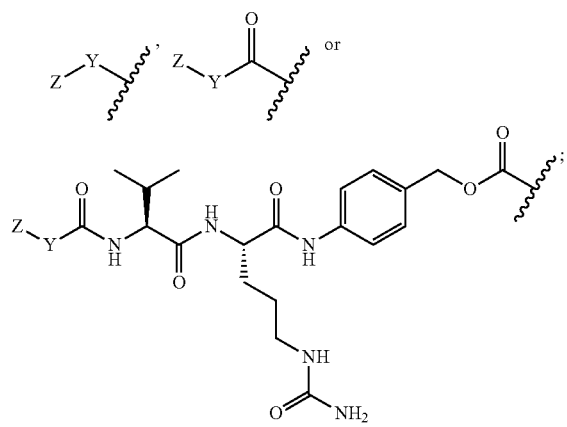

Y is —C$_2$-C$_{20}$ alkylene-, —C$_2$-C$_{20}$ heteroalkylene-, —C$_3$-C$_8$ carbocyclo-, -arylene-, —C$_3$-C$_8$heterocyclo-, —C$_1$-C$_{10}$alkylene-arylene-, -arylene-C$_1$-C$_{10}$alkylene-, —C$_1$-C$_{10}$alkylene-(C$_3$-C$_8$-carbocyclo)-, —(C$_3$-C$_8$-carbocyclo)-C$_1$-C$_{10}$alkylene-, —C$_1$-C$_{10}$alkylene-(C$_3$-C$_8$heterocyclo)-, or -(C$_3$-C$_8$ heterocyclo)-C$_1$-C$_{10}$alkylene-;

Z is

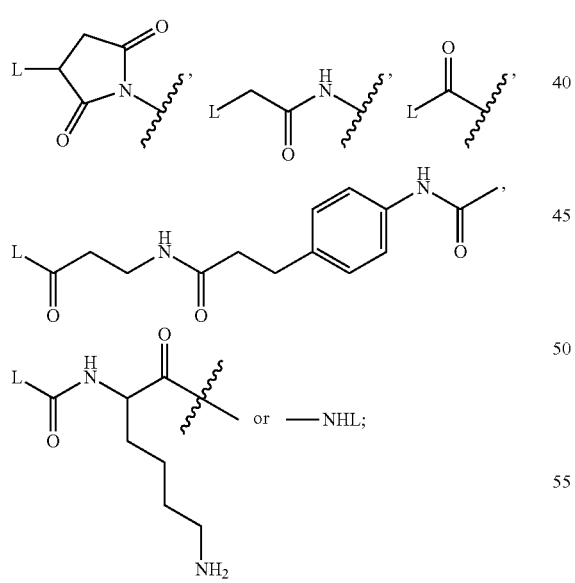

L is an antibody;

R² is hydrogen, C$_1$-C$_8$ alkyl or C$_1$-C$_8$ haloalkyl;

R$^{3A}$ and R$^{3B}$ are either of the following:

(i) R$^{3A}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, aralkyl or halogen; and R$^{3B}$ is C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, halogen or aralkyl; or (ii) R$^{3A}$ and R$^{3B}$ taken together are C$_2$-C$_8$ alkylene or C$_1$-C$_8$ heteroalkylene;

R$^{4A}$ and R$^{4B}$ are either of the following:

(i) R$^{4A}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; and R$^{4B}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; or (ii) R$^{4A}$ and R$^{4B}$ taken together are C$_2$-C$_8$ alkylene or C$_1$-C$_8$ heteroalkylene;

R⁵ is

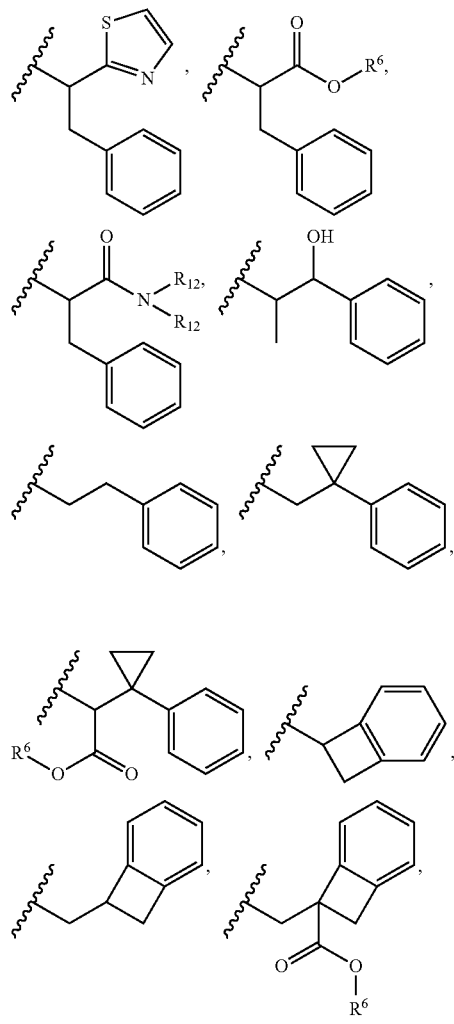

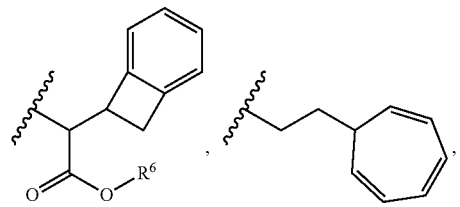

-continued

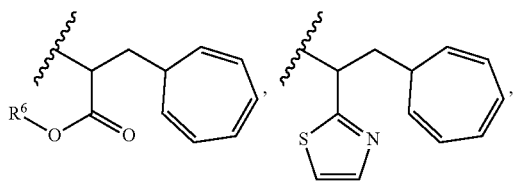

C₁-C₁₀ heterocyclyl, C₃-C₈ carbocycly and C₆-C₁₄ aryl optionally substituted with 1, 2, 3, 4 or 5 groups independently selected from the group consisting of —C₁-C₈ alkyl, —C₁-C₈ alkyl-N(R')₂, —C₁-C₈ alkyl-C(O)R', —C₁-C₈ alkyl-C(O)OR'—O—(C₁-C₈ alkyl), —C(O)R', —OC(O)R', —C(O)OR', —C(O)N(R')₂, —NHC(O)R', —S(O)₂R', —S(O)R', —OH, halogen, —N₃, —N(R')₂, —CN, —NHC(=NH)NH₂, —NHCONH₂, —S(=O)₂R' and —SR', wherein each R' is independently selected from the group consisting of hydrogen, C₁-C₈ alkyl and unsubstituted aryl, or two R' can, together with the nitrogen to which they are attached, form a C₁-C₁₀ heterocyclyl;

or R⁵ is

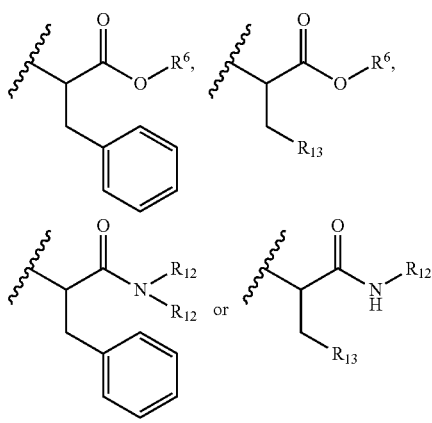

optionally substituted with 1, 2, 3, 4 or 5 groups independently selected from the group consisting of C₁-C₈ alkyl, —C₁-C₈ alkyl-N(R')₂, —C₁-C₈ alkyl-C(O)R', —C₁-C₈ alkyl-C(O)OR', —O—(C₁-C₈ alkyl), —C(O)R', —OC(O)R', —C(O)OR', —C(O)N(R')₂, —NHC(O)R', —S(O)₂R', —S(O)R', —OH, halogen, —N₃, —N(R')₂, —CN, —NHC(=NH)NH₂, —NHCONH₂, —S(=O)₂R', —SR' and arylene-R', wherein each R' is independently selected from the group consisting of hydrogen, C₁-C₈ alkyl, C₁-C₈ heterocyclyl, C₁-C₁₀ alkylene-C₃-C₈ heterocyclyl and aryl, or two R' can, together with the nitrogen to which they are attached, form a C₁-C₁₀ heterocyclyl;

R⁶ is hydrogen, —C₁-C₈ alkyl, —C₂-C₈ alkenyl, —C₂-C₈ alkynyl or —C₁-C₈ haloalkyl;

R¹² is hydrogen, C₁-C₄ alkyl, C₁-C₁₀ heterocyclyl or C₆-C₁₄ aryl;

R¹³ is C₁-C₁₀ heterocyclyl; and

X is O or S;

provided that when R³ᴬ is hydrogen X is S.

Another aspect of the invention relates to compound of formula IIIb:

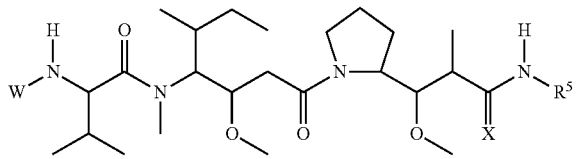

or a pharmaceutically acceptable salt or solvate thereof, wherein, independently for each occurrence, W is

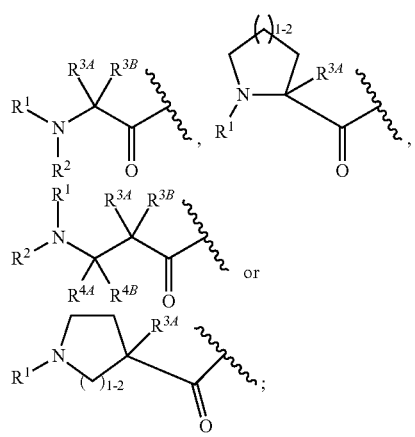

R¹ is hydrogen, C₁-C₈ alkyl or C₁-C₈ haloalkyl;

R² is hydrogen, C₁-C₈ alkyl or C₁-C₈ haloalkyl;

R³ᴬ and R³ᴮ are either of the following:

(i) R³ᴬ is hydrogen, C₁-C₈ alkyl, C₁-C₈ haloalkyl, C₃-C₈ carbocyclyl, C₁-C₁₀ heterocyclyl, aryl, heteroaralkyl, aralkyl or halogen; and R³ᴮ is C₁-C₈ alkyl, C₁-C₈ haloalkyl, C₃-C₈ carbocyclyl, C₁-C₁₀ heterocyclyl, aryl, heteroaralkyl, halogen or aralkyl; or (ii) R³ᴬ and R³ᴮ taken together are C₂-C₈ alkylene or C₁-C₈ heteroalkylene;

R⁴ᴬ and R⁴ᴮ are either of the following:

(i) R⁴ᴬ is hydrogen, C₁-C₈ alkyl, C₁-C₈ haloalkyl, C₃-C₈ carbocyclyl, C₁-C₁₀ heterocyclyl, aryl, heteroaralkyl or aralkyl; and R⁴ᴮ is hydrogen, C₁-C₈ alkyl, C₁-C₈ haloalkyl, C₃-C₈ carbocyclyl, C₁-C₁₀ heterocyclyl, aryl, heteroaralkyl or aralkyl; or (ii) R⁴ᴬ and R⁴ᴮ taken together are C₂-C₈ alkylene or C₁-C₈ heteroalkylene;

R⁵ is

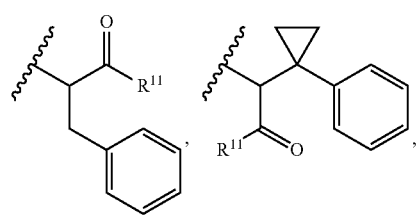

-continued

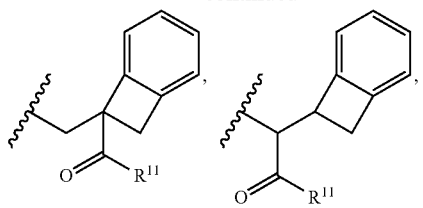

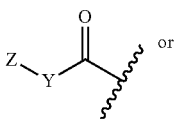

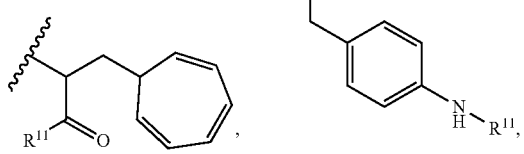

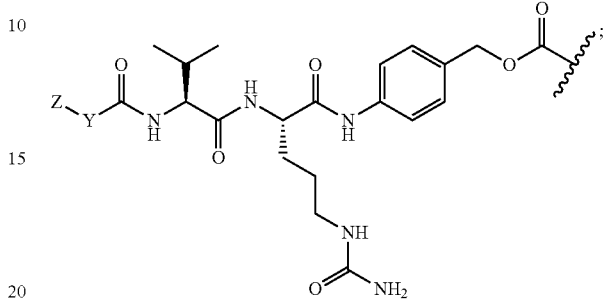

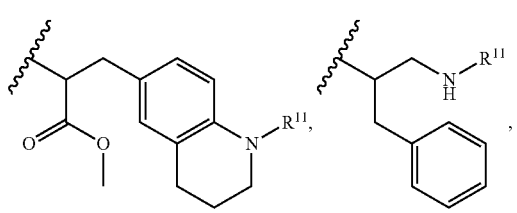

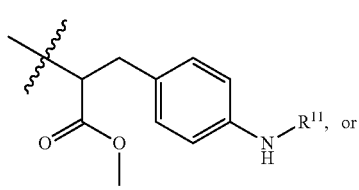

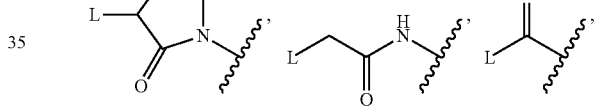

Y is —C$_2$-C$_{20}$ alkylene-, —C$_2$-C$_{20}$ heteroalkylene-, —C$_3$-C$_8$ carbocyclo-, -arylene-, —C$_3$-C$_8$heterocyclo-, —C$_1$-C$_{10}$alkylene-arylene-, -arylene-C$_1$-C$_{10}$alkylene-, —C$_1$-C$_{10}$alkylene-(C$_3$-C$_8$-carbocyclo)-, —(C$_3$-C$_8$-carbocyclo)-C$_1$-C$_{10}$alkylene-, —C$_1$-C$_{10}$alkylene-(C$_3$-C$_8$heterocyclo)-, or —(C$_3$-C$_8$ heterocyclo)-C$_1$-C$_{10}$alkylene-;

Z is

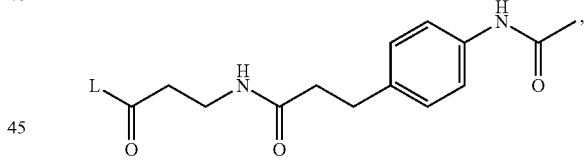

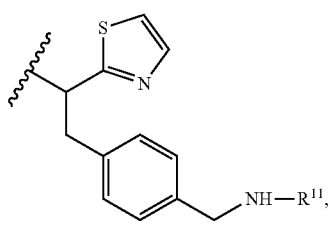

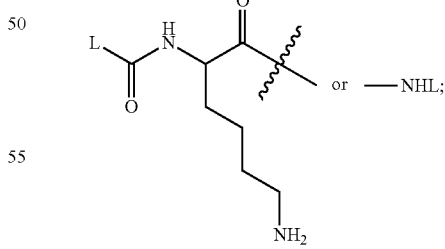

optionally substituted with 1, 2, 3, 4 or 5 groups independently selected from the group consisting of C$_1$-C$_8$ alkyl, —O—(C$_1$-C$_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, C$_1$-C$_8$ alkyl and unsubstituted aryl;

R$^{11}$ is

L is an antibody;

X is O or S.

Another aspect of the invention relates to compound of formula IIc:

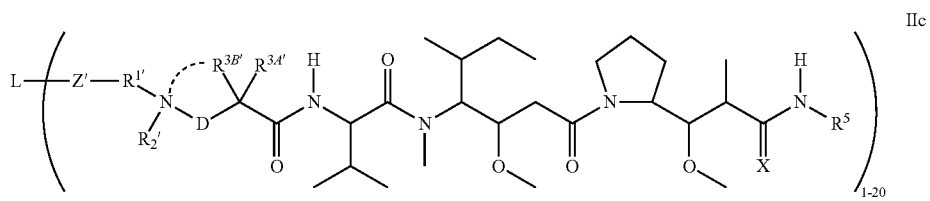

or a pharmaceutically acceptable salt or solvate thereof, wherein, independently for each occurrence, R$^{1'}$ is

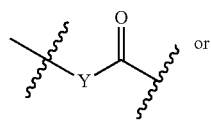 or

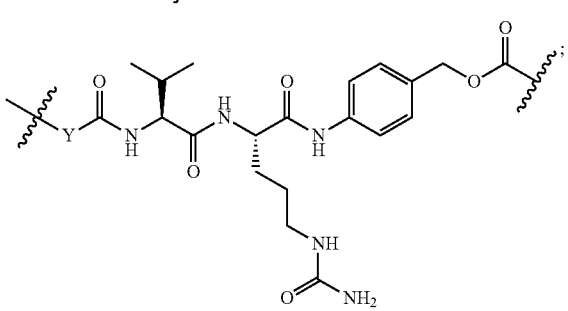

Y is —C$_2$-C$_{20}$ alkylene-, —C$_2$-C$_{20}$ heteroalkylene-, —C$_3$-C$_8$ carbocyclo-, -arylene-, —C$_3$-C$_8$heterocyclo-, —C$_1$-C$_{10}$alkylene-arylene-, -arylene-C$_1$-C$_{10}$alkylene-, —C$_1$-C$_{10}$alkylene-(C$_3$-C$_8$-carbocyclo)-, —(C$_3$-C$_8$-carbocyclo)-C$_1$-C$_{10}$alkylene-, —C$_1$-C$_{10}$alkylene-(C$_3$-C$_8$heterocyclo)-, or —(C$_3$-C$_8$ heterocyclo)-C$_1$-C$_{10}$alkylene-;

Z' is

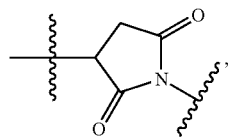

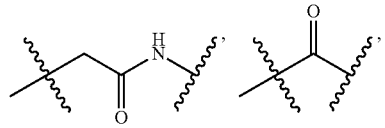

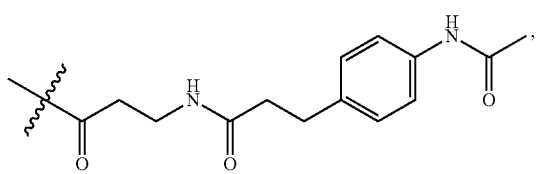

-continued

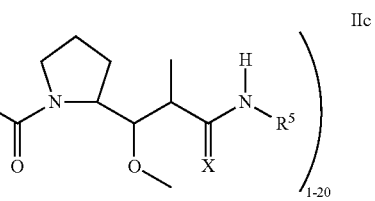, or —NH—;

L is an antibody;
D is —C(R$^{4A'}$)(R$^{4B'}$)— or is absent;
R$^{2'}$ is hydrogen, C$_1$-C$_8$ alkyl, C$_1$-C$_8$ haloalkyl, or is absent if ⁀ is present;
R$^{3A'}$ and R$^{3B'}$ are either of the following:
(i) R$^{3A'}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, aralkyl or halogen; and
R$^{3B'}$ is C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, halogen or aralkyl, or R$^{3B'}$ is C$_2$-C$_4$ alkylene and forms 5-7 member ring as indicated by ⁀; or
(ii) R$^{3A'}$ and R$^{3B'}$ taken together are C$_2$-C$_8$ alkylene or C$_1$-C$_8$ heteroalkylene;
R$^{4A'}$ and R$^{4B'}$ are either of the following:
(i) R$^{4A'}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; and
R$^{4B'}$ is hydrogen, C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl; or
(ii) R$^{4A'}$ and R$^{4B'}$ taken together are C$_2$-C$_8$ alkylene or C$_1$-C$_8$ heteroalkylene;
R$^5$ is

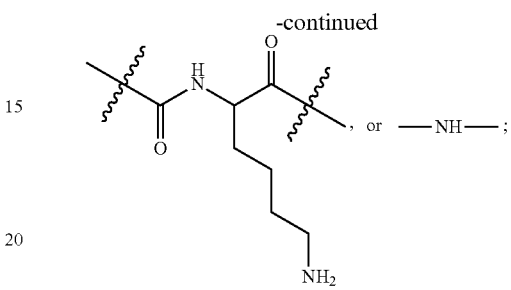

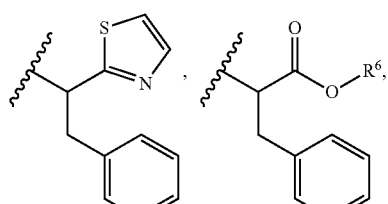

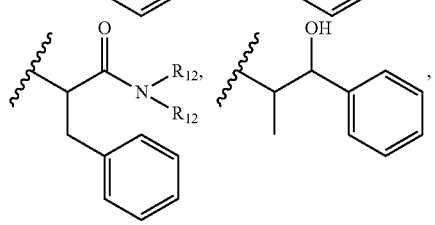

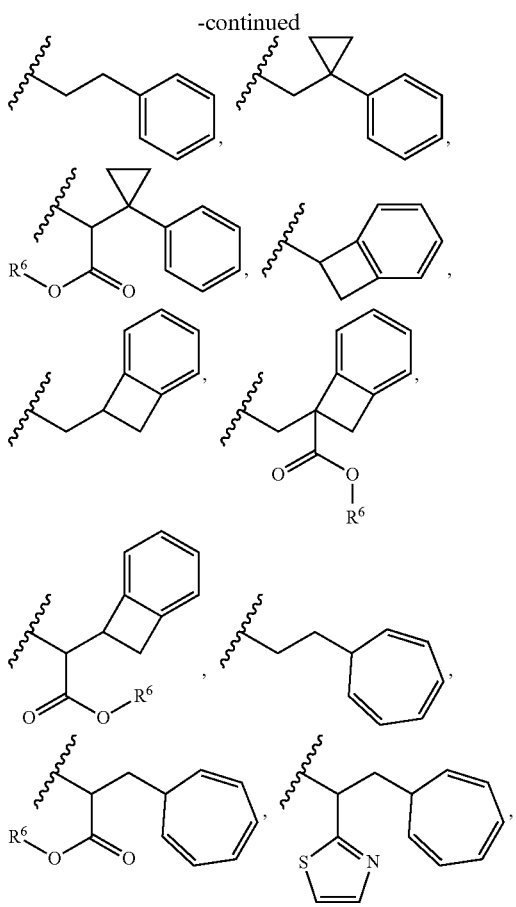

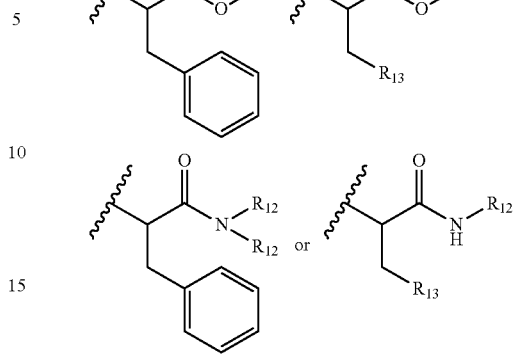

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$alkyl-N(R')$_2$, —$C_1$-$C_8$alkyl-C(O)R', —$C_1$-$C_8$alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or R$^5$ is optionally substituted with 1, 2, 3, 4 or 5 groups independently selected from the group consisting of $C_1$-$C_8$ alkyl, —$C_1$-$C_8$alkyl-N(R')$_2$, —$C_1$-$C_8$alkyl-C(O)R', —$C_1$-$C_8$alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

R$^6$ is hydrogen, —$C_1$-$C_8$ alkyl, —$C_2$-$C_8$ alkenyl, —$C_2$-$C_8$ alkynyl or —$C_1$-$C_8$ haloalkyl;

R$^{12}$ is hydrogen, $C_1$-$C_4$ alkyl, $C_1$-$C_{10}$ heterocyclyl or $C_6$-$C_{14}$ aryl;

R$^{13}$ is $C_1$-$C_{10}$ heterocyclyl; and

X is O or S;

provided that when R$^{34}$ is hydrogen X is S.

Another aspect of the invention relates to compound of formula IIIc:

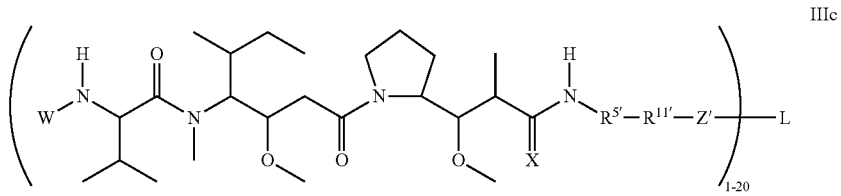

or a pharmaceutically acceptable salt or solvate thereof, wherein, independently for each occurrence, W is

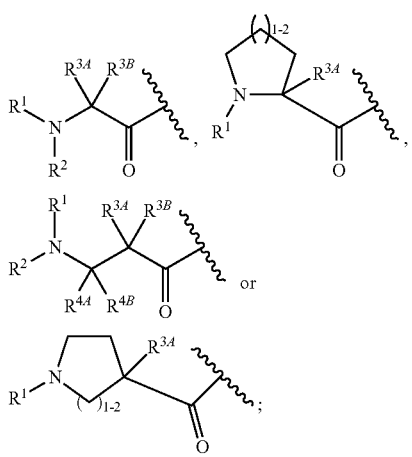

R¹ is hydrogen, $C_1$-$C_8$ alkyl or $C_1$-$C_8$ haloalkyl;

R² is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

R⁵ is

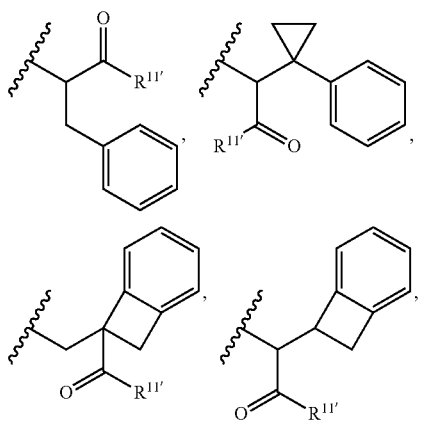

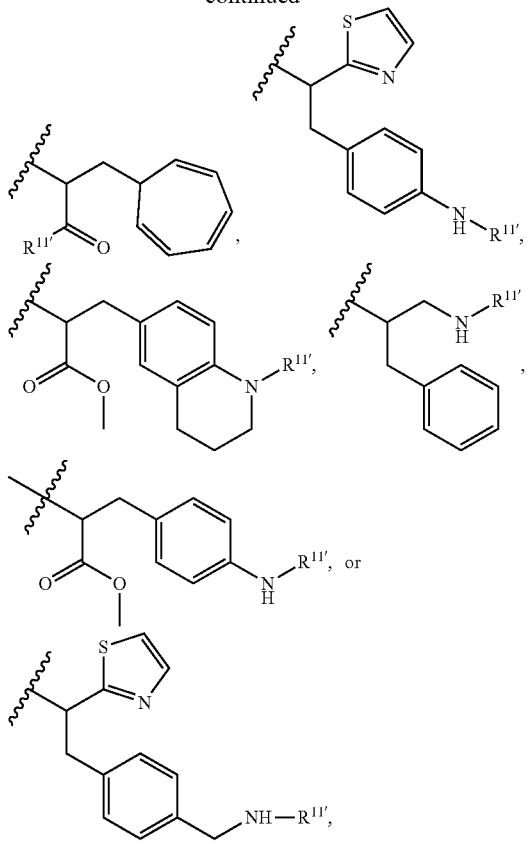

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

$R^{11'}$ is

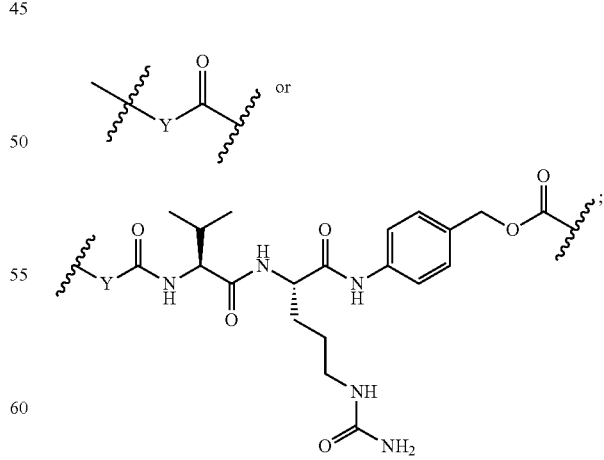

Y is —$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-

$C_1$-$C_{10}$alkylene-, —$C_1$-$C_{10}$alkylene-($C_3$-$C_8$heterocyclo)-, or -($C_3$-$C_8$ heterocyclo)-$C_1$-$C_{10}$alkylene-;

Z' is

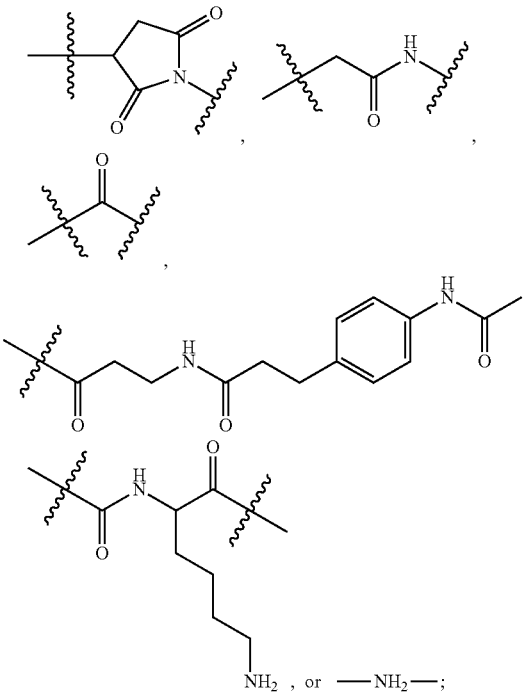

L is an antibody;
X is O or S.

Another aspect of the invention relates to compound of formula IId:

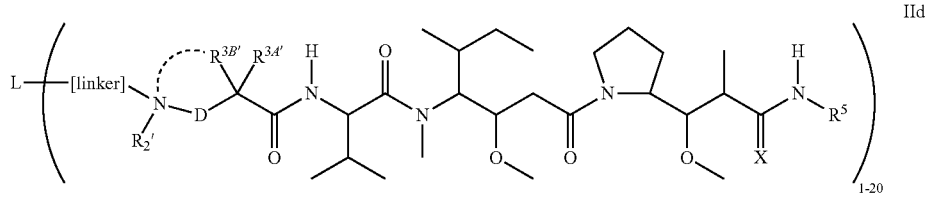

or a pharmaceutically acceptable salt or solvate thereof, wherein, independently for each occurrence,
L is an antibody;
[linker] is a divalent linker;
D is —C($R^{4A'}$)($R^{4B'}$)— or is absent;
$R^{2'}$ is hydrogen, $C_1$-$C_8$ alkyl, $C_1$-$C_8$ haloalkyl, or is absent if ⁓ is present;
$R^{3A'}$ and $R^{3B'}$ are either of the following:
  (i) $R^{3A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
  $R^{3B'}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl, or $R^{3B'}$ is $C_2$-$C_4$ alkylene and forms 5-7 member ring as indicated by ⁓ ; or
  (ii) $R^{3A'}$ and $R^{3B'}$ taken together are $C_2$-$C_8$ alkylene or $C_1$-$C_8$ heteroalkylene;
$R^{4A'}$ and $R^{4B'}$ are either of the following:
  (i) $R^{4A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
  $R^{4B'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
  (ii) $R^{4A'}$ and $R^{4B'}$ taken together are $C_2$-$C_8$ alkylene or $C_1$-$C_8$ heteroalkylene;
$R^5$ is

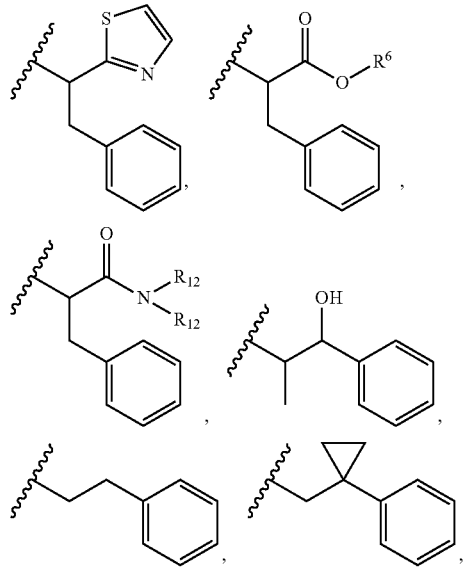

-continued

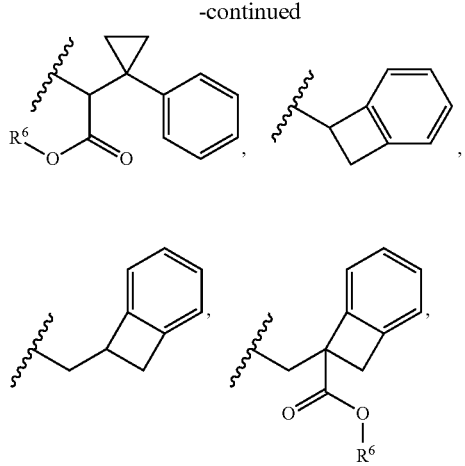

-continued

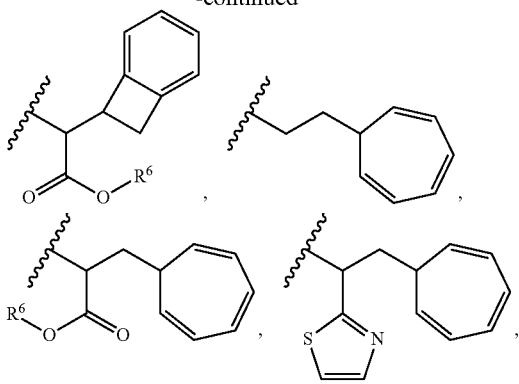

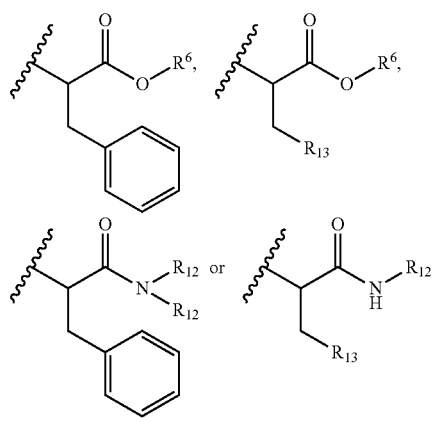

optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$heterocyclyl;

or R$^5$ is (=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

R$^6$ is hydrogen, —$C_1$-$C_8$ alkyl, —$C_2$-$C_8$ alkenyl, —$C_2$-$C_8$ alkynyl or —$C_1$-$C_8$ haloalkyl;

R$^{12}$ is hydrogen, $C_1$-$C_4$ alkyl, $C_1$-$C_{10}$ heterocyclyl or $C_6$-$C_{14}$ aryl;

R$^{13}$ is $C_1$-$C_{10}$ heterocyclyl; and

X is O or S;

provided that when R$^{3A}$ is hydrogen X is S.

Another aspect of the invention relates to compound of formula formula IIId:

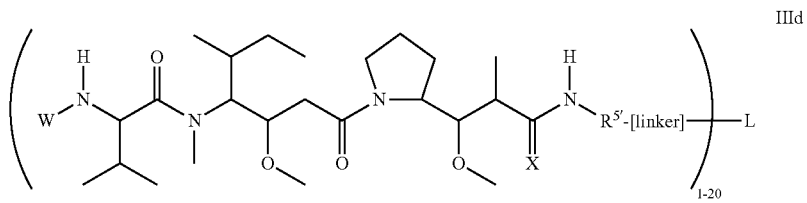

or a pharmaceutically acceptable salt or solvate thereof, wherein, independently for each occurrence, W is

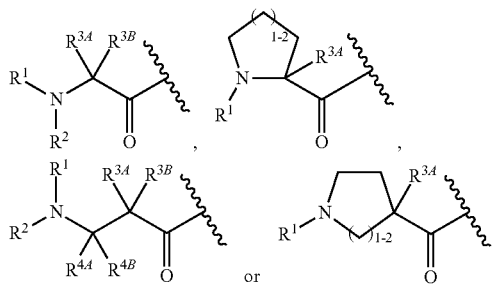

R$^1$ is hydrogen, $C_1$-$C_8$ alkyl or $C_1$-$C_8$ haloalkyl;

R$^2$ is hydrogen, $C_1$-$C_8$ alkyl or $C_1$-$C_8$ haloalkyl;

R$^{3A}$ and R$^{3B}$ are either of the following:

(i) R$^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and R$^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or (ii) R$^{3A}$ and R$^{3B}$ taken together are $C_2$-$C_8$ alkylene or $C_1$-$C_8$ heteroalkylene;

R$^{4A}$ and R$^{4B}$ are either of the following:

(i) R$^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and R$^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) R$^{4A}$ and R$^{4B}$ taken together are $C_2$-$C_8$ alkylene or $C_1$-$C_8$ heteroalkylene;

R⁵ is

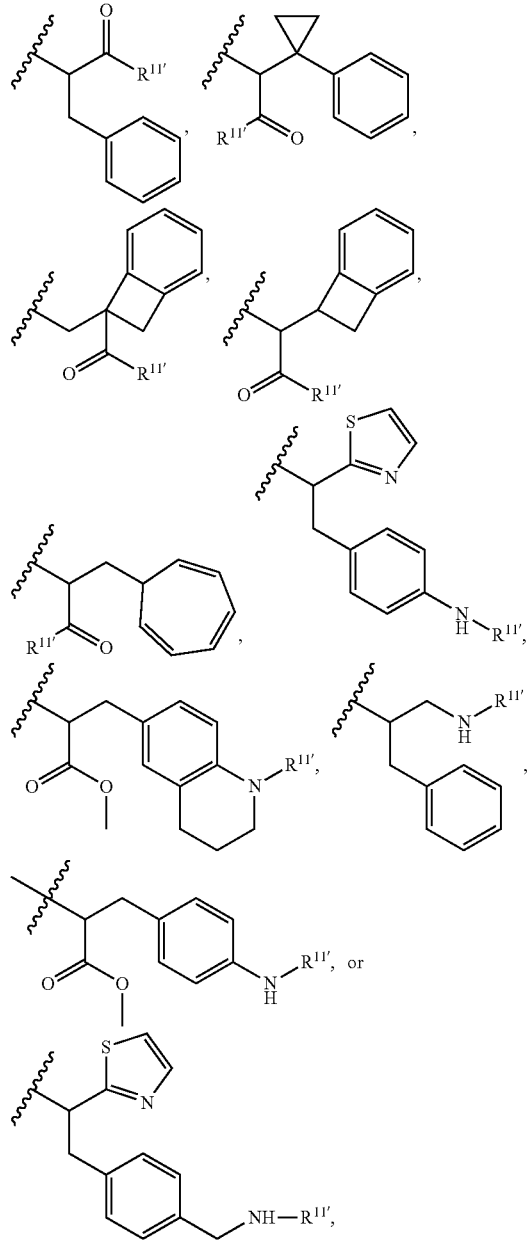

optionally substituted with 1, 2, 3, 4 or 5 groups independently selected from the group consisting of C₁-C₈ alkyl, —O—(C₁-C₈ alkyl), —C(O)R', —OC(O)R', —C(O)OR', —C(O)NH₂, —C(O)NHR', —C(O)N(R')₂, —NHC(O)R', —S(O)₂R', —S(O)R', —OH, halogen, —N₃, —NH₂, —NH(R'), —N(R')₂, —CN, —NHC(=NH)NH₂, —NHCONH₂, —S(=O)₂R' and —SR', wherein each R' is independently selected from the group consisting of hydrogen, C₁-C₈ alkyl and unsubstituted aryl;

[linker] is a divalent linker;

L is an antibody;

X is O or S.

In certain embodiments, the present invention relates to any of the aforementioned compounds and attendant definitions, wherein the compound is represented by

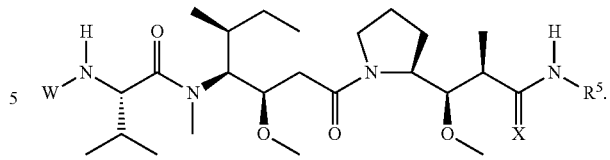

In certain embodiments, the present invention relates to any of the aforementioned compounds and attendant definitions, wherein W is

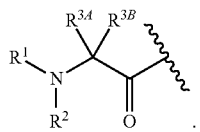

In certain embodiments, the present invention relates to any of the aforementioned compounds and attendant definitions, wherein W is

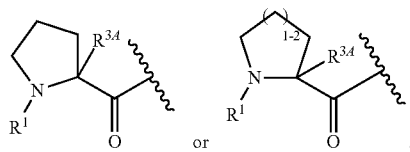

In certain embodiments, the present invention relates to any of the aforementioned compounds and attendant definitions, wherein W is

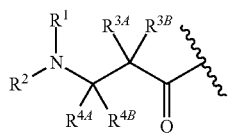

In certain embodiments, the present invention relates to any of the aforementioned compounds and attendant definitions, wherein W is

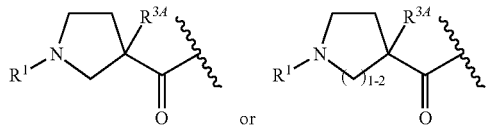

In certain embodiments of the invention W is:

W is

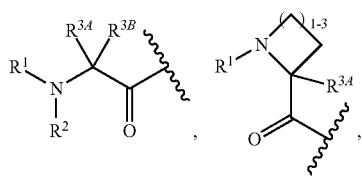

-continued

[Chemical structures showing two substituent groups with R¹, R², R³ᴬ, R³ᴮ, R⁴ᴬ, R⁴ᴮ substituents]

In certain embodiments, the present invention relates to any of the aforementioned compounds and attendant definitions, wherein $R^1$ is hydrogen, $C_1$-$C_8$ alkyl or $C_1$-$C_8$ haloalkyl.

In certain embodiments, the present invention relates to any of the aforementioned compounds and attendant definitions, wherein $R^1$ is hydrogen.

In certain embodiments, the present invention relates to any of the aforementioned compounds and attendant definitions, wherein $R^1$ is $C_1$-$C_8$ alkyl.

In certain embodiments, the present invention relates to any of the aforementioned compounds and attendant definitions, wherein $R^1$ is methyl.

In certain embodiments, the present invention relates to any of the aforementioned compounds and attendant definitions, wherein $R^2$ is hydrogen, $C_1$-$C_8$ alkyl or $C_1$-$C_8$ haloalkyl.

In certain embodiments, the present invention relates to any of the aforementioned compounds and attendant definitions, wherein $R^2$ is hydrogen.

In certain embodiments, the present invention relates to any of the aforementioned compounds and attendant definitions, wherein $R^2$ is $C_1$-$C_8$ alkyl.

In certain embodiments, the present invention relates to any of the aforementioned compounds and attendant definitions, wherein $R^2$ is methyl.

In certain embodiments, the present invention relates to any of the aforementioned compounds and attendant definitions, wherein $R^1$ is hydrogen; and $R^2$ is methyl.

In certain embodiments, the present invention relates to any of the aforementioned compounds and attendant definitions, wherein $R^1$ is methyl; and $R^2$ is methyl.

In certain embodiments, the present invention relates to any of the aforementioned compounds and attendant definitions, wherein $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl.

In certain embodiments, the present invention relates to any of the aforementioned compounds and attendant definitions, wherein $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen.

In certain embodiments, the present invention relates to any of the aforementioned compounds and attendant definitions, wherein $R^{3A}$ is halogen.

In certain embodiments, the present invention relates to any of the aforementioned compounds and attendant definitions, wherein $R^{3A}$ is hydrogen.

In certain embodiments, the present invention relates to any of the aforementioned compounds and attendant definitions, wherein $R^{3A}$ is $C_1$-$C_8$ alkyl.

In certain embodiments, the present invention relates to any of the aforementioned compounds and attendant definitions, wherein $R^{3A}$ is methyl.

In certain embodiments, the present invention relates to any of the aforementioned compounds and attendant definitions, wherein $R^{3B}$ is $C_1$-$C_8$ alkyl.

In certain embodiments, the present invention relates to any of the aforementioned compounds and attendant definitions, wherein $R^{3B}$ is methyl.

In certain embodiments, the present invention relates to any of the aforementioned compounds and attendant definitions, wherein $R^{3B}$ is isopropyl.

In certain embodiments, the present invention relates to any of the aforementioned compounds and attendant definitions, wherein $R^{3B}$ is $C_3$-$C_8$ carbocyclyl.

In certain embodiments, the present invention relates to any of the aforementioned compounds and attendant definitions, wherein $R^{3B}$ is cylohexyl.

In certain embodiments, the present invention relates to any of the aforementioned compounds and attendant definitions, wherein $R^{3A}$ is $C_1$-$C_8$ alkyl; and $R^{3B}$ is $C_1$-$C_8$ alkyl.

In certain embodiments, the present invention relates to any of the aforementioned compounds and attendant definitions, wherein $R^{3A}$ is methyl; and $R^{3B}$ is methyl.

In certain embodiments, the present invention relates to any of the aforementioned compounds and attendant definitions, wherein $R^{3A}$ is hydrogen; and $R^{3B}$ is $C_1$-$C_8$ alkyl.

In certain embodiments, the present invention relates to any of the aforementioned compounds and attendant definitions, wherein $R^{3A}$ is hydrogen; and $R^{3B}$ is isopropyl.

In certain embodiments, the present invention relates to any of the aforementioned compounds and attendant definitions, wherein $R^{3A}$ and $R^{3B}$ taken together are $C_2$-$C_8$ alkylene or $C_1$-$C_8$ heteroalkylene.

In certain embodiments, the present invention relates to any of the aforementioned compounds and attendant definitions, wherein $R^{3A}$ and $R^{3B}$ taken together are $C_2$-$C_8$ alkylene.

In certain embodiments, the present invention relates to any of the aforementioned compounds and attendant definitions, wherein $R^{3A}$ and $R^{3B}$ taken together are —$CH_2CH_2$—.

In certain embodiments, the present invention relates to any of the aforementioned compounds and attendant definitions, wherein $R^{3A}$ and $R^{3B}$ taken together are —$CH_2CH_2CH_2$—.

In certain embodiments, the present invention relates to any of the aforementioned compounds and attendant definitions, wherein $R^{3A}$ and $R^{3B}$ taken together are —$CH_2CH_2CH_2CH_2$—.

In certain embodiments, the present invention relates to any of the aforementioned compounds and attendant definitions, wherein $R^{3A}$ and $R^{3B}$ taken together are $C_1$-$C_8$ heteroalkylene.

In certain embodiments, the present invention relates to any of the aforementioned compounds and attendant definitions, wherein $R^{3A}$ and $R^{3B}$ taken together are —$CH_2OCH_2$—.

In certain embodiments, the present invention relates to any of the aforementioned compounds and attendant definitions, wherein $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl.

In certain embodiments, the present invention relates to any of the aforementioned compounds and attendant definitions, wherein $R^{4A}$ is hydrogen.

In certain embodiments, the present invention relates to any of the aforementioned compounds and attendant definitions, wherein $R^{4A}$ is $C_1$-$C_8$ alkyl.

In certain embodiments, the present invention relates to any of the aforementioned compounds and attendant definitions, wherein $R^{4A}$ is methyl.

In certain embodiments, the present invention relates to any of the aforementioned compounds and attendant definitions, wherein $R^{4B}$ is hydrogen.

In certain embodiments, the present invention relates to any of the aforementioned compounds and attendant definitions, wherein $R^{4B}$ is $C_1$-$C_8$ alkyl.

In certain embodiments, the present invention relates to any of the aforementioned compounds and attendant definitions, wherein $R^{4B}$ is methyl.

In certain embodiments, the present invention relates to any of the aforementioned compounds and attendant definitions, wherein $R^{4A}$ is $C_1$-$C_8$ alkyl; and $R^{4B}$ is $C_1$-$C_8$ alkyl.

In certain embodiments, the present invention relates to any of the aforementioned compounds and attendant definitions, wherein $R^{4A}$ is methyl; and $R^{4B}$ is methyl.

In certain embodiments, the present invention relates to any of the aforementioned compounds and attendant definitions, wherein $R^{4A}$ is hydrogen; and $R^{4B}$ is hydrogen.

In certain embodiments, the present invention relates to any of the aforementioned compounds and attendant definitions, wherein $R^{4A}$ is hydrogen; and $R^{4B}$ is $C_1$-$C_8$ alkyl.

In certain embodiments, the present invention relates to any of the aforementioned compounds and attendant definitions, wherein $R^{4A}$ and $R^{4B}$ taken together are $C_2$-$C_8$ alkylene or $C_1$-$C_8$ heteroalkylene.

In certain embodiments, the present invention relates to any of the aforementioned compounds and attendant definitions, wherein $R^{4A}$ and $R^{4B}$ taken together are $C_2$-$C_8$ alkylene.

In certain embodiments, the present invention relates to any of the aforementioned compounds and attendant definitions, wherein $R^{4A}$ and $R^{4B}$ taken together are —$CH_2CH_2$—.

In certain embodiments, the present invention relates to any of the aforementioned compounds and attendant definitions, wherein $R^{4A}$ and $R^{4B}$ taken together are —$CH_2CH_2CH_2$—.

In certain embodiments, the present invention relates to any of the aforementioned compounds and attendant definitions, wherein $R^{4A}$ and $R^{4B}$ taken together are —$CH_2CH_2CH_2CH_2$—.

In certain embodiments, the present invention relates to any of the aforementioned compounds and attendant definitions, wherein $R^{4A}$ and $R^{4B}$ taken together are $C_1$-$C_8$ heteroalkylene.

In certain embodiments, the present invention relates to any of the aforementioned compounds and attendant definitions, wherein $R^{4A}$ and $R^{4B}$ taken together are —$CH_2OCH_2$—.

In certain embodiments, the present invention relates to any of the aforementioned compounds and attendant definitions, wherein $R^5$ is

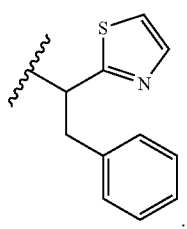 [SMILES: *C(Cc1ccccc1)c1nccs1]

In certain embodiments, the present invention relates to any of the aforementioned compounds and attendant definitions, wherein $R^5$ is

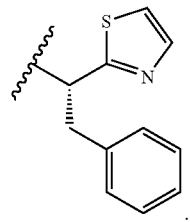

In certain embodiments, the present invention relates to any of the aforementioned compounds and attendant definitions, wherein $R^5$ is

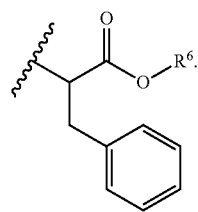

In certain embodiments, the present invention relates to any of the aforementioned compounds and attendant definitions, wherein $R^5$ is

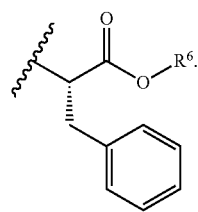

In certain embodiments, the present invention relates to any of the aforementioned compounds and attendant definitions, wherein $R^5$ is

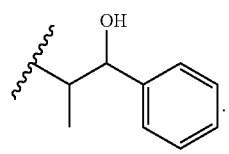 [SMILES: *C(C)C(O)c1ccccc1]

In certain embodiments, the present invention relates to any of the aforementioned compounds and attendant definitions, wherein $R^5$ is

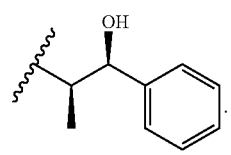 [SMILES: *[C@H](C)[C@@H](O)c1ccccc1]

In certain embodiments, the present invention relates to any of the aforementioned compounds and attendant definitions, wherein $R^5$ is

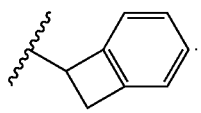 [SMILES: *C1Cc2ccccc21 ; "."]

In certain embodiments, the present invention relates to any of the aforementioned compounds and attendant definitions, wherein $R^5$ is

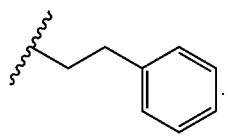

In certain embodiments, the present invention relates to any of the aforementioned compounds and attendant definitions, wherein $R^5$ is

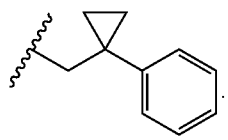 [SMILES: *CC1(c2ccccc2)CC1]

In certain embodiments, the present invention relates to any of the aforementioned compounds and attendant definitions, wherein $R^5$ is

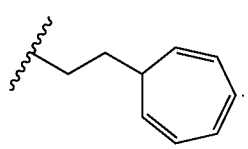 [SMILES: *CCC1C=CC=CC=C1 ; "."]

In certain embodiments, the present invention relates to any of the aforementioned compounds and attendant definitions, wherein $R^5$ is

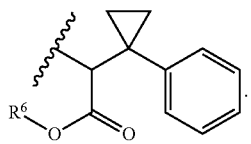

In certain embodiments, the present invention relates to any of the aforementioned compounds and attendant definitions, wherein $R^5$ is

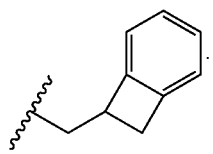 [SMILES: *CC1Cc2ccccc21]

In certain embodiments, the present invention relates to any of the aforementioned compounds and attendant definitions, wherein $R^5$ is

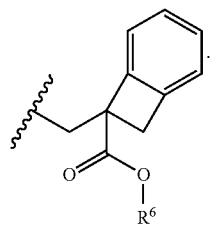

In certain embodiments, the present invention relates to any of the aforementioned compounds and attendant definitions, wherein $R^5$ is

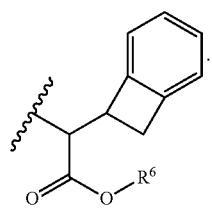

In certain embodiments, the present invention relates to any of the aforementioned compounds and attendant definitions, wherein $R^5$ is

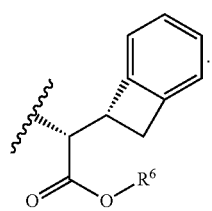

In certain embodiments, the present invention relates to any of the aforementioned compounds and attendant definitions, wherein $R^5$ is

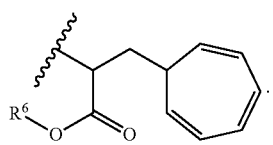

In certain embodiments, the present invention relates to any of the aforementioned compounds and attendant definitions, wherein $R^5$ is

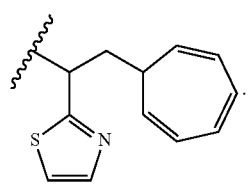 [SMILES: *C(CC1C=CC=CC=C1)c1nccs1 ; "."]

In certain embodiments, the present invention relates to any of the aforementioned compounds and attendant definitions, wherein $R^6$ is hydrogen.

In certain embodiments, the present invention relates to any of the aforementioned compounds and attendant definitions, wherein $R^6$ is $C_1$-$C_8$ alkyl.

In certain embodiments, the present invention relates to any of the aforementioned compounds and attendant definitions, wherein $R^6$ is methyl.

In certain embodiments, the present invention relates to any of the aforementioned compounds and attendant definitions, wherein X is O.

In certain embodiments, the present invention relates to any of the aforementioned compounds and attendant definitions, wherein X is S.

In certain embodiments, the present invention relates to any of the aforementioned compounds, or a pharmaceutically acceptable salt or solvate thereof, and attendant definitions, wherein the compound is selected from the group consisting of:

N-Methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide;

$N^2$-[(1-Aminocyclopentyl)carbonyl]-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide;

2-Methylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide;

N-Methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide;

N-Methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide;

N-Methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide;

2-Methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide;

2-Methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide;

$N^2$-[(1-Aminocyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

$N^2$-[(1-Aminocyclopropyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

1-Amino-N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]cyclohexanecarboxamide;

2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

2-Methylalanyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide;

2-Methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide;

2-Methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide;

2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide;

2-Methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

$N^2$-[(3-Aminooxetan-3-yl)carbonyl]-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide;

N,2-Dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide;

N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide;

N,2-Dimethylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide;

N,2-Dimethylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

$N^2$-(3-Amino-2,2-dimethylpropanoyl)-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

$N^2$-(3-Amino-2,2-dimethylpropanoyl)-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide;

2-Methyl-L-prolyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

2-Methylalanyl-N-[(3R,4S,5S)-1-{(2S)-2-[(1R,2R)-3-{[1-(bicyclo[4.2.0]octa-1,3,5-trien-7-yl)-2-methoxy-2-oxoethyl]amino}-1-methoxy-2-methyl-3-oxopropyl]pyrrolidin-1-yl}-3-methoxy-5-methyl-1-oxoheptan-4-yl]-N-methyl-L-valinamide;

2-Methylalanyl-N-[(3R,4S,5S)-1-{(2S)-2-[(1R,2R)-3-{[bicyclo[4.2.0]octa-1,3,5-trien-7-yl(carboxy)methyl]

amino}-1-methoxy-2-methyl-3-oxopropyl]pyrrolidin-1-yl}-3-methoxy-5-methyl-1-oxoheptan-4-yl]-N-methyl-L-valinamide;

2-Methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3 oxopropyl]pyrrolidin-1-yl}-5-methyl-1-oxoheptan-4-yl]-N-methyl-L-valinamide;

2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide;

2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

Methyl N-[(2R,3R)-3-{(2S)-1-[(3R,4S,5S)-4-{[N-(3-amino-2,2-dimethylpropanoyl)-L-valyl](methyl)amino}-3-methoxy-5-methylheptanoyl]pyrrolidin-2-yl}-3-methoxy-2-methylpropanoyl]-L-phenylalaninate;

N,2-dimethylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

2-methyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

2-methyl-L-prolyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-{(1S,2R)-4-{(2S)-2-[(1R,2R)-3-{[(1S)-1-benzyl-2-(methylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N,2-dimethylalanyl-N-{(1S,2R)-4-{(2S)-2-[(1R,2R)-3-{[(1S)-2-amino-1-benzyl-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N,2-dimethylalanyl-N-{(1S,2R)-4-{(2S)-2-[(1R,2R)-3-{[(1S)-1-benzyl-2-oxo-2-(propylamino)ethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N,2-dimethylalanyl-N-{(1S,2R)-4-{(2S)-2-[(1R,2R)-3-{R1S)-1-benzyl-2-(diethylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N,2-dimethylalanyl-N-{(1S,2R)-4-{(2S)-2-[(1R,2R)-3-{[(1S)-1-benzyl-2-(tert-butylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N,2-dimethylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

3-methyl-D-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

3-methyl-L-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

L-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

D-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

1,2-dimethyl-L-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

1,2-dimethyl-D-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide;

N~2~-[2,2-dimethyl-3-(methylamino)propanoyl]-N-{(1S,2R)-2-methoxy-4-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-1-[(1S)-1-methylpropyl]-4-oxobutyl}-N-methyl-L-valinamide;

Methyl N-{(2R,3R)-3-[(2S)-1-{(3R,4S,5S)-4-[{N-[2,2-dimethyl-3-(methylamino)propanoyl]-L-valyl}(methyl)amino]-3-methoxy-5-methylheptanoyl}pyrrolidin-2-yl]-3-methoxy-2-methylpropanoyl}-L-phenylalaninate;

Methyl N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalaninate;

Methyl N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalaninate;

N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalanine;

N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalanine;

Methyl N-{(2R,3R)-3-[(2S)-1-{(3R,4S,5S)-4-[N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate;

Methyl N-{(2R,3R)-3-[(2S)-1-{(3R,4S,5S)-4-[N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate;

(2S)—N-[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide;

(2R)—N-[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide;

2-methyl-L-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide;

N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-2-{[(3R)-3-fluoropyrrolidin-3-yl]carbonyl}-N-methyl-L-valinamide;

N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-2-{[(3S)-3-fluoropyrrolidin-3-yl]carbonyl}-N-methyl-L-valinamide;

(2S)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide;

(2R)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide;

N-2-{[(3R)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

N-2-{[(3S)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

1,2-dimethyl-L-prolyl-N-[(3R,4S,5S)-3-methoxy-1-{(2S)-2-[(1R,2R)-1-methoxy-3-{[(2S)-1-methoxy-1-oxo-3-(1,2,3,4-tetrahydroquinolin-6-yl)propan-2-yl]amino}-2-methyl-3-oxopropyl]pyrrolidin-1-yl}-5-methyl-1-oxoheptan-4-yl]-N-methyl-L-valinamide;

1,2-dimethyl-L-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

1,2-dimethyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine;

N-{(2R,3R)-3-[(2S)-1-{(3R,4S,5S)-4-[(N-{[(3S)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine;

2-methylalanyl-N-[(3R,4S,5S)-1-{(2S)-2-[(1R,2R)-3-{[(2R,4S)-4-carboxy-1-phenylpentan-2-yl]amino}-1-methoxy-2-methyl-3-oxopropyl]pyrrolidin-1-yl}-3-methoxy-5-methyl-1-oxoheptan-4-yl]-N-methyl-L-valinamide;

2-methylalanyl-N-[(3R,4S,5S)-1-{(2S)-2-[(1R,2R)-3-(bicyclo[1.1.1]pent-1-ylamino)-1-methoxy-2-methyl-3-oxopropyl]pyrrolidin-1-yl}-3-methoxy-5-methyl-1-oxoheptan-4-yl]-N-methyl-L-valinamide;

2-methylalanyl-N-[(3R,4S,5S)-3-methoxy-1-{(2S)-2-[(1R,2R)-1-methoxy-3-{[(1R)-2-methoxy-2-oxo-1-(1-phenylcyclopropyl)ethyl]amino}-2-methyl-3-oxopropyl]pyrrolidin-1-yl}-5-methyl-1-oxoheptan-4-yl]-N-methyl-L-valinamide;

2-methylalanyl-N-[(3R,4S,5S)-3-methoxy-1-{(2S)-2-[(1R,2R)-1-methoxy-3-{[(1S)-2-methoxy-2-oxo-1-(1-phenylcyclopropyl)ethyl]amino}-2-methyl-3-oxopropyl]pyrrolidin-1-yl}-5-methyl-1-oxoheptan-4-yl]-N-methyl-L-valinamide;

2-methylalanyl-N-[(3R,4S,5S)-1-{(2S)-2-[(1R,2R)-3-({(1R)-1-[(7R)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan-4-yl]-N-methyl-L-valinamide;

2-methylalanyl-N-[(3R,4S,5S)-1-{(2S)-2-[(1R,2R)-3-({(1S)-1-[(7S)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

2-methylalanyl-N-[(3R,4S,5S)-1-{(2S)-2-[(1R,2R)-3-({(1S)-1-[(7R)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan-4-yl]-N-methyl-L-valinamide;

N,N,2-trimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

N,N,2-trimethylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide;

2-methylalanyl-N-[(3R,4S,5S)-1-{(2S)-2-[(1R,2R)-3-{[(R)-carboxy(1-phenylcyclopropyl)methyl]amino}-1-methoxy-2-methyl-3-oxopropyl]pyrrolidin-1-yl}-3-methoxy-5-methyl-1-oxoheptan-4-yl]-N-methyl-L-valinamide;

difluoro {2-methylalanyl-N-[(3R,4S,5S)-1-{(2S)-2-[(3R,4R,7S)-7-benzyl-15-{2-[(3,5-dimethyl-1H-pyrrol-2-yl-kappaN)methylidene]-2H-pyrrol-5-yl-kappaN}-4-methyl-5,8,13-trioxo-2-oxa-6,9,12-triazapentadecan-3-yl]

pyrrolidin-1-yl}-3-methoxy-5-methyl-1-oxoheptan-4-yl]-N-methyl-L-valinamidato}boron;

2-methyl-D-prolyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide;

methyl N-{(2R,3R)-3-[(2S)-1-{(3R,4S,5S)-4-[{N-[(3-aminooxetan-3-yl)carbonyl]-L-valyl}(methyl)amino]-3-methoxy-5-methylheptanoyl}pyrrolidin-2-yl]-3-methoxy-2-methylpropanoyl}-L-phenylalaninate;

2-methylalanyl-N-{(3R,4S,5S)-1-[(2S)-2-{(3R,4R,7S,12S)-7-benzyl-14-[3-chloro-4-(propan-2-yloxy)phenyl]-4-methyl-[2-[4-(8-methylimidazo[1,2-a]pyridin-2-yl)benzyl]-5,8,14-trioxo-2,9-dioxa-6,13-diazatetradecan-3-yl}pyrrolidin-1-yl]-3-methoxy-5-methyl-1-oxoheptan-4-yl}-N-methyl-L-valinamide;

2-methylalanyl-N-[(3R,4S,5S)-1-{(2S)-2-[(1R,2R)-3-{[(2S)-1-{[4-(5-fluoro-1,3-benzothiazol-2-yl)-2-methylphenyl]amino}-1-oxo-3-phenylpropan-2-yl]amino}-1-methoxy-2-methyl-3-oxopropyl]pyrrolidin-1-yl}-3-methoxy-2-methyl-1-oxoheptan-4-yl]-N-methyl-L-valinamide;

1,2-dimethyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide;

N,2-dimethylalanyl-N-[(3R,4S,5S)-1-{(2S)-2-[(1R,2R)-3-{[(2S)-3-(1H-indol-3-yl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-[(3R,4S,5S)-3-methoxy-1-{(2S)-2-[(1R,2R)-1-methoxy-2-methyl-3-oxo-3-{[(2S)-1-oxo-3-phenyl-1-(prop-2-en-1-yloxy)propan-2-yl]amino}propyl]pyrrolidin-1-yl}-5-methyl-1-oxoheptan-4-yl]-N-methyl-L-valinamide;

2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-[(3R,4S,5S)-3-methoxy-1-{(2S)-2-[(1R,2R)-1-methoxy-2-methyl-3-oxo-3-({(2S)-1-oxo-3-phenyl-1-[(1H-1,2,3-triazol-4-ylmethyl)amino]propan-2-yl}amino)propyl]pyrrolidin-1-yl}-5-methyl-1-oxoheptan-4-yl]-N-methyl-L-valinamide;

N,2-dimethylalanyl-N-[(3R,4S,5S)-3-methoxy-1-{(2S)-2-[(1R,2R)-1-methoxy-2-methyl-3-oxo-3-{[(2S)-1-oxo-3-phenyl-1-(prop-2-yn-1-ylamino)propan-2-yl]amino}propyl]pyrrolidin-1-yl}-5-methyl-1-oxoheptan-4-yl]-N-methyl-L-valinamide;

N,2-dimethylalanyl-N-[(3R,4S,5S)-1-{(2S)-2-[(1R,2R)-3-{[(2S)-3-(1H-imidazol-4-yl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-[(3R,4S,5S)-1-{(2S)-2-[(1R,2R)-3-{[(2S)-3-(4-hydroxyphenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide;

N,2-dimethylalanyl-N-[(3R,4S,5S)-1-{(2S)-2-[(1R,2R)-3-{[(1R)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide;

1,2-dimethyl-L-prolyl-N-[(3R,4S,5S)-3-methoxy-1-{(2S)-2-[(1R,2R)-1-methoxy-2-methyl-3-oxo-3-{[(2S)-1-oxo-3-phenyl-1-(piperazin-1-yl)propan-2-yl]amino}propyl]pyrrolidin-1-yl}-5-methyl-1-oxoheptan-4-yl]-N-methyl-L-valinamide;

1,2-dimethyl-L-prolyl-N-[(3R,4S,5S)-1-{(2S)-2-[(1R,2R)-3-{[(2S)-1-amino-3-phenylpropan-2-yl]amino}-1-methoxy-2-methyl-3-oxopropyl]pyrrolidin-1-yl]-3-methoxy-5-methyl-1-oxoheptan-4-yl}-N-methyl-L-valinamide;
and 2-methyl-D-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide.

In certain embodiments, the present invention relates to any of the aforementioned compounds and attendant definitions, wherein $R^1$ is

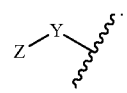

In certain embodiments, the present invention relates to any of the aforementioned compounds and attendant definitions, wherein $R^1$ is

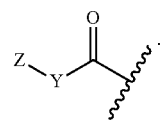

In certain embodiments, the present invention relates to any of the aforementioned compounds and attendant definitions, wherein $R^1$ is

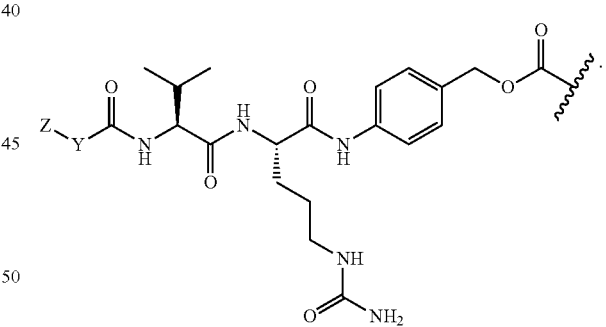

In certain embodiments, the present invention relates to any of the aforementioned compounds and attendant definitions, wherein Y is $C_2$-$C_{20}$ alkylene.

In certain embodiments, the present invention relates to any of the aforementioned compounds and attendant definitions, wherein Y is —$(CH_2)_p$—; and p is 1-10.

In certain embodiments, the present invention relates to any of the aforementioned compounds and attendant definitions, wherein p is 1. In certain embodiments, the present invention relates to any of the aforementioned compounds and attendant definitions, wherein p is 2. In certain embodiments, the present invention relates to any of the aforementioned compounds and attendant definitions, wherein p is 3. In certain embodiments, the present invention relates to any of the aforementioned compounds and attendant definitions, wherein p is 4. In certain embodiments, the present invention relates to any of the aforementioned compounds and attendant definitions, wherein p is 5. In certain embodiments, the present invention relates to any of the aforementioned compounds and attendant definitions, wherein p is 6. In certain embodiments, the present invention relates to any of the aforementioned compounds and attendant definitions, wherein p is 7. In certain embodiments, the present invention relates to any of the aforementioned compounds and attendant definitions, wherein p is $_8$. In certain embodiments, the present invention relates to any of the aforementioned compounds and attendant definitions, wherein p is 9. In certain embodiments, the present invention relates to any of the aforementioned compounds and attendant definitions, wherein p is 10.

In certain embodiments, the present invention relates to any of the aforementioned compounds and attendant definitions, wherein Y is $C_2$-$C_{20}$ heteroalkylene.

In certain embodiments, the present invention relates to any of the aforementioned compounds and attendant definitions, wherein Y is —$(CH_2CH_2O)_qCH_2CH_2$—; and q is 1-10.

In certain embodiments, the present invention relates to any of the aforementioned compounds and attendant definitions, wherein q is 1. In certain embodiments, the present invention relates to any of the aforementioned compounds and attendant definitions, wherein q is 2. In certain embodiments, the present invention relates to any of the aforementioned compounds and attendant definitions, wherein q is 3. In certain embodiments, the present invention relates to any of the aforementioned compounds and attendant definitions, wherein q is 4. In certain embodiments, the present invention relates to any of the aforementioned compounds and attendant definitions, wherein q is 5. In certain embodiments, the present invention relates to any of the aforementioned compounds and attendant definitions, wherein q is 6. In certain embodiments, the present invention relates to any of the aforementioned compounds and attendant definitions, wherein q is 7. In certain embodiments, the present invention relates to any of the aforementioned compounds and attendant definitions, wherein q is 8. In certain embodiments, the present invention relates to any of the aforementioned compounds and attendant definitions, wherein q is 9. In certain embodiments, the present invention relates to any of the aforementioned compounds and attendant definitions, wherein q is 10.

In certain embodiments, the present invention relates to any of the aforementioned compounds and attendant definitions, wherein Z is

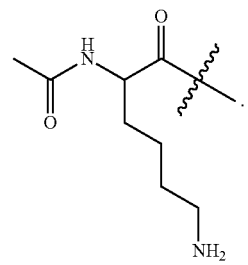

In certain embodiments, the present invention relates to any of the aforementioned compounds and attendant definitions, wherein Z is

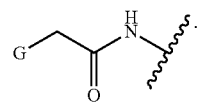

In certain embodiments, the present invention relates to any of the aforementioned compounds and attendant definitions, wherein Z is

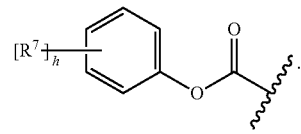

In certain embodiments, the present invention relates to any of the aforementioned compounds and attendant definitions, wherein Z is

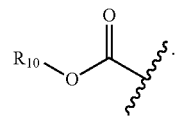

In certain embodiments, the present invention relates to any of the aforementioned compounds and attendant definitions, wherein Z is

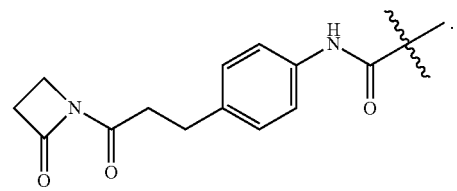 [SMILES: *C(=O)Nc1ccc(CCC(=O)N2CCC2=O)cc1]

In certain embodiments, the present invention relates to any of the aforementioned compounds and attendant definitions, wherein Z is In certain embodiments, the present invention relates to any of the aforementioned compounds and attendant definitions, wherein $R^7$ is F or Cl; and h is 4 or 5.

In certain embodiments, the present invention relates to any of the aforementioned compounds and attendant definitions, wherein $R^7$ is F; and h is 3, 4 or 5.

In certain embodiments, the present invention relates to any of the aforementioned compounds and attendant definitions, wherein $R^7$ is F; and h is 5.

In certain embodiments, the present invention relates to any of the aforementioned compounds and attendant definitions, wherein Z is —NH₂.

In certain embodiments, the present invention relates to any of the aforementioned compounds and attendant definitions, wherein G is Cl. In certain embodiments, the present invention relates to any of the aforementioned compounds and attendant definitions, wherein G is Br. In certain embodiments, the present invention relates to any of the aforementioned compounds and attendant definitions, wherein G is I.

In certain embodiments, the present invention relates to any of the aforementioned compounds and attendant definitions, wherein the compound is selected from the group consisting of the compounds of Table 18B.

In certain embodiments, the present invention relates to any of the aforementioned compounds and attendant definitions, wherein the compound is selected from the group consisting of:

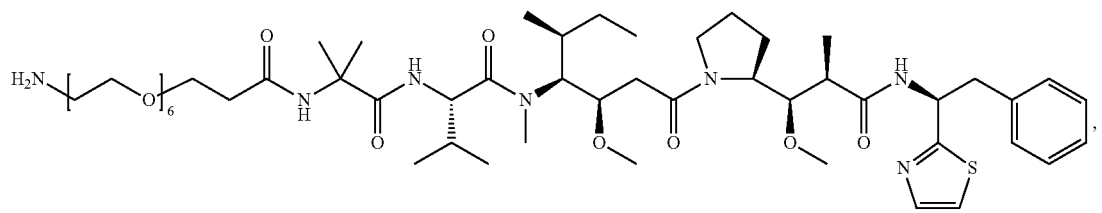

,

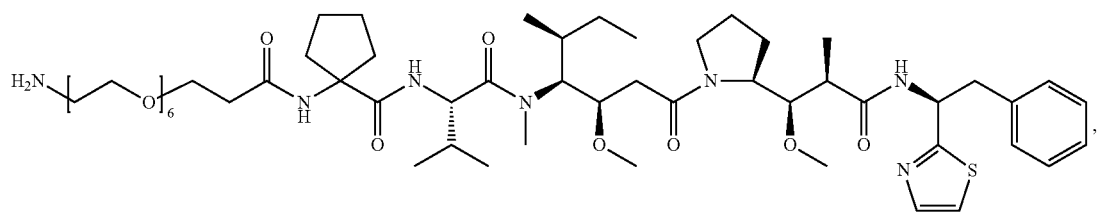

,

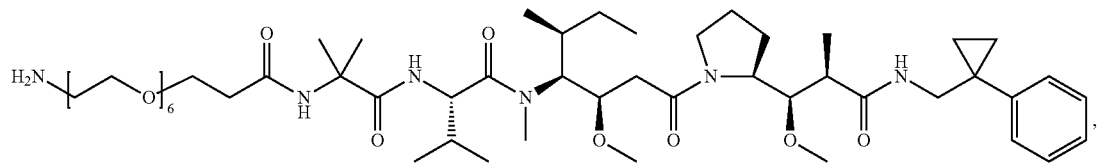

,

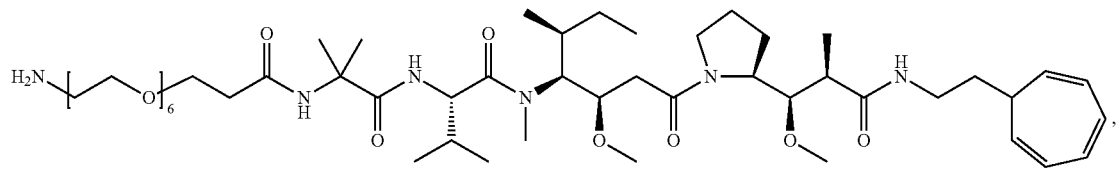

,

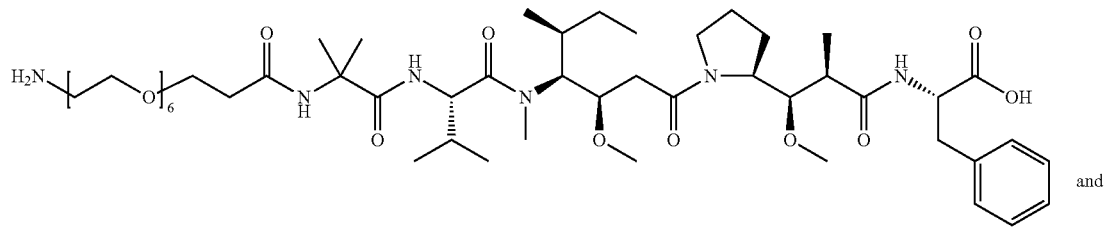

and

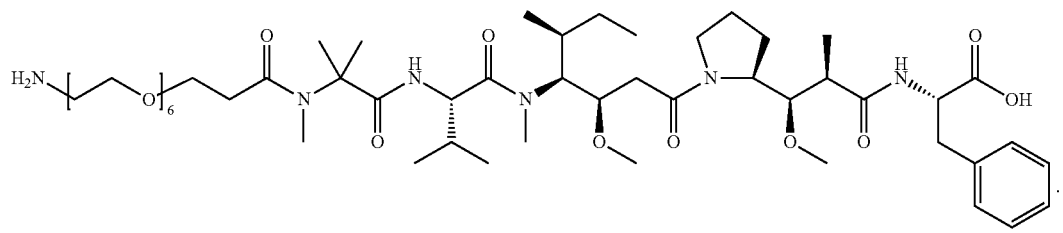

.

In certain embodiments, the present invention relates to any of the aforementioned compounds and attendant definitions, wherein Z is

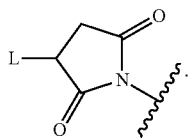

In certain embodiments, the present invention relates to any of the aforementioned compounds and attendant definitions, wherein Z is

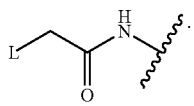

In certain embodiments, the present invention relates to any of the aforementioned compounds and attendant definitions, wherein Z is

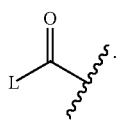

In certain embodiments, the present invention relates to any of the aforementioned compounds and attendant definitions, wherein Z is —NHL.

In certain embodiments, the present invention relates to any of the aforementioned compounds and attendant definitions, wherein Z is

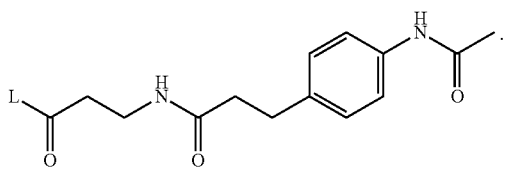

In certain embodiments, the present invention relates to any of the aforementioned compounds and attendant definitions, wherein Z is

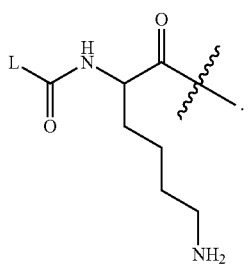

In certain embodiments, the present invention relates to any of the aforementioned compounds and attendant definitions, wherein L is H(C)—.

In certain embodiments, the present invention relates to any of the aforementioned compounds and attendant definitions, wherein L is an antibody selected from a murine antibody for the treatment of ovarian cancer such as oregovomab (OVAREX®); a murine $IgG_{2a}$ antibody for the treatment of colorectal cancer such as edrecolomab (PANOREX®); an anti-EGFR IgG chimeric antibody for the treatment of epidermal growth factor positive cancers, such as head and neck cancer, for instance cetuximab (ERBITUX®); a humanized antibody for the treatment of sarcoma, such as a Humanized Monoclonal Antibody to the Vitronectin Receptor ($\alpha_v\beta_3$) like Vitaxin®; a humanized $IgG_1$ antibody for the treatment of chronic lymphocytic leukemia (CLL) such as alemtuzumab (CAMPATH I/H®); SMART ID10 which is a humanized anti-HLA-DR antibody for the treatment of non-Hodgkin's lymphoma; 131I Lym-1 (ONCOLYM®)which is a radiolabeled murine anti-HLA-Dr10 antibody for the treatment of non-Hodgkin's lymphoma; a humanized anti-CD2 mAb for the treatment of Hodgkin's Disease or non-Hodgkin's lymphoma such as ALLOMUNE®; labetuzumab (CEACIDE®) which is a humanized anti-CEA antibody for the treatment of colorectal cancer; bevacizumab (AVASTIN®) which is a humanized anti-VEGF-A mAb for the treatment of brain, colon, kidney, or lung cancer; Ibritumomab tiuxetan (ZEVALIN®) which is an anti-CD20 monoclonal antibody to the treatment of non-Hodgkin's lymphoma; ofatumumab (ARZERRA®) which is a human anti-CD20 monoclonal antibody for the treatment of chronic lymphocytic leukemia; panitumumab (VECTIBIX®) which is a human anti-EGFR monoclonal antibody for the treatment of colon cancer; rituximab (RITUXAN®) which is an anti-CD20 chimeric monoclonal antibody for the treatment of chronic lymphocytic leukemia and non-Hodgkin's lymphoma; tositumomab (BEXXAR®) which is an anti-CD20 monoclonal antibody for the treatment of non-Hodgkin's lymphoma; trastuzumab (HERCEPTIN®) which is an anti-HER2 receptor monoclonal antibody for the treatment of breast and stomach cancer; ipilimumab (YERVOY®) which is an anti-CTLA4 human monoclonal antibody for the treatment of melanoma; gemtuzumab and inotuzumab ozogamicin.

In another specific embodiment, L includes antibodies selected from anti-I-13 antibodies, including anti-I-13 antibodies used in the treatment of cancer, for instance anti-IL-13Rα2 antibodies.

In yet another specific embodiment, L includes antibodies selected from anti-Notch antibodies, including anti-Notch antibodies used in the treatment of cancer.

In certain embodiments, the antibody L is bound to the linker via a sulfur bond or via a sulfur-sulfur bond.

Another aspect of the invention relates to an antibody drug conjugate comprising any of the aforementioned compounds.

Another aspect of the invention relates to an antibody drug conjugate comprising an antibody and any one of the aforementioned compounds.

In certain embodiments, the present invention relates to any of the aforementioned antibody drug conjugates and attendant definitions, wherein the compound is covalently bound to the antibody.

In certain embodiments, the present invention relates to any of the aforementioned antibody drug conjugates and attendant definitions, wherein the compound in said antibody drug conjugate is selected from the group consisting of the compounds of Table 18B,

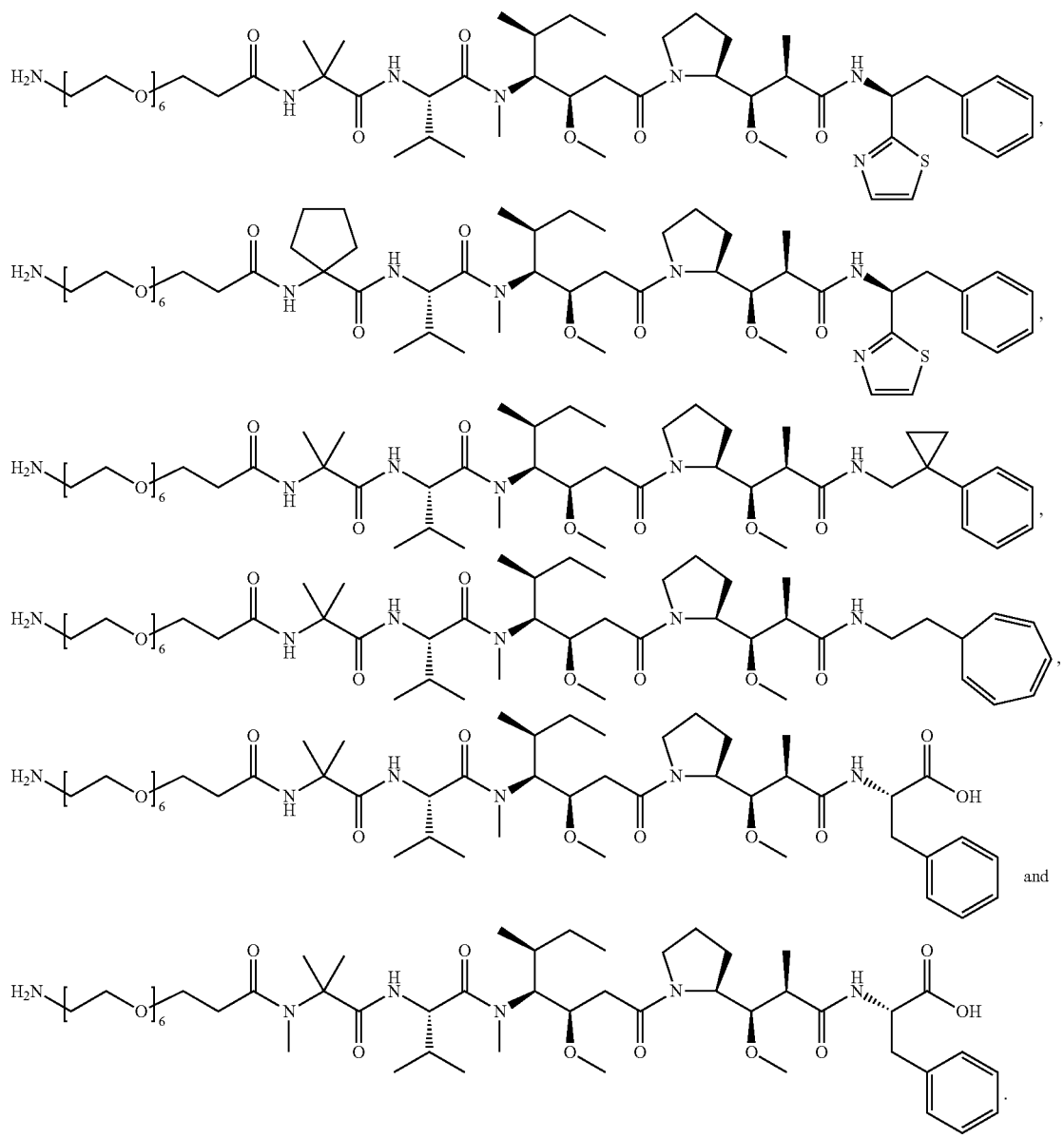

In certain embodiments, the present invention relates to any of the aforementioned antibody drug conjugates and attendant definitions, wherein the antibody drug conjugate comprises between 2, 3, 4, 5, 6, 7, 8, 9 or 10 compounds of the invention.

In certain embodiments, the present invention relates to any of the aforementioned antibody drug conjugates and attendant definitions, wherein the antibody drug conjugate comprises 3 or 4 compounds of the invention.

The Antibody Unit (Ab)

As noted above, the term "antibody" (or "Ab") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-$\alpha$ and TGF-$\beta$, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. No. 4,816,567; and U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques.

The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX® which is a murine antibody for the treatment of ovarian cancer; PANOREX® (Glaxo Wellcome, NC) which is a murine IgG$_{2a}$ antibody for the treatment of colorectal cancer; Cetuximab ERBITUX® (Imclone Systems Inc., NY) which is an anti-EGFR IgG chimeric antibody for the treatment of epidermal growth factor positive cancers, such as head and neck cancer; Vitaxin® (MedImmune, Inc., MD) which is a humanized antibody for the treatment of sarcoma; CAMPATH I/H® (Leukosite, MA) which is a humanized IgG$_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM® (Techniclone, Inc., CA) which is a radiolabeled murine anti-HLA-Dr10 antibody for the treatment of non-Hodgkin's lymphoma; ALLOMUNE® (BioTransplant, CA) which is a humanized anti-CD2 mAb for the treatment of Hodgkin's Disease or non-Hodgkin's lymphoma; CEACIDE® (Immunomedics, NJ) which is a humanized anti-CEA antibody for the treatment of colorectal cancer; AVASTIN® (Genentech/Roche, CA) which is a humanized anti-VEGF-A mAb for the treatment of brain, colon, kidney, or lung cancer; ZEVALIN® (Spectrum Pharmaceuticals, NV) which is an anti-CD20 monoclonal antibody to the treatment of non-Hodgkin's lymphoma; ARZERRA® (GSK, UK) which is a human anti-CD20 monoclonal antibody for the treatment of chronic lymphocytic leukemia; VECTIBIX® (Amgen, CA) which is a human anti-EGFR monoclonal antibody for the treatment of colon cancer; RITUXAN® (Genentech/BioGen, CA) which is an anti-CD20 chimeric monoclonal antibody for the treatment of chronic lymphocytic leukemia and non-Hodgkin's lymphoma; BEXXAR® (GSK, UK) which is an anti-CD20 monoclonal antibody for the treatment of non-Hodgkin's lymphoma; HERCEPTIN® (Genentech, CA) which is an anti-HER2 receptor monoclonal antibody for the treatment of breast and stomach cancer; YERVOY® (BMS, NJ) which is an anti-CTLA4 human monoclonal antibody for the treatment of melanoma; MYLOTARG® (Wyeth/Pfizer, NY) which is anti-CD33 humanized monoclonal antibody conjugated to calicheamicin for the treatment of acute myelogenous leukemia; and, inotuzumab ozogamicin (Wyeth/Pfizer, NY) which is an anti-CD22 humanized monoclonal antibody conjugated to calicheamicin for the treatment of acute lymphocytic leukemia and non-Hodgkin's lymphoma.

In another specific embodiment, anti-IL13 antibodies, including anti-IL13 antibodies used in the treatment of cancer, can be used.

In another specific embodiment, anti-Notch antibodies, including anti-Notch antibodies used in the treatment of cancer, can be used.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Synthesis of Compounds and Antibody Drug Conjugates Thereof

The compounds and conjugates of the invention can be made using the synthetic procedures outlined below in the Exemplification.

As described in more detail below, the compounds and conjugates of the invention can be prepared using a section of a linker unit having a reactive site for binding to the compound.

Linker

A linker (sometimes referred to as "[linker]" herein) is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells.

In one embodiment, the linker has the formula: is

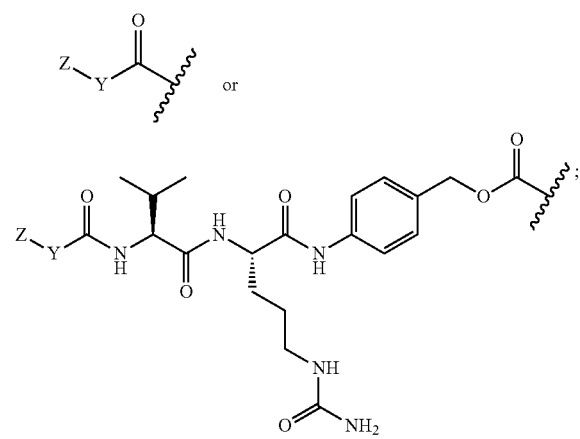

wherein

Y is $C_2$-$C_{20}$ alkylene or $C_2$-$C_{20}$ heteroalkylene; $C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z is

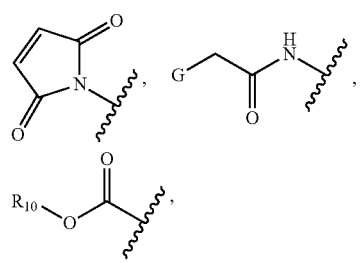

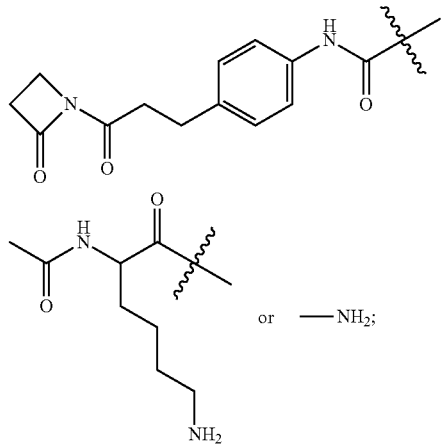

$R^7$ is independently selected for each occurrence from the group consisting of F, Cl, I, Br, $NO_2$, CN and $CF_3$;

$R^{10}$ is hydrogen, —$C_1$-$C_{10}$alkyl, —$C_3$-$C_8$-carbocycle, aryl, —$C_1$-$C_{10}$heteroalkyl, —$C_3$-$C_8$heterocyclo, —$C_1$-$C_{10}$alkylene-aryl, -arylene-$C_1$-$C_{10}$alkyl, —$C_1$-$C_{10}$alkylene-($C_3$-$C_8$-carbocyclo), —($C_3$-$C_8$ carbocyclo)-$C_1$-$C_{10}$alkyl, —$C_1$-$C_{10}$alkylene-($C_3$-$C_8$heterocyclo), and —($C_3$-$C_8$ heterocyclo)-$C_1$-$C_{10}$alkyl, where aryl on $R_{10}$ comprising aryl is optionally substituted with $[R_7]_h$; and h is 1, 2, 3, 4 or 5.

In an ADC the linker serves to attach the payload to the antibody.

In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

As described in more detail below, the conjugates can be prepared using a section of the linker having a reactive site for binding to a compound of the invention and introducing another section of the linker unit having a reactive site for an antibody. In one aspect, a linker unit has a reactive site which has an electrophilic group that is reactive with a nucleophilic group present on an antibody unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a Linker unit and forms a covalent bond to a linker unit. Useful electrophilic groups include, but are not limited to, maleimide and haloacetamide groups.

In another embodiment, a linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

As used herein, "mc-" previously known as "MalC-" refers to

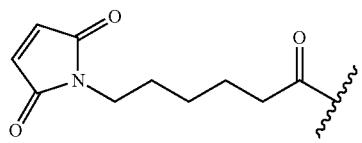 [SMILES: *C(=O)CCCCCN1C(=O)C=CC1=O]

As used herein, "mcValCitPABC-" previously known as "MalCValCitPABC-" refers to

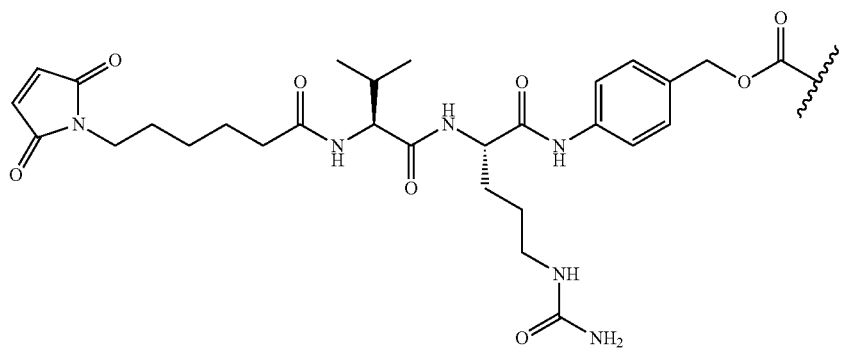 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

As used herein, "Ma1PegXC2-" refers to

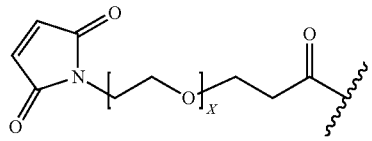

As used herein, "AmPegXC2-" refers to

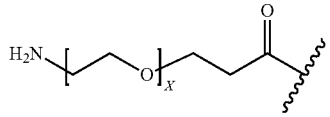

As used herein, "mcValCitPABCAmPegXC2-" refers to

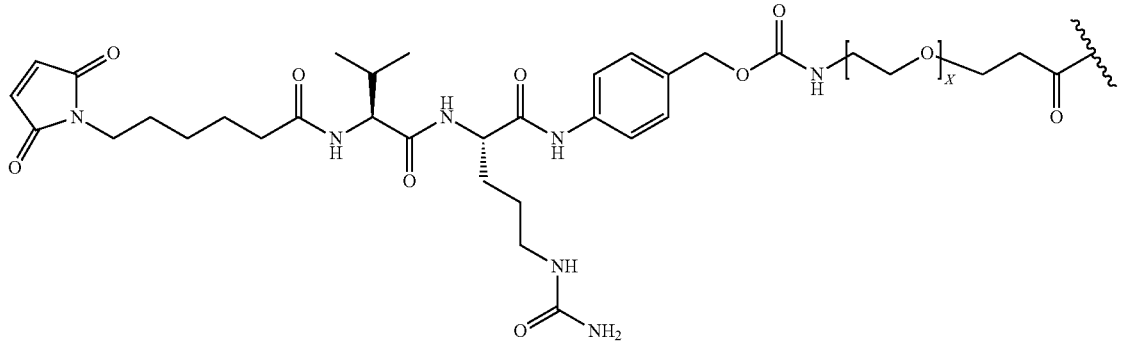

As used herein, "Ma1PegXC2ValCitPABC-" refers to
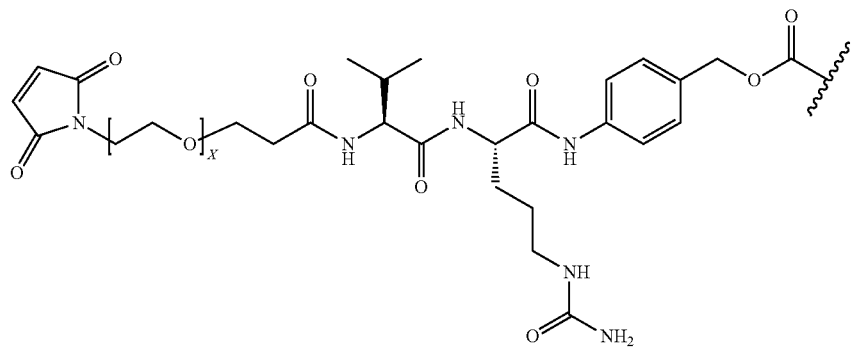
As used herein, "2BrAcPegXC2" refers to
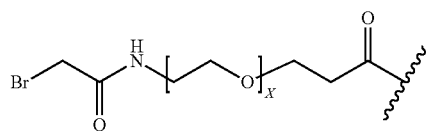
As used herein, "mv-" refers to
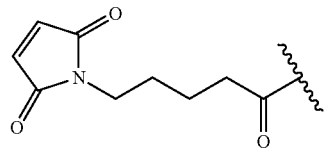 [SMILES: *C(=O)CCCCN1C(=O)C=CC1=O]
As used herein, "mb-" refers to
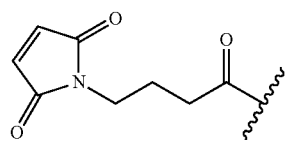 [SMILES: *C(=O)CCCN1C(=O)C=CC1=O]
As used herein, "me-" refers to
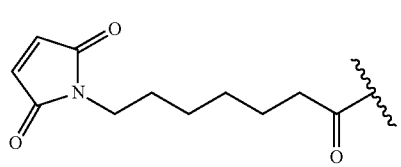 [SMILES: *C(=O)CCCCCCN1C(=O)C=CC1=O]
As used herein, "MalC6-" refers to
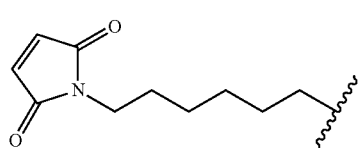 [SMILES: *CCCCCCN1C(=O)C=CC1=O]
As used herein, "PFPCOPe2XC2ValCitPABC-" refers
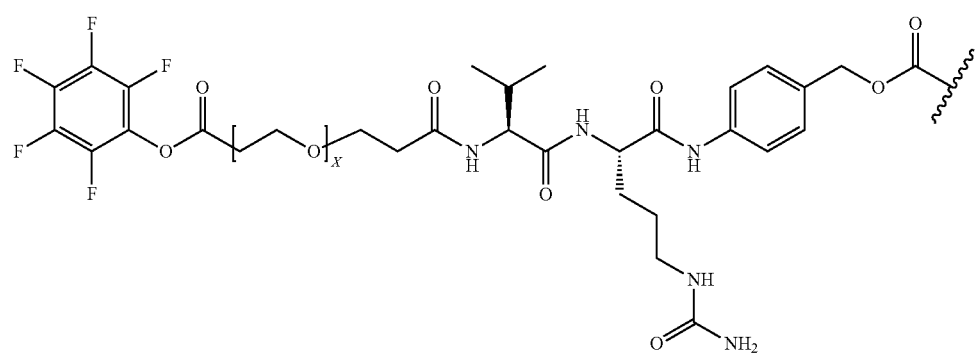

As used herein, "PFPCOPegXC2AmPegYC2-" refers to
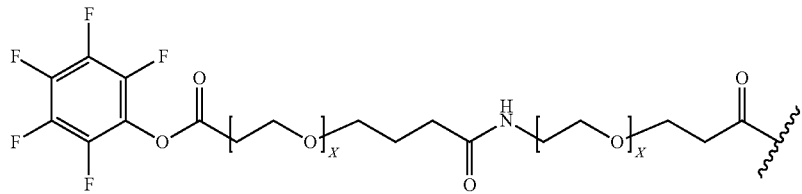
As used herein, "PFPCOPegXC2AlaAlaAsnPABC-" refers to
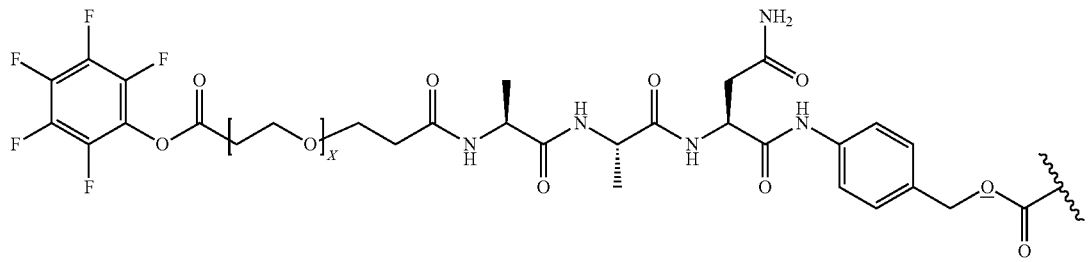
As used herein, "PFPCOPegXC2-" refers to
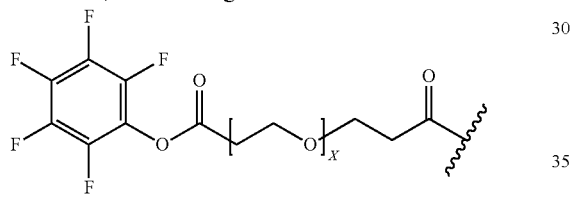
As used herein, "PFPCOPegXC2AmPegYC2PABC-" refers to
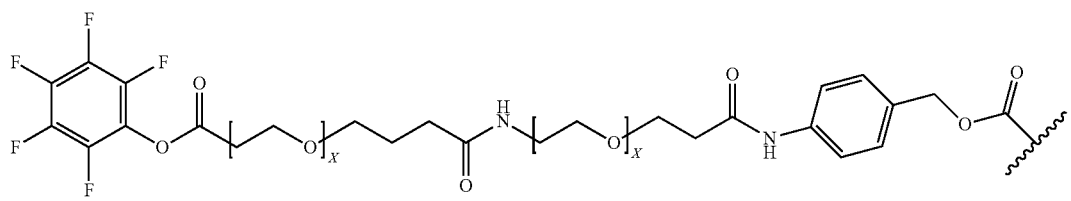
As used herein, "mcGly-" refers to
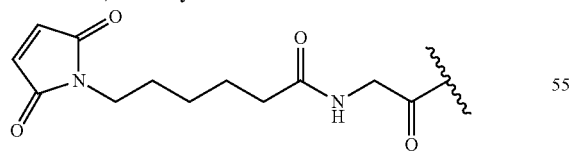
As used herein, "AzCOC2Ph4AmCOPeg2C2-" refers to
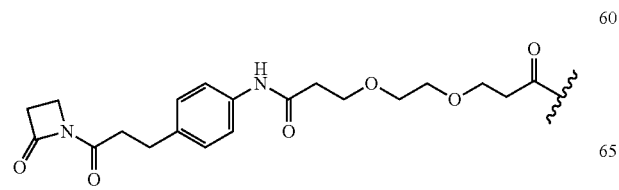

As used herein, "AzCOC2Ph4AmPeglC1-" refers to

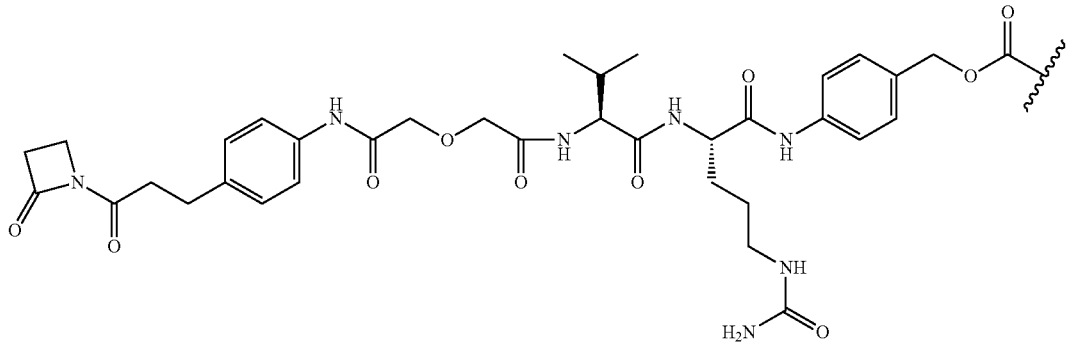 [SMILES: *C(=O)OCc1ccc(NC(=O)[C@H](CCCNC(N)=O)NC(=O)[C@@H](NC(=O)COCC(=O)Nc2ccc(CCC(=O)N3CCC3=O)cc2)C(C)C)cc1]

As used herein, "AcLysValCitPABC-" refers to

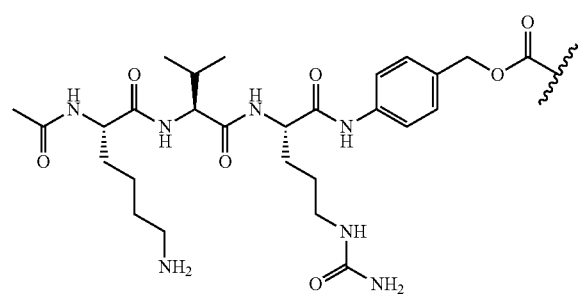 [SMILES: *C(=O)OCc1ccc(NC(=O)[C@H](CCCNC(N)=O)NC(=O)[C@@H](NC(=O)[C@H](CCCCN)NC(C)=O)C(C)C)cc1]

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. For example, compounds of the invention may be conjugated as described in International Patent Application Serial No. PCT/IB2011/054899, whose entire contents are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering in the presence of transglutaminase, Z is $NH_2$.

Conjugation to the Human Light Chain Kappa Domain Constant Region

In certain embodiments, a compound of the invention may be covalently attached to the side chain of $K^{188}$ of the human light chain kappa domain constant region (CLκ) (full light chain numbering according to Kabat). K188 may also be termed CLκ K80, when counting only the human kappa constant region, for example, of SEQ ID NOs: 1, 2, 3 and 4).

For example, compounds of the invention may be conjugated as described in U.S. patent application Ser. No. 13/180, 204, or WO2012/007896 whose entire contents are incorporated herein by reference. In certain embodiments, to facilitate conjugation to K188 CLκ (CLκ-K80), Z is

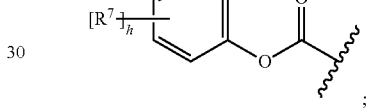

$R^7$ is independently selected for each occurrence from the group consisting of F, Cl, I, Br, $NO_2$, CN and $CF_3$; and h is 1, 2, 3, 4 or 5.

In certain embodiments, to facilitate conjugation to $K^{188}$ CLκ (CLκ-K80), Z is

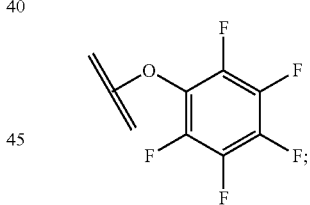

The present invention further provides antibody drug conjugates comprising an antibody, or antigen binding portions thereof, comprising a constant kappa domain covalently conjugated to a toxin of the invention, characterized in that at least one toxin of the invention is covalently conjugated to K80 of SEQ ID NO:1, SEQ ID NO:2, SEQ ID NO:3 or SEQ ID NO: 4 (Table 1). In some aspects, the number of toxins of the invention covalently conjugated to the at K80 may be a range whose lower limit is selected from the group consisting of about 1.5, about 1.6, about 1.7, about 1.8, about 1.9, and about 2.0, and whose upper limit is selected from the group consisting of about 2.0, about 2.1, about 2.2, about 2.3, about 2.4, about 2.5. In some aspects, p is about 2.

Conjugation of the toxin with the constant light domain of an antibody is particularly desirable to minimize, or prevent, any interference with binding of the Fc portion of the antibody to Fc receptors (such as FcγR and FcRn) or binding of the antibody to its respective target. Conversely, conjugation of the respective toxin to the Fc portion of an antibody may decrease the antibody half-life in vivo and/or its capacity to interact with the immune system (effector function). Conjugation of the toxin in the variable heavy chain (VH) or variable light chain (VL) region of the antibody carries a risk of diminishing the binding of the antibody to its cognate.

Furthermore, whereas conjugation to CLκ-K80 is reliable and robust, conjugation to other antibody surface lysines, each of slightly different reactivity and pI can result in an heterogeneous sample of conjugated antibodies that can release conjugated molecules at inopportune or irregular times, such as during circulation and prior to delivery of the Effector Moiety to the target by antibody recognition.

In addition, the present invention provides for known polymorphisms of the kappa chain V/A at position 45 and A/L at position 83 (giving the 3 identified human constant kappa polymorphisms Km(1):V45/L83 (SEQ ID NO:2), Km(1,2): A45/L83 (SEQ ID NO:3), and Km(3) A45/V83 (SEQ ID NO:4)). The variability of residues at positions 45 and 83 in SEQ ID NO:1 may be selected so as to only provide for any one, two or all three of the Km(1), Km(1,2), and Km(3) polymorphisms.

TABLE 1

| SEQ ID NO | DESCRIPTION | SEQUENCE |
|---|---|---|
| 1 | hLC constant region GENUS | TVAAPSVFIF PPSDEQLKSG TASVVCLLNN FYPREAKVQW KVDNxLQSGN SQESVTEQDS KDSTYSLSST LTLSKADYEK HKxYACEVTH QGLSSPVTKS FNRGEC |
| 2 | h LC constant region Km(1) polymorphism (V45/L83) | TVAAPSVFIF PPSDEQLKSG TASVVCLLNN FYPREAKVQW KVDNVLQSGN SQESVTEQDS KDSTYSLSST LTLSKADYEK HKLYACEVTH QGLSSPVTKS FNRGEC |
| 3 | h LC constant region Km(1, 2) polymorphism A45/L83 | TVAAPSVFIF PPSDEQLKSG TASVVCLLNN FYPREAKVQW KVDNALQSGN SQESVTEQDS KDSTYSLSST LTLSKADYEK HKLYACEVTH QGLSSPVTKS FNRGEC |
| 4 | h LC constant region Km(3) polymorphism A45/V83 | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGEC |

Wherein x at position 45 is A or V, and x at position 83 is L or V.

In certain embodiments, the invention provides for a composition comprising a compound of the invention covalently conjugated to an antibody (or antigen binding portion thereof), wherein at least about 50%, or at least about 60%, or at least about 70%, or at least about 80%, or at least about 90% of the compound of the invention in the composition is conjugated to the antibody or antigen binding portion thereof at $K^{188}$ CLκ.

In certain embodiments, the compounds of the invention

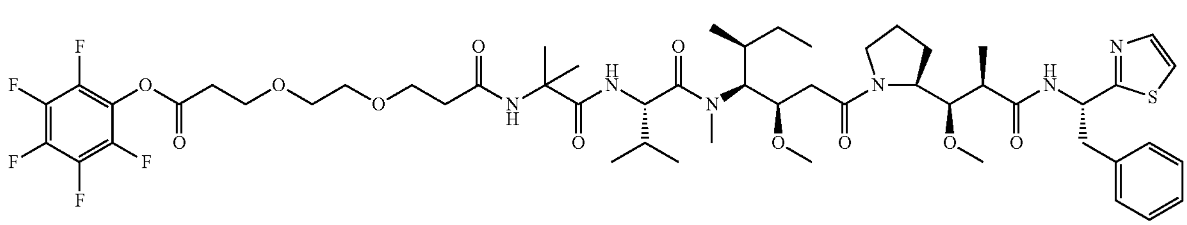

,

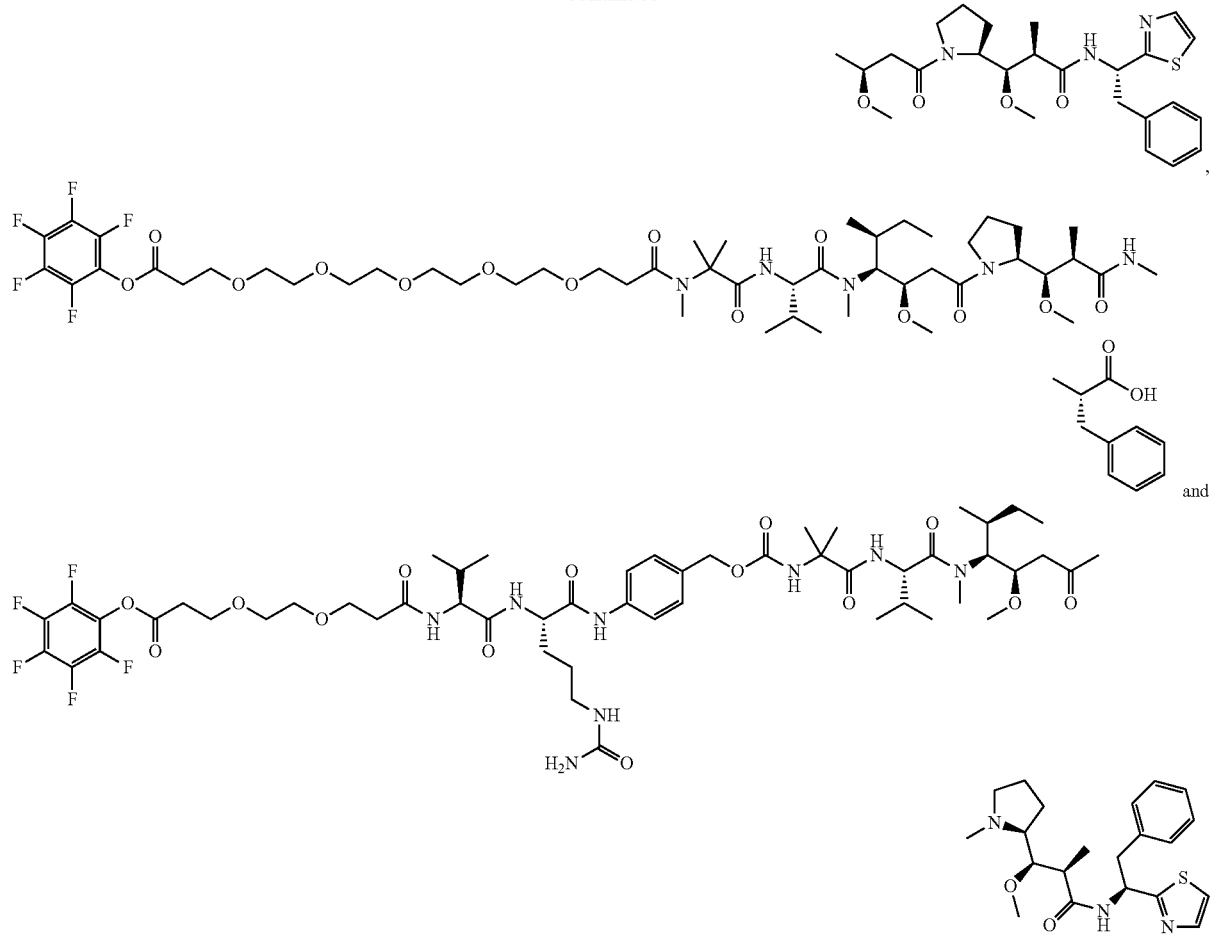

may be conjugated to the combining site of a catalytic antibody, such as aldolase antibodies, or antigen binding portion thereof. Aldolase antibodies contain combining site portions that, when unencumbered (for example by conjugation), catalyze an aldol addition reaction between an aliphatic ketone donor and an aldehyde acceptor. The contents of US Patent Application Publication No. US 2006/205670 are incorporated herein by reference, in particular pages 78-118 describing linkers, and paragraphs [0153]-[0233] describing antibodies, useful fragments, variants and modifications thereof, h38C2, combining sites and complimentary determining regions (CDRs), and related antibody technology (Table 2, and exemplary compounds below):

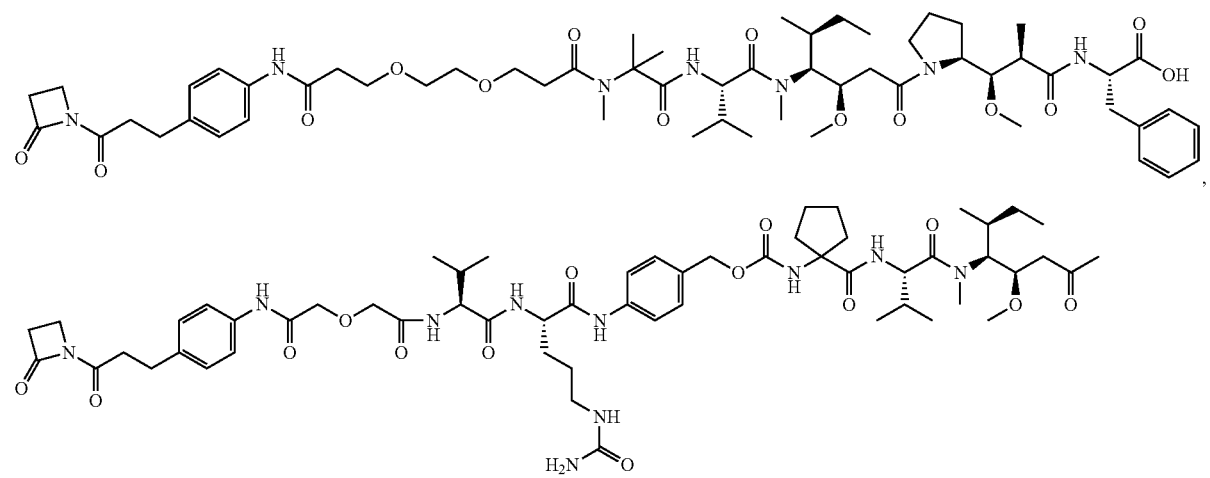

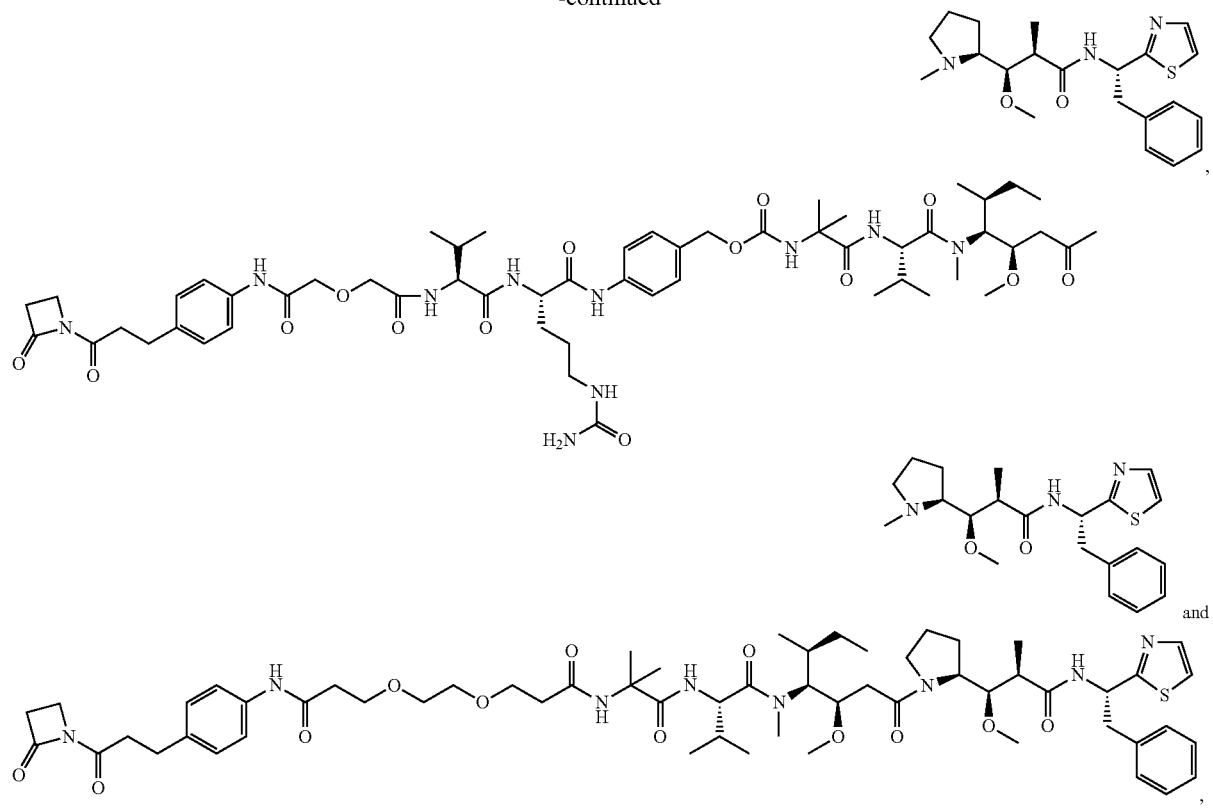

and

The term "combining site" includes the CDRs and the adjacent framework residues that are involved in antigen binding.

TABLE 2

| SEQ ID NO | DESCRIPTION | SEQUENCE |
|---|---|---|
| 5 | h38C2 VL | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IK |
| 6 | h38C2 VH | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSS |
| 7 | h38C2 LC | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 8 | h38C2 HC | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP |

TABLE 2 -continued

| SEQ ID NO | DESCRIPTION | SEQUENCE |
|---|---|---|
| | | APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |

Conjugation with Linkers Comprising Succinimides, Including Ring-Opened Versions In certain embodiments, the present invention includes a compound of the invention conjugated via a succinimide-based linker or a ring-opened succinimide-based linker. The stability of the succinimide-cysteine linkage has become an area of increasing interest. Succinimides can be transferred both in vitro and in vivo to exogenous thiol nucleophiles, presumably through a retro-Michael reaction resulting in a maleimide that is subsequently attacked by a thiol. It is believed that hydrolysis of the ring results in a species that is resistant to the retro-Michael reaction. This renders the resulting conjugate more stable and potentially more efficacious. Conditions may be optimized to forcibly open the succinimide ring on the conjugate. Basic conditions resulted in facile hydrolysis of the ring. For instance, linkers containing a polyethylene glycol (PEG) chain can be hydrolysed at pH 9.2 at 37° C. in approximately 12 h, and linkers containing an alkyl chain, such as "mc" may require a higher temperature and longer reaction time in order to drive the ring-opening to completion.

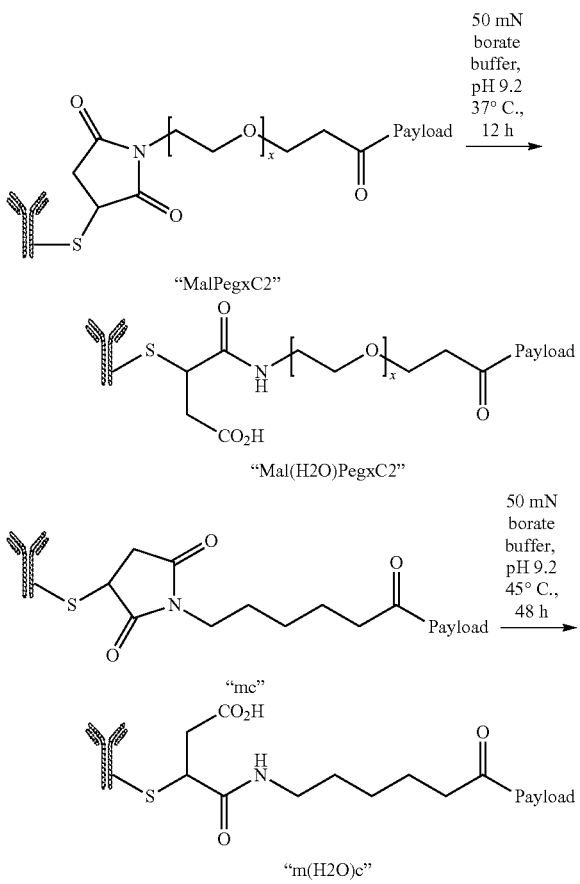

Example of Forced Hydrolysis of Maleimide-Based Conjugates

In order to assess the stability of these conjugates and prioritize samples for in vivo evaluation, an assay was developed that involves the treatment of the maleimide-linked conjugates with excess aqueous glutathione (GSH) or plasma. Aliquots of the reaction mixture were analyzed at various timepoints to determine the loading of the conjugate, using the methodology described above. The results (Table 24) indicate that the drug-antibody linkage is slowly cleaved in a GSH-dependent manner. As expected, the rate of cleavage is highly dependent upon the hydrolysis of the succinimide ring. Importantly, these results appear to translate to improved PK exposure, as measured by an increase in area-under-curve (AUC) of the conjugate and by an increase in the conjugate/Ab exposure ratio.

Method for Assessing the Stability of ADCs

The ADC sample (30 ng) in PBS is mixed with glutathione (GSH) solution to produce final concentration of GSH of 0.5 mM and 3 mg/mL protein concentration. A control sample (without GSH) was likewise prepared from 30 ng ADC diluted to 3 mg/mL in PBS. The GSH-treated ADC sample and the control ADC sample were incubated at 37° C. and were sampled at 0, 3, and 6 days. Aliquots were reduced with excess TCEP, acidified by adding 0.1% formic acid solution with 10% acetonitrile and analyzed by for loading by LC/MS as described below.

Sample analysis: Analysis was performed using an Aglient 1100 capillary HPLC coupled with Waters Xevo G2 Q-TOF mass spectrometer. The analytes were loaded onto a Zorbax Poroshell 300SB C8 column (0.5 mm×75 mm, maintained at 80° C.) with 0.1% formic acid, and eluted using a gradient of 20-40% buffer B (80% acetonitrile, 18% 1-propanol, 2% water with 0.1% formic acid) at a flow rate of 20 µl/min over 5.5 minutes. Mass spectrometric detection was carried out in positive, sensitivity mode with capillary voltage set at 3.3 kV. Data analysis was performed with MaxEnt 1 function in MassLynx and intensities were used for loading calculation based on the previously described formula.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the a compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carriers) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof.

For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, microparticles, microcapsules, capsules, etc., and can be used to administer a compound of the invention and/or antibody drug conjugate thereof. In certain embodiments, more than one compound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as silastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer.

Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

Released Species

Further embodiments of the invention include the chemical species released, inside or in the vicinity of the cancer cell or tumor cell by what is believed to be enzymatic and/or hydrolytic cleavage by one or more cancer cell or tumor cell-associated proteases. Such compounds include the species described herein, and also include compounds such as those described in the structure:

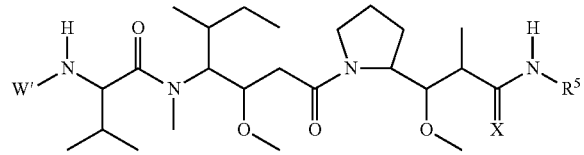

IV or a pharmaceutically acceptable salt or solvate thereof, wherein, independently for each occurrence, W is

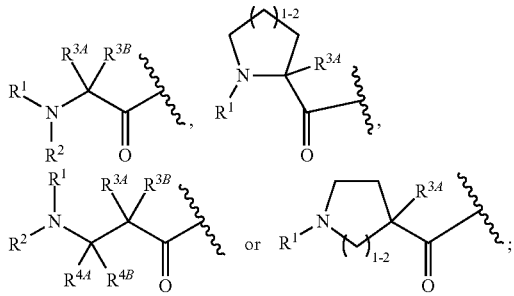

$R^1$ is

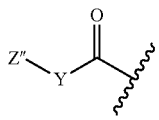

Y is $C_2$-$C_{20}$ alkylene or $C_2$-$C_{20}$ heteroalkylene; $C_3$-$C_8$ carbocyclo-, -arylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or -($C_3$-$C_8$ heterocyclo)-$C_1$-$C_{10}$alkylene-;

Z" is

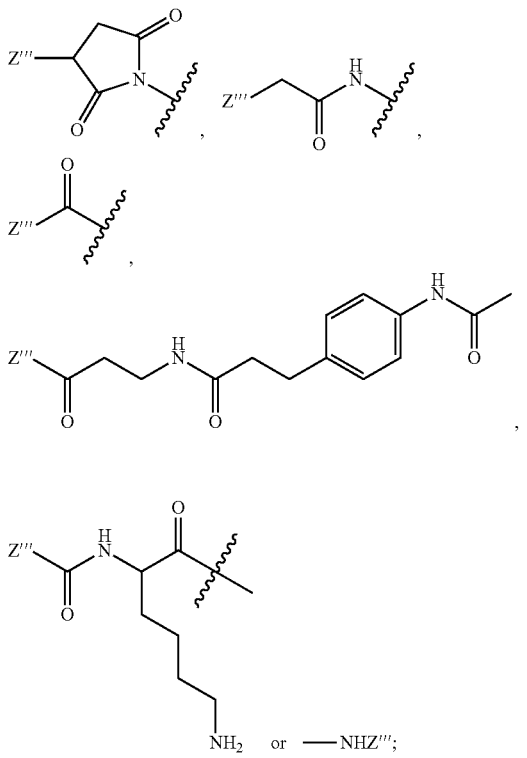

Z'" is

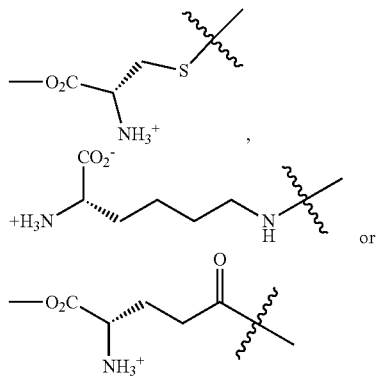

G is halogen, —OH, —SH or —S—$C_1$-$C_6$ alkyl;
$R^2$ is hydrogen, $C_1$-$C_8$ alkyl or $C_1$-$C_8$ haloalkyl;
$R^{3A}$ and $R^{3B}$ are defined as either of the following:
(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{3B}$ is $C_1$-$C_8$ alkyl, $C_1$-$C_8$ haloalkyl, $C_3$-$C_8$ carbocyclyl, $C_1$-$C_1$ heterocyclyl, aryl, heteroaralkyl, halogen or aralkyl; or
(ii) $R^{3A}$ and $R^{3B}$ taken together are $C_2$-$C_8$ alkylene or $C_1$-$C_8$ heteroalkylene;
$R^{4A}$ and $R^{4B}$ are defined as either of the following:
(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(ii) $R^{4A}$ and $R^{4B}$ taken together are $C_2$-$C_8$ alkylene or $C_1$-$C_8$ heteroalkylene;
$R^5$ is

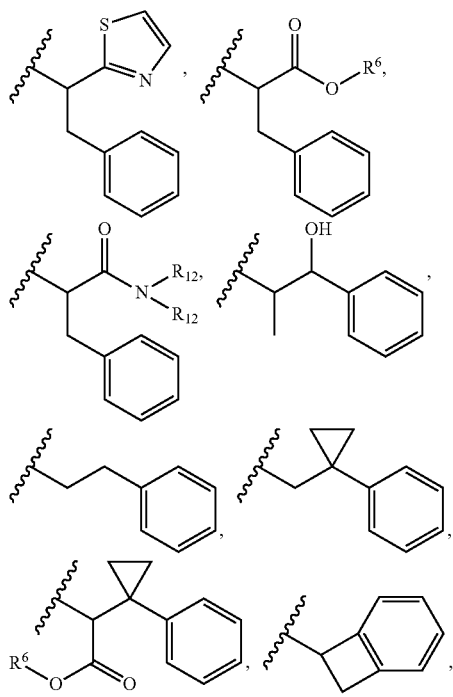

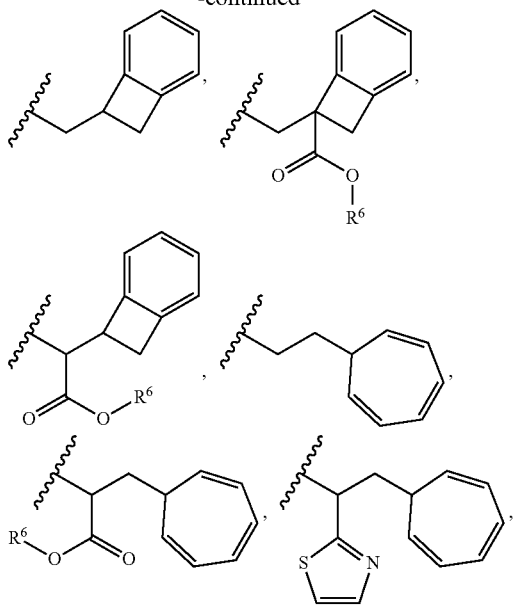

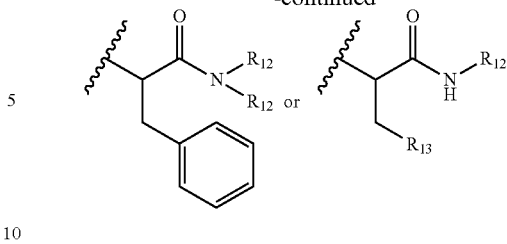

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or R$^5$ is

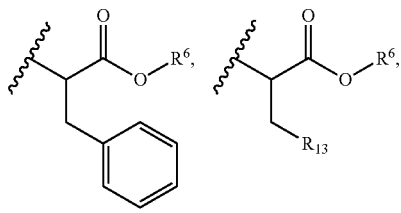

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$ heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

R$^6$ is hydrogen, —$C_1$-$C_8$ alkyl, —$C_2$-$C_8$ alkenyl, —$C_2$-$C_8$ alkynyl or —$C_1$-$C_8$ haloalkyl;

R$^{12}$ is hydrogen, $C_1$-$C_4$ alkyl, $C_1$-$C_{10}$ heterocyclyl or $C_6$-$C_{14}$ aryl;

R$^{13}$ is $C_1$-$C_{10}$ heterocyclyl; and

R$^7$ is independently selected for each occurrence from the group consisting of F, Cl, I, Br, NO$_2$, CN and CF$_3$;

R$^{10}$ is hydrogen, —$C_1$-$C_{10}$alkyl, —$C_3$-$C_8$-carbocycle, aryl, —$C_1$-$C_{10}$heteroalkyl, —$C_3$-$C_8$heterocyclo, —$C_1$-$C_{10}$alkylene-aryl, -arylene-$C_1$-$C_{10}$alkyl, —$C_1$-$C_{10}$alkylene-($C_3$-$C_8$-carbocyclo), —($C_3$-$C_8$ carbocyclo)-$C_1$-$C_{10}$alkyl, —$C_1$-$C_{10}$alkylene-($C_3$-$C_8$heterocyclo), and —($C_3$-$C_8$ heterocyclo)-$C_1$-$C_{10}$alkyl, where aryl on R$_{10}$ comprising aryl is optionally substituted with [R$_7$]$_h$;

h is 1, 2, 3, 4 or 5; and

X is O or S.

Of particular interest are compounds of formula IV having the structures:

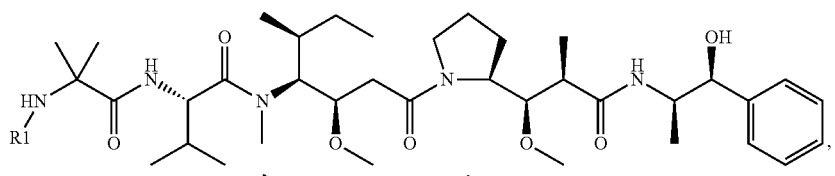

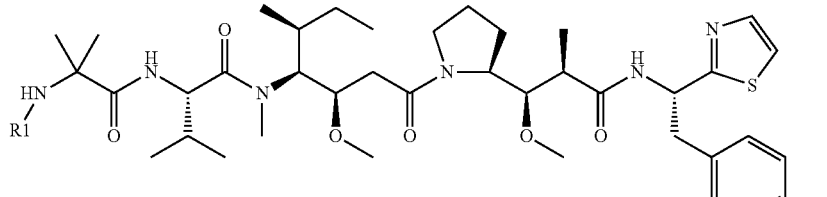

and

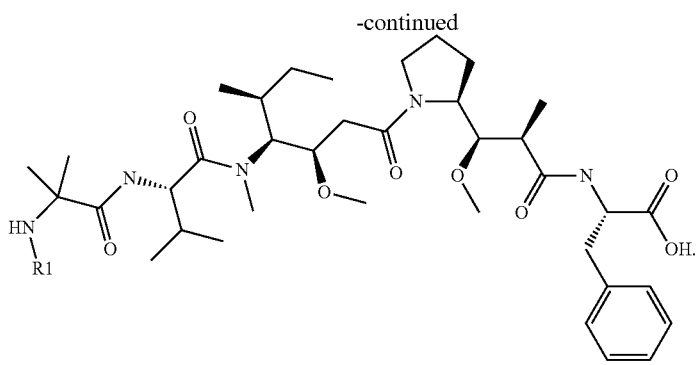

The invention is further described in the following examples, which are not intended to limit the scope of the invention.

EXEMPLIFICATION

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction Protocol (length of reaction and temperature) may vary. In general, reactions were followed by thin layer chromatography (TLC) or mass spectrometry, and subjected to work-up when appropriate. Purifications may vary between experiments: in general, solvents and the solvent ratios used for eluants/gradients were chosen to provide appropriate Rfs or retention times.

Optical rotations were performed on a Perkin-Elmer polarimeter 343 (Serial number 9506).

HRMS were performed on an Agilent 6220 TOF LC/MS.

Compound names were generated with ACD Labs software.

HPLC and LC-MS Conditions Used for Analysis

Protocol A:
Column: Phenomenex Luna C18 (2), 150×3.0 mm, 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 25° C.; Detection: DAD 215 nm, 254 nm; MS (+) range 150-2000 daltons; Injection volume: 10 μL; Instrument: Agilent 1200 LCMS.

Protocol B:
Column: Phenomenex Luna C18 (2), 150×3.0 mm, 5 μm; Mobile phase A: 0.1% formic acid in water (v/v); Mobile phase B: 0.1% formic acid in acetonitrile (v/v); Gradient: 50% B over 1.5 minutes, 50% to 100% B over 6.5 minutes, then 100% B over 3 minutes; Flow rate: 0.75 mL/minute. Temperature: 25° C.; Detection: DAD 215 nm; MS (+) range 150-2000 daltons; Injection volume: 10 μL; Instrument: Agilent 1200 LCMS.

Protocol C:
Column: Phenomenex Luna C18 (2), 150×3.0 mm, 5 μm; Mobile phase A: 0.02% trifluoroacetic acid in water (v/v); Mobile phase B: 0.02% trifluoroacetic acid in methanol (v/v); Gradient: 50% to 100% B over 10 minutes; Flow rate: 0.75 mL/minute. Temperature: not controlled; Detection: DAD 215 nm, 254 nm; Injection volume: 10 μL; Instrument: Agilent 1100 HPLC.

Protocol D:
Column: Phenomenex Luna C18 (2), 150×3.0 mm, 5 μm; Mobile phase A: 0.02% trifluoroacetic acid in water (v/v); Mobile phase B: 0.02% trifluoroacetic acid in methanol (v/v); Gradient: 5% to 100% B over 8 minutes; Flow rate: 0.75 mL/minute. Temperature: not controlled; Detection: DAD 215 nm, 254 nm; Injection volume: 10 μL; Instrument: Agilent 1100 HPLC.

Protocol E:
Column: Phenomenex Lux Amylose-2, 250×4.6 mm, 5 μm; Mobile phase A: heptane; Mobile phase B: ethanol (denaturated); Gradient: 5% to 100% B over 10 minutes; Flow rate: 1.5 mL/minute. Temperature: not controlled; Detection: DAD 215 nm, 254 nm; MS (+) range 150-1500 daltons; Injection volume: 10 μL; Instrument: Agilent 1100 LCMS.

Protocol F:
Column: Waters Acquity UPLC BEH, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 0.7 minute, 95% B over 0.1 minute; Flow rate: 1.25 mL/minute. Temperature: 60° C.; Detection: 200-450 nm; MS (+) range 100-1200 daltons; Injection volume: 5 μL; Instrument: Waters Acquity.

Protocol G:
Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 0% to 100% B over 8.5 minutes; Flow rate: 1.5 mL/minute. Temperature: not controlled; Detection: DAD 210 nm; Injection volume: 10 μL; Instrument: Agilent 1100 HPLC.

Protocol H:
Column: Phenomenex Gemini-NX, C18, 4.6×50 mm, 3 μm, 110 Å; Mobile phase A: 0.1% formic acid in water (v/v); Mobile phase B: 0.1% formic acid in acetonitrile (v/v); Gradient: 0% to 100% B over 4.10 minutes, linear then 100% B over 0.4 minute; Flow rate: 1.5 mL/minute. Temperature: 60° C.; Detection: DAD 200-450 nm; MS (+) range 100-2000 daltons; Injection volume: 5 μL; Instrument: Agilent.

Protocol I:
Column: Atlantis T3, 75×3.0 mm, 3 μm; Mobile phase A: 0.05% trifluoroacetic acid in water (v/v); Mobile phase B: acetonitrile; Gradient: 5% to 95% B over 5.75 minutes; Flow rate: 1.2 mL/minute. Temperature: 45° C.; Detection: DAD 215 nm, 230 nm, 254 nm; MS (+) range: 150-1200 daltons; Injection volume: 5 μL; Instrument: Agilent 1100 LCMS.

Protocol J:
Column: Phenomenex Luna Phenyl-Hexyl, 150×3.0 mm, 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B over 1 minute; Flow rate: 0.75 mL/minute. Temperature: 25° C.; Detection: DAD 215 nm, 254 nm; MS (+) range 150-2000 daltons; Injection volume: 10 μL; Instrument: Agilent 1200 LCMS.

Protocol K:
Column: Symmetry-C18, 50×2.1 mm, 3.5 μm; Mobile phase A: 0.1% formic acid in water (v/v); Mobile phase B: 0.1% formic acid in methanol (v/v); Gradient: 10% to 90% B over 6.5 minutes; Flow rate: 0.7 mL/minute. Temperature: room temperature; Detection: DAD 215 nm; MS (+) range 100-1500 daltons; Injection volume: 3 μL; Instrument: Waters 996 PDA.

Protocol L:
Column: XBridge C-18, 150×4.6 mm, 3.5 μm; Mobile phase A: 5 mM aqueous ammonium acetate solution; Mobile phase B: acetonitrile; Gradient: 10% B over 3 minutes then 10% to 80% B over 14 minutes; Flow rate: 0.7 mL/minute. Temperature: room temperature; Detection: DAD 215 nm; MS (+) range 100-1500 daltons; Injection volume: 3 μL; Instrument: Waters 996 PDA.

Protocol M:
Column: Phenomenex Luna, 150×3.0 mm, 5 μm; Mobile phase A: 0.1% formic acid in water (v/v); Mobile phase B: 0.1% formic acid in methanol (v/v); Gradient: 50% B over 1.5 minutes, 50% to 80% B over 8.5 minutes, then 80% B over 10 minutes; Flow rate: 0.75 mL/minute. Temperature: 45° C.; Detection: DAD 215 nm, 254 nm; MS (+) range 90-2000 daltons; Injection volume: 10 μL; Instrument: Agilent 1200 LCMS.

Protocol N:
Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 0% to 100% B over 23.5 minutes; Flow rate: 1.5 mL/minute. Temperature: not controlled; Detection: DAD 210 nm; Injection Volume: 10 μL; Instrument: Agilent 1100 HPLC Protocol O:
Column: Column: Agilent Poroshell 300SB-C8, 75×2.1 mm, 2.6 μm; Mobile phase A: 0.1% formic acid in water (v/v); Mobile phase B: 0.1% formic acid in acetonitrile (v/v); Gradient: 20% B to 45% B over 4 minutes; Flow rate: 1.0 mL/minute. Temperature: 60° C.; Detection: 220 nm; MS (+) range 400-2000Da; Injection volume: 10 μL; Instrument: Agilent 1100 LC, Waters MicromassZQ MS. Deconvolution was performed using MaxEntl.

Protocol P:
Column: Column: TSK-gel G3000SWx1, 300×7.8 mm, 10 μm; Mobile phase: Phosphate buffer saline (PBS, 1×), pH 7.4 with 2% acetonitrile; Isocratic; Flow rate: 1 mL/minute. Temperature: room temperature; Injection Volume: 5 μL; Instrument: Agilent 1100 HPLC.

Protocol Q:
Column: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol Q1:
Column: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 1.5 minute, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol Q2:
Column: Xtimate C18, 2.1×30 mm, 3 μm; Mobile phase A: 0.1% trifluoroacetic acid in water (v/v); Mobile phase B: 0.1% trifluoroacetic acid in acetonitrile (v/v); Gradient: 10% to 80% B over 0.9 minutes, 80% B over 0.6 minutes; 100% B for 0.5 minutes; Flow rate: 1.2 mL/minute. Detection: DAD 220 nM; Temperature: 25° C.; Injection volume: 1 μL; Instrument: Agilent.

Protocol Q3:
Column: Xtimate C18, 2.1×30 mm, 3 μm; Mobile phase A: 0.1% trifluoroacetic acid in water (v/v); Mobile phase B: 0.1% trifluoroacetic acid in acetonitrile (v/v); Gradient 0% to 60% B over 0.9 minutes, 60% B over 0.6 minutes; 100% B for 0.5 minutes; Flow rate: 1.2 mL/minute. Detection: DAD 220 nM; Temperature: 25° C.; Injection volume: 1 μl; Instrument: Agilent.

Protocol R:
Column: Phenomenex Luna, 150×3.0 mm, 5 nm; Mobile phase A: 0.1% formic acid in water (v/v); Mobile phase B: 0.1% formic acid in methanol (v/v); Gradient: 5% B over 1.5 minutes, 5% to 100% B over 8.5 minutes, then 100% B over 1 minute; Flow rate: 0.75 mL/minute. Temperature: 45° C.; Detection: DAD 215 nm, 254 nm; MS (+) range 150-2000 daltons; Injection volume: 10 mL; Instrument: 305 RP Agilent 1200 LCMS.

Protocol S:
Column: Phenomenex Luna, 150×3.0 mm, 5 nm; Mobile phase A: 0.1% trifluoroacetic acid in water (v/v); Mobile phase B: 0.1% trifluoroacetic in acetonitrile (v/v); Gradient: 5% B over 1.5 minutes, 5% to 95% B over 8.5 minutes, then 100% B over 1 minute; Flow rate: 1.0 mL/minute. Temperature: not controlled; Detection: DAD 210 nM; MS (+) range 150-2000 daltons; Injection volume: 10 mL; Instrument: 305 RP Agilent 1100 HPLC.

Protocol T:
Column: Atlantis dC18, 50×4.6 mm, 5 nm; Mobile phase A: 0.05% trifluoroacetic acid in water (v/v); Mobile phase B: 0.05% trifluoroacetic acid in acetonitrile (v/v); Gradient: 5% to 95% B over 4.0 minutes; then hold at 95% B over 1 minute; Flow rate: 2 mL/minute. Temperature: room temperature; Detection: DAD 215 nm; MS (+) range 160-1000 daltons; Injection volume: 3 mL; Instrument: Waters 996 PDA.

Protocol U:
Column: Phenomenex Luna C18 (2), 150×3.0 mm, 5 nm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 45° C.; Detection: DAD 215 nm, 254 nm; MS (+) range 150-2000 daltons; Injection volume: 10 mL; Instrument: Agilent 1200 LCMS.

Protocol V:
Column: HPLC-V Ultimate XB-C18, 50×3.0 mm, 3 nm; Mobile phase A: 0.225% trifluoroacetic acid in water (v/v); Mobile phase B: 0.225% trifluoroacetic acid in acetonitrile (v/v); Gradient: 30% to 90% B over 6 minutes; Flow rate: 1.2 mL/minute. Temperature: 40° C.; Detection: DAD 220 nm; Injection volume: 1 mL; Instrument: SHIMADZU.

Protocol W:
Column: HPLC-V Ultimate XB-C18, 50×3.0 mm, 3 nm; Mobile phase A: 0.1% trifluoroacetic acid in water (v/v); Mobile phase B: 0.1% trifluoroacetic acid in acetonitrile (v/v); Gradient: 10% to 80% B over 6 minutes; Flow rate: 1.2 mL/minute. Temperature: 40° C.; Detection: DAD 220 nm; Injection volume: 3 µL; Instrument: SHIMADZU.

Protocol X:
Column: YMC-pack ODS-A, 150×4.6 mm, 5 µm; Mobile phase A: 0.1% trifluoroacetic acid in water (v/v); Mobile phase B: 0.1% trifluoroacetic acid in acetonitrile (v/v); Gradient: 10% to 80% B over 6 minutes; Flow rate: 1.2 mL/minute. Detection: DAD 220 nm. Temperature: 40° C.; Injection volume: 3 µL; Instrument: SHIMADZU.

Protocol Y:
Column: YMC-pack ODS-A, 150×4.6 mm, 5 µm; Mobile Phase A: 0.1% trifluoroacetic acid in water (v/v); Mobile Phase B: 0.1% trifluoroacetic acid in acetonitrile (v/v); Gradient: 0% to 95% B over 10 minutes, then 95% B for 5 minutes; Flow rate 1.5 mL/minute; Detection: DAD 220 nm; Instrument: Agilent 1100.

Protocol Z:
Column: Xtimate C18, 2.1×30 µm, 3 µm; Mobile Phase A: 0.1% trifluoroacetic acid in water (v/v); Mobile phase B: 0.1% trifluoroacetic acid in acetonitrile (v/v); Gradient: 0% to 60% B over 2 minutes; Flow rate: 1.2 ml/min. Temperature: 50° C.; Detection: 220 nm, MS (+) range 100-1000 daltons; Injection volume: 1 µL; Instrument: SHIMADZU.

Protocol AB:
Column: Phenomenex Luna C18 (2), 150×2.0 mm, 5 µm; Mobile phase A: 0.1% formic acid in water (v/v); Mobile phase B: 0.1% formic acid in acetonitrile (v/v); Gradient: 5% to 100% B over 10 minutes, then 100% B for 2 minute; Flow rate: 0.5 mL/minute. Temperature: 25° C.; Detection: DAD 210 nm, 254 nm; MS (+) range 150-2000 daltons; Injection volume: 5 µL; Instrument: Agilent 1100 LCMS.

Protocol BB:
Column: Phenomenex Luna C18 (2), 150×2.0 mm, 5 µm; Mobile phase A: 0.1% formic acid in water (v/v); Mobile phase B: 0.1% formic acid in acetonitrile (v/v); Gradient: 5% B over 2.0 minutes, 5% to 100% B over 12 minutes, and 100% B for 2 minute, then 100% to 5% B over 1.5 min; Flow rate: 0.75 mL/minute. Temperature: 25° C.; Detection: DAD 215 nm, 254 nm; MS (+) range 150-2000 daltons; Injection volume: 5 µL; Instrument: Agilent.

Protocol CB:
Column: Waters XBridge C18, 4.6×50 mm, 5 µm; Mobile phase A: 0.03% ammonium hydroxide in water (v/v); Mobile phase B: 0.03% ammonium hydroxide in acetonitrile (v/v); Gradient: 5% to 95% B over 4.0 minutes, then 95% B for 1 minute; Flow rate: 2 mL/minute. Temperature: 25° C.; Detection: DAD 215 nm, MS (+) range 160-1000 daltons; Injection volume: 4 µL; Instrument: Waters ZQ/Alliance 2795 HPLC.

Protocol DB:
Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to /95% B over 4.0 minutes, then 95% B for 1 minute. Flow rate: 2 mL/minute. Temperature: 25° C.; Detection: DAD 215 nm, MS (+) range 160-1000 daltons; Injection volume: 4 µL; Instrument: Waters ZQ/Alliance 2795 HPLC.

Protocol EB:
Column: XBridge RP18, 2.1×50 mm, 5 µm; Mobile phase A: 0.02% ammonium hydroxide in water (v/v); Mobile phase B: 0.02% ammonium hydroxide in acetonitrile (v/v); Gradient 10% to 80% B % over 6 minutes, then 80% for 2 minutes; Flow rate: 1.2 mL/minute. Detection: DAD 220 nm.; Temperature: 50° C.

Protocol FB:
Column: Phenomenex Luna C18 (2), 150×2.0 mm, 5 µm; Mobile phase A: 0.1% formic acid in water (v/v); Mobile phase B: 0.1% formic acid in acetonitrile (v/v); Gradient: 5% B over 2.0 minutes, 5% to 100% B over 10 minutes, and 100% B for 2 minute; Flow rate: 0.50 mL/minute. Temperature: 25° C.; Detection: DAD 215 nm, 254 nm; MS (+) range 150-2000 daltons; Injection volume: 5 µL; Instrument: Agilent 1200 LCMS.

In some instances some minor alterations to analysis LC-MS and HPLC conditions were made such as but not limited a change in gradient or flow rate which is indicated by the symbol *.

HPLC Conditions Used for Purification

Method A:
Column: Phenomenex Lux Amylose-2, 250×21.2 mm, 5 µm; Mobile phase A: Heptane; Mobile phase B: Ethanol (denatured); Gradient: 5% to 100% B over 6 min; Flow Rate: 27 mL/minute; Detection: DAD 210-360 nm; MS (+) range 150-2000 daltons; Instrument: Waters FractionLynx.

Method B:
Column: Phenomenex Luna C18(2), 150×21.2 mm, 5 µm; Mobile phase A: 0.02% acetic acid in water; Mobile phase B: 0.02% acetic acid in acetonitrile; Gradient: 5% B over 1.5 minutes, 5% to 45% B over 8.5 minutes; Flow rate: 27 mL/minute; Detection: DAD 215 nm, 254 nm; MS (+) range 150-2000 daltons; Instrument: Waters FractionLynx.

Method C:
Column: Phenomenex Luna C18, 100×30 mm, 10 µm; Mobile phase A: 0.02% trifluoroacetic acid in water (v/v); Mobile phase B: 0.02% trifluoroacetic acid in methanol (v/v); Gradient: 10% to 90% B over 20 minutes; Flow rate: 20 mL/minute. Temperature: not controlled; Detection: DAD 210 nm, 254 nm; Injection Volume: variable; Instrument: Gilson.

Method D:
Column: Phenomenex Synergi Max-RP, 150×21.2 mm, 4 µMI; Mobile phase A: 0.1% formic acid in water; Mobile phase B: 0.1% formic acid in acetonitrile; Gradient: 30% B for 1.5 minutes, 30% to 60% B over 8.5 minutes, 60 to 100% B over 0.5 minutes then 100% B over 2 minutes; Flow rate: 27 mL/minute; Detection: DAD 210-360 nm; MS (+) range 150-2000 daltons; Instrument: Waters FractionLynx.

Method E1:
Column: Phenomenex Luna C18(2), 150×21.2 mm, 5 µm; Mobile phase A: 0.1% formic acid in water; Mobile phase B: 0.1% formic acid in acetonitrile; Gradient: 40% B for 1.5 minutes, 40% to 80% B over 8.5 minutes, 80 to 100% B over 0.5 minute then 100% B over 2 minutes; Flow rate: 27 mL/minute; Detection: Detection: DAD 210-360 nm; MS (+) range 150-2000 daltons; Instrument: Waters FractionLynx LCMS.

Method E2:
Column: Phenomenex Luna Phenyl-hexyl, 150×21.2 mm, 5 µm. The rest of the Protocols are identical to those described for Method E1.

Method F:

Column: Phenomenex Synergi Max-RP, 150×21.2 mm, 4 µm; Mobile phase A: 0.1% formic acid in water; Mobile phase B: 0.1% formic acid in methanol; Gradient: 44% B for 1.5 minutes, 44% to 77% B over 8.5 minutes, then 77% B over 10 minutes; Flow rate: 27 mL/minute; Detection: DAD 210-360 nm; MS (+) range 150-2000 daltons; Instrument: Waters FractionLynx LCMS.

Method G:

Column: PrincetonSFC 2-ethylpyridine, 250×21.2 mm, 5 µm; Mobile phase A: heptane; Mobile phase B: ethanol (denaturated); Gradient: 1% B for 1.5 minutes, 1% to 50% B over 8.5 minutes; Flow rate: 27 mL/minute; Detection: DAD 210-360 nm; MS (+) range 150-2000 daltons; Instrument: Waters FractionLynx LCMS.

Method H:

Column: Phenomenex Luna C18(2), 150×21.2 mm, 5 µm; Mobile phase A: 0.02% acetic acid in water; Mobile phase B: 0.02% acetic acid in acetonitrile; Gradient: 20% B over 1.5 minutes, 20% to 60% B over 10.5 minutes; Flow rate: 27 mL/minute; Detection: DAD 210-360 nm; MS (+) range 150-2000 daltons; Instrument: Waters FractionLynx LCMS.

Method I:

Column: Phenomenex Luna C18(2), 150×21.2 mm, 5 µm; Mobile phase A: 0.1% formic acid in water; Mobile phase B: 0.1% formic acid in methanol; Gradient: 40% B over 1.5 minutes, 40% to 70% B over 8.5 minutes then 70% B over 10 minutes; Flow rate: 27 mL/minute; Detection: DAD 210-360 nm; MS (+) range 150-2000 daltons; Instrument: Waters FractionLynx LCMS.

Method J:

Column: Phenomenex Luna C18, 100×30 mm, 5 µm; Mobile phase A: 0.02% trifluoroacetic acid in water (v/v); Mobile phase B: 0.02% trifluoroacetic acid in acetonitrile (v/v); Gradient: 10% to 90% B over 20 minutes; Flow rate: 20 mL/minute. Temperature: not controlled; Detection: DAD 210 nm, 254 nm; Injection Volume: variable; Instrument: Gilson.

Method K:

Column: Phenomenex Luna C18(2), 150×21.2 mm, 5 µm; Mobile phase A: 0.1% formic acid in water; Mobile phase B: 0.1% formic acid in acetonitrile; Gradient: 20% B for 1.5 minutes, 20% to 50% B over 8.5 minutes, 50 to 100% B over 0.5 minute then 100% B over 2 minutes; Flow rate: 27 mL/minute; Detection: Detection: DAD 210-360 nm; MS (+) range 150-2000 daltons; Instrument: Waters Fraction Lynx LCMS.

Method L:

Column: Phenomenex Luna C18(2), 150×21.2 mm, 5 µm; Mobile phase A: 0.1% formic acid in water; Mobile phase B: 0.1% formic acid in acetonitrile; Gradient: 30% B for 1.5 minutes, 30% to 50% B over 8.5 minutes, 50 to 100% B over 0.5 minute then 100% B over 2 minutes; Flow rate: 27 mL/minute; Detection: Detection: DAD 210-360 nm; MS (+) range 150-2000 daltons; Instrument: Waters Fraction Lynx LCMS.

Method M:

Column: Waters Sunfire, C18, 19×100 mm, 5 µm; Mobile phase A: 0.05% trifluoroacetic acid in water (v/v); Mobile phase B: 0.05% trifluoroacetic acid in acetonitrile (v/v); Gradient: 0 to 100% over 8.5 minutes. Flow rate 25 mL/minute. Detection: DAD 215 nm MS (+) range 160-1000 daltons; Instrument: Waters FractionLynx.

Method N:

Column: Waters Sunfire, C18, 19×100 mm, 5 µm; Mobile phase A: 0.05% formic acid in water (v/v); Mobile phase B: 0.05% formic acid in acetonitrile (v/v); Gradient: 0 to 100% over 8.5 minutes. Flow rate 25 mL/minute. Detection: DAD 215 nm MS (+) range 160-1000 daltons; Instrument: Waters FractionLynx.

Method O:

Column: Phenomenex Luna C18, 21.2×150 mm, 5 µm; Mobile phase A: 0.1% formic acid in water (v/v) acid in water (v/v); Mobile phase B: 0.1% formic acid in acetonitrile (v/v); Gradient(v/v); Gradient 20% B over 1.5 minutes, 20% to 40% B over 8.5 minutes, 40 to 100% B over 0.5 minutes, then hold 100% B for 1.5 minutes. Flow rate: 27 mL/minute. Detection: DAD 210-360 nm; MS (+) range 150-2000 daltons; Instrument: Waters FractionLynx.

Method P:

Column: Phenomenex Gemini C18, 21.2×250 mm, 5 µm; Mobile phase A: 0.225% ammonia hydroxide in water (pH 10) (v/v); Mobile phase B: 0.225% ammonia hydroxide in acetonitrile (v/v); Gradient: 45% to 85% B over 10 minutes. Flow rate 35 mL/minute. Detection: DAD 220 nm MS (+) range 100-1200 daltons; Instrument Shimadzu MS Trigger.

Method Q:

Column: Column. Phenomenex Synergi C18, 50×250 mm, 10 µm; Mobile phase A: 0.1% trifluoroacetic acid in water (v/v) Mobile phase B: Acetonitrile ; Gradient 10% to 40% B over 25 minutes. Flow rate 100 mL/minute. Detection: UV/Vis 220 nm; Instrument: Shimadzu LC-8A.

Method R:

Column: Phenomenex Luna C18 (2), 250×21.2 mm, 5 µm; Mobile phase A: 0.1% TFA in water (v/v); Mobile phase B: 0.1% TFA in acetonitrile (v/v); Gradient: 10% to 100% over 30 minutes; Flow rate variable. Temperature: 25° C.; Detection: DAD 215 nm, 254 nm; MS (+) range 150-2000 daltons; Injection volume: 1.8 mL: Instrument: Agilent 1100 Prep HPLC.

In some instances some minor alterations to purification conditions were made such as but not limited to a change in gradient or flow rate which is indicated by the symbol *.

General Procedures

General Procedure A:

Fmoc removal using diethylamine or piperidine. To a solution of the Fmoc-containing compound in dichloromethane or N,N-dimethylformamide (also referred to as DMF), was added an equal volume of diethylamine or piperidine. Reaction progress was monitored by LC-MS (or HPLC or TLC). Solvents were removed in vacuo, and in some cases the residue was azeotroped one to four times with heptane. Residue was usually diluted with dichloromethane and a small amount of methanol before being reduced down onto silica and purified by chromatography on silica gel, eluting with methanol in dichloromethane (or other appropriate mixture of solvents) to afford the desired material (or crude material was used as is).

General Procedure B:

Boc removal or t-Bu ester cleavage using trifluoroacetic acid. To a solution of the Boc-containing compound or tert-butyl ester-containing compound in dichloromethane at 0° C. (or at room temperature) was added trifluoroacetic acid, to afford a ratio of 1:4 trifluoroacetic acid:dichloromethane. Reaction progress was monitored by LC-MS (or HPLC or TLC). Solvents were removed in vacuo. The residue was azeotroped three times with heptane to afford the desired material.

General Procedure C:

Boc removal or tert-butyl ester (also refers to t-Bu ester) cleavage using hydrochloric acid in dioxane. To either a solution of Boc-containing compound or tert-butyl ester-containing compound in dioxane (or in some cases no solution, or other relevant solvent) was added a 4 M solution of hydrochloric acid in dioxane. Reaction progress was monitored by LC-MS (or HPLC or TLC). The reaction was concentrated in vacuo and in some cases azeotroped one to four time with heptanes.

General Procedure D:

Coupling with O-(7-azabenzotriazol-1-yl)-N,N,N;N'-tetramethyluronium hexafluorophosphate (HATU). To a stirring solution of the amine (1.0 eq.) and acid (1.0-2.0 eq.) in dichloromethane, N,N-dimethylformamide (also referred to as DMF), or a mixture of both, HATU (1.0-2.0 eq.) was added followed by triethylamine (2.0-4.0 eq.) or diisopropylethylamine (2.0-4.0 eq., also referred to as Hunig's base). Reaction progress was monitored by LC-MS (or HPLC or TLC); the reaction was usually completed within three hours. Solvents were removed in vacuo. The residue was purified by silica gel or reverse phase chromatography or in some cases azeotroped three times with heptanes, diluted with a small amount of ethyl acetate before being reduced down onto silica or C18 bonded silica and purified by silica gel or reverse phase chromatography.

General Procedure E:

coupling with N-[6-(2,5-dioxo-2,5-dihydro-1H-pyrrol-1-yl)hexanoyl]-L-valyl-$N^5$-carbamoyl-N-[4-({[(4-nitrophenoxy)carbonyl]oxy}methyl)phenyl]-L-ornithinamide (MalcValCitPABC-PNP). To a mixture of the payload amine (1 eq.) and N-[6-(2,5-dioxo-2,5-dihydro-1H-pyrrol-1-yl)hexanoyl]-L-valyl-$N^5$-carbamoyl-N-[4-({[(4-nitrophenoxy)carbonyl]oxy}methyl)phenyl]-L-ornithinamide (MalcValCit-PABC-PNP, Eur. Pat. Appl. (1994), EP624377, 1.0-2.0 eq.) in N,N-dimethylformamide or dimethylacetamide (also referred to as DMA), pyridine (0.0-4.0 eq.), diisopropylethylamine (0.0-4.0 eq.), 2,6-dimethylpyridine (0.0-4.0 eq., also referred to as 2,6-Luditine) and 1-hydroxybenzotriazole hydrate (0.01-1.1 eq. also referred to as HOBT) or 3H-[1,2,3]triazolo[4,5-b]pyridin-3-ol (0.01-1.1 eq., also referred to as HOAT) was added. After stirring at 40° C.-50° C. for 1-48 hours, the reaction mixture was concentrated in vacuo and azeotroped three times with heptane. The crude material was purified by reverse phase chromatography according to the specified method to afford the desired material.

General Procedure F:

Conjugation of commercial HERCEPTIN® antibody with linker-payload via internal disulfides. Commercially available HERCEPTIN® antibody (Genentech Inc) was dialyzed into Dulbecco's Phosphate Buffered Saline (DPBS, Lonza). The dialyzed antibody was reduced with addition of x equivalents of tris(2-carboxyethyl)phosphine hydrochloride (TCEP, 5 mM in distilled water) and diluted to 15 mg/mL final antibody concentration using DPBS, 5 mM 2,2',2'',2'''-(ethane-1,2-diyldinitrilo)tetraacetic acid (EDTA), pH 7.0-7.4 (Buffer A). The reaction was incubated at 37° C. for 1-2 hours and then cooled to room temperature. Conjugation was performed by addition of y equivalents of linker-payload (5-10 mM in dimethylacetamide (DMA)). DMA was added to achieve 10-20% (v/v) total organic solvent component in final reaction mixture, and Buffer A added to achieve 10 mg/mL final antibody concentration. The reaction was incubated for 1-2 hours at room temperature. The reaction mixture was then buffer exchanged into DPBS (pH 7.4) using GE Healthcare Sephadex G-25 M buffer exchange columns per manufacturer's instructions. Crude material was purified by size exclusion chromatography (SEC) using GE AKTA Explorer system with GE Superdex column and PBS (pH 7.4) eluent.

General Procedure G:

Conjugation reactions were performed in the upper portion of a centrifugal ultrafiltration device such as Amicon Ultra 50k Ultracel filters (part #UFC805096, GE). A 132 mM stock solution of L-cysteine was prepared in PBS containing 50 mM EDTA. This solution (50 µL) was added to a mixture of the respective mutant antibody (5 mg) in 950 µL of PBS containing 50 mM EDTA. The final cysteine concentration in the reaction mixture was 6.6 mM. After allowing the reaction to stand at room temperature (about 23° C.) for 1.5 hours the reaction tube was centrifuged to concentrate the material to approximately 100 µL. The mixture was diluted to 1 mL with PBS containing 50 mM EDTA. This process was repeated 4 times in order to remove all the cysteine reductant. The resulting material was diluted to 1 mL in PBS containing 50 mM EDTA and treated with 16 µL of a 5 mM solution of the maleimide linker-payload (from Table 18A in dimethyl acetamide (DMA) (approximately 5 equivalents). After standing at room temperature (about 23° C.) for 1.5 hours the reaction tube was centrifuged to concentrate the material to approximately 100 µL. The mixture was diluted to 1 mL with PBS. This process was repeated 2 times in order to remove the excess maleimide reactant. The antibody conjugates were generally purified by size exclusion chromatography (SEC) using GE AKTA Explorer system with a GE Superdex200 column and PBS (pH7.4) eluent. The loading of the drug onto the intended site of conjugation was determined using a variety of methods including mass spectrometry (MS), reverse phase HPLC, and hydrophobic interaction chromatography (HIC), as has been described elsewhere. The reported value (in Tables 19A and 19B) is generally obtained by LC-MS under reducing conditions.

General Procedure H:

A 20 mM TCEP solution (generally 50 to 100 molar equivalents) was added to the antibody (typically 5 mg) such that the final antibody concentration was 5 mg/mL in PBS containing 50 mM EDTA. After allowing the reaction to stand at 37° C. for 1.5 hours, the antibody was buffer exchanged into PBS containing 50 mM EDTA using a 50 kD MW cutoff spin concentration device (3×3 mL wash, 10× concentration per cycle). Alternative methods such as TFF or dialysis are also useful in particular circumstances. The resulting antibody was re-suspended in 1 mL of PBS containing 50 mM EDTA and treated with a freshly prepared 50 mM solution of DHA (dehydroascorbate) in 1:1 PBS/EtOH (final DHA concentration is typically 1 mM) and allowed to stand at 4° C. overnight. The antibody/DHA mixture was buffer exchanged into PBS containing 50 mM EDTA using a 50 kD MW cutoff spin concentration device (3×3 mL wash, 10× concentration per cycle). The resulting antibody was re-suspended in 1 mL of PBS containing 50 mM EDTA and treated with 10 mM maleimide linker-payload in DMA (typically 5-10 equivalents). After standing for 1.5 hours, the material was buffer exchanged (as above) into 1 mL of PBS (3×3 mL washes, 10× concentration per cycle). Purification by SEC (as described previously) was performed as needed to remove any aggregated material.

General Procedure I:

The initial conjugation of the linker-payload was performed using the previously described method (General Procedure F). The resulting antibody-drug-conjugate was buffer exchanged into a 50 mM borate buffer (pH 9.2) using an ultrafiltration device (50 kd MW cutoff). The resulting solution was heated to either 37° C. for 24 hours (for the maleimide-Peg linkers) or to 45° C. for 48 hours (for the maleimide-caproyl linkers). The resulting solution was cooled, buffer-exchanged into PBS, and purified by SEC (as described previously) in order to remove any aggregated material. LCMS analysis of the material indicated that the succinimide ring had completely opened (90% or more). Note that in examples where a methyl ester is present in the payload, the ester is hydrolyzed to the carboxylic acid under the described conditions.

General Procedure J:

The pentafluorophenyl esters were conjugated to the shown antibody following the procedure previously outlined in WO2012007896 A1

General Procedure K:

The conjugation of amino-alkyl linkers was accomplished via enzyme-mediated ligation as described in WO2012059882 A2.

General Procedure L:

N-[(9H-fluoren-9-ylmethoxy)carbonyl]-2-methylalanyl-N-[(3R,4S,5S)-1-(2S)-2-[(1R,2R)-2-carboxy-1-methoxypropyl]pyrrolidin-1-yl]-3-methoxy-5-methyl-1-oxoheptan-4-yl]-N-methyl-L-valinamide (prepared in the same manner as #136) was coupled to the relevant amino acid or amine moiety using HATU (1.0-2.0 eq.) in the presence of Hunig's base (1.-5.0 eq.) in a solution of DMF, dichloromethane, or in some cases a solution of both (or a solution of one or more solvents). Reaction was monitored by LC-MS (or TLC or HPLC). Reaction was concentrated in vacuo and purified usually by silica chromatography or by prep HPLC. Fmoc protection was then removed as described in general procedure A followed by concentration in vacuo and purified by silica chromatography or by prep HPLC.

General Procedure M.

151 was coupled to the relevant amine using HATU (1.0-2.0 eq., or other appropriate coupling reagent) in the presence of Hunig's base (1.0-5.0 eq.) in a solution of DMF, dichloromethane, or in some cases a solution of both (or a solution of one or more solvents). Reaction was monitored by LC-MS (or TLC or HPLC). Reaction was concentrated in vacuo. Boc de-protection was then performed as described in general procedure B, concentrated in vacuo and purified by silica chromatography or by prep HPLC.

General Procedure N.

1-(9H-fluoren-9-yl)-3-oxo-2,7,10,13,16,19,22-heptaoxa-4-azapentacosan-25-oic acid (or other appropriate Fmoc-AmPegXC2—COOH) was coupled to the relevant cytotoxic pentapeptide (or the cytotoxic pentapeptide containing a protecting group on a reactive moiety other than the N-terminus) using HATU (1.0-2.0 eq., or other appropriate coupling reagent) in the presence of Hunig's base (1.0-5.0 eq. or other appropriate base) in a solution of DMF, dichloromethane, or in some cases a solution of both (or a solution of one or more solvents). Reaction was monitored by LC-MS (or TLC or HPLC). Reaction was concentrated in vacuo. Fmoc de-protection was performed according to general procedure A. In some cases a second de-protection was performed in order to remove a protecting group on a reactive moiety on the cytotoxic pentapeptide using general procedure B (or other relevant procedure known in the literature based on the protecting group). The reaction was concentrated in vacuo and purified by silica chromatography or by prep HPLC.

General Procedure O.

The appropriate Fmoc-AmPegXC2—COOH is coupled to the relevant cytotoxic pentapeptide (or the cytotoxic pentapeptide containing a protecting group on a reactive moiety other than the N-terminus) and Fmoc de-protection is performed according to general procedure N. The reaction is concentrated in vacuo and then purified by silica chromatography or prep HPLC (or the crude material can be used as is). The appropriate PABC sequence (such as mcValCitPABC, or derivative of) is then installed according to general procedure E. In some cases if a protecting group is present on cytotoxic pentapeptide portion of the molecule de-protection is then performed using general procedure A or general procedure B (or other relevant procedure known in the literature based on the protecting group). The reaction is concentrated in vacuo and purified by silica chromatography or by prep HPLC.

General Procedure P.

Followed procedure E replacing mcValCitPABC-PNP, with MalPeg3C2ValCitPABC-PNP (prepared in a similar manner to mcValCitPABC-PNP).

General Procedure Q.

The appropriate Fmoc-AmPegXC2-COOH is coupled to the relevant cytotoxic pentapeptide (or the cytotoxic pentapeptide containing a protecting group on a reactive moiety other than the N-terminus) and Fmoc de-protection is performed as described in general procedure N. The reaction is concentrated in vacuo and then purified by silica chromatography or by prep HPLC (or the crude material can be used as is). To a stirring solution of this residue in DMF at 0° C. (or a slightly higher temperature in some cases) bromoacetic acid (1.0-2.0 eq.) was added followed by Hunig's base (1.0-5.0 eq.) and HATU (1.0-2.0 eq.) The reaction was allowed to warm to room temperature and stir at room temperature while being monitored by LC-MS (or TLC or HPLC). Reaction was concentrated in vacuo and purified by prep HPLC.

General Procedure R.

Followed procedure E replacing mcValCitPABC-PNP, with N-(6-{[(9H-fluoren-9-ylmethoxy)carbonyl]amino}hexanoyl)-L-valyl-N-5~-carbamoyl-N-[4-({[(4-nitrophenoxy)carbonyl]oxy}methyl)phenyl]-L-ornithinamide (prepared in a similar manner to mcValCitPABC-PNP). Fmoc de-protection was then performed (general procedure B) followed by prep HPLC purification.

General Procedure S.

To a stirring solution of 6-(2,5-dioxo-2,5-dihydro-1H-pyrrol-1-yl)hexanal (1.0-3.0 eq.) in methanol the relevant cytotoxic pentapeptide (1.0 eq) was added followed by formic acid. The reaction was allowed to stir at room temperature for 1-40 minutes followed by the addition of sodium (cyanokappaC)(trihydrido)borate(1-) (3.0-6.0 eq., also referred to as sodium cyanborohydride). The reaction was monitored by LC-MS (or TLC or HPLC). In some cases additional 6-(2,5-dioxo-2,5-dihydro-1H-pyrrol-1-yl)hexanal (1.0-3.0 eq.) was added. The reaction was concentrated in vacuo followed by purification using prep HPLC.

General Procedure T.

4-[3-oxo-3-(2-oxoazetidin-1-yl)propyl]anilinium is prepared as described in the literature (Bioorganic and Medicinal Chemistry Letters. 2012, vol. 22, #13, 4249-4253) which is then coupled to bis(pentafluorophenyl) 3,3'-[ethane-1,2-diylbis(oxy)]dipropanoate using HATU in dichloromethane followed by coupling to the desired cytotoxic pentapeptide. Material is then purified by prep HPLC.

General Procedure U.

Fmoc-ValCitPABC-PNP is coupled to the desired cytotoxic pentapeptide following general procedure E and then Fmoc is removed following general procedure A. This residue is then coupled to [2-oxo-2-({4-[3-oxo-3-(2-oxoazetidin-1-yl)propyl]phenyl}amino) ethoxy]acetic acid (which is prepared by coupling 4-[3-oxo-3-(2-oxoazetidin-1-yl)propyl]anilinium with 1,4-dioxane-2,6-dione following general procedure D). Material is then purified by prep HPLC.

General Procedure V.

Bis(pentafluorophenyl) 3,3'-[ethane-1,2-diylbis(oxy)]dipropanoate or bis(pentafluorophenyl) 4,7,10,13,16-pentaoxanonadecane-1,19-dioate is coupled to the desired cytotoxic pentapeptide (or in some cases coupled to the desired cytotoxic pentapeptide containing a protecting group on a reactive moiety other than the N-terminus) following general procedure D. If a protecting group is present, the protecting group is then removed (using relevant procedures described in the literature). Material is then purified by prep HPLC.

General Procedure W.

4-({[(4-nitrophenoxy)carbonyl]oxy}methyl)phenyl 1-(9H-fluoren-9-yl)-3-oxo-2,7,10-trioxa-4-azamidecan-13-oate is coupled to the desired cytotoxic pentapeptide following general procedure E. Fmoc is removed following general procedure A. Bis(pentafluorophenyl) 3,3'-[ethane-1,2-diylbis(oxy)]dipropanoate is coupled to this residue following general procedure D. Material is then purified by prep HPLC.

General Procedure X1.

N-[(9H-fluoren-9-ylmethoxy)carbonyl]-L-alanyl-L-alanyl-N~1~-[4-({[(4-nitrophenoxy)carbonyl]oxy}methyl)phenyl]-N~4~-trityl-L-aspartamide is coupled to the desired cytotoxic pentapeptide following general procedure E. Fmoc is removed following general procedure A and trityl protecting group is removed following general procedure B. Bis(pentafluorophenyl) 3,3'-[ethane-1,2-diylbis(oxy)]dipropanoate is coupled to this residue following general procedure D. Material is purified by prep HPLC.

General Procedure X2.

N-{3-[2-(3-ethoxy-3-oxopropoxy)ethoxy]propanoyl}-L-valyl-N~5~-carbamoyl-N-[4-({[(4-nitrophenoxy)carbonyl]oxy}methyl)phenyl]-L-ornithinamide is coupled to the desired cytotoxic pentapeptide following general procedure E. Ethyl ester is removed using lithium hydroxide in THF and water. NHS ester is then formed by coupling residue with 1-hydroxypyrrolidine-2,5-dione using N,N'-dicyclohexylcarbodiimide in THF. Material is purified by prep HPLC.

General Procedure X3.

N-[(9H-fluoren-9-ylmethoxy)carbonyl]-D-valyl-N~5~-carbamoyl-N-[4-({[(2-carboxypropan-2-yl)carbamoyl]oxy}methyl)phenyl]-L-ornithinamide is coupled to #50 following general procedure D in DMSO and acetonitrile. Fmoc is removed following general procedure A followed by coupling with bis(pentafluorophenyl) 3,3'-[ethane-1,2-diylbis(oxy)]dipropanoate using Hunig's base in acetonitrile. Material is purified by prep HPLC.

General Procedure X4.

N-[1-(9H-fluoren-9-yl)-3,5,12-trioxo-2,7,10-trioxa-4-azadodecan-12-yl]-2-methylalanine is coupled to #250 following general procedure D in acetonitrile. Fmoc is removed following general procedure A followed by coupling with bis(pentafluorophenyl) 3,3'-[ethane-1,2-diylbis(oxy)]dipropanoate using Hunig's base in acetonitrile. Material is purified by prep HPLC.

General Procedure X5.

L-valyl-N~5~-carbamoyl-N-[4-(hydroxymethyl)phenyl]-L-ornithinamide is coupled to N~2~-acetyl-N~6~-(tert-butoxycarbonyl)-L-lysine following general procedure D. This resulting residue is coupled with bis(4-nitrophenyl)carbonate with Hunig's base in DMF, followed by coupling with the desired cytotoxic pentapeptide following general procedure E. Boc de-protection is then performed following general procedure B in acetonitrile. Residue is purified by prep HPLC.

In some instances minor alterations to reaction conditions were made such as but not limited to order of reagent and reactant addition and or the amount of reagent or reactant which is indicated by the symbol *. Furthermore, these general procedures are provided as exemplary only and are non-limiting.

In addition to the General Procedures provided above, relevant dolastatin and auristatin references include the following: Petit et al. *J. Am. Chem. Soc.* 1989, 111, 5463; Petit et al. *Anti-Cancer Drug Design* 1998, 13, 243 and references cited therein; Petit et al. *J. Nat. Prod.* 2011, 74, 962; WO 96/33212; WO 95/09864; EP 0695758; WO 07/8848; WO 01/18032; WO 09/48967; WO 09/48967; WO 09/117,531; WO 08/8603; U.S. Pat. No. 7,750,116; U.S. Pat. No. 5,985,837; and US 2005/9751; all of which are hereby incorporated by reference in their entireties.

MS Analysis and Sample Preparation

Samples were prepped for LC-MS analysis by combining about 20 µL of sample (approximately 1 mg/mL of ADC in PBS) with 20 µL of 20 mM dithiothreitol (DTT). After allowing the mixture to stand at room temperature for 5 minutes, the samples were analyzed according to protocol 0.

The following calculation was performed in order to establish the total loading (DAR) of the conjugate:

Loading=2*[LC1/(LC1+LC0)]+2*[HC1/(HC0+HC1+HC2+HC3)]+4*[HC2/(HC0+HC1+HC2+HC3)]+6*[HC3/(HC0+HC1+HC2+HC3)]

Where the indicated variables are the relative abundance of: LC0=unloaded light chain, LC1=single loaded light chain, HC0=unloaded heavy chain, HC1=single loaded heavy chain, HC2=double loaded heavy chain, and HC3=triple loaded heavy chain.

LC-MS conditions used are Protocol F for retention time below one minute and Protocol H for the remaining experiments unless otherwise indicated.

Preparation of N-[(9H-Fluoren-9-ylmethoxy)carbonyl]-N-methyl-L-valyl-N-[(2R,3S,4S)-1-carboxy-2-methoxy-4-methylhexan-3-yl]-N-methyl-L-valinamide (#8)

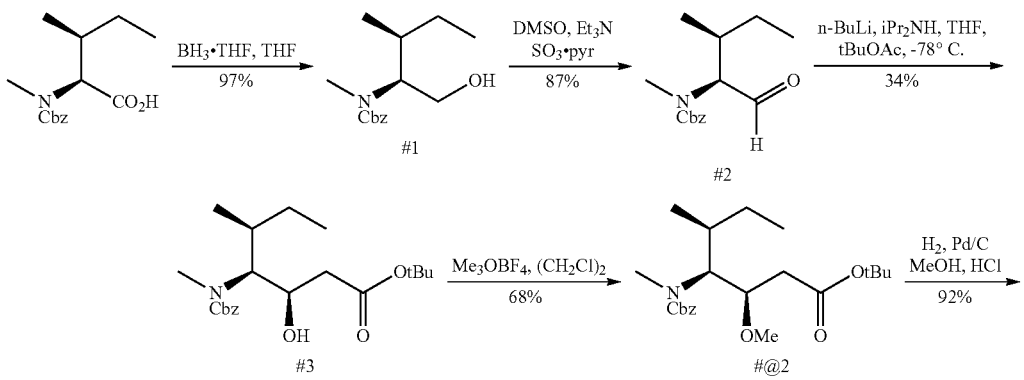

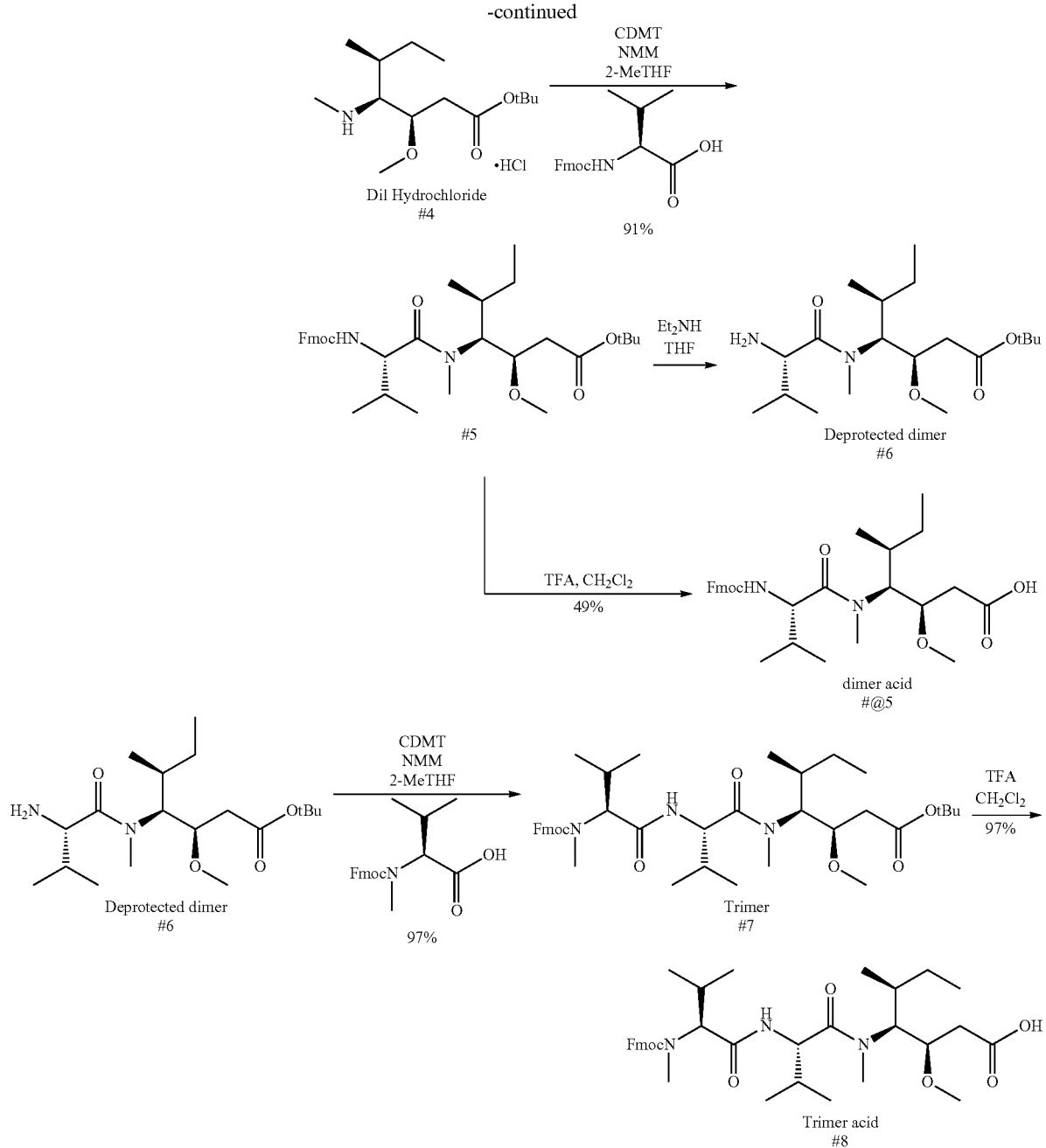

Step 1

Synthesis of benzyl[(2S,3S)-1-hydroxy-3-methyl-pentan-2-yl]methylcarbamate (#1)

To a solution of N-[(benzyloxy)carbonyl]-N-methyl-L-isoleucine (52.37 g, 187.5 mmol, 1 eq.) in tetrahydrofuran (524 mL, 0.35 M) was added borane-tetrahydrofuran complex (1 M in tetrahydrofuran, 375 mL, 375 mmol, 2 eq.) slowly over 1 hour and the reaction was allowed to stir for 18 hours at room temperature. The reaction was cooled to 0° C. and water (30 mL) was added over 30 minutes. The reaction mixture was diluted with 1 M aqueous sodium carbonate solution (100 mL) and tert-butyl methyl ether (250 mL). The aqueous layer was back-extracted with tert-butyl methyl ether (100 mL). The combined organic layers were washed with 1 M aqueous sodium carbonate solution (100 mL), washed with brine (200 mL), dried over magnesium sulfate, filtered, and concentrated in vacuo to provide #1 (48.44 g, 97% yield) as a pale yellow oil, which was used in the next step without further purification. $^1$H NMR (400 MHz, DMSO-$d_6$), presumed to be a mixture of rotamers: δ 7.26-7.41 (m, 5H), [5.06 (AB quartet, $J_{AB}$=12.9 Hz, $\Delta v_{AB}$=22.8 Hz) and 5.06 (AB quartet, $J_{AB}$=9.0 Hz, $\Delta v_{AB}$=9.0 Hz), total 2H], [4.65 (t, J=5.3 Hz) and 4.59 (t, J=5.4 Hz), total 1H], 3.67-3.80 (m, 1H), 3.51-3.60 (m, 1H), 3.41-3.51 (m, 1H), 2.75 and 2.71 (2 s, total 3H), 1.49-1.64 (br m, 1H), 1.24-1.37 (br m, 1H), 0.90-1.02 (br m, 1H), 0.74-0.87 (m, 6H).

Step 2

Synthesis of benzyl methyl[(2S,3S)-3-methyl-1-oxopentan-2-yl]carbamate (#2)

To a solution of #1 (8.27 g, 31.2 mmol, 1 eq.) in dimethyl sulfoxide (41.35 mL, 0.75 M), was added triethylamine (8.70 mL, 64.0 mmol, 2.05 eq.) and the mixture was cooled to 0° C. Sulfur trioxide pyridine complex (10.18 g, 63.96 mmol, 2.05 eq.) was then added portion-wise, while keeping the internal temperature below 8° C. The reaction was allowed to reach room temperature and was stirred for 18 hours. The reaction was poured into water (100 mL) and tert-butyl methyl ether (100 mL). The aqueous layer was back-extracted with tert-butyl methyl ether (50 mL) and the combined organic layers were washed with brine (100 mL), dried over magnesium sulfate, filtered, concentrated in vacuo and purified by silica gel chromatography (Gradient: 10% to 60% ethyl acetate in heptane) to provide #2 (7.14 g, 87%) as a colorless oil. $^1$H NMR (400 MHz, DMSO-$d_6$), presumed to be a mixture of rotamers, characteristic signals: δ 9.61 (s, 1H), 7.26-7.42 (m, 5H), 5.01-5.13 (m, 2H), 4.04-4.12 (m, 1H), 2.86 and 2.82 (2 s, total 3H), 1.94-2.11 (br m, 1H), 1.26-1.42 (br m, 1H).

Step 3

Synthesis of tert-butyl (3R,4S,5S)-4-{[(benzyloxy)carbonyl](methyl)amino}-3-hydroxy-5-methylheptanoate (#3)

Lithium diisopropylamine was prepared by adding n-butyllithium (2.5 M solution in tetrahydrofuran, 35.9 mL, 89.8 mmol, 1.4 eq.) to a solution of diisopropylamine (13.8 mL, 96.3 mmol, 1.5 eq.) in tetrahydrofuran (50 mL, 1.3 M) at −78° C. After 1 hour, tert-butyl acetate (15.7 mL, 116 mmol, 1.8 eq.) was added drop-wise and the reaction mixture was stirred for an additional 1.5 hours while being allowed to slowly warm to −20° C. The reaction mixture was recooled to −78° C. and a solution of the aldehyde #2 (16.9 g, 64.2 mmol, 1 eq.) in tetrahydrofuran (10 mL) was added. The reaction mixture was stirred for 1.5 hours and then quenched by addition of water (100 mL). After extraction with diethyl ether (2×100 mL), the combined organic layers were dried over sodium sulfate, concentrated in vacuo and purified by silica gel chromatography (Gradient: 0% to 20% acetone in heptane) to provide #3 (8.4 g, 34%) as a colorless oil. LC-MS: m/z 402.4 [M+Na$^+$], retention time=3.91 minutes; $^1$H NMR (400 MHz, DMSO-$d_6$), presumed to be a mixture of rotamers: δ 7.27-7.39 (m, 5H), 5.01-5.12 (m, 2H), [4.93 (d, J=7.2 Hz) and 4.98 (br d, J=7.2 Hz), total 1H], 4.03-4.15 (br m, 1H), 3.68-3.85 (br m, 1H), 2.65 and 2.72 (2 br s, total 3H), 2.28-2.37 (m, 1H), 2.09-2.17 (m, 1H), 1.74-1.90 (br m, 1H), 1.41-1.51 (m, 1H), 1.39 (s, 9H), 0.92-1.01 (m, 1H), 0.77-0.92 (m, 6H).

Step 4

Synthesis of tert-butyl (3R,4S,5S)-4-{[(benzyloxy)carbonyl](methyl)amino}-3-methoxy-5-methylheptanoate (#@2)

To a solution of #3 (8.4 g, 22 mmol, 1 eq.) in 1,2-dichloroethane (25 mL, 0.88 M) were added molecular sieves (4 Å, 0.7 g) and Proton sponge (1,8-bis(dimethylamino)naphthalene) (13.4 g, 59.2 mmol, 2.7 eq.), followed by trimethyloxonium tetrafluoroborate (9.10 g, 61.6 mmol, 2.8 eq.). After stirring overnight, the reaction mixture was filtered through Celite. The filtrate was concentrated in vacuo and the residue was purified by silica gel chromatography (Gradient: 0% to 40% 1:1 acetone:ethyl acetate in heptane) to give #@2 (8.7 g, 68%) as a colorless oil. $^1$H NMR (400 MHz, DMSO-$d_6$), presumed to be a mixture of rotamers: δ 7.28-7.40 (m, 5H), 5.01-5.13 (m, 2H), 3.89-4.08 (br m, 1H), 3.70-3.82 (m, 1H), 3.18 and 3.26 (2 s, total 3H), 2.66 and 2.71 (2 br s, total 3H), 2.44-2.53 (m, 1H, assumed; partially obscured by solvent peak), 2.17-2.24 (m, 1H), 1.71-1.86 (br m, 1H), 1.39 and 1.39 (2 s, total 9H), 1.31-1.40 (m, 1H), 0.94-1.08 (m, 1H), 0.76-0.91 (m, 6H).

Step 5

Synthesis of tert-butyl (3R,4S,5S)-3-methoxy-5-methyl-4-(methylamino)heptanoate, hydrochloride salt (#4)

To a solution of #@2 (13.37 g, 33.98 mmol, 1 eq.) in methanol (134 mL, 0.1 M) and concentrated hydrochloric acid (3.1 mL, 37.4 mmol, 1.1 eq.) was added 10% palladium on carbon (50% wet) (0.1 wt %; 1.34 g, 3.40 mmol). The mixture was hydrogenated at 45 psi for 3 hours, then purged with nitrogen, filtered through Celite and concentrated in vacuo to provide #4 (9.20 g, 92%) as a white solid. $^1$H NMR (400 MHz, CDCl$_3$) δ 9.65 (br s, 1H), 8.97 (br s, 1H), 3.98-4.04 (m, 1H), 3.40 (s, 3H), 3.06-3.13 (br m, 1H), 2.82 (br dd, J=6, 5 Hz, 3H), 2.74-2.80 (m, 1H), 2.68 (dd, half of ABX pattern, J=16.3, 4.2 Hz, 1H), 2.00-2.10 (br m, 1H), 1.73-1.84 (m, 1H), 1.46 (s, 9H), 1.38-1.45 (m, 1H), 1.13 (d, J=7.0 Hz, 3H), 0.99 (t, J=7.4 Hz, 3H).

Step 6

Synthesis of tert-butyl (3R,4S,5S)-4-[{N-[(9H-fluoren-9-ylmethoxy)carbonyl]-L-valyl}(methyl)amino]-3-methoxy-5-methylheptanoate (#5)

To a mixture of N-[(9H-fluoren-9-ylmethoxy)carbonyl]-L-valine (18.53 g, 54.60 mmol, 1.3 eq.) and 2-chloro-4,6-dimethoxy-1,3,5-triazine (CDMT) (9.58 g, 54.6 mmol, 1.3 eq.) in 2-methyltetrahydrofuran (118.00 mL, 0.34 M) was added N-methylmorpholine (6.52 mL, 59.1 mmol, 1.5 eq.) followed by #4 (11.80 g, 39.9 mmol, 1 eq.). After 3 hours, the reaction was quenched with water (50 mL) and stirred for 15 minutes. The aqueous layer was separated and back-extracted with 2-methyltetrahydrofuran (50 mL). The combined organic layers were washed with saturated aqueous sodium bicarbonate solution (50 mL), dried over magnesium sulfate, filtered, and concentrated in vacuo to give a colorless oil, which was purified by silica gel chromatography (Gradient: 5% to 40% ethyl acetate in heptane) to give #5 (26.2 g, 91%) as a colorless foam. LC-MS (Protocol I) m/z 581.3 [M+H$^+$] 1604.3 [M+Na$^+$], retention time=4.993 minutes; $^1$H NMR (400 MHz, DMSO-$d_6$), possibly a mixture of rotamers, characteristic major signals: δ 7.88 (d, J=7.4 Hz, 2H), 7.71 (d, J=7.4 Hz, 2H), 7.62 (d, J=8.6 Hz, 1H), 7.41 (dd, J=7.4, 7.4 Hz, 2H), 7.27-7.34 (m, 2H), 4.13-4.32 (m, 4H), 3.70-3.82 (br m, 1H), 3.24 (s, 3H), 2.92 (br s, 3H), 2.54 (dd, J=15.7, 2.4 Hz, 1H), 2.17 (dd, J=15.4, 9.4 Hz, 1H), 1.95-2.07 (m, 1H), 1.70-1.83 (br m, 1H), 1.40 (s, 9H), 0.83-0.94 (m, 9H), 0.69 (t, J=7.2 Hz, 3H).

Step 7A

Synthesis of tert-butyl (3R,4S,5S)-3-methoxy-5-methyl-4-[methyl(L-valyl)amino]heptanoate (#6)

To a solution of #5 (26 g, 42 mmol, 1 eq.) in tetrahydrofuran (260 mL, 0.16 M) was added diethylamine (22 mL) over 30 minutes. The reaction was stirred for about 6 hours and the suspension was then filtered through Celite and washed with additional tetrahydrofuran (25 mL). The filtrate was concentrated in vacuo to provide a pale yellow oil, which was redissolved in 2-methyltetrahydrofuran (50 mL) and concentrated again to ensure complete removal of diethylamine. The crude oil of #6 (>15.25 g) was taken into the next step without further purification.

Step 7B

Synthesis of (3R,4S,5S)-4-[{N-[(9H-fluoren-9-yl-methoxy)carbonyl]-L-valyl}(methyl)amino]-3-methoxy-5-methylheptanoic acid (#@5)

According to general procedure B, from #5 (1.62 g, 2.79 mmol, 1 eq.), dichloromethane (10 mL, 0.3 M) and trifluoroacetic acid (3 mL) was synthesized #@5 (1.42 g, 97%) as a solid which was used without further purification. LC-MS m/z 525.3 [M+H$^+$] 1547.3 [M+Na] retention time=0.95 minute; $^1$H NMR (400 MHz, DMSO-d$_6$), characteristic signals: δ 7.89 (d, J=7.6 Hz, 2H), 7.71 (d, J=7.4 Hz, 2H), 7.59 (d, J=8.8 Hz, 1H), 7.41 (dd, J=7.6, 7.4 Hz, 2H), 7.28-7.34 (m, 2H), 4.14-4.32 (m, 4H), 3.24 (s, 3H), 2.92 (br s, 3H), 2.51-2.57 (m, 1H, assumed; partially obscured by solvent peak), 2.20 (dd, J=15.9, 9.5 Hz, 1H), 1.95-2.06 (m, 1H), 1.70-1.83 (br m, 1H), 1.22-1.36 (br m, 1H), 0.84-0.93 (m, 9H), 0.70 (t, J=7.3 Hz, 3H).

Step 8

Synthesis of N-[(9H-fluoren-9-ylmethoxy)carbonyl]-N-methyl-L-valyl-N—[(3R,4S,5S)-1-tert-butoxy-3-methoxy-5-methyl-1-oxoheptan-4-yl]-N-methyl-L-valinamide (#7)

To a mixture of N-[(9H-fluoren-9-ylmethoxy)carbonyl]-N-methyl-L-valine (19.54 g, 55.29 mmol, 1.3 eq.) and #6 (15.25 g, 42.54 mmol, 1 eq.) in 2-methyltetrahydrofuran (152 mL, 0.28 M) was added 2-chloro-4,6-dimethoxy-1,3,5-triazine (CDMT) (9.71 g, 55.3 mmol, 1.3 eq.). After 10 minutes, N-methylmorpholine (6.6 mL, 60 mmol, 1.4 eq.) was slowly added, while keeping the internal temp below 25° C. The reaction was stirred for 4 hours and was then quenched by the addition of water (50 mL). After stirring for 15 minutes, the aqueous layer was separated and back-extracted with 2-methyltetrahydrofuran (50 mL). The combined organic layers were washed with saturated aqueous sodium bicarbonate solution (100 mL), then were dried over magnesium sulfate, filtered, and concentrated in vacuo. The resulting yellow foam was purified by silica gel chromatography (Gradient: 5% to 35% ethyl acetate in heptane) to give #7 (32 g, 97%). $^1$H NMR (400 MHz, DMSO-d$_6$), presumed to be a mixture of rotamers, characteristic signals: δ 7.89 (d, J=7.4 Hz, 2H), 7.62 (d, J=7.4 Hz, 2H), 7.41 (br dd, J=7.4, 7.4 Hz, 2H), 7.29-7.34 (m, 2H), 4.52-4.69 (br m, 1H), 3.70-3.82 (br m, 1H), 3.22 and 3.25 (2 br s, total 3H), 2.94 and 2.96 (2 br s, total 3H), 2.78 and 2.81 (2 br s, total 3H), 2.11-2.23 (m, 1H), 1.90-2.10 (m, 2H), 1.68-1.83 (br m, 1H), 1.40 (s, 9H), 1.21-1.33 (br m, 1H).

Step 9

Synthesis of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (#8)

To #7 (32 g, 46 mmol, 1 eq.) in dichloromethane (160 mL, 0.29 M) was added drop-wise over 10 minutes trifluoroacetic acid (17.4 mL, 231 mmol, 5 eq.). After 6 hours, the same amount of trifluoroacetic acid was added and the reaction was continued for 18 hours. The reaction mixture was diluted with toluene (320 mL) and concentrated in vacuo to provide #8 (35.8 g, 97%) as a pinkish oil, which was used in the next step without further purification. $^1$H NMR (400 MHz, DMSO-d$_6$), presumed to be a mixture of rotamers, characteristic signals: δ 7.90 (d, J=7.0 Hz, 2H), 7.62 (d, J=7.4 Hz, 2H), 7.41 (br dd, J=7.4, 7.0 Hz, 2H), 7.29-7.35 (m, 2H), 4.54-4.68 (br m, 1H), [4.09 (d, J=11 Hz) and 4.22 (d, J=10.9 Hz), total 1H], 3.74-3.84 (br m, 1H), 3.22 and 3.24 (2 br s, total 3H), 2.94 and 2.96 (2 br s, total 3H), 2.78 and 2.80 (2 br s, total 3H), 2.13-2.24 (m, 1H), 1.89-2.10 (br m, 2H), 1.70-1.81 (br m, 1H).

Preparation of (2R,3R)-3-[(2S)-1-(tert-Butoxycarbonyl)pyrrolidin-2-yl]-3-methoxy-2-methylpropanoic acid (#11; "Boc-Dap-acid")

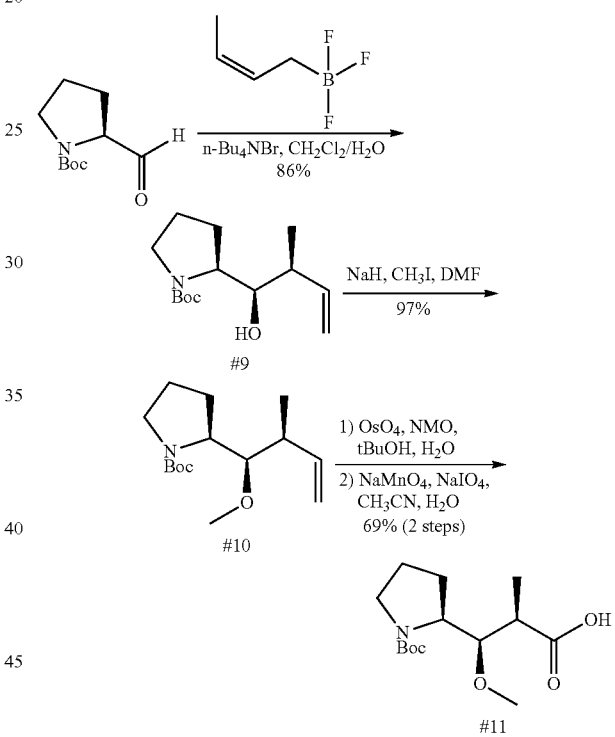

Step 1

Synthesis of tert-butyl (2S)-2-[(1R,2S)-1-hydroxy-2-methylbut-3-en-1-yl]pyrrolidine-1-carboxylate (#9)

To a solution of tert-butyl (2S)-2-formylpyrrolidine-1-carboxylate (10 g, 50 mmol, 1 eq.) in dichloromethane (120 mL, 0.42 M) was added potassium (2Z)-2-buten-1-yltrifluoroborate (9.76 g, 60.2 mmol, 1.2 eq.) followed by tetra-n-butylammonium bromide (3.24 g, 5.02 mmol, 0.1 eq.) and water (60 mL). After 13 hours, the reaction was diluted with dichloromethane (150 mL) and water (150 mL). The aqueous layer was separated and back-extracted with dichloromethane (100 mL). The combined organic layers were washed with aqueous sodium chloride solution (5% wt, 200 mL), washed with water (200 mL), and concentrated in vacuo to afford #9 (~13 g) as an orange oil, which was used without further purification. ¹H NMR (400 MHz, CDCl₃) δ 5.61-5.86 (br m, 1H), 4.97-5.09 (m, 2H), 3.80-3.98 (br m, 2H), 3.45-3.67 (br m, 1H), 3.21-3.29 (m, 1H), 2.14-2.26 (m, 1H), 1.80-2.04 (m, 3H), 1.65-1.76 (m, 1H), 1.47 (s, 9H), 1.12 (d, J=6.6 Hz, 3H).

Step 2

Synthesis of tert-butyl (2S)-2-[(1R,2S)-1-methoxy-2-methylbut-3-en-1-yl]pyrrolidine-1-carboxylate (#10)

Sodium hydride (60% in mineral oil, 3.38 g, 84.4 mmol, 1.1 eq.) was combined with hexane (40 mL), and the mixture was subjected to rapid mechanical stirring for 5 minutes. The solids were allowed to settle and the hexane was removed. This procedure was repeated twice to remove mineral oil. N,N-Dimethylformamide (59 mL, 1.3 M) was added and the mixture was cooled to 0° C.; methyl iodide (5 mL; 81 mmol, 1.05 eq.) was then added drop-wise, followed by drop-wise addition of a solution of #9 (19.6 g, 76.8 mmol, 1 eq.) in N,N-dimethylformamide (59 mL) over 5 minutes, while keeping the temperature between 0° C. and 5° C. The reaction was stirred at 0° C. for 2 hours. The reaction was quenched with saturated aqueous ammonium chloride solution (150 mL), poured into aqueous sodium chloride solution (5% wt, 300 mL), and the mixture was extracted with ethyl acetate (3×50 mL). The combined organic layers were washed with 10% aqueous sodium chloride solution (2×300 mL), washed with water (200 mL), and concentrated in vacuo. The resulting water-wet oil was reconcentrated from ethyl acetate (150 mL) and purified by silica gel chromatography (Gradient: 2% to 10% ethyl acetate in heptane) to afford #10 (15.0 g, 73%) as a colorless oil. ¹H NMR (400 MHz, CDCl₃), presumed to be a mixture of rotamers: δ 5.60-5.83 (m, 1H), 4.91-5.06 (m, 2H), 3.81-3.95 (br m, 1H), 3.43 (s, 3H), 3.36-3.61 (m, 2H), 3.19-3.31 (m, 1H), 2.09-2.21 (m, 1H), 1.86-2.02 (br m, 2H), 1.62-1.85 (br m, 2H), 1.47 and 1.49 (2 s, total 9H), 1.09 (d, J=6.6 Hz, 3H).

Step 3

Synthesis of (2R,3R)-3-[(2S)-1-(tert-butoxycarbonyl)pyrrolidin-2-yl]-3-methoxy-2-methylpropanoic acid (#11)

To #10 (25.0 g, 92.8 mmol, 1 eq.) in tert-butanol (100 mL, 0.93 M) was immediately added water (30.00 mL) followed by N-methylmorpholine-N-oxide (25.97 g, 192.1 mmol, 2.07 eq.) and osmium tetroxide (235.93 mg, 928.04 μmol, 0.01 eq.) After 12 hours, the mixture was concentrated in vacuo using water (20 mL) to azeotropically remove residual tert-butanol. The residue was partitioned between ethyl acetate (500 mL) and water (500 mL) plus brine (150 mL). The aqueous layer was re-extracted with ethyl acetate (250 mL). The combined organic layers were washed with aqueous sodium chloride solution (10 wt %, 200 mL), washed with water (150 mL), and concentrated in vacuo to afford a water-wet pale brown oil that was re-concentrated from ethyl acetate (100 mL) to remove any remaining water. This crude diol (34.76 g) was used without further purification.

To the crude diol (34.76 g, ≤92.8 mmol, 1 eq.) in acetonitrile (347 mL, 0.1 M) and water (174 mL) was added sodium permanganate (2.03 g, 5.73 mmol, 0.05 eq.). The mixture was cooled to 0° C. and sodium periodate (51.46 g, 240.6 mmol, 2.1 eq.) was added portion-wise over 30 minutes, while keeping the internal temperature below 5° C. The reaction was stirred at 0° C. for 4 hours and was then poured into a solution of sodium thiosulfate pentahydrate (65.40 g, 263.5 mmol, 2.3 eq.) in water (100 mL). The mixture was filtered through Celite and the filtrate was concentrated in vacuo. The residue was partitioned between ethyl acetate (200 mL) and water (200 mL). The aqueous layer was back-extracted with ethyl acetate (250 mL), and the combined organic layers were washed with a 10% aqueous citric acid solution. As the desired product was very soluble in water, all the aqueous layers were combined, treated with Celite (100 g) and concentrated in vacuo to yield an off-white paste. Ethyl acetate (150 mL) was added and the mixture was re-concentrated to remove any residual water; this operation was repeated one more time. The paste was treated with ethyl acetate (150 mL) and placed in vacuo at 50° C. for 10 minutes and filtered (repeated twice). These filtrates were combined with the previous organic layer (from the citric acid wash), concentrated, diluted with ethyl acetate (200 mL) and filtered through Celite to remove solids. Finally, this filtrate was concentrated to yield #11 (22.9 g, 69% over two steps) as a yellowish/brown foam. LCMS (Protocol I): m/z 310.1 [M+Na⁺], 232.1 [(M-2-methylprop-1-ene)+H⁺], 188.1 [(M−Boc)+H⁺], retention time=3.268 minutes; ¹H NMR (400 MHz, DMSO-d₆), characteristic signals: δ 3.61-3.85 (br m, 2H), 3.20-3.45 (br m, 4H), 3.03-3.17 (br m, 1H), 1.59-1.93 (br m, 4H), 1.40 (br s, 9H), 1.02-1.18 (br m, 3H).

Preparation of (2R,3R)-3-Methoxy-2-methyl-N-[(1S)-2-phenyl-1-(1,3-thiazol-2-yl)ethyl]-3-[(2S)-pyrrolidin-2-yl]propanamide, trifluoroacetic acid salt (#19) and (2R,3R)-3-methoxy-2-methyl-N-[(1S)-2-phenyl-1-(1,3-thiazol-2-yl)ethyl]-3-[(2S)-pyrrolidin-2-yl]propanethioamide, trifluoroacetic acid salt (#18)

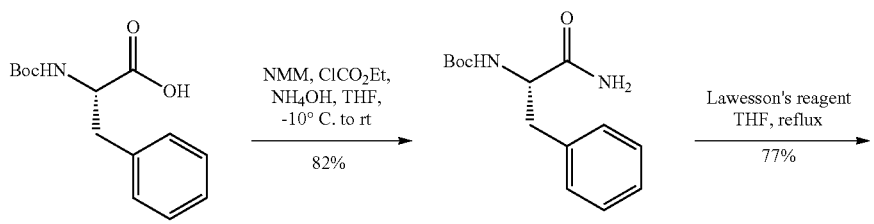

12

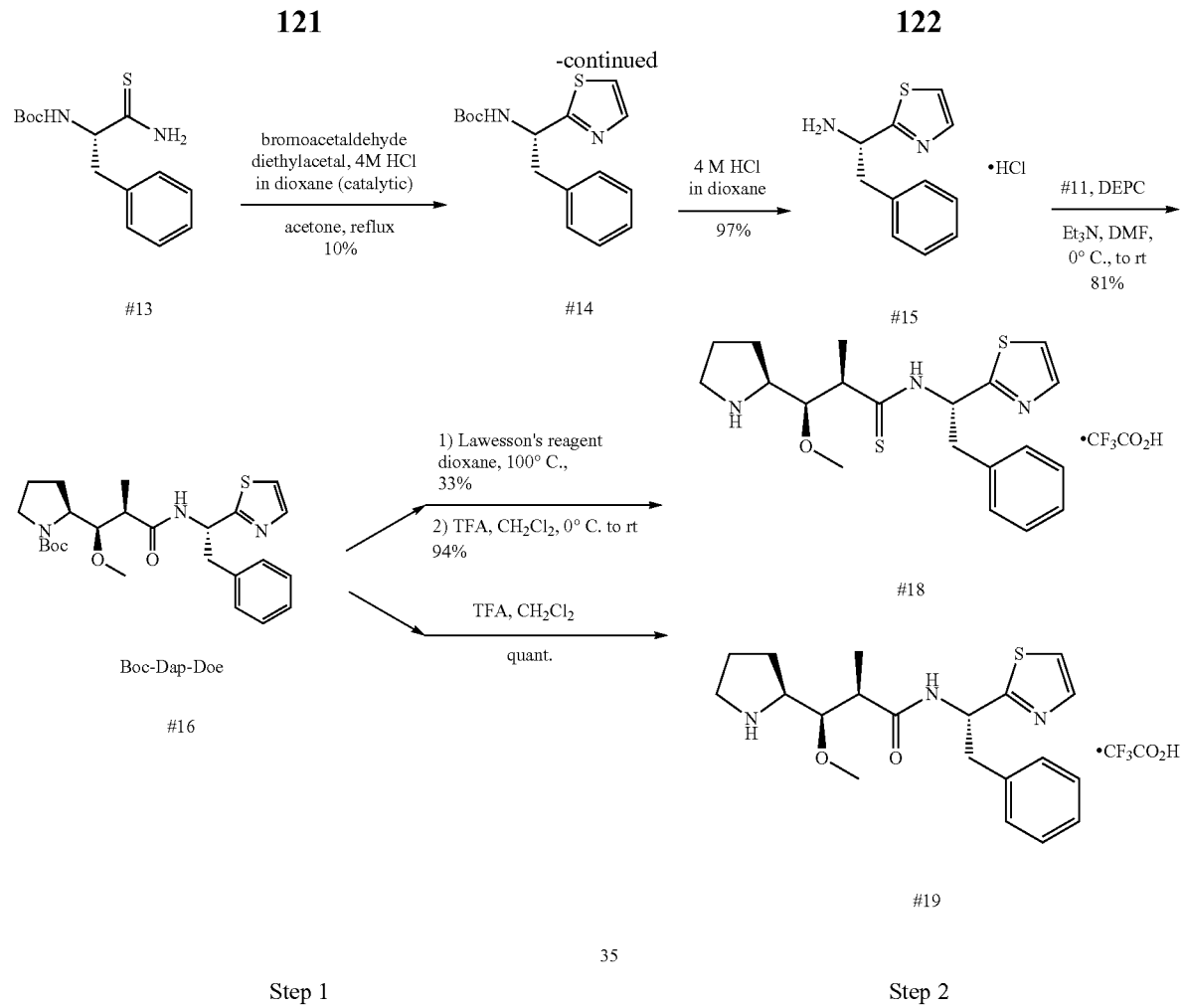

Step 1

Synthesis of Nα-(tert-butoxycarbonyl)-L-phenylalaninamide (#12)

To a solution of Boc-Phe-OH (30.1 g, 113 mmol, 1 eq.) in tetrahydrofuran (378 mL, 0.3 M) cooled to −10° C. were added N-methylmorpholine (13.6 mL, 124 mmol, 1.09 eq.), and ethyl chloroformate (11.8 mL, 124 mmol, 1.09 eq.). After 20 minutes, a 30% aqueous ammonium hydroxide solution (45 mL, 350 mmol, 3.1 eq.) was added. The mixture was stirred at room temperature for 18 hours before being concentrated in vacuo. The residue was diluted with ethyl acetate and washed sequentially with 1 N aqueous potassium bisulfate solution, water and brine. The organic layer was then dried over sodium sulfate, filtered, and concentrated in vacuo. The white solid was dissolved (this required heating with stirring) in ethyl acetate (about 400 mL); the solution was then allowed to cool to room temperature before adding hexane (1000 mL). After a few minutes, a white material started to precipitate from the reaction mixture. The solid was collected by filtration, washed with heptane (2×~150 mL), and dried under vacuum for 18 hours to give #12 (24.50 g, 82%) as a solid. LC-MS: m/z 263.2 [M−H$^+$], 309.2 [M+HCO$_2^-$], retention time=1.85 minutes; $^1$H NMR (400 MHz, DMSO-d$_6$), presumed to be a mixture of rotamers, major rotamer: δ 7.35 (br s, 1H), 7.22-7.30 (m, 5H), 7.00 (br s, 1H), 6.78 (d, J=8.6 Hz, 1H), 4.09 (ddd, J=10, 9, 4.5 Hz, 1H), 2.95 (dd, J=13.8, 4.4 Hz, 1H), 2.72 (dd, J=13.7, 10.1 Hz, 1H), 1.30 (s, 9H).

Step 2

Synthesis of tert-butyl [(2S)-1-amino-3-phenyl-1-thioxopropan-2-yl]carbamate (#13)

To a solution of #12 (14.060 g, 53.192 mmol, 1 eq.) in tetrahydrofuran (180 mL, 0.296 M), was added 2,4-bis(4-methoxyphenyl)-1,3,2,4-dithiadiphosphetane-2,4-dithione (Lawesson's reagent) (12.70 g, 31.40 mmol, 0.59 eq.) and the reaction was refluxed for 90 minutes. The reaction was cooled to room temperature and quenched by addition of saturated aqueous sodium bicarbonate solution. The mixture was extracted twice with ethyl acetate and the combined organic layers were dried over sodium sulfate, filtered, and concentrated in vacuo. The residue was dissolved in ethyl acetate, concentrated in vacuo onto silica and purified by silica gel chromatography (Gradient: 0% to 100% ethyl acetate in heptane), affording #13 (11.50 g, 77%) as a white solid. LC-MS: m/z 279.4 [M−H$^+$], 225.2 [(M−2-methylprop-1-ene)+H$^+$], 181.2 [(M−Boc)+H$^+$]; $^1$H NMR (400 MHz, DMSO-d$_6$), presumed to be a mixture of rotamers, major rotamer: δ 9.60 (br s, 1H), 9.19 (br s, 1H), 7.23-7.32 (m, 5H), 6.82 (d, J=8.8 Hz, 1H), 4.44 (ddd, J=9.4, 9.1, 4.4 Hz, 1H), 3.00 (dd, J=13.7, 4.5 Hz, 1H), 2.79 (dd, J=13.6, 9.9 Hz, 1H), 1.29 (s, 9H).

Step 3

Synthesis of tert-butyl [(1S)-2-phenyl-1-(1,3-thiazol-2-yl)ethyl]carbamate (#14)

To a mixture of #13 (5.65 g, 20.2 mmol, 1 eq.) in acetone (101 mL, 0.2 M) was added bromoacetaldehyde diethyl acetal (8.76 mL, 58.2 mmol, 2.89 eq.) and 2 drops of 4 M hydrochloric acid in dioxane. The mixture was degassed with nitrogen three times before being heated to reflux. After 2 hours, the reaction was cooled to room temperature and concentrated in vacuo. The residue was dissolved in ethyl acetate, washed with saturated aqueous sodium bicarbonate solution and washed with brine. The organic layer was dried over sodium sulfate, filtered, and concentrated in vacuo. The resulting crude orange oil was diluted with ethyl acetate before being concentrated in vacuo onto silica and purified by silica gel chromatography (Gradient: 0% to 35% ethyl acetate in heptane) and then by reverse phase chromatography (Method A) to give #14 (625 mg, 10%); HPLC (Protocol E): m/z 304.5 [M+H$^+$], 248.9 [(M−2-methylprop-1-ene)+H$^+$], retention time=7.416 minutes; $^1$H NMR (400 MHz, DMSO-d$_6$), presumed to be a mixture of rotamers, major rotamer: δ 7.75 (d, J=3.3 Hz, 1H), 7.75 (br d, J=8.6 Hz, 1H), 7.61 (br d, J=3.1 Hz, 1H), 7.25-7.30 (m, 5H), 4.99 (ddd, J=10.5, 8.9, 4.5 Hz, 1H), 3.29-3.36 (m, 1H, assumed; partially obscured by water signal), 2.98 (dd, J=13.8, 10.6 Hz, 1H), 1.31 (s, 9H).

Step 4

Synthesis of (1S)-2-phenyl-1-(1,3-thiazol-2-yl)ethanamine, hydrochloride salt (#15)

According to general procedure C, from #14 (1.010 g, 3.318 mmol, 1 eq.), dioxane (10 mL, 0.33 M) and a 4 M solution of hydrochloric acid in dioxane (20 mL, 80 mmol, 20 eq.) was synthesized #15 (775 mg, 97%). $^1$H NMR (400 MHz, DMSO-d$_6$) δ 8.95-9.07 (br m, 3H), 7.86 (d, J=3.2 Hz, 1H), 7.73 (d, J=3.2 Hz, 1H), 7.18-7.28 (m, 3H), 7.10-7.15 (m, 2H), 4.98-5.07 (m, 1H), 3.49 (dd, J=13.3, 4.9 Hz, 1H), 3.18 (dd, J=13.4, 10.2 Hz, 1H).

Step 5

Synthesis of tert-butyl (2S)-2-[(1R,2R)-1-methoxy-2-methyl-3-oxo-3-{[(1S)-2-phenyl-1-(1,3-thiazol-2-yl)ethyl]amino}propyl]pyrrolidine-1-carboxylate (#16)

To a solution of #11 (280 mg, 0.974 mmol, 1 eq.) and #15 (460 mg, 1.44 mmol, 1.48 eq.) in N,N-dimethylformamide (3 mL, 0.32 M) at 0° C. was added diethylphosphoryl cyanide (DEPC) (93% purity, 212 μL, 1.30 mmol, 1.34 eq.), followed by triethylamine (367 μL, 2.63 mmol, 2.7 eq.). After 2 hours at 0° C., the reaction mixture was warmed to room temperature for 18 hours. The reaction mixture was then diluted with ethyl acetate:toluene (2:1, 30 mL) and was washed successively with 1 M aqueous sodium bisulfate solution (35 mL) and 50% saturated aqueous sodium bicarbonate solution (4×25 mL). The organic layer was dried over sodium sulfate, filtered, concentrated in vacuo, and purified by silica gel chromatography (12% to 100% ethyl acetate in heptane) to give #16 as a light amber oil (374 mg, 81%). LC-MS: m/z 474.4 [M+H$^+$], 374.4 [(M−2-methylprop-1-ene)+H$^+$] retention time=3.63 minutes; $^1$H NMR (400 MHz, DMSO-d$_6$), characteristic signals: δ 8.66 (d, J=8.5 Hz, 1H), 7.78 (d, J=3.3 Hz, 1H), 7.64 (d, J=3.3 Hz, 1H), 7.21-7.31 (m, 4H), 7.14-7.20 (m, 1H), 5.40 (ddd, J=11.4, 8.5, 4.0 Hz, 1H), 3.23 (br s, 3H), 2.18 (dq, J=9.7, 6.7 Hz, 1H), 1.06 (d, J=6.6 Hz, 3H).

Step 6A

Synthesis of tert-butyl (2S)-2-[(1R,2R)-1-methoxy-2-methyl-3-{[(1S)-2-phenyl-1-(1,3-thiazol-2-yl)ethyl]amino}-3-thioxopropyl]pyrrolidine-1-carboxylate (#17)

A mixture of #16 (350 mg, 0.739 mmol, 1 eq.) and 2,4-bis(4-methoxyphenyl)-1,3,2,4-dithiadiphosphetane-2,4-dithione (Lawesson's reagent) (324 mg, 0.776 mmol, 1.05 eq.) in toluene (6 mL, 0.1 M) was warmed to 100° C. After 10 minutes, the mixture was cooled to room temperature. Insoluble material was removed by filtration and the filtrate was concentrated in vacuo. The residue was purified by silica gel chromatography (Gradient: 12% to 80% ethyl acetate in heptane) and then by reverse phase chromatography (Method E2) to give #17 (120 mg, 33%); HPLC (Protocol J): m/z 490.2 [M+H$^+$], retention time=10.069 minutes; [α]$^{20}_D$−110 (c 0.24, MeOH); $^1$H NMR (400 MHz, CD$_3$OD), characteristic signals: δ 7.78 (d, J=3.3 Hz, 1H), 7.51 (d, J=3.3 Hz, 1H), 7.32-7.37 (m, 2H), 7.24-7.30 (m, 2H), 7.17-7.23 (m, 1H), 6.52-6.61 (br m, 1H), 3.62 (br dd, J=15, 4 Hz, 1H), 3.37 (s, 3H), 2.98-3.09 (br m, 1H), 2.53-2.64 (br m, 1H), 1.60-1.78 (m, 2H), 1.49 (s, 9H), 1.27 (d, J=6.5 Hz, 3H).

Step 6B

Synthesis of (2R,3R)-3-methoxy-2-methyl-N-[(1S)-2-phenyl-1-(1,3-thiazol-2-yl)ethyl]-3-[(2S)-pyrrolidin-2-yl]propanethioamide, trifluoroacetic acid salt (#18)

According to general procedure B, from #17 (198 mg, 0.404 mmol, 1 eq.), dichloromethane (6 mL, 0.07 M) and trifluoroacetic acid (2 mL) was synthesized #18 (185 mg, 91%), which was used without further purification. LC-MS: m/z 390.1 [M+H$^+$], retention time=0.57 minutes; $^1$H NMR (400 MHz, DMSO-d$_6$) δ 10.91 (d, J=8.2 Hz, 1H), 9.07-9.20 (br m, 1H), 7.86-8.00 (br m, 1H), 7.83 (d, J=3.2 Hz, 1H), 7.69 (d, J=3.3 Hz, 1H), 7.27-7.36 (m, 4H), 7.21-7.26 (m, 1H), 6.33 (ddd, J=11.3, 8.3, 4.4 Hz, 1H), 3.76-3.82 (m, 1H), 3.56 (dd, J=14.6, 4.3 Hz, 1H), 3.45 (s, 3H), 3.28 (dd, J=14.6, 11.3 Hz, 1H), 3.02-3.12 (br m, 1H), 2.89-3.00 (br m, 1H), 2.72-2.89 (m, 2H), 1.69-1.83 (br m, 1H), 1.43-1.58 (m, 2H), 1.20-1.33 (m, 1H), 1.22 (d, J=6.6 Hz, 3H).

Step 7

Synthesis of (2R,3R)-3-methoxy-2-methyl-N-[(1S)-2-phenyl-1-(1,3-thiazol-2-yl)ethyl]-3-[(2S)-pyrrolidin-2-yl]propanamide, trifluoroacetic acid salt (#19)

According to general procedure B, from #16 (607 mg, 1.28 mmol, 1 eq.), dichloromethane (10 mL, 0.13 M) and trifluoroacetic acid (2 mL) was synthesized #19 (640 mg, quantitative), which was used in the next step without further purification. $^1$H NMR (400 MHz, DMSO-d$_6$) δ 8.96-9.07 (br m, 1H), 8.89 (d, J=8.8 Hz, 1H), 7.87-8.00 (br m, 1H), 7.80 (d, J=3.2 Hz, 1H), 7.66 (d, J=3.3 Hz, 1H), 7.28-7.34 (m, 4H), 7.20-7.27 (m, 1H), 5.43 (ddd, J=11.3, 8.6, 4.2 Hz, 1H), 3.42-3.50 (m, 2H), 3.36 (s, 3H), 3.04-3.14 (br m, 1H), 2.99 (dd, J=14.2, 11.5 Hz, 1H), 2.92-3.02 (m, 1H), 2.78-2.88 (br m, 1H), 2.34-2.42 (m, 1H), 1.73-1.84 (br m, 1H), 1.55-1.68 (m, 1H), 1.38-1.53 (m, 2H), 1.15 (d, J=6.9 Hz, 3H).

Preparation of (2R,3R)-3-Methoxy-2-methyl-N-(2-phenylethyl)-3-[(2S)-pyrrolidin-2-yl]propanethioamide, hydrochloride salt (#23) and (2R,3R)-3-methoxy-2-methyl-N-(2-phenylethyl)-3-[(2S)-pyrrolidin-2-yl]propanamide, hydrochloride salt (#24)
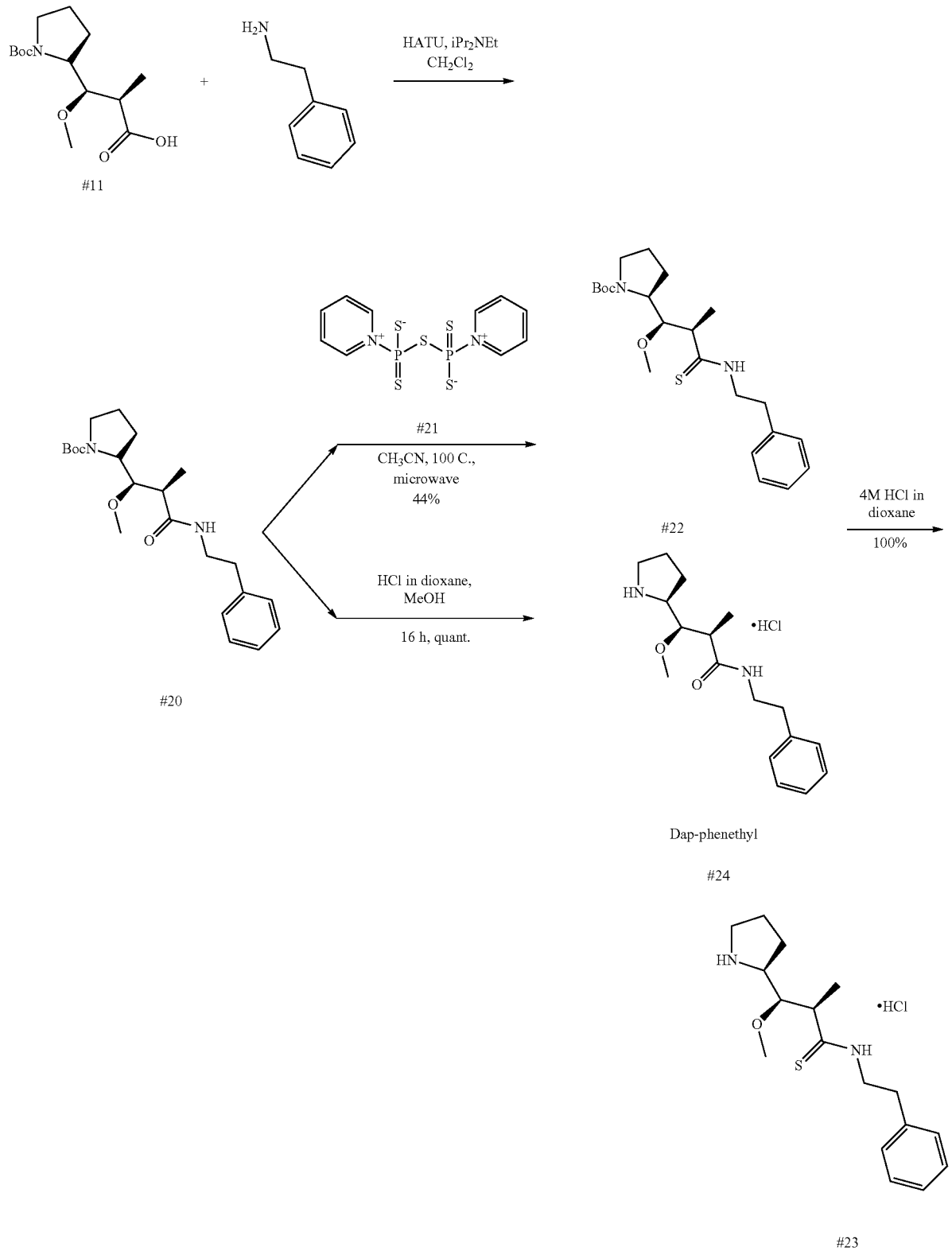

Step 1A

Synthesis of tert-butyl (2S)-2-{(1R,2R)-1-methoxy-2-methyl-3-oxo-3-[(2-phenylethyl)amino]propyl}pyrrolidine-1-carboxylate (#20)

To #11 (22 g, 77 mmol, 1 eq.) in dichloromethane (383 mL, 0.2 M) and N,N-dimethylformamide (30 mL) were added diisopropylethylamine (26.9 mL, 153 mmol, 2 eq.), 2-phenylethylamine (11.6 mL, 91.9 mmol, 1.2 eq.) and HATU (39.0 g, 99.5 mmol, 1.3 eq.). The reaction was stirred for 18 hours and then concentrated in vacuo. The residue was taken up in ethyl acetate (700 mL) and washed sequentially with 1 M aqueous hydrochloric acid solution (2×200 mL) and brine. The organic layer was dried over sodium sulfate, filtered and evaporated in vacuo. The crude material was taken up in dichloromethane and filtered. The filtrate was purified by silica gel chromatography (Gradient: 0% to 100% ethyl acetate in heptane) to give #20 (24 g, 80%) as an off-white solid. LC-MS: m/z 392.2 [M+2H$^+$], 291.1 [(M−Boc)+H$^+$], retention time=0.88 minutes; $^1$H NMR (400 MHz, DMSO-d$_6$), presumed to be a mixture of rotamers: δ 7.80-7.89 (br m, 1H), 7.23-7.29 (m, 2H), 7.15-7.23 (m, 3H), 3.72-3.82 and 3.55-3.62 (2 br m, total 1H), 3.45-3.55 (br m, 1H), 3.31-3.44 (br m, 2H), 3.29 (s, 3H), 3.12-3.25 (br m, 1H), 2.98-3.12 (br m, 1H), 2.71 (t, J=7.1 Hz, 2H), 2.09-2.19 (m, 1H), 1.71-1.83 (br m, 2H), 1.60-1.70 (br m, 1H), 1.49-1.60 (br m, 1H), 1.41 (s, 9H), 1.03 (d, J=6.8 Hz, 3H).

Step 1B

Synthesis of dipyridinium-1-ylpentathiodiphosphonate (#21)

Phosphorous pentasulfide (4.45 g, 2.19 mL, 20 mmol, 1 eq.) was added to pyridine (56 mL, 0.36 M) at 80° C. and the mixture was heated at reflux (115° C.) for 1 hour. The mixture was cooled to room temperature and the product was collected by filtration to give #21 as a yellow solid (4.57 g, 60%); mp: 165-167° C. (decomposition); $^1$H NMR (400 MHz, DMSO-d$_6$) δ 8.78-8.84 (m, 4H), 8.22-8.30 (m, 2H), 7.76-7.83 (m, 4H).

Step 2A

Synthesis of tert-butyl (2S)-2-{(1R,2R)-1-methoxy-2-methyl-3-[(2-phenylethyl)amino]-3-thioxopropyl}pyrrolidine-1-carboxylate (#22)

A mixture of #20 (1.200 g, 3.073 mmol, 1 eq.) and #21 (1.40 g, 3.69 mmol, 1.2 eq.) in acetonitrile (15 mL, 0.20 M) was subjected to microwave radiation at 100° C. for 30 minutes. The reaction mixture was then cooled to room temperature, diluted with ethyl acetate (150 mL), and washed sequentially with 0.5 M aqueous hydrochloric acid solution (100 mL) and brine (2×50 mL). The organic layer was dried over magnesium sulfate, filtered, and concentrated in vacuo. The residue was purified by silica gel chromatography (Gradient: 20% to 80% ethyl acetate in heptane) to give #22 (670 mg, 54%) as a white wax-like solid; mp: 107-109° C.; LC-MS: m/z 407.4 [M+H$^+$], 351.3 [(M−2-methylprop-1-ene)+H$^+$], 307.3 [(M−Boc)+H$^+$], retention time=0.99 minutes; $^1$H NMR (400 MHz, CD$_3$CN), presumed to be a mixture of rotamers: δ 8.28 (br s, 1H), 7.19-7.33 (m, 5H), 3.81-4.05 (br m, 2H), 3.60-3.81 (br m, 2H), 3.38-3.51 (br m, 1H), 3.36 (s, 3H), 3.02-3.17 (br m, 1H), 2.89-3.02 (m, 2H), 2.50-2.62 (br m, 1H), 1.71-1.85 (br m, 2H), 1.53-1.66 (br m, 2H), 1.45 (br s, 9H), 1.23 (d, J=6.7 Hz, 3H).

Step 3

Synthesis of (2R,3R)-3-methoxy-2-methyl-N-(2-phenylethyl)-3-[(2S)-pyrrolidin-2-yl]propanethioamide, hydrochloride salt (#23)

According to procedure C, from #22 (325 mg, 0.799 mmol, 1 eq.), dioxane (5 mL, 0.2 M) and a 4 M hydrochloric acid solution in dioxane (4 mL, 16 mmol, 20 eq.) was synthesized #23 (274 mg, quantitative) as a white foam; LC-MS: 308.2 [M+H$^+$], retention time=0.55 minutes.

Step 2B

Synthesis of (2R,3R)-3-methoxy-2-methyl-N-(2-phenylethyl)-3-[(2S)-pyrrolidin-2-yl]propanamide, hydrochloride salt (#24)

To #20 (7.00 g, 17.9 mmol, 1 eq.) in dioxane (50 mL, 0.36 M) and methanol (2 mL) was added a 4 M solution of hydrochloric acid in dioxane (20 mL, 80 mmol, 4.4 eq.). After stirring for 18 hours, the mixture was concentrated to afford #24 (5.86 g, quantitative) as a gum, which was used without further purification; LC-MS: 292.2 [M+H$^+$], retention time=0.47 minutes.

Preparation of N-Methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#26)

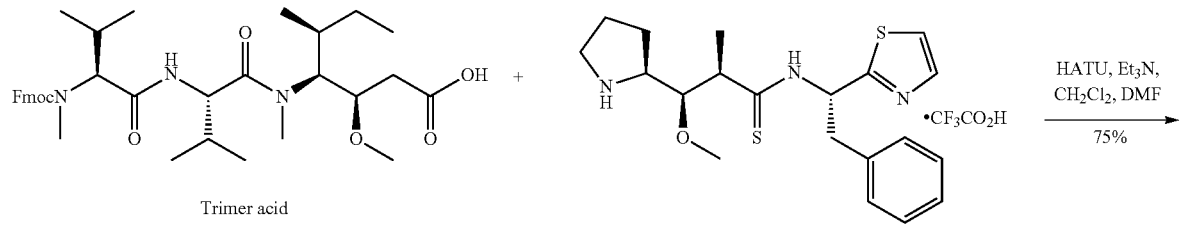

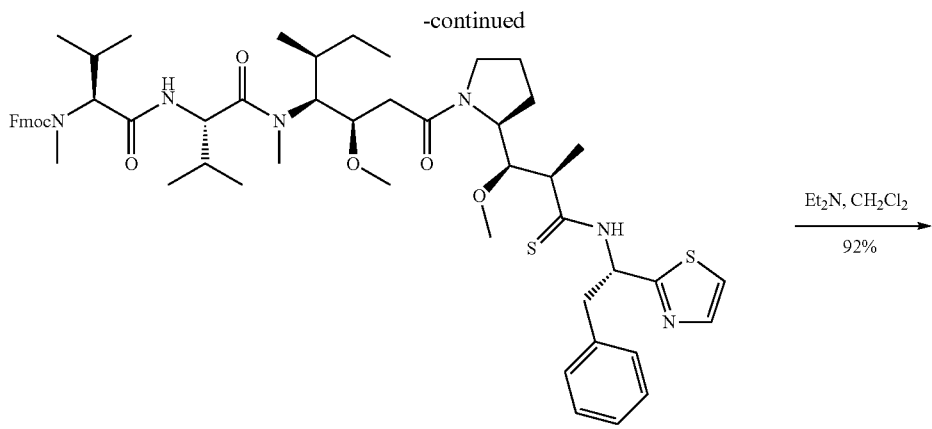

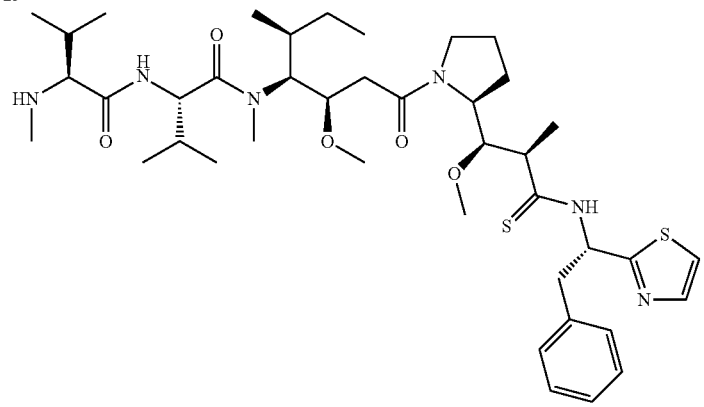

Step 1

Synthesis of N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#25)

According to general procedure D, from #8 (480 mg, 0.753 mmol, 1 eq.), dichloromethane (10 mL, 0.07 M), N,N-dimethylformamide (2 mL), the amine #18 (401 mg, 0.941 mmol, 1.25 eq.), HATU (372 mg, 0.979 mmol, 1.3 eq.) and triethylamine (367 μL, 2.64 mmol, 3.5 eq.) was synthesized the crude desired material, which was purified by silica gel chromatography (Gradient: 0% to 30% acetone in heptane) to afford #25 (711 mg, 75%) as a solid. LC-MS: m/z 1009.7 [M+H$^+$], retention time=1.15 minutes; HPLC (Protocol B): m/z 505.3 [M+2H$^+$]/2, retention time=10.138 minutes; $^1$H NMR (400 MHz, DMSO-d$_6$), presumed to be a mixture of rotamers, characteristic signals: δ [10.54 (br d, J=8 Hz) and 10.81 (br d, J=8 Hz), total 1H], 7.89 (br d, J=7 Hz, 2H), [7.80 (d, J=3.3 Hz) and 7.83 (d, J=3.2 Hz), total 1H], [7.64 (d, J=3.2 Hz) and 7.69 (d, J=3.2 Hz), total 1H], 7.62 (br d, J=7 Hz, 2H), 7.37-7.44 (m, 2H), 7.28-7.35 (m, 4H), 7.20-7.27 (m, 2H), 7.12-7.18 (m, 1H), 6.27-6.35 and 6.40-6.48 (2 m, total 1H), [1.14 (d, J=6.4 Hz) and 1.17 (d, J=6.3 Hz), total 3H].

Step 2

Synthesis of N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#26)

According to general procedure A, from #25 (701 mg, 0.694 mmol) in dichloromethane (10 mL, 0.07 M) and diethylamine (10 mL) was synthesized the crude desired material, which was purified by silica gel chromatography (Gradient: 0% to 10% methanol in dichloromethane) to give a glass-like solid. Diethyl ether and heptane were added and the mixture was concentrated in vacuo, producing #26 (501 mg, 92%) as a white solid. HPLC (Protocol A): m/z 787.4 [M+H$^+$], retention time=7.229 minutes, (purity >97%); $^1$H NMR (400 MHz, DMSO-d$_6$), presumed to be a mixture of rotamers, characteristic signals: δ [10.54 (br d, J=8 Hz) and 10.81 (br d, J=8. Hz), total 1H], [7.99 (br d, J=9 Hz) and 8.00 (br d, J=9 Hz), total 1H], [7.80 (d, J=3.3 Hz) and 7.83 (d, J=3.3 Hz), total 1H], [7.65 (d, J=3.2 Hz) and 7.69 (d, J=3.3 Hz), total 1H], 7.29-7.34 (m, 2H), 7.19-7.28 (m, 2H), 7.13-7.19 (m, 1H), [6.31 (ddd, J=11, 8, 4.5 Hz) and 6.45 (ddd, J=11.5, 8, 4.5 Hz), total 1H], [4.57 (dd, J=8.9, 8.7 Hz) and 4.63 (dd, J=8.7, 8.7 Hz), total 1H], 3.16, 3.21, 3.24 and 3.25 (4 s, total 6H), 2.96 and 3.03 (2 br s, total 3H), [1.14 (d, J=6.6 Hz) and 1.17 (d, J=6.4 Hz), total 3H].

Preparation of N²-[(1-Anainocyclopentyl)carbonyl]-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#30)
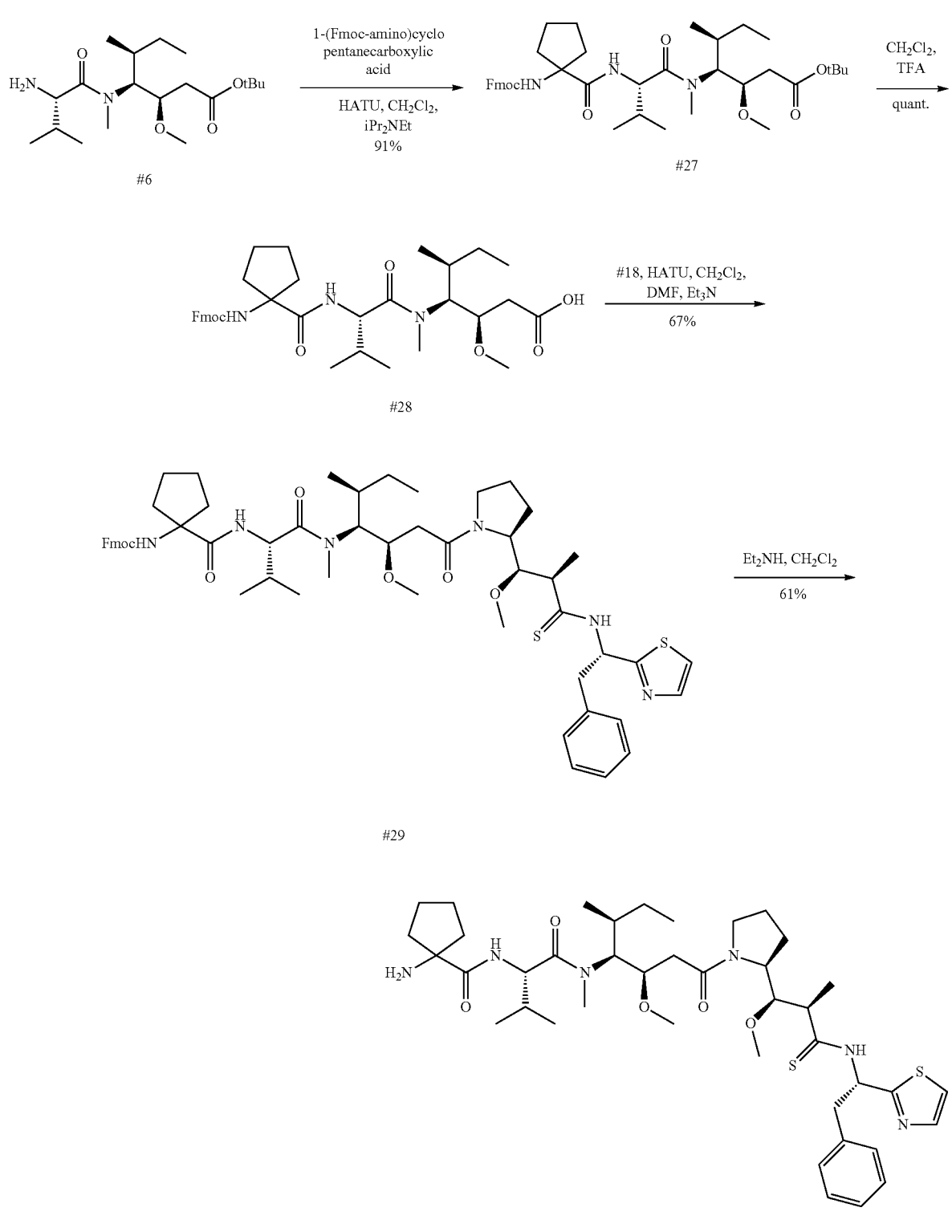

Step 1

Synthesis of tert-butyl (3R,4S,5S)-4-[{N-[(1-{[(9H-fluoren-9-ylmethoxy)carbonyl]amino}cyclopentyl)carbonyl]-L-valyl}(methyl)amino]-3-methoxy-5-methylheptanoate (#27)

To #6 (287 mg, 0.801 mmol, 1 eq.) in dichloromethane (4 mL, 0.2 M) were added 1-{[(9H-fluoren-9-ylmethoxy)carbonyl]amino}cyclopentanecarboxylic acid (309 mg, 0.879 mmol, 1.1 eq.), diisopropylethylamine (281 μL, 1.60 mmol, 2 eq.) and HATU (376 mg, 0.960 mmol, 1.2 eq.). The mixture was stirred for 18 hours and diluted with ethyl acetate (15 mL). The reaction mixture was washed with 1 M aqueous hydrochloric acid solution (2×5 mL) and with brine (5 mL). The organic layer was dried over sodium sulfate, filtered, and concentrated in vacuo. The crude material was purified by silica gel chromatography (Gradient: 0% to 60% ethyl acetate in heptane) to provide #27 (502 mg, 91%) as a white foam. LC-MS: m/z 692.3 [M+H$^+$], 714.3 [M+Na$^+$], 636.3 [(M−2-methylprop-1-ene)+H$^+$], retention time=1.13 minutes; $^1$H NMR (400 MHz, DMSO-d$_6$), characteristic signals: δ 7.89 (br d, J=7.4 Hz, 2H), 7.67-7.75 (m, 2H), 7.60 (br s, 1H), 7.38-7.44 (m, 2H), 7.30-7.36 (m, 2H), 7.21 (br d, J=8.8 Hz, 1H), 4.44-4.59 (m, 2H), 4.17-4.27 (m, 3H), 3.68-3.78 (br m, 1H), 3.21 (s, 3H), 2.88 (br s, 3H), 2.09-2.20 (m, 2H), 1.39 (s, 9H).

Step 2

Synthesis of (3R,4S,5S)-4-[{N-[(1-{[(9H-fluoren-9-ylmethoxy)carbonyl]amino}cyclopentyl)carbonyl]-L-valyl}(methyl)amino]-3-methoxy-5-methylheptanoic acid (#28)

To a solution of #27 (500 mg, 0.723 mmol) in dichloromethane (7 mL, 0.1 M) was added trifluoroacetic acid (3 mL). The reaction mixture initially became orange, then darkened over time. After stirring for 18 hours, the solvent was removed in vacuo to give #28 (460 mg, quantitative) as a dark brown glass, which was used without further purification. LC-MS: m/z 636.3 [M+H$^+$].

Step 3

Synthesis of N$^2$-[(1-{[(9H-fluoren-9-ylmethoxy)carbonyl]amino}cyclopentyl)carbonyl]-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#29)

According to general procedure D, from #28 (50 mg, 0.079 mmol, 1 eq.) dichloromethane (3 mL, 0.03 M), N,N-dimethylformamide (0.5 mL), amine #18 (44 mg, 0.087 mmol, 1.1 eq.), triethylamine (33.0 μL, 0.237 mmol, 3 eq.) and HATU (36 mg, 0.95 mmol, 1.2 eq.) was synthesized the crude desired material, which was purified by silica gel chromatography (Gradient: 0% to 30% acetone in heptane) to give #29 (59 mg, 67%) as a solid. LC-MS: m/z 1007.5 [M+H$^+$], retention time=1.11 minutes; $^1$H NMR (400 MHz, DMSO-d$_6$), presumed to be a mixture of rotamers, characteristic signals: δ [10.54 (br d, J=8 Hz) and 10.80 (br d, J=8 Hz), total 1H], 7.89 (br d, J=7 Hz, 2H), [7.80 (d, J=3.3 Hz) and 7.82 (d, J=3.1 Hz), total 1H], 7.68-7.75 (m, 2H), [7.64 (d, J=3.2 Hz) and 7.68 (d, J=3.2 Hz), total 1H], 7.38-7.44 (m, 2H), 7.27-7.36 (m, 4H), 7.12-7.25 (m, 4H), [6.30 (ddd, J=11, 8, 4.5 Hz) and 6.39-6.48 (m), total 1H], [4.50 (br dd, J=8, 8 Hz) and 4.54-4.59 (m), total 1H], 4.17-4.29 (m, 3H), 2.89 and 2.96 (2 br s, total 3H), [1.13 (d, J=6.5 Hz) and 1.16 (d, J=6.4 Hz), total 3H].

Step 4

Synthesis of N$^2$-[(1-aminocyclopentyl)carbonyl]-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#30)

According to general procedure A, from #29 (54 mg, 0.054 mmol) in dichloromethane (6 mL, 0.9 mM) and diethylamine (4 mL) was synthesized the crude desired material, which was purified by silica gel chromatography (Gradient: 0% to 10% methanol in dichloromethane) to give example #30 (26 mg, 61%) as a solid. HPLC (Protocol A): retention time=7.233 minutes, m/z 785.4 [M+H$^+$], (purity >72%). $^1$H NMR (400 MHz, DMSO-d$_6$), presumed to be a mixture of rotamers, characteristic signals: δ [10.54 (br d, J=8 Hz) and 10.82 (br d, J=8 Hz), total 1H], 8.19-8.27 (m, 1H), [7.80 (d, J=3.2 Hz) and 7.83 (d, J=3.2 Hz), total 1H], [7.65 (d, J=3.3 Hz) and 7.69 (d, J=3.3 Hz), total 1H], 7.28-7.33 (m, 2H), 7.20-7.27 (m, 2H), 7.14-7.19 (m, 1H), [6.31 (ddd, J=11, 8, 4.5 Hz) and 6.44 (ddd, J=11, 8, 4 Hz), total 1H], [4.53 (dd, J=9, 8 Hz) and 4.60 (dd, J=9, 7.5 Hz), total 1H], 3.24 and 3.25 (2 s, total 3H), 3.17 and 3.21 (2 s, total 3H), 2.93 and 3.00 (2 br s, total 3H), [1.14 (d, J=6.5 Hz) and 1.17 (d, J=6.5 Hz), total 3H].

Preparation of 2-Methylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#34)

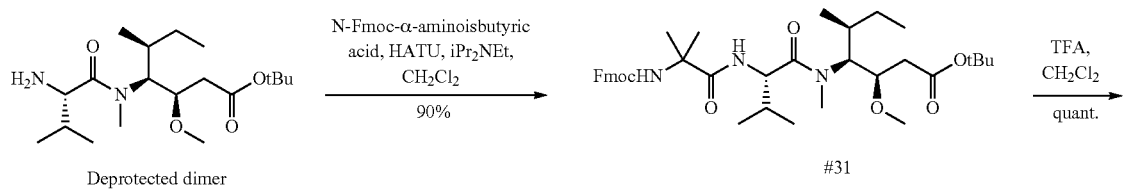

Deprotected dimer
6

31

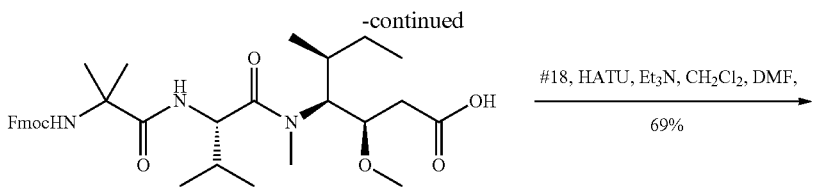

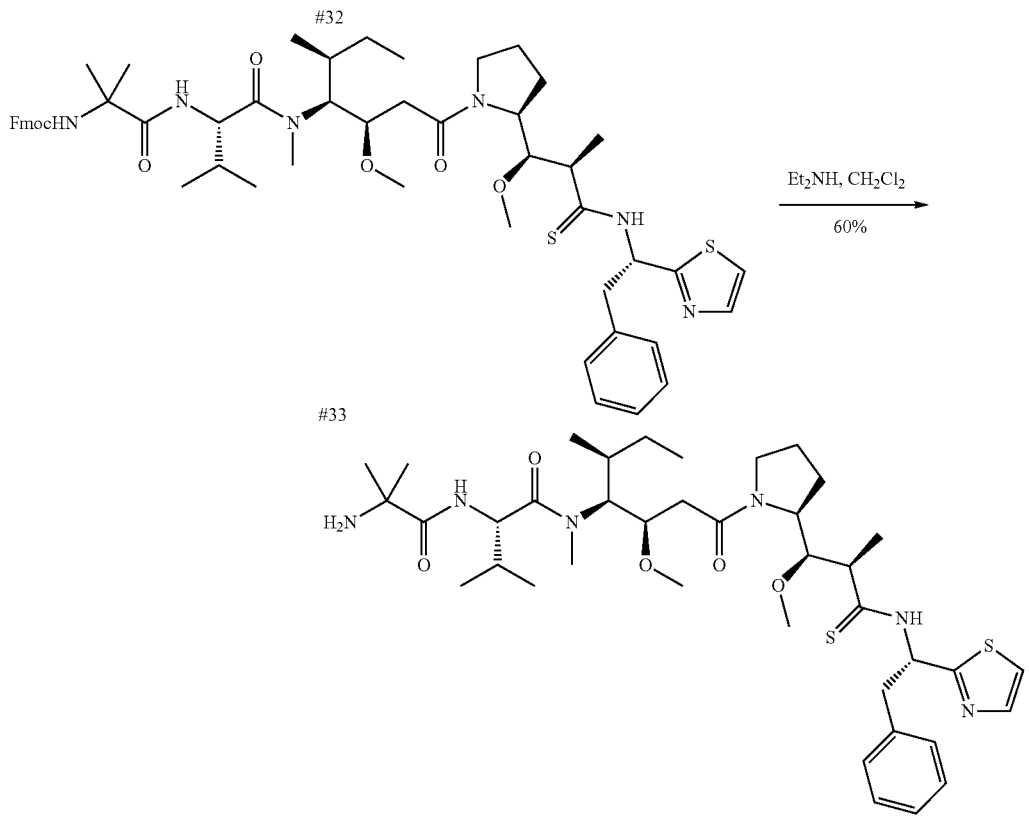

Step 1

Synthesis of N-[(9H-fluoren-9-ylmethoxy)carbonyl]-2-methylalanyl-N-[(3R,4S,5S)-1-tert-butoxy-3-methoxy-5-methyl-1-oxoheptan-4-yl]-N-methyl-L-valinamide (#31)

To a solution of #6 (70% pure, 3.13 g, 6.1 mmol, 1 eq.) in dichloromethane (40 mL, 0.15 M) were added N-[(9H-fluoren-9-ylmethoxy)carbonyl]-2-methylalanine (1.99 g, 6.12 mmol, 1 eq.), diisopropylethylamine (2.67 mL, 15.3 mmol, 2.5 eq.) and HATU (2.79 g, 7.35 mmol, 1.2 eq.). The reaction mixture was stirred for 18 hours, diluted with ethyl acetate, washed with 1 M aqueous hydrochloric acid solution and washed with brine. The organic layer was dried over sodium sulfate, filtered, and concentrated in vacuo onto silica. The material was then purified by silica gel chromatography (Gradient: 0% to 45% ethyl acetate in heptane) to provide #31 (3.65 g, 90%) as a solid. LC-MS: m/z 665.5 [M+H$^+$], 688.5 [M+Na$^+$], 610.5 [(M−2-methylprop-1-ene)+H$^+$]; HPLC (Protocol C): retention time=9.455 (purity >94%); $^1$H NMR (400 MHz, DMSO-d$_6$), characteristic signals: δ 7.89 (d, J=7.4 Hz, 2H), 7.67-7.74 (m, 2H), 7.39-7.48 (m, 3H), 7.31-7.36 (m, 2H), 7.29 (br d, J=8.8 Hz, 1H), 4.47-4.60 (br m, 1H), 4.47 (dd, J=8.6, 8.0 Hz, 1H), 4.18-4.28 (m, 3H), 3.69-3.79 (br m, 1H), 3.21 (s, 3H), 2.88 (br s, 3H), 2.15 (dd, J=15.5, 9.3 Hz, 1H), 1.91-2.01 (m, 1H), 1.67-1.81 (br m, 1H), 1.39 (s, 9H), 1.36 (br s, 3H), 1.30 (s, 3H), 0.75 (d, J=6.6 Hz, 3H), 0.66-0.73 (br m, 3H).

Step 2

Synthesis of N-[(9H-fluoren-9-ylmethoxy)carbonyl]-2-methylalanyl-N-[(2R,3S,4S)-1-carboxy-2-methoxy-4-methylhexan-3-yl]-N-methyl-L-valinamide (#32)

According to general procedure B, from #31 (500 mg, 0.751 mmol) in dichloromethane (7 mL, 0.1 M) and trifluoroacetic acid (3 mL) was synthesized #32 as a glass (458 mg, quantitative), which was used in the next step without further purification. LC-MS: m/z 611.4 [M+2H$^+$], 632.2 [M+Na$^+$], retention time=0.94 minute.

Step 3

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#33)

According to general procedure D, from #32 (53.0 mg, ≤0.083 mmol, 1 eq.), dichloromethane (4 mL, 0.02 M), N,N-dimethylformamide (1 mL), amine #18 (43.8 mg, 0.0870 mmol, 1 eq.), triethylamine (36 µL, 0.26 mmol, 3 eq.) and HATU (39.5 mg, 0.104 mmol, 1.2 eq.) was synthesized the crude desired material, which was purified by silica gel chromatography (Gradient: 0% to 30% acetone in heptane) to give #33 (60 mg, 69% over two steps). LC-MS: m/z 981.4 [M+H$^+$], retention time=1.090 minutes; $^1$H NMR (400 MHz, DMSO-d$_6$), presumed to be a mixture of rotamers, characteristic signals: δ [10.54 (br d, J=8 Hz) and 10.80 (br d, J=8 Hz), total 1H], 7.86-7.91 (m, 2H), [7.80 (d, J=3.3 Hz) and 7.82 (d, J=3.3 Hz), total 1H], 7.68-7.74 (m, 2H), [7.64 (d, J=3.2 Hz) and 7.68 (d, J=3.3 Hz), total 1H], 7.38-7.44 (m, 2H), 7.20-7.36 (m, 6H), 7.12-7.17 (m, 1H), 6.27-6.34 and 6.40-6.47 (2 m, total 1H), 3.22 and 3.24 (2 s, total 3H), 3.14 and 3.18 (2 s, total 3H), 2.90 and 2.97 (2 br s, total 3H), 1.37 (br s, 3H), 1.31 (2 br s, total 3H), [1.13 (d, J=6.6 Hz) and 1.16 (d, J=6.5 Hz), total 3H].

Step 4

Synthesis of 2-methylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#34)

According to general procedure A, from #33 (55 mg, 0.055 mmol, 1 eq.) in dichloromethane (6 mL, 0.009 M) and diethylamine (4 mL) was synthesized the crude desired material, which was purified by silica gel chromatography (Gradient: 0% to 5% methanol in dichloromethane) to give #34 (25 mg, 60%) as a solid. HPLC (Protocol A): m/z 759.4 [M+H$^+$], retention time=7.088 minutes, (purity >75%). $^1$H NMR (400 MHz, DMSO-d$_6$), presumed to be a mixture of rotamers, characteristic signals: δ [10.54 (br d, J=8 Hz) and 10.81 (br d, J=8 Hz), total 1H], 8.01-8.08 (m, 1H), [7.80 (d, J=3.1 Hz) and 7.83 (d, J=3.3 Hz), total 1H], [7.65 (d, J=3.2 Hz) and 7.69 (d, J=3.2 Hz), total 1H], 7.29-7.33 (m, 2H), 7.20-7.27 (m, 2H), 7.13-7.19 (m, 1H), 6.27-6.35 and 6.40-6.48 (2 m, total 1H), [4.49 (dd, J=9, 8 Hz) and 4.56 (dd, J=9, 8 Hz), total 1H], 3.24 and 3.25 (2 s, total 3H), 3.17 and 3.21 (2 s, total 3H), 2.92 and 2.99 (2 br s, total 3H), 1.20 and 1.21 (2 s, total 3H), 1.12 and 1.13 (2 s, total 3H), 0.75-0.81 (m, 3H).

Preparation of N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide (#36)

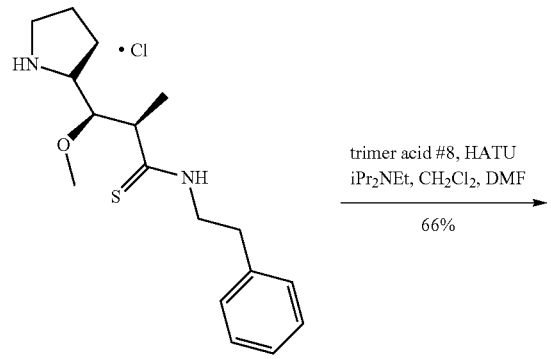

23

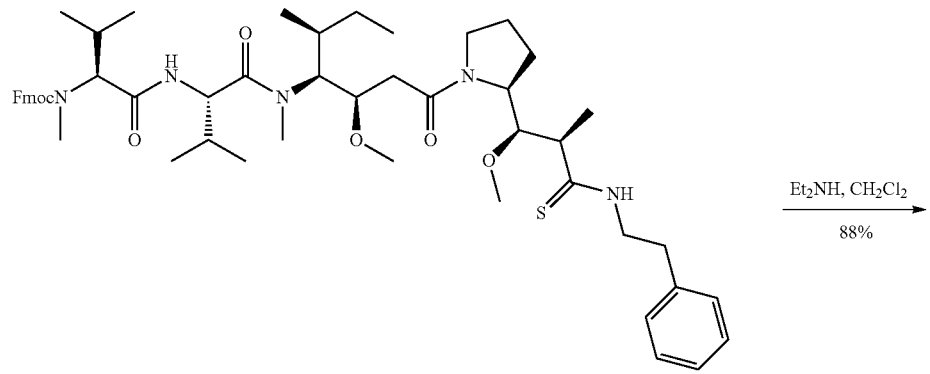

35

-continued

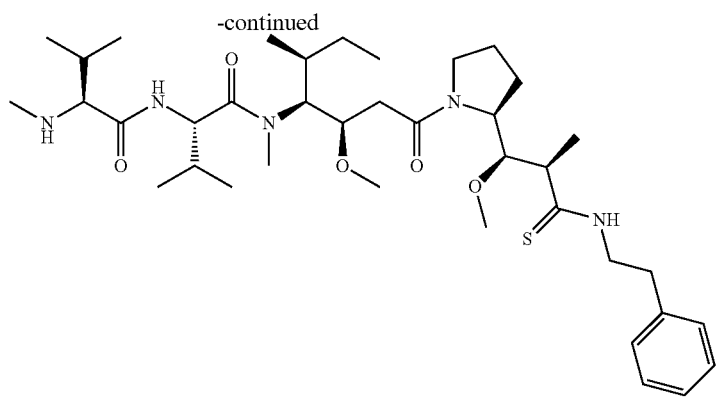

36

Step 1

Synthesis of N-[(9H-fluoren-9-ylmethoxy)carbonyl]-N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide (#35)

To a mixture of #23 (337 mg, 0.983 mmol, 1 eq.) in dichloromethane (8 mL, 0.1 M) and N,N-dimethylformamide (1 mL) were added #8 (564 mg, 0.885 mmol, 0.9 eq.), diisopropylethylamine (383 mg, 2.95 mmol, 3 eq.) and HATU (472 mg, 1.18 mmol, 1.2 eq.). After 2 hours, the mixture was diluted with dichloromethane, washed sequentially with 0.1 M aqueous hydrochloric acid and with brine, dried over magnesium sulfate, filtered, and concentrated in vacuo. The residue was purified by reverse phase chromatography (Method G) to give #35 (600 mg, 66%); LC-MS: m/z 926.6 [M+H$^+$], retention time=1.16 minutes; $^1$H NMR (400 MHz, DMSO-d$_6$), presumed to be a mixture of rotamers, characteristic signals: δ [9.94 (br t, J=5 Hz) and 10.16-10.23 (br m), total 1H], 7.90 (d, J=7.2 Hz, 2H), [7.71 (br d, J=7 Hz) and 8.06 (br d, J=8 Hz), total 1H], 7.60-7.65 (m, 2H), 7.41 (br dd, J=7, 7 Hz, 2H), 7.15-7.36 (m, 7H), 3.29 (s, 3H), 1.16-1.22 (m, 3H).

Step 2

Synthesis of N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide (#36)

According to general procedure A, from #35 (465 mg, 0.502 mmol, 1 eq.) in dichloromethane (5 mL, 0.1 M) and diethylamine (5 mL) was synthesized the crude desired material, which was purified by silica gel chromatography (Gradient: 0% to 10% methanol in dichloromethane) to give #36 (310 mg, 88%) as a solid. LC-MS: m/z 704.6 [M+H$^+$], retention time=0.74 minutes; HRMS: m/z calculated for C$_{38}$H$_{66}$N$_5$O$_5$S: 704.4779. found: 704.477 [M+H$^+$]; $^1$H NMR (400 MHz, CD$_3$OD), presumed to be a mixture of rotamers, characteristic signals: δ 7.23-7.30 (m, 4H), 7.15-7.22 (m, 1H), [4.68 (d, J=8.6 Hz) and 4.74 (d, J=8.0 Hz), total 1H], 3.39 and 3.40 (2 s, total 3H), 3.12 and 3.22 (2 br s, total 3H), [2.82 (d, J=6.0 Hz) and 2.84 (d, J=6.0 Hz), total 1H], 2.29 and 2.30 (2 s, total 3H), [1.27 (d, J=6.8 Hz) and 1.29 (d, J=6.6 Hz), total 3H], [0.84 (t, J=7.4 Hz) and 0.87 (t, J=7.4 Hz), total 3H].

Preparation of N-methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, trifluoroacetic acid salt (#41) and N-Methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#42)

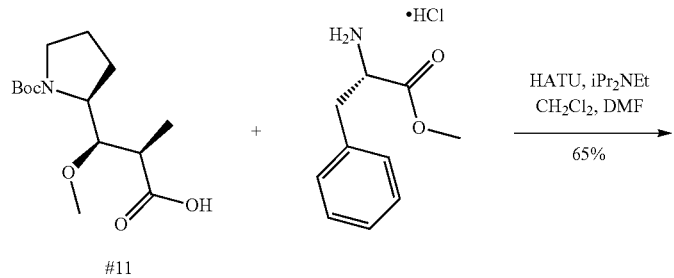

11

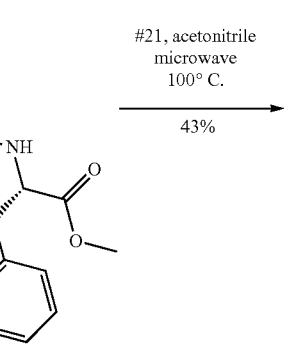

37

-continued
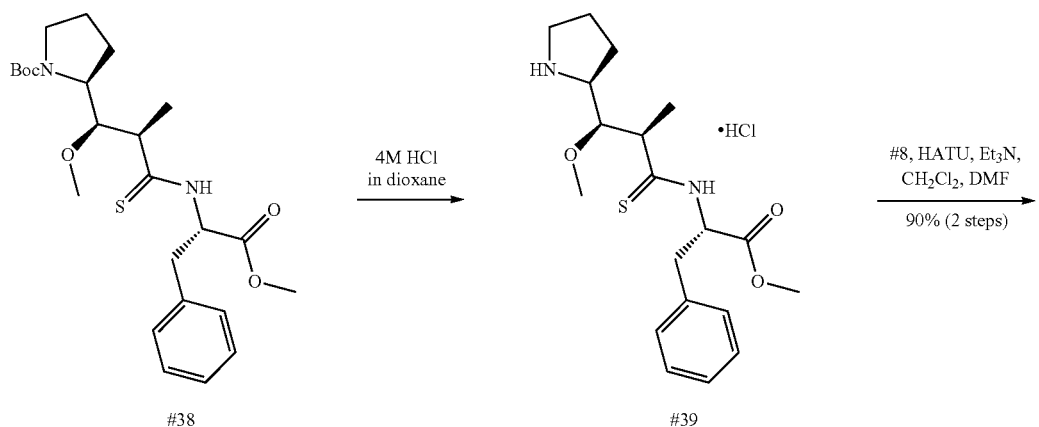
38 → #39
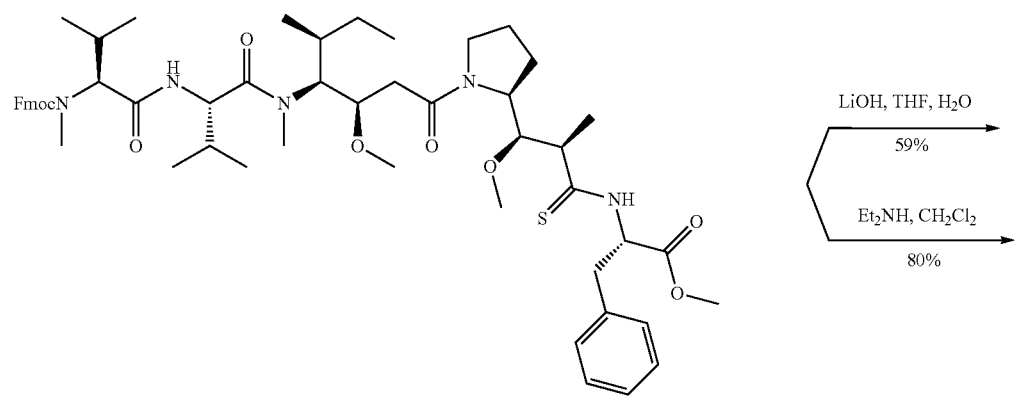
40

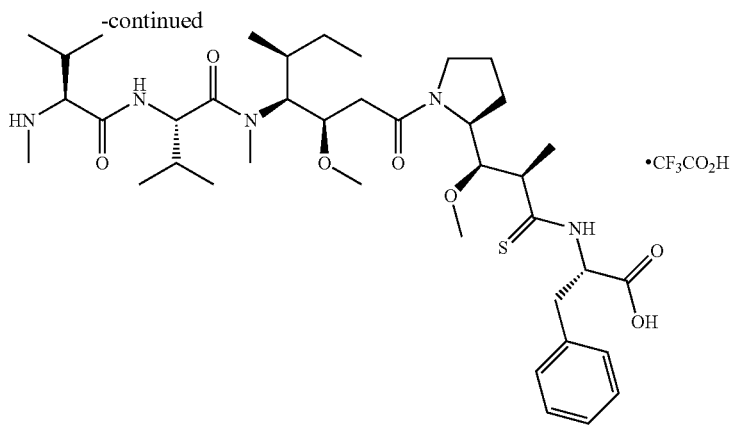

41

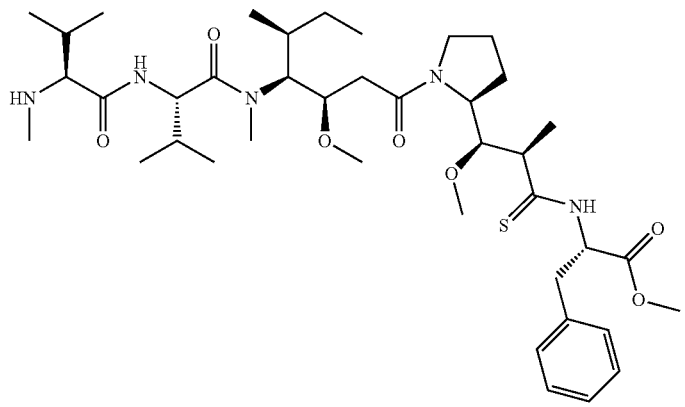

42

Step 1

Synthesis of methyl N-{(2R,3R)-3-[(2S)-1-(tert-butoxycarbonyl)pyrrolidin-2-yl]-3-methoxy-2-methylpropanoyl}-L-phenylalaninate (#37)

To a mixture of #11 (2.7 g, 9.4 mmol, 1 eq.) in dichloromethane (30 mL, 0.3 M) and N,N-dimethylformamide (3 mL) were added diisopropylethylamine (3.30 mL, 18.8 mmol, 2 eq.), L-phenylalanine methyl ester hydrochloride (2.03 g, 9.40 mmol, 1.2 eq.) and HATU (4.79 g, 12.2 mmol, 1.3 eq.). The reaction was stirred for 18 hours and then concentrated in vacuo. The residue was taken up in ethyl acetate (100 mL) and washed sequentially with 1 M hydrochloric acid (2×50 mL) and brine. The organic layer was dried over sodium sulfate, filtered and evaporated in vacuo. The crude material was taken up in dichloromethane and filtered. The filtrate was purified by silica gel chromatography (Gradient: 0% to 100% ethyl acetate in heptane) to give #37 (2.76 g, 65%) as an off-white solid. LC-MS: m/z 449.3 [M+H$^+$], 349.2 [(M−Boc)+H$^+$] retention time=0.88 minutes; $^1$H NMR (400 MHz, DMSO-d$_6$), presumed to be a mixture of rotamers, characteristic signals: δ 8.28 (d, J=8.2 Hz, 1H), 7.14-7.29 (m, 5H), 4.50 (ddd, J=10.9, 8.1, 4.4 Hz, 1H), 3.64 (s, 3H), 3.23 (s, 3H), 2.15-2.24 (m, 1H), 1.56-1.76 (m, 2H), 1.31-1.55 (m, 11H), 1.02 (d, J=6.6 Hz, 3H).

Step 2

Synthesis of methyl N-{(2R,3R)-3-[(2S)-1-(tert-butoxycarbonyl)pyrrolidin-2-yl]-3-methoxy-2-methylpropanethioyl}-L-phenylalaninate (#38)

A mixture of #37 (1.52 g, 3.39 mmol, 1 eq.) and #21 (1.68 g, 4.41 mmol, 1.3 eq.) in acetonitrile (12 mL, 0.28 M) was subjected to microwave radiation at 100° C. for 1 hour. The mixture was partitioned between water and ethyl acetate. The aqueous layer was back-extracted with ethyl acetate. The combined organic layers were washed with 10% aqueous citric acid solution and with brine, dried over sodium sulfate, filtered, and concentrated in vacuo. The material was dissolved in a small amount of ethyl acetate and concentrated onto silica in vacuo. Purification by silica gel chromatography (Gradient: 0% to 30% ethyl acetate in heptane) provided #38 (680 mg, 43%); LC-MS: m/z 465.2 [M+H$^+$], 487.3 [M+Na$^+$], 365.2 [(M−Boc)+H$^+$], retention time=0.97 minutes; HPLC (Protocol B): 465.2 [M+H⁺], 487.2 [M+Na⁺], 365.2 [(M−Boc)+H⁺], retention time=7.444 minutes (purity >98%); ¹H NMR (400 MHz, DMSO-d₆), presumed to be a mixture of rotamers, characteristic signals: δ 10.23 (br d, J=7.5 Hz, 1H), 7.17-7.28 (m, 5H), 5.24 (ddd, J=11, 7.5, 4.5 Hz, 1H), 3.66 (s, 3H), 3.28 (s, 3H), 3.21 (dd, J=14.3, 4.4 Hz, 1H), 3.07 (dd, J=14.2, 11.2 Hz, 1H), 2.65-2.74 (m, 1H), 1.54-1.71 (m, 2H), 1.37 (s, 9H), 1.17 (d, J=6.4 Hz, 3H).

Step 3

Synthesis of methyl N-{(2R,3R)-3-methoxy -2-methyl-3-[(2S)-pyrrolidin-2-yl]propanethioyl}-L-phenylalaninate, hydrochloride salt (#39)

According to general procedure C, at 0° C. from #38 (660 mg, 1.42 mmol, 1 eq.), dioxane (10 mL, 0.14 M) and 4 M hydrochloric acid solution in dioxane (20 mL, 80 mmol, 60 eq.) was synthesized #39 (590 mg) as an off-white solid, which was used in the next step without further purification. LC-MS: m/z 365.2 [M+H⁺], retention time=0.58 minutes; ¹H NMR (400 MHz, DMSO-d₆) δ 10.67 (d, J=7.7 Hz, 1H), 9.42-9.54 (br m, 1H), 8.21-8.33 (br m, 1H), 7.20-7.35 (m, 5H), 5.25 (ddd, J=11.1, 7.6, 4.4 Hz, 1H), 3.76 (dd, J=8.9, 3.0 Hz, 1H), 3.68 (s, 3H), 3.39 (s, 3H), 3.24 (dd, J=14.2, 4.5 Hz, 1H), 3.13 (dd, J=14.3, 11.0 Hz, 1H), 2.93-3.09 (m, 3H), 2.85-2.93 (m, 1H), 1.72-1.84 (m, 1H), 1.36-1.60 (m, 3H), 1.22 (d, J=6.6 Hz, 3H).

Step 4

Synthesis of N-[(9H-fluoren-9-ylmethoxy)carbonyl]-N-methyl-L-valyl-N—R3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#40)

According to general procedure D, from #8 (247 mg, 0.387 mmol, 1 eq.), #39 (186 mg, ≤0.450 mmol, 1.2 eq.), dichloromethane (10 mL, 0.04 M), N,N-dimethylformamide (2 mL), HATU (176 mg, 0.464 mmol, 1.2 eq.) and triethylamine (189 mL, 1.35 mmol, 3.5 eq.) was synthesized the crude desired material, which was purified by silica gel chromatography (Gradient: 0% to 25% acetone in heptane) to give #40 (410 mg, 90% over 2 steps) as an off-white solid. LC-MS: m/z 984.7 [M+H⁺], 1006.7 [M+Na⁺], retention time=1.15 minutes; HPLC (Protocol C): retention time=9.683 minutes (purity >99%); ¹H NMR (400 MHz, DMSO-d₆), presumed to be a mixture of rotamers, characteristic signals: δ [10.19 (br d, J=7 Hz) and 10.49 (br d, J=8 Hz), total 1H], 7.90 (d, J=7.5 Hz, 2H), 7.60-7.65 (m, 2H), 7.38-7.45 (m, 2H), 7.29-7.35 (m, 2H), 7.14-7.28 (m, 5H), [5.20 (ddd, J=11, 7, 4 Hz) and 5.35-5.43 (m), total 1H], 3.65 and 3.69 (2 s, total 3H), [1.15 (d, J=6.5 Hz) and 1.18 (d, J=6.4 Hz), total 3H].

Step 5A

Synthesis of N-methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, trifluoroacetic acid salt (#41)

To a solution of #40 (401 mg, 0.407 mmol, 1 eq.) in tetrahydrofuran (10 mL, 0.03 M) was added a solution of lithium hydroxide (24.4 mg, 1.02 mmol, 2.5 eq.) in water (5 mL). After 4 hours, the reaction was concentrated in vacuo and then azeotroped three times with heptane. The crude material was dissolved in dimethyl sulfoxide (7 mL) and purified by reverse phase chromatography (Method C, 7 injections of 1 mL). The appropriate fractions were concentrated (Genevac) before being diluted with a small amount of methanol in dichloromethane. The mixture was concentrated in vacuo to a glass-like solid. Diethyl ether was then added, followed by heptane, and the mixture was concentrated in vacuo to afford #41 (180 mg, 59%) as a white solid. LC-MS: m/z 748.6 [M+H⁺], retention time=0.68 minutes; HPLC (Protocol A): 748.4 [M+H⁺], retention time=6.922 minutes; ¹H NMR (400 MHz, DMSO-d₆), presumed to be a mixture of rotamers, characteristic signals: δ 12.9 and 13.1 (2 v br s, total 1H), [10.12 (br d, J=8 Hz) and 10.45 (br d, J=8 Hz), total 1H], 8.75-8.90 (m, 2H), 8.62-8.73 (br m, 1H), 7.13-7.29 (m, 5H), [5.20 (ddd, J=11, 7.5, 4 Hz) and 5.40 (ddd, J=11.5, 8, 4 Hz), total 1H], 4.55-4.73 (m, 2H), 3.23 and 3.25 (2 s, total 3H), 3.16 and 3.18 (2 s, total 3H), 2.97 and 3.01 (2 br s, total 3H), 1.13-1.20 (m, 3H), 0.73-0.81 (m, 3H).

Step 5B

Synthesis of N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#42)

According to general procedure A, from #40 (561 mg, 0.570 mmol, 1 eq.), dichloromethane (10 mL, 0.057 M) and diethylamine (10 mL) was synthesized #42 (348 mg, 80%) as a white solid after silica gel chromatography (Gradient: 0% to 10% methanol in dichloromethane). LC-MS: m/z 762.7 [M+H⁺], retention time=0.74 minutes; HPLC (Protocol A): 762.4 [M+H⁺], retention time=7.315 minutes (purity >95%); ¹H NMR (400 MHz, DMSO-d₆), presumed to be a mixture of rotamers, characteristic signals: δ [10.20 (br d, J=7.5 Hz) and 10.50 (br d, J=8 Hz), total 1H], 7.95-8.03 (m, 1H), 7.15-7.29 (m, 5H), [5.20 (ddd, J=11, 7.5, 5 Hz) and 5.39 (ddd, J=11, 7.5, 4 Hz, total 1H], [4.57 (dd, J=8.8, 8.7 Hz) and 4.61 (dd, J=8.7, 8.6 Hz), total 1H], 3.65 and 3.69 (2 s, total 3H), 3.24 and 3.25 (2 s, total 3H), 3.16 and 3.17 (2 s, total 3H), 2.96 and 2.99 (2 br s, total 3H), 2.69-2.79 (m, 1H), 2.62-2.68 (m, 1H), 2.14 and 2.15 (2 br s, total 3H), [1.15 (d, J=6.6 Hz) and 1.18 (d, J=6.5 Hz), total 3H], [0.75 (t, J=7.4 Hz) and 0.76 (t, J=7.3 Hz), total 3H].

Preparation of 2-Methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, hydrochloride salt (#44) and 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide, hydrochloride salt (#45)

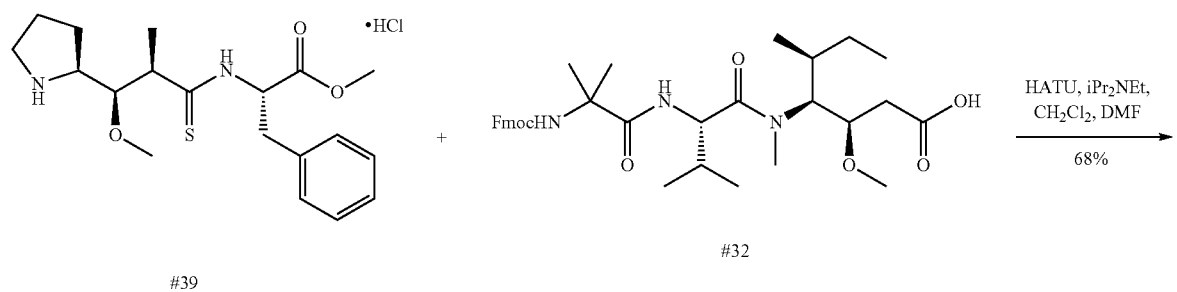

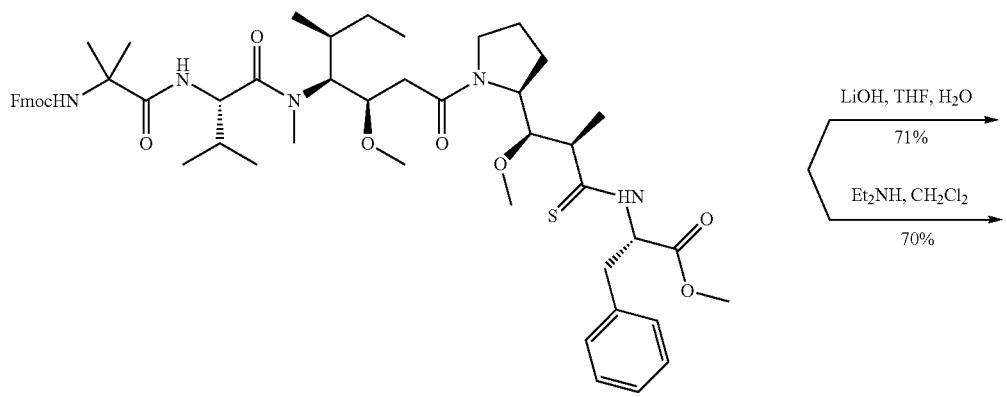

-continued

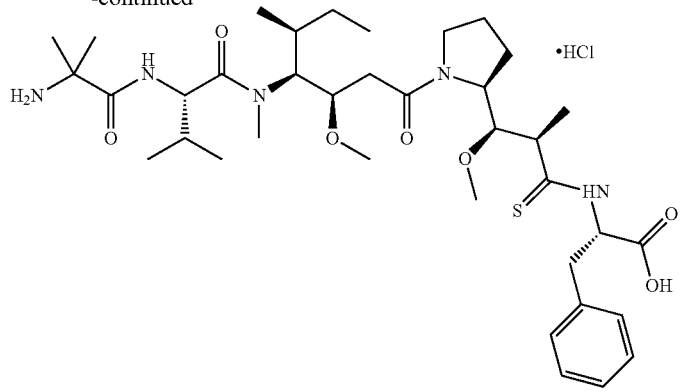

44

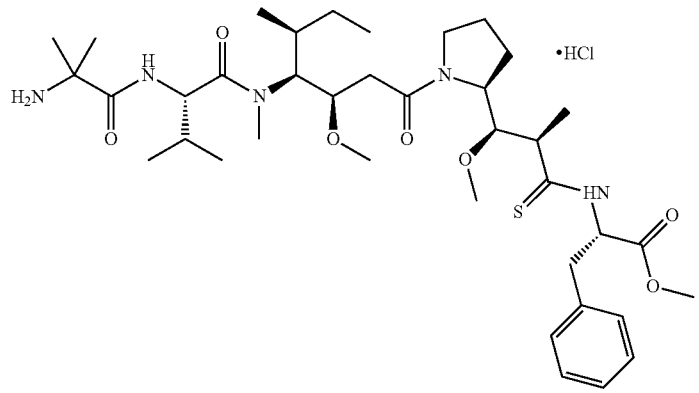

45

Step 1

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#43)

To a solution of #32 (321 mg, 0.881 mmol, 1 eq.) in dichloromethane (5 mL, 0.1 M) and N,N-dimethylformamide (1 mL) were added #39 (484 mg, ≤0.769 mmol, 0.9 eq.), HATU (353 mg, 0.881 mmol, 1 eq.) and diisopropylethylamine (463 μL, 2.64 mmol, 3 eq.). After stirring for 18 hours, the mixture was diluted with dichloromethane, washed with water and with brine, dried over magnesium sulfate, filtered, and concentrated onto silica in vacuo. The residue was purified by silica gel chromatography (Gradient: 0% to 30% acetone in heptane) to give #43 (574 mg, 68% over two steps) as a white solid. LC-MS: m/z 956.6 [M+H$^+$], retention time=4.49 minutes; $^1$H NMR (400 MHz, CD$_3$OD), presumed to be a mixture of rotamers, characteristic signals: δ 7.80 (d, J=7.5 Hz, 2H), 7.64-7.72 (m, 2H), 7.16-7.35 (m, 7H), [5.43 (dd, J=11, 4.5 Hz) and 5.58 (dd, J=11.5, 4 Hz), total 1H], 3.72 and 3.75 (2 s, total 3H), 3.34 and 3.35 (2 s, total 3H), 3.26 and 3.29 (2 s, total 3H), 3.05 and 3.11 (2 br s, total 3H), 1.39 and 1.40 (2 s, total 3H), [1.24 (d, J=6.7 Hz) and 1.29 (d, J=6.4 Hz), total 3H].

Step 2A

Synthesis of 2-methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, hydrochloride salt (#44)

To a solution of #43 (100 mg, 0.105 mmol, 1 eq.) in tetrahydrofuran (5 mL, 0.02 M) was added a solution of lithium hydroxide (10 mg, 0.417 mmol, 3 eq.) in water (3 mL). After 3 hours, the reaction was concentrated in vacuo and purified by reverse phase chromatography (Method C) to give a trifluoroacetic acid salt, which was dissolved in methanol, treated with a 4 M hydrochloric acid solution in dioxane, and concentrated in vacuo to give #44 (56 mg, 71%) as a white solid. LC-MS: m/z 720.6 [M+H$^+$], retention time=0.67 minutes; HPLC (Protocol D): retention time=8.851 minutes; $^1$H NMR (400 MHz, CD$_3$OD), presumed to be a mixture of rotamers, characteristic signals: δ 7.17-7.31 (m, 5H), 3.34 and 3.35 (2 s, total 3H), 3.10 and 3.16 (2 br s, total 3H), 1.62 and 1.64 (2 s, total 3H), 1.53 and 1.55 (2 s, total 3H), [1.26 (d, J=6.5 Hz) and 1.30 (d, J=6.5 Hz), total 3H], 0.84-0.91 (m, 3H).

Step 2B

Synthesis of 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide, hydrochloride salt (#45)

According to general procedure A, from #43 (176 mg, 0.184 mmol, 1 eq.), dichloromethane (4 mL, 0.05 M) and diethylamine (4 mL) was synthesized the crude desired material, which was purified by reverse phase chromatography (Method C). The resulting trifluoroacetic acid salt was dissolved in methanol, treated with a 4 M solution of hydrochloric acid in dioxane, and concentrated in vacuo to give #45 (100 mg, 70%) as a white solid. LC-MS: m/z 734.6 [M+H$^+$], retention time=0.72 minutes; $^1$H NMR (400 MHz, CD$_3$OD), presumed to be a mixture of rotamers, characteristic signals: δ 7.18-7.31 (m, 5H), 5.41-5.47 and 5.55-5.62 (2 m, total 1H), 3.73 and 3.76 (2 s, total 3H), 3.35 and 3.36 (2 s, total 3H), 3.10 and 3.15 (2 br s, total 3H), 1.62 and 1.64 (2 s, total 3H), 1.53 and 1.55 (2 s, total 3H), [1.25 (d, J=6.6 Hz) and 1.29 (d, J=6.5 Hz), total 3H], 0.84-0.91 (m, 3H).

Preparation of N$^2$-[(1-Aminocyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#47)

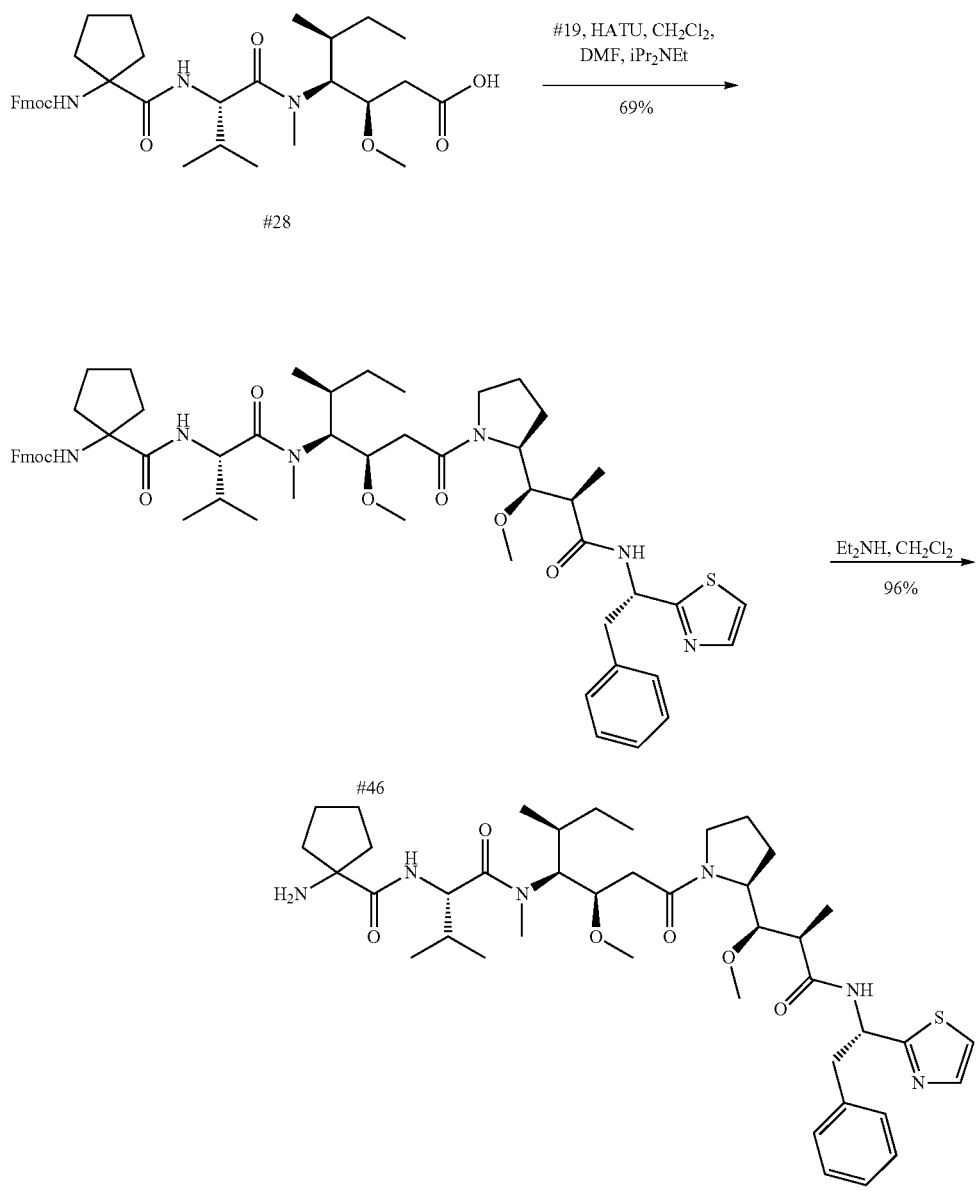

Step 1

Synthesis of N²-[(1-{[(9H-fluoren-9-ylmethoxy)carbonyl]amino}cyclopentyl)-carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#46)

To a solution of #19 (353 mg, 0.944 mmol, 1 eq.) in dichloromethane (10 mL, 0.094 M) were added #28 (600 mg, 0.944 mmol, 0.9 eq.), diisopropylethylamine (498 µL, 2.83 mmol, 3 eq.) and HATU (444 mg, 1.13 mmol, 1.2 eq.). After stirring for two days, the mixture was concentrated in vacuo and the residue was diluted with ethyl acetate (60 mL), washed with 1 M aqueous hydrochloric acid solution and with brine, dried over sodium sulfate, filtered, and concentrated in vacuo. The residue was diluted with dichloromethane and filtered. The filtrate was concentrated under reduced pressure onto silica and purified by silica gel chromatography (Gradient: 40% to 100% ethyl acetate in heptane) to give #46 (644 mg, 69%) as a white solid. LC-MS: m/z 991.8 [M+H⁺], retention time=1.07 minutes; ¹H NMR (400 MHz, DMSO-d₆), presumed to be a mixture of rotamers, characteristic signals: δ 7.89 (br d, J=7.4 Hz, 2H), [7.77 (d, J=3.3 Hz) and 7.79 (d, J=3.3 Hz), total 1H], 7.66-7.76 (m, 2H), [7.62 (d, J=3.3 Hz) and 7.65 (d, J=3.3 Hz), total 1H], 7.37-7.44 (m, 2H), 7.11-7.36 (m, 7H), [5.38 (ddd, J=11, 8, 4 Hz) and 5.48-5.57 (m), total 1H], 3.13, 3.17, 3.18 and 3.24 (4 s, total 6H), 2.90 and 3.00 (2 br s, total 3H), [1.05 (d, J=6.6 Hz) and 1.09 (d, J=6.8 Hz), total 3H].

Step 2

Synthesis of N²-[(1-aminocyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#47)

To a mixture of #46 (500 mg, 0.504 mmol, 1 eq.) in tetrahydrofuran (8 mL, 0.06 M) was added diethylamine (4 mL). After stirring for 18 hours, the reaction mixture was concentrated in vacuo and the residue was purified by silica gel chromatography (Gradient: 0% to 10% methanol in dichloromethane) to give #47 (374 mg, 96%) as a white solid. LC-MS: m/z 769.6 [M+H⁺], retention time=0.70 minutes; ¹H NMR (400 MHz, DMSO-d₆), presumed to be a mixture of rotamers, characteristic signals: δ [8.64 (br d, J=8.4 Hz) and 8.87 (br d, J=8.6 Hz), total 1H], [8.22 (br d, J=9.4 Hz) and 8.26 (br d, J=9.4 Hz), total 1H], [7.77 (d, J=3.3 Hz) and 7.80 (d, J=3.3 Hz), total 1H], [7.63 (d, J=3.1 Hz) and 7.66 (d, J=3.3 Hz), total 1H], 7.13-7.31 (m, 5H), [5.39 (ddd, J=11.1, 8.5, 4.2 Hz) and 5.54 (ddd, J=11.7, 8.8, 4.1 Hz), total 1H], [4.53 (dd, J=9.2, 7.6 Hz) and 4.64 (dd, J=9.2, 6.6 Hz), total 1H], 3.16, 3.20, 3.21 and 3.25 (4 s, total 6H), 2.93 and 3.03 (2 br s, total 3H), [1.05 (d, J=6.8 Hz) and 1.10 (d, J=6.6 Hz), total 3H], 0.73-0.80 (m, 3H).

Preparation of N²-[(1-Anainocyclopropyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#51) and 1-anaino-N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]cyclohexanecarboxamide (#52)

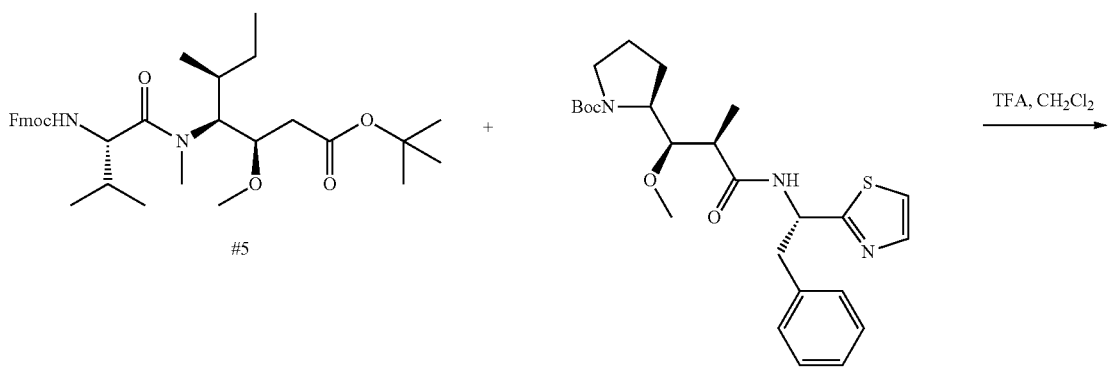

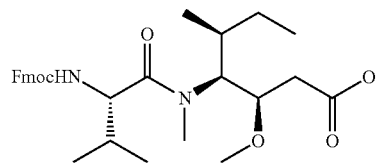
+
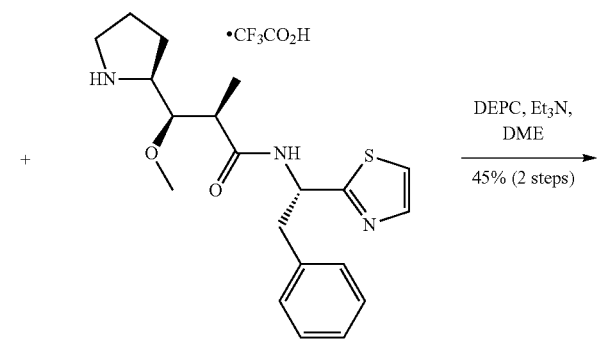
48
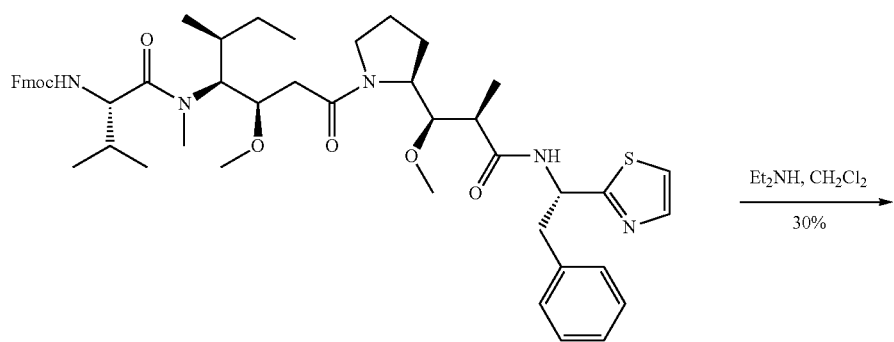
49
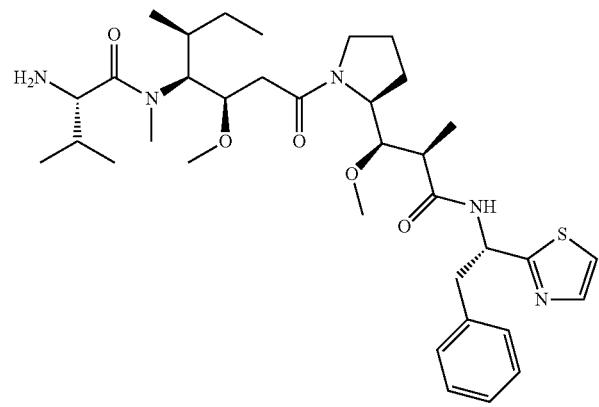
50

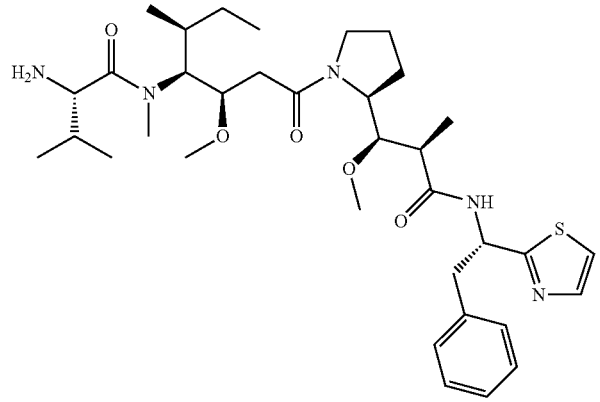
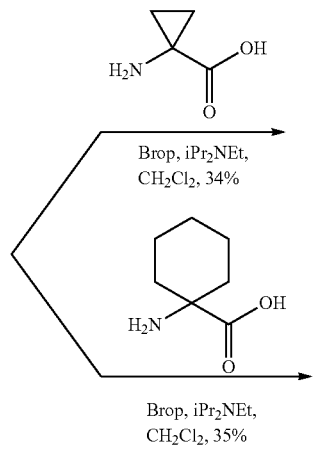
50
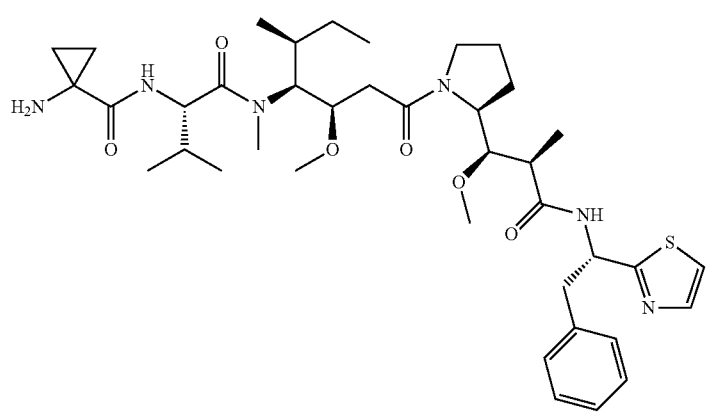
51
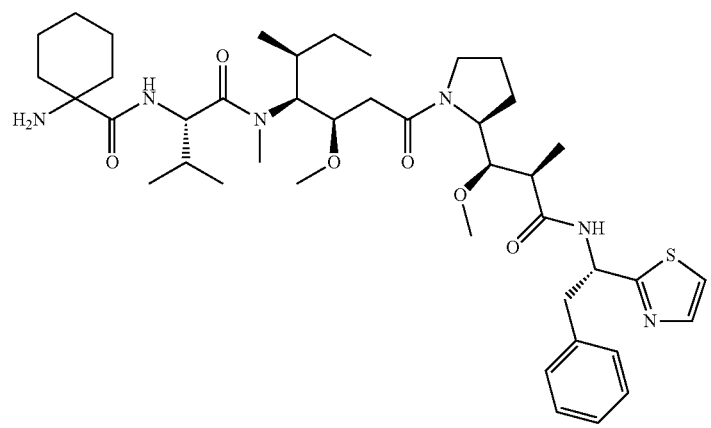
52

Step 1

Synthesis of (2R,3R)-3-methoxy-2-methyl-N-[(1S)-2-phenyl-1-(1,3-thiazol-2-yl)ethyl]-3-[(2S)-pyrrolidin-2-yl]propanamide, trifluoroacetic acid salt and (3R,4S,5S)-4-[{N-[(9H-fluoren-9-ylmethoxy)carbonyl]-L-valyl}(methyl)amino]-3-methoxy-5-methyl-heptanoic acid (#48)

To a solution of #16 (1.0 g, 2.11 mmol, 1 eq.) and #5 (1.22 g, 2.11 mmol, 1 eq.) in dichloromethane (20 mL, 0.1 M) at 0° C. was added trifluoroacetic acid (6 mL). After 3 hours, the mixture was concentrated in vacuo to give the mixture #48 (1.8 g), which was used in the next step without further purification; LC-MS (Protocol K): m/z 374.2 [M+H$^+$], retention time=2.093 minutes, 525.2 [M+H$^+$], retention time=4.875 minutes.

Step 2

Synthesis of N$^2$-[(9H-fluoren-9-ylmethoxy)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#49)

To a solution of #48 (1.8 g, ≤2.1 mmol, 1 eq.) and diethyl cyanophosphonate (DEPC) (0.51 g, 3.2 mmol, 1.5 eq.) in 1,2-dimethoxyethane (30 mL, 0.07 M) at 0° C. was added triethylamine (1.47 mL, 10.6 mmol, 5 eq.). After stirring at room temperature for 2 hours, the mixture was concentrated in vacuo and the residue was purified by silica gel chromatography (10% to 50% ethyl acetate in petroleum ether) to give #49 (0.8 g, 45%). R$_f$ 0.6 (10% methanol in dichloromethane); LC-MS (Protocol K): m/z 881.3 [M+H$^+$], 903.3 [M+Na$^+$], retention time=4.837 minutes.

Step 3

Synthesis of N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#50)

According to general procedure A, from #49 (0.70 g, 0.79 mmol, 1 eq.), dichloromethane (15 mL, 0.05 M) and diethylamine (10 mL) was synthesized #50 (160 mg, 30%) after purification by silica gel chromatography (Gradient: 0% to 5% methanol in dichloromethane). R$_f$ 0.4 (10% methanol in dichloromethane); LC-MS (Protocol K): m/z 658.3 [M+H$^+$], 680.3 [M+Na$^+$], retention time=2.760 minutes.

Step 4A

Synthesis of N$^2$-[(1-aminocyclopropyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#51)

To a solution of #50 (100 mg, 0.15 mmol, 1 eq.), bromotris(dimethylamino)phosphonium hexafluorophosphate (Brop, 70 mg, 0.18 mmol, 1.2 eq.) and diisopropylethylamine (0.08 mL, 0.45 mmol, 3 eq.) in dichloromethane (15 mL, 0.01 M) at 0° C. was added 1-aminocyclopropanecarboxylic acid (18 mg, 0.18 mmol, 1.2 eq.). After 2 hours, the mixture was quenched with water and extracted twice with ethyl acetate. The combined organic layers were dried over sodium sulfate, filtered, and concentrated in vacuo. The residue was purified by silica gel chromatography (Gradient: 0% to 5% methanol in dichloromethane) to give #51 (45 mg, 34%). R$_f$ 0.5 (10% methanol in dichloromethane). LC-MS (Protocol L): m/z 741.44 [M+H$^+$]; $^1$H NMR (300 MHz, DMSO-d$_6$), presumed to be a mixture of rotamers, characteristic signals: δ [8.64 (br d, J=8 Hz) and 8.88 (br d, J=8 Hz), total 1H], [8.16 (br d, J=9 Hz) and 8.22 (br d, J=10 Hz), total 1H], [7.77 (d, J=3.5 Hz) and 7.79 (d, J=3.5 Hz), total 1H], [7.63 (d, J=3.5 Hz) and 7.65 (d, J=3 Hz), total 1H], 7.10-7.32 (m, 5H), 5.33-5.60 (m, 1H), 3.16, 3.20, 3.21 and 3.26 (4 s, total 6H), 2.93 and 3.02 (2 br s, total 3H), [1.05 (d, J=6.3 Hz) and 1.10 (d, J=6.3 Hz), total 3H].

Step 4B

Synthesis of 1-amino-N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl] (methyl)amino}-3-methyl-1-oxobutan-2-yl]cyclohexanecarboxamide (#52)

To a solution of #50 (120 mg, 0.18 mmol, 1 eq.), Brop (84 mg, 0.21 mmol, 1.2 eq.) and diisopropylethylamine (0.1 mL, 0.54 mmol, 3 eq.) in dichloromethane (15 mL, 0.009 M) at 0° C. was added 1-aminocyclohexanecarboxylic acid (31 mg, 0.21 mmol, 1.2 eq.). After 2 hours, the mixture was quenched with water and extracted twice with ethyl acetate. The combined organic layers were dried over sodium sulfate, filtered, and concentrated in vacuo. The residue was purified by silica gel chromatography (Gradient: 0% to 5% methanol in dichloromethane) to give #52 (50 mg, 35%). R$_f$ 0.6 (10% methanol in dichloromethane). LC-MS (Protocol K): m/z 783.79 [M+H$^+$]; $^1$H NMR (400 MHz, DMSO-d$_6$), presumed to be a mixture of rotamers, characteristic signals: δ [8.64 (br d, J=8 Hz) and 8.87 (br d, J=9 Hz), total 1H], 8.18-8.28 (m, 1H), [7.77 (d, J=3.5 Hz) and 7.80 (d, J=3.3 Hz), total 1H], [7.63 (d, J=3.3 Hz) and 7.66 (d, J=3.3 Hz), total 1H], 7.12-7.31 (m, 5H), 5.35-5.43 and 5.49-5.57 (2 m, total 1H), [4.51 (dd, J=9, 8 Hz), and 4.61 (dd, J=9, 7 Hz), total 1H], 3.16, 3.19, 3.21 and 3.25 (4 s, total 6H), 2.93 and 3.02 (2 br s, total 3H), [1.05 (d, J=6.8 Hz) and 1.10 (d, J=6.8 Hz), total 3H].

Preparation of 2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

dimethylformamide (3 mL), the amine #19 (2.5 g, 3.4 mmol, 1.2 eq.), HATU (1.29 g, 3.38 mmol, 1.2 eq.) and triethylamine (1.57 mL, 11.3 mmol, 4 eq.) was synthesized the crude desired material, which was purified by silica gel chromatography (Gradient: 0% to 55% acetone in heptane), producing #53 (2.42 g, 74%) as a solid. LC-MS: m/z 965.7 [M+H$^+$],

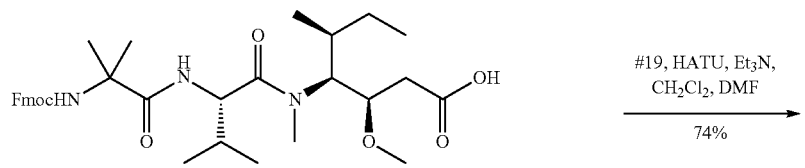

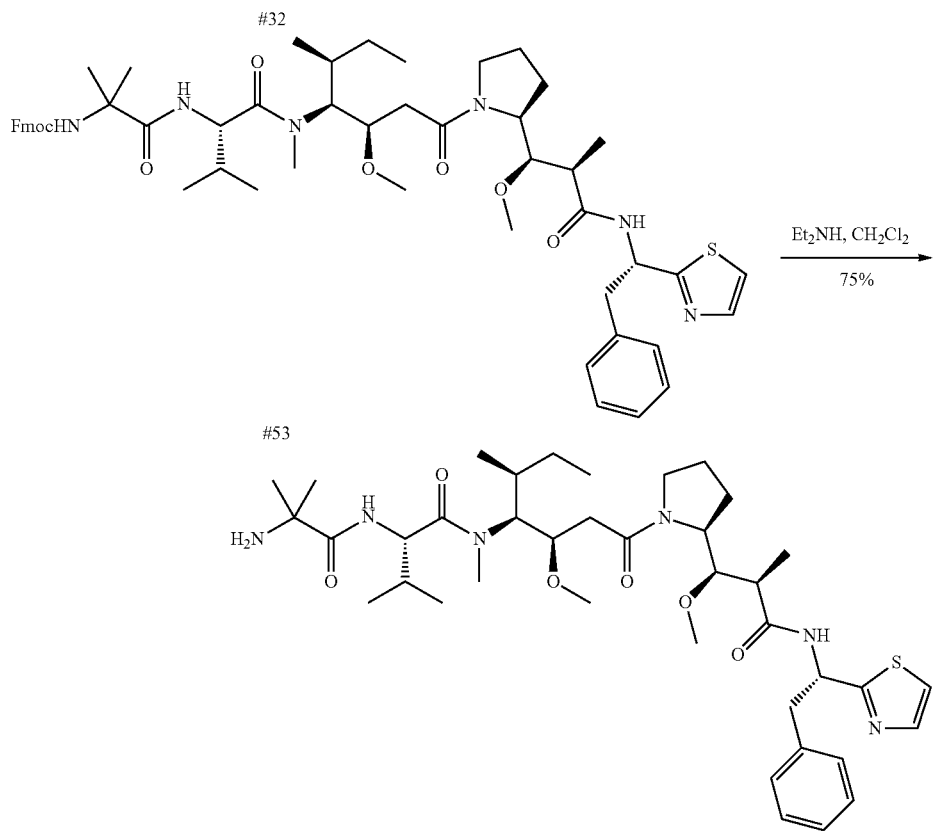

Step 1

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53)

According to general procedure D, from #32 (2.05 g, 2.83 mmol, 1 eq.) in dichloromethane (20 mL, 0.1 M) and N,N-

987.6 [M+Na$^+$], retention time=1.04 minutes; HPLC (Protocol A): m/z 965.4 [M+H$^+$], retention time=11.344 minutes (purity >97%); $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24

(4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2

Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

According to general procedure A, from #53 (701 mg, 0.726 mmol) in dichloromethane (10 mL, 0.07 M) was synthesized the crude desired material, which was purified by silica gel chromatography (Gradient: 0% to 10% methanol in dichloromethane). The residue was diluted with diethyl ether and heptane and was concentrated in vacuo to afford #54 (406 mg, 75%) as a white solid. LC-MS: m/z 743.6 [M+H$^+$], retention time=0.70 minutes; HPLC (Protocol A): m/z 743.4 [M+H$^+$], retention time=6.903 minutes, (purity >97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

Preparation of 2-Methylalanyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, acetic acid salt (#56)

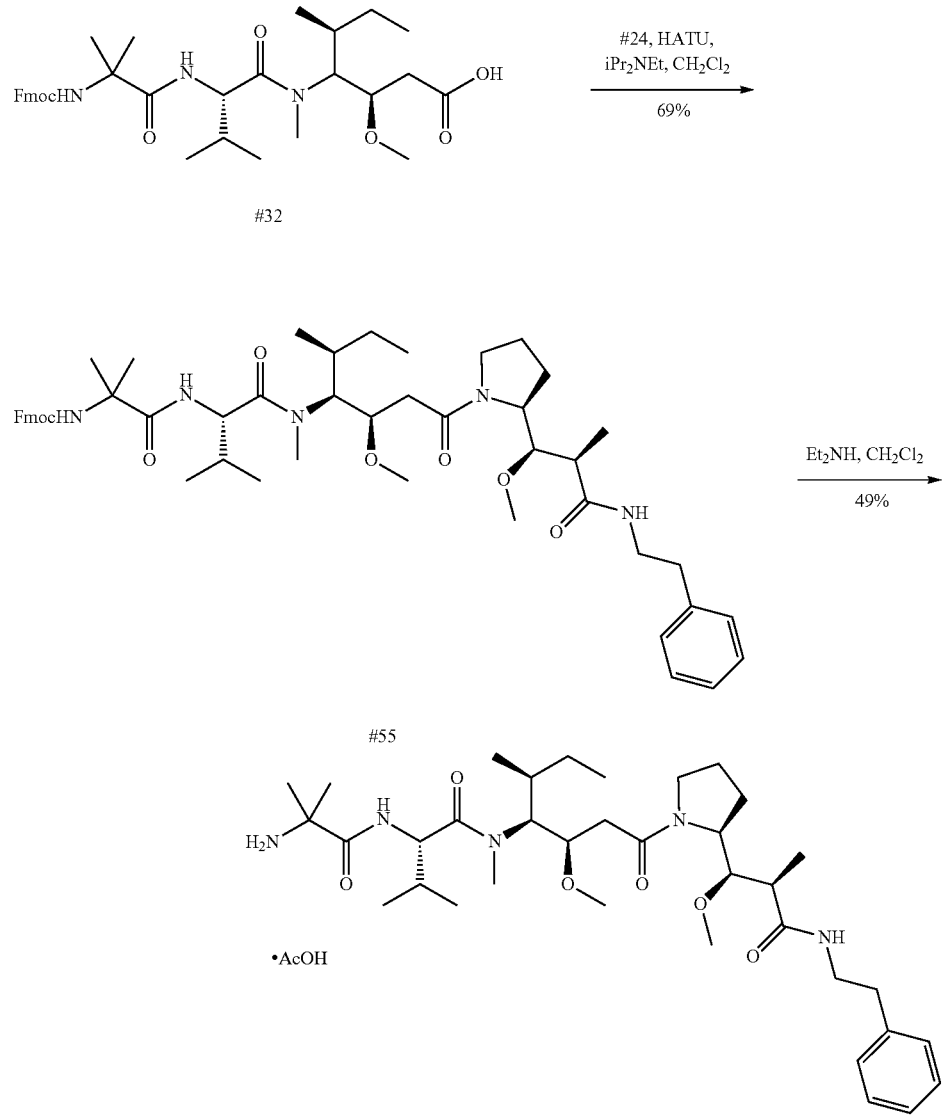

Step 1

Synthesis of N-[(9H-fluoren-9-ylmethoxy)carbonyl]-2-methylalanyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide (#55)

To a solution of #24 (104 mg, 0.256 mmol, 1 eq.) in dichloromethane (10 mL, 0.094 M) were added #32 (156 mg, 0.256 mmol, 0.9 eq.), diisopropylethylamine (135 μL, 0.768 mmol, 3 eq.) and HATU (120 mg, 0.307 mmol, 1.2 eq.). After stirring for 18 hours, the mixture was concentrated in vacuo and the residue was diluted with ethyl acetate (10 mL), washed with 1 M aqueous hydrochloric acid solution (2×5 mL) and with brine, dried over sodium sulfate, filtered, and concentrated in vacuo. The residue was diluted with dichloromethane and filtered. The filtrate was concentrated under reduced pressure onto silica and purified by silica gel chromatography (Gradient: 0% to 100% ethyl acetate in heptane) to give #55 (44 mg, 19%) as a white solid. LC-MS: m/z 884.5 [M+2H$^+$], retention time=1.04 minutes.

Step 2

Synthesis of 2-methylalanyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, acetic acid salt (#56)

To a mixture of #55 (44 mg, 0.050 mmol, 1 eq.) in tetrahydrofuran (1 mL, 0.05 M) was added diethylamine (0.5 mL). After stirring for 18 hours, the reaction mixture was concentrated in vacuo and the residue was purified by reverse phase chromatography (Method B) to give #56 (16.2 mg, 49%) as a solid. LC-MS: m/z 660.8 [M+H$^+$], retention time=2.23 minutes; HPLC (Protocol A): m/z 660.5 [M+H$^+$], 682.4 [M+Na$^+$], retention time=6.865 minutes.

Preparation of 2-Methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide (#60)

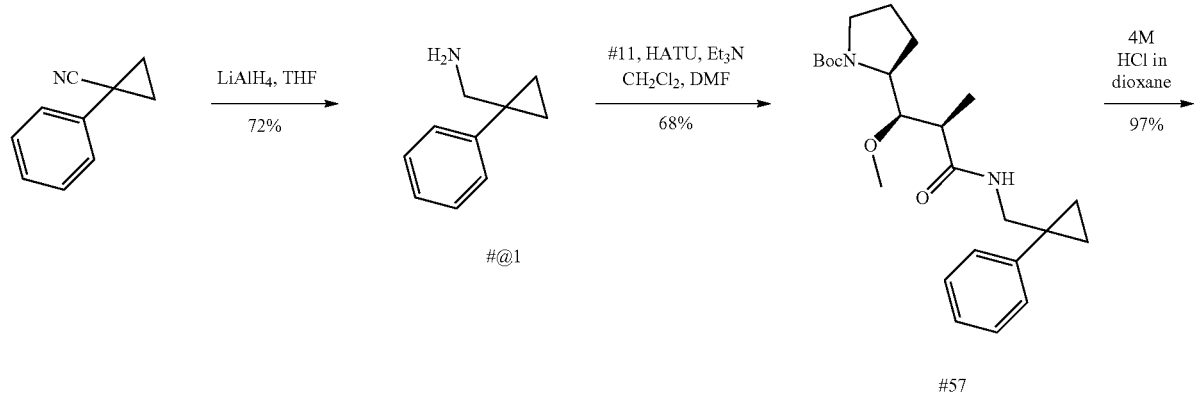

@1

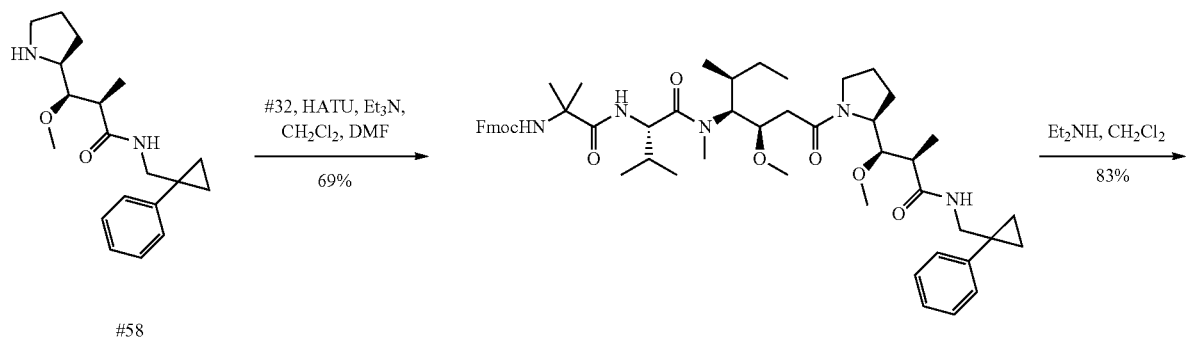

58

59

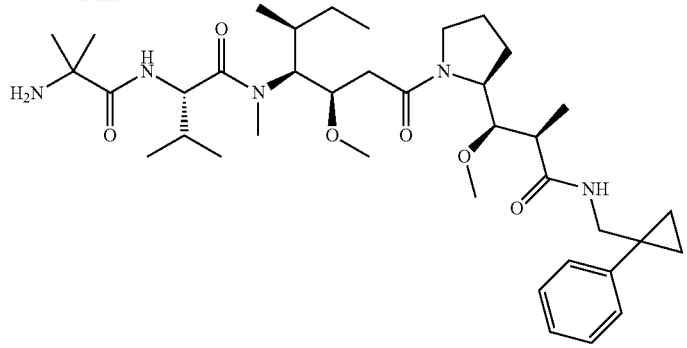

60

Step 1

Synthesis of 1-(1-phenylcyclopropyl)methanamine #@1

To a solution of 1-phenylcyclopropanecarbonitrile (50 g, 0.34 mol, 1 eq.) in tetrahydrofuran (500 mL, 0.7 M) at 0° C. was added lithium aluminum hydride (23 g, 0.35 mol, 1.03 eq.). The reaction mixture was stirred at 0° C. for one hour and then at reflux for one hour. The reaction mixture was then cooled down and quenched with water (23 mL) and a 15% aqueous sodium hydroxide solution (69 mL). The mixture was filtered and concentrated in vacuo to afford #*1 (36 g, 72%). LC-MS: m/z 148.1 [M+H$^+$], retention time=0.86 minutes; $^1$H NMR (400 MHz, CDCl$_3$) δ 7.2-7.4 (m, 5H), 2.78 (s, 2H), 1.19 (br s, 2H), 0.72-0.84 (m, 4H).

Step 2

Synthesis of tert-butyl (2S)-2-[(1R,2R)-1-methoxy-2-methyl-3-oxo-3-{[(1-phenylcyclopropyl)methyl]amino}propyl]pyrrolidine-1-carboxylate (#57)

According to general procedure D, from #11 (2.15 g, 7.48 mmol, 1.1 eq.) in dichloromethane (20 mL, 0.3 M) and N,N-dimethylformamide (4 mL), 1-(1-phenylcyclopropyl)methanamine #@1 (1.001 g, 6.799 mmol, 1 eq.), HATU (3.10 g, 8.16 mmol, 1.2 eq.) and triethylamine (2.84 mL, 20.4 mmol, 3 eq.) was synthesized the crude desired material, which was purified by silica gel chromatography (Gradient: 0% to 100% ethyl acetate in heptane), producing #57 (1.93 g, 68%) as a solid. HPLC (Protocol A at 45° C.): m/z 417.3 [M+H$^+$], retention time=10.575 minutes; $^1$H NMR (400 MHz, DMSO-d$_6$), presumed to be a mixture of rotamers: δ 7.75-7.81 (m, 1H), 7.20-7.27 (m, 4H), 7.12-7.19 (m, 1H), 3.33-3.62 and 3.71-3.80 (br multiplets, total 4H), 3.28 (s, 3H), 2.97-3.17 (br m, 2H), 2.14-2.24 (m, 1H), 1.67-1.80 (br m, 2H), 1.45-1.65 (m, 2H), 1.41 (s, 9H), 1.00 (d, J=6.6 Hz, 3H), 0.67-0.93 (m, 4H).

Step 3

Synthesis of (2R,3R)-3-methoxy-2-methyl-N-[(1-phenylcyclopropyl)methyl]-3-[(2S)-pyrrolidin-2-yl]propanamide, hydrochloride salt (#58)

According to general procedure C, from #57 (566 mg, 1.36 mmol, 1 eq.) in dioxane (4 mL, 0.3 M) and 4 M hydrochloric acid solution in dioxane (4 mL, 16 mmol, 11.7 eq.) was synthesized #58 (466 mg, 97%); LC-MS: m/z 318.2 [M+H$^+$], 339.2 [M+Na$^+$], retention time=0.56 minute; $^1$H NMR (400 MHz, DMSO-d$_6$) δ 9.53 (br s, 1H), 8.48 (br s, 1H), 8.11 (br dd, J=5.7, 5.6 Hz, 1H), 7.23-7.30 (m, 4H), 7.14-7.21 (m, 1H), 3.58 (dd, J=7.5, 3.9 Hz, 1H), 3.50 (dd, J=13.7, 6.3 Hz, 1H), 3.34 (s, 3H), 3.21-3.29 (br m, 1H), 3.18 (dd, J=13.8, 5.0 Hz, 1H), 3.04-3.13 (br m, 2H), 2.42-2.50 (m, 1H), 1.56-1.89 (m, 4H), 1.04 (d, J=6.9 Hz, 3H), 0.71-0.91 (m, 4H).

Step 4

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide (#59)

According to general procedure D, from #32 (550 mg, 0.902 mmol, 1 eq.), #58 (350 mg, 0.992 mmol, 1.1 eq.) dichloromethane (10 mL, 0.08 M) and N,N-dimethylformamide (2 mL), HATU (446 mg, 1.17 mmol, 1.3 eq.) and triethylamine (0.503 mL, 3.61 mmol, 4 eq.) was synthesized the crude desired material, which was purified by silica gel chromatography (Gradient: 0% to 30% acetone in heptane), producing #59 (618 mg, 69%) as an off-white solid. LC-MS: m/z 908.7 [M+H$^+$], 930.7 [M+Na$^+$], retention time=1.07 minutes; HPLC (Protocol B at 45° C.): m/z 908.5 [M+H$^+$], retention time=8.721 minutes (purity >97%); $^1$H NMR (400 MHz, DMSO-d$_6$), presumed to be a mixture of rotamers, characteristic signals: δ 7.89 (d, J=7.5 Hz, 2H), 7.38-7.44 (m, 2H), 7.30-7.36 (m, 2H), [4.49 (dd, J=8.5, 7.8 Hz) and 4.59 (dd, J=8.7, 6.9 Hz), total 1H], 4.18-4.26 (m, 3H), 3.93-4.01 (br m, 1H), 3.23 and 3.26 (2 s, total 3H), 3.16 and 3.16 (2 s, total 3H), 2.91 and 3.05 (2 br s, total 3H), 1.36 and 1.37 (2 br s, total 3H), 1.30 and 1.32 (2 br s, total 3H), [1.00 (d, J=6.7 Hz) and 1.02 (d, J=6.6 Hz), total 3H], 0.67-0.78 (m, 7H).

Step 5

Synthesis of 2-methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide (#60)

According to general procedure A, from #59 (605 mg, 0.666 mmol, 1 eq.) dichloromethane (10 mL, 0.067 M) and diethylamine (10 mL) was synthesized #60 (379 mg, 83%); HPLC (Protocol A at 45° C.) m/z 685.5 [M+H⁺], retention time=7.072 minutes; $^1$H NMR (400 MHz, DMSO-d$_6$), presumed to be a mixture of rotamers, characteristic signals: δ [8.03 (br d, J=9.6 Hz) and 8.07 (br d, J=9.4 Hz), total 1H], [7.74 (br dd, J=7, 4 Hz) and 7.99 (br dd, J=5.9, 5.7 Hz), total 1H], 7.20-7.27 (m, 4H), 7.11-7.17 (m, 1H), [4.49 (dd, J=9, 7 Hz) and 4.58 (dd, J=9, 7.5 Hz), total 1H], 3.96-4.04 (br m, 1H), 3.24 and 3.27 (2 s, total 3H), 3.18 and 3.19 (2 s, total 3H), 2.93 and 3.07 (2 br s, total 3H), 1.20 and 1.21 (2 s, total 3H), 1.12 and 1.14 (2 s, total 3H), [1.00 (d, J=6.7 Hz) and 1.03 (d, J=6.7 Hz), total 3H].

Preparation of 2-Methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide (#66)

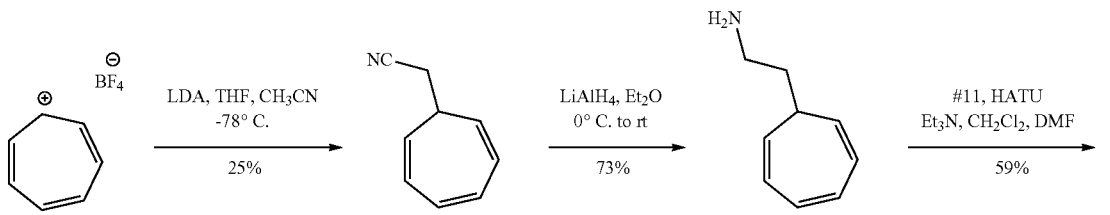

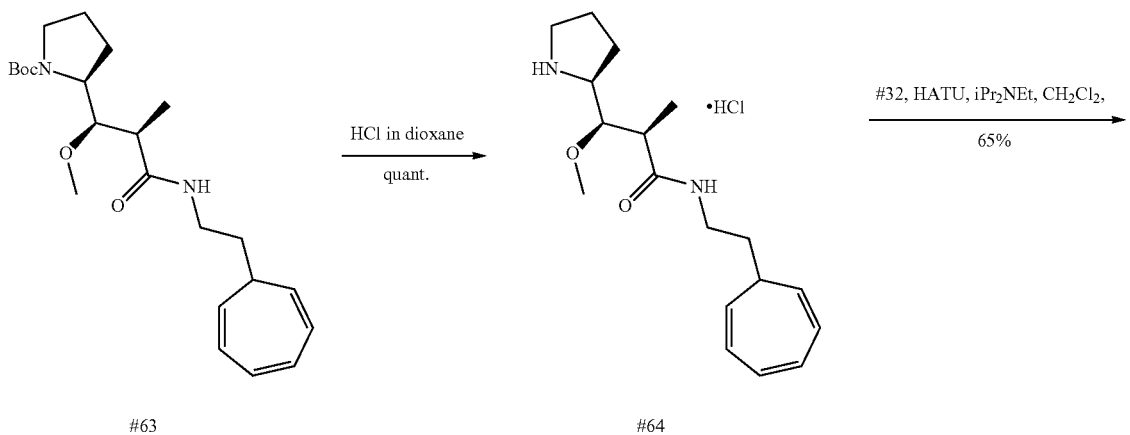

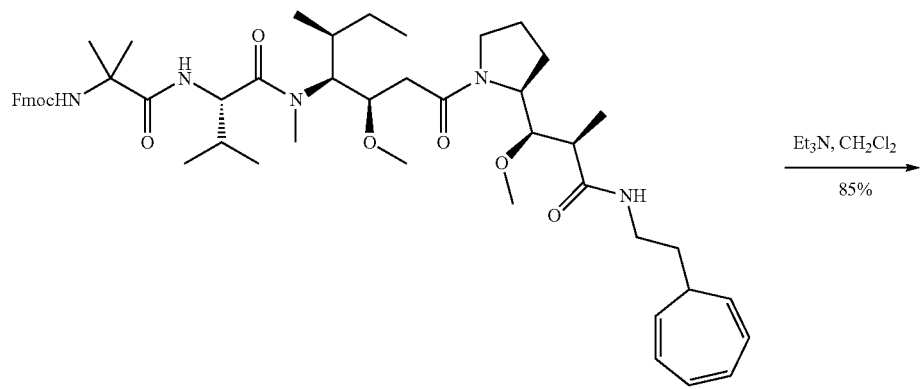

-continued

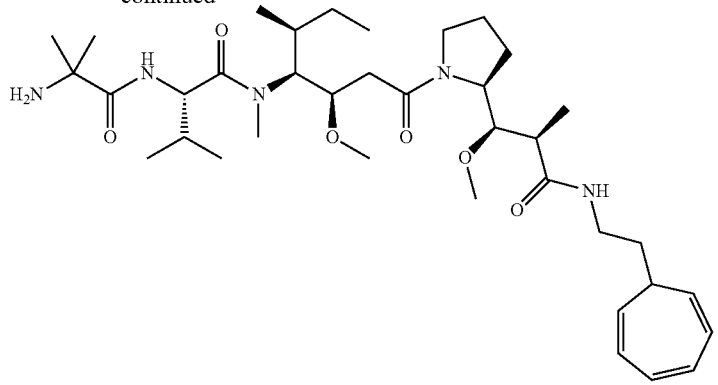

66

Step 1

Synthesis of cyclohepta-2,4,6-trien-1-ylacetonitrile (#61)

To a solution of anhydrous acetonitrile (3.12 mL, 56.2 mmol, 1 eq.) in tetrahydrofuran (281 mL, 0.2 M) was added lithium diisopropylamine (1.8 M in heptane/ethylbenzene/tetrahydrofuran, 31.2 mL, 56.2 mmol, 1 eq.) at −78° C. After 20 minutes at −78° C., tropylium tetrafluoroborate (10 g, 56 mmol, 1 eq.) was added. After 10 minutes, the reaction was concentrated in vacuo and the residue was diluted with ethyl acetate and washed with water. The organic layer was dried over sodium sulfate, filtered, and concentrated in vacuo to provide a brown oil, which was purified by silica gel chromatography (Gradient: 0% to 10% ethyl acetate in heptane) to provide #61 (1.88 g, 25%) as a yellow oil. $^1$H NMR (400 MHz, CDCl$_3$) δ 6.69-6.71 (m, 2H), 6.27-6.32 (m, 2H), 5.28-5.33 (m, 2H), 2.61 (d, J=7.2 Hz, 2H), 2.26-2.34 (m, 1H).

Step 2

Synthesis of 2-(cyclohepta-2,4,6-trien-1-yl)ethanamine (#62)

To a suspension of lithium aluminum hydride (911 mg, 24.0 mmol, 1.4 eq.) in anhydrous diethyl ether (75 mL, 0.23 M) at 0° C. was slowly added, drop-wise over 15 minutes, a solution of #61 (2.25 g, 17.2 mmol, 1 eq.) in diethyl ether (15 mL). The reaction was warmed to room temperature. After 5 hours, the reaction was cooled to 0° C. and quenched by addition of water (1 mL), then filtered through a small pad of Celite and washed with methanol. The filtrate was dried over sodium sulfate, filtered, and concentrated in vacuo to provide #62 (1.683 g, 73%) as a golden oil. LC-MS: m/z 136.1 [M+H$^+$], retention time=0.23 minutes; $^1$H NMR (400 MHz, CDCl$_3$) δ 6.64-6.67 (m, 2H), 6.16-6.21 (m, 2H), 5.16-5.21 (m, 2H), 2.84-2.89 (m, 2H), 1.86-1.92 (m, 2H), 1.62-1.70 (m, 1H).

Step 3

Synthesis of tert-butyl (2S)-2-[(1R,2R)-3-{[2-(cyclohepta-2,4,6-trien-1-yl)ethyl]amino}-1-methoxy-2-methyl-3-oxopropyl]pyrrolidine-1-carboxylate (#63)

To a solution of #11 (3.57 g, 12.4 mmol, 1 eq.) in dichloromethane (100 mL, 0.1 M) and N,N-dimethylformamide (4 mL) was added HATU (5.36 g, 13.7 mmol, 1.1 eq.). After 20 minutes, triethylamine (5.20 mL, 37.3 mmol, 3 eq.) was added, followed by #62 (1.68 g, 12.4 mmol, 1 eq.), and the mixture was stirred for 18 hours. The reaction was concentrated in vacuo and the residue was taken up in ethyl acetate and washed with water (50 mL). The aqueous layer was back-extracted with ethyl acetate (3 times) and the combined organic layers were dried, filtered, and concentrated in vacuo to provide a brown oil, which was purified by silica gel chromatography (Gradient: 0% to 100% ethyl acetate in heptane) to provide #63 (2.95 g, 59% yield) as a viscous oil. LC-MS: m/z 405.4 [M+H$^+$], 427.4 [M+Na$^+$], retention time=0.75 minutes; $^1$H NMR (400 MHz, CDCl$_3$), presumed to be a mixture of rotamers: δ 6.63-6.68 (m, 2H), 6.16-6.23 (m, 2H), 5.19 (br dd, J=9.0, 5.8 Hz, 2H), 3.51-3.63 and 3.71-3.90 (2 br multiplets, total 3H), 3.42 (s, 3H), 3.18-3.29 and 3.34-3.47 (2 br multiplets, total 3H), 2.27-2.45 (br m, 1H), 1.6-2.00 (m, 7H), 1.47 and 1.50 (2 br s, total 9H), 1.16-1.29 (br m, 3H).

Step 4

Synthesis of (2R,3R)—N-[2-(cyclohepta-2,4,6-trien-1-yl)ethyl]-3-methoxy-2-methyl-3-[(2S)-pyrrolidin-2-yl]propanamide, hydrochloride salt (#64)

Intermediate #63 (400 mg, 0.989 mmol, 1 eq.) was treated with a 4 M solution of hydrochloric acid in dioxane (10 mL, 40 mmol, 40 eq.). After 1 hour, the reaction mixture was concentrated in vacuo and the residue was taken up in dichloromethane and washed with 1 M sodium hydroxide solution. The aqueous layer was back-extracted with dichloromethane and the combined organic layers were dried over sodium sulfate, filtered, and concentrated in vacuo to provide #64 (301 mg, quantitative) as a brown oil, which slowly began to solidify upon standing. LC-MS: m/z 305.3 [M+H$^+$], retention time=0.54 minutes; HPLC (Protocol G): retention time=4.848 minutes; $^1$H NMR (400 MHz, CDCl$_3$), characteristic signals: δ 6.64-6.67 (m, 2H), 6.16-6.22 (m, 2H), 6.08-6.14 (br m, 1H), 5.16-5.22 (m, 2H), 3.44 (s, 3H), 3.31 (dd, J=6.3, 4.5 Hz, 1H), 2.98-3.04 (m, 1H), 2.94 (ddd, J=10.5, 7.2, 5.6 Hz, 1H), 2.81 (ddd, J=10.5, 7.7, 6.7 Hz, 1H), 2.57 (qd, J=7.1, 4.5 Hz, 1H), 1.90-1.97 (m, 2H), 1.49-1.55 (m, 1H), 1.18 (d, J=7.1 Hz, 3H).

Step 5

Synthesis of N-[(9H-fluoren-9-ylmethoxy)carbonyl]-2-methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide (#65)

According to general procedure D, from #32 (678 mg, 0.937 mmol, 1 eq.) in dichloromethane (9.37 mL, 0.1 M), the amine #64 (300 mg, 0.985 mmol, 1.1 eq.), HATU (427 mg, 1.12 mmol, 1.2 eq.) and diisopropylethylamine (494 μL, 2.81 mmol, 3 eq.) was synthesized the crude desired material, which was purified by silica gel chromatography (Gradient: 0% to 50% acetone in heptane), producing #65 (546 mg, 65%) as a solid. LC-MS: m/z 896.7 [M+H$^+$], 918.7 [M+Na$^+$], retention time=1.06 minutes.

Step 6

Synthesis of 2-methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide (#66)

To a solution of #65 (540 mg, 0.603 mmol, 1 eq.) in dichloromethane (10 mL, 0.06 M) was added triethylamine (10 mL) and the reaction mixture was stirred for 2 hours. The mixture was concentrated in vacuo and the residue was purified by silica gel chromatography (Gradient: 0% to 10% methanol in dichloromethane) to give #66 (347 mg, 85%) as a colorless solid. HPLC (Protocol A at 45° C.): m/z 674.5 [M+H$^+$], retention time=7.015 minutes. $^1$H NMR (400 MHz, DMSO-d$_6$), presumed to be a mixture of rotamers, characteristic signals: δ [8.03 (br d, J=9 Hz) and 8.05 (br d, J=9 Hz), total 1H], [7.77 (br dd, J=5.5, 5.5 Hz) and 7.98 (br dd, J=5.5, 5.5 Hz), total 1H], 6.54-6.65 (m, 2H), 6.10-6.19 (m, 2H), 5.11-5.19 (m, 2H), [4.48 (dd, J=9, 8 Hz) and 4.54 (dd, J=9, 7.5 Hz), total 1H], 3.94-4.04 (br m, 1H), 3.26 and 3.29 (2 s, total 3H), 3.17 and 3.19 (2 s, total 3H), 2.93 and 3.06 (2 br s, total 3H), 1.20 and 1.21 (2 s, total 3H), 1.12 and 1.13 (2 s, total 3H), [1.04 (d, J=6.8 Hz) and 1.07 (d, J=6.7 Hz), total 3H].

Preparation of 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#69) and 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#70)

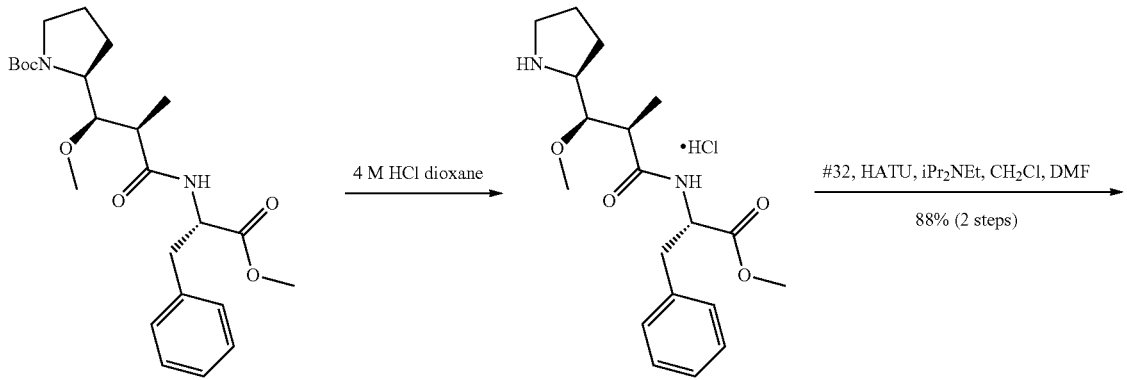

37    #67

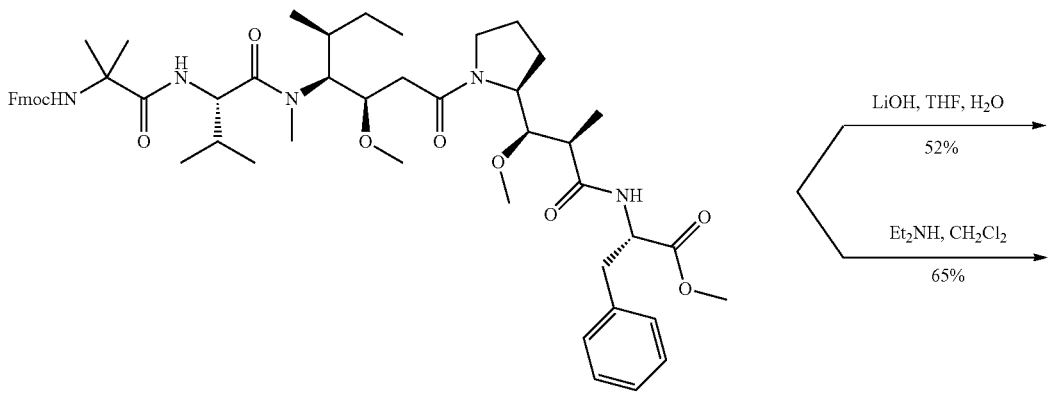

68

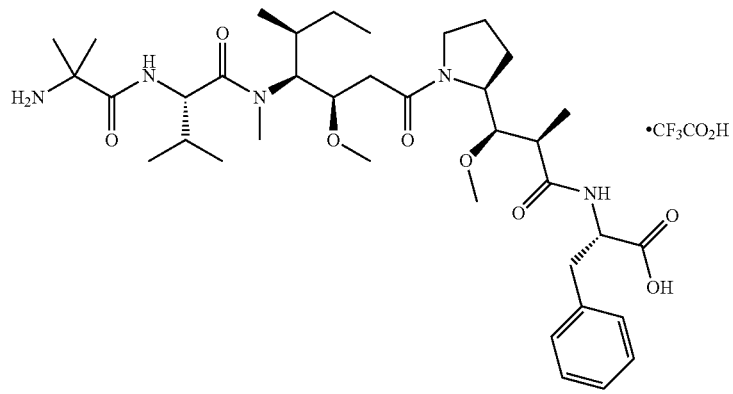

69

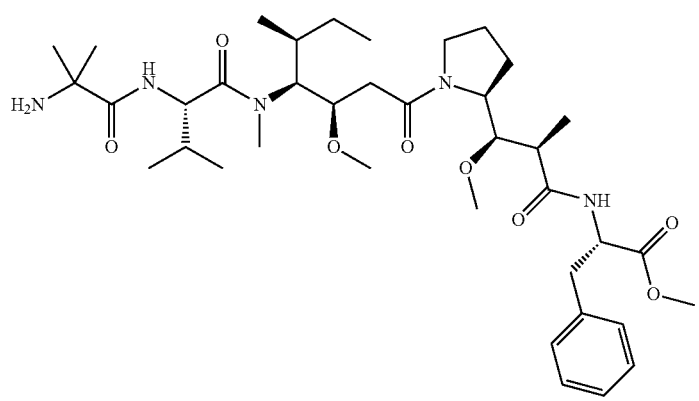

70

Step 1

Synthesis of methyl N-{(2R,3R)-3-methoxy-2-methyl-3-[(2S)-pyrrolidin-2-yl]propanoyl}-L-phenylalaninate, hydrochloride salt (#67)

According to general procedure C, from #37 (2.39 g, 5.33 mmol, 1 eq.), dioxane (10 mL, 0.53 M) and a 4 M hydrochloric acid solution in dioxane (10 mL, 40 mmol, 7.5 eq.) was synthesized #67 (2.21 g) as a white solid, which was used in the next step without further purification. LC-MS: m/z 349.2 [M+H$^+$], retention time=0.53 minutes; $^1$H NMR (400 MHz, DMSO-d$_6$) δ 9.45-9.58 (br m, 1H), 8.63 (d, J=8.1 Hz, 1H), 8.51-8.62 (br m, 1H), 7.25-7.33 (m, 4H), 7.18-7.25 (m, 1H), 4.50 (ddd, J=10.8, 8.1, 4.5 Hz, 1H), 3.65 (s, 3H), 3.54 (dd, J=6.8, 4.5 Hz, 1H), 3.20 (s, 3H), 3.11 (dd, J=13.8, 4.5 Hz, 1H), 2.99-3.14 (br m, 3H), 2.89 (dd, J=13.8, 10.9 Hz, 1H), 2.44-2.50 (m, 1H, assumed; partially obscured by solvent peak), 1.77-1.89 (m, 1H), 1.60-1.73 (m, 2H), 1.46-1.57 (m, 1H), 1.05 (d, J=6.8 Hz, 3H).

Step 2

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#68)

According to general procedure D, from #32 (353 mg, 0.488 mmol, 1 eq.) in dichloromethane (10 mL, 0.04 M), amine #67 (271 mg, ≤0.588 mmol, 1.3 eq.), HATU (223 mg, 0.586 mmol, 1.2 eq.) and diisopropylethylamine (238 μL, 1.71 mmol, 3.5 eq.) was synthesized the crude desired material, which was purified by silica gel chromatography (Gradient: 0% to 40% acetone in heptane), affording #68 (404 mg, 88% over two steps) as a solid. LC-MS: m/z 940.7 [M+H$^+$], 962.7 [M+Na$^+$], retention time=1.04 minutes; HPLC (Protocol C): retention time=9.022 minutes; $^1$H NMR (400 MHz, DMSO-d$_6$), presumed to be a mixture of rotamers, characteristic signals: δ [8.25 (br d, J=8 Hz) and 8.48 (br d, J=8 Hz), total 1H], 7.89 (d, J=7.4 Hz, 2H), 7.67-7.75 (m, 2H), 7.38-7.44 (m, 2H), 7.31-7.36 (m, 2H), 7.14-7.24 (m, 5H), 4.43-4.69 (m, 3H), 4.17-4.26 (m, 3H), 3.91-3.99 (br m, 1H), 3.63 and 3.65 (2 s, total 3H), 3.19 and 3.24 (2 s, total 3H), 3.14 and 3.15 (2 s, total 3H), 2.90 and 2.99 (2 br s, total 3H), 1.36 and 1.37 (2 br s, total 3H), 1.30 and 1.32 (2 s, total 3H), [1.02 (d, J=6.8 Hz) and 1.06 (d, J=6.6 Hz), total 3H].

Step 3A

Synthesis of 2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#69)

To a solution of #68 (143 mg, 0.152 mmol, 1 eq.) in tetrahydrofuran (5 mL, 0.02 M) was added a solution of lithium hydroxide (9.10 mg, 0.378 mmol, 2.5 eq.) in water (3 mL). After 5 hours, the reaction was concentrated in vacuo, azeotroped three times with heptane, dissolved in dimethyl sulfoxide (2.2 mL) and purified by reverse phase chromatography (Method C) to give #69 (56 mg, 52%). HPLC (Protocol A at 45° C.): 704.4 [M+H$^+$], retention time=6.623 minutes; $^1$H NMR (400 MHz, DMSO-d$_6$), presumed to be a mixture of rotamers, characteristic signals: δ 8.08-8.22 and 8.37-8.49 (2 m, total 5H), 7.12-7.28 (m, 5H), 3.18, 3.20 and 3.24 (3 s, total 6H), 2.95 and 3.04 (2 br s, total 3H), 1.52 and 1.53 (2 s, total 3H), 1.39 and 1.41 (2 s, total 3H), [1.02 (d, J=6.8 Hz) and 1.05 (d, J=6.6 Hz), total 3H], 0.74-0.81 (m, 3H).

Step 3B

Synthesis of 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#70)

According to general procedure A, from #68 (240 mg, 0.255 mmol, 1 eq.), dichloromethane (10 mL, 0.026 M) and diethylamine (10 mL) was synthesized #70 (120 mg, 65%) as a white solid/glass mix after silica gel chromatography (Gradient: 0% to 10% methanol in dichloromethane). HPLC (Protocol A at 45° C.): m/z 762.7 [M+H$^+$], 740.4 [M+Na$^+$], retention time=6.903 minutes; $^1$H NMR (400 MHz, DMSO-d$_6$), presumed to be a mixture of rotamers, characteristic signals: δ [8.26 (d, J=8.1 Hz) and 8.49 (d, J=8.3 Hz), total 1H], [8.03 (d, J=9.5 Hz) and 8.07 (d, J=9.5 Hz), total 1H], 7.14-7.27 (m, 5H), 3.63 and 3.67 (2 s, total 3H), 3.16, 3.18, 3.20 and 3.25 (4 s, total 6H), 2.92 and 3.01 (2 br s, total 3H), 1.20 and 1.22 (2 s, total 3H), 1.12 and 1.13 (2 s, total 3H), [1.02 (d, J=6.8 Hz) and 1.06 (d, J=6.7 Hz), total 3H], 0.74-0.80 (m, 3H).

Preparation of N$^2$-[(3-Aminooxetan-3-yl)carbonyl]-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, acetic acid salt (#75)

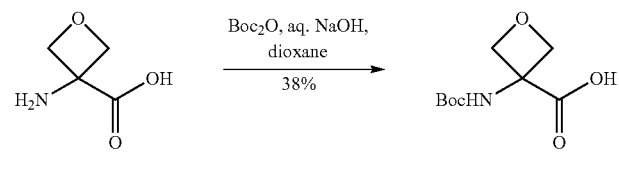

71

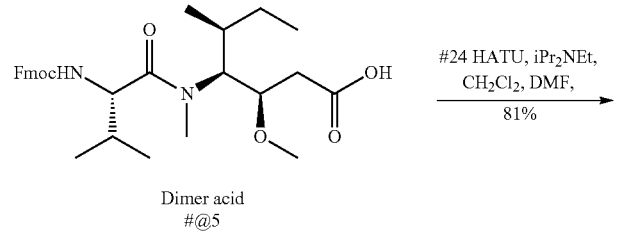

Dimer acid
@5

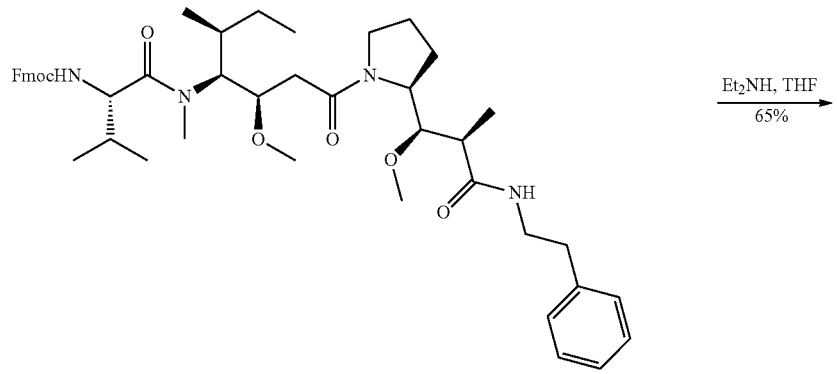

Fmoc-tetramer
72

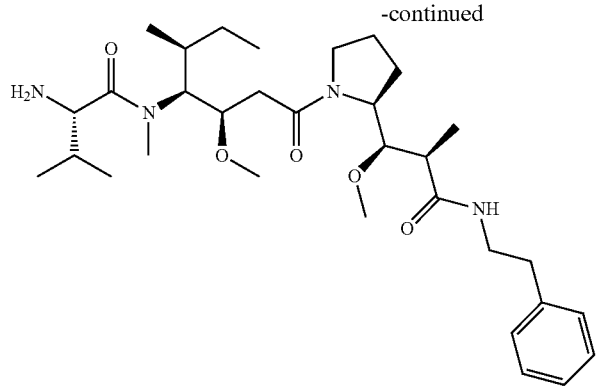

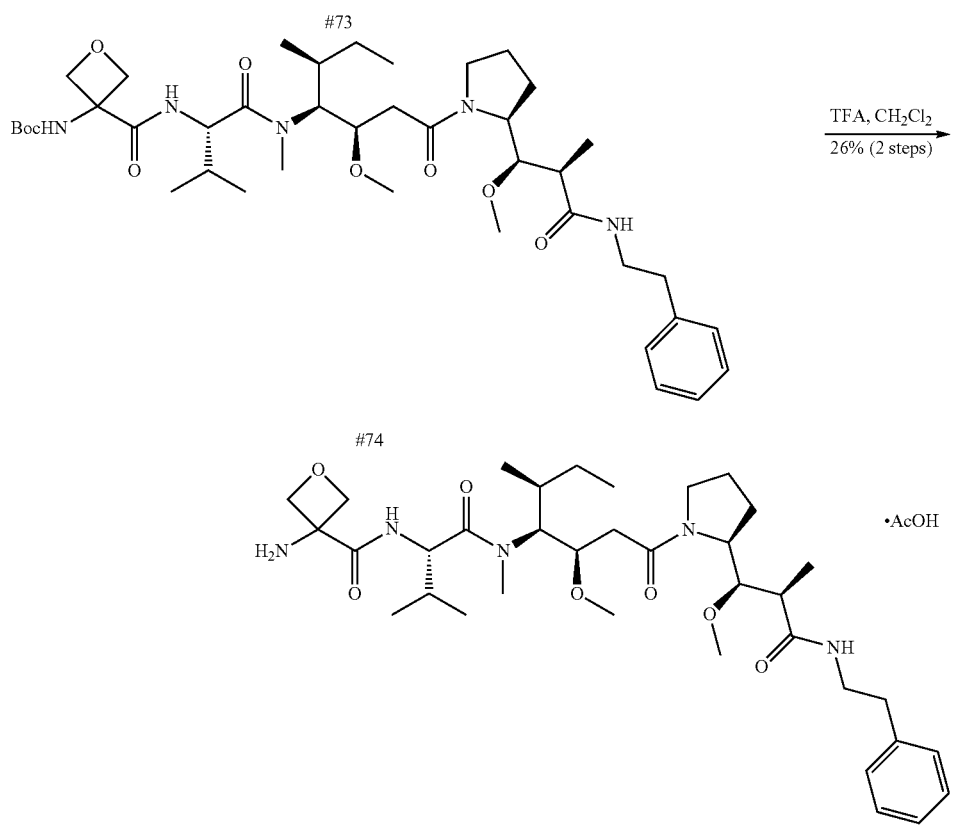

Step 1

Synthesis of 3-[(tert-butoxycarbonyl)amino]oxetane-3-carboxylic acid (#71)

To 1-aminooxetane-3-carboxylic acid (1.00 g, 8.54 mmol, 1 eq.) in dioxane (15 mL, 0.5 M) was added a solution of sodium hydroxide (1.55 g, 38.7 mmol, 4.5 eq.) in water (15 mL) followed by di-tert-butyl dicarbonate (2.09 g, 9.29 mmol, 1.1 eq.) A white solid formed. The reaction was stirred for 18 hours and then concentrated in vacuo. The residue was taken up in ethyl acetate and washed with 1 M aqueous hydrochloric acid solution and with brine. The organic layer was dried over sodium sulfate, filtered, and concentrated in vacuo to give #71 (633 mg, 38%) as a white solid. $^1$H NMR (400 MHz, DMSO-$d_6$), presumed to be a mixture of rotamers: δ 12.93 (br s, 1H), 7.59 and 7.93 (2 br s, total 1H), 4.71-4.78 (m, 2H), 4.47 (d, J=6.4 Hz, 2H), 1.30 and 1.38 (2 s, total 9H).

Step 2

Synthesis of $N^2$-[(9H-fluoren-9-ylmethoxy)carbonyl]-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide (#72)

To #@5 (9.47 g, 18.0 mmol, 1 eq.) and #24 (5.90 g, 18.0 mmol, 1 eq.) in dichloromethane (250 mL, 0.072 M) were added diisopropylethylamine (9.52 mL, 54.2 mmol, 3 eq.) and HATU (8.49 g, 21.7 mmol, 1.2 eq.). The reaction was stirred for 18 hours and then concentrated in vacuo. The residue was taken up in ethyl acetate (300 mL) and was washed with 1 M aqueous hydrochloric acid solution (2×100 mL) and with brine. The organic layer was dried over sodium sulfate, filtered, and concentrated in vacuo. The residue was taken up in dichloromethane (250 mL) and filtered. The filtrate was concentrated in vacuo onto silica and purified by silica gel chromatography (Gradient: 0% to 50% acetone in heptane) to provide #72 (11.61 g, 81%) as a light yellow solid. LC-MS: m/z 797.6 [M+H$^+$], 819.6 [M+Na$^+$], retention time=1.06 minutes; $^1$H NMR (400 MHz, DMSO-d$_6$), presumed to be a mixture of rotamers, characteristic signals: δ 3.26 and 3.28 (2 s, total 3H), 3.18 and 3.20 (2 s, total 3H), 2.95 and 3.10 (2 br s, total 3H), 1.01-1.09 (m, 3H), 0.67-0.78 (m, 3H).

Step 3

Synthesis of N-{(3R,4S,5S)-3-methoxy-1—R2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide (#73)

To #72 (5.16 g, 6.47 mmol, 1 eq.) in tetrahydrofuran (10 mL, 0.65 M) was added diethylamine (10 mL). After 2 hours, the reaction was concentrated in vacuo and the residue was purified by silica gel chromatography (Gradient: 0% to 10% methanol in dichloromethane) to give #73 (2414 mg, 65%). LC-MS: m/z 576.5 [M+H$^+$], retention time=0.64 minutes; $^1$H NMR (400 MHz, DMSO-d$_6$), presumed to be a mixture of rotamers, characteristic signals: δ 7.80-7.88 and 7.99-8.10 (2 m, total 1H), 7.14-7.31 (m, 5H), 3.17 and 3.18 (2 s, total 3H), 2.87 and 3.03 (2 br s, total 3H), 1.02-1.08 (m, 3H).

Step 4

Synthesis of N$^2$-({3-[(tert-butoxycarbonyl)amino]oxetan-3-yl}carbonyl)-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide (#74)

To #73 (100 mg, 0.174 mmol, 1 eq.) in dichloromethane (4 mL, 0.04) and N,N-dimethylformamide (0.5 mL) was added #71 (45.2 mg, 0.208 mmol, 1.2 eq.), followed by diisopropylethylamine (92 µL, 0.521 mmol, 3 eq.) and HATU (102 mg, 0.260 mmol, 1.5 eq.). After 16 hours, the reaction was concentrated in vacuo and the residue was taken up in ethyl acetate (6 mL) and washed with 1 M aqueous hydrochloric acid solution (2×2 mL) and with brine. The organic layer was dried over sodium sulfate, filtered, and concentrated in vacuo. The crude material was purified by reverse phase chromatography (Method C) to give #74 (140 mg), which was used in the next step without further purification. LC-MS: m/z 774.7 [M+H$^+$], 796.6 [M+Na$^+$], retention time=0.91 minute.

Step 5

Synthesis of N$^2$-[(3-aminooxetan-3-yl)carbonyl]-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, acetic acid salt (#75)

To #74 (140 mg, ≤0.181 mmol, 1 eq.) in dichloromethane (3 mL, 0.06 M) was added trifluoroacetic acid (1 mL). After 1 hour, the reaction was concentrated in vacuo and the residue was taken up in ethyl acetate (6 mL) and washed with saturated aqueous sodium bicarbonate solution (2 mL) and with brine. The organic layer was dried over sodium sulfate, filtered, and concentrated in vacuo. Half of the crude material was purified by reverse phase chromatography (Method B) to give #75 (16 mg, 26%, over two steps). LC-MS: m/z 674.6 [M+H$^+$], retention time=0.68 minutes; HPLC (Protocol A at 45° C.): m/z 674.5 [M+H$^+$], retention time=7.128 minutes; $^1$H NMR (400 MHz, DMSO-d$_6$), presumed to be a mixture of rotamers, characteristic signals: δ 7.80-7.87 and 8.02-8.07 (2 m, total 2H), 7.23-7.30 (m, 2H), 7.14-7.22 (m, 3H), 4.28-4.33 (m, 2H), 3.96-4.04 (br m, 1H), 3.17 and 3.19 (2 s, total 3H), 2.96 and 3.10 (2 br s, total 3H), [1.04 (d, J=7.0 Hz) and 1.07 (d, J=6.6 Hz), total 3H].

Preparation of N,2-Dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#79) and N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, trifluoroacetic acid salt (#80)

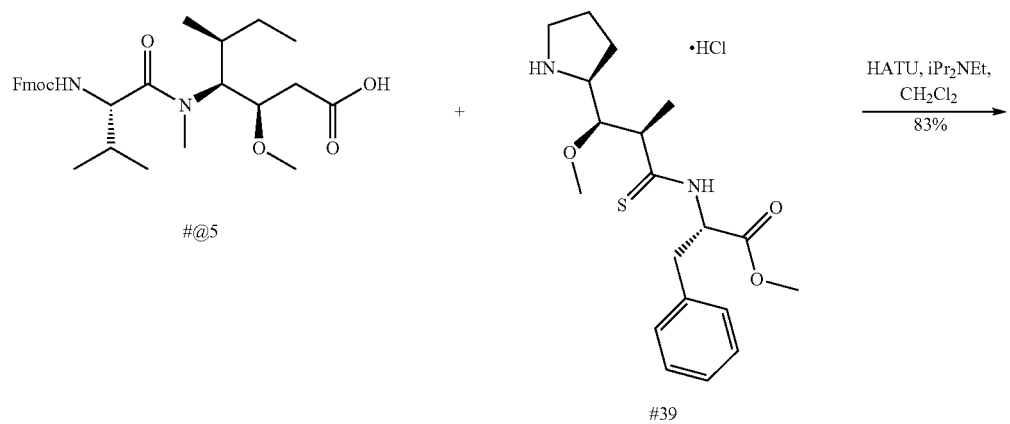

183
-continued
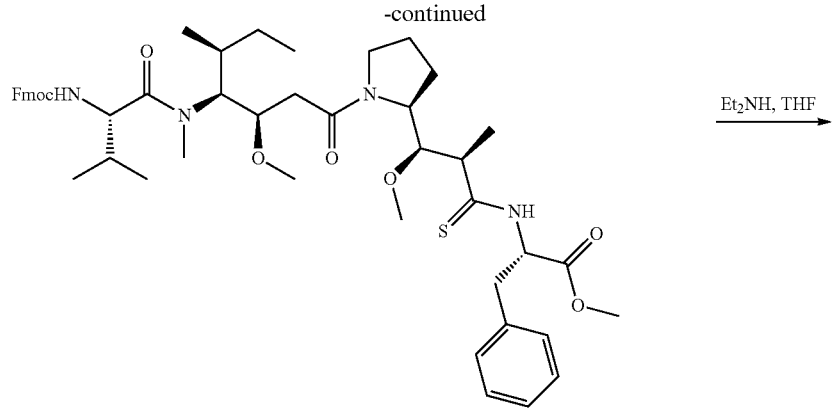
76
Et₂NH, THF →
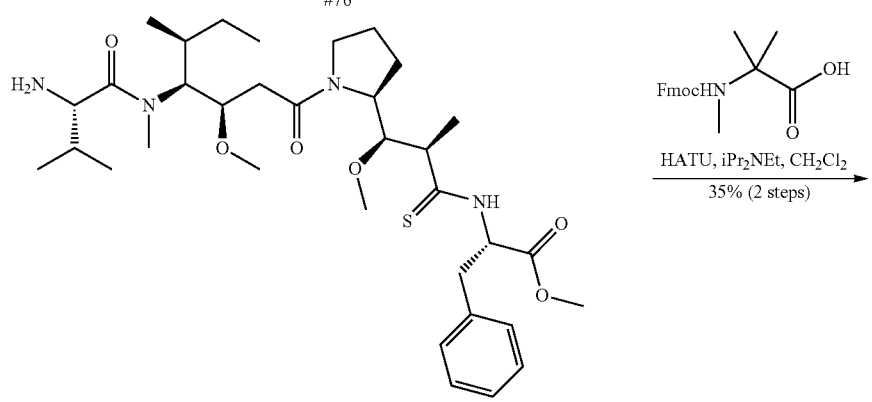
77
FmocHN-C(CH₃)₂-COOH (N-Me)
HATU, iPr₂NEt, CH₂Cl₂
35% (2 steps)
184
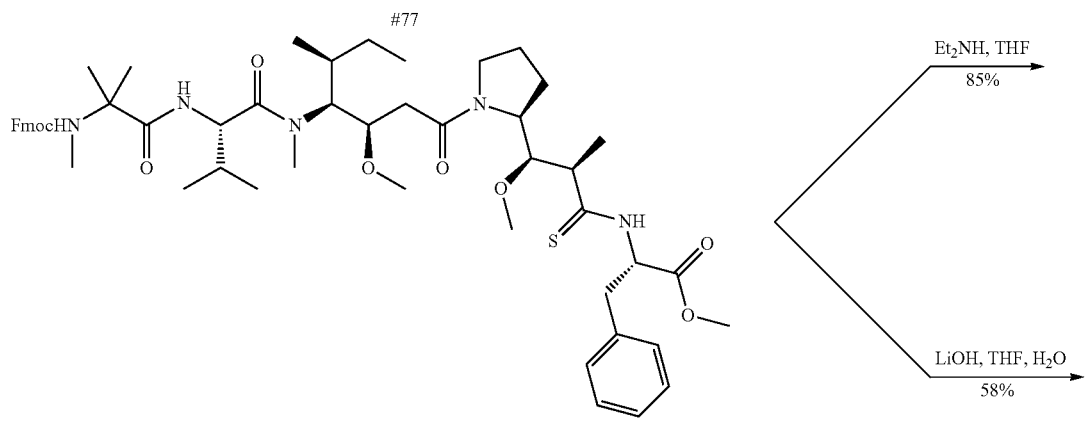
78
Et₂NH, THF
85%
LiOH, THF, H₂O
58%
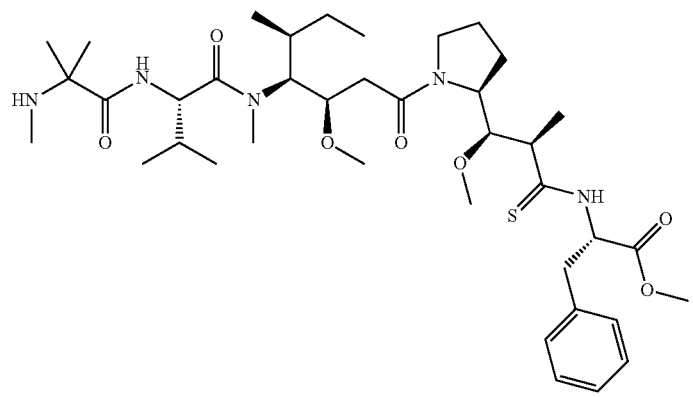
79

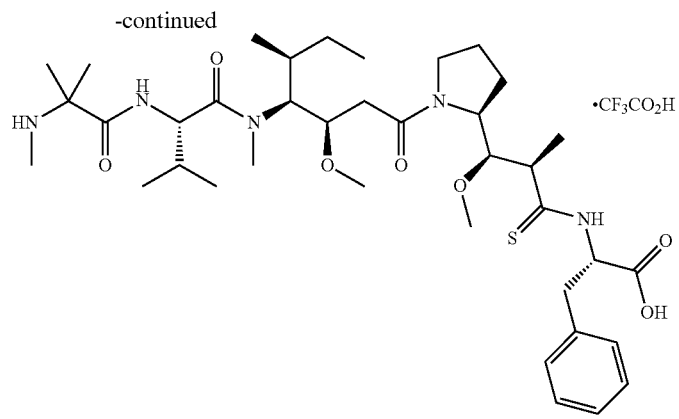

80

Step 1

Synthesis of methyl N-{(2R,3R)-3-[(2S)-1-{(3R,4S,5S)-4-[{N-[(9H-fluoren-9-ylmethoxy)carbonyl]-L-valyl}(methyl)amino]-3-methoxy-5-methylheptanoyl}pyrrolidin-2-yl]-3-methoxy-2-methylpropanethioyl}-L-phenylalaninate (#76)

According to general procedure D, from #@5 (260 mg, 0.648 mmol, 1 eq.), #39 (340 mg, ≤0.629 mmol, 1 eq.), dichloromethane (10 mL, 0.065 M), HATU (296 mg, 0.778 mmol, 1.2 eq.) and diisopropylethylamine (339 µL, 1.94 mmol, 3 eq.) was synthesized the crude desired material, which was purified by silica gel chromatography (Gradient: 0% to 40% acetone in heptane) to give #76 (466 mg, 83% over two steps) as a solid. LC-MS: m/z 871.5 [M+H$^+$], 893.5 [M+Na$^+$], retention time=1.10 minutes; HPLC (Protocol C): retention time=9.249 minutes (purity >99%); $^1$H NMR (400 MHz, DMSO-d$_6$), presumed to be a mixture of rotamers, characteristic signals: δ [10.19 (br d, J=7.4 Hz) and 10.49 (br d, J=7.8 Hz), total 1H], 7.89 (br d, J=7.4 Hz, 2H), 7.68-7.75 (m, 2H), 7.54-7.60 (m, 1H), 7.41 (br dd, J=7.4, 7.4 Hz, 2H), 7.28-7.36 (m, 2H), 7.15-7.28 (m, 5H), [5.20 (ddd, J=10.9, 7.3, 4.4 Hz) and 5.34-5.43 (m), total 1H], 3.65 and 3.69 (2 s, total 3H), 3.24 and 3.25 (2 s, total 3H), 3.17 (br s, 3H), 2.93 and 2.98 (2 br s, total 3H), [1.15 (d, J=6.6 Hz) and 1.18 (d, J=6.6 Hz), total 3H].

Step 2

Synthesis of methyl N-{(2R,3R)-3-methoxy-3-[(2S)-1-{(3R,4S,5S)-3-methoxy-5-methyl-4-[methyl(L-valyl)amino]heptanoyl}pyrrolidin-2-yl]-2-methylpropanethioyl}-L-phenylalaninate (#77)

According to general procedure A, from #76 (460 mg, 0.528 mmol, 1 eq.) tetrahydrofuran (8 mL, 0.07 M) and diethylamine (8 mL) was synthesized #77 (399 mg), which was used in the next step without further purification; LC-MS m/z 649.5 [M+H$^+$], retention time=0.73 minutes; $^1$H NMR (400 MHz, DMSO-d$_6$), presumed to be a mixture of rotamers, characteristic product signals: δ [10.20 (d, J=7.4 Hz) and 10.49 (d, J=7.4 Hz), total 1H], 7.15-7.28 (m, 5H), [5.20 (ddd, J=10.9, 7.2, 4.5 Hz) and 5.34-5.42 (m), total 1H], 3.65 and 3.68 (2 s, total 3H), 3.24 and 3.25 (2 s, total 3H), 3.15 and 3.15 (2 s, total 3H), 2.83 and 2.88 (2 br s, total 3H), [1.15 (d, J=6.6 Hz) and 1.18 (d, J=6.6 Hz), total 3H].

Step 3

Synthesis of N-[(9H-fluoren-9-ylmethoxy)carbonyl]-N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#78)

According to general procedure D, from #77 (399 mg, ≤0.52 mmol, 1 eq.), N-[(9H-fluoren-9-ylmethoxy)carbonyl]-N,2-dimethylalanine (213 mg, 0.628 mmol, 1.2 eq.), dichloromethane (5 mL, 0.1 M), HATU (239 mg, 0.628 mmol, 1.2 eq.) and diisopropylethylamine (282 µL, 1.62 mmol, 3.1 eq.) was synthesized the crude desired material, which was purified by silica gel chromatography (Gradient: 0% to 50% acetone in heptane), providing #78 (231 mg, 46% over two steps). LC-MS: m/z 970.7 [M+H$^+$], 992.6 [M+Na$^+$], retention time=1.11 minutes; HPLC (Protocol C): retention time=9.260 minutes; $^1$H NMR (400 MHz, DMSO-d$_6$), presumed to be a mixture of rotamers, characteristic signals: δ [10.19 (d, J=7.4 Hz) and 10.47 (d, J=7.8 Hz), total 1H], 7.89 (d, J=7.4 Hz, 2H), 7.61-7.67 (m, 2H), 7.41 (br dd, J=7.4, 7.4 Hz, 2H), 7.14-7.36 (m, 8H), [5.20 (ddd, J=11, 7, 5 Hz) and 5.38 (ddd, J=11, 8, 4 Hz), total 1H], [4.41 (dd, J=8.6, 8.4 Hz) and 4.46 (dd, J=8.2, 8.2 Hz), total 1H], 3.65 and 3.68 (2 s, total 3H), 3.23 and 3.24 (2 s, total 3H), 3.13 (br s, 3H), 2.88 and 2.93 (2 br s, total 3H), 2.84 and 2.85 (2 s, total 3H), 1.31 and 1.32 (2 s, total 3H), [1.15 (d, J=6.6 Hz) and 1.18 (d, J=6.4 Hz), total 3H].

Step 4A

Synthesis of N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide (#79)

According to general procedure A, from #78 (223 mg, 0.230 mmol, 1 eq.), dichloromethane (6 mL, 0.04 M) and diethylamine (6 mL) was synthesized #79 (146 mg, 85%) as a white solid after silica gel chromatography (Gradient: 0% to 5% methanol in heptane then 0% to 10% methanol in dichloromethane). HPLC (Protocol A at 45° C.): 749.4 [M+H$^+$], retention time=7.315 minutes; $^1$H NMR (400 MHz, DMSO-d$_6$), presumed to be a mixture of rotamers, characteristic signals: δ [10.20 (d, J=7.6 Hz) and 10.50 (d, J=8.0 Hz), total 1H], 7.79-7.88 (m, 1H), 7.15-7.29 (m, 5H), [5.20 (ddd, J=11, 7, 4 Hz) and 5.38 (ddd, J=11, 8, 4 Hz), total 1H], [4.50 (dd, J=8.8, 8.6 Hz) and 4.56 (dd, J=9, 8 Hz), total 1H], 3.65 and 3.69 (2 s, total 3H), 3.24 and 3.25 (2 s, total 3H), 3.16 (br s, 3H), 2.93 and 2.97 (2 br s, total 3H), 2.10 and 2.11 (2 s, total 3H).

Step 4B

Synthesis of N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide, trifluoroacetic acid salt (#80)

To a solution of #78 (170 mg, 0.175 mmol, 1 eq.) in tetrahydrofuran (3 mL, 0.04 M) was added a solution of lithium hydroxide (12.6 mg, 0.525 mmol, 3 eq.) in water (1.5 mL). After stirring overnight, the solvent was removed in vacuo. The residue was azeotroped three times with heptane. The residue was then diluted with dimethyl sulfoxide (2.2 mL) and purified by reverse phase chromatography (Method C) to afford #80 (74 mg, 58%) as a solid. LC-MS: m/z 734.6 [M+H$^+$], retention time=0.69 minutes; HPLC (Protocol A at 45° C.): 734.4 [M+H$^+$], retention time=6.903 minutes (purity >96%); $^1$H NMR (400 MHz, DMSO-d$_6$), presumed to be a mixture of rotamers, characteristic signals: δ 12.9 and 13.1 (2 v br s, total 1H), [10.12 (d, J=7.4 Hz) and 10.46 (d, J=7.8 Hz), total 1H], 8.77-8.89 (br m, 2H), [8.47 (d, J=8.6 Hz) and 8.51 (d, J=8.6 Hz), total 1H], 7.21-7.29 (m, 4H), 7.14-7.21 (m, 1H), [5.16-5.23 (m) and 5.38 (ddd, J=11.3, 8.2, 3.9 Hz), total 1H], [4.51 (dd, J=9.0, 9.0 Hz) and 4.57 (dd, J=9.4, 8.6 Hz), total 1H], 3.24 and 3.24 (2 s, total 3H), 3.18 and 3.19 (2 s, total 3H), 2.96 and 3.00 (2 br s, total 3H), 1.51 and 1.53 (2 s, total 3H), 1.40 and 1.42 (2 s, total 3H), 1.14-1.19 (m, 3H), 0.74-0.81 (m, 3H).

Preparation of N,2-Dimethylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#84)

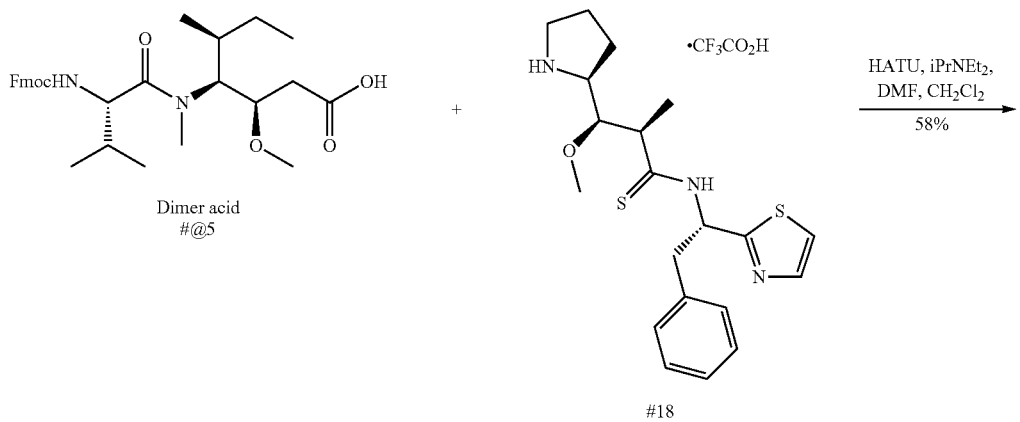

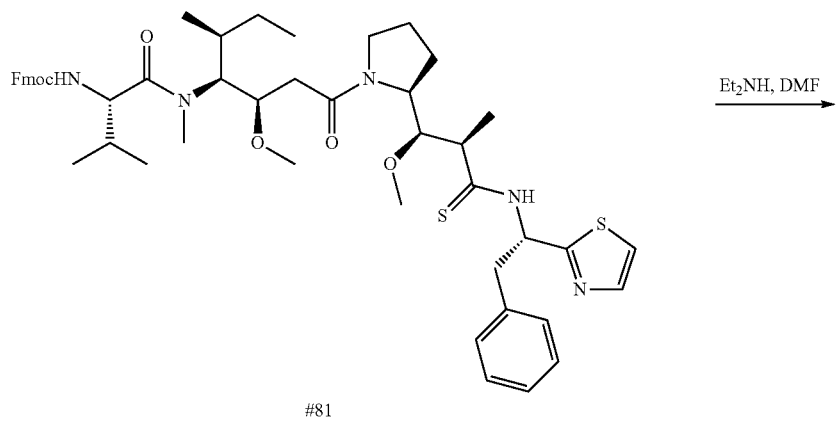

-continued

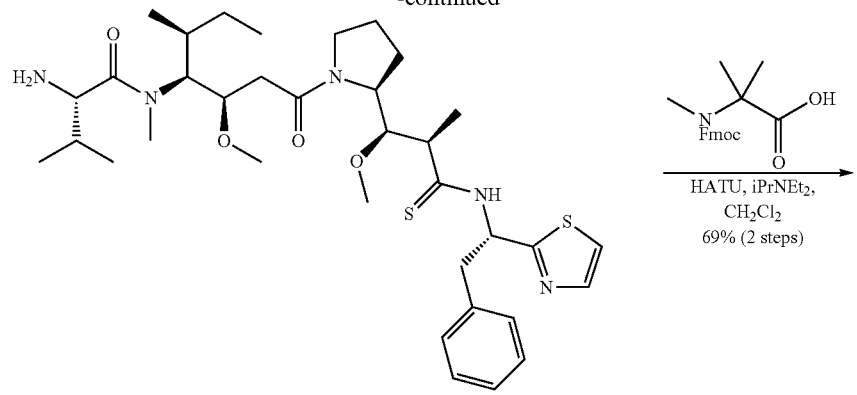

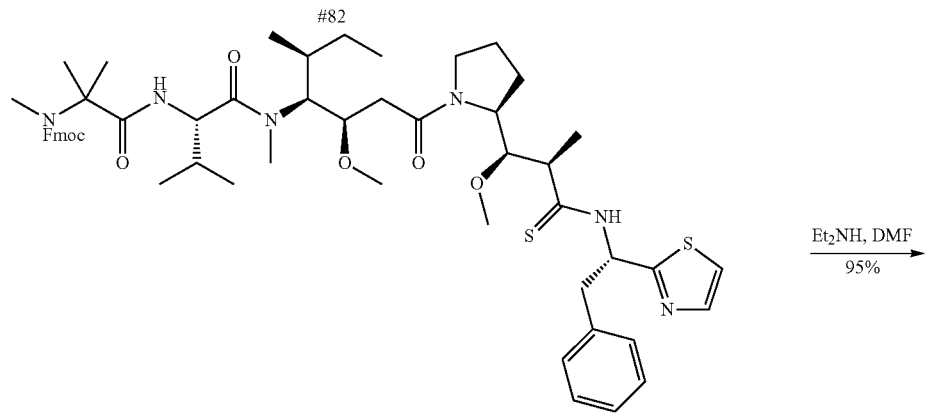

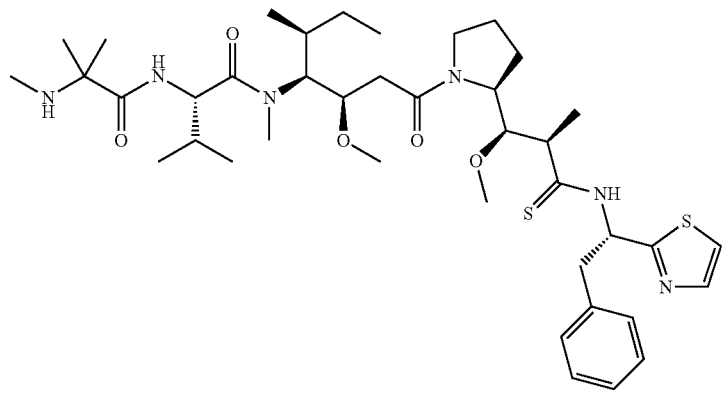

Step 1

Synthesis of N²-[(9H-fluoren-9-ylmethoxy)carbonyl]-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#81)

According to general procedure D, from #@5 (620 mg, 1.18 mmol, 1 eq.) dichloromethane (10 mL, 0.1 M), amine #18 (604 mg, 1.42 mmol, 1.2 eq.), diisopropylethylamine (618 μL, 3.54 mmol, 3 eq.) and HATU (539 mg, 1.42 mmol, 1.2 eq.) was synthesized the crude desired material, which was purified by silica gel chromatography (Gradient: 0% to 30% acetone in heptane) to give #81 (737 mg, 58%). HPLC (Protocol C): retention time=9.235 minutes; ¹H NMR (400 MHz, DMSO-$d_6$), presumed to be a mixture of rotamers, characteristic signals: δ [10.54 (br d, J=8 Hz) and 10.81 (br d, J=8 Hz), total 1H], 7.89 (d, J=7.6 Hz, 2H), [7.80 (d, J=3.3 Hz) and 7.83 (d, J=3.1 Hz), total 1H], 7.70-7.75 (m, 2H), [7.64 (d, J=3.1 Hz) and 7.68 (d, J=3.3 Hz), total 1H], 7.55-7.60 (m, 1H), 7.38-7.44 (m, 2H), 7.13-7.35 (m, 7H), [6.31 (ddd, J=11, 8, 4.5 Hz) and 6.40-6.48 (m), total 1H], 3.23 and 3.24 (2 s, total 3H), 3.17 and 3.22 (2 s, total 3H), 2.94 and 3.01 (2 br s, total 3H), [1.14 (d, J=6.4 Hz) and 1.17 (d, J=6.2 Hz), total 3H].

Step 2

Synthesis of N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#82)

According to general procedure A, from #81 (733 mg, 0.818 mmol, 1 eq.) in dichloromethane (7 mL, 0.1 M) and diethylamine (7 mL) was synthesized #82 (670 mg), which was used in the next step without further purification. LC-MS: m/z 674.5 [M+H$^+$], retention time=1.29 minutes; $^1$H NMR (400 MHz, DMSO-d$_6$), presumed to be a mixture of rotamers, characteristic product signals: δ [10.55 (br d, J=8 Hz) and 10.84 (br d, J=8 Hz), total 1H], [7.64 (d, J=3.1 Hz) and 7.69 (d, J=3.3 Hz), total 1H], 7.13-7.33 (m, 5H), 6.27-6.35 and 6.38-6.47 (2 m, total 1H), 3.23 and 3.25 (2 s, total 3H), 3.15 and 3.19 (2 s, total 3H), 2.84 and 2.91 (2 br s, total 3H).

Step 3

Synthesis of N-[(9H-fluoren-9-ylmethoxy)carbonyl]-N,2-dimethylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#83).

According to general procedure D, from #82 (670 mg, ≤0.818 mmol, 1 eq.), dichloromethane (5 mL, 0.16 M), N-[(9H-fluoren-9-ylmethoxy)carbonyl]-N,2-dimethylalanine (304 mg, 0.896 mmol, 1.1 eq.), HATU (372 mg, 0.978 mmol, 1.2 eq.) and diisopropylethylamine (440 μL, 2.53 mmol, 3.1 eq.) was synthesized the crude desired material, which was purified by silica gel chromatography (Gradient: 0% to 30% acetone in heptane) to give #83 (556 mg, 69% over two steps). LC-MS: m/z 994.7 [M+H$^+$], retention time=0.69 minutes; HPLC (Protocol C): retention time=9.333 minutes (purity >98%); $^1$H NMR (400 MHz, DMSO-d$_6$), presumed to be a mixture of rotamers, characteristic signals: δ [10.53 (br d, J=8 Hz) and 10.80 (br d, J=8 Hz), total 1H], 7.86-7.91 (m, 2H), [7.80 (d, J=3.3 Hz) and 7.82 (d, J=3.2 Hz), total 1H], [7.64 (d, J=3.2 Hz) and 7.68 (d, J=3.2 Hz), total 1H], 7.62-7.66 (m, 2H), 7.38-7.44 (m, 2H), 7.28-7.36 (m, 5H), 7.19-7.26 (m, 2H), 7.12-7.17 (m, 1H), [6.31 (ddd, J=11, 8, 4.5 Hz) and 6.44 (ddd, J=11, 8.5, 4.5 Hz), total 1H], [4.42 (dd, J=9, 8 Hz) and 4.48 (dd, J=8, 8 Hz), total 1H], 3.22 and 3.24 (2 s, total 3H), 3.13 and 3.17 (2 s, total 3H), 2.89 and 2.97 (2 br s, total 3H), 2.84 and 2.85 (2 s, total 3H), [1.13 (d, J=6.4 Hz) and 1.16 (d, J=6.4 Hz), total 3H].

Step 4

Synthesis of N,2-dimethylalanyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide (#84)

According to general procedure A, from #83 (552 mg, 0.555 mmol, 1 eq.) in dichloromethane (10 mL, 0.05 M) and diethylamine (10 mL) was synthesized the crude desired material, which was diluted with methanol, concentrated in vacuo onto silica, and purified by silica gel chromatography (Gradient: 0% to 10% methanol in dichloromethane) to give #84 (406 mg, 95%) as a white solid. LC-MS: m/z 772.8 [M+H$^+$], retention time=1.35 minutes; HPLC (Protocol A): 774.4 [M+H$^+$], retention time=7.390 minutes; $^1$H NMR (400 MHz, DMSO-d$_6$), presumed to be a mixture of rotamers, characteristic signals: δ [10.54 (br d, J=8 Hz) and 10.81 (br d, J=8 Hz), total 1H], 7.78-7.84 (m, 2H), [7.65 (d, J=3.1 Hz) and 7.69 (d, J=3.3 Hz), total 1H], 7.29-7.34 (m, 2H), 7.20-7.28 (m, 2H), 7.14-7.19 (m, 1H), 6.27-6.35 and 6.40-6.48 (2 m, total 1H), [4.51 (dd, J=9, 8 Hz) and 4.57 (dd, J=9, 8 Hz), total 1H], 3.24 and 3.25 (2 s, total 3H), 3.16 and 3.21 (2 s, total 3H), 2.94 and 3.00 (2 br s, total 3H), 2.09 and 2.10 (2 s, total 3H), 1.08 and 1.09 (2 s, total 3H), 0.73-0.80 (m, 3H).

N,2-Dimethylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#88)

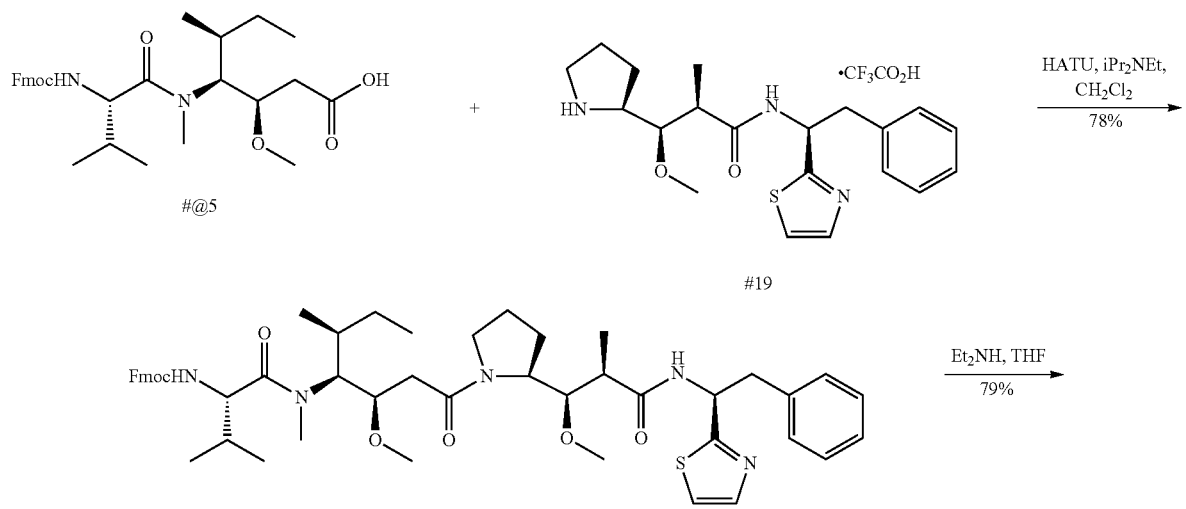

-continued

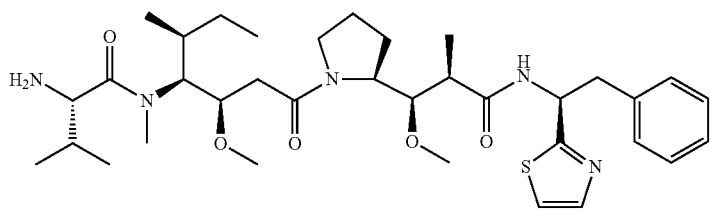

86

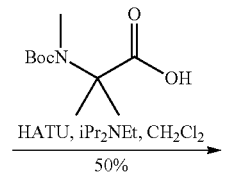

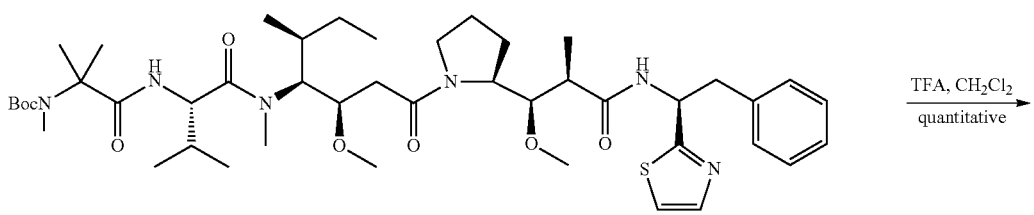

87

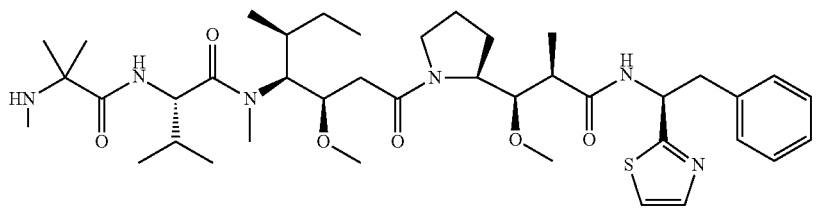

88

Step 1

Synthesis of N²-[(9H-fluoren-9-ylmethoxy)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#85)

To a mixture of #@5 (5.48 g, 10.4 mmol, 1 eq.) and #19 (3.90 g, 10.4 mmol, 1 eq.) in dichloromethane (50 mL, 0.2M) was added diisopropylethylamine (5.51 mL, 31.3 mmol, 3 eq.) followed by HATU (4.91 g, 12.5 mmol, 1.2 eq.). After stirring overnight, the reaction mixture was concentrated in vacuo. The residue was taken up in ethyl acetate (100 mL) and washed with 1 M aqueous hydrochloric acid solution (2×30 mL) and with brine (30 mL). The organic layer was dried over sodium sulfate, filtered, and concentrated in vacuo. The residue was taken up in dichloromethane and filtered; the filtrate was purified by silica gel chromatography (Gradient; 0% to 50% acetone in heptane) to afford #85 (7.20 g, 78%) as a solid. LC-MS: m/z 880.6 [M+H⁺], retention time=1.07 minutes.

Step 2

Synthesis of N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#86)

According to general procedure A, from #85 (5.00 g, 5.68 mmol, 1 eq.) in tetrahydrofuran (10 mL, 0.56 M) and diethylamine (3 mL) was synthesized the crude desired material, which was purified by silica gel chromatography (Gradient: 0% to 10% methanol in dichloromethane) to give #86 (2.952 g, 79%) as a solid. LC-MS: m/z 658.5 [M+H⁺], 680.5 [M+Na⁺] retention time=0.66 minute; ¹H NMR (400 MHz, DMSO-d₆), presumed to be a mixture of rotamers, characteristic signals: δ [8.64 (br d, J=8.4 Hz) and 8.90 (br d, J=8.8 Hz), total 1H], [7.77 (d, J=3.3 Hz) and 7.80 (d, J=3.3 Hz), total 1H], [7.63 (d, J=3.3 Hz) and 7.66 (d, J=3.3 Hz), total 1H], 7.12-7.31 (m, 5H), [5.39 (ddd, J=11.2, 8.4, 4.2 Hz) and 5.54 (ddd, J=11.9, 8.9, 4.0 Hz), total 1H], 3.15, 3.19, 3.20 and 3.26 (4 s, total 6H), 2.86 and 2.98 (2 br s, total 3H), [1.06 (d, J=6.6 Hz) and 1.11 (d, J=6.6 Hz), total 3H].

Step 3

Synthesis of N-(tert-butoxycarbonyl)-N,2-dimethylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#87)

To a mixture of #86 (80.3 mg, 0.122 mmol, 1 eq.) in dichloromethane (4 mL, 0.03 M) was added N-(tert-butoxycarbonyl)-N,2-dimethylalanine (29.1 mg, 0.134 mmol, 1.1 eq.) followed by diisopropylethylamine (64 μL, 0.365 mmol, 3 eq.) and HATU (71.7 mg, 0.183 mmol, 1.5 eq.) After stirring overnight, the reaction mixture was concentrated in vacuo. The residue was taken up in ethyl acetate (6 mL) and washed with 1 M aqueous hydrochloric acid solution (2×2 mL) and with brine. The organic solvent was dried over sodium sulfate, filtered, and concentrated in vacuo. The residue was taken up in dichloromethane and filtered; the filtrate was concentrated in vacuo onto silica and purified by silica gel chromatography (Gradient: 0% to 50% acetone in heptane) to afford #87 (58 mg, 50%) as a white solid. LC-MS: m/z 857.7 [M+H$^+$], 879.7 [M+Na$^+$], retention time=0.99 minute; $^1$H NMR (400 MHz, DMSO-d$_6$), presumed to be a mixture of rotamers, characteristic signals: δ [8.64 (br d, J=8 Hz) and 8.87 (br d, J=9 Hz), total 1H], [7.77 (d, J=3.3 Hz) and 7.80 (d, J=3.3 Hz), total 1H], [7.63 (d, J=3.2 Hz) and 7.66 (d, J=3.2 Hz), total 1H], 7.13-7.31 (m, 5H), [6.95 (br d, J=8 Hz) and 7.06 (br d, J=8 Hz), total 1H], 5.35-5.42 and 5.51-5.58 (2 m, total 1H), 3.15, 3.19, 3.20 and 3.26 (4 s, total 6H), 2.94 and 3.03 (2 br s, total 3H), 2.83 and 2.84 (2 s, total 3H), [1.05 (d, J=6.7 Hz) and 1.11 (d, J=6.7 Hz), total 3H].

Step 4

Synthesis of N,2-dimethylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#88)

To a mixture of #87 (58 mg, 0.068 mmol, 1 eq.) in dichloromethane (8 mL) was added trifluoroacetic acid (2 mL). After stirring overnight, the reaction mixture was concentrated in vacuo. The residue was taken up in ethyl acetate (10 mL), washed with saturated aqueous sodium bicarbonate solution, dried over sodium sulfate, filtered, and concentrated in vacuo to give #88 (52 mg, quantitative). LC-MS 757.6 [M+H$^+$], retention time=0.69 minute; $^1$H NMR (400 MHz, DMSO-d$_6$), presumed to be a mixture of rotamers, characteristic signals: δ [8.64 (br d, J=8.6 Hz) and 8.87 (br d, J=8.6 Hz), total 1H], 7.80-7.85 (m, 1H), [7.77 (d, J=3.3 Hz) and 7.80 (d, J=3.1 Hz), total 1H], [7.63 (d, J=3.1 Hz) and 7.66 (d, J=3.3 Hz), total 1H], 7.20-7.31 (m, 4H), 7.13-7.19 (m, 1H), [5.39 (ddd, J=11, 8.5, 4 Hz) and 5.49-5.56 (m), total 1H], [4.51 (dd, J=9, 8 Hz) and 4.61 (dd, J=9, 8 Hz), total 1H], 3.16, 3.20, 3.21 and 3.25 (4 s, total 6H), 2.94 and 3.03 (2 br s, total 3H), 2.10 and 2.10 (2 s, total 3H), 1.16 (br s, 3H), 1.04-1.12 (m, 6H), 0.72-0.80 (m, 3H).

Preparation of N$^2$-(3-Amino-2,2-dimethylpropanoyl)-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, trifluoroacetic acid salt (#95

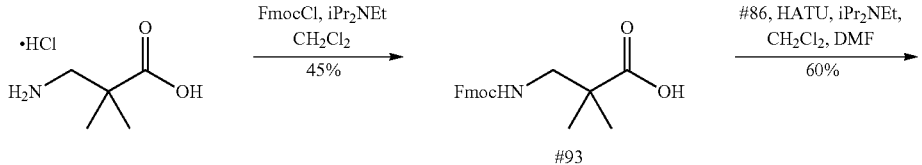

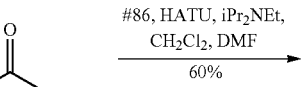

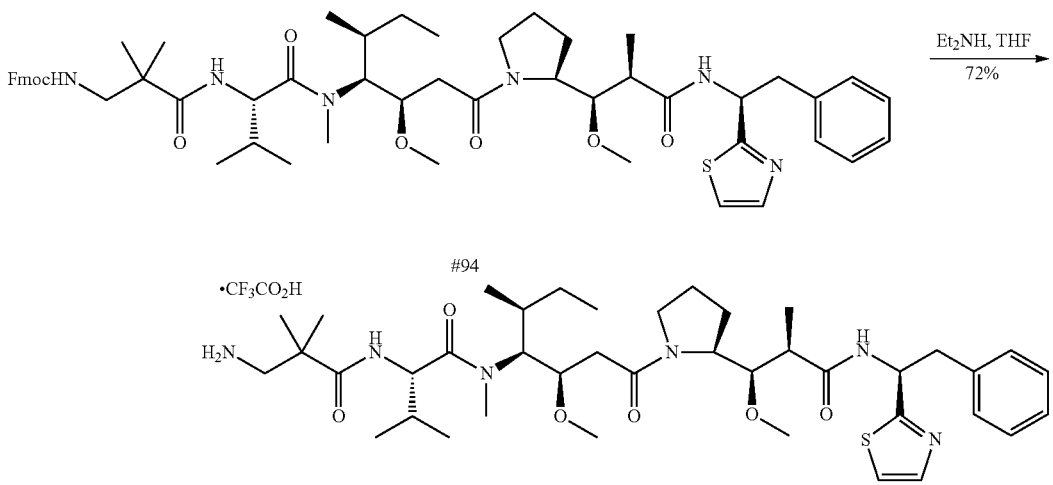

Step 1

Synthesis of 3-{[(9H-fluoren-9-ylmethoxy)carbonyl]amino}-2,2-dimethylpropanoic acid (#93)

To 3-amino-2,2-dimethylpropanoic acid, hydrochloride salt (250 mg, 1.63 mmol, 1 eq.) in dichloromethane (4 mL, 0.4 M) was added diisopropylethylamine (859 μL, 4.88 mmol, 3 eq.) followed by (9H-fluoren-9-ylmethoxy)carbonyl chloride (473 mg, 1.79 mmol, 1.1 eq.) The reaction was stirred for 18 hours and then concentrated in vacuo. The residue was taken up in ethyl acetate (3 mL) and washed with 1 M aqueous hydrochloric acid solution (2×1 mL) and with brine. The organic layer was dried over sodium sulfate, filtered, and purified by silica gel chromatography (Gradient: 0% to 100% ethyl acetate in heptane) to give #93 (250 mg, 45%) as an oil. $^1$H NMR (400 MHz, DMSO-$d_6$) δ 12.22 (s, 1H), 7.89 (d, J=7.4 Hz, 2H), 7.72 (d, J=7.4 Hz, 2H), 7.38-7.44 (m, 2H), 7.27-7.35 (m, 3H), 4.18-4.30 (m, 3H), 3.16 (d, J=6.2 Hz, 2H), 1.05 (s, 6H).

Step 2

Synthesis of $N^2$-(3-{[(9H-fluoren-9-ylmethoxy)carbonyl]amino}-2,2-dimethylpropanoyl)-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#94)

To #86 (100 mg, 0.152 mmol, 1 eq.) in dichloromethane (4 mL, 0.038 M) and N,N-dimethylformamide (0.5 mL) was added #93 (51.6 mg, 0.152 mmol, 1 eq.) followed by diisopropylethylamine (80.0 μL, 0.457 mmol, 3 eq.) and HATU (89.8 mg, 0.229 mmol, 1.5 eq.). The reaction was stirred for 18 hours and then concentrated in vacuo. The residue was taken up in ethyl acetate (6 mL) and was washed with 1 M aqueous hydrochloric acid solution (2×2 mL) and with brine. The organic layer was dried over sodium sulfate, filtered, and concentrated in vacuo. The residue was taken up in dichloromethane (250 mL) and filtered; the filtrate was concentrated in vacuo onto silica and purified by silica gel chromatography (Gradient: 0% to 50% acetone in heptane) to provide #94 (90 mg, 60%) as a white solid. LC-MS: m/z 979.8 [M+H$^+$], 1002.7 [M+Na$^+$], retention time=1.15 minutes; $^1$H NMR (400 MHz, DMSO-$d_6$), presumed to be a mixture of rotamers, characteristic product signals: δ [8.64 (br d, J=8.6 Hz) and 8.86 (br d, J=8.6 Hz), total 1H], 7.86-7.91 (m, 2H), [7.77 (d, J=3.3 Hz) and 7.79 (d, J=3.3 Hz), total 1H], 7.67-7.73 (m, 2H), [7.63 (d, J=3.3 Hz) and 7.65 (d, J=3.3 Hz), total 1H], 6.87-6.95 (m, 1H), [5.39 (ddd, J=11, 8, 4 Hz) and 5.52 (ddd, J=11.5, 9, 4 Hz), total 1H], [4.44 (dd, J=8.4, 8.4 Hz) and 4.55 (dd, J=8.4, 8.4 Hz), total 1H], 3.16, 3.20, 3.21 and 3.25 (4 s, total 6H), 2.96 and 3.06 (2 br s, total 3H), 0.69-0.77 (m, 3H).

Step 3

Synthesis of $N^2$-(3-amino-2,2-dimethylpropanoyl)-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, trifluoroacetic acid salt (#95)

To #94 (86 mg, 0.088 mmol, 1 eq.) in tetrahydrofuran (2 mL, 0.04 M) was added diethylamine (10 mL). After stirring overnight, the reaction was concentrated in vacuo and the residue was purified by reverse phase chromatography (Method C) to give #95 (55 mg, 72%). LC-MS: m/z 757.5 [M+H$^+$], retention time=0.74 minutes; $^1$H NMR (400 MHz, DMSO-$d_6$), presumed to be a mixture of rotamers, characteristic signals: δ [8.66 (br d, J=8 Hz) and 8.92 (br d, J=9 Hz), total 1H], [7.91 (br d, J=8 Hz) and 7.97 (br d, J=9 Hz), total 1H], [7.78 (d, J=3.3 Hz) and 7.81 (d, J=3.1 Hz), total 1H], 7.65-7.74 (br m, 3H), [7.63 (d, J=3.3 Hz) and 7.67 (d, J=3.3 Hz), total 1H], 7.12-7.31 (m, 5H), [5.35-5.42 (m) and 5.45-5.52 (m), total 1H], [4.44 (dd, J=9, 9 Hz) and 4.55 (dd, J=9, 9 Hz), total 1H], 3.17, 3.20, 3.22 and 3.25 (4 s, total 6H), 2.96 and 3.05 (2 br s, total 3H), 1.25 and 1.25 (2 s, total 3H), 1.14 and 1.15 (2 s, total 3H), [1.06 (d, J=6.6 Hz) and 1.10 (d, J=6.4 Hz), total 3H], 0.72-0.80 (m, 3H).

Preparation of $N^2$-(3-Amino-2,2-dimethylpropanoyl)-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, trifluoroacetic acid salt (#97)

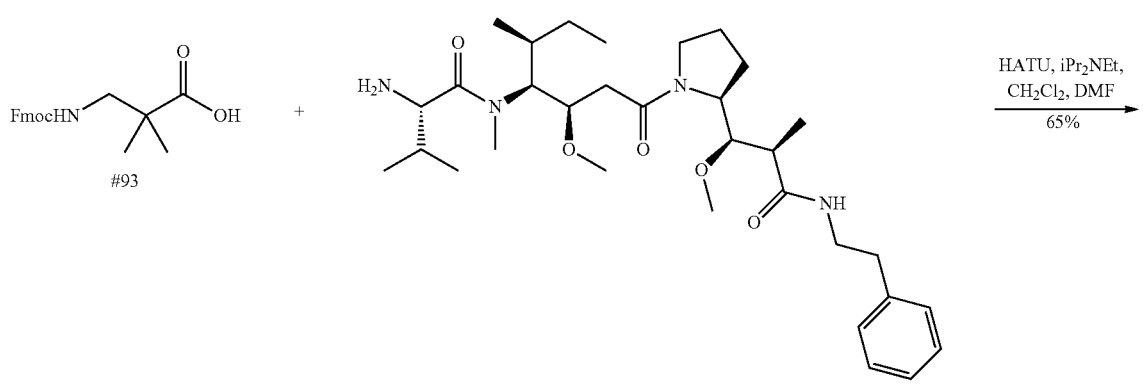

73

-continued

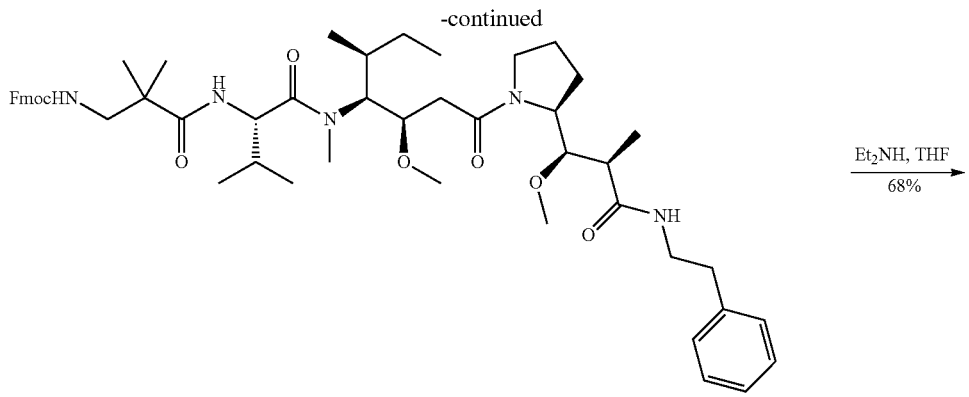
96

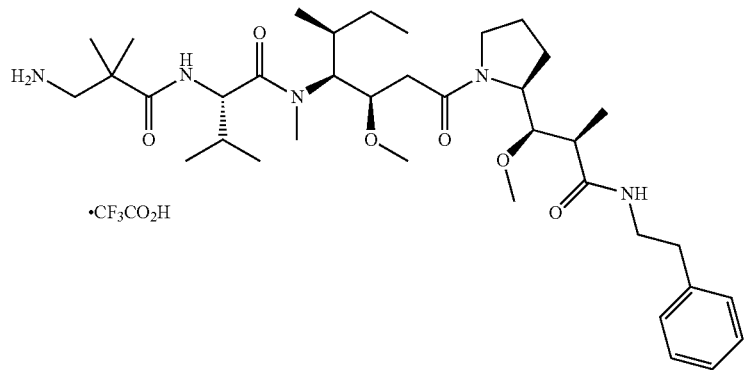
97

Step 1

Synthesis of $N^2$-(3-{[(9H-fluoren-9-ylmethoxy)carbonyl]amino}-2,2-dimethylpropanoyl)-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide (#96)

To #73 (100 mg, 0.174 mmol, 1 eq.) in dichloromethane (4 mL, 0.04 M) and N,N-dimethylformamide (0.5 mL) was added #93 (59.1 mg, 0.174 mmol, 1 eq.), followed by diisopropylethylamine (92 µL, 0.52 mmol, 3 eq.) and HATU (102 mg, 0.260 mmol, 1.5 eq.). The reaction was stirred for 18 hours and then concentrated in vacuo. The residue was taken up in ethyl acetate (6 mL) and was washed with 1 M aqueous hydrochloric acid solution (2×2 mL) and with brine. The organic layer was dried over sodium sulfate, filtered, and concentrated in vacuo. Purification by silica gel chromatography (Gradient: 0% to 50% acetone in heptane) provided #96 (102 mg, 65%) as a white solid. LC-MS: m/z 896.7 [M+H$^+$], 918.8 [M+Na$^+$], retention time=1.14 minutes; $^1$H NMR (400 MHz, DMSO-d$_6$), presumed to be a mixture of rotamers, characteristic product signals: δ 7.88 (d, J=7.4 Hz, 2H), [7.83 (br dd, J=6, 5 Hz) and 8.03 (br dd, J=6, 5 Hz), total 1H], 7.67-7.73 (m, 2H), 7.36-7.48 (m, 3H), 7.22-7.35 (m, 4H), 7.13-7.21 (m, 3H), 6.86-6.96 (m, 1H), [4.44 (dd, J=8.6, 8.6 Hz) and 4.50 (dd, J=8.6, 8.6 Hz), total 1H], 3.18, 3.19, 3.26 and 3.29 (4 s, total 6H), 2.96 and 3.11 (2 br s, total 3H), 0.70-0.77 (m, 3H).

Step 2

Synthesis of $N^2$-(3-amino-2,2-dimethylpropanoyl)-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide, trifluoroacetic acid salt (#97)

To #96 (98 mg, 0.11 mmol, 1 eq.) in tetrahydrofuran (2 mL, 0.04 M) was added diethylamine (0.5 mL). After stirring overnight, the reaction was concentrated in vacuo and the residue was purified by reverse phase chromatography (Method C) to give #97 (58 mg, 68%). LC-MS: m/z 674.4 [M+H$^+$], 696.4 [M+Na$^+$], retention time=0.74 minutes; HPLC (Protocol A): 674.5 [M+H$^+$], retention time=7.072 minutes; $^1$H NMR (400 MHz, DMSO-d$_6$), presumed to be a mixture of rotamers, characteristic signals: δ [7.92 (br d, J=8 Hz) and 7.97 (br d, J=8 Hz), total 1H], [7.86 (br dd, J=6, 5 Hz) and 8.07 (br dd, J=6, 5 Hz), total 1H], 7.64-7.74 (br m, 3H), 7.15-7.29 (m, 5H), [4.44 (dd, J=9, 9 Hz) and 4.50 (dd, J=9, 9 Hz), total 1H], 3.26 and 3.29 (2 s, total 3H), 3.18 and 3.20 (2 s, total 3H), 2.96 and 3.10 (2 br s, total 3H), 1.24 and 1.25 (2 s, total 3H), 1.14 and 1.16 (2 s, total 3H), 1.02-1.07 (m, 3H), 0.73-0.80 (m, 3H).

Preparation of 2-methyl-L-prolyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino]propyl}pyrrolidin-1-yl}-5-methyl-1-oxoheptan-4-yl]-N-methyl-L-vaLinamide, trifluoroacetic acid salt (#98)

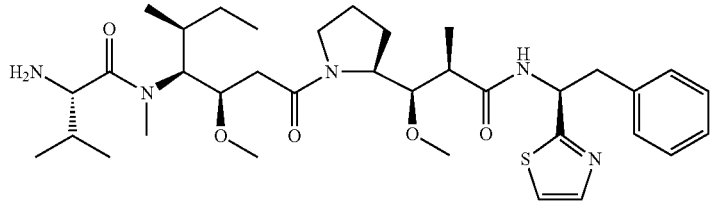

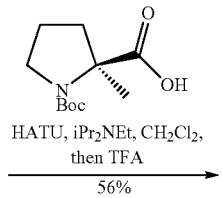

86

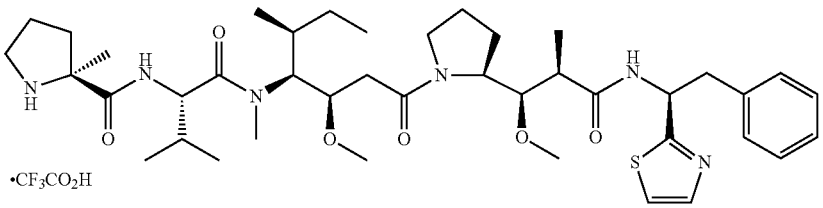

98

To a mixture 1-(tert-butoxycarbonyl)-2-methyl-L-proline (65.1 mg, 0.284 mmol, 1.1 eq.) and #86 (170 mg, 0.258 mmol, 1 eq.) in dichloromethane (5 mL, 0.03 M) was added HATU (0.108 mg, 0.284 mmol, 1.1 eq.) followed by diisopropylethylamine (139 µL, 0.800 mmol, 3.1 eq.). After stirring overnight, the reaction mixture was cooled to 0° C., dichloromethane (3 mL) was added followed by the slow addition of trifluoroacetic acid (2 mL). The reaction mixture was stirred at 0° C. for 5 minutes, allowed to warm to room temperature and then stirred at room temperature for 30 minutes before being concentrated in vacuo. The residue was azeotroped two times with heptane, diluted with a small amount of dichloromethane and methanol before being concentrated in vacuo onto silica The residue was purified by silica gel chromatography (Gradient: 0% to 10% methanol in dichloromethane) and then by reverse phase chromatography (Method C) to afford #98 (128 mg, 56%) as a white solid. LC-MS: m/z 769.4 [M+H$^+$], retention time=1.28 minutes; HPLC (Protocol A at 45° C.) m/z 769.4 [M+H$^+$], retention time=7.146 minutes (purity >98%); $^1$HNMR (400 MHz, DMSO-d$_6$), presumed to be a mixture of rotamers, characteristic signals: δ 9.03-9.15 (br m, 1H), 8.77-8.86 (br m, 1H), 8.69-8.76 (m, 1H), [8.66 (d, J=8.2 Hz) and 8.92 (d, J=8.6 Hz), total 1H], [7.78 (d, J=3.1 Hz) and 7.80 (d, J=3.5 Hz), total 1H], [7.63 (d, J=3.1 Hz) and 7.67 (d, J=3.1 Hz), total 1H], 7.12-7.31 (m, 5H), [5.38 (ddd, J=11, 8, 4 Hz) and 5.47 (ddd, J=11, 9, 4 Hz), total 1H], [4.46 (dd, J=9.4, 9.0 Hz) and 4.55 (dd, J=9.0, 8.6 Hz), total 1H], 3.17, 3.20, 3.22 and 3.25 (4 s, total 6H), 2.98 and 3.04 (2 br s, total 3H), [1.06 (d, J=7.0 Hz) and 1.09 (d, J=6.6 Hz), total 3H], 0.73-0.80 (m, 3H).

Preparation of methyl amino(bicyclo[4.2.0]octa-1,3,5-trien-7-yl)acetate, hydrochloride salt (#102)

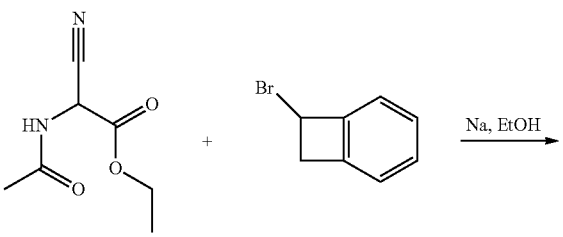

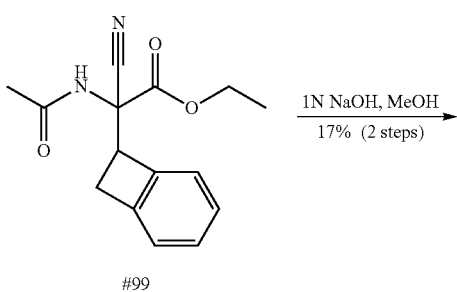

99

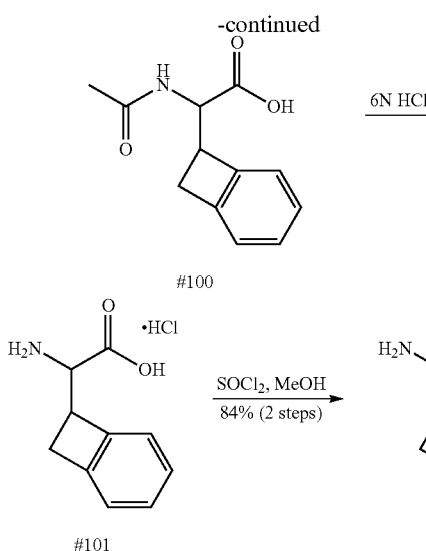

Step 1

Synthesis of ethyl (acetylamino)(bicyclo[4.2.0]octa-1,3,5-trien-7-yl)cyanoacetate (#99)

Sodium (464 mg, 20.2 mmol, 1.2 eq.) was allowed to react with absolute ethanol (40 mL, 0.42 M); to the resulting mixture was added ethyl 2-(acetylamino)-2-cyanoacetate (3.44 g, 20.2 mmol, 1.2 eq.). After 20 minutes at 60° C., 7-bromobicyclo[4.2.0]octa-1,3,5-triene (3.092 g, 16.89 mmol, 1 eq.) was added and the reaction mixture was heated at reflux overnight, then filtered and concentrated in vacuo. The residue was diluted with water and extracted with ethyl acetate. The organic layer was washed with brine, dried over sodium sulfate, filtered, and concentrated in vacuo to give a dark oil, which was purified by silica gel chromatography (Gradient: 0% to 50% ethyl acetate in heptane) to give #99 (4.38 g) as a yellow gum. LC-MS: m/z 273.2 [M+H$^+$], retention time=2.36 minutes.

Step 2

Synthesis of (acetylamino)(bicyclo[4.2.0]octa-1,3,5-trien-7-yl)acetic acid (#100)

To a mixture of #99 (4.38 mg, <16.1 mmol, 1 eq.) in methanol (30 mL, 0.53 M) was added a 1 N aqueous solution of sodium hydroxide (38 mL, 38 mmol, 2.4 eq.). The reaction mixture was heated at reflux overnight, then concentrated in vacuo, diluted with water (40 mL), and acidified with a 1 N aqueous solution of hydrochloric acid (40 mL). The aqueous layer was extracted with dichloromethane (3×30 mL). The combined organic layers were dried over sodium sulfate, filtered and concentrated in vacuo. The resulting oil was purified by silica gel chromatography (Solvent A: dichloromethane; Solvent B: 20% methanol in dichloromethane containing 0.02% trifluoroacetic acid; Gradient: 0% to 40% B) then by supercritical fluid chromatography (Column: Chiralpak AD-H, 250×21 mm; Eluent: 85:15 carbon dioxide/methanol; Flow Rate: 65 g/min; Detection: 210 nm; Instrument: Berger minigram preparative SFC system). The second eluting peak was isolated to give #100 (600 mg, 17% over two steps) as a single enantiomer (retention time=3.37 minutes, purity >99%). LC-MS: m/z 220.3 [M+H$^+$], retention time=2.10 minutes; $^1$H NMR (400 MHz, CD$_3$OD) δ 7.14-7.24 (m, 2H), 7.03-7.09 (m, 2H), 4.59 (d, J=8.6 Hz, 1H), 3.87 (ddd, J=8.5, 5.3, 2.4 Hz, 1H), 3.35 (dd, J=14.5, 5.4 Hz, 1H, assumed; partially obscured by solvent peak), 3.10 (dd, J=14.4, 2.4 Hz, 1H), 2.00 (s, 3H). Optical rotation: [α]$_D^{25}$+70.9° (c 0.67, methanol)

Step 3

Synthesis of amino(bicyclo[4.2.0]octa-1,3,5-trien-7-yl)acetic acid, hydrochloride salt (#101)

A mixture of #100 (200 mg, 0.912 mmol, 1 eq.) and 6 N aqueous hydrochloric acid (12.3 mL, 73.8 mmol, 81 eq.) was heated at reflux overnight. The reaction mixture was concentrated in vacuo to give the single enantiomer #101 (195 mg) as an off-yellow solid, which was used in the next step without further purification.

Step 4

Synthesis of methyl amino(bicyclo[4.2.0]octa-1,3,5-trien-7-yl)acetate, hydrochloride salt (#102)

To a mixture of #101 (195 mg, <0.913 mmol, 1 eq.) in methanol (20 mL, 0.04 M) was added thionyl chloride (0.666 mL, 9.13 mmol, 10 eq.). After two hours at reflux, the reaction mixture was concentrated in vacuo to give the single enantiomer #102 (175 mg, 84% over two steps) as a light-colored solid. LC-MS: m/z 192.3 [M+H$^+$], retention time=0.80 minutes; GC-MS: m/z 192 [M+H$^+$], retention time=3.206 minutes; $^1$H NMR (400 MHz, CD$_3$OD) δ 7.24-7.33 (m, 2H), 7.11-7.18 (m, 2H), 4.40 (d, J=6.9 Hz, 1H), 3.99-4.05 (m, 1H), 3.78 (s, 3H), 3.46 (dd, J=14.8, 5.4 Hz, 1H), 3.23 (dd, J=14.8, 2.5 Hz, 1H).

Preparation of (2R,3R)-3-Methoxy-2-methyl-3-[(2S)-pyrrolidin-2-yl]propanoic acid, hydrochloride salt (#103)

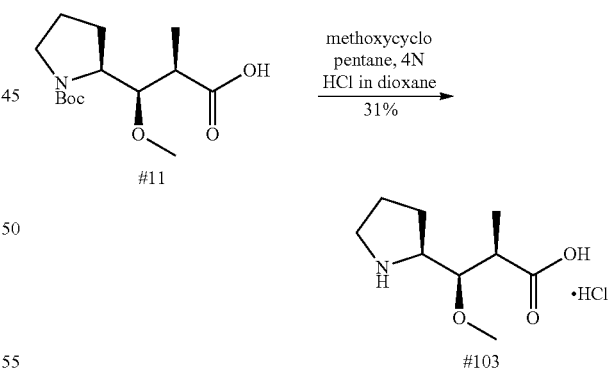

To a mixture of #11 (4.09 g, 14.2 mmol, 1 eq.) in cyclopentyl methyl ether (10 mL, 0.14 M) was added a 4 N solution of hydrogen chloride in dioxane (37 mL, 100 mmol, 7 eq.). After three hours, the reaction mixture was concentrated in vacuo and azeotroped three times with heptane to give #103 (1000 mg, 31%) as a gum, which was used in the next step without further purification. $^1$H NMR (400 MHz, DMSO-d$_6$) δ 9.92-10.06 (br s, 1H), 8.66-8.80 (br s, 1H), 3.89 (dd, J=5.2, 4.9 Hz, 1H), 3.43-3.53 (m, 1H), 3.39 (s, 3H), 3.06-3.17 (m, 2H), 2.66 (qd, J=7.1, 4.6 Hz, 1H), 1.71-2.03 (m, 4H), 1.11 (d, J=7.1 Hz, 3H).

Preparation of 2-Methylalanyl-N-[(3R,4S,5S)-1-{(2S)-2-[(1R,2R)-3-{[1-(bicyclo[4.2.0]octa-1,3,5-trien-7-yl)-2-methoxy-2-oxoethyl]amino}-1-methoxy-2-methyl-3-oxopropyl]pyrrolidin-1-yl}-3-methoxy-5-methyl-1-oxoheptan-4-A-N-methyl-L-valinamide, trifluoroacetic acid salt (#107) and 2-methylalanyl-N-[(3R,4S,5S)-1-{(2S)-2-[(1R,2R)-3-{[bicyclo[4.2.0]octa-1,3,5-trien-7-yhcarboxy)methyl]amino}-1-methoxy-2-methyl-3-oxopropyl]pyrrolidin-1-yl}-3-methoxy-5-methyl-1-oxoheptan-4-A-N-methyl-L-valinamide, trifluoroacetic acid salt (#108)

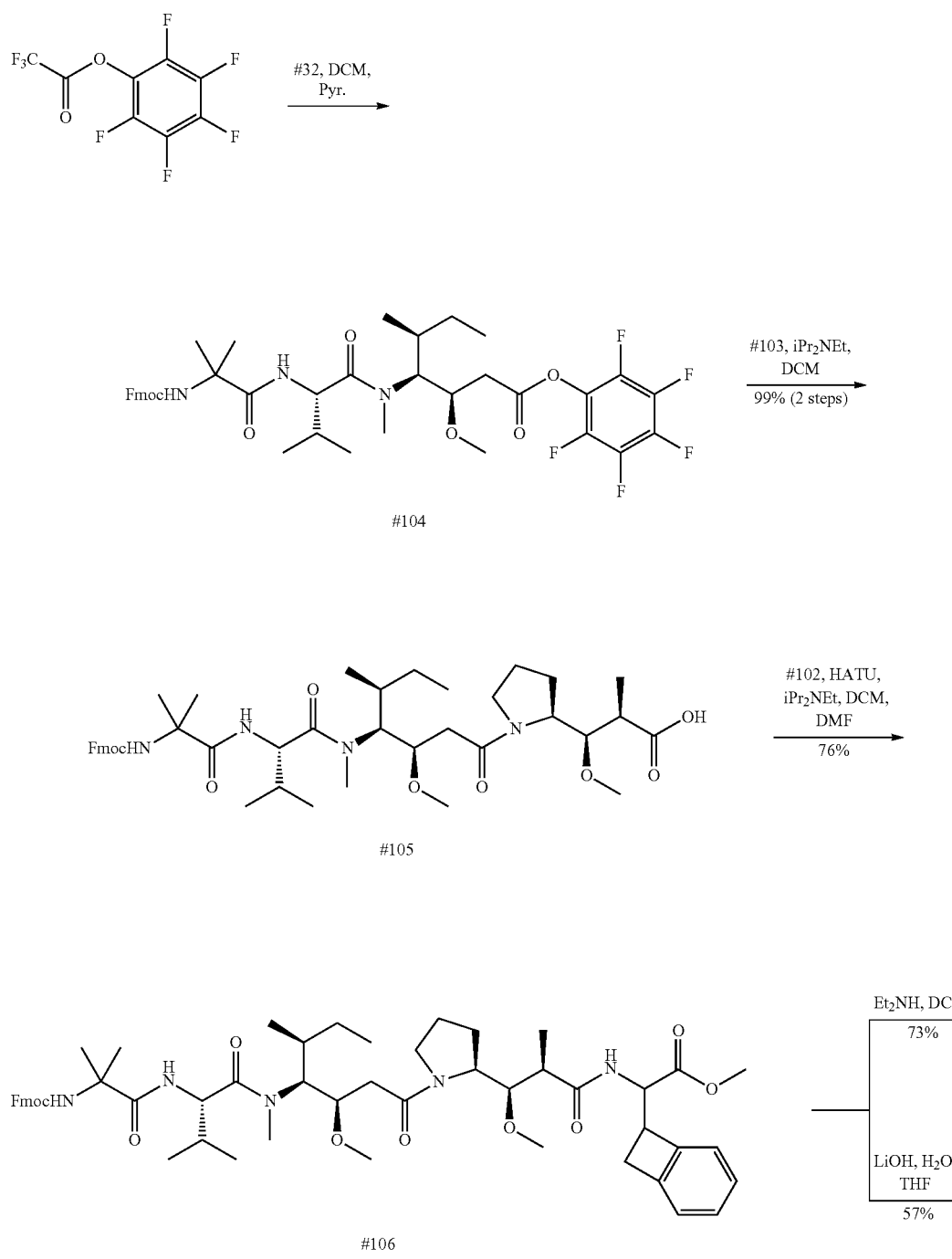

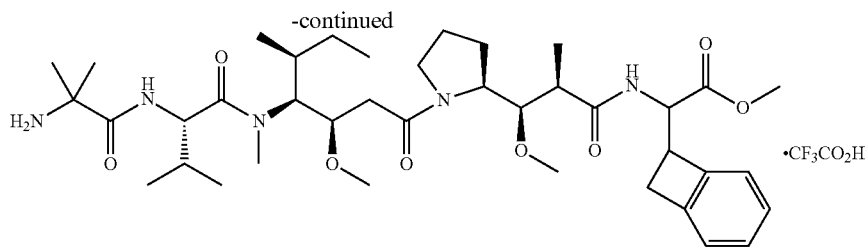

107

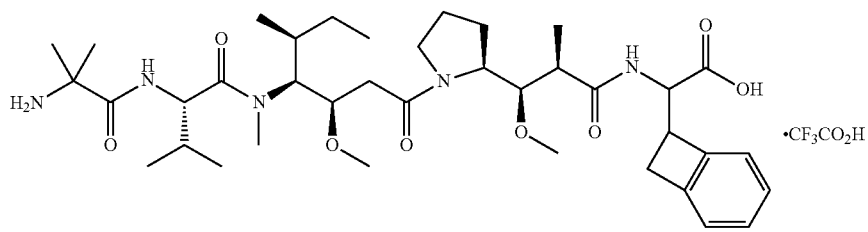

108

Step 1

Synthesis of N-[(9H-fluoren-9-ylmethoxy)carbonyl]-2-methylalanyl-N-[(3R,4S,5S)-3-methoxy-5-methyl-1-oxo-1-(pentafluorophenoxy)heptan-4-yl]-N-methyl-L-valinamide (#104)

To #32 (4.00 g, 6.56 mmol, 1 eq.) in dichloromethane (20 mL, 0.33 M) and pyridine (1.06 mL, 13.1 mmol, 2 eq.) was added drop-wise pentafluorophenyl trifluoroacetate (2.25 mL, 13.1 mmol, 2 eq.). The reaction mixture was stirred for one hour.

To a second flask containing #32 (360 mg, 0.59 mmol) in dichloromethane (0.6 mL, 1 M) and pyridine (0.095 mL, 1.2 mmol, 2 eq.) was added drop-wise pentafluorophenyl trifluoroacetate (0.203 mL, 1.18 mmol). This reaction mixture was stirred for 15 minutes.

The two reaction mixtures were combined, washed twice with 1 N aqueous hydrochloric acid, dried over sodium sulfate, filtered and concentrated in vacuo. The resulting yellow oil was dissolved in ethyl acetate, pre-adsorbed onto silica gel and purified by silica gel chromatography (Gradient: 0% to 40% ethyl acetate in heptane) to give #104 (4.6 g, 83%) as a white foam containing some impurities. LC-MS: m/z 798.3 [M+Na$^+$], retention time=1.23 minutes.

Step 2

Synthesis of N-[(9H-fluoren-9-ylmethoxy)carbonyl]-2-methylalanyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (#105)

To a mixture of #104 (2.00 g, <2.58 mmol, 1 eq.) in dichloromethane (6 mL, 0.4 M) was added a solution of #103 (483 mg, 2.16 mmol, 1 eq.) in dichloromethane (2 mL) followed by diisopropylethylamine (1.35 mL, 7.73 mmol, 3 eq.). The reaction mixture was stirred for 16 hours, then adsorbed onto silica and purified by silica gel chromatography (Gradient: 0% to 20% methanol in dichloromethane) to give #105 (1.67 g, 83%) as a white foam. Fractions containing the desired product with impurities (0.571 g) were collected separately.

The above reaction and purification were repeated in a similar fashion using #104 (2.60 g, <3.35 mmol, 1 eq.), #103 (750 mg, 3.35 mmol, 1 eq.), dichloromethane (10 mL, 0.3 M) and diisopropylethylamine (1.35 mL, 7.73 mmol, 2.3 eq.) to give #105 (2.4 g, 92%) as a tan foam. Fractions containing impure product (1.7 g) were combined with the previous impure fractions and purified as described above to afford additional #105 (1.30 g, quantitative yield for both reactions over two steps). LC-MS: m/z 779.3 [M+H$^+$], 802.3 [M+Na$^+$], retention time=1.05 minutes.

Step 3

Synthesis of N-[(9H-fluoren-9-ylmethoxy)carbonyl]-2-methylalanyl-N-[(3R,4S,5S)-1-{(2S)-2-[(1R,2R)-3-{[1-(bicyclo[4.2.0]octa-1,3,5-trien-7-yl)-2-methoxy-2-oxoethyl]amino}-1-methoxy-2-methyl-3-oxopropyl]pyrrolidin-1-yl}-3-methoxy-5-methyl-1-oxoheptan-4-yl]-N-methyl-L-valinamide (#106)

To a mixture of #105 (225 mg, 0.289 mmol, 1 eq.) in dichloromethane (15 mL, 0.02 M) and N,N-dimethylformamide (1 mL) was added HATU (136 mg, 0.347 mmol, 1.2 eq.). After five minutes, a solution of amine #102 (72.4 mg, 0.318 mmol, 1 eq.) and diisopropylamine (203 mL, 1.16 mmol, 3 eq.) in dichloromethane (5 mL) was added. After 24 hours, the reaction mixture was washed with brine, dried over sodium sulfate, filtered, concentrated in vacuo onto silica gel, and purified by silica gel chromatography (Gradient: 0% to 50% acetone in heptane) to give the single enantiomer #106 (210 mg, 76%) as a clear oil. LC-MS: m/z 953.1 [M+H$^+$], retention time=3.99 minutes; $^1$H NMR (400 MHz, CDCl$_3$), presumed to be a mixture of rotamers, characteristic signals: 7.76 (d, J=7.5 Hz, 2H), 7.57-7.64 (m, 2H), 7.40 (dd, J=7.5, 7.4 Hz, 2H), 7.28-7.34 (m, 2H), 4.82-4.88 (m, 1H), 3.95-4.01 (m, 1H), 3.76 and 3.82 (2 s, total 3H), 3.30, 3.31, 3.34 and 3.35 (4 s, total 6H), [1.20 (d, J=7.0 Hz) and 1.20 (d, J=7.0 Hz), total 3H].

Step 4A

Synthesis of 2-methylalanyl-N-[(3R,4S,5S)-1-{(2S)-2-[(1R,2R)-3-{[1-(bicyclo[4.2.0]octa-1,3,5-trien-7-yl)-2-methoxy-2-oxoethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#107)

According to general procedure A, from #106 (25 mg, 0.026 mmol, 1 eq.) in dichloromethane (10 mL, 0.003 M) and diethylamine (4 mL) was synthesized the crude desired material, which was purified by reverse phase chromatography (Method C) to give the single enantiomer #107 (16 mg, 73%) as a solid. LC-MS: m/z 730.8 [M+H⁺], retention time=2.13 minutes; HPLC (Protocol N): retention time=9.889 minutes.

Step 4B

Synthesis of 2-methylalanyl-N-[(3R,4S,5S)-1-{(2S)-2-[(1R,2R)-3-{[bicyclo[4.2.0]octa-1,3,5-trien-7-yl(carboxy)methyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#108)

The single enantiomer #108 (94.5 mg, 57%) was synthesized from #106 (190 mg, 0.200 mmol) according to a procedure similar to the one described for synthesis of #41 from #40. LC-MS: m/z 716.8 [M+H⁺], retention time=2.06 minutes; HPLC (Protocol N): retention time=9.137 minutes.

Preparation of 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#112)

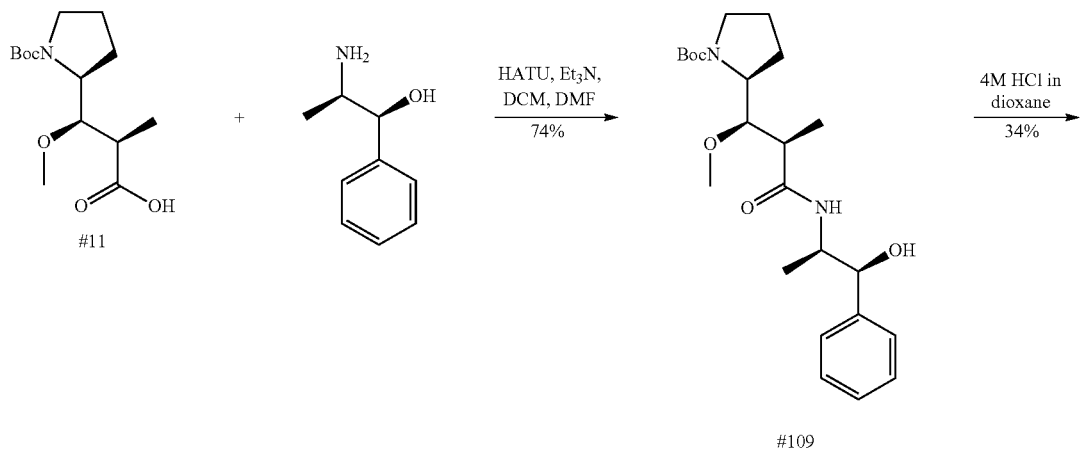

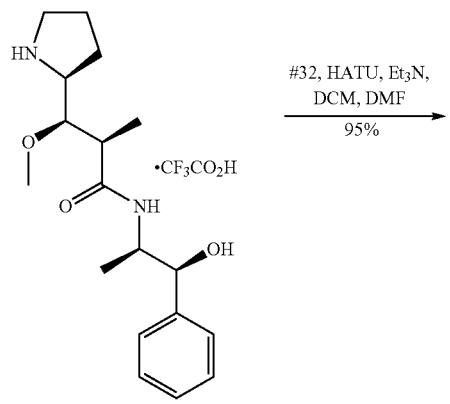

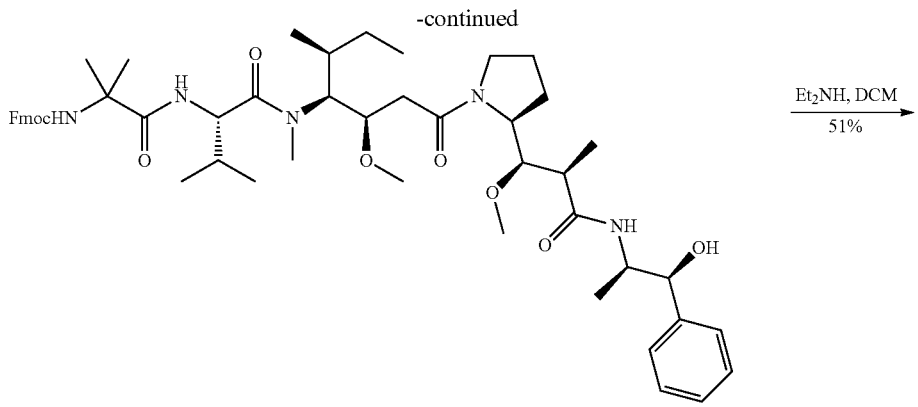

111

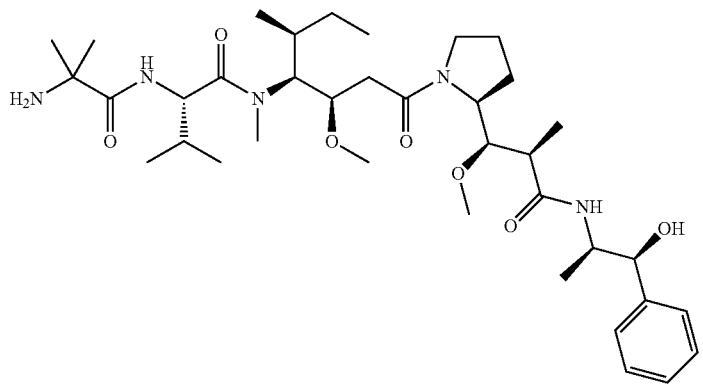

112

Step 1

Synthesis of tert-butyl (2S)-2-[(1R,2R)-3-{[(1S,2R)-1-hydroxy-1-phenylpropan-2-yl]amino}-1-methoxy-2-methyl-3-oxopropyl]pyrrolidine-1-carboxylate (#109)

To a solution of #11 (2.00 g, 6.96 mmol, 1 eq.) in dichloromethane (21 mL, 0.3 M) and N,N-dimethylformamide (3 mL) was added HATU (3270 mg, 8.35 mmol, 1.2 eq.). After two minutes, the amine (1R,2S)-(+)-norephedrine (1.07 mg, 6.96 mmol, 1 eq.) and triethylamine (1.94 mL, 13.9 mmol, 2 eq.) were added. After two hours, the reaction mixture was diluted with ethyl acetate (100 mL), washed with a 1 M aqueous solution of hydrochloric acid and with brine, dried over sodium sulfate, filtered, concentrated in vacuo, and purified by silica gel chromatography (Gradient: 0% to 60% ethyl acetate in heptane) to provide #109 (2.18 g, 74%) as a white solid. LC-MS: m/z 321.3 [(M−Boc)+H$^+$], retention time=3.14 minutes; $^1$H NMR (400 MHz, DMSO-d$_6$), presumed to be a mixture of rotamers, characteristic signals: δ 7.64 (d, J=8.6 Hz, 1H), 7.24-7.33 (m, 4H), 7.15-7.21 (m, 1H), 5.35 (br d, J=5 Hz, 1H), 4.45 (br dd, J=5, 5 Hz, 1H), 3.91-4.00 (m, 1H), 3.30-3.39 (m, 1H), 3.26 (s, 3H), 2.94-3.07 (m, 1H), 2.04-2.14 (m, 1H), 1.46-1.78 (m, 4H), 1.40 (s, 9H), 0.97-1.04 (m, 6H).

Step 2

Synthesis of (2R,3R)—N-[(1S,2R)-1-hydroxy-1-phenylpropan-2-yl]-3-methoxy-2-methyl-3-[(2S)-pyrrolidin-2-yl]propanamide, trifluoroacetic acid salt (#110)

According to general procedure C, at 0° C. from #109 (414 mg, 0.984 mmol, 1 eq.), dioxane (5 mL, 0.2 M) and a 4 M solution of hydrogen chloride in dioxane (15 mL, 60 mmol, 60 eq.) was synthesized the crude desired compound, which was purified by reverse phase chromatography (Method C) to give #110 (120 mg, 34%) as a viscous liquid. LC-MS: m/z 321.1 [M+H$^+$], retention time=0.55 minutes; $^1$H NMR (400 MHz, DMSO-d$_6$), characteristic signals: δ 7.90 (d, J=8.6 Hz, 1H), 7.28-7.36 (m, 4H), 7.20-7.27 (m, 1H), 4.46 (d, J=6.2 Hz, 1H), 3.48 (dd, J=8.6, 2.3 Hz, 1H), 3.38 (s, 3H), 2.92-3.16 (m, 3H), 2.24-2.35 (m, 1H), 1.49-1.88 (m, 4H), 1.09 (d, J=6.6 Hz, 3H), 1.01 (d, J=6.6 Hz, 3H).

Step 3

Synthesis of N-[(9H-fluoren-9-ylmethoxy)carbonyl]-2-methylalanyl-N—[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#111)

According to general procedure D, from #32 (140 mg, 0.230 mmol, 1 eq.), #110 (110 mg, 0.253 mmol, 1.1 eq.), dichloromethane (3 mL, 0.08 M), N,N-dimethylformamide (0.5 mL), HATU (96.2 mg, 0.253 mmol, 1.1 eq) and triethylamine (96 μL, 0.69 mmol, 3 eq.) was synthesized the crude desired product, which was purified by silica gel chromatography (Gradient: 0% to 40% acetone in heptane) to give #111 (220 mg, 95%). LC-MS: m/z 912.4 [M+H$^+$], 935.4 [M+Na$^+$], retention time=2.15 minutes; HPLC (Protocol B): m/z 912.5 [M+H$^+$], 934.5 [M+Na$^+$], retention time=10.138 minutes (purity >94%); $^1$H NMR (400 MHz, DMSO-d$_6$), presumed to be a mixture of rotamers, characteristic signals: δ 7.89 (d, J=7.8 Hz, 2H), 7.66-7.75 (m, 2H), 7.41 (dd, J=7.4, 7.4 Hz, 2H), 7.12-7.20 (m, 1H), [5.33 (d, J=4.7 Hz) and 5.38 (d, J=4.7 Hz), total 1H], 3.15, 3.18, 3.22 and 3.23 (4 s, total 6H), 1.30, 1.33, 1.36 and 1.39 (4 s, total 6H), 0.95-1.06 (m, 6H).

Step 4

Synthesis of 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#112)

According to general procedure A, from #111 (210 mg, 0.230 mmol) in dichloromethane (5 mL, 0.05 M) and diethylamine (5 mL) was synthesized the crude desired material, which was purified by silica gel chromatography (Gradient: 0% to 10% methanol in dichloromethane) to give a mixture of an oil and solid. Diethyl ether and heptane were added and the mixture was concentrated in vacuo, producing #112 (81 mg, 51%) as a white solid. LC-MS: m/z 690.4 [M+H$^+$], retention time=1.10 minutes; HPLC (Protocol A): m/z 690.5 [M+H$^+$], 712.4 [M+Na$^+$], retention time=7.229 minutes (purity >90%); $^1$H NMR (400 MHz, DMSO-d$_6$), presumed to be a mixture of rotamers, characteristic signals: δ [7.62 (br d, J=8 Hz), 7.88 (br d, J=8 Hz), 8.07 (br d, J=9 Hz) and 8.11 (br d, J=9 Hz), total 2H], 7.15-7.34 (m, 5H), [5.34 (d, J=4 Hz) and 5.41 (d, J=5 Hz), total 1H], 3.18, 3.21, 3.23 and 3.25 (4 s, total 6H), 2.93 and 3.08 (2 br s, total 3H), 1.15, 1.18, 1.21 and 1.25 (4 s, total 6H).

Preparation of N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (115)

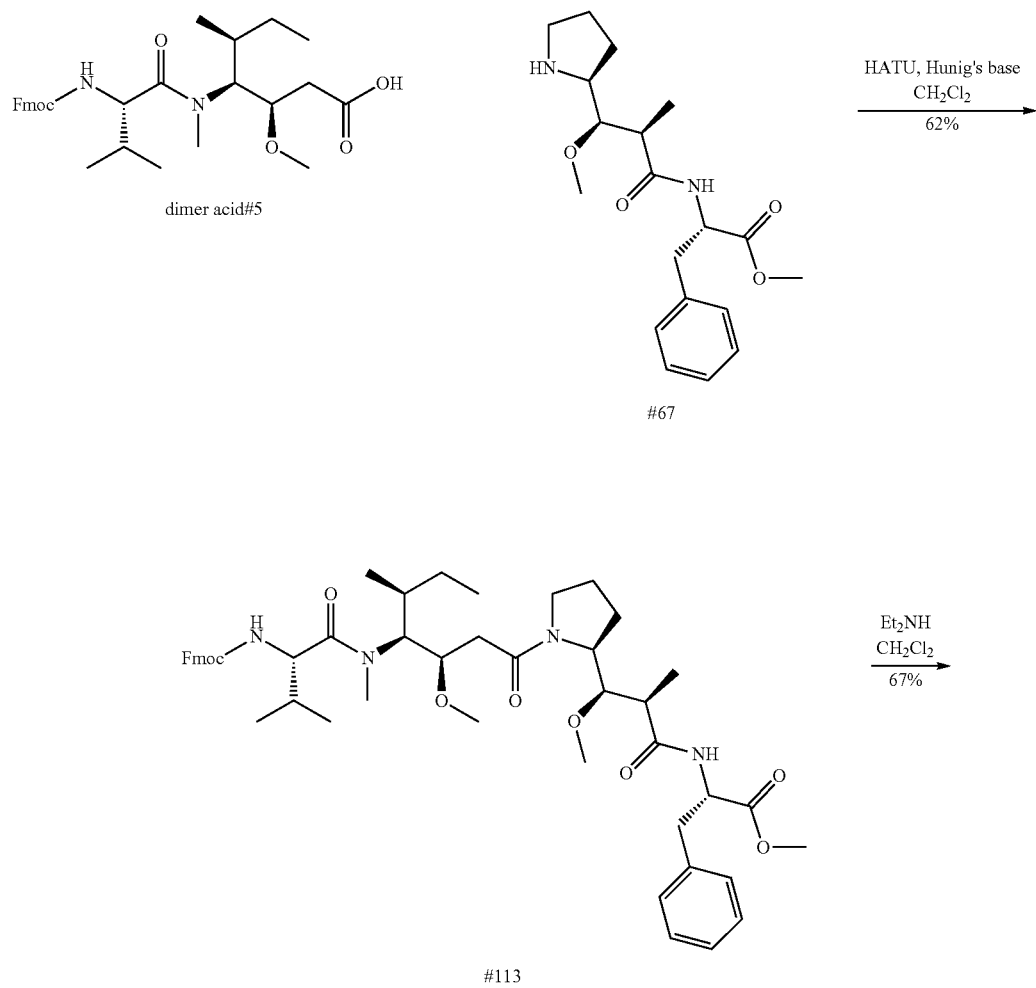

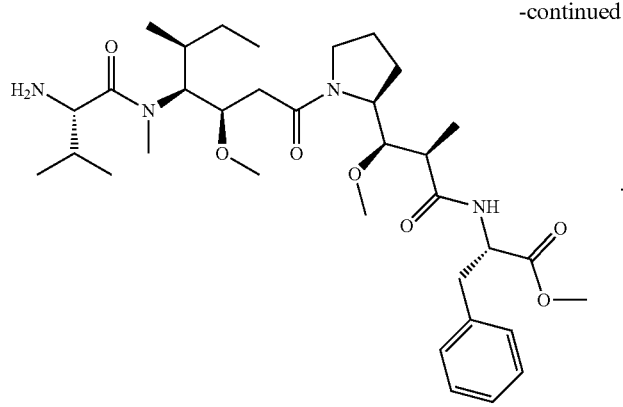

114

1. N-[(9H-fluoren-9-ylmethoxy)carbonyl]-N,2-dimethylalanine HATU, Hunig's base, CH$_2$Cl$_2$
2. LiOH, THF, water
   64%

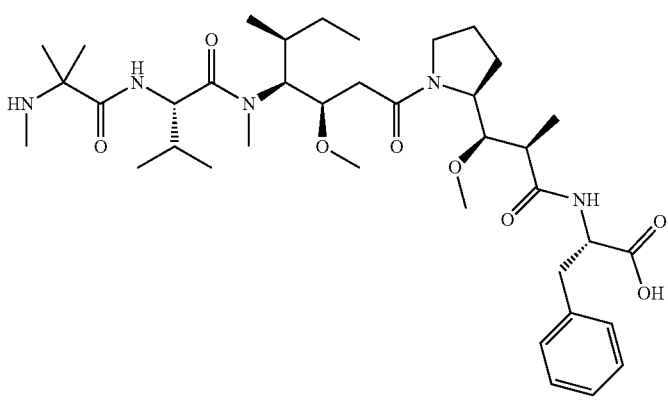

115

Step 1

Synthesis of methyl N-{(2R,3R)-3-[(2S)-1-{(3R,4S,5S)-4-[{N-[(9H-fluoren-9-ylmethoxy)carbonyl]-L-valyl}(methyl)amino]-3-methoxy-5-methylheptanoyl}pyrrolidin-2-yl]-3-methoxy-2-methylpropanoyl}-L-phenylalaninate (#113).

To a stirring mixture of dimer acid#5 (12.1 g, 23.0 mM) and #67 (11.5 g, 23.0 mM) in 75 mL of dichloromethane under nitrogen, HATU (10.8 g, 27.6 mM) was added followed by Hunig's base (12.1 mL, 69.0 mM). The reaction was allowed to stir at room temperature for 15 hours. Reaction was concentrated to a smaller volume, taken up with ethyl acetate and washed with 1 N HCl two times. The organic layer was then washed with brine, dried over sodium sulfate, filtered, and concentrated in vacuo. Residue was then purified by silica gel chromatography (Gradient: 0% to 70% acetone in heptanes), producing #113 (12.3 g, 62%) as a white solid. LC-MS (Protocol Q): m/z 855.3 [M+H$^+$], 877.2 [M+Na$^+$], retention time=2.32 minutes; HPLC (Protocol R): /z 855.5 [M+H$^+$], retention time=9.596 minutes (purity >97%).

Step 2

Synthesis of methyl N-{(2R,3R)-3-methoxy-3-[(2S)-1-{(3R,4S,5S)-3-methoxy-5-methyl-4-[methyl(L-valyl)amino]heptanoyl}pyrrolidin-2-yl]-2-methylpropanoyl}-L-phenylalaninate (#114)

According to general procedure A, from #113 (12 g, 14 mmol, 1 eq.), dichloromethane (60 mL, 0.24 M) and diethylamine (40 mL, 390 mM) was synthesized #114 (5.9 g, 67%) white/slight yellow solid after purification by silica gel chromatography (Gradient: 0% to 25% methanol in dichloromethane). LC-MS (Protocal Q): m/z 633.0 [M+H$^+$], retention time=1.19 minutes. HPLC (Protocol A): /z 633.5 [M+H$^+$], retention time=7.142 minutes (purity >98%).

Step 3

Synthesis of N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide-trifluoroacetic acid salt (#115)

To a stirring mixture of N-[(9H-fluoren-9-ylmethoxy)carbonyl]-N,2-dimethylalanine (167 mg, 0.493 mM), #114 (260 mg, 0.411 mM), and HATU (188 mg, 0.493 mM) in 10 mL of dichloromethane, Hunig's base (0.14 mL, 0.82 mM) was added. The reaction was allowed to stir at room temperature for 1 hour and 20 minutes. Reaction was reduced down. THF (9 mL) was added to crude material and to this stirring mixture lithium hydroxide (49.2 mg, 2.06 mM) dissolved in 3 mL of water was added. The reaction was allowed to stir at room temperature for 4 hours. Reaction was concentrated down followed by purification by medium pressure reverse phase C18 chromatography (Gradient: 5% to 45% water in acetonitrile with 0.02% TFA in each phase) #115 (218 mg, 64%) white solid. LC-MS (Protocol Q): m/z 718.7 [M+H$^+$], 740.6 [M+Na$^+$], retention time=1.21 minutes. HPLC (Protocol A at 45° C.): m/z 718.4 [M+H$^+$], retention time=6.903 minutes. $^1$H NMR (400 MHz, DMSO-d$_6$), δ 8.81-8.95 (m), 8.44-8.50 (m), 8.42 (d), 8.15 (d), 7.14-7.28 (m), 4.71-4.78 (m), 4.57-4.66 (m), 4.49-4.56 (m), 4.41-4.48 (m), 3.94-4.05 (m), 3.72-3.79 (m), 3.39-3.60 (m), 2.95-3.33 (m), 2.78-2.89 (m), 2.69 (s), 2.43-2.50 (m), 2.08-2.42 (m), 1.60-1.92 (m), 1.20-1.57 (m), 0.84-1.11 (m), 0.74-0.83 (m).

Preparation of 2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3 oxopropyl]pyrrolidin-1-yl}-5-methyl-1-oxoheptan-4-yl]-N-methyl-L-valinamide, trifluoroacetic acid salt (#117) and 2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#118)

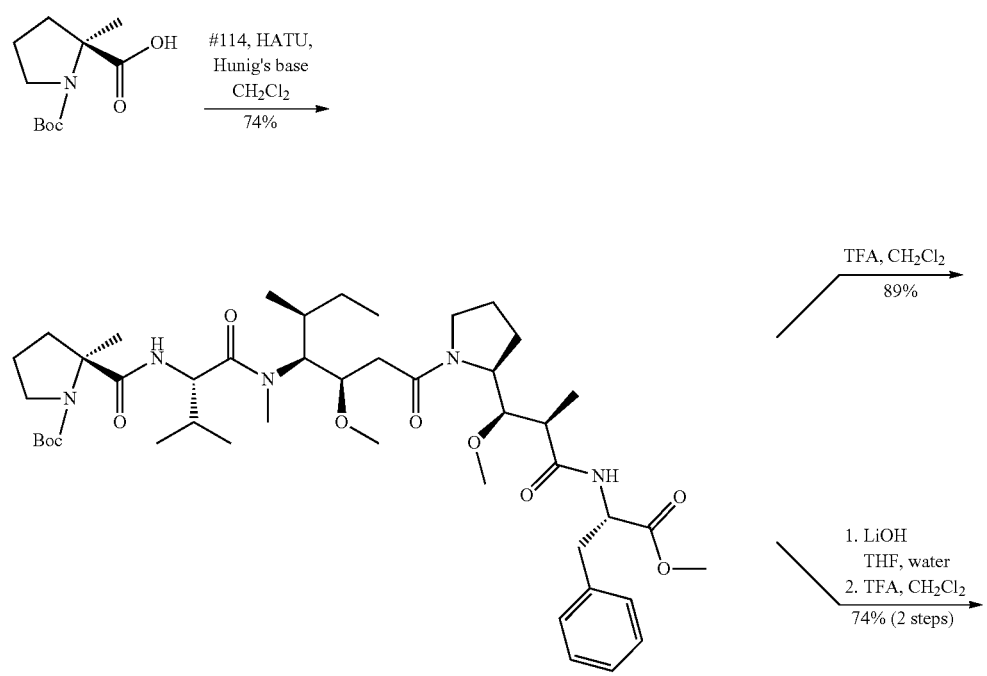

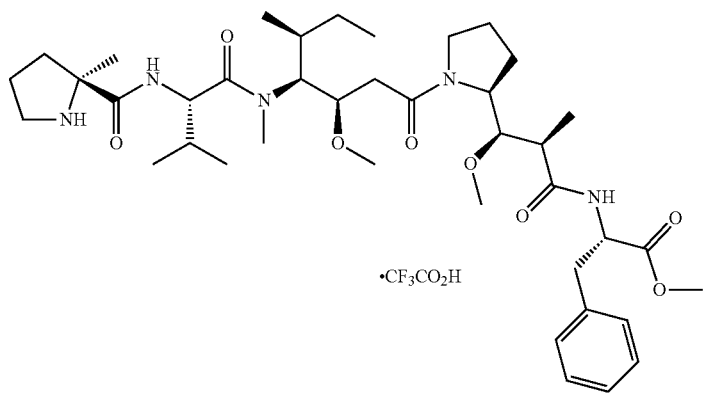

-continued

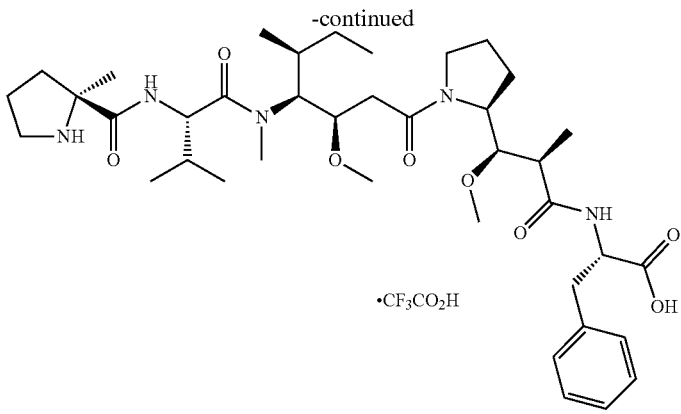

•CF₃CO₂H

118

Step 1

Synthesis of 1-(tert-butoxycarbonyl)-2-methyl-L-prolyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#116)

To a stirring solution of #114 (1.02 g, 1.61 mmol, 1.0 eq.) and 1-(tert-butoxycarbonyl)-2-methyl-L-proline (443 mg, 1.93 mmol, 1.2 eq.) in 12 mL of dichloromethane, HATU (735 mg, 1.93 mmol, 1.2 eq.) was added followed by Hunig's base (1.12 mL, 6.45 mmol, 4.0 eq.). The reaction was allowed to stir at room temperature for 2 hours. The reaction was reduced down, diluted with ethyl acetate before being washed with 0.5 N HCl and brine. Organics where then dried over sodium sulfate, reduced to a smaller volume, and then reduced down on silica. Silica chromatography was then performed (Gradient: 0%-45% acetone in heptanes) producing #116 (1.02 g, 74%) as a white solid. LC-MS (Protocol Q): m/z 844.3 [M+H⁺], 867.2 [M+Na⁺], retention time=2.15 minutes.

Step 2A

Synthesis of 2-methyl-L-prolyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#117)

To a stirring solution of #116 (450 mg, 0.533 mmol, 1.0 eq.) in 7 mL of dichloromethane at 0° C., TFA (3 mL, 40 mmol, 70 eq.) was added. The reaction was allowed to stir at 0° C. for 5 minutes and then allowed to warm to room temperature while stirring for 20 minutes. Reaction was reduced down, diluted with dichloromethane and a small amount of methanol before being reduced down onto silica. Silica chromatography was then performed (Gradient: 0%-20% methanol in ethyl acetate) producing #117 (396 mg, 89%) as a white solid. LC-MS (Protocol Q): m/z 744.5 [M+H⁺], 767.2 [M+Na⁺], retention time=1.40 minutes; HPLC (Protocol A at 45° C.): m/z 744.5 [M+H⁺], retention time=7.149 minutes (purity >91%). ¹H NMR (400 MHz, DMSO-d₆), δ 8.73-9.14 (m), 8.66 (br d), 8.50 (d), 8.22 (d), 7.12-7.25 (m), 4.67-4.74 (m), 4.41-4.63 (m), 3.93-4.00 (m), 3.73 (dd), 3.63 (d), 3.46-3.57 (m), 3.38-3.45 (m), 3.26-3.23 (m), 3.22-3.25 (m), 3.06-3.22 (m), 2.99-3.05 (m), 2.93-2.97 (m), 2.80-2.89 (m), 2.75-2.78 (m), 2.64-2.67 (m), 2.46-2.50 (m), 2.27-2.43 (m), 2.00-2.26 (m), 1.85-1.99 (m), 1.70-1.83 (m), 1.52-1.69 (m), 1.33-1.51 (m), 1.18-1.31 (m), 0.98-1.07 (m), 0.93-0.97 (m), 0.82-0.92 (m), 0.71-0.78 (m).

Step 2B

Synthesis of 2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#118)

To a stirring solution of #116 (435 mg, 0.515 mmol), in 4 mL of THF under nitrogen, LiOH (24.7 mg, 1.03 mmol, 2.0 eq.) dissolved in 2 mL of water was added. The reaction was allowed to stir at room temperature until LC-MS indicated saponification of methyl ester. Reaction was concentrated in vacuo and then placed underneath vacuum. Reaction was diluted with dichloromethane and placed underneath nitrogen. To this stirring mixture TFA (3 mL, 40.5 mmol, 80 eq.) was added. Reaction was allowed to stir at room temperature for 30 minutes. Reaction was then reduced down. Residue was purified by medium pressure reverse phase C18 chromatography (Gradient: 5% to 60% acetonitrile in water with 0.02% TFA in each phase) #118 (396 mg, 89%) as a white solid. LC-MS (Protocol Q): m/z 730.2 [M+H⁺], retention time=1.18 minutes; HPLC (Protocol A at 45° C.): m/z 730.5 [M+H⁺], retention time=7.088 minutes (purity >98%). ¹H NMR (400 MHz, DMSO-d₆), δ 9.04-9.13 (m), 8.75-8.87 (m), 8.70 (d), 8.38 (d), 8.11 (d), 7.10-7.24 (m), 4.66-4.74 (m), 4.48-4.64 (m), 4.37-4.47 (m), 3.91-3.99 (m), 3.77 (m), 3.47-3.56 (m), 3.33-3.47 (m), 3.08-3.30 (m), 2.93-3.07 (m), 2.75-2.86 (m), 2.63-2.69 (m), 2.45-2.50 (m), 2.28-2.44 (m), 2.03-2.27 (m), 1.88-2.02 (m), 1.68-1.86 (m), 1.55-1.67 (m), 1.30-1.47 (m), 1.17-1.29 (m), 0.98-1.05 (m), 0.93-0.97 (m), 0.83-0.92 (m), 0.71-0.79 (m).

Preparation of 2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#123)
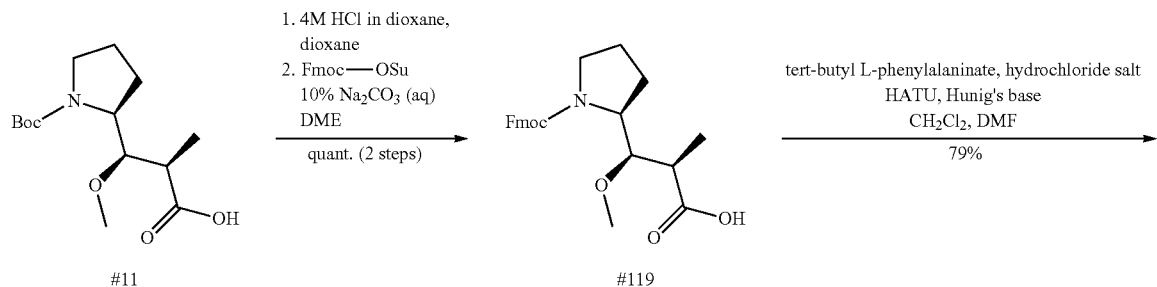
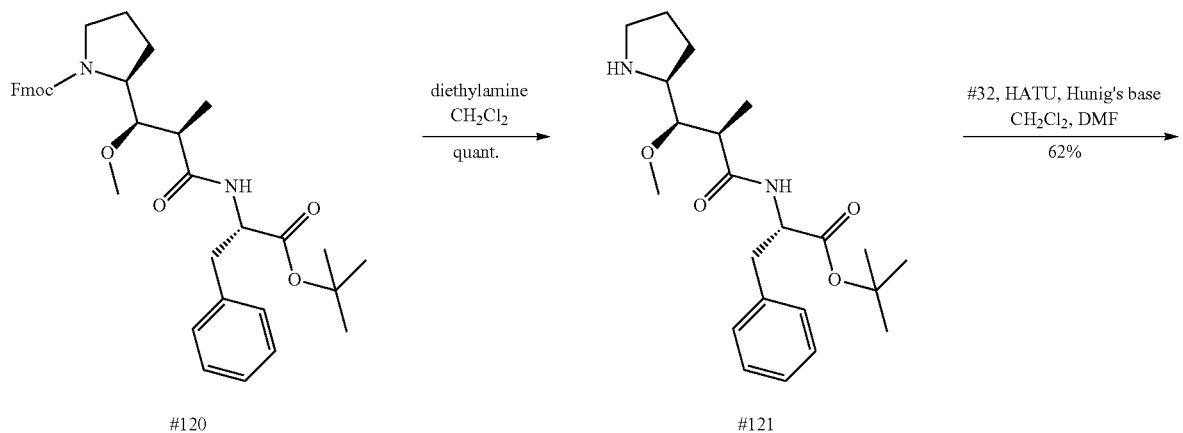
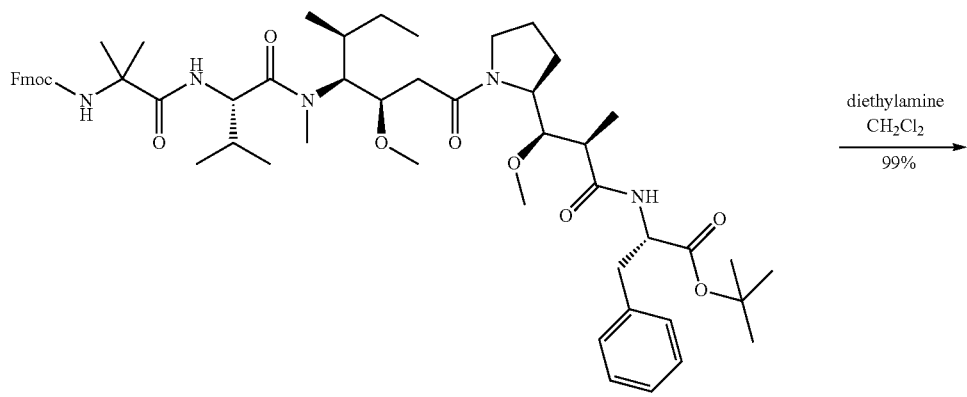

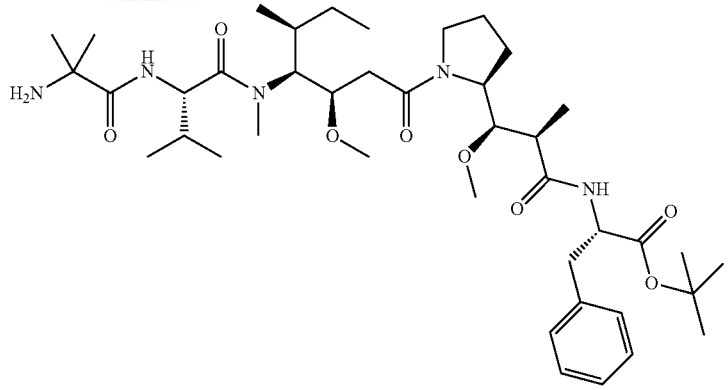

123

Step 1

Synthesis of (2R,3R)-3-{(2S)-1-[(9H-fluoren-9-yl-methoxy)carbonyl]pyrrolidin-2-yl}-3-methoxy-2-methylpropanoic acid (#119)

To a stirring solution of #11 (2.4 g, 8.4 mmol, 1.0 eq.) in 10 mL of dioxane under nitrogen, 4M HCl in dioxane (20 mL, 80 mM, 10 eq.) was added. The reaction was allowed to stir at room temperature for 3 hours before being concentrated in vacuo and placed underneath high vacuum. Crude material was then dissolved with 30 mL of 10% $Na_2CO_3$. This solution was then added to a stirring solution of 1-{[(9H-fluoren-9-ylmethoxy)carbonyl]oxy}pyrrolidine-2,5-dione (2.96 g, 8.77 mmol, 1.05 eq.) in 30 mL of DME. Reaction was allowed to stir at room temperature until TLC (20% methanol/40% ethyl acetate/40% heptanes) indicated the consumption of Boc de-protected starting material. The reaction was concentrated in vacuo to a smaller volume, washed twice with ether, acidified to pH 2 using concentrated HCl and then extracted three times with a solution of 90% dichloromethane 10% methanol. The organics where washed with saturated sodium bicarbonate and brine before being dried over sodium sulfate, filtered, and concentrated in vacuo to a brown solid #119 (3.4 g, quant.). LC-MS (Protocol Q): m/z 410.0 [M+H$^+$], retention time=1.81 minutes.

Step 2

Synthesis tert-butyl N-[(2R,3R)-3-{(2S)-1[(9H-fluoren-9-ylmethoxy)carbonyl]pyrrolidin-2-yl}-3-methoxy-2-methylpropanoyl]-L-phenylalaninate (#120)

To a stirring solution of tert-butyl L-phenylalaninate, hydrochloride salt (1.67 g, 6.5 mmol, 1.0 eq.) and #119 (5.9 g, 6.5 mmol, 1.0 eq.) in 50 mL of dichloromethane and 5 mL of DMF, HATU (2.9 g, 7.9 mmol, 1.2 eq.) was added followed by Hunig's base (5.6 mL, 32 mmol, 5.0 eq.). The reaction was allowed to stir at room temperature for 45 minutes. Reaction was reduced down, diluted with ethyl acetate, washed with 0.5 N HCl and brine before being concentrated down onto silica. Silica chromatography was then performed (Gradient: 0%-25% acetone in heptane) producing #120 (3.14 g, 79%) as a white yellow solid. LC-MS (Protocol Q): m/z 613.1 [M+H$^+$] retention time=2.37 minutes.

Step 3

Synthesis of tert-butyl N-{(2R,3R)-3-methoxy-2-methyl-3-[(2S)-pyrrolidin-2-yl]propanoyl}-L-phenylalaninate (#121)

To a stirring solution of #120 (2.87 g, 4.68 mmol, 1.00 eq.) in 20 mL of dichloromethane, diethylamine (10 mL, 95 mM, 20.5 eq.) was added. The reaction was allowed to stir at room temperature for 2 hours. Another (10 mL, 95 mmol, 20.5 eq.) of diethylamine was added and the reaction was allowed to stir at room temperature for 3 more hours. Reaction was concentrated in vacuo and placed underneath high vacuum producing #121 (1.8 g, quant.) yellow white oil solid mix. LC-MS (Protocol Q): m/z 391.1 [M+H$^+$] retention time=1.05 minutes.

Step 4

Synthesis of N-[(9H-fluoren-9-ylmethoxy)carbonyl]-2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#122)

To a stirring solution of #121 (0.55 g, 1.0 mmol, 1.0 eq.) in 10 mL of dichloromethane and 1 mL of DMF, #32 (0.62 g, 1.0 mmol, 1.0 eq.) was added followed by HATU (0.42 g, 1.1 mmol, 1.1 eq.) and Hunig's base (0.72 mL, 4.1 mmol, 4.0 eq.). The reaction was allowed to stir at room temperature for approximately 21 hours. Reaction was reduced down, diluted with ethyl acetate, and then washed with 0.5 N HCl and brine. Organic layer was dried over sodium sulfate, filtered, and concentrated to a smaller volume before being concentrated down onto silica. Silica chromatography was then performed (Gradient: 0%-40% acetone in heptane) producing #122 (0.62 g, 62%) as a white solid. LC-MS (Protocol Q): m/z 982.3 [M+H$^+$] retention time=2.44 minutes.

Step 5

Synthesis 2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#123)

To a stirring mixture of #122 (600 mg, 0.611 mmol, 1.00 eq.) in 15 mL of dichloromethane, diethylamine (5 mL, 50 mmol, 80 eq.) was added. The reaction was allowed to stir at room temperature for 3 hours. Reaction was concentrated in vacuo and mixture was purified by Silica Chromatography (Gradient: 0%-40% methanol in dichloromethane) producing #123 (0.46 g, 99%) as a solid. LC-MS (Protocol Q1): m/z 760.3 [M+H$^+$] retention time=0.83 minutes. $^1$H NMR (400 MHz, CD$_3$OD), δ 7.14-7.30 (m), 4.70-4.78 (m), 4.56-4.64 (m), 4.05-4.19 (m), 3.87 (dd), 3.79-3.84 (m), 3.72-3.77 (m), 3.62-3.70 (m), 3.46-3.56 (m), 3.37-3.45 (m), 3.33-3.36 (m), 3.16-3.24 (m), 3.09-3.11 (m), 2.98-3.05 (m), 2.95 (d), 2.91 (d), 2.87 (d), 2.83 (d), 2.73-2.79 (m), 2.40-2.51 (m), 2.29-2.39 (m), 2.16-2.28 (m), 2.04-2.15 (m), 2.01 (s), 1.73-1.96 (m), 1.50-1.68 (m), 1.47-1.49 (m), 1.46 (s), 1.43 (s), 1.38 (s), 1.35 (d), 1.23-1.32 (m), 1.17-1.22 (m), 1.15 (d), 1.04-1.11 (m), 0.94-1.03 (m), 0.82-0.91 (m).

Preparation of methyl N-[(2R,3R)-3-{(2S)-1-[(3R, 4S,5S)-4-{[N-(3-amino-2,2-dimethylpropanoyl)-L-valyl](methyl)amino}-3-methoxy-5-methylheptanoyl]pyrrolidin-2-yl}-3-methoxy-2-methylpropanoylpL-phenylalaninate (#126)

aqueous layer was acidified to pH<2 with concentrated HCl and then extracted three times with a 10% methanol 90% dichloromethane solution. The organics where combined before being washed with 1M HCl and brine. The organic layer was dried over sodium sulfate and concentrated in vacuo producing #124 (2.2 g, 98%) as a white solid. LC-MS (Protocol Q1): m/z 362.0 [M+Na$^+$] retention time=0.89 minutes.

Step 2

Synthesis of methyl N-[(2R,3R)-3-{(2S)-1-[(3R,4S, 5S)-4-{[N-(3-{[(9H-fluoren-9-ylmethoxy)carbonyl] amino}-2,2-dimethylpropanoyl)-L-valyl] (methyl) amino}-3-methoxy-5-methylheptanoyl]pyrrolidin-2-yl}-3-methoxy-2-methylpropanoyl]-L-phenylalaninate (#125)

To a stirring solution of #114 (200 mg, 0.316 mmol, 1.00 eq.) in 2 mL of dichloromethane, #124 (107 mg, 0.316 mmol, 1.00 eq.) was added followed by Hunig's base (0.167 mL, 0.948 mmol, 3.00 eq.) and HATU (149 mg, 0.379 mmol, 1.20

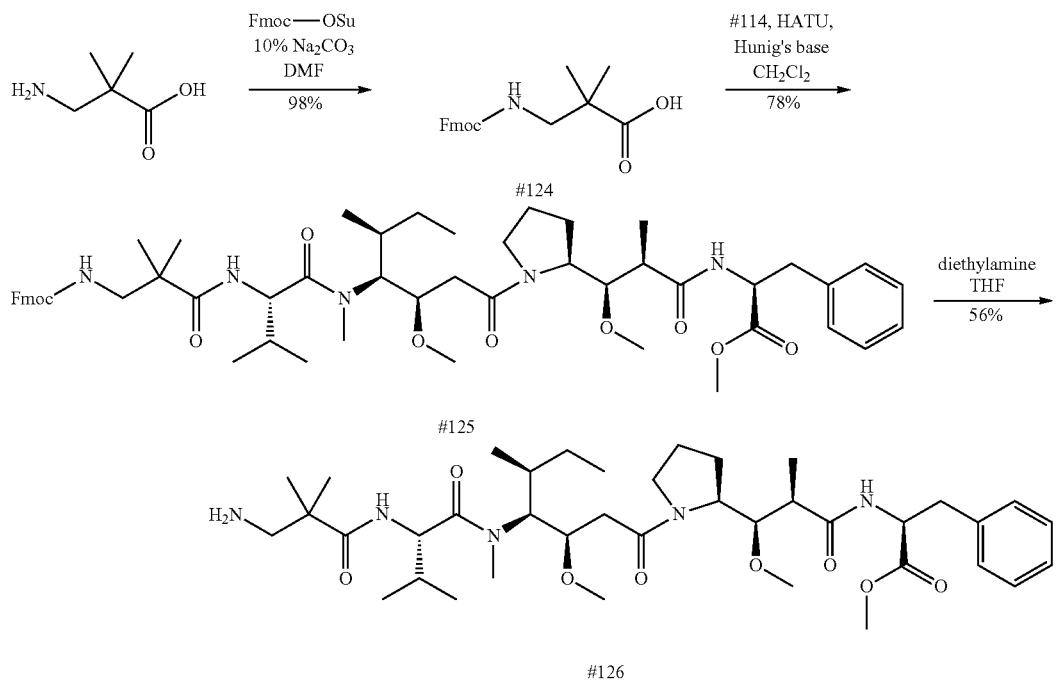

Step 1

Synthesis of 3-{[(9H-fluoren-9-ylmethoxy)carbonyl] amino}-2,2-dimethylpropanoic acid (#124)

A solution of 3-amino-2,2-dimethylpropanoic acid hydrochloride (1.0 g, 6.5 mmol, 1.0 eq.) in 10 mL of 10% Na$_2$CO$_3$ was added to a solution of 1-{[(9H-fluoren-9-ylmethoxy) carbonyl]oxy}pyrrolidine-2,5-dione (2.3 g, 6.5 mmol, 1.0 eq.) in 10 mL of DME. The reaction was allowed to stir at room temperature overnight. Reaction was concentrated to a smaller volume and then washed two times with ether. The eq.). The reaction was allowed to stir at room temperature for ~12 hours. The reaction was concentrated to a smaller volume, taken up in 10 mL of ethyl acetate, and washed two times with 5 mL of 1M HCl, and once with 5 mL of brine. The organic layer was dried over sodium sulfate and decanted. Organics where concentrated in vacuo and the crude material was taken up in dichloromethane. The precipitate was filtered. The organic layer was concentrated in vacuo and the residue was purified by silica chromatography (Gradient: 0%-50% acetone in heptane) producing #125 (235 mg, 78%) as a white solid. LC-MS (Protocol Q): m/z 954.2 [M+H$^+$] retention time=2.28 minutes.

Step 3

Synthesis of methyl N-[(2R,3R)-3-{(2S)-1-[(3R,4S,5S)-4-{[N-(3-amino-2,2-dimethylpropanoyl)-L-valyl](methyl)amino}-3-methoxy-5-methylheptanoyl]pyrrolidin-2-yl}-3-methoxy-2-methylpropanoyl]-L-phenylalaninate (#126)

To a stirring solution of #125 (235 mg, 0.246 mmol, 1.00 eq.) in 2 mL of THF, (1 mL, 10 mM, 40.6 eq.) of diethylamine was added. The reaction was allowed to stir at room temperature for 3 hours. Reaction was concentrated in vacuo and the residue was purified by silica chromatography (Gradient: 0%-30% methanol in ethyl acetate) producing #126 (101 mg, 56%) as a white solid. LC-MS (Protocol Q): m/z 732.2 [M+H$^+$] retention time=1.32 minutes. $^1$H NMR (400 MHz, DMSO-d$_6$), δ 8.51 (dd), 8.28 (d), 7.15-7.29 (m), 5.77 (s), 4.55-4.77 (m), 4.44-4.54 (m), 3.94-4.10 (m), 3.73-3.79 (m), 3.66 (d), 3.49-3.60 (m), 3.40-3.48 (m), 3.10-3.36 (m), 3.00-3.09 (m), 2.83-2.98 (m), 2.57-2.77 (m), 2.19-2.46 (m), 1.87-2.14 (m), 1.61-1.86 (m), 1.36-1.55 (m), 1.23-1.36 (m), 1.12-1.22 (m), 0.97-1.11 (m), 0.82-0.96 (m), 0.73-0.81 (m).

Preparation of N,2-dimethylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#130)

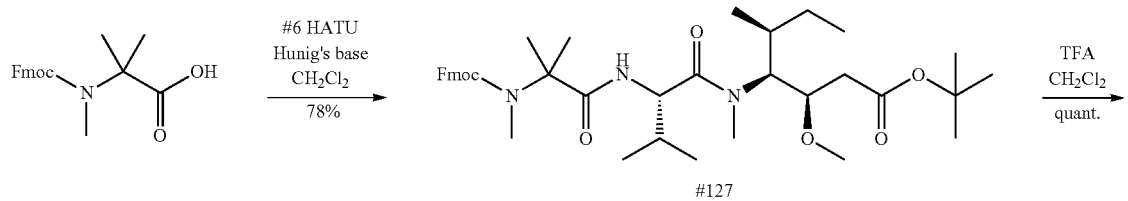

127

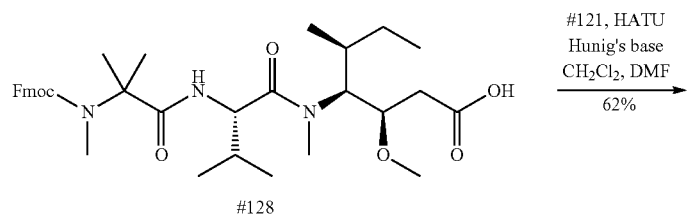

128

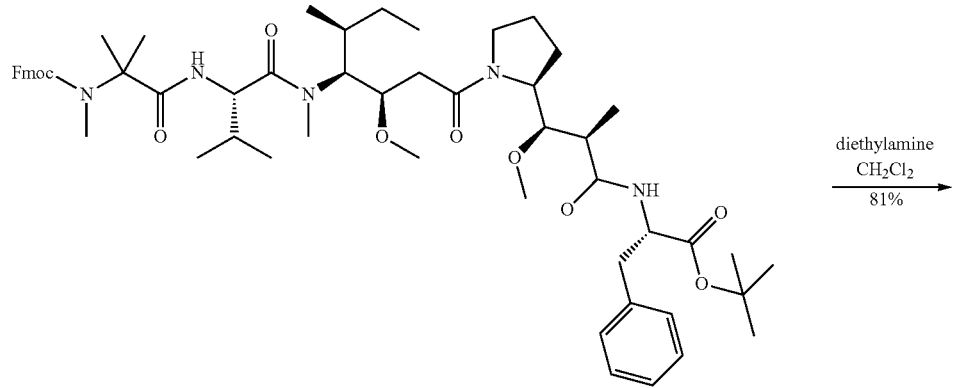

129

-continued

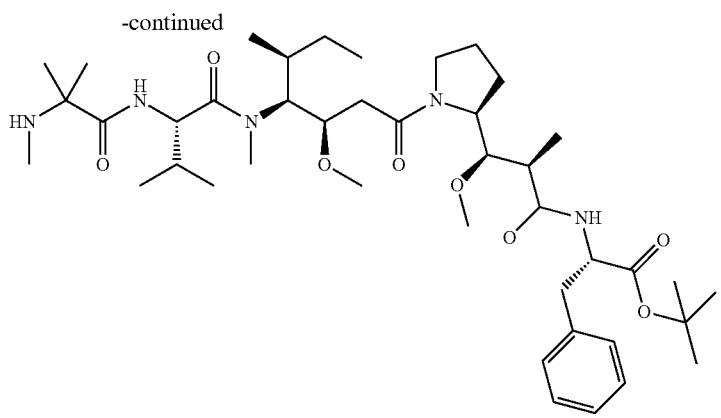

130

Step 1

Synthesis of N-[(9H-fluoren-9-ylmethoxy)carbonyl]-N,2-dimethylalanyl-N-[(3R,4S,5S)-1-tert-butoxy-3-methoxy-5-methyl-1-oxoheptan-4-yl]-N-methyl-L-valinamide (#127)

To a round bottom flask containing #6 (4.7 g, 7.9 mmol, 1.0 eq.) and N-[(9H-fluoren-9-ylmethoxy)carbonyl]-N,2-dimethylalanine (3.2 g, 9.4 mmol, 1.2 eq.) and a stir bar under nitrogen, 50 mL of dichloromethane was added followed by HATU (3.6 g, 9.4 mmol, 1.2 eq.) and Hunig's base (5.5 mL, 32 mmol, 4.0 eq.). The reaction was allowed to stir at room temperature for ~12 hours. Reaction was reduced to a smaller volume, taken up in ethyl acetate, before being washed with 1 N HCl, and brine. Organics where then dried over sodium sulfate, filtered and then reduced down onto silica. Residue was purified by Silica Chromatography (Gradient: 0%-30% acetone in heptane) producing #127 (4.2 g, 78%) as a white solid. LC-MS (Protocol Q): m/z 680.2 [M+H$^+$] retention time=2.52 minutes.

Step 2

Synthesis N-[(9H-fluoren-9-ylmethoxy)carbonyl]-N,2-dimethylalanyl-N-[(2R,3S,4S)-1-carboxy-2-methoxy-4-methylhexan-3-yl]-N-methyl-L-valinamide, (#128)

To a stirring solution of #127 (4.2 g, 6.1 mmol, 1.0 eq.) in 21 mL of dichloromethane under nitrogen, (7 mL, 90 mmol, 10 eq.) of TFA was added. The reaction was allowed to stir at room temperature for ~4 hours. Reaction was concentrated in vacuo, azeotroped once with heptane, and then placed underneath high vacuum yielding #128 as a white slight yellow solid (3.8 g, quant.). LC-MS (Protocol Q): m/z 624.2 [M+H$^+$] retention time=2.01 minutes.

Step 3

Synthesis of N-[(9H-fluoren-9-ylmethoxy)carbonyl]-N,2-dimethylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#129)

To a stirring solution of #128 (1.67 g, 3.1 mmol, 1.0 eq.) in 20 of dichloromethane and 2 mL of DMF, #121 (2.4 g, 3.1 mmol, 1.0 eq.) was added followed by HATU (1.29 g, 3.39 mmol, 1.1 eq.) and then Hunig's base (2.2 mL, 12.3 mmol, 4.0 eq.). The reaction was allowed to stir at room temperature for -2 hours. Reaction was reduced down, diluted with ethyl acetate before being washed with 0.5 N HCl and brine. Organics where dried over sodium sulfate and then reduced down onto silica. Residue was purified by Silica Chromatography (Gradient: 0%-50% acetone in heptanes) producing #129 (1.9 g, 62%) as a white solid. LC-MS (Protocol Q): m/z 996.3 [M+H$^+$] retention time=2.53 minutes.

Step 4

Synthesis of N,2-dimethylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#130)

To a stirring solution of #129 (823 mg, 0.826 mmol, 1.00 eq.) in 15 mL of dichloromethane, diethylamine (4 mL, 40 mmol, 50 eq.) was added. The reaction was allowed to stir at room temperature for ~14½ hours. The reaction was concentrated in vacuo and azeotroped once with heptanes. Residue with diluted with dichloromethane and a small amount of methanol before being reduced down onto silica. Residue was purified by Silica Chromatography (Gradient: 0%-20% methanol in ethyl acetate) producing #130 (518 mg, 81%) as a white solid. LC-MS (Protocol Q): m/z 774.3 [M+H$^+$] retention time=1.48 minutes. HPLC (Protocol A at 25° C.): m/z 774.5 [M+H$^+$], retention time=7.733 minutes (purity >98%). $^1$H NMR (400 MHz, DMSO-d$_6$), δ 8.36 (d). 8.14 (d), 7.81 (t), 7.14-7.25 (m), 7.01-7.07 (m), 4.87-4.94 (m), 4.78-4.85 (m), 4.67-4.76 (m), 4.46-4.65 (m), 4.29-4.40 (m), 3.93-4.03 (m), 3.70-3.81 (m), 3.49-3.60 (m), 3.38-3.47 (m), 3.29-3.36 (m), 3.15-3.28 (m), 2.98-3.13 (m), 2.94 (br s), 2.74-2.89 (m), 2.64-2.69 (m), 2.18-2.45 (m), 2.02-2.14 (m), 1.90-2.01 (m), 1.62-1.87 (m), 1.40-1.55 (m), 1.37 (d), 1.20-1.33 (m), 1.16 (d), 1.01-1.10 (m), 0.90-0.98 (m), 0.82-0.89 (m), 0.69-0.79 (m).

Preparation of 2-methyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt (#131)

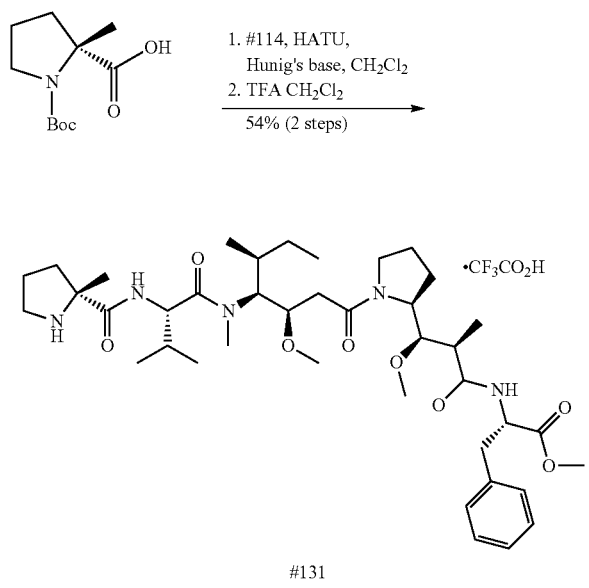

131

Step 1

Synthesis of 2-methyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide trifluoroacetic acid salt (#131)

To a stirring solution of #114 (164 mg, 0.259 mmol, 1.0 eq.) and 1-(tert-butoxycarbonyl)-2-methyl-D-proline (71.3 mg, 0.311 mmol, 1.2 eq.) in 4 mL of dichloromethane, HATU (118 mg, 0.311 mmol, 1.2 eq.) was added followed by Hunig's base (0.180 mL, 1.04 mmol, 4 eq.). The reaction was allowed to stir at room temperature for ~30 minutes. Reaction was reduced down. Reaction was taken up in 3.5 mL of dichloromethane and placed under nitrogen. To this stirring solution, TFA (1.5 mL, 20 mmol, 76 eq.) was added. The reaction was allowed to stir at room temperature for ~1 hour. Reaction was reduced down and placed underneath high vacuum. Purification by (Method J*) affords #131 (119 mg, 54%) as a white solid. HPLC (Protocol A at 45° C.): m/z 744.5 [M+H$^+$], retention time=7.342 minutes (purity >98%). $^1$H NMR (400 MHz, DMSO-d$_6$), δ 9.08-9.18 (m), 8.79-8.89 (m), 8.76 (t), 8.54 (d), 8.29 (d), 7.14-7.31 (m), 4.70-4.79 (m), 4.57-4.66 (m), 4.45-4.55 (m), 3.96-4.04 (m), 3.74-3.80, 3.66 (d), 3.48-3.61 (m), 3.40-3.48 (m), 3.09-3.34 (m), 3.00-3.09 (m), 2.95-3.00 (m), 2.83-2.93 (m), 2.36-2.53 (m), 2.21-2.35 (m), 2.10-2.19 (m), 1.99-2.10 (m), 1.61-1.09 (m), 1.36-1.53 (m), 1.21-1.35 (m), 1.02-1.10 (m), 0.94-1.0 (m), 0.86-0.93 (m), 0.73-0.82 (m).

Preparation of 2-methyl-L-prolyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#134)

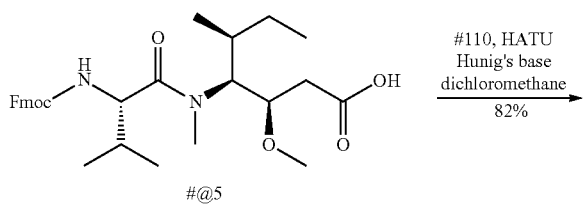

@5

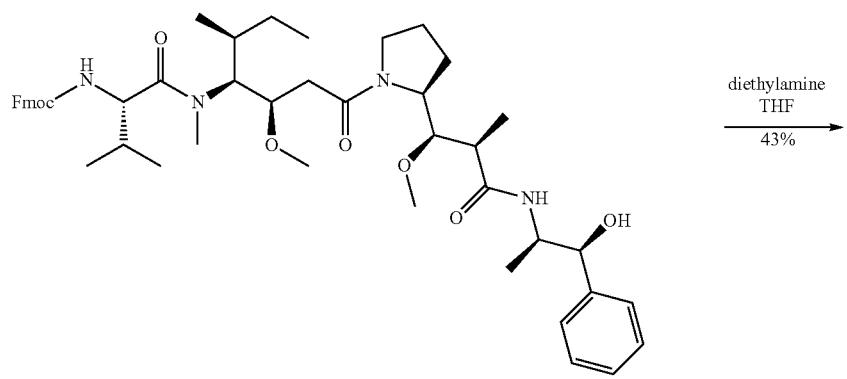

132

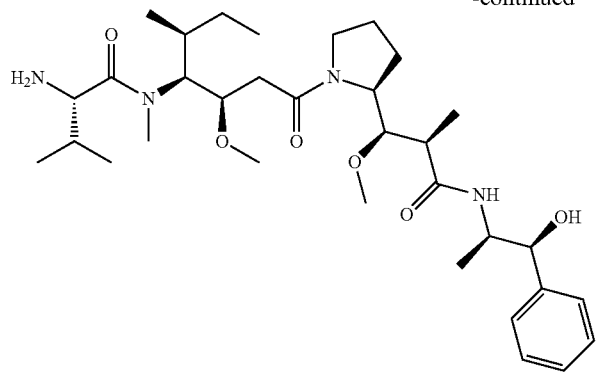

133

1. 1-(tert-butoxycarbonyl)-2-methyl-L-proline
   HATU, Hunig's base
   dichloromethane
2. 4M HCl in dioxane
   dioxane 86% (2 steps)

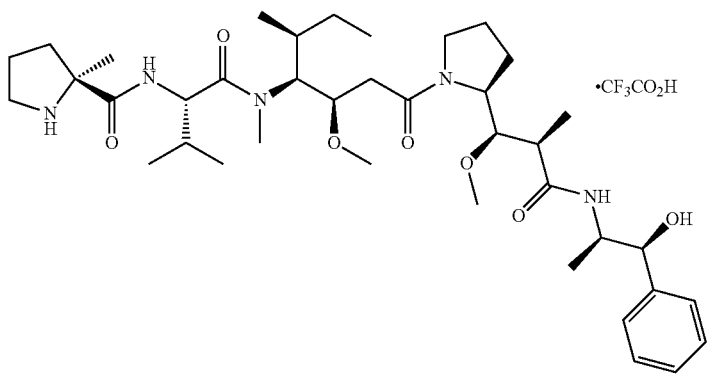

134

Step 1

Synthesis of N~2~-[(9H-fluoren-9-ylmethoxy)carbonyl]-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#132)

To a flask containing #@5 (1.14 g, 2.17 mmol, 1.0 eq.), 10 mL of dichloromethane was added followed by Hunig's base (1.15 mL, 6.52 mmol, 3.0 eq.), HATU (1.02 g, 2.61 mmol, 1.2 eq.), and #110 (0.776 g, 2.17 mmol, 1.0 eq.). Reaction was allowed to stir at room temperature for 30 minutes and then concentrated in vacuo. Crude material was taken up in 50 mL of ethyl acetate, washed two times with 25 mL of 1 M HCl, and once with 25 mL of brine. Organics where dried over sodium sulfate and decanted. Organics where concentrated in vacuo, taken up in 30 mL of dichloromethane, and the resulting precipitate was filtered off Organics where concentrated in vacuo and the residue was purified by silica chromatography (Gradient: 0%-50% acetone in heptanes) producing #132 (1.33 g, 81%) as a solid. LC-MS (Protocol Q): m/z 849.2 [M+Na$^+$] retention time=2.19 minutes.

Step 2

Synthesis of N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#133)

To a stirring solution of #132 (1.33 g, 1.60 mmol, 1.0 eq) in 10 mL of THF diethylamine (5 mL, 50 mM, 31.3 eq) was added. The reaction was allowed to stir at room temperature for 4 hours. Reaction was concentrated in vacuo and the residue was purified by silica chromatography (Gradient: 0%-30% methanol in ethyl acetate) producing #133 (418 mg, 43%) as a white solid. LC-MS (Protocol Q1): m/z 605.2 [M+H$^+$] retention time=1.48 minutes.

Step 3

Synthesis of 2-methyl-L-prolyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#134)

HATU (151 mg, 0.398 mmol, 1.2 eq), #133 (201 mg, 0.332 mmol, 1.0 eq.) and 1-(tert-butoxycarbonyl)-2-methyl-L-proline (91.3 mg, 0.398 mM, 1.2 eq.) where combined in a round bottom flask containing a stir bar under nitrogen. 5 mL of dichloromethane was added followed by Hunig's base (0.231 mL, 1.33 mmol, 4.0 eq.). The reaction was allowed to stir at room temperature for ~15 hours. Reaction was then concentrated in vacuo and placed underneath high vacuum. 4 mL of dioxane was then added to the residue followed by 4M HCl in dioxane (4 mL, 20 mmol, 50 eq.). Reaction was then allowed to stir at room temperature for 1 hour. Reaction was then concentrated in vacuo and the residue was purified by medium pressure reverse phase C18 chromatography (Gradient: 5% to 90% acetonitrile in water with 0.02% TFA in each phase) #134 (237 mg, 86%) as a white solid. LC-MS (Protocol Q): m/z 716.3 [M+H$^+$], retention time=1.16 minutes; HPLC (Protocol A at 45° C.): /z 716.5 [M+H$^+$], retention time=6.930 minutes (purity >98%). $^1$H NMR (400 MHz, DMSO-d$_6$), 9.12-9.21 (m), 8.79-8.90 (m), 8.70-8.78 (m), 7.95 (d), 7.64 (d), 7.25-7.36 (m), 7.16-7.23 (m), 4.74-4.80 (m), 4.61-4.69 (m), 4.41-4.59 (m), 3.91-4.06 (m), 3.78 (dd), 3.54-3.64 (m), 3.45-3.51 (m), 3.17-3.36 (m), 3.02-3.15 (m), 3.00 (br s), 2.40-2.48 (m), 2.24-2.35 (m), 1.91-2.21 (m), 1.68-1.90 (m), 1.61-1.68 (m), 1.48-1.59 (m), 1.22-1.35 (m), 0.97-1.09 (m), 0.84-0.97 (m), 0.74-0.83 (m).

Preparation of N,2-dimethylalanyl-N-{(1S,2R)-4-{(2S)-2-[(1R,2R)-3-{[(1S)-1-benzyl-2-(methylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#140), N,2-dimethylalanyl-N-{(1S,2R)-4-{(2S)-2-[(1R,2R)-3-{[(1S)-2-amino-1-benzyl-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#141), N,2-dimethylalanyl-N-{(1S,2R)-4-{(2S)-2-[(1R,2R)-3-{[(1S)-1-benzyl-2-oxo-2-(propylamino)ethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#142), N,2-dimethylalanyl-N-{(1S,2R)-4-{(2S)-2-[(1R,2R)-3-{[(1S)-1-benzyl-2-(diethylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#143), and N,2-dimethylalanyl-N-{(1S,2R)-4-{(2S)-2-[(1R,2R)-3-{[(1S)-1-benzyl-2-(tert-butylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#144)

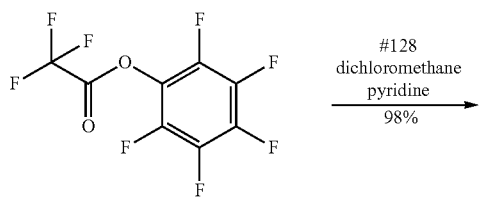

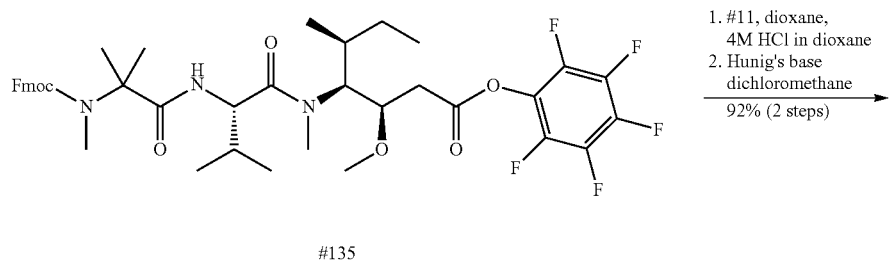

135

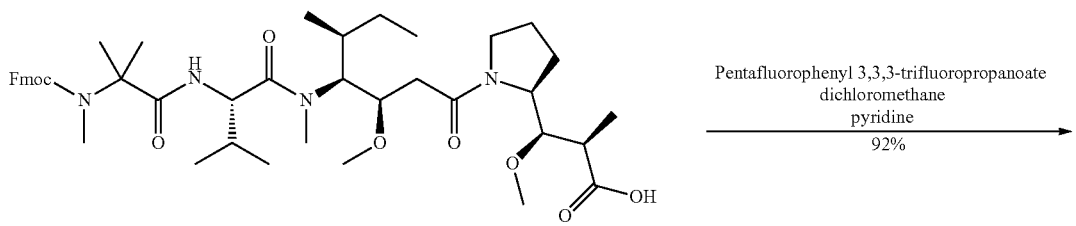

136

-continued
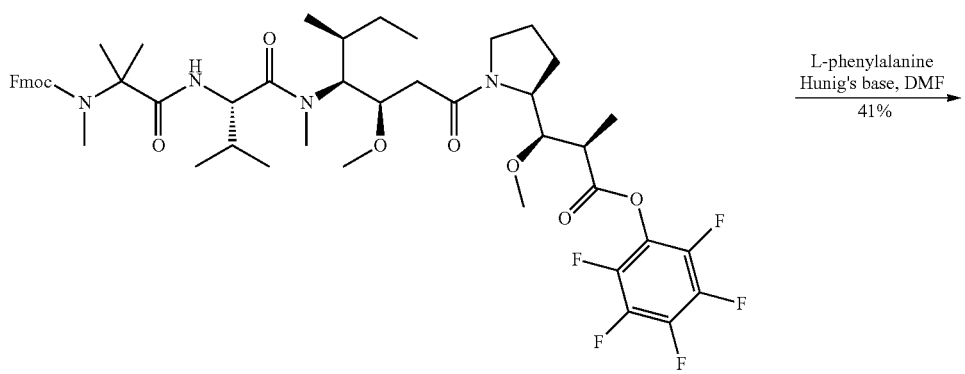
137
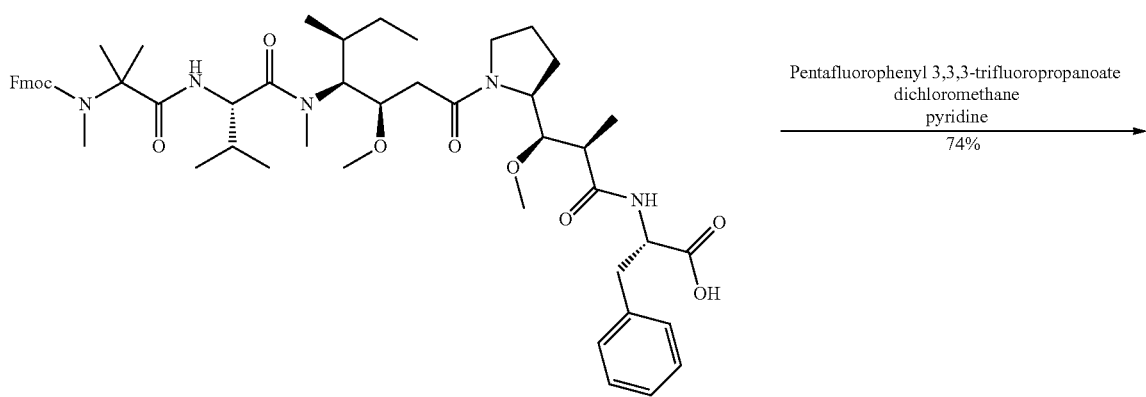
138
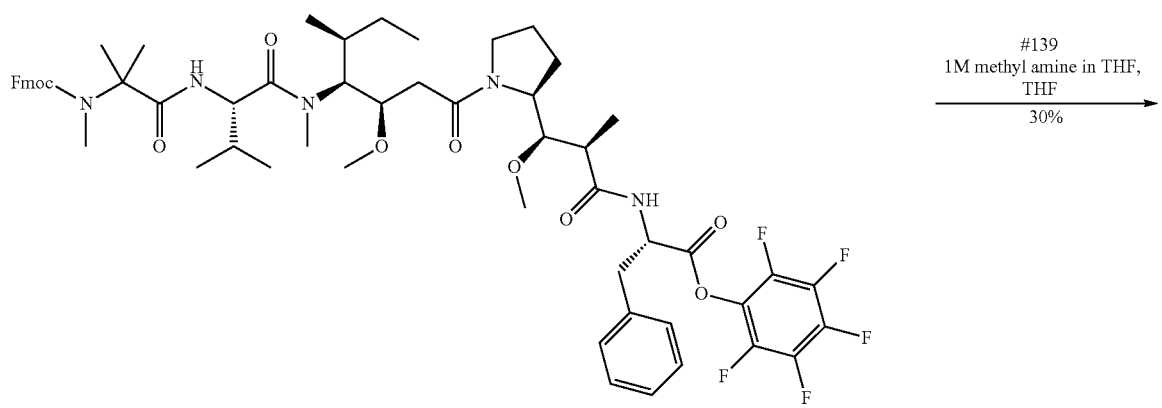
139

-continued
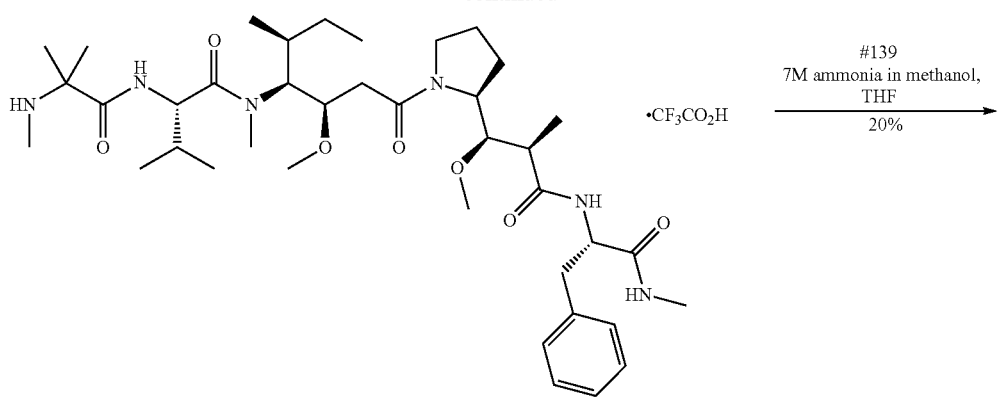
140
139
7M ammonia in methanol, THF
20%
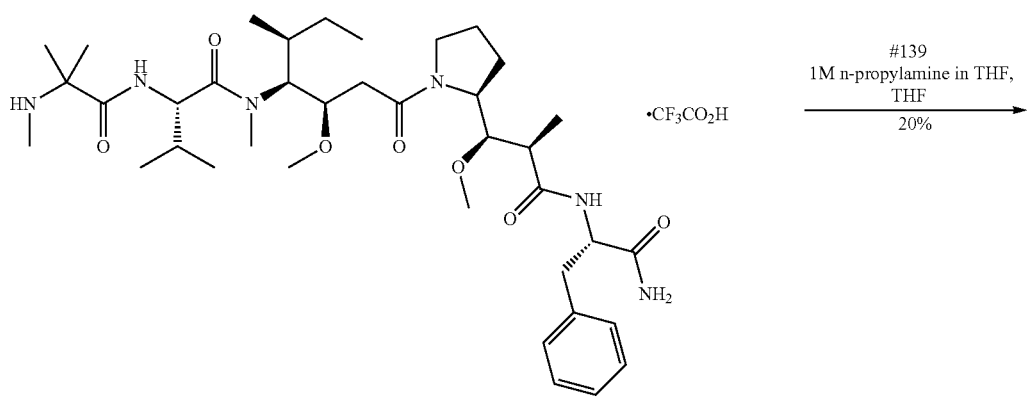
141
139
1M n-propylamine in THF, THF
20%
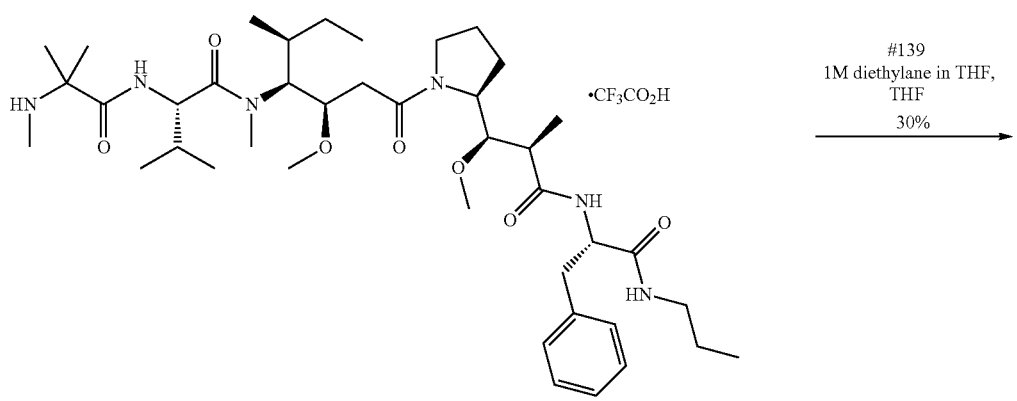
142
139
1M diethylane in THF, THF
30%

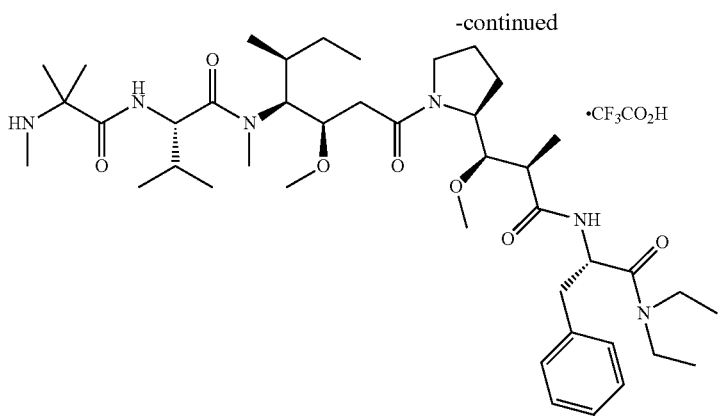
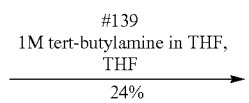

143

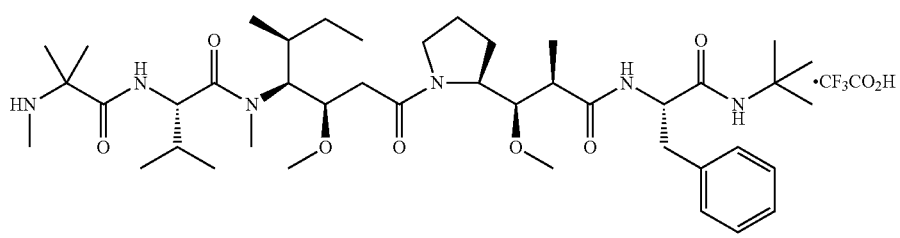

144

Step 1

Synthesis of N-[(9H-fluoren-9-ylmethoxy)carbonyl]-N,2-dimethylalanyl-N-[(3R,4S,5S)-3-methoxy-5-methyl-1-oxo-1-(pentafluorophenoxy)heptan-4-yl]-N-methyl-L-valinamide (#135)

Pentafluorophenyl 3,3,3-trifluoropropanoate (2.44 mL, 13.4 mmol, 2.0 eq.) was added to a solution of #128 (4.18 g, 6.70 mmol, 1.0 eq.) in 50 mL of dichloromethane followed by pyridine (1.61 mL, 20.1 mmol, 3.0 eq.). Reaction was allowed to stir at room temperature for ~12 hours. Reaction was concentrated in vacuo and the residue was purified by silica chromatography (Gradient: 0%-70% acetone in heptanes) producing #135 (5.2 g, 98%) as a white foam. LC-MS (Protocol Q1): m/z 812.1 [M+Na$^+$] retention time=1.24 minutes.

Step 2

Synthesis of N-[(9H-fluoren-9-ylmethoxy)carbonyl]-N,2-dimethylalanyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (#136)

To a stirring solution of 4M HCl in dioxane (10 mL, 25 mmol, 3.7 eq.) in 10 mL of dioxane #11 (2.31 g, 8.05 mmol, 1.2 eq.) was added. The reaction was allowed to stir at room temperature for 6 hours. The reaction was concentrated in vacuo producing a yellow gum. A solution of #135 (5.3 g, 6.7 mmol, 1.0 eq.) in 30 mL of dichloromethane was added to the previous residue followed by Hunig's base (3.5 mL, 20 mmol, 3 eq.). The reaction was allowed to stir at room temperature for 4 hours. The reaction was diluted with dichloromethane before being washed with a 1% HCl aqueous solution and then brine. The organics layer was dried over sodium sulfate, concentrated in vacuo, and the residue was purified by silica chromatography (Gradient: 20%-50% ethyl acetate in heptanes followed by 93% ethyl acetate 6.6% methanol and 0.4% acetic acid) producing #136 (4.87 g, 92%) as a off white solid. LC-MS (Protocol Q1): m/z 793.3 [M+H$^+$] retention time=1.07 minutes.

Step 3

Synthesis of N-[(9H-fluoren-9-ylmethoxy)carbonyl]-N,2-dimethylalanyl-N-[(3R,4S,5S)-3-methoxy-1-{(2S)-2-[(1R,2R)-1-methoxy-2-methyl-3-oxo-3-(pentafluorophenoxy)propyl]pyrrolidin-1-yl}-5-methyl-1-oxoheptan-4-yl]-N-methyl-L-valinamide (#137)

Pentafluorophenyl 3,3,3-trifluoropropanoate (1.3 mL, 7.1 mmol, 2.0 eq.) was added to a solution of #136 (2.8 g, 3.5 mmol, 1.0 eq.) in 30 mL of dichloromethane followed by the addition of pyridine (0.85 mL, 10.6 mM). The reaction was allowed to stir at room temperature for 2 hours. The reaction was concentrated in vacuo, and the residue was purified by silica chromatography (Gradient: 0%-70% acetone in heptane) producing #137 (3.1 g, 92%) as a white powder. LC-MS (Protocol Q1): m/z 959.2 [M+H$^+$] retention time=1.28 minutes.

Step 4

Synthesis of N-[(9H-fluoren-9-ylmethoxy)carbonyl]-N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide(#138)

To a stirring solution of #137 (493 mg, 0.514 mmol, 1.0 eq.) in 4 mL of DMF, L-phenylalanine (84.9 mg, 0.514 mmol, 1.0 eq) was added followed by Hunig's base (0.27 mL, 1.54 mmol, 3.0 eq.). The reaction was allowed to stir at room temperature for ~12 hours. Reaction was concentrated in vacuo and residue was purified by silica chromatography (Gradient: 0%-100% ethyl acetate in heptane) producing #138 (200 mg, 41%) as a white foam. LC-MS (Protocol Q1): m/z 940.3 [M+H$^+$] retention time=1.08 minutes.

Step 5

Synthesis of N-[(9H-fluoren-9-ylmethoxy)carbonyl]-N,2-dimethylalanyl-N-[(3R,4S,5S)-3-methoxy-1-{(2S)-2-[(1R,2R)-1-methoxy-2-methyl-3-oxo-3-{[(2S)-1-oxo-1-(pentafluorophenoxy)-3-phenylpropan-2-yl]amino}propyl]pyrrolidin-1-yl}-5-methyl-1-oxoheptan-4-yl]-N-methyl-L-valinamide (#139)

To a stirring solution of #138 (200 mg, 0.213 mmol, 1.0 eq.) in 5 mL of dichloromethane, Pentafluorophenyl 3,3,3-trifluoropropanoate (126 mg, 0.426 mM, 2.0 eq.) was added followed by pyridine (0.051 mL, 0.64 mmol, 3.0 eq.). The reaction was allowed to stir at room temperature for ~12 hours. Reaction was concentrated in vacuo and the residue was purified by silica chromatography (Gradient: 0%-100% ethyl acetate in heptanes) producing #139 (174 mg, 74%) as a yellow oil. LC-MS (Protocol Q1): m/z 1128 [M+Na$^+$] retention time=1.23 minutes.

Step 6A

Synthesis of N,2-dimethylalanyl-N-{(1S,2R)-4-{(2S)-2-[(1R,2R)-3-{[(1S)-1-benzyl-2-(methylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#140)

To a stirred solution of #139 (20 mg, 0.018 mmol, 1.0 eq.) in 1 mL of THF methylamine (1M in THF, 0.18 mL, 0.18 mmol, 10 eq.) was added, and the mixture was stirred at room temperature for 3 hours. The reaction was reduced down, and diluted with dmso, and subjected to purification (Method J*). The fractions were collected and concentrated in vacuo to give #140 (4.0 mg, 30%) as a white solid. LC-MS (Protocol Q1): m/z 731.2 [M+H$^+$], retention time=0.70 minutes. $^1$H NMR (400 MHz, methanol-d$_4$), 7.30-7.41 (m), 4.71-4.78 (m), 4.58-4.69 (m), 4.04-4.15 (m), 3.86-3.98 (m), 3.73-3.78 (m), 3.61-3.70 (m), 3.50-3.58 (m), 3.32-3.47 (m), 3.23-3.26 (m), 3.17-3.22 (m), 3.07-3.15 (m), 2.95-2.98 (m), 2.76-2.91 (m), 2.68-2.75 (m), 2.63-2.66 (m), 2.43-2.51 (m), 2.22-2.28 (m), 1.99-2.11 (m), 1.74-1.96 (m), 1.21-1.31 (m), 1.17-1.20 (m), 0.92-1.10 (m), 0.79-0.89 (m).

Step 6B

Synthesis of N,2-dimethylalanyl-N-{(1S,2R)-4-{(2S)-2-[(1R,2R)-3-{[(1S)-2-amino-1-benzyl-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#141)

Following the same procedure as #140 using #139 (20 mg, 0.018 mmol, 1.0 eq.), ammonia solution (7M in methanol, 0.026 mL, 0.18 mmol, 10 eq.) and purification (Method J*), #141 (3.0 mg, 20%) was obtained as a white solid. LC-MS (Protocol Q): m/z 717.2 [M+H$^+$], retention time=0.79 minutes. $^1$H NMR (400 MHz, methanol-d$_4$), 7.22-7.30 (m), 7.14-7.21 (m), 4.57-4.4.80 (m), 4.02-4.17 (m), 3.92-3.98 (m), 3.84-3.91 (m), 3.32-3.74 (m), 3.17-3.27 (m), 3.06-3.14 (m), 2.77-3.05 (m), 2.65 (s), 2.43-2.51 (m), 2.21-2.26 (m), 1.98-2.13 (m), 1.70-1.94 (m), 1.32-1.69 (m), 1.16-1.31 (m), 0.89-1.13 (m), 0.80-0.88 (m).

Step 6C

Synthesis of N,2-dimethylalanyl-N-{(1S,2R)-4-{(2S)-2-[(1R,2R)-3-{[(1S)-1-benzyl-2-oxo-2-(propylamino)ethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#142)

Following the same procedure as #140 using #139 (20 mg, 0.018 mmol, 1.0 eq.) n-propylamine (1M in THF, 0.18 mL, 0.18 mmol, 10. eq) and purification (Method J*), #142 (3.0 mg, 20%) was obtained as a white solid. LC-MS (Protocol Q): m/z 759.2 [M+H$^+$], retention time=0.74 minutes. $^1$H NMR (400 MHz, methanol-d$_4$), 7.15-7.29 (m), 4.71-4.79 (m), 4.52-4.68 (m), 4.04-4.17 (m), 3.87-3.99 (m), 3.73-3.99 (m), 3.73-3.79 (m), 3.50-3.70 (m), 3.34-3.49 (m), 3.06-3.23 (m), 2.79-2.99 (m), 2.44-2.50 (m), 2.28-2.43 (m), 2.22-2.27 (m), 1.75-2.10 (m), 1.34-1.61 (m), 1.16-1.29 (m), 0.92-1.10 (m), 0.77-0.89 (m).

Step 6D

Synthesis of N,2-dimethylalanyl-N-{(1S,2R)-4-{(2S)-2-[(1R,2R)-3-{[(1S)-1-benzyl-2-(diethylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#143)

Following the same procedure as #140 using #139 (20 mg, 0.018 mmol, 1.0 eq.) diethylamine (1M in THF, 0.18 mL, 0.18 mmol, 10 eq.) and purification (Method J*), #143 (4.0 mg, 30%) was obtained as a white solid. LC-MS (Protocol Q): m/z 773.3 [M+H$^+$], retention time=0.77 minutes. $^1$H NMR (400 MHz, methanol-d$_4$), 7.16-7.33 (m), 5.10-5.17 (m), 4.96-5.07 (m), 4.68-4.75 (m), 4.60-4.65 (m), 3.61-4.23 (m), 3.35-3.67 (m), 3.16-3.26 (m), 2.99-3.15 (m), 2.78-2.94 (m), 2.30-2.52 (m), 2.19-2.28 (m), 1.73-2.13 (m), 1.83-1.45 (m), 1.19-1.31 (m), 0.92-1.18 (m), 0.80-0.89 (m).

Step 6E

Synthesis of N,2-dimethylalanyl-N-{(1S,2R)-4-{(2S)-2-[(1R,2R)-3-{[(1S)-1-benzyl-2-(tert-butylamino)-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt #144

Following the same procedure as #140 using #139 (20 mg, 0.018 mmol, 1.0 eq.) tert-butylamine (1M in THF, 0.18 mL, 0.18 mmol, 10 eq.) and purification (Method J*), #144 (3.4 mg, 24%) was obtained as a white solid. LC-MS (Protocol Q1): m/z 773.3 [M+H$^+$], retention time=0.74 minutes. $^1$H NMR (400 MHz, DMSO-d$_6$), δ 8.21 (d), 8.03-7.98 (m), 7.92 (d), 7.81-7.62 (m), 7.46-7.16 (m), 4.83-4.69 (m), 4.68-4.56 (m), 4.21-4.07 (m), 3.92-3.86 (m), 3.83-3.80 (m), 3.74-3.65 (m), 3.60-3.48 (m), 3.47-3.36 (m), 3.28-3.13 (m), 3.11-3.01 (m), 2.96-2.82 (m), 2.69-2.62 (m), 2.54-2.43 (m), 2.38-2.12 (m), 2.00-1.76 (m), 1.69-1.161 (m), 1.60-1.53 (m), 1.52-0.98 (m), 0.94-0.86 (m).

Preparation of N,2-dimethylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#145)

Step 1

Synthesis of N,2-dimethylalanyl-N-{(1S,2R)-4-{(2S)-2-[(1R,2R)-3-{[(1R,2S)-2-hydroxy-1-methyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#145)

To a stirring solution of #137 (300 mg, 0.313 mmol, 1.0 eq.) in 3 mL of DMF, (1S,2R)-2-amino-1-phenylpropan-1-ol (54.8 mg, 0.344 mmol, 1.1 eq.) was added followed by Hunig's base (0.164 mL, 0.939 mmol, 3.0 eq). The reaction was allowed to stir at room temperature for ~12 hours. Piperidine 20% solution in DMF (1 mL, 2.2 mmol, 7.0 eq.) was then added and the reaction was allowed to stir at room temperature for 2 hours. Purification (Method J*) followed by concentration of appropriate test tubes produced #145 (190 mg, 74%) as a white powder. LC-MS (Protocol Q): m/z 704.3 [M+H$^+$], retention time=0.67 minutes. $^1$H NMR (400 MHz, CD$_3$OD), δ 7.97 (d), 7.73 (d), 7.37-7.41 (m), 7.27-7.36 (m), 7.19-7.25 (m), 4.70-4.75 (m), 4.58-4.63 (m), 4.49-4.54 (m), 4.14-4.30 (m), 4.04-4.11 (m), 3.87 (dd), 3.63-3.77 (m), 3.51-3.58 (m), 3.46-3.49 (m), 3.38-3.43 (m), 3.25-3.37 (m), 3.15-3.23 (m), 3.11-3.14 (m), 3.01-3.02 (m), 2.59-2.64 (m), 2.52-2.55 (m), 2.44-2.52 (m), 2.41-2.43 (m), 2.07-2.26 (m), 1.73-2.0 (m), 1.65-1.73 (m), 1.59-1.65 (m), 1.51-1.59 (m), 1.32-1.46 (m), 1.23-1.26 (m), 1.08-1.21 (m), 0.94-1.07 (m), 0.83-0.92 (m).

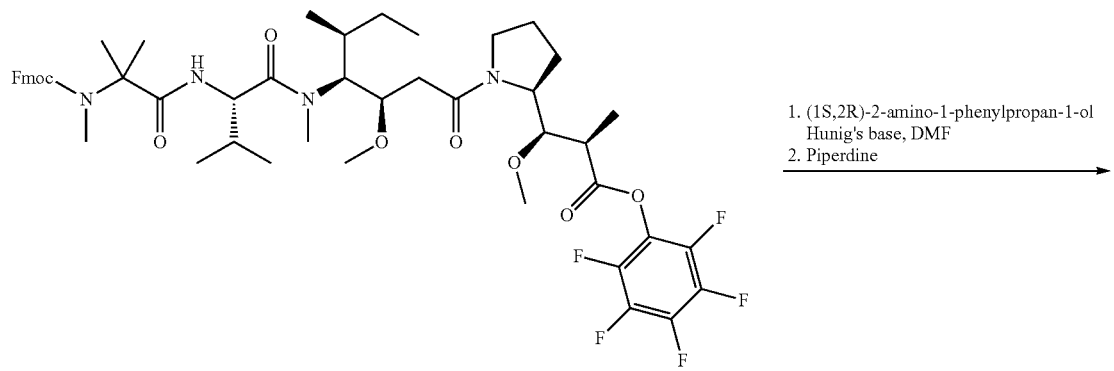

137

1. (1S,2R)-2-amino-1-phenylpropan-1-ol
   Hunig's base, DMF
2. Piperdine

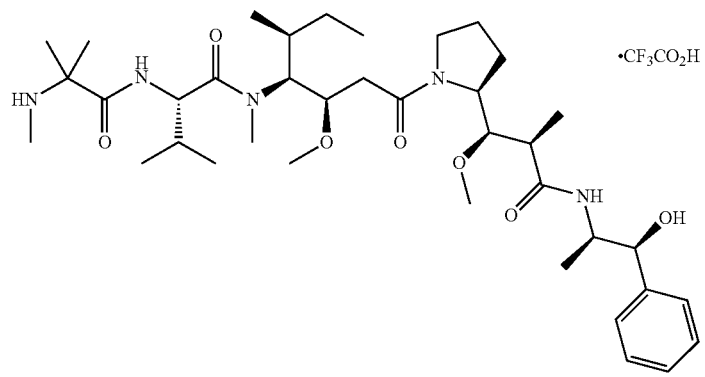

145

Preparation of 3-methyl-D-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#146), 3-methyl-L-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#147), L-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#148), and D-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#149)

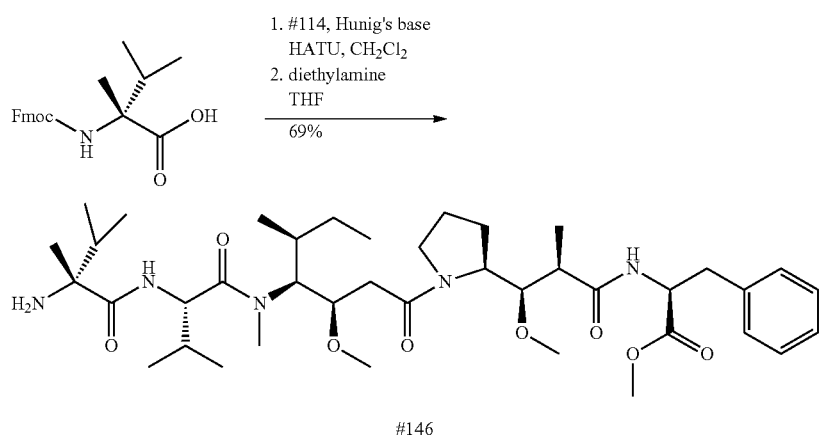

146

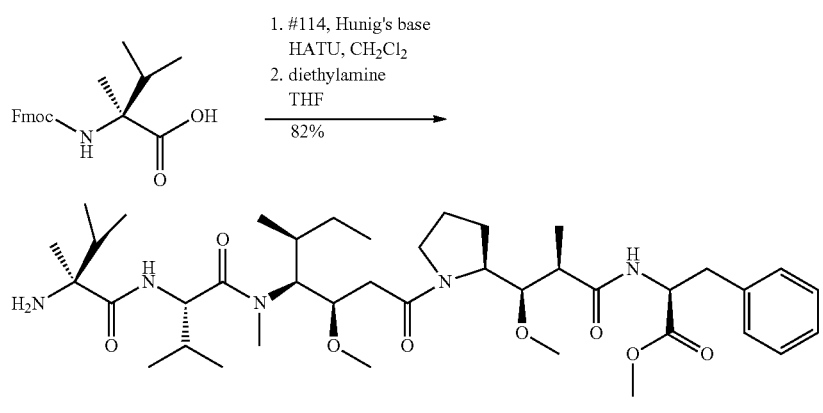

147

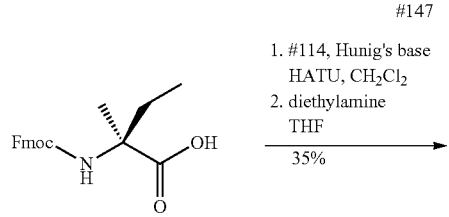

-continued

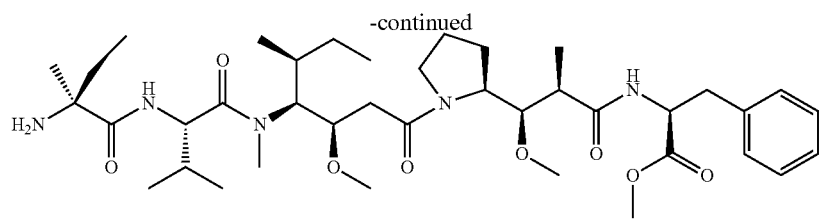

148

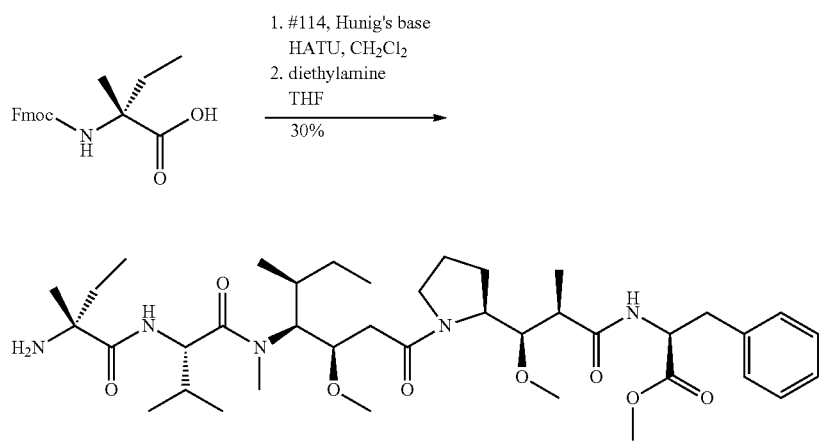

149

Step 1A

Synthesis of 3-methyl-D-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#146)

A solution of #114 (225 mg, 0.356 mmol, 1.0 eq.) in 2 mL of dichloromethane was added to a solution of N-[(9H-fluoren-9-ylmethoxy)carbonyl]-3-methyl-D-isovaline (126 mg, 0.356 mmol, 1.0 eq.) in 4 mL of dichloromethane. Hunig's base (0.188 mL, 1.07 mmol, 3.0 eq.) was added followed by HATU (167 mg, 0.427 mmol, 1.2 eq). The reaction was allowed to stir at room temperature for 12 hours. The reaction was concentrated in vacuo and then taken up in ethyl acetate before being washed two times with 1M HCl and once with brine. The organic layer was dried over sodium sulfate and decanted. The organic solvent was removed in a genevac. THF (4 mL) was added followed diethylamine (2 mL, 19 mmol, 53.4 eq.). The reaction was allowed to stir for ~12 hours. Reaction was concentrated using a genevac followed by silica chromatography (Gradient: 0%-30% methanol in ethyl acetate) producing #146 (183 mg, 69%) as a solid. LC-MS (Protocol Q): m/z 746.4 [M+H$^+$] retention time=1.37 minutes. $^1$H NMR (400 MHz, DMSO-d$_6$), δ 8.55 (d), 8.26-8.36 (m), 7.88-8.03 (m), 7.81 (d), 7.41-7.53 (m), 7.13-7.30 (m), 7.01 (s), 4.71-4.79 (m), 4.44-4.70 (m), 3.96-4.04 (m), 3.70-3.80 (m), 3.62-3.69 (m), 3.40-3.61 (m), 2.76-3.35 (m), 2.67-2.71 (m), 2.56-2.58 (m), 2.06-2.46 (m), 1.61-1.90 (m), 1.14-1.54 (m), 0.72-1.12 (m).

Step 1B

Synthesis of 3-methyl-L-isovalyl-N-{(1S,2R)-4-{(2S)-2-[(1R,2R)-3-{[(1S)-1-benzyl-2-methoxy-2-oxoethyl]amino}-1-methoxy-2-methyl-3-oxopropyl]pyrrolidin-1-yl}-2-methoxy-1-[(1S)-1-methylpropyl]-4-oxobutyl]-N-methyl-L-valinamide (#147)

A solution of #114 (224 mg, 0.354 mmol, 1.0 eq.) in 2 mL of dichloromethane was added to a solution of N-[(9H-fluoren-9-ylmethoxy)carbonyl]-3-methyl-L-isovaline (125 mg, 0.354 mmol, 1.0 eq.) in 4 mL of dichloromethane. Hunig's base (0.187 mL, 1.06 mmol, 3.0 eq.) was added followed by HATU (167 mg, 0.425 mmol, 1.2 eq.). The reaction was allowed to stir at room temperature for 12 hours. The reaction was concentrated in vacuo and then taken up in ethyl acetate before being washed two times with 1M HCl and once with brine. The organic layer was dried over sodium sulfate and decanted. The organic solvent was removed in a genevac. THF (4 mL) was added followed diethylamine (2 mL, 19 mmol, 53.7 eq.). The reaction was allowed to stir for ~12 hours. Reaction was concentrated using a genevac followed by silica chromatography (Gradient: 0%-30% methanol in ethyl acetate) producing #147 (216 mg, 82%) as a solid. LC-MS (Protocol Q): m/z 746.6 [M+H$^+$] retention time=1.29 minutes. $^1$H NMR (400 MHz, DMSO-d$_6$), δ 8.56 (m), 8.31-8.39 (m), 8.50 (d), 8.30 (br d), 7.87-8.01 (m), 7.80 (d), 7.40-7.53 (m), 7.14-7.30 (m), 4.45-4.78 (m), 3.94-4.04 (m), 3.70-3.79 (m), 3.61-3.69 (m), 3.42-3.59 (m), 2.97-3.37 (m), 2.80-2.92 (m), 2.32-2.49 (m), 2.05-2.30 (m), 1.61-1.89 (m), 1.37-1.56 (m), 1.14-1.135 (m), 0.70-1.11 (m).

Step 1C

Synthesis of L-isovalyl-N-{(1S,2R)-4-{(2S)-2-[(1R, 2R)-3-{[(1S)-1-benzyl-2-methoxy-2-oxoethyl] amino}-1-methoxy-2-methyl-3-oxopropyl]pyrrolidin-1-yl}-2-methoxy-1-[(1S)-1-methylpropyl]-4-oxobutyl}-N-methyl-L-valinamide (#148)

A solution of #114 (447 mg, 0.707 mmol, 1.0 eq.) in 2 mL of dichloromethane was added to a solution of N-[(9H-fluoren-9-ylmethoxy)carbonyl]-L-isovaline (240 mg, 0.707 mmol, 1.0 eq.) in 4 mL of dichloromethane. Hunig's base (0.373 mL, 2.12 mmol, 3.0 eq.) was added followed by HATU (332 mg, 0.425 mmol, 1.2 eq.). The reaction was allowed to stir at room temperature for 12 hours. The reaction was concentrated in vacuo and then taken up in ethyl acetate before being washed two times with 1M HCl and once with brine. The organic layer was dried over sodium sulfate and decanted. The organic solvent was removed in a genevac. THF (4 mL) was added followed by diethylamine (2 mL, 19 mmol, 26.9 eq.). The reaction was allowed to stir for ~12 hours. Reaction was concentrated using a genevac followed by silica chromatography (Gradient: 0%-30% methanol in ethyl acetate) producing #148 (182 mg, 35%) as a solid. LC-MS (Protocol Q1): m/z 732.3 [M+H$^+$] retention time=0.71 minutes. $^1$H NMR (400 MHz, DMSO-d$_6$), δ 8.56 (d), 8.46-8.52 (m), 8.30 (d), 8.02-8.15 (m), 7.98 (d), 7.80 (d), 7.40-7.53 (m), 7.15-7.30 (m), 4.70-4.80 (m), 4.44-4.69 (m), 3.96-4.05 (m), 3.70-3.79 (m), 3.62-3.69 (m), 3.41-3.59 (m), 2.99-3.35 (m), 2.31-2.95 (m), 2.67-2.71 (m), 2.55-2.59 (m), 2.32-2.48 (m), 2.20-2.31 (m), 1.97-2.19 (m), 1.61-1.88 (m), 1.37-1.56 (m), 1.20-1.34 (m), 1.14-1.19 (m), 1.02-1.11 (m), 0.97-1.01 (m), 0.86-0.96 (m), 0.71-0.83 (m).

Step 1D

Synthesis of D-isovalyl-N-{(1S,2R)-4-{(2S)-2-[(1R, 2R)-3-{[(1S)-1-benzyl-2-methoxy-2-oxoethyl] amino}-1-methoxy-2-methyl-3-oxopropyl]pyrrolidin-1-yl}-2-methoxy-1-[(1S)-1-methylpropyl]-4-oxobutyl}-N-methyl-L-valinamide (#149)

A solution of #114 (447 mg, 0.707 mmol, 1.0 eq.) in 2 mL of dichloromethane was added to a solution of N-[(9H-fluoren-9-ylmethoxy)carbonyl]-D-isovaline (240 mg, 0.707 mmol, 1.0 eq.) in 4 mL of dichloromethane. Hunig's base (0.373 mL, 2.12 mmol, 3 eq.) was added followed by HATU (332 mg, 0.425 mmol, 1.2 eq.). The reaction was allowed to stir at room temperature for 12 hours. The reaction was concentrated in vacuo and then taken up in ethyl acetate before being washed two times with 1M HCl and once with brine. The organic layer was dried over sodium sulfate and decanted. The organic solvent was removed in a genevac. THF (4 mL) was added followed by diethylamine (2 mL, 19 mmol, 26.9 eq.). The reaction was allowed to stir for ~12 hours. Reaction was concentrated using a genevac followed by silica chromatography (Gradient: 0%-30% methanol in ethyl acetate) producing #149 (154 mg, 30%) as a solid. LC-MS (Protocol Q): m/z 732.0 [M+H$^+$] retention time=1.24 minutes. $^1$H NMR (400 MHz, DMSO-d$_6$), δ 8.55 (d), 8.38-8.46 (m), 8.29 (d), 8.03-8.14 (m), 7.97 (d), 7.81 (d), 7.40-7.53 (m), 7.14-7.28 (m), 7.02 (s), 4.71-4.79 (m), 4.43-4.69 (m), 3.96-4.05 (m), 3.71-3.80 (m), 3.62-3.70 (m), 3.49-3.60 (m), 3.40-3.48 (m), 3.15-3.34 (m), 3.10-3.14 (m), 3.01-3.09 (m), 2.94-3.00 (m), 2.83-2.93 (m), 2.65-2.71 (m), 2.55-2.59 (m), 2.32-2.48 (m), 2.04-2.31 (m), 1.61-1.89 (m), 1.37-1.52 (m), 1.21-1.35 (m), 1.15-1.20 (m), 1.02-1.10 (m), 0.75-1.01 (m).

Preparation of 1,2-dimethyl-L-prolyl-N-{(1S,2R)-4-{(2S)-2-[(1R,2R)-3-{[(1S)-1-carboxy-2-phenylethyl] amino}-1-methoxy-2-methyl-3-oxopropyl]pyrrolidin-1-yl}-2-methoxy-1-[(1S)-1-methylpropyl]-4-oxobutyl}-N-methyl-L-valinamide (#151)

Step 1

Synthesis of 1,2-dimethyl-L-proline (#150)

A parr flask containing 2-methyl-L-proline (1.0 g, 7.7 mmol, 1.0 eq.), 40 mL of methanol, Formaldehyde 37 wt. % in water (2.1 mL, 77 mmol, 10 eq.), and Palladium 10 wt. % on Carbon (313 mg, 2.94 mmol, 0.38 eq.) was placed on a parr shaker and allowed to shake under 40 psi of hydrogen for ~12 hours. Hydrogen was removed and the reaction was filtered through a pad of celite which was rinsed with a solution of 50% methanol 50% dichloromethane. Residue was concentrated in vacuo yielding #150 (1.1 g, 100%) as a white slight black colored solid. LC-MS (Protocol Q): m/z 144.0 [M+H$^+$] retention time=0.17 minutes.

Step 2

Synthesis of 1,2-dimethyl-L-prolyl-N-{(1S,2R)-4-{(2S)-2-[(1R,2R)-3-{[(1S)-1-carboxy-2-phenylethyl] amino}-1-methoxy-2-methyl-3-oxopropyl]pyrrolidin-1-yl}-2-methoxy-1-[(1S)-1-methylpropyl]-4-oxobutyl}-N-methyl-L-valinamide (#151)

To a stirring mixture of #114 (125 mg, 0.198 mmol, 1.0 eq), #150 (37 mg, 0.26 mmol, 1.3 eq.), and HATU (98 mg, 0.26 mmol, 1.3 eq.) in 5 mL of dichloromethane, Hunig's base (0.14 mL, 0.80 mmol, 4.1 eq.) was added. The reaction was allowed to stir at room temperature for 1 hour. Reaction was concentrated in vacuo. THF (6 mL) was added to crude material. To this stirring mixture LiOH (14 mg, 0.59 mmol, 3.0 eq) dissolved in 2 mL of water was added. Reaction was allowed to stir at room temperature for 90 minutes. Reaction was concentrated in vacuo and residue was purified by medium pressure reverse phase C18 chromatography (Gradient: 5% to 40% acetonitrile in water with 0.02% TFA in each phase) #151 (147 mg, 69%) as a white solid. LC-MS (Protocol Q): m/z 744.3 [M+H$^+$], retention time=1.19 minutes; HPLC (Protocol A at 45° C.): m/z 744.4 [M+H$^+$], retention time=6.631 minutes (purity >98%). $^1$H NMR (400 MHz, DMSO-d$_6$), δ 9.57-9.71 (m), 8.75 (d), 8.42 (d), 8.15 (d), 7.14-7.29 (m), 4.70-4.79 (m), 4.40-4.68 (m), 3.95-4.03 (m), 3.73-3.80 (m), 3.37-3.61 (m), 2.97-3.31 (m), 2.79-2.88 (m), 2.66-2.76 (m), 2.54-2.58 (m), 2.31-2.43 (m), 1.94-2.29 (m), 1.57-1.91 (m), 1.21-1.52 (m), 0.85-1.10 (m), 0.74-0.82 (m)

Preparation of 1,2-dimethyl-D-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#153)

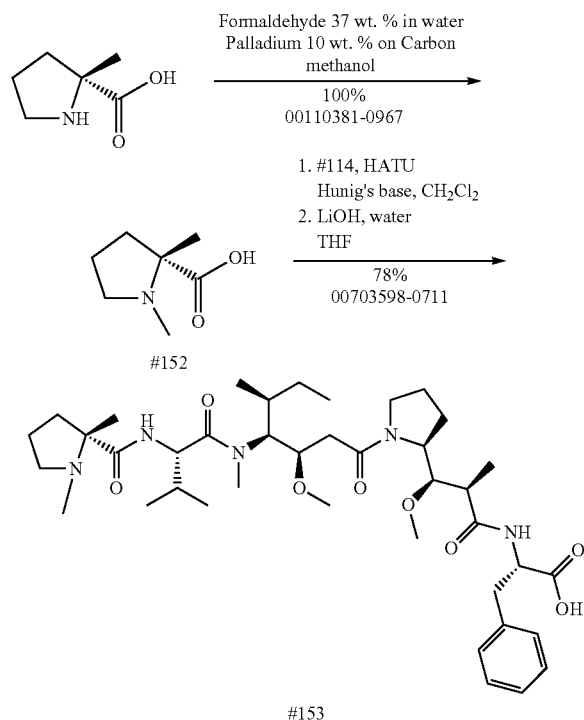

152

153

Step 1

Synthesis of 1,2-dimethyl-D-proline (#152)

To a parr flask containing 2-methyl-D-proline (432 mg, 3.34 mmol, 1.0 eq.), Formaldehyde 37 wt. % in water (1.0 mL, 37 mM, 11 eq.), 3.5 mL of methanol and 1 mL of water, Palladium 10 wt. % on Carbon (108 mg, 0.304 mmol, 0.304 eq.) was added. The flask was placed on a parr shaker and allowed to shake under 30 psi of hydrogen for ~48 hours. Hydrogen was removed and reaction was washed through a pad of celite, which was subsequently washed with methanol. The organics where concentrated in vacuo and then azeotroped with toluene affording #152 (517 mg, 100%) as a solid. $^1$H NMR (400 MHz, methanol-d$_4$): δ [3.61-3.56 (m, 1H), 3.07-2.96 (m, 1H), 2.68 (br s, 3H), 2.34-2.22 (m, 1H), 2.01-1.88 (m, 1H), 1.87-1.73 (m, 1H), 1.40 (br s, 3H)].

Step 2

Synthesis of 1,2-dimethyl-D-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#153)

To a stirring mixture of #114 (240 mg, 0.379 mmol, 1.0 eq.), #152 (71 mg, 0.49 mmol, 1.3 eq.), and HATU (188 mg, 0.49 mmol, 1.3 eq.) in 10 mL of dichloromethane, Hunig's base (0.27 mL, 4.1 mM, 4.1 eq.) was added. The reaction was allowed to stir at room temperature for 1 hour. Reaction was concentrated in vacuo. THF (6 mL) was added to crude material. To this stirring mixture LiOH (36 mg, 1.5 mmol, 4 eq.) dissolved in 2 mL of water was added. Reaction was allowed to stir at room temperature for 1 hour. Reaction was concentrated in vacuo and residue was purified by medium pressure reverse phase C18 chromatography (Gradient: 5% to 40% acetonitrile in water with 0.02% TFA in each phase) #153 (220 mg, 78%) as a white solid. LC-MS (Protocol Q): m/z 744.8 [M+H$^+$], retention time=1.16 minutes; HPLC (Protocol A at 45° C.): /z 744.4 [M+H$^+$], retention time=6.713 minutes (purity >98%). $^1$H NMR (400 MHz, DMSO-d$_6$), δ 9.72-9.85 (m), 8.65 (t), 8.41 (d), 8.14 (d), 7.14-7.28 (m), 4.69-4.79 (m), 4.38-4.53 (m), 3.95-4.04 (m), 3.73-3.79 (m), 3.37-3.62 (m), 3.13-3.33 (m), 2.95-3.10 (m), 2.79-2.89 (m), 2.67-2.75 (m), 2.00-2.46 (m), 1.61-1.90 (m), 1.22-1.54 (m), 1.02-1.09 (m), 0.95-1.01 (m), 0.85-0.94 (m), 0.75-0.83 (m)

Preparation of N~2~-[2,2-dimethyl-3-(methylamino)propanoyl]-N-{(1S,2R)-2-methoxy-4-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-1-[(1S)-1-methylpropyl]-4-oxobutyl}-N-methyl-L-valinamide, trifluoroacetic acid salt (#154)

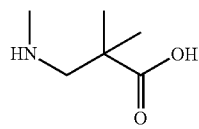

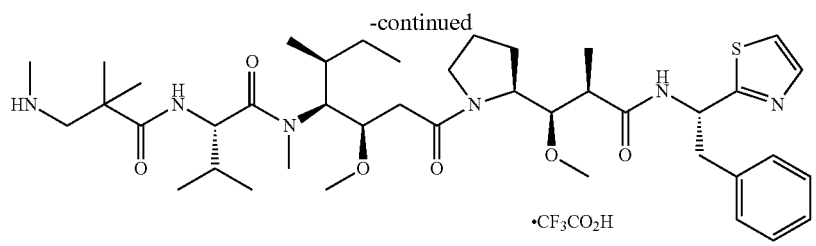

154

Step 1

Synthesis of N~2~-[2,2-dimethyl-3-(methylamino)propanoyl]-N-{(1S,2R)-2-methoxy-4-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-1-[(1S)-1-methylpropyl]-4-oxobutyl}-N-methyl-L-valinamide, trifluoroacetic acid salt (#154)

Preparation of methyl N-{(2R,3R)-3-[(2S)-1-{(3R,4S,5S)-4-[{N-[2,2-dimethyl-3-(methylamino)propanoyl]-L-valyl}(methyl)amino]-3-methoxy-5-methylheptanoyl}pyrrolidin-2-yl]-3-methoxy-2-methylpropanoyl}-L-phenylalaninate, trifluoroacetic acid salt (#155)

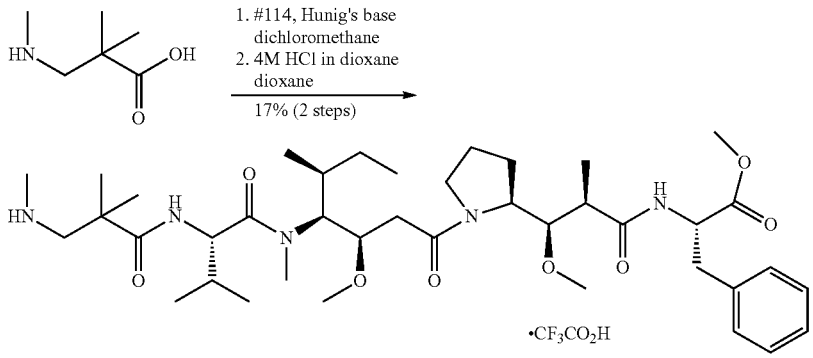

155

To vial containing #50 (100 mg, 0.152 mmol, 1.0 eq.) and 1 mL of dichloromethane, 2,2-dimethyl-3-(methylamino)propanoic acid (36 mg, 0.152 mmol, 1.0 eq.) was added followed by Hunig's base (0.080 mL, 0.456 mmol, 3.0 eq.) and HATU (66 mg, 0.17 mmol, 1.1 eq.). The reaction was allowed to stir at room temperature for 1 hour. The reaction was concentrated in vacuo and then taken up in ethyl acetate before being washed two times with 1M HCl and once with brine. The organic layer was dried over sodium sulfate and decanted. The reaction was concentrated in vacuo. Dioxane (1 ml) was added followed by 4M HCl in dioxane (1.0 mL, 4.0 mmol, 26 eq.). The reaction was allowed to stir at room temperature for ~12 hours. The reaction was concentrated in vacuo. The crude material was purified by medium pressure reverse phase C18 chromatography (Gradient: 10% to 100% acetonitrile in water with 0.02% TFA in each phase) yielding #154 (55.8 mg, 41%) as a solid. LC-MS (Protocol Q): m/z 771.8 [M+H$^+$]. $^1$H NMR (400 MHz, DMSO-d$_6$), δ 8.70 (d), 8.45 (d), 7.90-8.15 (m), 7.82 (d), 7.75 (d), 7.55 (dd), 7.40 (dd), 6.90-7.10 (m), 5.10-5.30 (m), 4.45-4.55 (b), 4.30-4.45 (m), 4.20-4.30 (m), 3.75-3.90 (m), 3.50-3.60 (m), 3.15-3.40 (m), 3.05-3.15 (m), 2.85-3.05 (m), 2.60-2.85 (m), 2.25-2.40 (m), 1.80-2.25 (m), 1.70-1.80 (m), 1.20-1.60 (m), 0.80-1.10 (m), 0.05-0.80 (m).

Step 1

Synthesis of methyl N-{(2R,3R)-3-[(2S)-1-{(3R,4S,5S)-4-[{N-[2,2-dimethyl-3-(methylamino)propanoyl]-L-valyl}(methyl)amino]-3-methoxy-5-methylheptanoyl}pyrrolidin-2-yl]-3-methoxy-2-methylpropanoyl}-L-phenylalaninate, trifluoroacetic acid salt (#155)

To vial containing #114 (96.2 mg, 0.152 mmol, 1.0 eq.) and 1 mL of dichloromethane, 2,2-dimethyl-3-(methylamino)propanoic acid (36.1 mg, 0.152 mmol, 1.0 eq.) was added followed by Hunig's base (0.080 mL, 0.456 mmol, 3.0 eq.) and HATU (66 mg, 0.17 mmol, 1.1 eq.). The reaction was allowed to stir at room temperature for 1 hour. The reaction was concentrated in vacuo and then taken up in ethyl acetate before being washed two times with 1M HCl and once with brine. The organic layer was dried over sodium sulfate and decanted. The reaction was concentrated in vacuo. Dioxane (1 ml) was added followed by 4M HCl in dioxane (1.0 mL, 4.0 mmol, 26 eq.). The reaction was allowed to stir at room temperature for ~12 hours. The reaction was concentrated in vacuo. The crude material was purified by medium pressure reverse phase C18 chromatography (Gradient: 10% to 100% acetonitrile in water with 0.02% TFA in each phase) yielding #155 (22.2 mg, 17%). $^1$H NMR (400 MHz, DMSO-$d_6$), δ 8.55 (d), 8.22 (d), 8.15-8.35 (m), 7.90-8.05 (m) 7.10-7.25 (m) 4.70-4.80 (m), 4.55-4.65 (m), 4.45-4.52 (m), 3.93-4.00 (m), 3.72-3.78 (m), 3.60-3.70 (m), 3.50-3.60 (m), 3.40-3.50 (m), 2.80-3.30 (m), 2.45-2.60 (m), 2.00-2.45 (m), 1.60-1.80 (m), 1.35-1.50 (m), 1.10-1.35 (m).

Preparation of methyl N-{(2R,3R)-3-methoxy-3-[(2S)-1-{(3R,4S,5S)-3-methoxy-5-methyl-4-[methyl (N-{[(2S)-2-methylpiperidin-2-yl]carbonyl}-L-valyl) amino]heptanoyl}pyrrolidin-2-yl]-2-methylpropanoyl}-L-phenylalaninate, trifluoroacetic acid salt (#158) and methyl N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalaninate, trifluoroacetic acid salt (#159)

Step 1

(Synthesis of (2S)-1-(tert-butoxycarbonyl)-2-methylpiperidine-2-carboxylic acid (#156) and (2R)-1-(tert-butoxycarbonyl)-2-methylpiperidine-2-carboxylic acid (#157)

1-(tert-butoxycarbonyl)-2-methylpiperidine-2-carboxylic acid (500 mg, 2.06 mmol, 1 eq.) was separated by supercritical fluid chromatography (Column: Chiralcel OJ-H, 250×21 mm; Eluent: 90:10 carbon dioxide/ethanol; Flow Rate: 65 g/min; to give the corresponding enantiomers. The first eluting peak (retention time=1.57 minutes) was isolated to give #156 as a gum (140 mg, 28%) (stereochemistry arbitrarily assigned as the S enantiomer). $^1$H NMR (400 MHz, CDCl$_3$) δ 3.83-3.90 (m, 1H), 2.93-3.01 (m, 1H), 1.87-1.97 (m, 1H), 1.67-1.77 (m, 3H), 1.48-1.66 (m, 2H), 1.46 (s, 3H), 1.44 (s, 9H). Optical rotation: [α]$_D$25−21.7° (c 0.40, chloroform). The second eluting peak (retention time=2.22 minutes) was isolated to give #157 as an oil (255 mg, 51%) (stereochemistry arbitrarily assigned as the R enantiomer). $^1$H NMR (400 MHz, CDCl$_3$) δ 3.83-3.90 (m, 1H), 2.93-3.01 (m, 1H), 1.87-

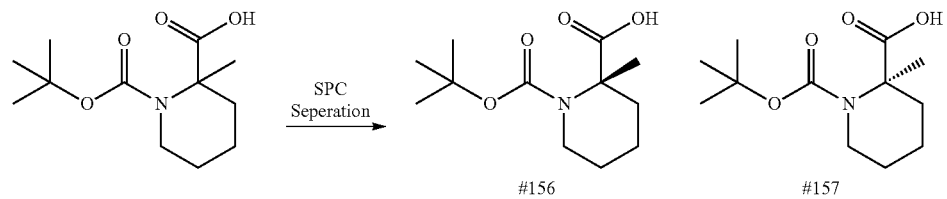

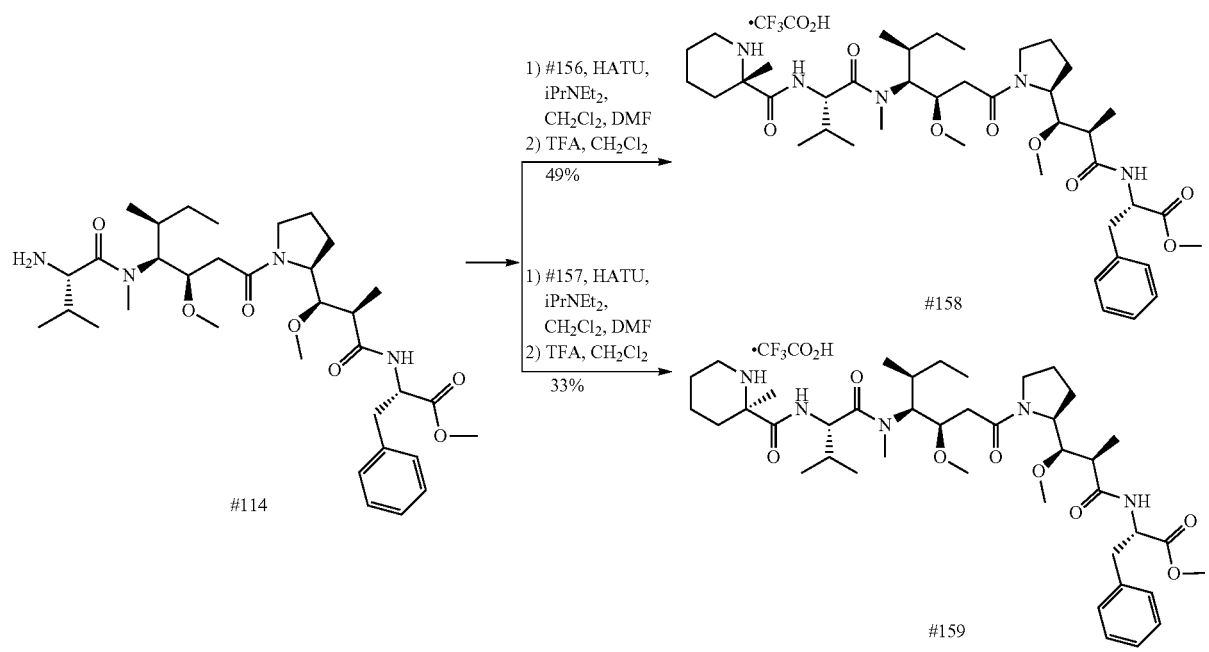

221.97 (m, 1H), 1.67-1.77 (m, 3H), 1.48-1.66 (m, 2H), 1.46 (s, 3H), 1.44 (s, 9H). Optical rotation: [α]$_D$25+30.2° (chloroform).

Step 2A

Synthesis of methyl N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L valyl)amino]heptanoyl}pyrrolidin-2-yl]-2-methylpropanoyl}-L-phenylalaninate, trifluoroacetic acid salt (#158)

To a solution of #156 (8.3 mg, 0.034 mmol, 1 eq.) in dichloromethane (0.3 mL) and N,N-dimethylformamide (0.05 mL), was added N,N-diisopropylethylamine (0.018 mL, 0.102 mmol, 3 eq.), followed by HATU (16.1 mg, 0.041 mmol, 1.2 eq.). The reaction was stirred for 15 minutes and #114 (23.4 mg, 0.037 mmol, 1.1 eq.) was added and stirred at room temperature for 18 hours. The reaction was diluted with dichloromethane (2.5 mL) and 10% citric acid (1.5 mL) was added. The layers were separated using a phase separator cartridge and the aqueous layer extracted with dichloromethane (2×2.5 mL) and the combined organic layers were concentrated in vacuo. The residue was dissolved in dichloromethane (4 mL) and trifluoroacetic acid (0.5 mL) was added. The reaction was stirred at room temperature for 2 hours, then concentrated in vacuo. Purification by reverse phase chromatography (method M*) afforded #158 (10.6 mg, 49%). HPLC (Protocol T): m/z 758.4 [M+H$^+$], retention time=2.53 minutes (purity >99%). $^1$H NMR (400 MHz, DMSO-d$_6$), δ 8.74-8.90 (m), 8.49-8.55 (m), 8.24 (d), 8.08-8.12 (m), 7.94-8.01 (m), 7.14-7.26 (m), 4.71-4.77 (m), 4.57-4.68 (m), 4.44-4.55 (m), 3.94-4.0 (m), 3.73-3.78 (m), 3.40-3.72 (m), 3.16-3.32 (m), 2.98-3.16 (m), 2.82-2.92 (m), 2.47-2.56 (m), 2.38-2.44 (m), 2.20-2.37 (m), 2.08-2.19 (m) 1.74-1.88 (m), 1.61-1.73 (m), 1.52-1.59 (m), 1.22-1.52 (m), 1.05 (dd), 0.94-1.00 (m), 0.85-0.93 (m), 0.74-0.79 (m).

Step 2B

Synthesis of methyl N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalaninate, trifluoroacetic acid salt (#159)

To a solution of #157 (7.8 mg, 0.032 mmol, 1 eq.) in dichloromethane (0.3 mL) and N,N-dimethylformamide (0.05 mL), was added N, N-diisopropylethylamine (0.017 mL, 0.096 mmol, 3 eq.) followed by HATU (14.9 mg, 0.038 mmol, 1.2 eq.). The reaction was stirred for 15 minutes and #114 (22.1 mg, 0.035 mmol, 1.1 eq.) was added and stirred at room temperature for 3 hours and then concentrated in vacuo. Purification of the residue by silica gel chromatography (Gradient: 0 to 80% acetone in heptane) afforded a white solid which was dissolved in dioxane (0.2 mL) and 4N HCl in dioxane (0.2 mL) was added. The reaction was stirred at room temperature for 2 hours and additional 4N HCl in dioxane (0.1 mL) was added. The reaction was stirred for 2 hours at room temperature, concentrated in vacuo. Purification by reverse phase chromatography (Method M*) afforded #159 (6.6 mg, 33%). HPLC (Protocol T): m/z 758.4 [M+H$^+$], retention time=2.46 minutes (purity=89%). $^1$H NMR (400 MHz, DMSO-d$_6$), δ 8.86-8.95 (m), 8.75-8.84 (m), 8.48-8.54 (m), 8.33-8.45 (m), 8.22-8.27 (m), 8.17-8.19 (m), 7.99-8.12 (m), 7.83-7.91 (m), 7.13-7.29 (m), 7.04-7.08 (m), 4.69-4.76 (m), 4.55-4.66 (m), 4.45-4.53 (m), 3.96-4.01 (m), 3.41-3.78 (m), 3.28-3.33 (m), 3.24-3.27 (m), 3.16-3.23 (m), 3.11-3.15 (m), 3.02-3.10 (m), 2.93-3.02 (m), 2.91-2.93 (m), 2.84-2.91 (m), 2.76-2.82 (m), 2.69-2.71 (m), 2.60-2.63 (m), 2.53-2.55 (m), 2.47-2.53 (m), 2.40-2.46 (m), 2.30-2.38 (m), 2.20-2.30 (m), 2.06-2.17 (m), 1.75-1.87 (m), 1.52-1.74 (m), 1.35-1.51 (m), 1.14-1.34 (m), 1.01-1.08 (m), 0.92-1.0 (m), 0.85-0.94 (m), 0.74-0.82 (m).

Preparation of N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalanine, trifluoroacetic acid salt (#162) and N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalanine, trifluoroacetic acid salt. (#163)

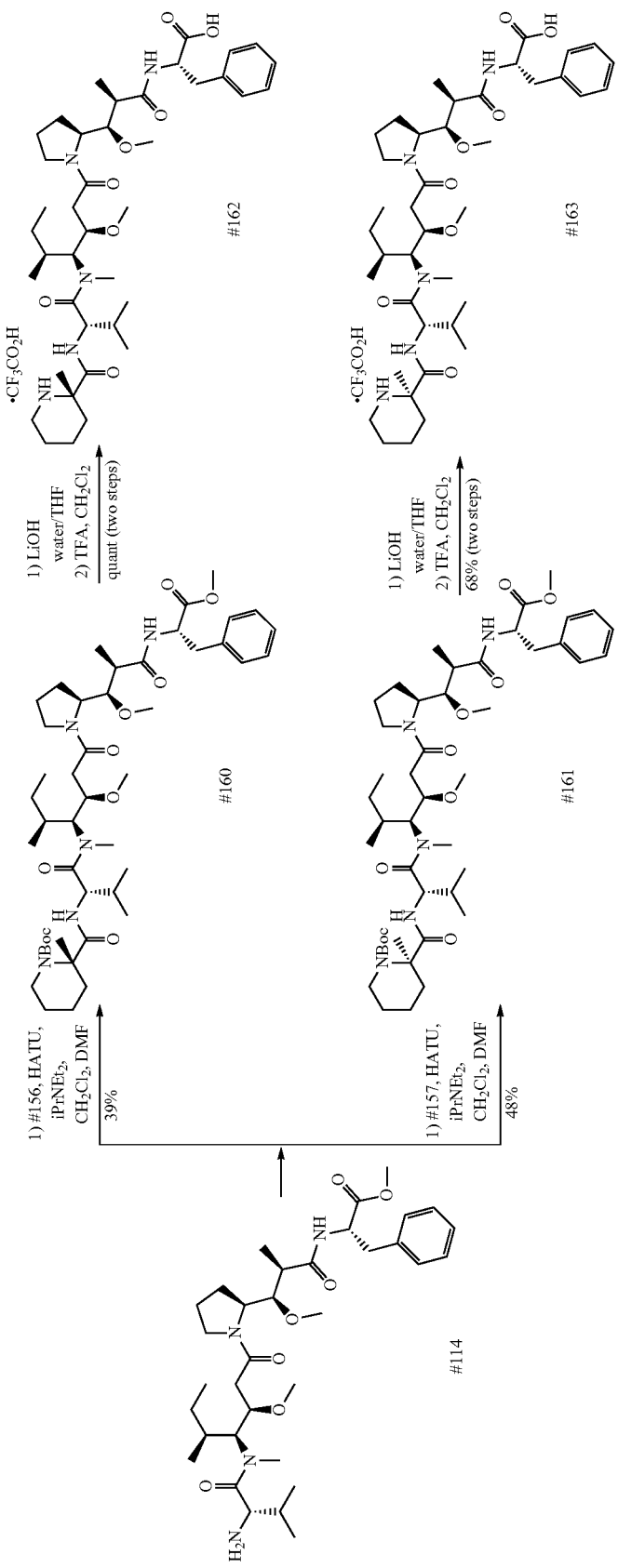

Step 1A

Synthesis of methyl N-{(2R,3R)-3-[(2S)-1-{(3R,4S,5S)-4-[(N-{[(2S)-1-(tert-butoxycarbonyl)-2-methylpiperidin-2-yl]carbonyl}-L-valyl)(methyl)amino]-3-methoxy-5-methylheptanoyl}pyrrolidin-2-yl]-3-methoxy-2-methylpropanoyl}-L-phenylalaninate (#160)

To a solution of #156 (106 mg, 0.436 mmol, 1 eq.) in dichloromethane (3 mL) and N,N-dimethylformamide (0.5 mL) was added diisopropylethylamine (0.228 mL, 1.31 mmol, 3 eq.) followed by HATU (205 mg, 0.523 mmol, 1.2 eq.). The reaction was stirred for 15 minutes and #114 (276 mg, 0.436 mmol, 1 eq.) was added and stirred at room temperature for 2 hours. The reaction was diluted with dichloromethane (10 mL) and washed with 10% citric acid (3×5 mL). The organic layer was dried over sodium sulfate, filtered and the filtrate concentrated in vacuo. Purification of the residue by silica gel chromatography (Gradient: 0 to 80% acetone in heptane) afforded #160 (145 mg, 39%). LC-MS (protocol Q1): m/z 858.8 [M+H$^+$], retention time=1.12 minutes.

Step 1B

Synthesis of methyl N-{(2R,3R)-3-[(2S)-1-{(3R,4S,5S)-4-[(N-{[(2R)-1-(tert-butoxycarbonyl)-2-methylpiperidin-2-yl]carbonyl}-L-valyl)(methyl)amino]-3-methoxy-5-methylheptanoyl}pyrrolidin-2-yl]-3-methoxy-2-methylpropanoyl}-L-phenylalaninate (#161)

To a solution of #157 (109 mg, 0.448 mmol, 1 eq.) in dichloromethane (3 mL) and N,N-dimethylformamide (0.5 mL), was added diisopropylethylamine (0.234 mL, 1.34 mmol, 3 eq.) followed by HATU (205 mg, 0.538 mmol, 1.2 eq.). The reaction stirred for 15 minutes and #114 (284 mg, 0.448 mmol, 1 eq.) was added. After stirring at room temperature for 2 hours, the mixture was diluted with dichloromethane (10 mL), washed with 10% citric acid (3×5 mL). The organic layer was dried over sodium sulfate, filtered and concentrated in vacuo. Purification of the residue by silica gel chromatography (Gradient: 0 to 100% acetone in heptane) afforded #161 (185 mg, 48%). LC-MS (Protocol Q): m/z 858.3 [M+H$^+$], retention time=2.25 minutes.

Step 2A

Synthesis of N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalanine, trifluoroacetic acid salt (#162)

To a solution of #160 (145 mg, 0.169 mmol, 1 eq.) in tetrahydrofuran (1.25 mL) was added lithium hydroxide (8 mg, 0.338 mmol, 2 eq.) dissolved in water (0.75 mL). The reaction was stirred at room temperature for 2 hours and evaporated to dryness in vacuo. The residue was dissolved in dichloromethane (2.5 mL) and trifluoroacetic acid (1 mL) was added. The reaction was stirred for 30 minutes, concentrated in vacuo and purified by medium pressure reverse phase C18 chromatography (Gradient: 0% to 100% acetonitrile in water with 0.02% TFA in each phase) to afford the title compound #162 (145 mg, quantitative) as a white solid. HPLC (Protocol U): m/z 744.5 [M+H+], retention time=7.121 minutes (purity=98%). $^1$H NMR (400 MHz, DMSO-d$_6$). δ 8.76-8.96 (m), 8.52-8.58 (m), 8.38-8.43 (m), 8.11-8.16 (m), 7.27-7.30 (m), 7.12-7.27 (m), 7.01-7.05 (m), 4.71-4.79 (m), 4.48-4.67 (m), 4.39-4.47 (m), 3.79-4.22 (m), 3.71-3.78 (m), 3.38-3.57 (m), 3.22-3.30 (m), 3.14-3.23 (m), 3.07-3.13 (m), 2.96-3.06 (m), 2.76-2.87 (m), 2.66-2.68 (m), 2.47-2.57 (m), 2.42-2.44 (m), 2.06-2.40 (m), 1.73-1.89 (m), 1.51-1.72 (m), 1.36-1.49 (m), 1.20-1.35 (m), 1.00-1.09 (m), 0.95-0.99 (m), 0.83-0.94 (m), 0.73-0.80 (m).

Step 2B

Synthesis of N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalanine, trifluoroacetic acid salt (#163)

Compound #161 (185 mg, 0.216 mmol, 1 eq.) was converted to the crude title compound #163, using the procedure described for the preparation of #162. The crude material was purified by medium pressure reverse phase C18 chromatography (Gradient: 0% to 85% acetonitrile in water with 0.02% TFA in each phase) to yield #163 (127 mg, 68%) as a white solid. HPLC (Protocol U): m/z 744.5 [M+H+], retention time=7.077 minutes (purity=98%). $^1$H NMR (400 MHz, DMSO-d$_6$). δ 8.79-8.99 (m), 8.36-8.49 (m), 8.12-8.17 (m), 7.31-7.34 (m), 7.11-7.27 (m), 7.05-7.09 (m), 4.71-4.77 (m), 4.54-4.68 (m), 4.40-4.53 (m), 3.88-4.39 (m), 3.71-3.77 (m), 3.39-3.58 (m), 3.22-3.32 (m), 3.10-3.22 (m), 3.04-3.09 (m), 2.92-3.03 (m), 2.77-2.88 (m), 2.68-2.71 (m), 2.47-2.57 (m), 2.43-2.45 (m), 2.30-2.42 (m), 2.03-2.29 (m), 1.74-1.88 (m), 1.52-1.73 (m), 1.37-1.51 (m), 1.17-1.37 (m), 1.00-1.07 (m), 0.95-0.99 (m), 0.84-0.93 (m), 0.73-0.81 (m).

Preparation of methyl N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate, trifluoroacetic acid salt (#172) and methyl N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate, trifluoroacetic acid salt (#173)

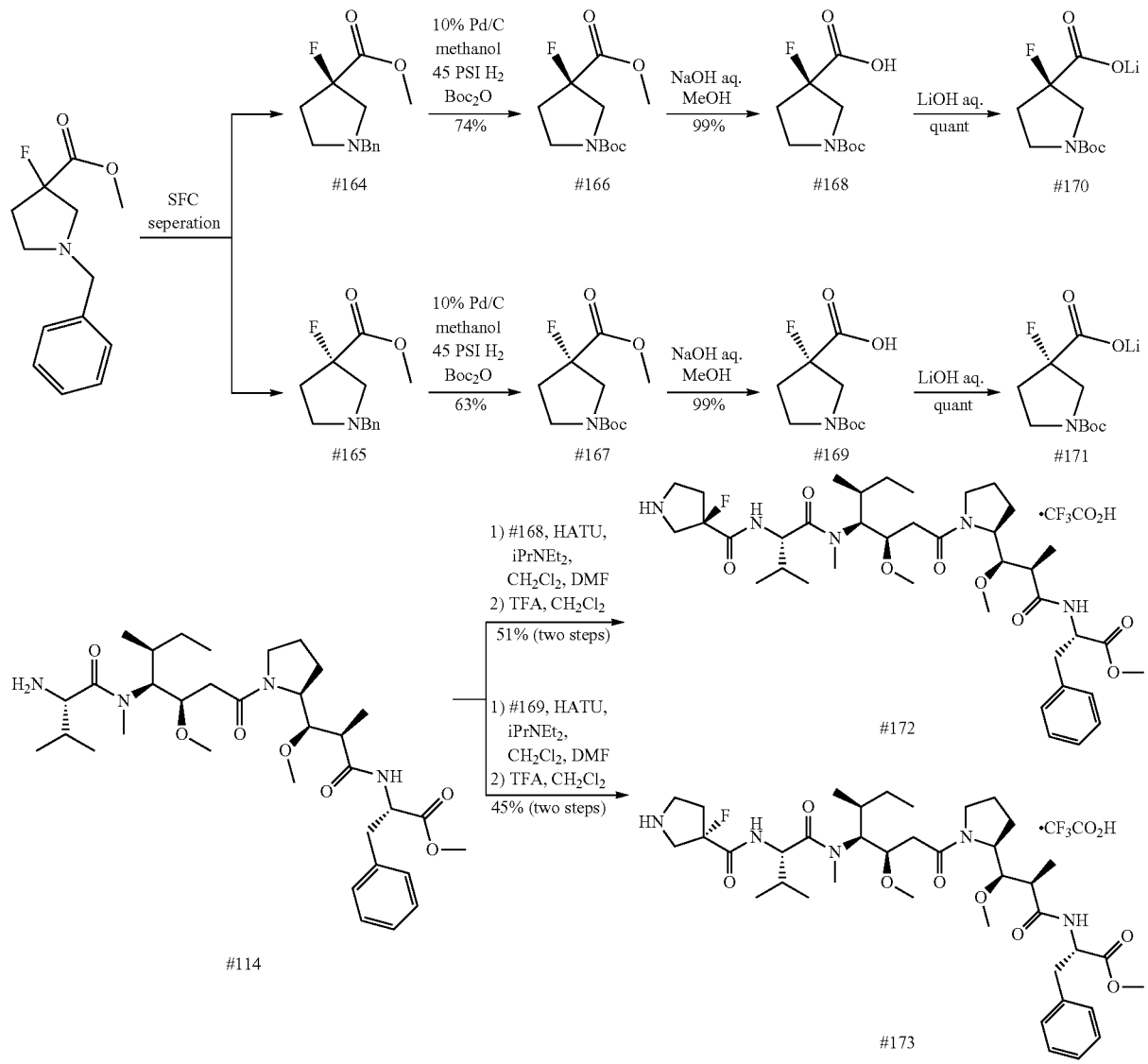

Step 1

Synthesis of methyl (3R)-1-benzyl-3-fluoropyrrolidine-3-carboxylate (#164) and methyl (3S)-1-benzyl-3-fluoropyrrolidine-3-carboxylate (#165)

Known (methyl 1-benzyl-3-fluoropyrrolidine-3-carboxylate (3900 mg, 16.4 mmol, 1 eq.) was separated by supercritical fluid chromatography (Column: Chiralpak IC, 250×21 mm; Eluent: 95:5 carbon dioxide/propanol; Flow Rate: 65 g/min; to give the corresponding enantiomers. The first eluting peak (retention time=3.37 minutes) was isolated to afford #164 (1720 mg, 36%) as a single enantiomer (stereochemistry arbitrarily assigned as R enantiomer). $^1$H NMR (400 MHz, TMS-CDCl$_3$; δ 7.17-7.30 (m, 5H), 3.74 (s, 3H), 3.65 (d, J=12.9 Hz, 1H), 3.63 (d, J=12.9 Hz, 1H), 2.86-3.03 (m, 3H), 2.61 (q, J=8.0 Hz, 1H), 2.34-2.46 (m, 1H), 2.13-2.26 (m, 1H). Optical rotation: [α]$_D$25+24.7° (chloroform). The second eluting peak (retention time=3.91 minutes) was isolated to afford #165 (1600 mg, 33%) as a single enantiomer (stereochemistry arbitrarily assigned as S enantiomer). $^1$H NMR (400 MHz, CDCl$_3$; (CH$_3$)$_4$Si), δ 7.17-7.30 (m, 5H), 3.74 (s, 3H), 3.65 (d, J=12.9 Hz, 1H), 3.63 (d, J=12.9 Hz, 1H), 2.86-3.03 (m, 3H), 2.61 (q, J=8.0 Hz, 1H), 2.34-2.46 (m, 1H), 2.13-2.26 (m, 1H). Optical rotation: [α]$_D$25-23.3° (chloroform).

Step 2A

Synthesis of 1-tert-butyl 3-methyl (3R)-3-fluoropyrrolidine-1,3-dicarboxylate (#166)

To a solution containing #164 (355 mg, 1.50 mmol, 1 eq.) and Di-tert-butyl carbonate (400 mg, 1.8 mmol, 1.2 eq.) in methanol (15.5 mL) was added 10% Pd/C (70 mg). The reaction was hydrogenated at 45 psi in a Parr shaker at for 22 hours, filtered over celite, and the filtrate concentrated in vacuo and purified by silica gel chromatography (Gradient: 0 to 30% ethyl acetate in heptane) to afford #166 as a clear oil. (272 mg, 74%). $^1$H NMR (400 MHz, CDCl$_3$), δ 3.87 (s, 3H), 3.85-3.66 (m, 3H), 3.56 (m, 1H), 2.53-2.28 (m, 2H), 1.51 (s, 9H).

Step 2B

Synthesis of 1-tert-butyl 3-methyl (3S)-3-fluoropyrrolidine-1,3-dicarboxylate (#167)

Compound #165 (362 mg, 1.53 mmol, 1 eq.) was converted to #167 in 63% yield using the method described above for #164. $^1$H NMR (400 MHz, CDCl$_3$), δ 3.87 (s, 3H), 3.85-3.66 (m, 3H), 3.56 (m, 1H), 2.53-2.28 (m, 2H), 1.51 (s, 9H).

Step 3A

Synthesis of (3R)-1-(tert-butoxycarbonyl)-3-fluoropyrrolidine-3-carboxylic acid (#168)

To a solution of #166 (272 mg, 1.10 mmol, 1 eq.) dissolved in methanol (2.96 mL) was added an aqueous solution of sodium hydroxide (2.5 M, 0.88 mL) and the reaction was stirred at room temperature for 3.5 hours. The reaction was quenched with 10% aqueous citric acid (5 mL), ethyl acetate (100 mL) was added, and the layers separated. The organic layer was washed with 10% citric acid, water, and brine, dried over sodium sulfate, filtered and concentrated in vacuo to afford #168 as a white solid. (253 mg, 99%). $^1$H NMR (400 MHz, CDCl$_3$), δ 3.96-3.69 (m, 3H), 3.59 (m, 1H), 2.59-2.33 (m, 2H), 1.51 (s, 9H). LC-MS (Protocol Q1): m/z 232.1 [M−H+], retention time=0.67 minutes. Chiral HPLC retention time: 3.39 min (purity=99%). (Column: Chiralpak AD-H, 4.6 mm×25 cm, mobile phase 5-60% CO$_2$/Methanol, flow rate 3.0 mL/min); Optical rotation: [α]$_D$25 4.8 (c=0.52, MeOH)

Step 3B

Synthesis of (3S)-1-(tert-butoxycarbonyl)-3-fluoropyrrolidine-3-carboxylic acid (#169)

To a solution of #167 (238 mg, 0.963 mmol, 1 eq.) dissolved in methanol (2.6 mL) was added an aqueous solution of sodium hydroxide (2.5 M, 0.88 mL) and the reaction was stirred at room temperature for 3 hours. The reaction was then quenched with 10% aqueous citric acid (5 mL) and ethyl acetate (100 mL) was added, and the layers were separated. The organic layer was washed with 10% citric acid, water, and brine, then dried over sodium sulfate, filtered and concentrated in vacuo to afford #169 as a white solid (221 mg, 99%). $^1$H NMR (400 MHz, CDCl$_3$), δ 3.96-3.69 (m, 3H), 3.59 (m, 1H), 2.59-2.33 (m, 2H), 1.51 (s, 9H). LC-MS (Protocol Q1): m/z 232.1 [M−H+], retention time=0.67 minutes. Chiral HPLC retention time: 3.95 min (purity=98%)(Column: Chiralpak AD-H, 4.6 mm×25 cm, mobile phase 5-60% CO$_2$/Methanol, flow rate 3.0 mL/min); Optical rotation: [α]$_D$25-3.6 (c=0.55, MeOH)

Step 4A

Synthesis of lithium (3R)-1-(tert-butoxycarbonyl)-3-fluoropyrrolidine-3-carboxylate (#170)

To a solution of #168 (50 mg, 0.21 mmol, 1 eq.) in methanol (0.2 mL) was added a solution of lithium hydroxide (9.2 mg, 0.38 mmol, 1.8 eq.) dissolved in water (0.1 mL). Next, tetrahydrofuran (0.3 mL) was added and the reaction was stirred at 45° C. for 18 hours. The reaction was concentrated in vacuo and the material was azeotroped (3×) with toluene (2 mL) to obtain #170 (51 mg, 100%) as a white solid which was used in the next step without further purification.

Step 4B

Synthesis of lithium (3S)-1-(tert-butoxycarbonyl)-3-fluoropyrrolidine-3-carboxylate (#171)

To a solution of #169 (75 mg, 0.32 mmol, 1 eq.) in methanol (0.3 mL) was added a solution of lithium hydroxide (13.8 mg, 0.572 mmol, 1.8 eq.) in water (0.4 mL). Next, tetrahydrofuran (0.45 mL) was added and the reaction was stirred at 45° C. for 18 hours. The reaction was concentrated in vacuo and the material was azeotroped (3×) with toluene (4 mL) to obtain #171 (77 mg, 100%) as a white solid, which was used in the next step without further purification.

Step 5A

Synthesis of methyl N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate, trifluoroacetic acid salt (#172)

To a suspension of #168 (36.9 mg, 0.158 mmol, 1 eq.) and #114 (100 mg, 0.158 mmol, 1.0 eq.) in N,N-dimethylformamide (0.8 mL) and dichloromethane (3.6 mL) was added N,N-diisopropylethylamine (0.083 mL, 0.474 mmol, 3 eq.) followed by HATU (60.7 mg, 0.158 mmol, 1.0 eq.) and the reaction was stirred at room temperature for 18 hours. The reaction was diluted with ethyl acetate and was washed successively with water, 10% aqueous citric acid (WN), and brine. The organic layer was dried over sodium sulfate and concentrated in vacuo to give 220 mg (164% of theory) of a crude intermediate. A portion of this crude intermediate (50 mg, 23%) was dissolved in dichloromethane (1.5 mL) and trifluoroacetic acid (0.4 mL) was added. The mixture was stirred at room temperature for 2 hours and evaporated to dryness in vacuo. Purification by reverse phase chromatography (Method M*) afforded #172 (15.8 mg, 51%) LC-MS (Protocol Q): m/z 748.9 [M+H$^+$] retention time=1.29 minutes. $^1$H NMR (DMSO-d$_6$), δ 9.16-9.43 (m), 8.48-8.53 (m), 8.40-8.44 (m), 8.34-8.39 (m), 8.22-8.30 (m), 8.09-8.16 (m), 7.87-7.91 (m), 7.77-7.83 (m), 7.12-7.24 (m), 4.56-4.72 (m), 4.41-4.54 (m), 3.92-4.00 (m), 3.70-3.75 (m), 3.39-3.66 (m), 3.20-3.25 (m), 3.12-3.20 (m), 2.97-3.11 (m), 2.94 (br s), 2.75-2.89 (m), 2.63-2.69 (m), 2.47-2.54 (m), 2.29-2.45 (m), 2.15-2.27 (m), 2.02-2.15 (m), 1.57-1.87 (m), 1.33-1.51 (m), 1.19-1.30 (m), 1.02 (dd), 0.82-0.97 (m), 0.70-0.79 (m).

Step 5B

Synthesis of methyl N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate, trifluoroacetic acid salt (#173)

To a suspension of #169 (36.9 mg, 0.158 mmol, 1 eq.) and #114 (100.0 mg, 0.158 mmol, 1 eq.) in N,N-dimethylformamide (0.8 mL) and dichloromethane (3.6 mL) was added N,N-diisopropylethylamine (0.083 mL, 0.474 mmol, 3 eq.) was added, followed by HATU (60.7 mg, 0.158 mmol, 1 eq.). The reaction was stirred at room temperature for 14 hours, diluted with ethyl acetate, and washed successively with water, 10% aqueous citric acid (W/V), and brine. The organic layer was dried over sodium sulfate and concentrated in vacuo to give 180 mg (134% of theory) of a crude intermediate. A portion of this crude intermediate (50 mg, 27%) was dissolved in dichloromethane (1.5 mL) and trifluoroacetic acid (0.4 mL) was added and the mixture stirred at room temperature for 2 hours and evaporated to dryness in vacuo. Purification by reverse phase chromatography (Method M*) afforded #173 (17.6 mg, 45%). LC-MS (Protocol Q): m/z 748.9 [M+H+] retention time=1.29 minutes. $^1$H NMR (DMSO-$d_6$) δ 9.35-9.50 (m), 9.22-9.34 (m), 8.47-8.52 (m), 8.39-8.45 (m), 8.30-8.37 (m), 8.22-8.24 (m), 8.09-8.13 (m), 7.80-7.85 (m), 7.67-7.72 (m), 7.09-7.24 (m), 6.97-6.98 (m), 4.65-4.72 (m), 4.55-4.64 (m), 4.41-4.50 (m), 3.92-3.99 (m), 3.42-3.75 (m), 3.32-3.39 (m), 3.25-3.31 (m), 3.21-3.24 (m), 3.11-3.20 (m), 3.06-3.11 (M), 2.97-3.05 (m), 2.95 (br s), 2.83-2.88 (m), 2.76-2.82 (m), 2.65-2.70 (m), 2.44-2.54 (m), 2.15-2.42 (m), 2.02-2.14 (m), 1.57-1.84 (m), 1.33-1.48 (m), 1.19-1.30 (m), 1.02 (dd), 0.92-0.97 (m), 0.82-0.91 (m), 0.70-0.77 (m).

Preparation of (2S)—N-[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide, hydrochloride salt (#178) and (2R)—N-[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide, hydrochloride salt (#180)

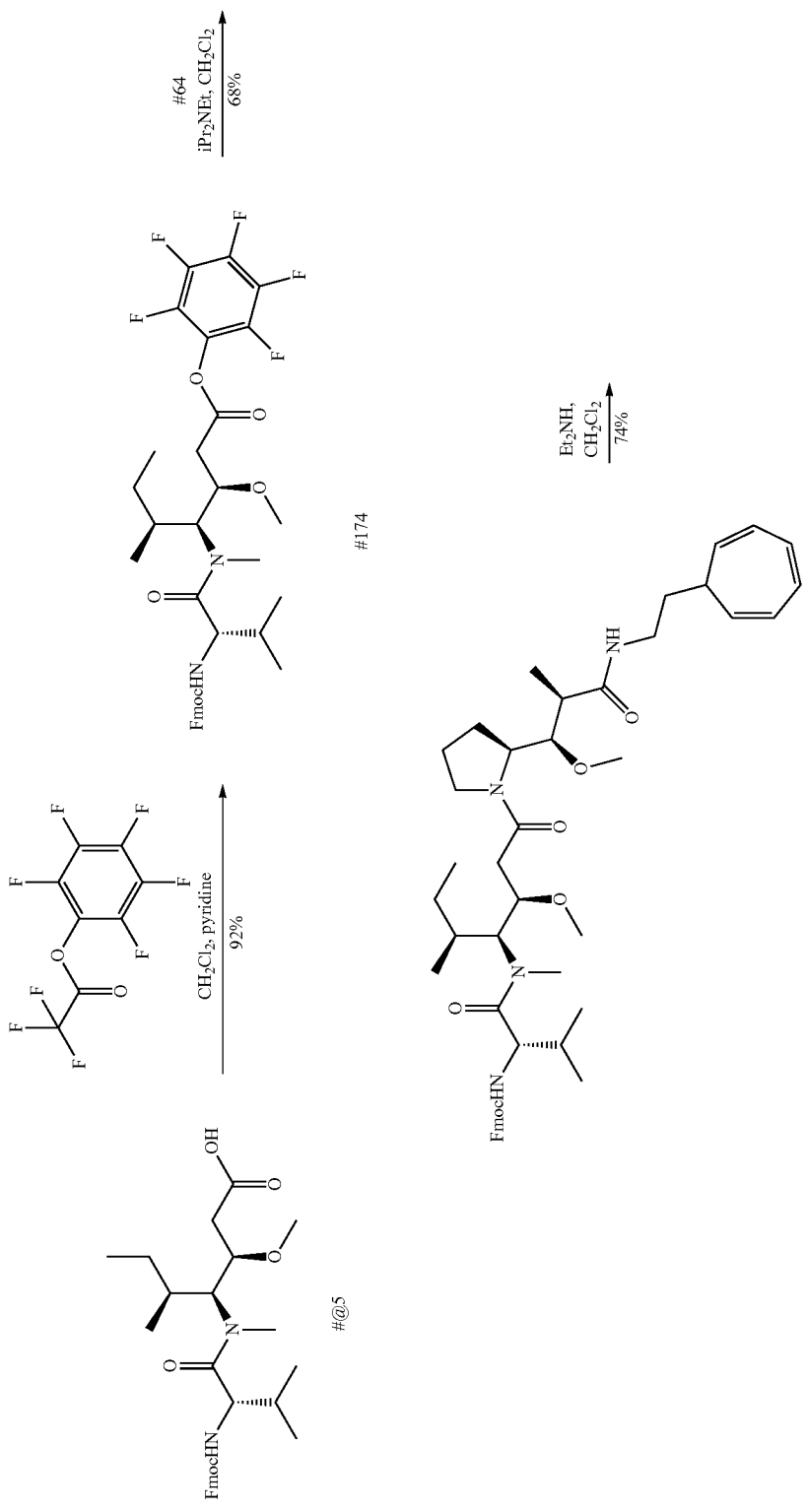

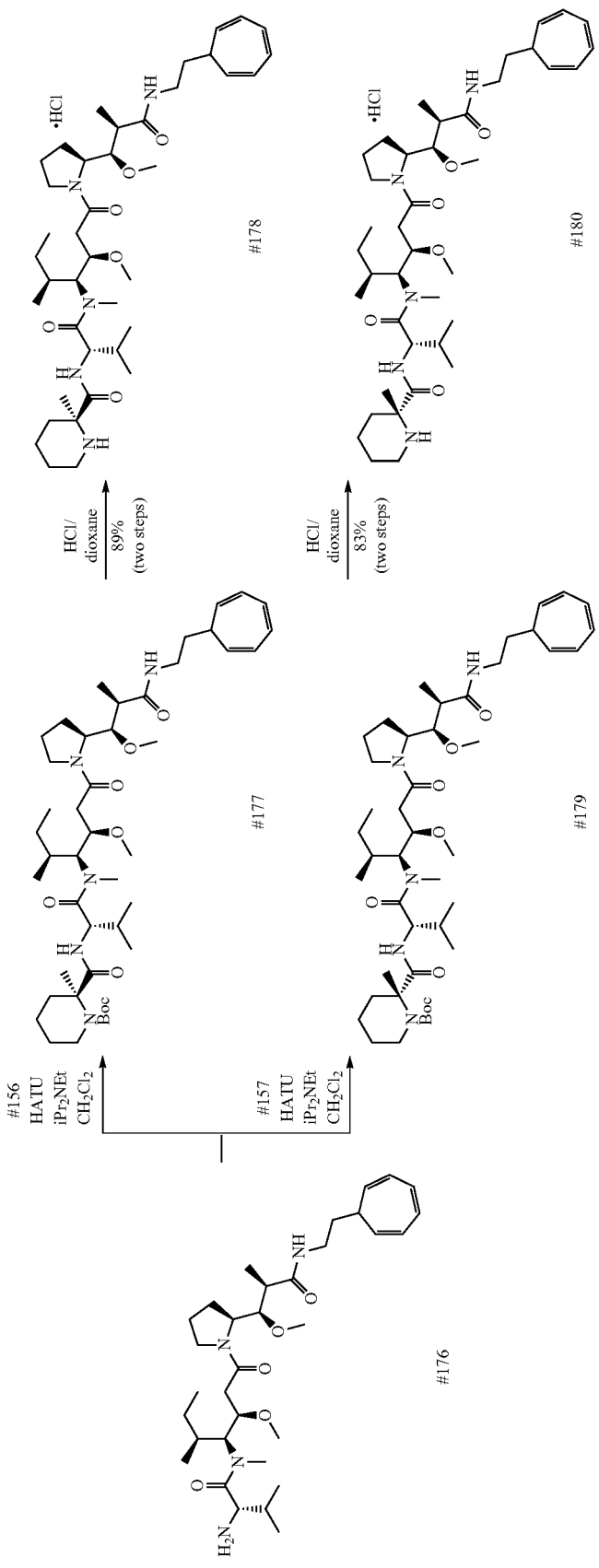

Step 1

Synthesis of pentafluorophenyl (3R,4S,5S)-4-[{N-[(9H-fluoren-9-ylmethoxy)carbonyl]-L-valyl}(methyl)amino]-3-methoxy-5-methylheptanoate (#174)

To a solution of #@5 (19.43 g, 37.03 mmol, 1 eq.) in dichloromethane (100 mL) and pyridine (5.86 g, 74.1 mmol, 2 eq.) was added pentafluorophenyl trifluoroacetate (20.7 g, 74.1 mmol, 2 eq.) and the reaction was stirred at room temperature for 1 hour. The reaction was concentrated in vacuo and purified by silica gel chromatography (Gradient: 0 to 52% ethyl acetate in heptane) to afford #174 (23.58 g, 92%) as a yellow oil. LC-MS (Protocol Q1): m/z 691.2 [M+H+], retention time=1.23 minutes.

Step 2

Synthesis of N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N~2~-[(9H-fluoren-9-ylmethoxy)carbonyl]-N-methyl-L-valinamide (#175)

To a solution of #174 (706 mg, 1.02 mmol, 1 eq.) and #64 (311 mg, 1.02 mmol, 1 eq.) in dichloromethane (3 mL) was added N,N-diisopropylethylamine (400 mg, 3.07 mmol, 3 eq.). After 18 hours of stirring at room temperature, the reaction was concentrated in vacuo and purified by silica gel chromatography (Gradient: 0 to 100% ethyl acetate in heptane) to afford #175 (560 mg, 68%) as a white solid. LC-MS (Protocol Q1): m/z 611.8 [M+H+], retention time=1.15 minutes.

Step 3

Synthesis of N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide (#176)

According to the general procedure A, from #175 (560 mg, 0.690 mmol, 1 eq.) in dichloromethane (9 mL), and N,N-diethylamine (6.0 mL), was synthesized the crude desired compound, which was purified by by silica gel chromatography (Gradient: 0 to 50% methanol in dichloromethane) to afford #176 (351 mg, 87%) as a yellow oil. LC-MS (Protocol Q1): m/z 589.5 [M+H$^+$], retention time=0.72 minutes.

Step 4A

Synthesis of tert-butyl (2S)-2-{[(2S)-1-{[(3R,4S,5S)-1-{(2S)-2-[(1R,2R)-3-{[2-(cyc lohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]carbamoyl}-2-methylpiperidine-1-carboxylate (#177)

According to the general procedure D, from #176 (100 mg, 0.170 mmol, 1 eq.), #156 (53.8 mg, 0.221 mmol, 1.3 eq.), dichloromethane (4.5 mL), HATU (84.9 mg, 0.221 mmol, 1.3 eq.) and N,N-diisopropylethylamine (0.123 mL, 0.697 mmol, 4.1 eq.), was synthesized the crude desired material, which was purified by silica gel chromatography (Gradient: 0 to 100% ethyl acetate in heptane) to afford #177 (145 mg, assume quantitative yield) as a white solid. LC-MS (Protocol Q1): m/z 814.7 [M+H$^+$], retention time=1.14 minutes.

Step 4B

Synthesis of tert-butyl (2R)-2-{[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]carbamoyl}-2-methylpiperidine-1-carboxylate (#179)

According to the general procedure D, from #176 (100 mg, 0.170 mmol, 1 eq.), #157 (53.8 mg, 0.221 mmol, 1.3 eq.), dichloromethane (4.5 mL), HATU (84.9 mg, 0.221 mmol, 1.3 eq.) and N,N-diisopropylethylamine (0.123 mL, 0.697 mmol, 4.1 eq.), was synthesized the crude desired material, which was purified by silica gel chromatography (Gradient: 0 to 100% ethyl acetate in heptane) to afford #179 (155 mg, assume quantitative yield) as a white solid. LC-MS (Protocol Q1): m/z 814.7 [M+H$^+$], retention time=1.14 minutes.

Step 5A

Synthesis of (2S)-N-[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide , hydrochloride salt (#178)

According to the general procedure C, from #177 (143 mg, 0.176 mmol, 1 eq.) and 4M solution of hydrochloric acid in dioxane (2.0 mL) was synthesized the desired material as a gum (145 mg). A portion of this crude residue (25 mg) was azeotroped with a mixture of methanol/acetonitrile to afford #178 (20 mg, 89% yield) as a white solid. $^1$H NMR (400 MHz, DMSO-d$_6$), δ 8.96-9.07 (m), 8.79-8.96 (m), 8.58 (d), 8.02-8.08 (m), 7.77-7.83 (m), 7.25-7.31 (m), 7.19-7.24 (m), 6.56-6.67 (m), 6.12-6.21 (m), 5.13-5.22 (m), 4.72-4.81 (m), 4.63-4.70 (m), 4.50-4.59 (m), 4.07-4.16 (m), 3.98-4.05 (m), 3.80-3.86 (m), 3.55-3.76 (m), 3.46-3.54 (m), 3.38-3.44 (m), 3.26-3.35 (m), 3.18-3.24 (m), 3.05-3.18 (m), 2.98-3.04 (m), 2.40-2.55 (m), 2.27-2.35 (m), 2.08-2.27 (m), 1.74-1.98 (m), 1.50-1.74 (m), 1.20-1.46 (m), 0.73-1.16 (m). LC-MS (Protocol Q1): m/z 714.6 [M+H$^+$], retention time=0.76 minutes. HPLC (Protocol U): m/z 714.5 [M+H$^+$] retention time=7.124 minutes (purity=91%).

Step 5B

Synthesis of (2R)—N-[(2S)-1-{[(3R,4S,5S)-1-{(2S)-2-[(1R,2R)-3-{[2-(cyc lohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]-2-methylpiperidine-2-carboxamide, hydrochloride salt (#180)

According to the general procedure C, from #179 (162 mg, 0.199 mmol, 1 eq.) and 4M solution of hydrochloric acid in dioxane (2.0 mL) was synthesized the desired material as a gum (155 mg). A portion of this gum (25 mg) was azeotroped with a 1/1 mixture of methanol/acetonitrile to afford #180 (20 mg, 83%) as a solid. $^1$H NMR (400 MHz, DMSO-d$_6$), δ 9.02-9.13 (m), 8.83-8.93 (m), 8.39-8.46 (m), 8.00-8.06 (m), 7.78 (t), 7.24-7.30 (m), 7.16-7.21 (m), 6.54-6.65 (m), 6.09-6.19 (m), 5.11-5.18 (m), 4.69-4.78 (m), 4.59-4.68 (m), 4.46-4.56 (m), 4.08-4.13 (m), 3.95-4.03 (m), 3.77-3.85 (m), 3.54-3.73 (m), 3.43-3.53 (m), 3.37-3.42 (m), 3.24-3.33 (m), 3.16-3.22 (m), 3.03-3.15 (m), 2.99-3.02 (m), 2.89-2.98 (m), 2.65-2.76 (m), 2.41-2.54 (m), 2.15-2.39 (m), 2.07-2.15 (m), 1.51-1.94 (m), 1.49 (d), 1.38 (t), 1.20-1.32 (m), 1.02-1.09 (m), 0.84-0.97 (m), 0.73-0.81 (m). LC-MS (Protocol Q1): m/z 714.6 [M+H$^+$], retention time=0.76 HPLC (Protocol U): m/z 714.4 [M+H$^+$], retention time=7.409 minutes (purity=90%).

Preparation of 2-methyl-L-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide, formic acid salt (#182) and N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-~2~-{[(3R)-3-fluoropyrrolidin-3-yl]carbonyl}-N-methyl-L-valinamide, trifluoroacetic acid salt (#184) and N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N~2~-{[(3S)-3-fluoropyrrolidin-3-yl]carbonyl}-N-methyl-L-valinamide, trifluoroacetic acid salt (#186)

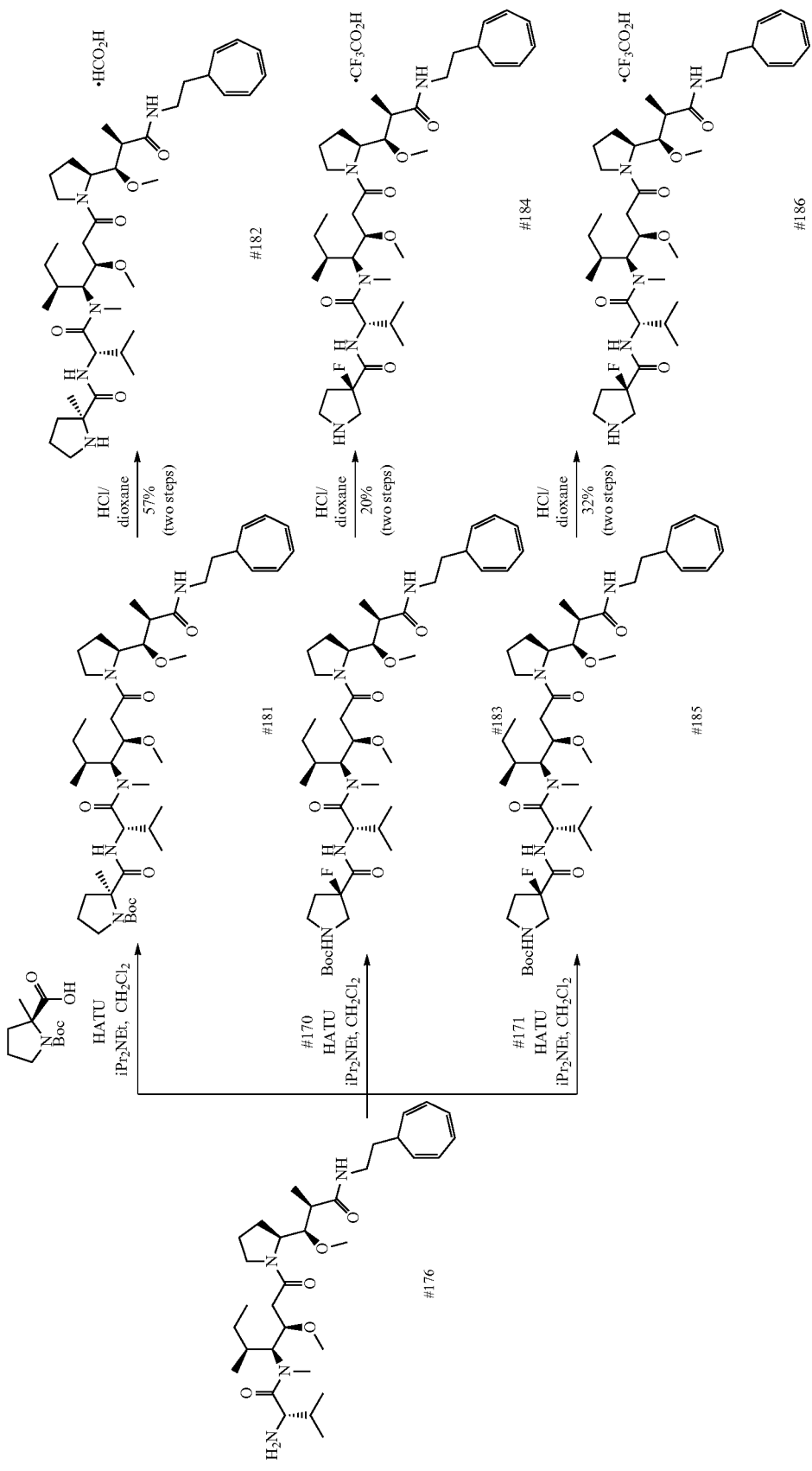

Step 1A

Synthesis of 1-(tert-butoxycarbonyl)-2-methyl-L-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide (#181)

According to the general procedure D, from #176 (100 mg, 0.170 mmol, 1 eq.), (S)-1-(tert-butoxycarbonyl)-2-methyl-L-proline (50.7 mg, 0.221 mmol, 1.3 eq.), dichloromethane (4.3 mL), HATU (84.9 mg, 0.221 mmol, 1.3 eq.) and N,N-diisopropylethylamine (0.123 mL, 0.697 mmol, 4.1 eq.), was synthesized the crude desired material, which was purified by silica gel chromatography (Gradient: 0 to 100% ethyl acetate in heptane) to afford #181 (142 mg, assume quantitative yield). LC-MS (Protocol Q1): m/z 800.6 [M+H$^+$], retention time=1.11 minutes.

Step 1B

Synthesis of tert-butyl (3R)-3-{[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]carbamoyl}-3-fluoropyrrolidine-1-carboxylate (#183)

To a solution of #170 (18.2 mg, 0.076 mmol, 1 eq.) in dichloromethane (1.8 mL) and N,N-dimethylformamide (0.3 mL) was added N,N-diisopropylethylamine (0.040 mL, 0.228 mmol, 3 eq.) followed by HATU (29.2 mg, 0.076 mmol, 1 eq.). After stirring for 10 minutes at room temperature, #176 (45 mg, 0.076 mmol, 1 eq.) was added. The reaction was stirred at room temperature for 18 hours and additional HATU (29 mg, 0.076 mmol, 1 eq.) was added. After 8 hours the reaction was concentrated in vacuo to provide #183 (61.0 mg, quantitative) which was taken into the next step without further purification. LC-MS (Protocol Q1): m/z 826.6 [M+Na$^+$], retention time=1.05 minutes.

Step 1C

Synthesis of tert-butyl (3S)-3-{[(2S)-1-{[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]carbamoyl}-3-fluorocyclopentanecarboxylate (#185)

To a solution of #171 (24 mg, 0.1 mmol, 1 eq.) in dichloromethane (2.35 mL) and N,N-dimethylformamide (0.33 mL) was added N,N-diisopropylethylamine (0.053 mL, 0.300 mmol, 3 eq.) followed by HATU (38.4 mg, 0.100 mmol, 1 eq.). After stirring at room temperature for 10 minutes, #176 (58.9 mg, 0.1 mmol, 1 eq.) was added. The reaction was stirred at room temperature for 18 hours and additional quantity of HATU (38.4 mg, 0.100 mmol, 1 eq.) and N,N-dimethylformamide (0.2 mL) was added and stirred for an additional 9 hours. The reaction was concentrated in vacuo to give #185 (80 mg, quantitative), which was taken into the next step without further purification. LC-MS (Protocol Q1): m/z 804.6 [M+H$^+$], retention time=1.05 minutes.

Step 2A

Synthesis of 2-methyl-L-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide, formic acid salt (#182)

According to the general procedure C, from #181 (136 mg, 0.170 mmol, 1 eq.) and 4M solution of hydrochloric acid in dioxane (2 mL) was synthesized the desired material as a gum (142 mg). A portion of this crude residue (20 mg, 14%) was azeotroped with a 1/1 mixture of methanol/acetonitrile and then purified by reverse phase chromatography (Method O) to obtain #182 (10 mg, 57% over two steps) as a solid. HPLC (Protocol U): m/z 700.4 [M+H$^+$], retention time=7.106 minutes (purity >90%). $^1$H NMR (400 MHz, DMSO-d$_6$), δ 8.25-8.39 (m), 8.20-8.25 (m), 7.96-7.99 (m), 7.74-7.77 (m), 6.55-6.63 (m), 6.10-6.18 (m), 5.11-5.18 (m), 4.66-4.72 (m), 4.51-4.61 (m), 4.46-4.50 (m), 3.96-4.01 (m), 3.37-3.86 (m), 3.20-3.36 (m), 3.11-3.19 (m), 3.03-3.11 (m), 2.98-3.03 (m), 2.90-2.96 (m), 2.77-2.79 (m), 2.65-2.73 (m), 2.57-2.63 (m), 2.47-2.56 (m), 2.36-2.46 (m), 2.26-2.32 (m), 2.14-2.25 (m), 2.03-2.10 (m), 1.92-2.03 (m), 1.72-1.92 (m), 1.64-1.72 (m), 1.60-1.64 (m), 1.50-1.59 (m), 1.39-1.48 (m), 1.23-1.32 (m), 1.18-1.22 (m), 1.12-1.14 (m), 1.01-1.09 (m), 0.83-1.00 (m), 0.74-0.83 (m), 0.70-0.74 (m).

Step 2B

Synthesis of N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N~2~-{[(3R)-3-fluoropyrrolidin-3-yl]carbonyl}-N-methyl-L-valinamide trifluoroacetic acid salt (#184)

According to the general procedure C, from #183 (61.1 mg, 0.076 mmol, 1 eq.), dichloromethane (0.3 mL), and a 4M solution of hydrochloric acid in dioxane (0.9 mL) was synthesized the crude desired material (140 mg). A portion of the crude material (98 mg, 69%) was purified by reverse phase chromatography (Method M*) to give #184 (7.6 mg, 20% over two steps). HPLC (Protocol T): m/z 704.5 [M+H+], retention time=2.50 minutes (purity=84%). $^1$H NMR (400 MHz, DMSO-d$_6$), δ 8.67-8.71 (m), 8.44-8.48 (m), 8.27-8.33 (m), 8.22-8.27 (m), 7.97-8.03 (m), 7.84-7.89 (m), 7.74-7.81 (m), 7.43-7.48 (m), 7.23-7.29 (m), 7.17-7.21 (m), 6.55-6.66 (m), 6.10-6.19 (m), 5.10-5.19 (m), 4.66-4.75 (m), 4.51-4.63 (m), 3.96-4.04 (m), 3.78-3.85 (m), 3.65-3.73 (m), 3.46-3.62 (m), 3.37-3.45 (m), 3.24-3.37 (m), 3.21-3.24 (m), 3.13-3.21 (m), 3.02-3.13 (m), 2.95-3.00 (m), 2.80-2.82 (m), 2.66-2.71 (m), 2.47-2.57 (m), 2.24-2.46 (m), 2.09-2.24 (m), 1.95-2.05 (m), 1.49-1.93 (m), 1.22-1.34 (m), 1.02-1.09 (m), 0.83-1.01 (m), 0.74-0.82 (m).

Step 2C

Synthesis of N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N~2~-{[(3S)-3-fluoropyrrolidin-3-yl]carbonyl}-N-methyl-L-valinamide, trifluoroacetic acid salt (#186)

According to the general procedure C, from #185 (80.3 mg, 0.1 mmol, 1 eq.), dichloromethane (0.4 mL), and a 4M solution of hydrochloric acid in dioxane (1.2 mL) was synthesized the crude desired material, in which a portion (94 mg, 53%) was purified by reverse phase chromatography (Method M*) to give #186 (11.8 mg, 32% over two steps). $^1$H NMR (400 MHz, DMSO-$d_6$), δ 8.85-9.07 (m), 8.29-8.41 (m), 7.99-8.04 (m), 7.76-7.84 (m), 6.56-6.68 (m), 6.12-6.21 (m), 5.12-5.21 (m), 4.87-4.99 (m), 4.69-4.79 (m), 4.49-4.67 (m), 3.98-4.06 (m), 3.80-3.87 (m), 3.64-3.76 (m), 3.55-3.64 (m), 3.47-3.54 (m), 3.39-3.46 (m), 3.26-3.39 (m), 3.22-3.25 (m), 3.18-3.22 (m), 3.06-3.14 (m), 2.98-3.01 (m), 2.55-2.57 (m), 2.42-2.49 (m), 2.11-2.38 (m), 2.09 (s), 1.78-1.97 (m), 1.72-1.77 (m), 1.51-1.71 (m), 1.24-1.36 (m), 1.07 (dd), 0.83-1.03 (m), 0.75-0.82 (m). HPLC (Protocol T): m/z 704.5 [M+H$^+$], retention time=2.48 minutes (purity=100%).

Preparation of (2S)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide, formate salt (#188) and (2R)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide, formate salt (#190) and N~2~-{[(3R)-3-fluoropyrrolidin-3-yl]carbonyl}-N-[(3R,4S,5S)-3-methoxy-1-{(2S)-2-[(1R,2R)-1-methoxy-2-methyl-3-oxo-3-[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, trifluoroacetic acid salt. (#192) and N~2~-{[(3S)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, trifluoroacetic acid salt. (#194)

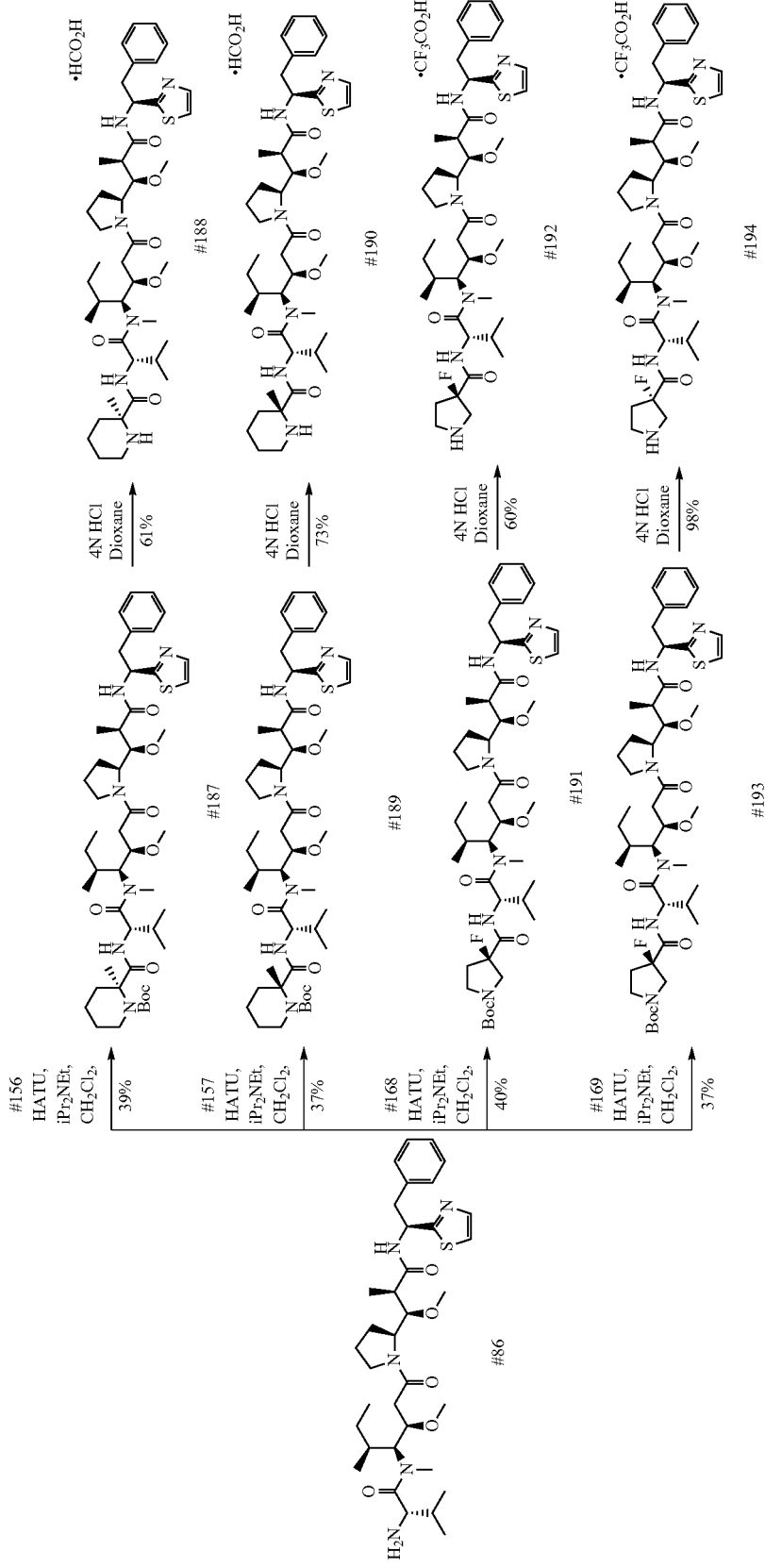

Step 1A

Synthesis of tert-butyl (2S)-2-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}-2-methylpiperidine-1-carboxylate (#187)

According to the general procedure D, from #86 (280 mg, 0.4 mmol, 1 eq.), #156 (100 mg, 0.4 mmol, 1 eq.), dichloromethane (5 mL), HATU (182 mg, 0.48 mmol, 1.2 eq.) and N,N-diisopropylethylamine (100 mg, 0.8 mmol, 2 eq.) was synthesized the crude desired material, which was purified by silica gel chromatography (Gradient: 0.01 to 0.05% methanol in dichloromethane) to afford #187 (220 mg, 62%) as a white solid. HPLC (Protocol V): m/z 883.57 [M+H$^+$], retention time=3.23 minutes (purity=95%).

Step 1B

Synthesis of tert-butyl (2R)-2-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}-2-methylpiperidine-1-carboxylate (#189)

According to the general procedure D, from #86 (400 mg, 0.6 mmol, 1 eq.), #157 (146 mg, 0.6 mmol, 1 eq.), dichloromethane (10 mL), HATU (259 mg, 0.72 mmol, 1.2 eq.) and N,N-diisopropylethylamine (158 mg, 1.2 mmol, 2 eq.) was synthesized the crude desired material, which was purified by silica gel chromatography (Gradient: 0.01 to 0.05% methanol in dichloromethane) to afford #189 (220 mg, 37%) as a white solid. HPLC (Protocol W): m/z 883.7 [M+H$^+$], retention time=4.12 minutes (purity=95%).

Step 1C

Synthesis of tert-butyl (3R)-3-fluoro-3-{[(2S)-1-{[(3R,4S,5S)-3-methoxy-1-{(2S)-2-[(1R,2R)-1-methoxy-2-methyl-3-oxo-3-{[(1S)-2-phenyl-1-(1,-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}pyrrolidine-1-carboxylate (#191)

According to the general procedure D, from #86 (300 mg, 0.45 mmol, 1 eq.), #168 (106 mg, 0.45 mmol, 1 eq.), dichloromethane (10 mL), HATU (194 mg, 0.54 mmol, 1.2 eq.) and diisopropylethylamine (117 mg, 0.9 mmol, 2 eq.) was synthesized the crude desired material, which was purified by reverse phase chromatography (Method P) to afford #191 (159 mg, 40%) as a white solid. HPLC (Protocol X): m/z 873.4 [M+H$^+$], retention time=3.32 minutes (purity=99%).

Step 1D

Synthesis of tert-butyl (3S)-3-fluoro-3-{[(2S)-1-{[(3R,4S,5S)-3-methoxy-1-{(2S)-2-[(1R,2R)-1-methoxy-2-methyl-3-oxo-3-{[(1S)-2-phenyl-1-(1,-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}pyrrolidine-1-carboxylate (#193)

According to the general procedure D, from #86 (300 mg, 0.45 mmol, 1 eq.), #169 (106 mg, 0.45 mmol, 1 eq.), dichloromethane (10 mL), HATU (194 mg, 0.54 mmol, 1.2 eq.) and diisopropylethylamine (117 mg, 0.9 mmol, 2 eq.) was synthesized the crude desired material, which was purified by reverse phase chromatography (Method P) to afford #193 (149 mg, 37%) as a white solid. HPLC (Protocol X): m/z 873.4 [M+H$^+$], retention time=3.34 minutes (purity=98%).

Step 2A

Synthesis of (2S)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide, formic acid salt (#188)

According to the general procedure C, from #187 (20 mg, 0.023 mmol, 1 eq.), dichloromethane (0.1 mL), acetonitrile (0.1 mL) and 4M solution of hydrochloric acid in dioxane (0.26 mL) was synthesized the crude desired material, which was purified by reverse phase chromatography (Method N*) to obtain #188 (11.6 mg, 61%,); HPLC (Protocol T): m/z 783.8 [M+H$^+$], retention time=2.53 minutes (purity=96%). $^1$H NMR (400 MHz, DMSO-d$_6$), δ 8.82-8.87 (m), 8.60-8.63 (m), 8.26-8.29 (m), 7.84-7.90 (m), 7.75-7.81 (m), 7.60-7.67 (m), 7.21-7.31 (m), 7.14-7.19 (m), 5.49-5.55 (m), 5.37-5.42 (m), 4.69-4.75 (m), 4.59-4.65 (m), 4.50-4.56 (m), 3.95-4.01 (m), 3.77-3.82 (m), 3.54-3.61 (m), 3.47-3.53 (m), 3.24-3.45 (m), 3.14-3.23 (m), 3.03-3.08 (m), 2.96-3.03 (m), 2.78-2.80 (m), 2.64-2.73 (m), 2.60-2.62 (m), 2.47-2.56 (m), 2.31-2.45 (m), 2.13-2.28 (m), 2.00-2.07 (m), 1.92-1.99 (m), 1.71-1.86 (m), 1.58-1.70 (m), 1.50-1.56 (m), 1.38-1.49 (m), 1.15-1.36 (m), 1.08-1.14 (m), 1.03-1.07 (m), 0.90-1.02 (m), 0.83-0.90 (m), 0.73-0.80 (m), 0.70-0.73 (m).

Step 2B

Synthesis of (2R)—N-[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]-2-methylpiperidine-2-carboxamide, formic acid salt. (#190)

According to the general procedure C, from #189 (20 mg, 0.022 mmol, 1 eq.), dichloromethane (0.1 mL), acetonitrile (0.1 mL) and 4M solution of hydrochloric acid in dioxane (0.26 mL) was synthesized the crude desired material, which was purified by reverse phase chromatography (Method N*) to obtain #190 (13.2 mg, 73%) HPLC (Protocol T): m/z 783.7 [M+H$^+$], retention time=2.5 minutes (purity=100%). $^1$H NMR (400 MHz, DMSO-d$_6$), δ 8.83-8.86 (m), 8.60-8.62 (m), 8.24-8.27 (m), 7.83-7.89 (m), 7.78-7.80 (m), 7.75-7.77 (m), 7.64-7.66 (m), 7.60-7.63 (m), 7.20-7.31 (m), 7.13-7.19 (m), 5.49-5.55 (m), 5.36-5.42 (m), 4.65-4.74 (m), 4.60-4.65 (m), 4.50-4.56 (m), 3.95-4.01 (m), 3.76-3.81 (m), 3.53-3.62 (m), 3.47-3.52 (m), 3.22-3.45 (m), 3.14-3.21 (m), 2.97-3.05 (m), 2.93-2.96 (m), 2.79-2.86 (m), 2.76-2.78 (m), 2.65-2.68 (m), 2.48-2.56 (m), 2.37-2.43 (m), 2.29-2.35 (m), 2.17-2.27 (m), 2.04-2.11 (m), 1.93-2.00 (m), 1.70-1.85 (m), 1.53-1.69 (m), 1.36-1.48 (m), 1.28-1.36 (m), 1.13-1.26 (m), 1.08-1.12 (m), 0.98-1.07 (m), 0.91-0.97 (m), 0.84-0.91 (m), 0.73-0.78 (m).

Step 2C

Synthesis of N~2~-{[(3R)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, trifluoroacetic acid salt. (#192)

According to the general procedure C, from #191 (10 mg, 0.011 mmol, 1 eq.), dichloromethane (0.1 mL), acetonitrile (0.1 mL) and 4M solution of hydrochloric acid in dioxane (0.13 mL) was synthesized the crude desired material, which was purified by reverse phase chromatography (Method M*) to obtain #192 (5.1 mg, 60%) HPLC (Protocol T): m/z 773.5 [M+H$^+$], retention time=2.43 minutes (purity=100%). $^1$H NMR (400 MHz, DMSO-d$_6$) δ 9.32-9.44 (m), 9.17-9.21 (m), 8.91 (d), 8.63-8.69 (m), 8.38-8.43 (m), 8.22-8.27 (m), 7.80 (dd), 7.66 (dd), 7.14-7.33 (m), 5.49-5.57 (m), 5.37-5.45 (m), 4.10-4.78 (m), 3.97-4.06 (m), 3.77-3.83 (m), 3.33-3.65 (m), 3.15-3.29 (m), 2.95-3.09 (m), 2.82-2.83 (m), 2.67-2.71 (m), 2.55-2.57 (m), 2.32-2.54 (m), 2.10-2.31 (m), 2.09 (s), 1.72-1.90 (m), 1.57-1.72 (m). 1.38-1.50 (m), 1.15-1.38 (m), 1.09 (dd), 0.85-1.0 (m), 0.75-0.83 (m).

Step 2D

Synthesis of N~2~-{[(3S)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide , trifluoroacetic acid salt. (#194)

According to the general procedure C, from #193 (10 mg, 0.011 mmol, 1 eq.), dichloromethane (0.1 mL), acetonitrile (0.1 mL) and 4M solution of hydrochloric acid in dioxane (0.13 mL) was synthesized the crude desired material, which was purified by reverse phase chromatography (Method M*) to obtain #194 (9 mg, 93%) HPLC (Protocol T): m/z 773.8 [M+H$^+$], retention time=2.42 minutes (purity=100%). $^1$H NMR (400 MHz, DMSO-d$_6$) δ 9.39-9.52 (m), 9.21-9.35 (m), 8.90 (d), 8.63-8.69 (m), 8.42-8.48 (m), 8.29-8.34 (m), 7.80 (dd), 7.66 (dd), 7.22-7.33 (m), 7.13-7.21 (m), 5.47-5.57 (m), 5.36-5.44 (m), 4.43-4.93 (m), 3.97-4.05 (m), 3.64-3.83 (m), 3.32-3.61 (m), 3.15-3.29 (m), 3.06-3.09 (m), 2.95-3.05 (m), 2.89-2.95 (m), 2.82-2.84 (m), 2.67-2.72 (m), 2.54-2.56 (m), 2.48-2.53 (m), 2.28-2.48 (m), 2.11-2.28 (m), 2.09 (s), 1.57-1.72 (m), 1.38-1.47 (m), 1.15-1.37 (m), 1.09 (dd), 0.85-0.99 (m), 0.78 (t).

Preparation of 1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, formate salt (#200) and 1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, formate salt (#201)

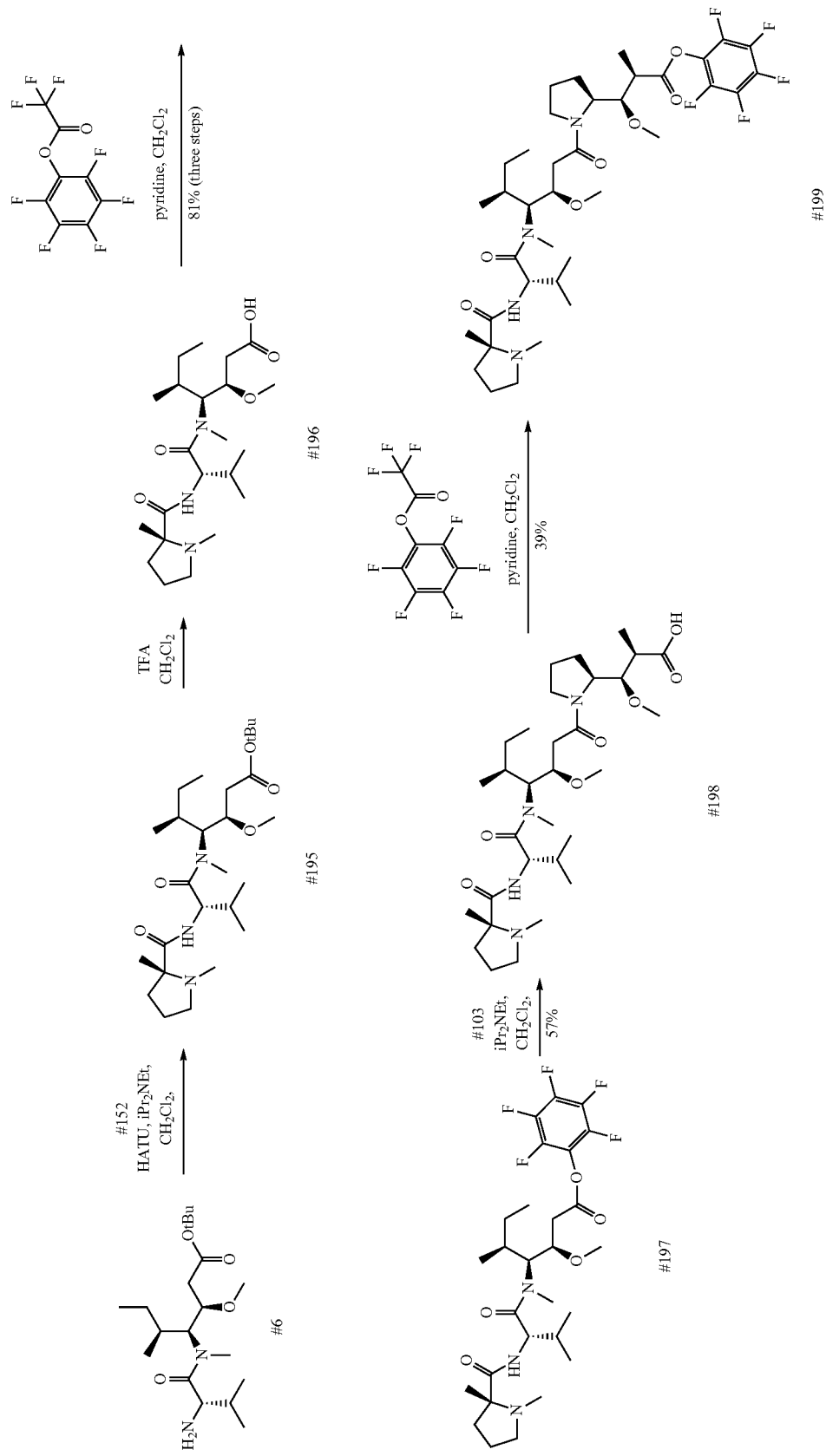

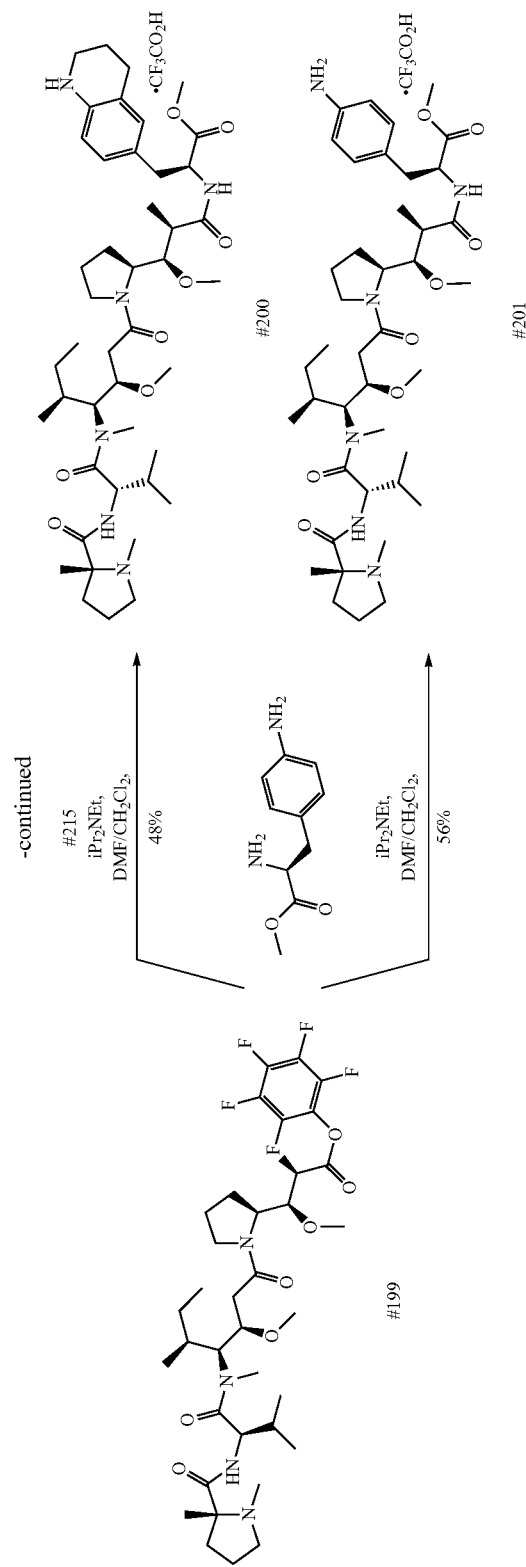

Step 1

Synthesis of 1,2-dimethyl-D-prolyl-N-[(3R,4S,5S)-1-tert-butoxy-3-methoxy-5-methyl-1-oxoheptan-4-yl]-N-methyl-L-valinamide (#195)

According to the general procedure D, from #6 (7.75 g, 21.6 mmol, 1 eq.), #152 (3.88 g, 21.6 mmol, 1 eq.), dichloromethane (100 mL), HATU (9.8 g, 25.9 mmol, 1.2 eq.), and diisopropylethylamine (11.1 g, 86.4 mmol, 4 eq.) was synthesized the crude desired material, which was purified by silica gel chromatography (Gradient: 20 to 55% ethyl acetate in petroleum ether) to afford #195 (11.1 g, quantitative yield) as a yellow oil.

Step 2

Synthesis of 1,2-dimethyl-D-prolyl-N-[(2R,3S,4S)-1-carboxy-2-methoxy-4-methylhexan-3-yl]-N-methyl-L-valinamide (#196)

According to the general procedure B, from #195 (11.1 g, 21.6 mmol, 1 eq.), dichloromethane (100 mL) and trifluoroacetic acid (40 mL) was synthesized the crude desired material, to obtain #196 (10.1 g, quantitative yield) which was used in the next step without further purification. LC-MS (Protocol Z): m/z 428.5 [M+H$^+$], retention time=0.9 minutes.

Step 3

Synthesis of 1,2-dimethyl-D-prolyl-N-[(3R,4S,5S)-3-methoxy-5-methyl-1-oxo-1-(pentafluorophenoxy)heptan-4-yl]-N-methyl-L-valinamide (#197)

To a cooled solution (0° C.) of #196 (4.0 g, 9.4 mmol, 1 eq.) in dichloromethane (40 mL) was added dropwise pyridine (2.95 g, 37.6 mmol, 4 eq.) followed by a solution of pentafluorophenyl trifluoroacetate (3.9 g, 13.6 mmol, 1.4 eq.) in dichloromethane (5 mL). The mixture was stirred at room temperature for one hour, and the solvent was concentrated in vacuo. The residue was purified by silica gel chromatography (Gradient: 1 to 10% methanol in dichloromethane) to afford compound #197 (4.5 g, 81.2% (over three steps) as white solid.

Step 4

Synthesis of 1,2-dimethyl-D-prolyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide, trifluoroacetic acid salt (#198)

To a cooled solution (0° C.) of #197 (4.0 g, 7.4 mmol, 1 eq.) in dichloromethane (25 mL) was added dropwise diisopropylethylamine (3.4 g, 26.3 mmol, 3.5 eq.) followed by a solution #103 (2.3 g, 7.6 mmol, 1.02 eq.) in dichloromethane (15 mL). After the addition, the mixture was stirred at room temperature for 16 hours and the solvent was removed in vacuo. The residue was purified by silica gel chromatography (Gradient: 1 to 10% methanol in dichloromethane) followed by a second purification by reverse phase chromatography (Method Q) to give #198 (1.57 g, 57.5%) as white solid HPLC (Protocol X): m/z 597.49 [M+H$^+$] retention time=8.879 minutes (purity=98%). Chiral HPLC retention time: 3.328 min (purity=98%) Column: Column: Chiralcel OJ-H, 250×4.6 mm, 5 μm; Mobile phase: methanol (0.05% diethylamine) in $CO_2$ from 5% to 40% over 15 minutes; Flow rate: 2.35 mL/minute.

Step 5

Synthesis of 1,2-dimethyl-D-prolyl-N-[(3R,4S, 5S)-3-methoxy-1-{(2S)-2-[(1R,2R)-1-methoxy-2-methyl-3-oxo-3-(p entafluorophenoxy)propyl]pyrrolidin-1-yl}-5-methyl-1-oxoheptan-4-yl]-N-methyl-L-valinamide (#199)

To a solution of #198 (280 mg, 0.394 mmol, 1 eq.) in dichloromethane (2 mL) was added pyridine (75 mg, 0.94 mmol, 2.4 eq.) followed by a solution of pentafluorophenyl trifluoroacetate (268 mg, 0.94 mmol, 2.4 eq.) in dichloromethane (1.5 mL). The mixture was stirred at room temperature for 2.5 hours, and the solvent was concentrated in vacuo. The residue was purified by silica gel chromatography (Gradient: 1 to 10% methanol in dichloromethane) to afford compound #199 (279 mg, 39%) as white solid. LC-MS (Protocol Q1): m/z 763.5 [M+H$^+$], retention time=0.93 minutes.

Step 6A

Synthesis of 1,2-dimethyl-D-prolyl-N-[(3R,4S,5S)-3-methoxy-1-{(2S)-2-[(1R,2R)-1-methoxy-3-{[(2S)-1-methoxy-1-oxo-3-(1,2,3,4-tetrahydroquinolin-6-yl)propan-2-yl]amino}-2-methyl-3-oxopropyl]pyrrolidin-1-yl}-5-methyl-1-oxoheptan-4-yl]-N-methyl-L-valinamide, trifluoroacetic acid salt (#200)

To a mixture of #199 (25 mg, 0.033 mmol, 1 eq) and #215 ((7.7 mg, 0.033 mmol, 1 eq.) in dichloromethane (1.5 mL), N,N-diisopropylethylamine (30.2 mg, 2.31 mmol, 7 eq.) was added. The reaction was stirred for 5 minutes and N,N-dimethylformamide (0.5 mL) was added. After stirring for 2½ hours, additional N,N-diisopropylethylamine (30.2 mg, 2.31 mmol, 7 eq.) was added. After 3½ hours, more N,N-dimethylformamide (0.75 mL) was added and the mixture stirred for 18 hours. Additional N,N-diisopropylethylamine (15.1 mg, 1.15 mmol, 3.6 eq.) and N,N-dimethylformamide (0.25 mL) were added and reaction stirred at room temperature for 48 hours. The reaction mixture was concentrated in vacuo and the crude product was purified by reverse phase chromatography (Method M*) to give #200 (12.9 mg, 48%). HPLC (Protocol T): m/z HPLC (Protocol 7): m/z 407.7, double charge [2+], retention time=1.69 minutes (purity=100%). $^1$H NMR (400 MHz, DMSO-d$_6$) δ 9.72-9.82 (m), 8.61-8.67 (m), 8.42-8.48 (m), 8.19-8.24 (m), 7.25-7.27 (m), 7.12-7.14 (m), 6.94-7.01 (m), 6.88-6.94 (m), 6.78-6.84 (m), 6.67-6.74 (m), 6.57-6.64 (m), 4.69-4.77 (m), 4.60-4.68 (m), 4.53-4.60 (m), 4.46-4.53 (m), 4.37-4.45 (m), 3.97-4.05 (m), 3.76-3.81 (m), 3.62-3.67 (m), 3.53-3.62 (m), 3.44-3.52 (m), 3.32-3.38 (m), 3.27-3.32 (m), 3.22-3.27 (m), 3.15-3.22 (m), 3.06-3.14 (m), 2.97-3.01 (m), 2.92-2.96 (m), 2.74-2.83 (m), 2.61-2.74 (m), 2.57-2.61 (m), 2.48-2.56 (m), 2.37-2.46 (m), 2.25-2.36 (m), 2.00-2.20 (m), 1.67-1.91 (m), 1.47-1.60 (m), 1.37-1.47 (m), 1.24-1.35 (m), 1.03-1.10 (m), 0.95-1.00 (m), 0.88-0.94 (m), 0.76-0.83 (m).

Step 6B

Synthesis of 1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#201)

To a mixture of #199 (25 mg, 0.033 mmol, 1 eq) and the commercially available methyl4-amino-L-phenylalaninate (8.8 mg, 0.033 mmol, 1 eq.) in dichloromethane (1.5 mL), N,N-diisopropylethylamine (30.2 mg, 2.31 mmol, 7 eq.) was added. The reaction was stirred for 5 minutes and N,N-dimethylformamide (0.5 mL) was added. After 4 hours, additional N,N-diisopropylethylamine (37.75 mg, 2.88 mmol, 8.25 eq.) was added and the mixture stirred for 50 minutes. Additional N,N-dimethylformamide (0.75 mL) was added and the reaction was stirred for 66 hours, concentrated in vacuo and the crude product was purified by reverse phase chromatography (Method M*) to give #201 (14.3 mg, 56%); HPLC (Protocol T): m/z 387.2, double charge [2+], retention time=1.50 minutes (purity=100%); $^1$H NMR (400 MHz, DMSO-$d_6$) δ 9.68-9.84 (m), 8.57-8.66 (m), 8.46-8.51 (m), 8.23-8.29 (m), 7.18-7.28 (m), 7.11-7.16 (m), 7.03-7.08 (m), 6.97-7.02 (m), 4.67-4.75 (m), 4.58-4.66 (m), 4.34-4.57 (m), 3.95-4.03 (m), 3.85-3.90 (m), 3.73-3.81 (m), 3.66-3.72 (m), 3.57-3.66 (m), 3.50-3.57 (m), 3.42-3.49 (m), 3.32-3.38 (m), 3.14-3.30 (m), 2.95-3.11 (m), 2.84-2.94 (m), 2.78-2.81 (m), 2.63-2.74 (m), 2.46-2.57 (m), 2.34-2.45 (m), 2.19-2.34 (m), 1.97-2.19 (m), 1.67-1.90 (m), 1.45-1.62 (m), 1.34-1.41 (m), 1.21-1.34 (m), 1.01-1.10 (m), 0.82-0.99 (m), 0.72-0.81 (m).

Preparation of 1,2-dimethyl-L-prolyl-N-[(3R,4S,5S)-3-methoxy-1-{(2S)-2-[(1R,2R)-1-methoxy-3-{[(2S)-1-methoxy-1-oxo-3-(1,2,3,4-tetrahydroquinolin-6-yl)propan-2-yl]amino}-2-methyl-3-oxopropyl]pyrrolidin-1-yl}-5-methyl-1-oxoheptan-4-yl]-N-methyl-L-valinamide, formate salt. (#207) and 1,2-dimethyl-L-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide formate salt (#208) and 1,2-dimethyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt (#209)

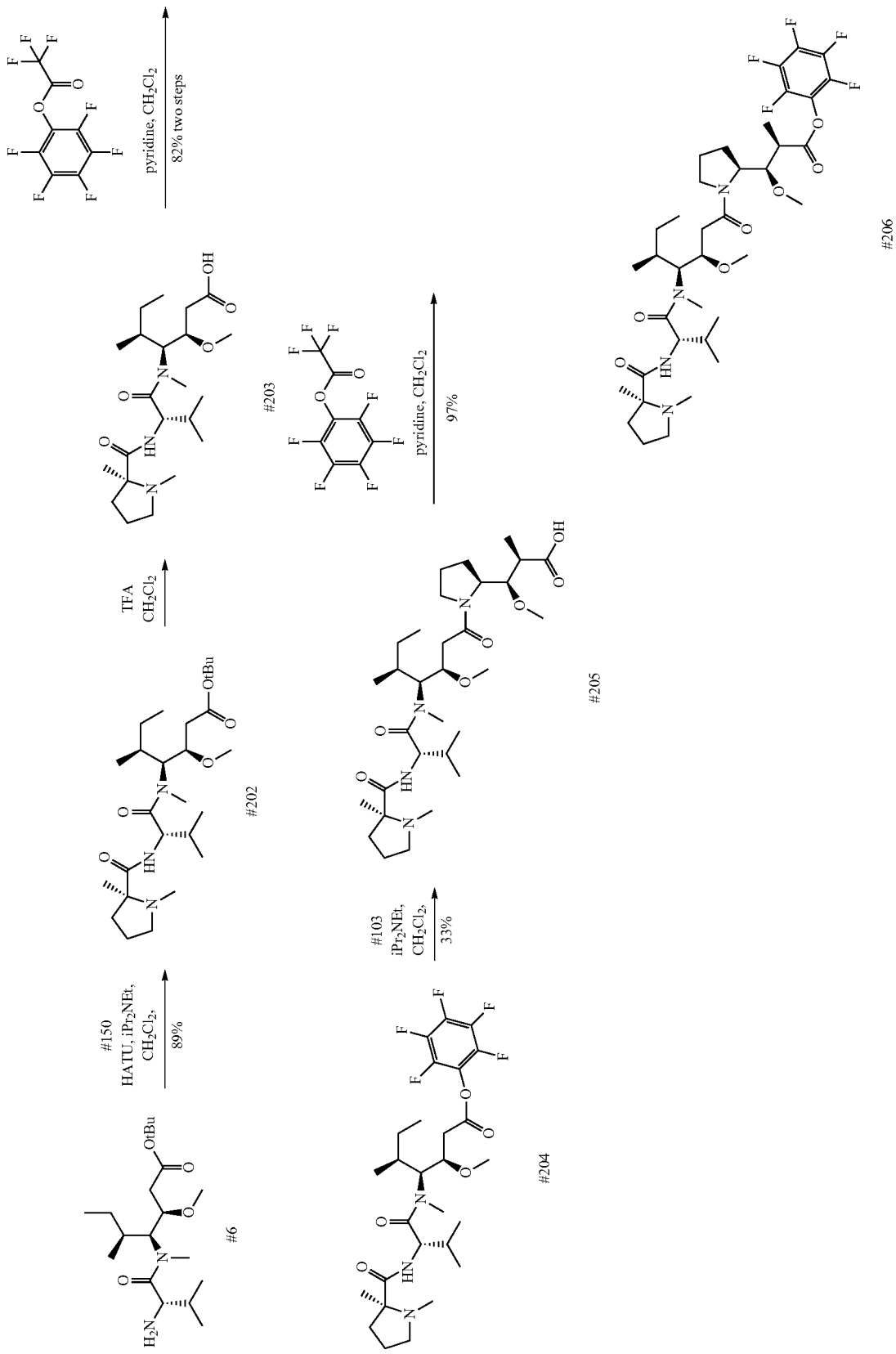

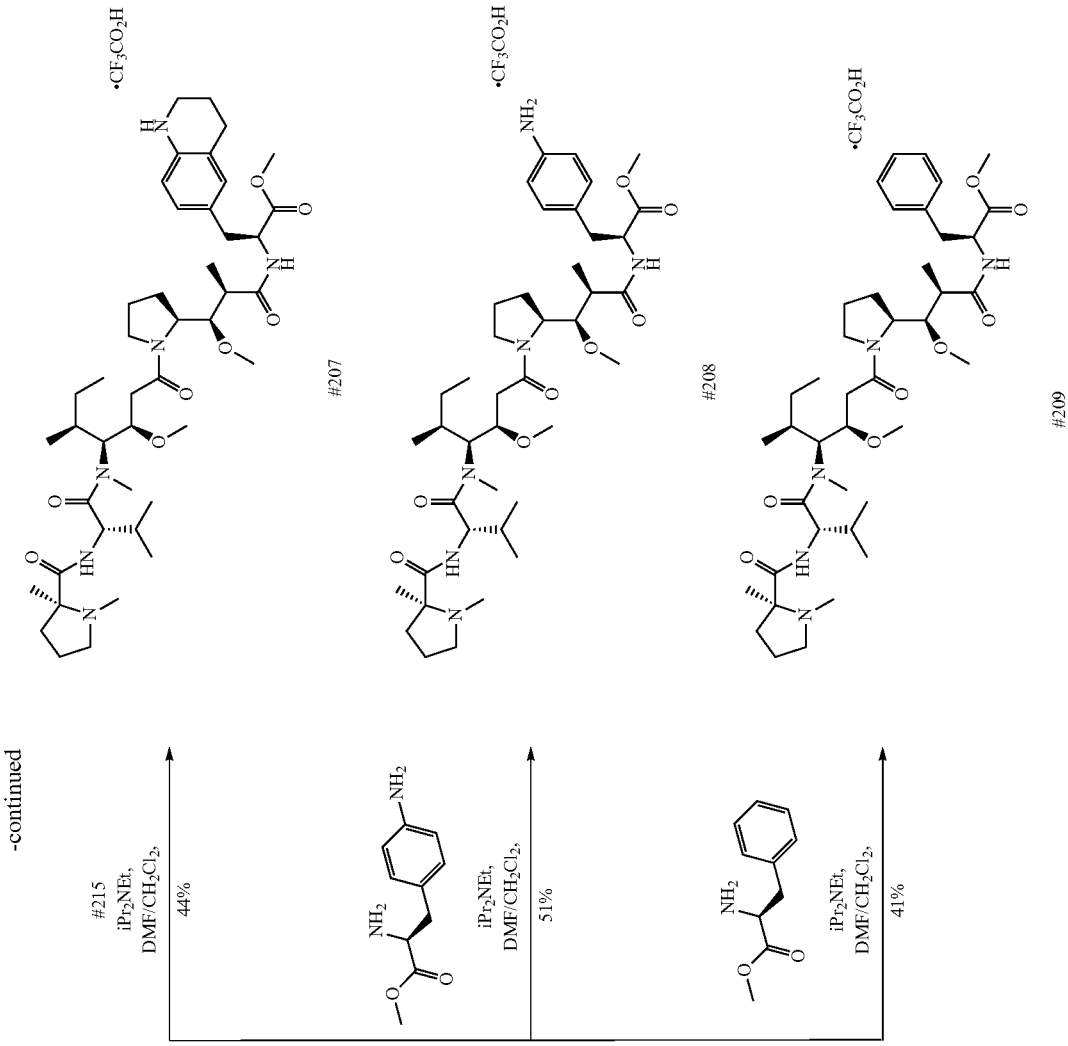
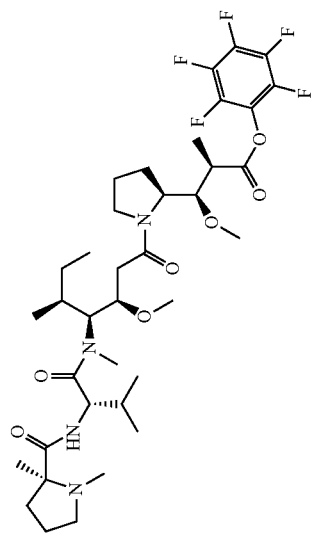

Step 1

Synthesis of 1,2-dimethyl-L-prolyl-N-[(3R,4S,5S)-1-tert-butoxy-3-methoxy-5-methyl-1-oxoheptan-4-yl]-N-methyl-L-valinamide (#202)

According to the general procedure D, from #6 (4.3 g, 12 mmol, 1 eq.), #150 (2.15 g, 12 mmol, 1 eq.), dichloromethane (50 mL), HATU (5.46 g, 14 mmol, 1.2 eq.), and diisopropylethylamine (8.17 mL) was synthesized the crude desired material, which was purified by silica gel chromatography (Gradient: 20 to 55% ethyl acetate in petroleum ether) to afford #202 (5.2 g, 89%) as a yellow oil. 1

Step 2

Synthesis of 1,2-dimethyl-L-prolyl-N-[(2R,3S,4S)-1-carboxy-2-methoxy-4-methylhexan-3-yl]-N-methyl-L-valinamide (#203)

According to the general procedure B, from #202 (5.2 g, 10.77 mmol, 1 eq.), dichloromethane (45 mL), and trifluoroacetic acid (20 mL) was synthesized the crude desired material, to obtain #203 (7 g, quantitative yield) which was used in the next step without further purification.

Step 3

Synthesis of 1,2-dimethyl-L-prolyl-N-[(3R,4S,5S)-3-methoxy-5-methyl-1-oxo-1-(pentafluorophenoxy)heptan-4-yl]-N-methyl-L-valinamide (#204)

To a cooled solution (0° C.) of #203 (7.0 g, 10.77 mmol, 1 eq.) in dichloromethane (15 mL) was added dropwise pyridine (3.41 g 43.08 mmol, 4 eq.) followed by a solution of pentafluorophenyl trifluoroacetate (6.03 g, 21.54 mmol, 2 eq.) in dichloromethane (7 mL). The mixture was stirred at room temperature for one hour, and the solvent was concentrated in vacuo. The residue was purified by silica gel chromatography (Gradient: 1 to 10% methanol in dichloromethane) to afford compound #204 (8 g, 82% over two steps) as yellow solid.

Step 4

Synthesis of 1,2-dimethyl-L-prolyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (#205)

To a cooled solution (0° C.) of #204 (8.0 g, 10.77 mmol, 1 eq.) in dichloromethane (25 mL) was added dropwise diisopropylethylamine (5.6 g, 43.08 mmol, 4 eq.) followed by a solution of #103 (3.22 g, 10.77 mmol, 1 eq.) in dichloromethane (15 mL). After the addition, the mixture was stirred at room temperature for 16 hours and the solvent was removed in vacuo. The residue was purified by silica gel chromatography (Gradient: 1 to 10% methanol in dichloromethane) to give #205 (2.2 g, 33%) as a yellow solid HPLC (Protocol X): m/z 597.42 [M+H$^+$], retention time=8.729 minutes (purity >97%), Chiral HPLC retention time: 2.87 min (purity=89%) Column. Chiralcel OD-3, 150×4.6 mm, 3 nm; Mobile phase: ethanol (0.05% diethylamine) in CO$_2$ from 5% to 40% over 12 minutes; Flow rate: 2.5 mL/minute.

Step 5

Synthesis of 1,2-dimethyl-L-prolyl-N-[(3R,4S,5S)-3-methoxy-1-{(2S)-2-[(1R,2R)-1-methoxy-2-methyl-3-oxo-3-(pentafluorophenoxy)propyl]pyrrolidin-1-yl}-5-methyl-1-oxoheptan-4-yl]-N-methyl-L-valinamide (#206)

To a solution of #198 (0.28 g, 0.47 mmol, 1 eq.) in dichloromethane (2 mL) was added pyridine (75 mg, 0.94 mmol, 2 eq.) followed by a solution of pentafluorophenyl trifluoroacetate (268 mg, 0.94 mmol, 2 eq.) in dichloromethane (1.5 mL). The mixture was stirred at room temperature for 2.5 hours, and the solvent was concentrated in vacuo. The residue was purified by silica gel chromatography (Gradient: 1 to 10% methanol in dichloromethane) to afford compound #206 (348 mg, 97%) as white solid. LC-MS (protocol Q1): m/z 763.5 [M+H$^+$], retention time=0.9 minutes.

Step 6A

Synthesis of 1,2-dimethyl-L-prolyl-N-[(3R,4S,5S)-3-methoxy-1-{(2S)-2-[(1R,2R)-1-methoxy-3-{[(2S)-1-methoxy-1-oxo-3-(1,2,3,4-tetrahydroquinolin-6-yl)propan-2-yl]amino}-2-methyl-3-oxopropyl]pyrrolidin-1-yl}-5-methyl-1-oxoheptan-4-yl]-N-methyl-L-valinamide, trifluoroacetic acid salt. (#207)

The title compound was prepared from #206 (25 mg, 0.033 mmol, 1 eq.) and #215 (7.7 mg, 0.033 mmol, 1 eq) using the method described above for preparation of #200. The crude product was purified by reverse phase chromatography (Method M*) to give #207 (11.7 mg, 44%). HPLC (Protocol T): m/z 407.6, double charge [2+], retention time=1.59 minutes (purity=100%). $^1$H NMR (DMSO-d$_6$) δ 9.57-9.69 (m), 8.68-8.76 (m), 8.42-8.47 (m), 8.23-8.29 (m), 8.18-8.23 (m), 7.24-7.27 (m), 6.95-7.01 (m), 6.89-6.94 (m), 6.80-6.86 (m), 6.70-6.78 (m), 6.60-6.67 (m), 4.69-4.77 (m), 4.60-4.68 (m), 4.46-4.60 (m), 4.34-4.46 (m), 3.95-4.03 (m), 3.87-3.91 (m), 3.79-3.85 (m), 3.74-3.79 (m), 3.60-3.66 (m), 3.49-3.60 (m), 3.41-3.49 (m), 3.12-3.35 (m), 3.04-3.12 (m), 2.89-3.04 (m), 2.68-2.83 (m), 2.61-2.67 (m), 2.45-2.55 (m), 2.34-2.44 (m), 2.08-2.33 (m), 2.05-2.08 (m), 1.92-2.05 (m), 1.75-1.91 (m), 1.65-1.75 (m), 1.59-1.64 (m), 1.34-1.58 (m), 1.20-1.31 (m), 1.01-1.09 (m), 0.94-0.99 (m), 0.84-0.93 (m), 0.80-0.83 (m), 0.72-0.80 (m).

Step 6B

Synthesis of 1,2-dimethyl-L-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (#208)

To a mixture of #206 (25.0 mg, 0.033 mmol, 1 eq.), and the commercially available methyl4-amino-L-phenylalaninate (8.8 mg, 0.033 mmol, 1 eq.) in dichloromethane (1.5 mL), N,N-diisopropylethylamine (30.2 mg, 2.31 mmol, 7 eq.) was added.

The reaction was stirred for 5 minutes and N,N-dimethylformamide (0.5 mL) was added. After 2½ hours, additional N,N-diisopropylethylamine (30.2 mg, 2.31 mmol, 7 eq.) was added. After stirring for 3½ hours, additional N,N-dimethylformamide (0.75 mL) was added and The reaction was stirred for 66 hours, concentrated in vacuo and the crude product was purified by reverse phase chromatography (Method M*) to give #208 (13 mg, 51%); HPLC (Protocol T): m/z 387.2, double charge [2+], retention time=1.58 minutes (purity=100%); $^1$H NMR (400 MHz, DMSO-$d_6$) δ 9.54-9.69 (m), 8.68-8.75 (m), 8.46-8.50 (m), 8.33-8.37 (m), 8.22-8.31 (m), 8.09-8.14 (m), 7.17-7.27 (m), 7.07-7.16 (m), 6.99-7.05 (m), 6.92-6.99 (m), 4.69-4.75 (m), 4.60-4.68 (m), 4.42-4.59 (m), 4.34-4.42 (m), 3.95-4.03 (m), 3.85-3.90 (m), 3.74-3.80 (m), 3.65-3.72 (m), 3.62-3.65 (m), 3.42-3.62 (m), 3.31-3.36 (m), 3.24-3.30 (m), 3.11-3.24 (m), 3.03-3.11 (m), 2.96-3.03 (m), 2.81-2.92 (m), 2.65-2.76 (m), 2.43-2.55 (m), 2.34-2.43 (m), 2.06-2.33 (m), 1.93-2.05 (m), 1.75-1.89 (m), 1.66-1.74 (m), 1.58-1.65 (m), 1.47-1.57 (m), 1.34-1.43 (m), 1.20-1.32 (m), 1.10-1.14 (m), 1.00-1.09 (m), 0.83-0.99 (m), 0.72-0.81 (m).

Step 6C

Synthesis of 1,2-dimethyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt (#209)

The title compound was prepared from #206 (25.0 mg, 0.033 mmol, 1 eq.) and methyl -L-phenylalaninate hydrochloride (7.1 mg, 0.033 mmol, 1 eq.) using the method described above for preparation of #200. The crude product was purified by reverse phase chromatography (Method M*) to give #209 (10.3 mg, 41%). HPLC (Protocol T): m/z 758.7 [M+H$^+$], retention time=1.787 minutes (purity=100%). $^1$H NMR (DMSO-$d_6$) δ 9.57-9.70 (m), 8.70-8.75 (m), 8.50-8.56 (m), 8.32-8.42 (m), 8.24-8.26 (m), 8.10-8.15 (m), 7.14-7.27 (m), 7.12-7.13 (m), 6.98-7.00 (m), 4.69-4.77 (m), 4.55-4.67 (m), 4.43-4.53 (m), 3.94-4.02 (m), 3.73-3.78 (m), 3.62-3.68 (m), 3.48-3.60 (m), 3.39-3.48 (m), 3.23-3.33 (m), 3.13-3.22 (m), 3.08-3.13 (m), 3.02-3.08 (m), 2.96-3.01 (m), 2.81-2.94 (m), 2.76-2.80 (m), 2.66-2.75 (m), 2.62-2.66 (m), 2.46-2.55 (m), 2.31-2.45 (m), 2.09-2.29 (m), 2.05-2.09 (m), 1.93-2.04 (m), 1.74-1.88 (m), 1.65-1.74 (m), 1.59-1.65 (m), 1.36-1.52 (m), 1.21-1.35 (m), 1.01-1.08 (m), 0.94-1.00 (m), 0.83-0.94 (m), 0.73-0.81 (m).

Preparation of methyl (2S)-2-amino-3-(1,2,3,4-tetrahydroquinolin-6-yl)propanoate

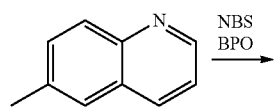

Step 1

Synthesis of 6-(bromomethyl)quinoline (#210)

A solution of 6-methylquinoline (5 g, 35 mmol, 1 eq.), N-Bromosuccinimide (8.1 g, 45.5 mmol, 1.3 eq.) and benzoyl peroxide (840 mg, 3.5 mmol, 0.1 eq.) in carbon tetrachloride (100 mL) was stirred at reflux for 3 hours and then cooled to room temperature. The reaction mixture was filtered and the filtrate was concentrated in vacuo. The residue was dissolved in tetrahydrofuran (100 mL) and filtered. The filtrate was directly used in the next step without further purification Step 2

Synthesis of 6-{[(2S,5R)-3,6-dimethoxy-5-(propan-2-yl)-2,5-dihydropyrazin-2-yl]methyl}quinoline (#211)

To a cooled solution (−70° C.) of (2R)-3,6-dimethoxy-2-(propan-2-yl)-2,5-dihydropyrazine (25.8 g, 140 mmol, 2 eq.) in tetrahydrofuran (200 mL) was added dropwise n-butyllithium (2.5 M, 64.4 mL, 161 mmol 2.3 eq.) and then stirred for 30 minutes. A solution of #210 (15.4 g, 70 mmol, 1 eq.) in tetrahydrofuran (150 mL) was added dropwise at −65° C. and then the solution was stirred for 2 hours at this temperature. The reaction was quenched by saturated aqueous ammonium chloride (100 mL) and extracted with ethyl acetate (100 mL). The organic phase was dried over sodium sulfate and concentrated in vacuo. The residue was purified by silica column chromatography (Gradient: 10 to 16% ethyl acetate in petroleum ether) to afford #211 (7.3 g, 32%, over two steps) as yellow solid. LC-MS (Protocol Z): m/z 326.2 [M+H$^+$], retention time=0.88 minutes.

Step 3

Synthesis of methyl (2S)-2-amino-3-(quinolin-6-yl)propanoate (#212)

To a solution of #211 (7.3 g, 22.5 mmol, 1 eq.) in water (25 mL) and acetonitrile (80 mL) was added trifluoroacetic acid (9 mL) at 0° C. and the solution was stirred at 10° C. overnight. The organic layer was removed in vacuo and the remaining aqueous layer was basified to pH 9 with sodium carbonate, which was directly used for the next step.

Step 4

Synthesis of methyl (2S)-2-[(tert-butoxycarbonyl)amino]-3-(quinolin-6-yl)propanoate (#213)

To a solution #212 (5.2 g, 22.5 mmol, 1 eq.) and triethylamine (9.1 g, 90 mmol, 4 eq.) in mixed solvent of methanol (30 mL) and water (50 mL) was added di-tert-butyl dicarbonate (17.5 g, 78.75 mmol, 3.5 eq.) at 0° C. and then the solution was stirred at 10° C. overnight. The reaction mixture was filtered and the filter cake was washed with methanol (20 mL×2). The filtrate was extracted with ethyl acetate (50 mL×2) and the organic phase was concentrated in vacuo. The residue was purified by silica column chromatography (Gradient: 25 to 50% ethyl acetate in petroleum ether) to afford #213 (5.5 g, 74% over two steps) as yellow oil. LC-MS (Protocol Z): m/z 331.2 [M+H$^+$], retention time=0.76 minutes.

Step 5

Synthesis of methyl (2S)-2-[(tert-butoxycarbonyl)amino]-3-(1,2,3,4-tetrahydroquinolin-6-yl)propanoate (#214)

A suspension of #213 (1.5 g, 4.55 mmol, 1 eq.) and palladium on carbon (150 mg) in ethanol (20 mL) was stirred at 50° C. under 30 psi of hydrogen overnight. The reaction mixture was filtered through a pad of celite and the filtrate was concentrated in vacuo. The residue was purified by silica column chromatography (Gradient: 40% ethyl acetate in petroleum ether) to afford #214 (1.2 g, 80%) as an oil. $^1$H NMR (400 MHz, CDCl$_3$): δ 6.70 (d, 2H), 6.40 (m, 1H), 4.95 (m, 1H), 4.49 (m, 1H), 3.77 (s, 3H), 3.28 (m, 2H), 2.97 (m, 2H), 2.71 (m, 2H), 1.95 (m, 2H), 1.26 (s, 9H), HPLC (Protocol Y): m/z 357.0 [M+Na$^+$] retention time=5.304 minutes (purity >98%). Chiral HPLC retention time: 4.64 min (purity=98%)(Column: Chiralcel OJ-H, 150×4.6 mm, 5 μm; Mobile phase: ethanol (0.05% diethylamine) in CO$_2$ from 5% to 40% over 15 minutes; Flow rate: 2.5 mL/minute.

Step 6

Synthesis of methyl (2S)-2-amino-3-(1,2,3,4-tetrahydroquinolin-6-yl)propanoate (#215)

To a solution of #214 (750 mg, 2.25 mmol, 1 eq.) in dichloromethane (20 mL) was added dropwise trifluoracetic acid (2 mL) at 0° C. and then the solution was stirred at 20° C. overnight. The reaction mixture was concentrated in vacuo and the residue was dissolved in water (20 mL). The solution was basified with sodium carbonate and extracted with ethyl acetate/tetrahydrofuran (30 mL×3). The organic phase was dried over sodium sulfate and concentrated in vacuo to afford #215 (450 mg, 85%) as a yellow oil. $^1$H NMR (400 MHz, CDCl$_3$): δ 6.70 (d, 2H), 6.40 (m, 1H), 3.73 (s, 3H), 3.67 (m, 1H), 3.30 (m, 2H), 2.96 (m, 1H), 2.75 (m, 3H), 1.96 (m, 2H), 1.50 (br, 2H), 1.26 (br, 1H), HPLC (Protocol Y): m/z 235.14 [M+H$^+$] retention time=4.35 minutes (purity >96%). Chiral HPLC retention time: 5.71 min (purity=98%). (Column: Chiralcel OJ-H, 150×4.6 mm, 5 μm; Mobile phase: ethanol (0.05% diethylamine) in CO$_2$ from 5% to 40% over 15 minutes; Flow rate: 2.5 mL/minute.

Preparation of N-{(2R,3R)-3-[(2S)-1-{(3R,4S,5S)-4-[(N-{[(3R)-3-fluoropyrrolidin-3-yl]carbonyl}-L-valyl)(methyl)anaino]-3-methoxy-5-methylheptanoyl}pyrrolidin-2-yl]-3-methoxy-2-methylpropanoyl}-L-phenylalanine, trifluoroacetic acid salt (#217) and N-{(2R,3R)-3-[(2S)-1-{(3R,4S,5S)-4-[(N-{[(3S)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine, trifluoroacetic acid salt (#219)

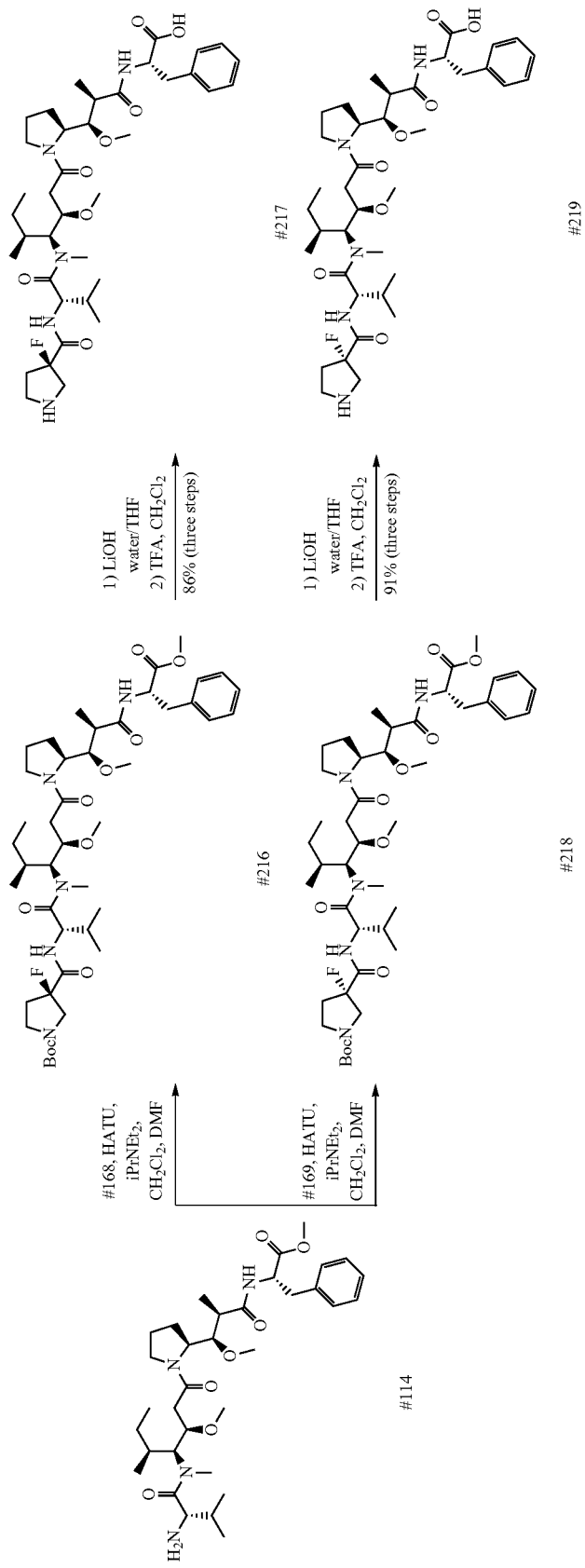

Step 1A

Synthesis of methyl N-{(2R,3R)-3-[(2S)-1-{(3R,4S,5S)-4-[(N-{[(3R)-1-(tert-butoxycarbonyl)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate (#216)

To a solution of #168 (36.9 mg, 0.158 mmol, 1 eq.) and #114 (100 mg, 0.158 mmol, 1 eq.) in dichloromethane (3.6 mL) and N,N-dimethylformamide (0.8 mL), was added diisopropylethylamine (0.083 mL, 0.474 mmol, 3 eq.) followed by HATU (60.7 mg, 0.158 mmol, 1 eq.). The reaction was allowed to stir at room temperature for 18 hours, diluted with ethyl acetate (25 mL), washed with water (1×), 10% citric acid (1×) and brine (1×). The organic layer was dried over sodium sulfate, filtered, and the filtrate concentrated in vacuo to give crude #216 (220 mg, 164% of theory) which was used in next step without further purification. HPLC (protocol Q): m/z 848.6 [M+H$^+$], retention time=2.10 minutes.

Step 1B

Synthesis of methyl N-{(2R,3R)-3-[(2S)-1-{(3R,4S,5S)-4-[(N-{[(3S)-1-(tert-butoxycarbonyl)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalaninate (#218)

To a solution of #169 (36.9 mg, 0.158 mmol, 1 eq.) and #114 (100 mg, 0.158 mmol, 1 eq.) in dichloromethane (3.6 mL) and N,N-dimethylformamide (0.8 mL), was added diisopropylethylamine (0.083 mL, 0.474 mmol, 3 eq.) followed by HATU (60.7 mg, 0.158 mmol, 1 eq.). The reaction was allowed to stir at room temperature for 18 hours, diluted with ethyl acetate (25 mL), washed with water (1×), 10% citric acid (1×) and brine (1×). The organic layer was dried over sodium sulfate, filtered, and the filtrate concentrated in vacuo to provide crude #218 (180 mg, 134% of theory) which was used in next step without further purification. HPLC (protocol Q): m/z 848.6 [M+H$^+$], retention time=2.10 minutes.

Step 2A

Synthesis of N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine, trifluoroacetic acid salt (#217)

To a solution of crude #216 (134 mg) in tetrahydrofuran (4 mL) was added lithium hydroxide (1M, 0.5 mL). The reaction was stirred at room temperature for 18 hours and concentrated in vacuo. The residue was dissolved in dichloromethane (2 mL) and trifluoroacetic acid (2 mL) was added. The reaction was stirred for 4 hours and concentrated in vacuo. The crude material was purified by reverse phase chromatography (Method M*) to obtain #217 (60 mg, 86% over two steps) as a gum. LC-MS (protocol Q): m/z 734.93 [M+H$^+$], retention time=1.19 minutes. $^1$H NMR (DMSO-d$_6$) 12.62-12.83 (m), 9.30-9.43 (m), 9.17-9.28 (m), 8.34-8.41 (m), 8.22-8.31 (m), 8.08-8.15 (m), 7.87-7.93 (m), 7.76-7.81 (m), 7.11-7.23 (m), 4.93-4.99 (m), 4.81-4.88 (m), 4.55-4.71 (m), 4.48-4.54 (m), 4.37-4.45 (m), 3.92-3.99 (m), 3.69-3.75 (m), 3.31-3.65 (m), 3.25-3.30 (m), 3.20-3.24 (m), 3.12-3.19 (m), 3.08-3.10 (m), 2.97-3.07 (m), 2.92-2.97 (m), 2.75-2.84 (m), 2.64-2.70 (m), 2.43-2.57 (m), 2.28-2.43 (m), 2.15-2.26 (m), 2.02-2.15 (m), 1.56-1.87 (m), 1.31-1.48 (m), 1.05-1.30 (m), 0.97-1.06 (m), 0.82-0.97 (m), 0.71-0.79 (m).

Step 2B

Synthesis of N-{(2R,3R)-3-[(2S)-1-{(3R,4S,5S)-4-[(N-[(3S)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine, trifluoroacetic acid salt (#219)

To a solution of crude #218 (100 mg) in tetrahydrofuran (4 mL) was added 1.0 M lithium hydroxide in water (0.5 mL). The reaction was stirred at room temperature for 18 hours and then concentrated in vacuo. The crude material was dissolved in dichloromethane (2 mL) and trifluoroacetic acid (2 mL) was added. The reaction was stirred for 4 hours and then concentrated in vacuo. The crude material was purified by reverse phase chromatography (Method M*) to obtain #219 as a gum (60 mg, 91% over two steps). LC-MS (protocol Q): m/z 734.97 [M+H$^+$], retention time=1.14 minutes. $^1$H NMR (400 MHz, DMSO-d$_6$), δ 12.62-12.85 (m), 9.32-9.43 (m), 9.13-9.26 (m), 8.39-8.46 (m), 8.30-8.39 (m), 8.25-8.29 (m), 8.08-8.13 (m), 7.79-7.85 (m), 7.67-7.72 (m), 7.10-7.23 (m), 4.94-5.01 (m), 4.83-4.89 (m), 4.64-4.73 (m), 4.56-4.63 (m), 4.44-4.50 (m), 4.37-4.44 (m), 3.92-3.99 (m), 3.60-3.74 (m), 3.24-3.55 (m), 3.11-3.24 (m), 3.07-3.10 (m), 3.02-3.06 (m), 2.98-3.02 (m), 2.93-2.97 (m), 2.75-2.85 (m), 2.68-2.69 (m), 2.63-2.67 (m), 2.45-2.55 (m), 2.26-2.44 (m), 2.15-2.25 (m), 2.03-2.14 (m), 1.55-1.87 (m), 1.31-1.47 (m), 1.15-1.31 (m), 0.98-1.05 (m), 0.91-0.98 (m), 0.82-0.91 (m), 0.71-0.78 (m).

Preparation of 2-methylalanyl-N-{(3R,4S,5S)-1-[(2S)-2-{(3R,4R,7S)-7-benzyl-4-methyl-18-[(4S,5R)-5-methyl-2-oxoimidazolidin-4-yl]-5,8,13-trioxo-2-oxa-6,9,12-triazaoctadecan-3-yl}pyrrolidin-1-yl]-3-methoxy-5-methyl-1-oxoheptan-4-yl}-N-methyl-L-valinamide (#257)

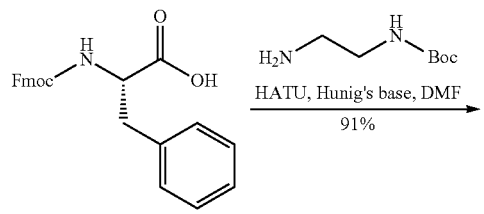

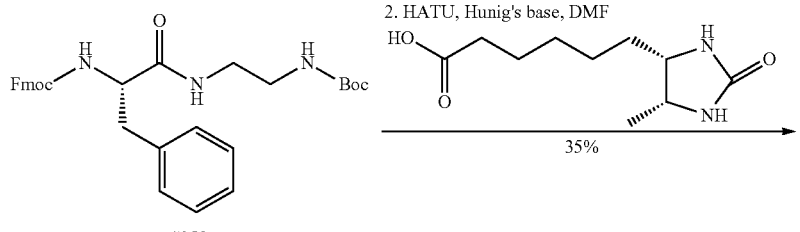

253

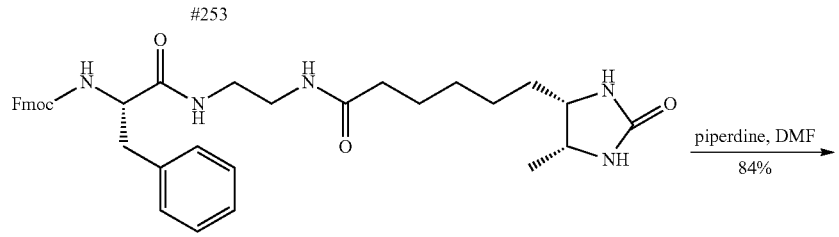

254

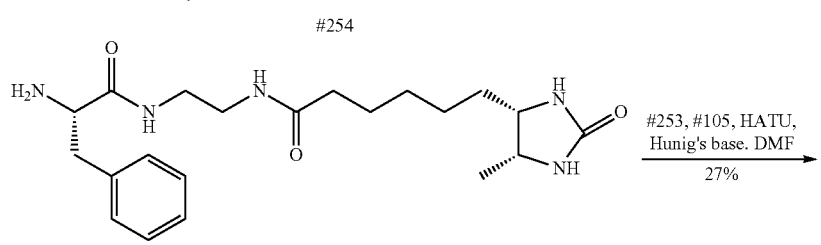

255

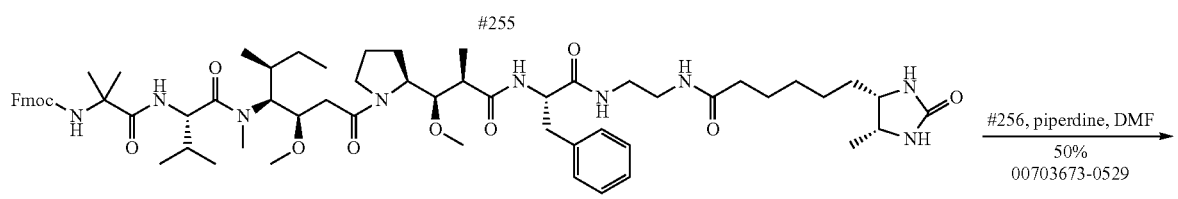

256

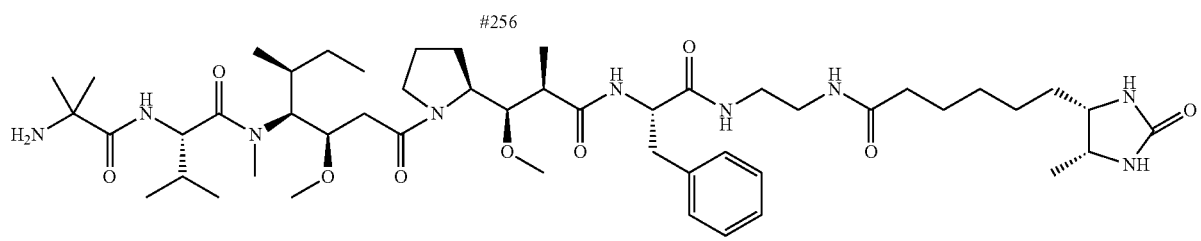

257

Step 1

Synthesis of 9H-fluoren-9-ylmethyl [(2S)-1-({2-[(tert butoxycarbonyl)amino]ethyl}amino)-1-oxo-3-phenylpropan-2-yl]carbamate (#253)

Following general procedure D using N-[(9H-fluoren-9-ylmethoxy)carbonyl]-L-phenylalanine (500 mg, 1.29 mmol, 1.0 eq), tert-butyl (2-aminoethyl)carbamate (207 mg, 1.29 mmol, 1.0 eq.), HATU (620 mg, 1.55 mmol, 1.2 eq.) and Hunig's base (0.452 mL, 2.58 mmol, 2.0 eq) in 6 mL of DMF #253 was yielded as a white solid (620 mg, 91%) following concentration of solvent and re-crystallization using ethyl acetate. LC-MS (Protocol Q1): m/z 552.3 [M+Na⁺], retention time=1.01 minutes.

Step 2

Synthesis of N-alpha-[(9H-fluoren-9-ylmethoxy)carbonyl]-N-[2-({6-[(4S,5R)-5-methyl-2-oxoimidazolidin-4-yl]hexanoyl}amino)ethyl]-L-phenylalaninamide (#254)

Boc protection was removed using general procedure C using #251 (88 mg, 0.17 mmol, 1.0 eq.) and 4M HCl (2.0 mL, 8.0 mmol, 48 eq.) followed by concentration in vacuo. Coupling reaction was then performed following general procedure D using crude residue, 6-[(4S,5R)-5-methyl-2-oxoimidazolidin-4-yl]hexanoic acid (35.6 mg, 0.166 mmol, 1.0 eq.), HATU (73.2 mg, 0.18 mmol, 1.1 eq.), and Hunig's base (0.087 mL, 0.50 mmol, 3.0 eq.) in 2 mL of DMF followed by purification (Method J) yielding #254 (35 mg, 34%) as a white solid. LC-MS (Protocol Q1): m/z 626.3 [M+H⁺], retention time=0.86 minutes.

Step 3

Synthesis of N-[2-{6-[(4S,5R)-5-methyl-2-oxoimidazolidin-4-yl]hexanoyl}amino)ethyl]-L-phenylalaninamide (#255)

Following general procedure A using #254 (35 mg, 0.056 mmol, 1.0 eq.), piperidine (0.10 mL, 1.0 mmol, 20 eq.) in 0.5 mL of DMF followed by purification using silica chromatography (0-30% methanol in dichloromethane) affords #253 (19 mg, 84%). LC-MS (Protocol Q1): m/z 404.2 [M+H$^+$], retention time=0.48 minutes.

Step 4

Synthesis of N-[(9H-fluoren-9-ylmethoxy)carbonyl]-2-methylalanyl-N-{(3R,4S,5S)-1-[(2S)-2-{(3R,4R,7S)-7-benzyl-4-methyl-18-[(4S,5R)-5-methyl-2-oxoimidazolidin-4-yl}-5,8,13-trioxo-2-oxa-6,9,12-triazaoctadecan-3-yl}pyrrolidin-1-yl]-3-methoxy-5-methyl-1-oxoheptan-4-yl]-N-methyl-L-valinamide (#256)

Following general procedure D using #105 (36.6 mg, 0.047 mmol, 1.0 eq.), #255 (19 mg, 0.047 mmol, 1.0 eq.), HATU (22.4 mg, 0.056 mmol, 1.2 eq.) and Hunig's base (0.025 mL, 0.141 mmol) in 1.5 mL of DMF following by purification (Method J) yielded #256 (15 mg, 27%) as a white solid. LC-MS (Protocol Q1): m/z 1164.8 [M+H$^+$], retention time=0.99 minutes.

Step 5

Synthesis of 2-methylalanyl-N-{(3R,4S,5S)-1-[(2S)-2-{(3R,4R,7S)-7-benzyl-4-methyl-18-[(4S,5R)-5-methyl-2-oxoimidazolidin-4-yl]-5,8,13-trioxo-2-oxa-6,9,12-triazaoctadecan-3-yl}pyrrolidin-1-yl]-3-methoxy-5-methyl-1-oxoheptan-4-yl}-N-methyl-L-valinamide (#257)

Following general procedure A using #256 (5 mg, 0.004 mmol, 1.0 eq.) and piperidine (0.02 mL, 0.2 mmol, 50 eq.) in 0.7 mL of DMF followed by purification (Method J) afforded #257 (2 mg, 50%) as a colorless glass. LC-MS (Protocol Q1): m/z 1164.8 [M+H$^+$], retention time=0.99 minutes. $^1$H NMR (400 MHz, DMSO-d$_6$), δ 8.44-8.52 (m), 8.06-8.20 (m), 7.96-8.01 (m), 7.69-7.83 (m), 7.20-7.28 (m), 7.11-7.19 (m), 3.38-3.83 (m), 3.19-3.26 (m), 3.03-3.12 (m), 2.98 (s), 2.91 (s), 2.75 (s), 2.65-2.70 (m), 2.01-2.36 (m), 1.65-1.87 (m), 1.39-1.57 (m), 1.13-1.37 (m), 1.04-1.08 (m), 0.74-1.01 (m).

Preparation of N-[5-(2,5-dioxo-2,5-dihydro-1H-pyrrol-1-yl)pentanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mv#115)

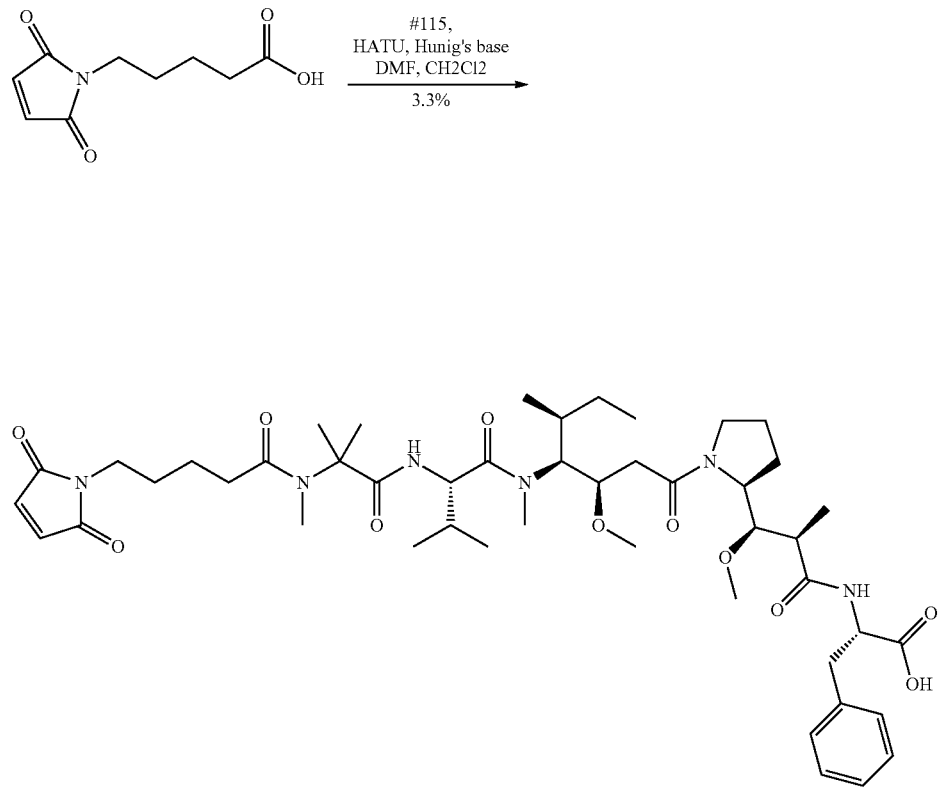

mv#115

Step 1

Preparation of N-[5-(2,5-dioxo-2,5-dihydro-1H-pyrrol-1-yl)pentanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mv#115)

To a stirring solution of 5-(2,5-dioxo-2,5-dihydro-1H-pyrrol-1-yl)pentanoic acid (12 mg, 0.061 mM) in 0.4 mL of dichloromethane, and 0.1 mL of DMF, HATU (23.2 mg, 0.061 mM) was added followed by Hunig's base (0.033 mL, 0.188 mM). The reaction was allowed to stir for 5 minutes before #115 (39 mg, 0.047 mM) was added as a solution in 0.4 mL of dichloromethane, and 0.1 mL of DMF. The reaction was allowed to stir at room temperature for 3 hours and 15 minutes before being quenched through the addition of water containing a small amount of TFA. Reaction was then reduced down. Crude material was dissolved with DMSO and purified by reverse phase chromatography (Method J). The appropriate fractions were concentrated then (Genevac). Material was then further purified by reverse phase chromatography (Method K) with the appropriate fractions being concentrated (Genevac). Material was then transferred to a small vial using dichloromethane and methanol before being reduced down (Genevac) to afford mv#115 (1.4 mg, 3.3%) oil/solid mix. HPLC (Protocol A at 45° C.): m/z 897.5 [M+H+], retention time=9.149 minutes (purity >97%).

Preparation of N-[6-(2,5-dioxo-2,5-dihydro-1H-pyrrol-1-yl)hexanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mc#115)

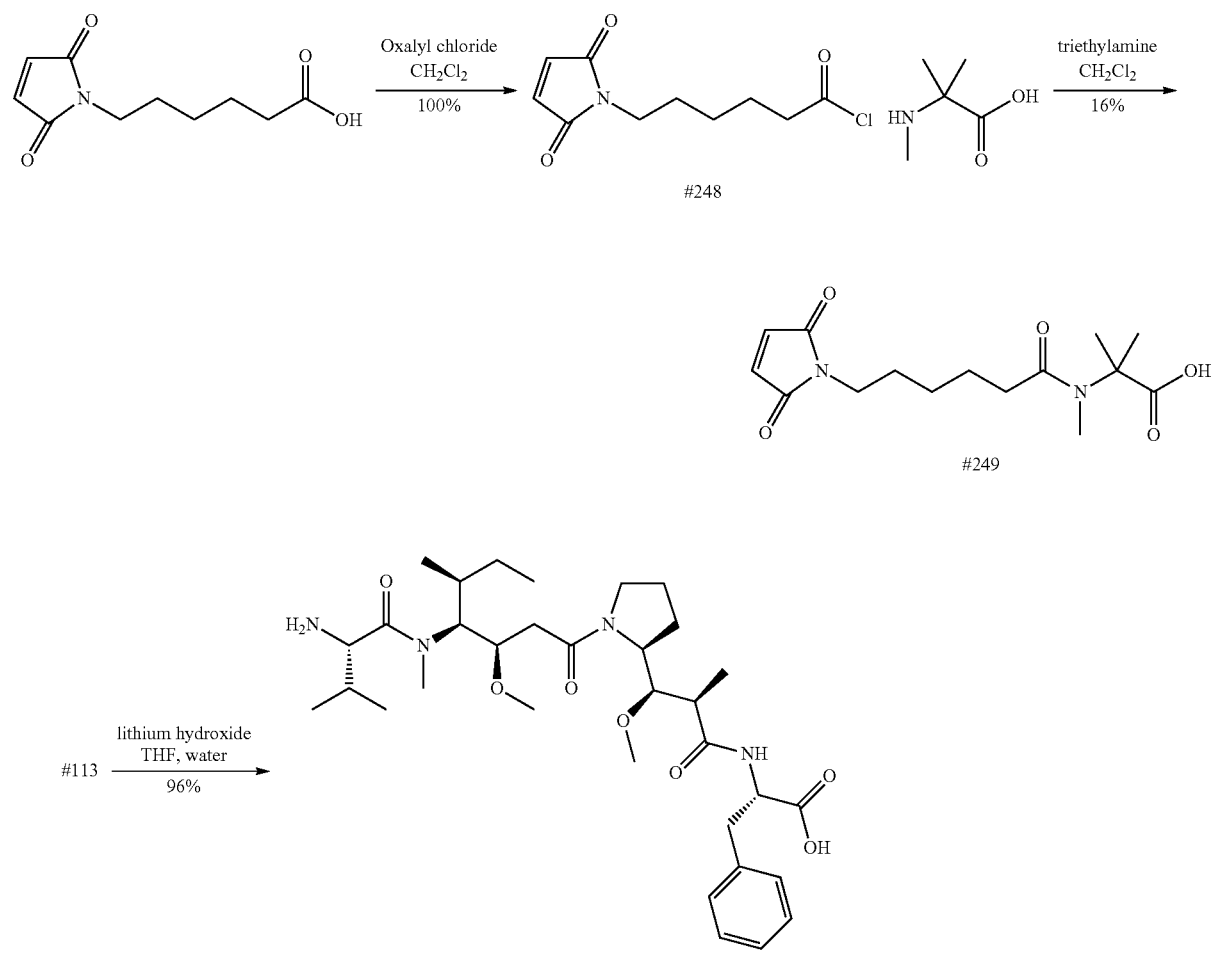

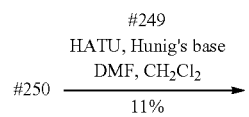

-continued

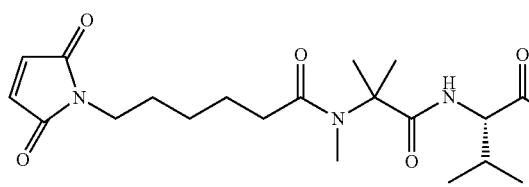
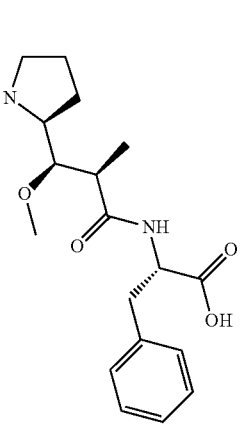

mc#115

Step 1

Synthesis of 6-(2,5-dioxo-2,5-dihydro-1H-pyrrol-1-yl)hexanoyl chloride (#248)

To a stirring solution of 6-(2,5-dioxo-2,5-dihydro-1H-pyrrol-1-yl)hexanoic acid (3.15 g, 14.9 mM) in 15 mL of dichloromethane, oxalyl chloride (1.61 mL, 17.9 mM) was added followed by one drop of DMF. The reaction was allowed to stir at room temperature for three hours. The reaction was concentrated in vacuo. The residue was dissolved in a one to one solution of heptane and dichloromethane and then concentrated in vacuo. This process was repeated two more times producing a solid #248 (3.43 g, 100%). $^1$H NMR (400 MHz, DMSO-$d_6$): δ [7.02 (s, 2H), 3.43 (m, 2H), 2.53 (m, 1H), $CH_{2.18}$ (m, 1H), 1.54 (m, 4H), 1.26 (m, 2H).]

Step 2

Synthesis of N-[6-(2,5-dioxo-2,5-dihydro-1H-pyrrol-1-yl)hexanoyl]-N,2-dimethylalanine (#249)

To a stirring solution of #248 (600 mg, 2.61 mM) in 10 mL of dichloromethane, N,2-dimethylalanine (306 mg, 2.61 mM) was added followed by triethylamine (1.09 mL, 7.84 mM). The reaction was allowed to stir at room temperature for three hours. Dichloromethane was added to the reaction and the organic layer was washed three times with water and two times with brine. The organic layer was separated and then dried over sodium sulfate before being concentrated in vacuo. The crude residue was purified by silica chromatography (0-30% methanol in dichloromethane) on silica which had been previously neutralized with triethylamine yielding a white solid #249 (127 mg, 16%). LC-MS (Protocol Q): m/z 309.0 [M−H$^-$], retention time=0.96 minutes.

Step 3

Synthesis of N-{(2R,3R)-3-methoxy-3-[(2S)-1-{(3R,4S,5S)-3-methoxy-5-methyl-4-[methyl(L-valyl)amino]heptanoyl}pyrrolidin-2-yl]-2-methylpropanoyl}-L-phenylalanine (#250)

To a stirring solution of #113 (2.10 g, 2.46 mM) in 10 mL of THF, lithium hydroxide (228 mg, 5.16 mM) was added followed by 3 mL of water. The reaction was allowed to stir at room temperature for 2 hours. The reaction was acidified though the addition of 1 M HCl and then concentrated in vacuo. The resulting white solid was taken up in 20 mL of acetonitrile and mL of water. The aqueous layer removed and the organic layer was washed once with water. The organic layer was dried over sodium sulfate, filtered, and concentrated in vacuo. Ethyl acetate (20 mL) was then added and the crude solid was allowed to stir for 30 minutes, before being filtered to yield a white solid #250 (1.42 g, 94%). LC-MS (Protocol Q): m/z 619.5 [M+H$^+$], retention time=1.10 minutes. HPLC (Protocol A at 45° C.) m/z 619.4 [M+H$^+$], retention time=6.732 minutes.

Step 4

Synthesis of N-[6-(2,5-dioxo-2,5-dihydro-1H-pyrrol-1-yl)hexanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mc#115)

To a stirring solution of #249 (382 mg, 1.23 mM) in 5 mL of dichloromethane, HATU (482 mg, 1.23 mM) was added followed by triethylamine (0.52 mL, 1.23 mM). The reaction was allowed to stir for 1 hour at room temperature followed by the addition of #250 (762 mg, 1.23 mM). The reaction was allowed to stir for 3 hours. Reaction was concentrated in vacuo. Reverse phase purification (MethodL) followed by lyophilization yielded a white solid mc#120 (124 mg, 11%). HPLC (Protocol A at 45° C.;) m/z 911.5 [M+H$^+$], retention time=9.676 minutes.

Preparation of N-[4-(2,5-dioxo-2,5-dihydro-1H-pyrrol-1-yl)butanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mb#115)

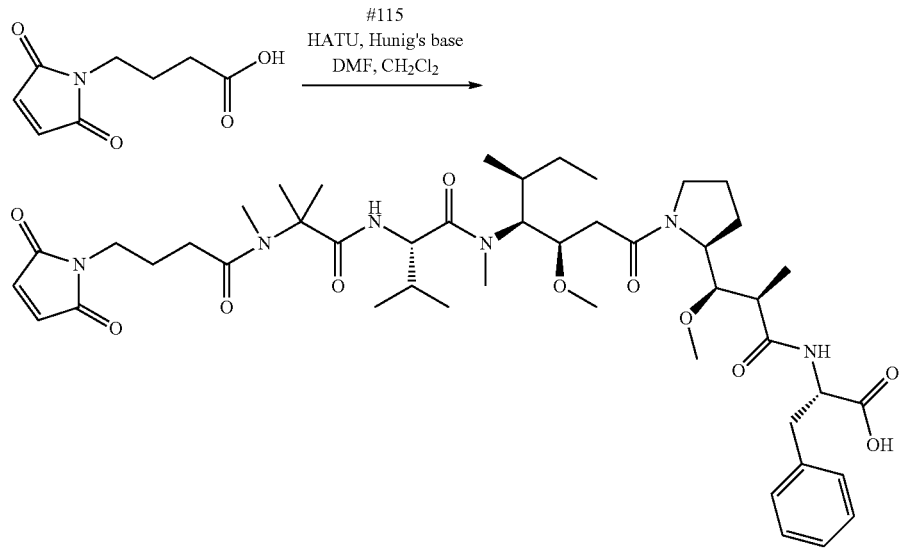

mb#115

Step 1

Synthesis of N-[4-(2,5-dioxo-2,5-dihydro-1H-pyrrol-1-yl)butanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (mb#115)

A stirring solution of 4-(2,5-dioxo-2,5-dihydro-1H-pyrrol-1-yl)butanoic acid (1.2 equivalents), HATU (1.2 equivalents), and Hunig's base (3 equivalents) in DMF and dichloromethane is allowed to stir for 30 minutes. Compound #115 (1 equivalent) is then added as a solution in dichloromethane and DMF. Reaction is monitored by LC-MS. Reaction is concentrated down and purification is completed by Isco medium pressure reverse phase chromatography (Gradient: 5%-100% water in acetonitrile).

Preparation of N-[7-(2,5-dioxo-2,5-dihydro-1H-pyrrol-1-yl)heptanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (me#115)

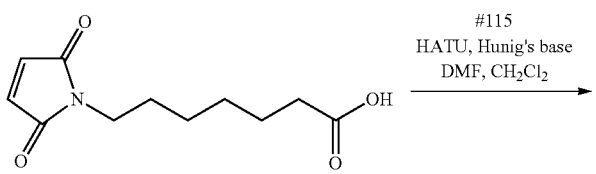

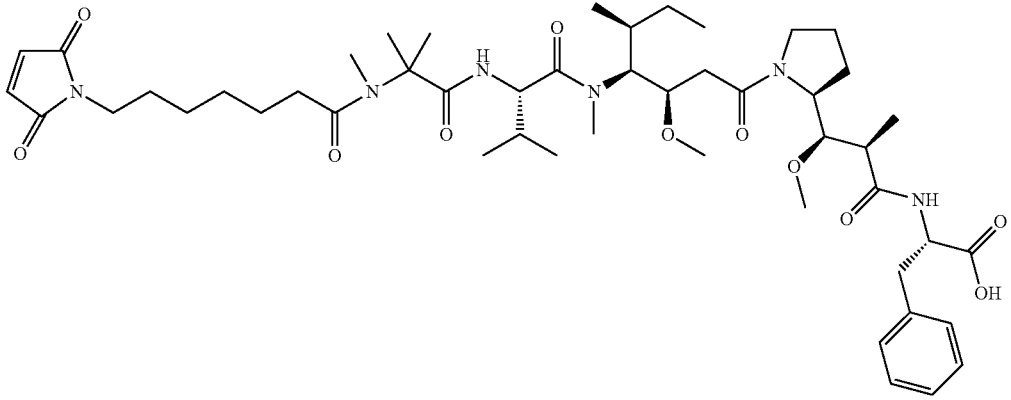

me#115

Step 1

Synthesis of N-[7-(2,5-dioxo-2,5-dihydro-1H-pyrrol-1-yl)heptanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (me#115)

A stirring solution 7-(2,5-dioxo-2,5-dihydro-1H-pyrrol-1-yl)heptanoic acid (1.2 equivalents), HATU (1.2 equivalents), and Hunig's base (3 equivalents) in DMF and dichloromethane is allowed to stir for 30 minutes. Compound #115 (1 equivalent) is then added as a solution in dichloromethane and DMF. Reaction is monitored by LC-MS. Reaction is concentrated down and purification is completed by Isco medium pressure reverse phase chromatography (Gradient: 5%-100% water in acetonitrile).

Preparation of N-[6-(2,5-dioxo-2,5-dihydro-1H-pyrrol-1-yOhexanoylPL-valyl-N~5~-carbamoyl-N-(4-{(8S,11S,12R)-[2-(2-{(2S)-2-[(1R,2R)-3-{[(1S)-1-carboxy-2-phenylethyl]amino}-1-methoxy-2-methyl-3-oxopropyl]pyrrolidin-1-yl}-2-oxoethyl)-8-isopropyl-4,5,5,10-tetramethyl-11-[(1S)-1-methylpropyl]-3,6,9-trioxo-2,13-dioxa-4,7,10-triazatetradec-1-yl}phenyl)-L-ornithinamide (mcValCitPABC#115)

$$\text{\#115} \xrightarrow[\text{HOAt, DMA}]{\substack{\text{mcValCitPABC-PNP} \\ \text{Hunig's base} \\ \text{2,6-Lutidine}}}$$

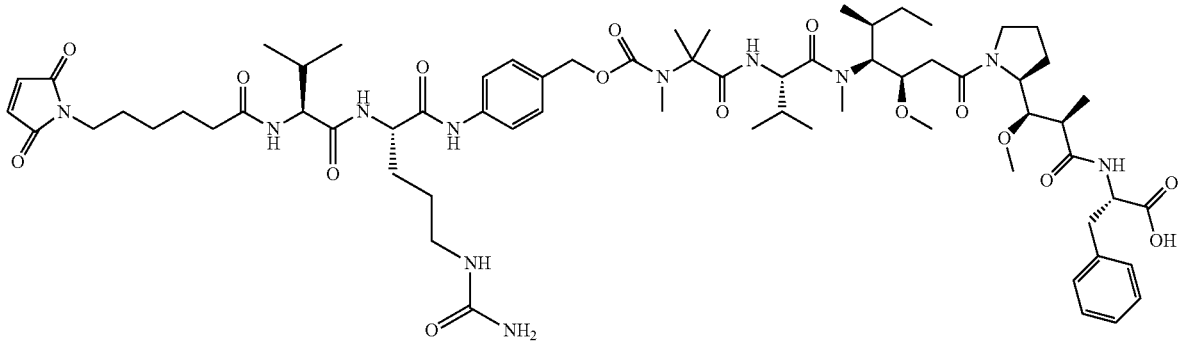

mcValCitPABC#115

Step 1

Synthesis of N-[6-(2,5-dioxo-2,5-dihydro-1H-pyrrol-1-yl)hexanoyl]-L-valyl-N~5~-carbamoyl-N-(4-{(8S,11S,12R)-12-(2-{(2S)-2-[(1R,2R)-3-{[(1S)-1-carboxy-2-phenylethyl]amino}-1-methoxy-2-methyl-3-oxopropyl]pyrrolidin-1-yl}-2-oxoethyl)-8-isopropyl-4,5,5,10-tetramethyl-11-[(1S)-1-methylpropyl]-3,6,9-trioxo-2,13-dioxa-4,7,10-triazatetradec-1-yl}phenyl)-L-ornithinamide (mcValCitPABC#115)

A solution of mcCValCitPABC (Linker # D, 1 equivalent) and #115 (1 equivalent) in DMF is prepared. Hunig's base (4 equivalents), 2,6-Luditine (4 equivalents), and HOAT (0.2 equivalents) is added. Reaction is monitored by LC-MS. Reaction is concentrated down and purification is completed by Isco medium pressure reverse phase chromatography (Gradient: 5%-100% water in acetonitrile).

Preparation of N-(21-amino-4,7,10,13,16,19-hexaoxahenicosan-1-oyl)-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (AmPeg6C2#115)

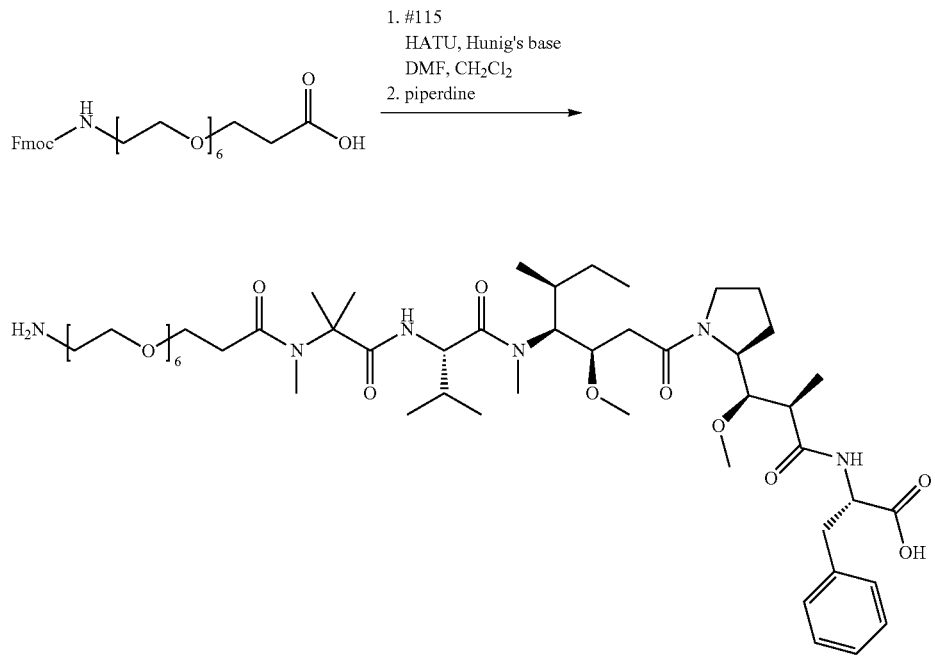

AmPeg6C2#115

Step 1

Synthesis of N-(21-amino-4,7,10,13,16,19-hexaoxahenicosan-1-oyl)-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (AmPeg6C2#115)

A solution of 1-(9H-fluoren-9-yl)-3-oxo-2,7,10,13,16,19,22-heptaoxa-4-azapentacosan-25-oic acid (1 equivalent), HATU (1 equivalent), and Hunig's base (3 equivalents) is allowed to stir for 30 minutes. Compound #115 is added as a solution in DMF. Reaction is monitored by LC-MS. When coupling reaction is near completion, piperidine (5 equivalents) is added. Fmoc de-protection is monitored by LC-MS. Reaction is concentrated down and purification is completed by Isco medium pressure reverse phase chromatography (Gradient: 5%-100% water in acetonitrile).

Preparation of 1,2-dimethyl-D-prolyl-N-[(3R,4S, 5S)-1-{(2S)-2-[(1R,2R)-3-({(2S)-3-[4-({N-[6-(2,5-dioxo-2,5-dihydro-1H-pyrrol-1-yl)hexanoyl]glycyl}amino)phenyl]-1-methoxy-1-oxopropan-2-yl}amino)-1-methoxy-2-methyl-3-oxopropyl]pyrrolidin-1-yl}-3-methoxy-5-methyl-1-oxoheptan-4-yl]-N-methyl-L-valinamide mcGly#201
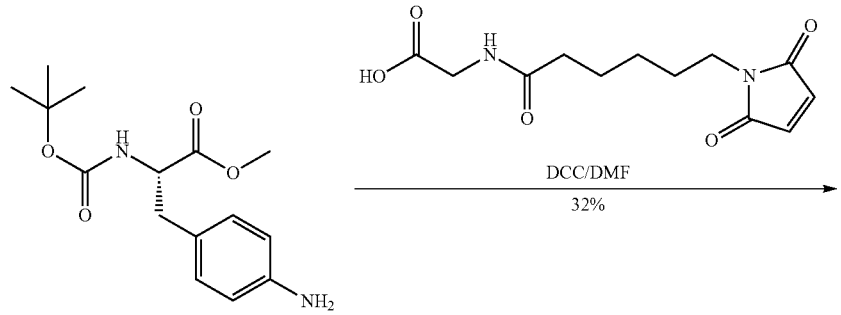
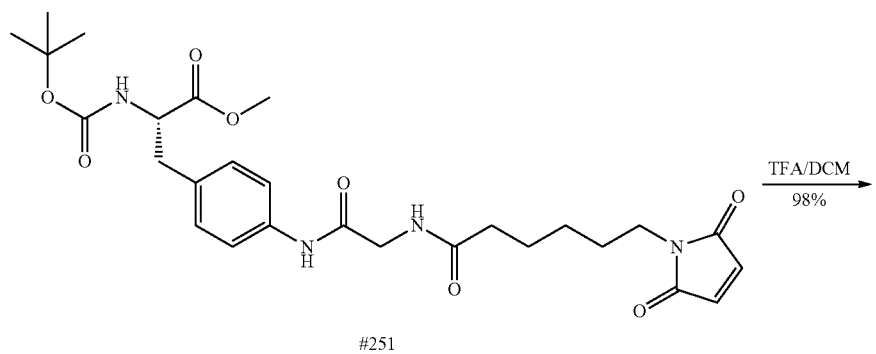
251
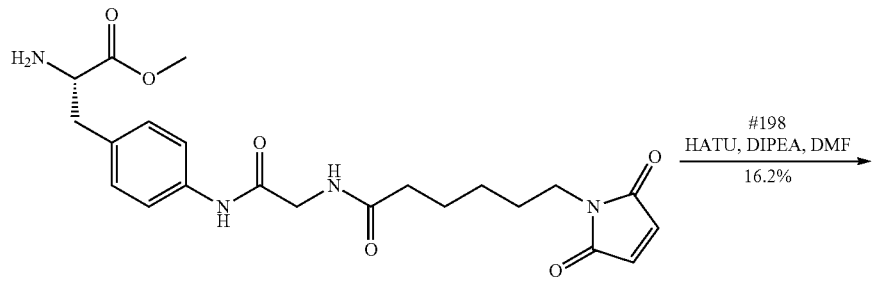
252
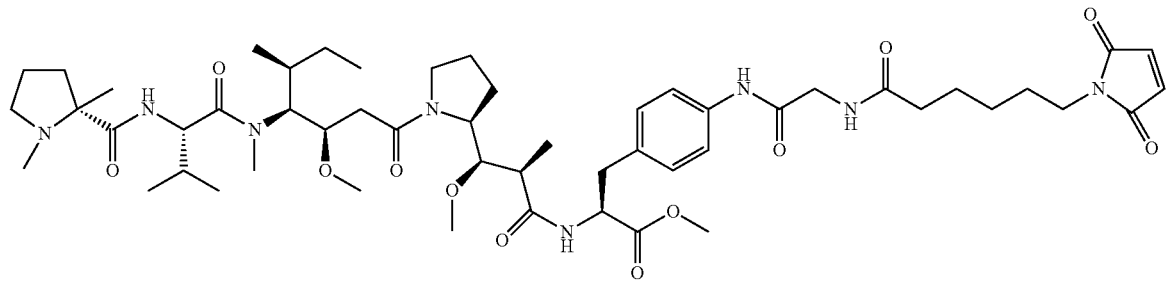
mcGly#201

Step 1

Synthesis of methyl N-(tert-butoxycarbonyl)-4-({N-[6-(2,5-dioxo-2,5-dihydro-1H pyrrol-1-yl)hexanoyl]glycyl}amino)-L-phenylalaninate (#251)

To a solution of methyl 4-amino-N-(tert-butoxycarbonyl)-L-phenylalaninate (4.1 g, 15.3 mmol, 1 eq.) in dry N,N-dimethylformamide (70 mL) was added N,N'-Dicyclohexyl-carbodiimide (2.9 g, 15.3 mmol, 1 eq.) at 0° C. The mixture was stirred at 0° C. for 30 minutes. A solution of 2-(6-(2,5-dioxo-2,5-dihydro-1H-pyrrol-1-yl)hexanamido)acetic acid (3 g, 10.2 mmol, 0.66 eq.) in dry N,N-dimethylformamide (20 mL) was added at 0° C. The mixture was stirred at room temperature for 3 days. The mixture was filtered. The filtrate was poured into ice water (200 mL) and extracted with EtOAc (200 mL×3). The extract was washed with brine (200 mL), dried over $Na_2SO_4$ and concentrated in vacuo to afford #251 (1.8 g, 32.3% yield) as a light yellow solid. HPLC (Protocol Q2) [M+Na$^+$] 567.3, retention time=1.02 min

Step 2

Synthesis of methyl 4-({N-[6-(2,5-dioxo-2,5-dihydro-1H-pyrrol-1-yl)hexanoyl]glycyl}amino)-L-phenylalaninate (#252)

To a solution of #251 (800 mg, 1.47 mmol, 1 eq.) in dichloromethane (16 mL) was added TFA (4.8 mL) at 0° C. The mixture was stirred at room temperature for 2 hours. The mixture was concentrated in vacuo. The residue was dissolved in water and filtered. The filtrate was lyophilized to afford #252 (800 mg, 97.5%) as a white solid. HPLC (Protocol Q3) [M+H$^+$] 1445.4, retention time=0.90 min.

Step 3

Synthesis of 1,2-dimethyl-D-prolyl-N-[(3R,4S,5S)-1-{(2S)-2-[(1R,2R)-3-({(2S)-3-[4-({N-[6-(2,5-dioxo-2,5-dihydro-1H-pyrrol-1-yl)hexanoyl]glycyl}amino)phenyl]-1-methoxy-1-oxopropan-2-yl}amino)-1-methoxy-2-methyl-3-oxopropyl]pyrrolidin-1-yl}-3-methoxy-5-methyl-1-oxoheptan-4-yl]-N-methyl-L-valinamide (mcGly#201)

To a solution of #198 (94 mg, 0.13 mmol, 1 eq.) and #252 (60.3 mg, 0.18 mmol, 1.4 eq.) in N,N-dimethylformamide (2 mL) was added HATU (64.2 mg, 0.13 mmol, 1 eq.) followed by N,N-diisopropylethylamine (66 mg, 0.52 mmol). The solution was stirred at room temperature for 1 hour. The reaction mixture was neutralized with aq. critic acid and concentrated to give crude product, which was purified by silica gel chromotography (eluted with MeOH/DCM from 1% to 7%), then purified again by preparative TLC (Methanol:dichloromethane: =1:10) to give mcGly#201 (25 mg, 16.2%) as a white solid ESI-MS: m/z 1023.59 [M+H$^+$], HPLC (ProtocolEB) retention time=4.0 minutes (Purity=96%). $^1$H NMR (DMSO-$d_6$) 9.88 (d, 1H), 8.48 (d, 0.5H), 8.24 (d, 0.5H), 8.11 (m, 1H), 7.82 (m, 1H), 7.47 (d, 2H), 7.15 (m, 2H), 7.01 (s, 2H), 4.67 (m, 3H), 3.96 (m, 4H), 3.65 (m, 4H), 3.40 (m, 4H), 3.27 (m, 7H), 3.16 (m, 5H), 2.24 (m, 8H), 1.50 (m, 11H), 1.19 (m, 21H).

Preparation of 1,2-dimethyl-L-prolyl-N-[(3R,4S,5S)-1-{(2S)-2-[(1R,2R)-3-{[(2S)-1-{[6-(2,5-dioxo-2,5-dihydro-1H-pyrrol-1-yl)hexyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (MalC6Am#151)

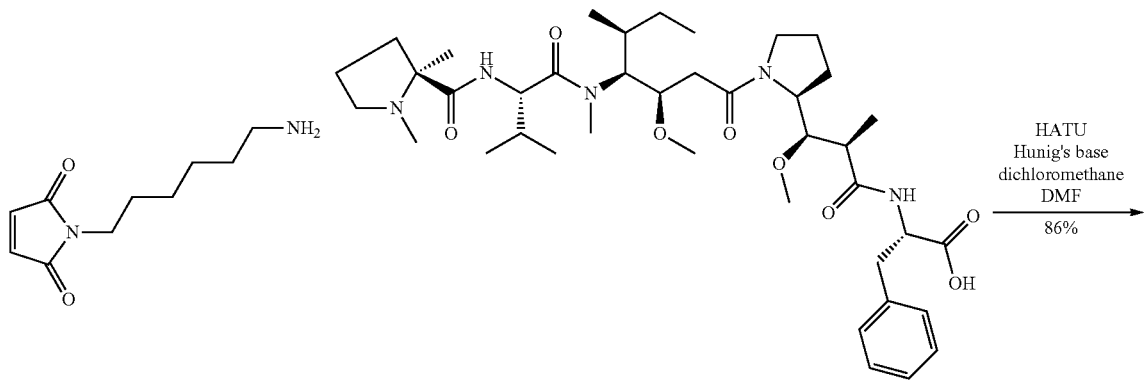

151

-continued

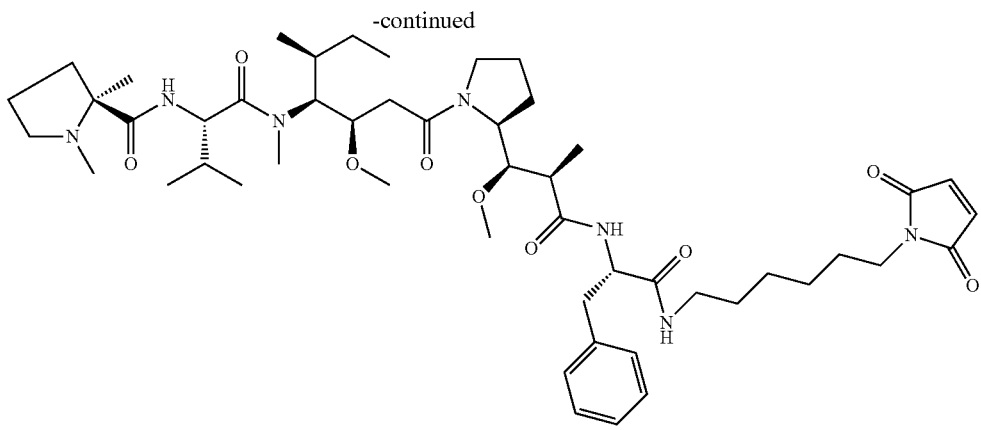

MalC6Am#151

Step 1

Synthesis of 1,2-dimethyl-L-prolyl-N-[(3R,4S,5S)-1-{(2S)-2-[(1R,2R)-3-{[(2S)-1-{[6-(2,5-dioxo-2,5-dihydro-1H-pyrrol-1-yl)hexyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (MalC6Am#151)

Following general procedure D using #151 (20 mg, 0.023 mmol, 1.0 eq.), 1-(6-aminohexyl)-1H-pyrrole-2,5-dione (7.0 mg, 0.030 mmol, 1.3 eq.), HATU (11.4 mg, 0.030 mmol, 1.3 eq.), and Hunig's base (0.016 mL, 0.092 mmol, 1.3 eq.) in 2 mL of dichloromethane, and 0.2 mL of DMF followed by purification using medium pressure reverse phase C18 chromatography (Gradient: 5% to 80% acetonitrile in water with 0.02% TFA in each phase) yielded MalC6 μm#151 (18.4 mg, 86%) as a clear oil/solid mix. LC-MS (Protocol Q): m/z 922.3 [M+H$^+$], retention time=1.43 minutes; HPLC (Protocol A at 45° C.): m/z 922.4 [M+H$^+$], retention time=7.203 minutes.

Preparation of N-[6-(2,5-dioxo-2,5-dihydro-1H-pyrrol-1-yl)hexanoyl]-L-valyl-N-(4-{(6S,9R,10R)-6-benzyl-10-[(2S)-1-{(3R,4S,5S)-4-[(1,2-dimethyl-L-prolyl-L-valyl)(methyl)amino]-3-methoxy-5-methylheptanoyl}pyrrolidin-2-yl]-9-methyl-3,8-dioxo-2,11-dioxa-4,7-diazadodec-1-yl}phenyl)-N~5~-carbamoyl-L-ornithinamide (mcValCitPABC#246)

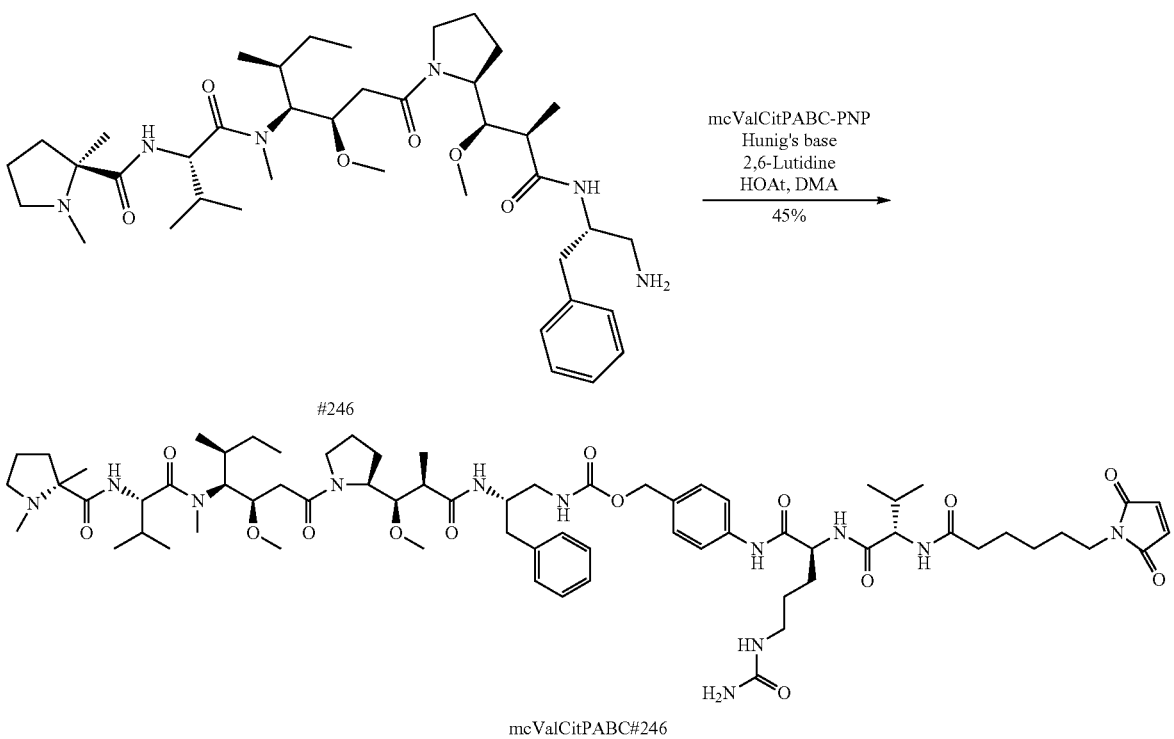

Step 1

Synthesis of N-[6-(2,5-dioxo-2,5-dihydro-1H-pyrrol-1-yl)hexanoyl]-L-valyl-N-(4-{(6S,9R,10R)-6-benzyl-10-[(2S)-1-{(3R,4S,5S)-4-[(1,2-dimethyl-L-prolyl-L-valyl)(methyl)amino]-3-methoxy-5-methylheptanoyl}pyrrolidin-2-yl]-9-methyl-3,8-dioxo-2,11-dioxa-4,7-diazadodec-1-yl}phenyl)-N~5~-carbamoyl-L-ornithinamide (mcValCitPABC#246)

Following general procedure E using #246 (29.2 mg, 0.035 mmol, 1.0 eq.), mcValCitPABC-PNP (28.8 mg, 0.039 mmol, 1.1 eq.), 2,6-Luditine (0.016 mL, 0.14 mmol, 4.0 eq.), Hunig's base (0.025 mL, 0.14 mmol, 4.0 rq.), and HOAT (4.8 mg, 0.035 mmol, 1.0 eq.) in 2.0 mL of DMA followed by purification using medium pressure reverse phase C18 chromatography (Gradient: 5% to 50% acetonitrile in water with 0.02% TFA in each phase) yielded mcValCitPABC#246 (21 mg, 45%) as a clear oil/solid mix. LC-MS (Protocol Q): m/z 1327.9 [M+H$^+$], retention time=1.36 minutes.

HERCEPTIN® In Vitro and In Vivo Studies

It is noted that for the following studies HERCEPTIN® in the absence of conjugated cytotoxic agents shows no significant in vitro potency or in vivo efficacy at equivalent antibody concentrations.

In vitro Cell Assay Procedure

Target expressing (BT474 (breast cancer), N87 (gastric cancer), HCC1954 (breast cancer), MDA-MB-361-DYT2 (breast cancer)) or non-expressing (MDA-MB-468) cells were seeded in 96-well cell culture plates for 24 hours before treatment. Cells were treated with 3-fold serially diluted antibody-drug conjugates or free compounds (i.e., no antibody conjugated to the drug) in duplicate at 10 concentrations. Cell viability was determined by CellTiter 96® AQ$_{ueous}$ One Solution Cell Proliferation MTS Assay (Promega, Madison Wis.) 96 hours after treatment. Relative cell viability was determined as percentage of untreated control. IC$_{50}$ values were calculated using a four parameter logistic model #203 with XLfit v4.2 (IDBS, Guildford, Surry, UK). Results are shown in Tables 20, 21A and 21B.

In vivo MDAMB-361 DYT2 Tumor Xenograft Model

In vivo efficacy studies of antibody-drug conjugates were performed with the Her2+MDAMB-361 DYT2 cell line. For efficacy studies, 10 million tumor cells in 50% matrigel were implanted subcutaneously into 6-8 week old irradiated nude mice. When the tumor sizes reached between 250-350 mm$^3$ drugs or vehicle were administered through bolus tail vein injection. Mice were injected with 1 mg/kg of antibody drug conjugates treated four times every four days (Q4dx4). Tumor volume is measured twice a week for the first 50 days and once weekly thereafter by a Caliper device and calculated with the following formula: Tumor volume=(length×width)/2. Results were compared across studies by normalizing the tumor regression of the drug-treated mice by dividing the tumor volume by the vehicle-treated tumor volume (T/C).

Figure 2:
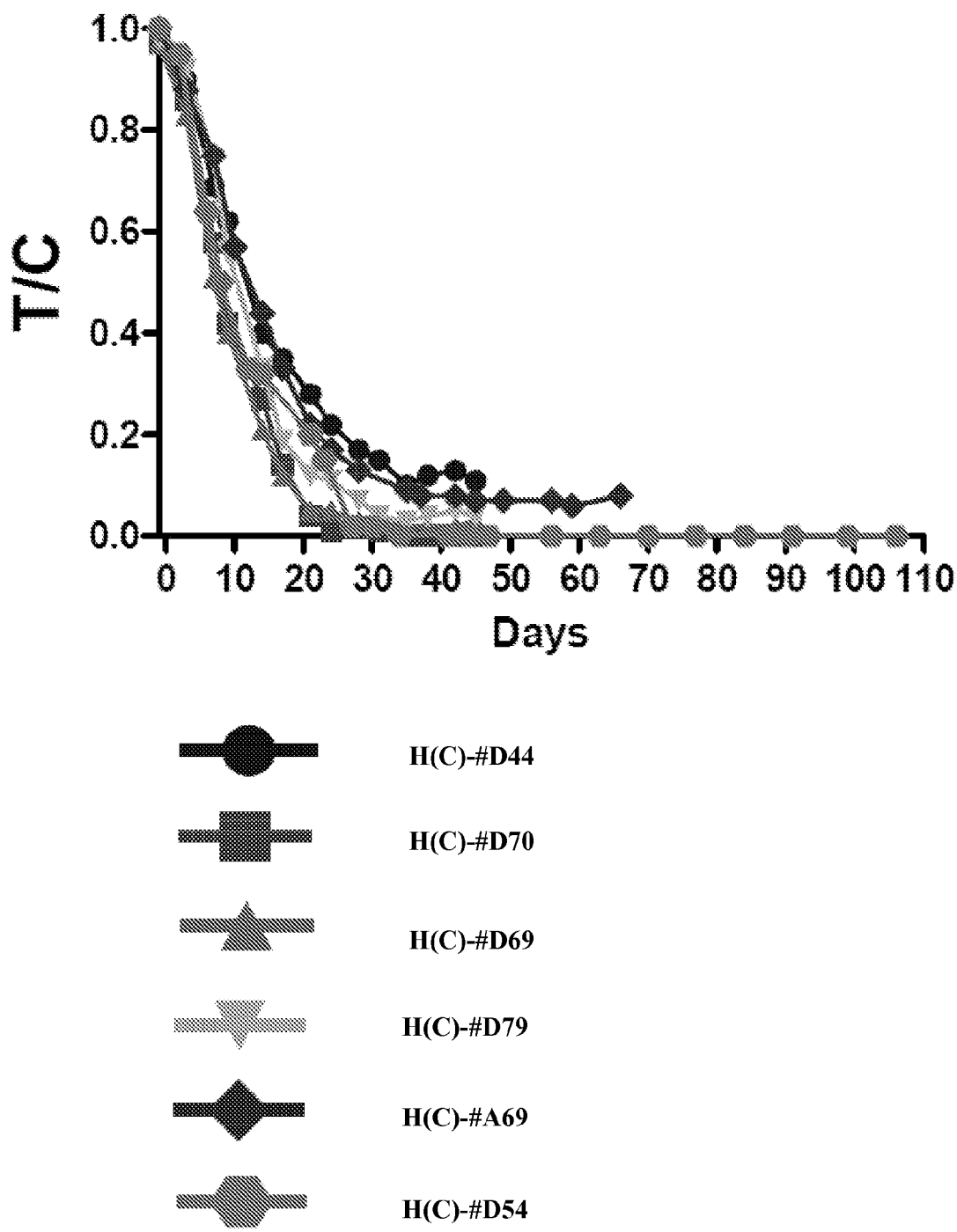
FIG. 2 depicts a graph of anti-tumor activity of six conjugates (each administered at 1 mg/kg, Q4dx4) plotted as drug-treated tumor volume/vehicle-treated tumor volume over time.

Six compounds were tested in the three different MDA-MB-361-DYT2 xenograft studies to determine their anti-tumor activity. The results of a representative study with four of the compounds demonstrates significant tumor regression from the vehicle-treated mice over the 50 day observation period (FIG. 1). To compare the results of compounds in the three studies, anti-tumor activity was normalized by dividing the drug-treated tumor volume by the vehicle-treated tumor volume (T/C). A plot of the six T/C values (FIG. 2) demonstrates that each of the six compounds causes complete (or almost complete) tumor regression over the observation period which was up to 107 days for one of the studies.

Figure 4A:
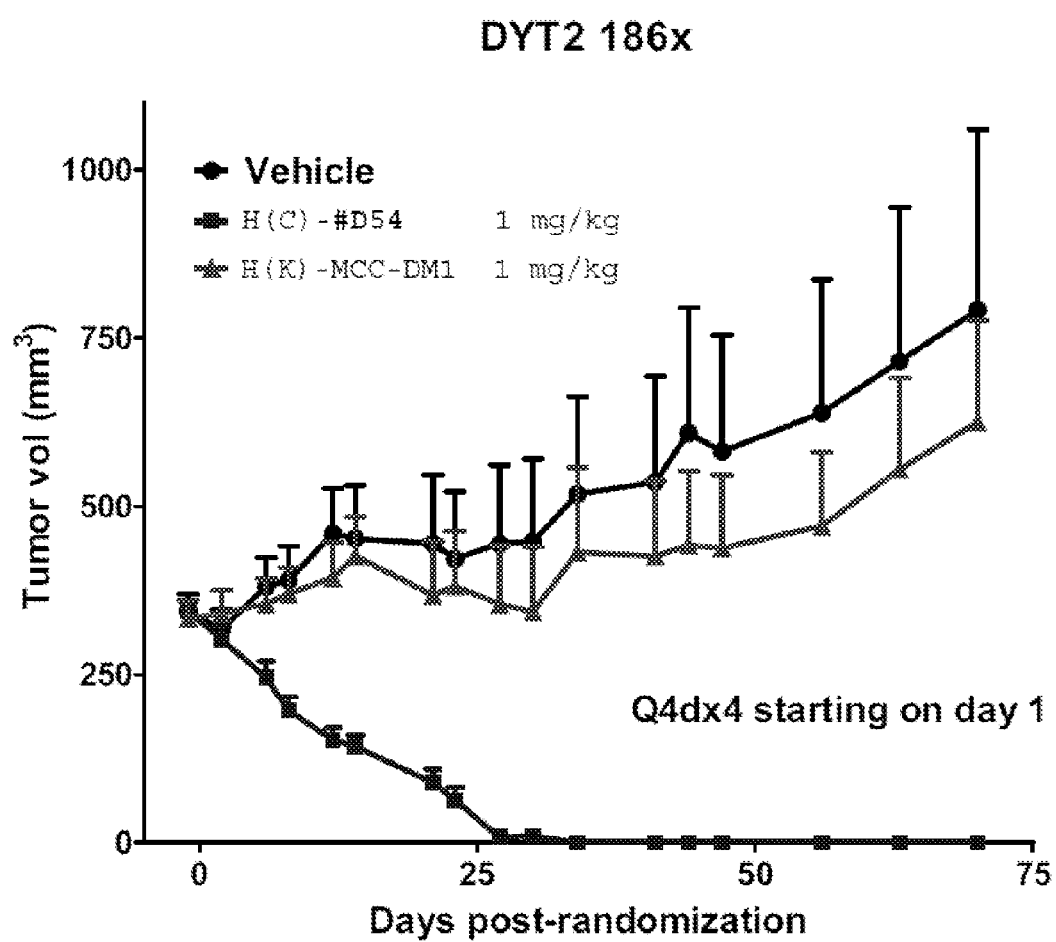
FIGS. 4A, 4B and 4C depict [A] results of testing of H(C)-#D54 and H(K)-MCC-DM1 in a MDA-MB-361-DYT2 mouse xenograft in vivo screening model; [B] results of the testing of H(C)-vcMMAE and H(C)-mcMMAF in a MDA-MB-361-DYT2 mouse xenograft in vivo screening model; and [α] a comparison of the calculated T/C for all four conjugates. Mice were treated q4dx4, starting on day 1.
Figure 4B:
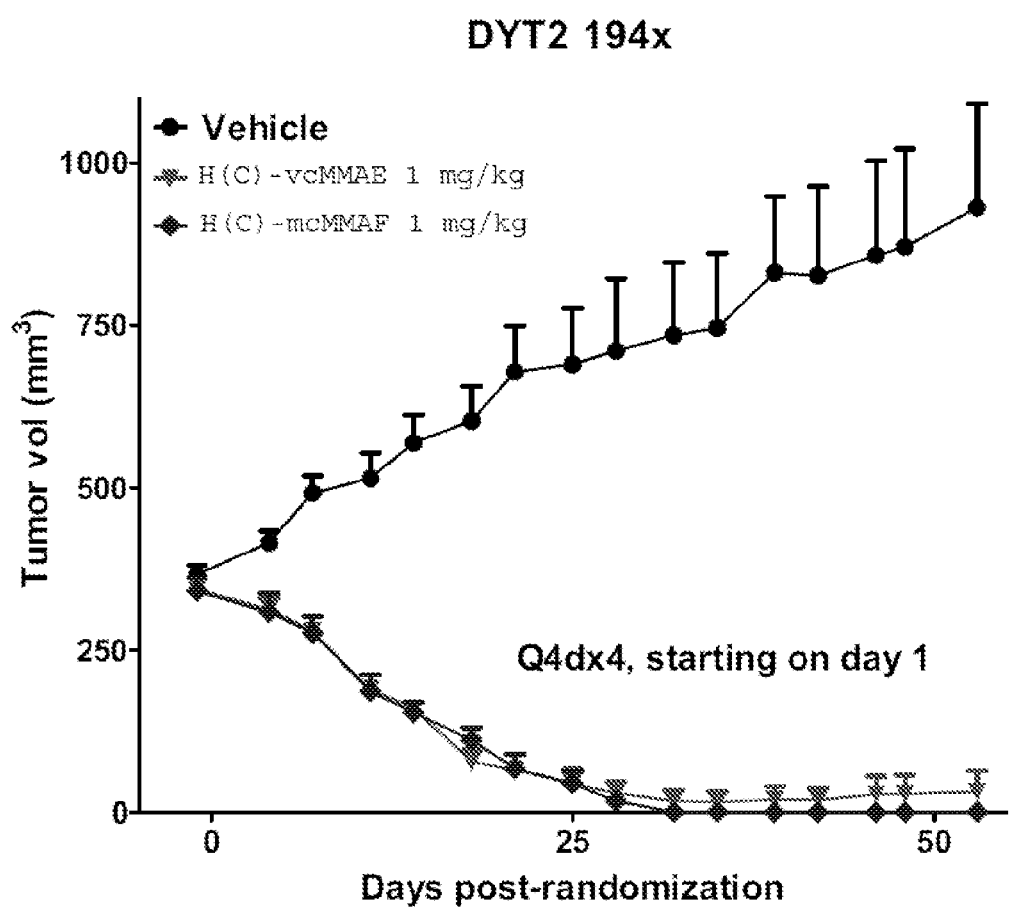
Figure 4C:
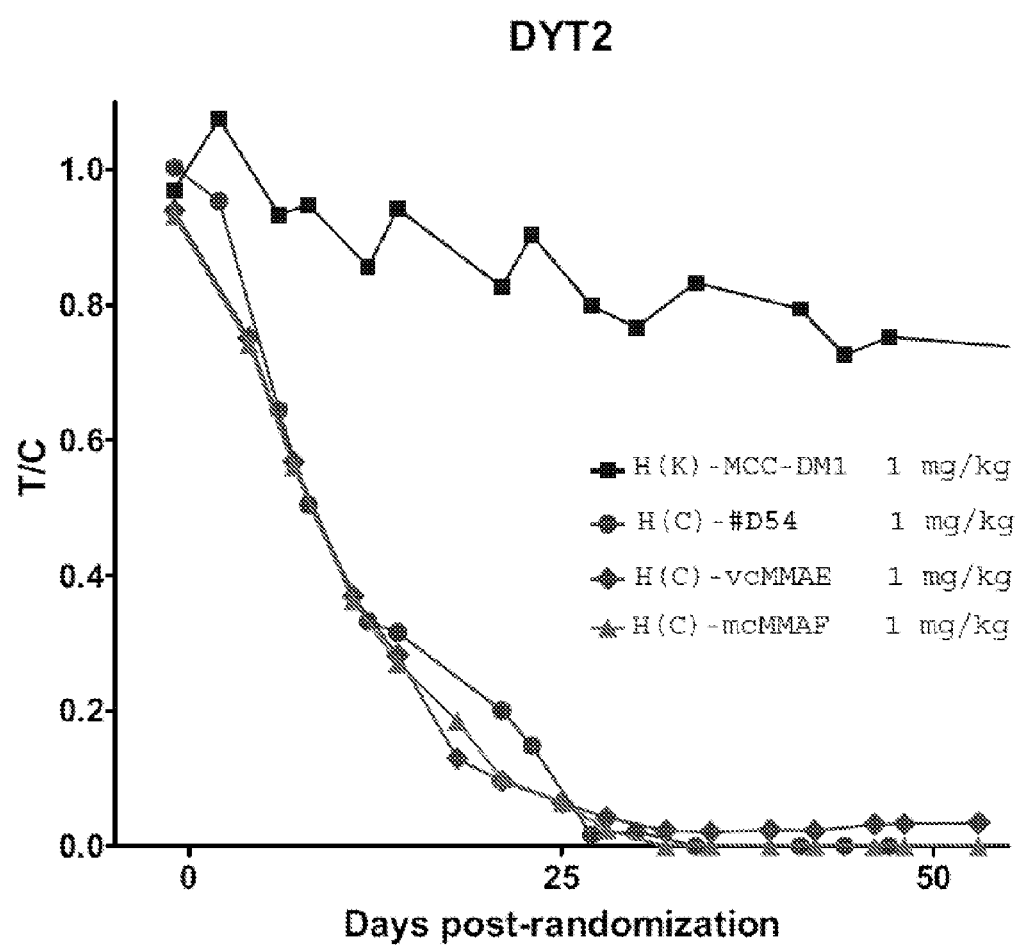
Figure 5A:
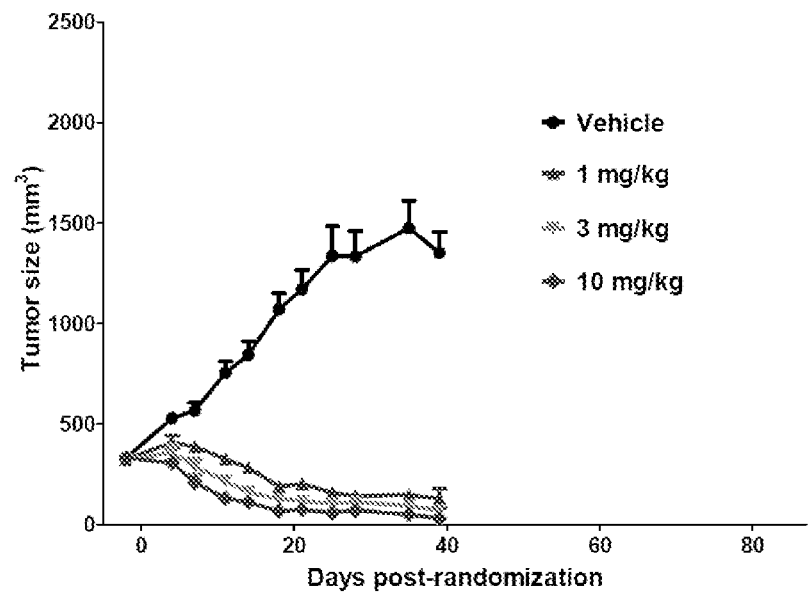
FIGS. 5A, 5B, 5C, 5D, 5E and 5F depict the dose response results of the testing [A] H(C)-#D54, [B] H(C)-vcMMAE, [α] H(C)-mcMMAF and [D] H(K)-MCC-DM1 in a N87 mouse xenograft in vivo model; [E] a comparison of H(C)-#D54 and H(C)-vcMMAE; and [F] a comparison of T/C for all four conjugates. Mice were treated q4dx4, starting on day 1.
Figure 5B:
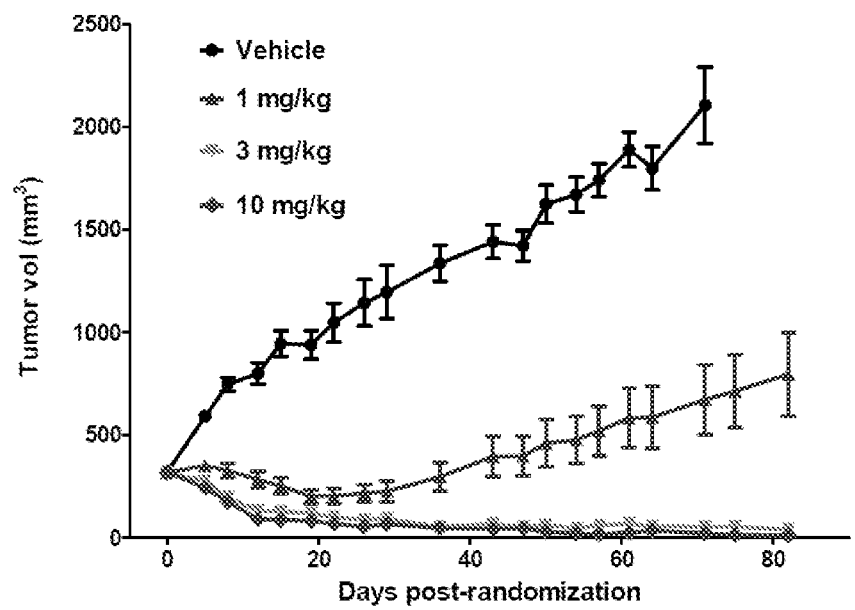
Figure 5C:
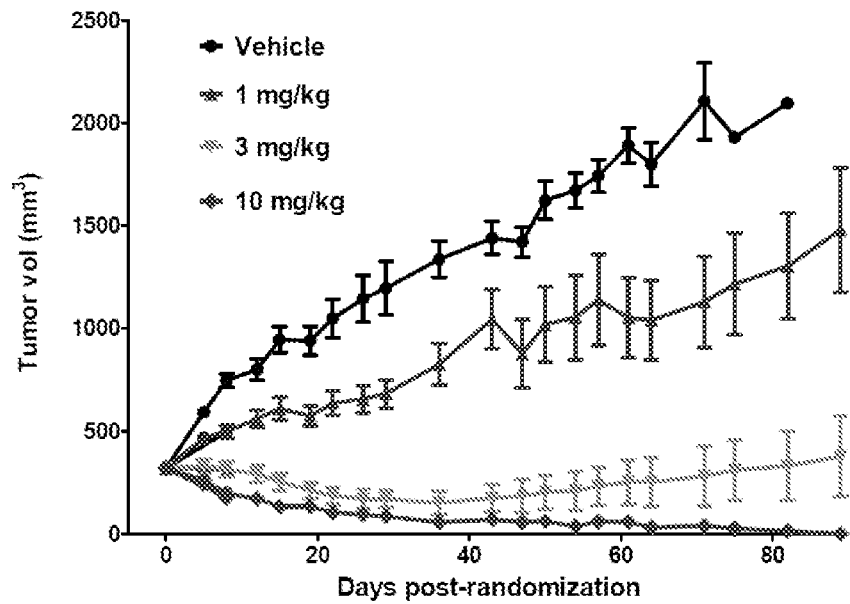
Figure 5D:
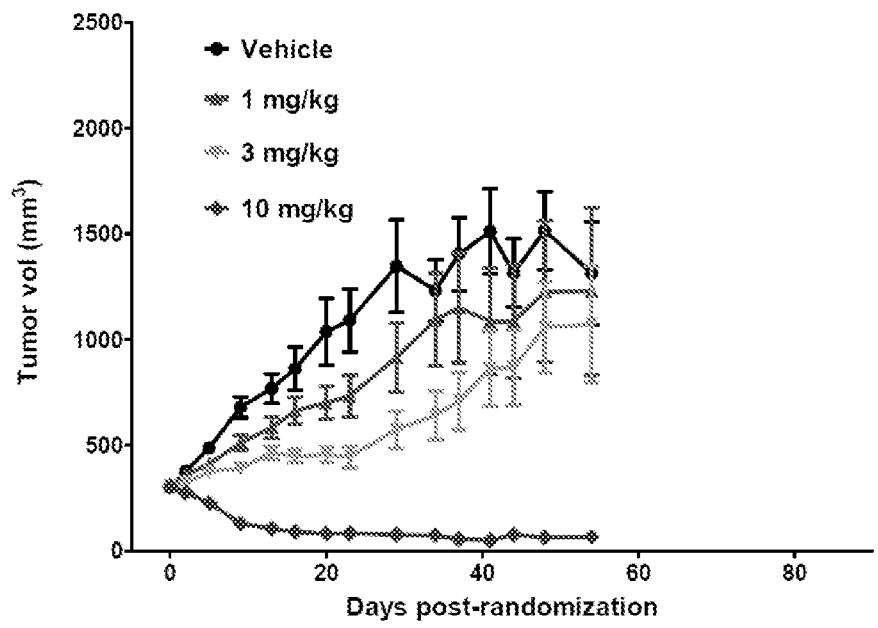
Figure 5E:
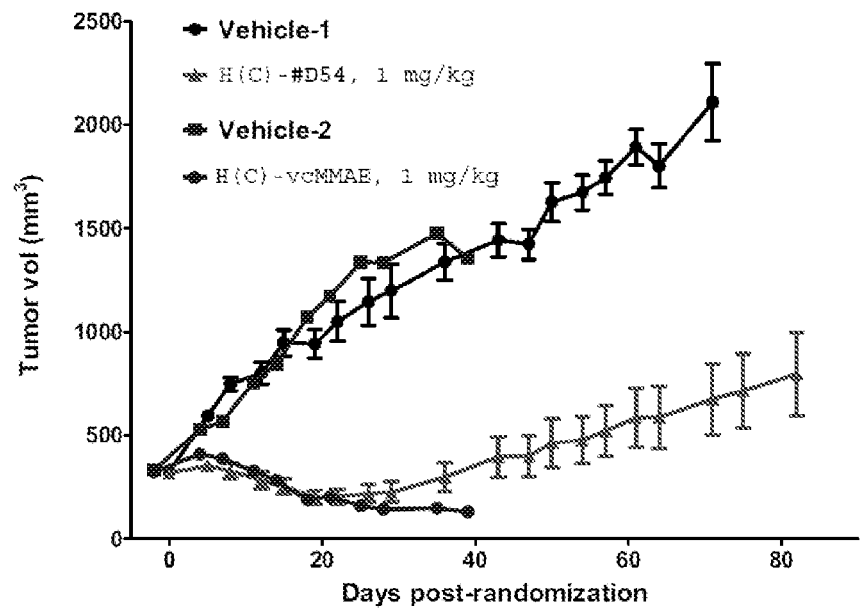
Figure 5F:
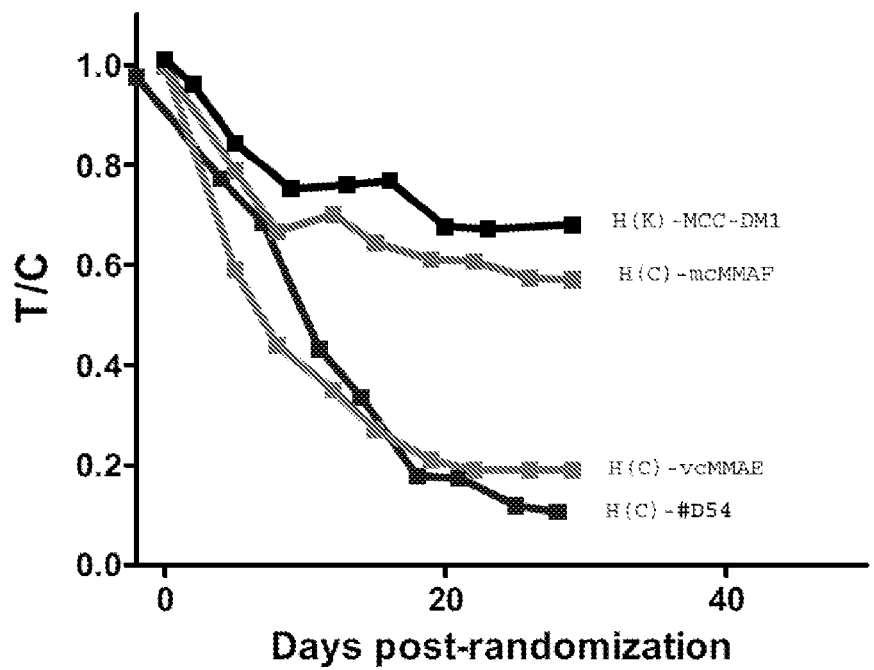
Figure 6:
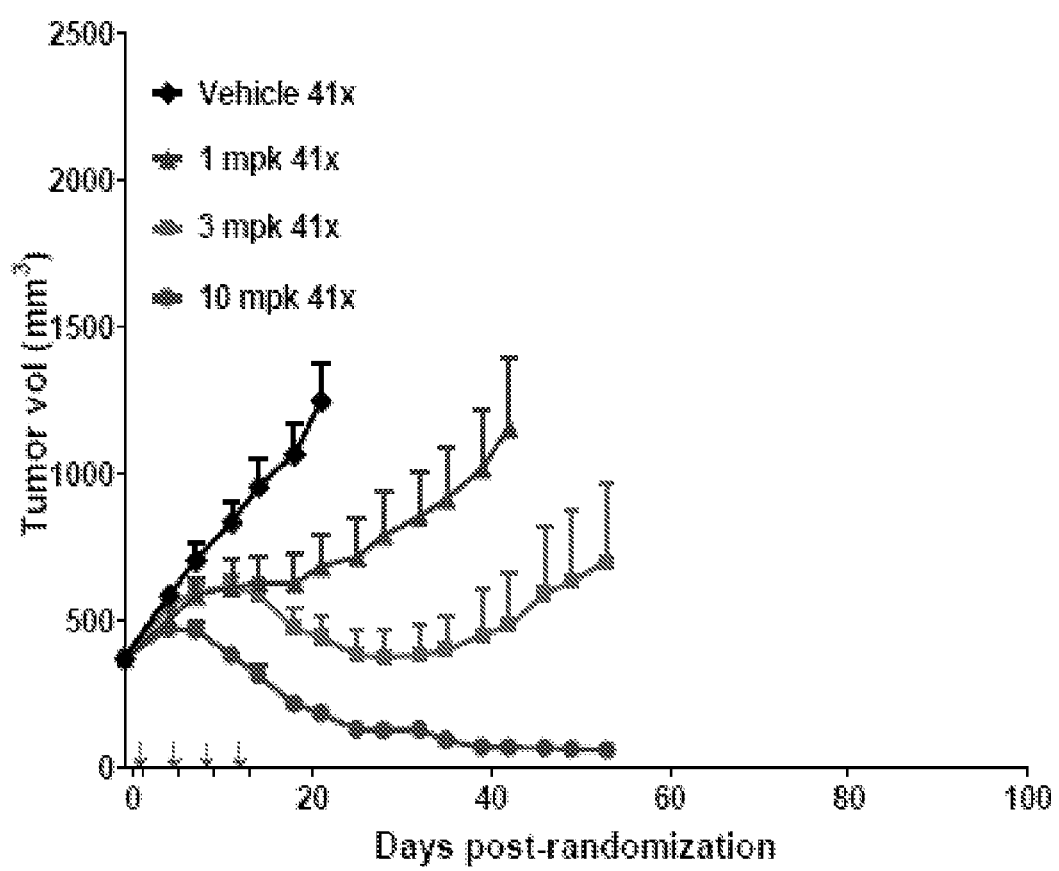
FIG. 6 depicts the dose response results of the testing H(C)-#A115 at 1 mpk, 3 mpk and 10 mpk, in a N87 mouse xenograft in vivo model. Mice were treated q4dx4, starting on day 1.
Figure 7:
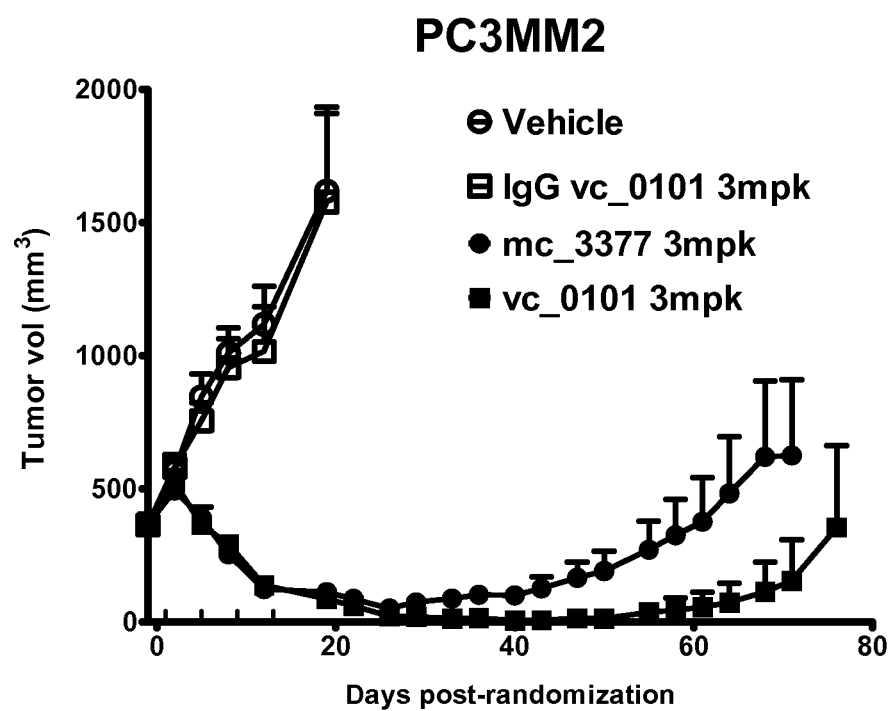
FIG. 7 shows data comparing humanized antibody hu08 conjugated to vc-0101 or mc-3377, tested in an in vivo xenograft model with PC3mM2 cells, a human prostate cancer cell line that expresses the IL-13Rα2 receptor.

Results of the testing of H(C)-#D54, H(C)-vcMMAE, H(C)-mcMMAF and H(K)-MCC-DM1 in the MDA-MB-361-DYT2 xenograft studies are shown in FIG. 4. Tumor volume in treatment group over control group (T/C) plot allows comparison between conjugates (see FIG. 5C). These results demonstrate that H(C)-#D54 displays equivalent efficacy to HERCEPTIN® conjugates with H(C)-vcMMAE, H(C)-mcMMAF and is superior to H(K)-MCC-DM1 in this model.

In Vivo N87 Tumor Xenograft Model (HERCEPTIN®)

In vivo efficacy studies of antibody-drug conjugates were performed with target-expressing xenograft models using the N87 cell lines. For efficacy study, 7.5 million tumor cells in 50% matrigel are implanted subcutaneously into 6-8 weeks old nude mice until the tumor sizes reach between 250 and 350 mm$^3$. Dosing is done through bolus tail vein injection. Depending on the tumor response to treatment, animals are injected with 1-10 mg/kg of antibody drug conjugates treated four times every four days. All experimental animals are monitored for body weight changes weekly. Tumor volume is measured twice a week for the first 50 days and once weekly thereafter by a Caliper device and calculated with the following formula: Tumor volume=(length×width)/2 Animals are humanely sacrificed before their tumor volumes reach 2500 mm$^3$. The tumor size is observed to decrease after the first week of treatment Animals may be monitored continuously for tumor re-growth after the treatment has discontinued.

Figure 3:
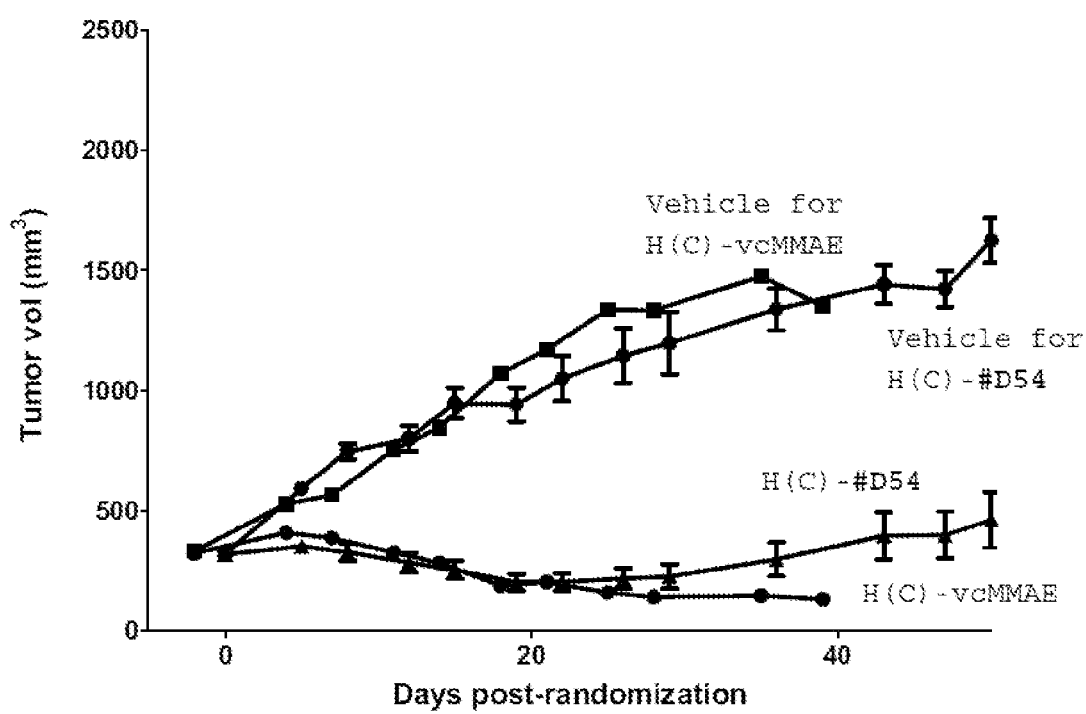
FIG. 3 depicts the results of the testing of H(C)-#D54 and H(C)-vcMMAE at 1 mg/kg s

Results of the testing of H(C)-#D54, H(C)-vcMMAE, H(C)-mcMMAF and H(K)-MCC-DM1 in the N87 mouse xenograft in vivo screening model are shown in FIGS. 3 and 5. These results demonstrate that H(C)-#D54 is superior/similar to the H(C)-vcMMAE conjugate and is more potent than the H(C)-mcMMAF and H(K)-MCC-DM1 conjugates in this model.

Pharmacokinetics and Toxicokinetics

Mouse pharmacokinetics and rat toxicokinetics were determined from single dose mouse pharmacokinetic and rat toxicology studies (see Tables 22 and 23). Mouse pharmacokinetics and rat toxicokinetics were determined from single dose mouse pharmacokinetic and rat toxicology studies. Mouse pharmacokinetics were determined from samples collected from nude mice that were administered a single 3 mg/kg dose. Samples were collected for up to 336 h. Rat toxicokinetics were determined in rats (Sprague-Dawley (Crl:CD (SD))) that were administered a single administration of H(C)-vc-MMAE or H(C)-#D54 at doses of 3, 10, and 30 mg/kg, or administered H(C)-mc-MMAD or H(C)-mc-MMAF at 10, 30, and 100 mg/kg. Samples were collected for up to 336 hours. Circulating concentrations of total antibody and ADC were measured using ELISA assays. Area under the curve (AUC) was calculated for the total antibody and ADC for each ADC. ADC to antibody AUC ratios were also calculated.

Exposure of H(C)-#D54 total antibody and ADC were greater than that observed for H(C)-vc-MMAE in mice at 3 mg/kg and at all doses evaluated in rats. The ADC to Ab AUC ratio for H(C)-#D54 was also greater than that observed for H(C)-vc-MMAE. These results suggest that H(C)-#D54 has greater exposure and that the ADC and/or linker payload are potentially more stable than H(C)-vc-MMAE.

Toxicity

The target independent toxicity of #D54 and comparator linker-payloads (mcValCitPABC-MMAD and mcValCitPABC-MMAE) conjugated to a non-cross reactive monoclonal antibody (IgG1) were assessed in a single-dose rat toxicity study with a two-week observation period. The doses of the antibody drug conjugates (ADCs) were 0, 3, 10 and 30 mg/kg with an n is 5 males/group and the linker-payload loading was similar among the conjugates (3.8, 3.2 and 4, respectively). These studies included at least daily clinical observations, weekly body weights, clinical pathology (end of in-life) and necropsy (Day 15-17) with microscopic examination of 9 or more tissues and any gross lesions.

Mortality with related body weight changes and signs of morbidity were observed at the mg/kg dose for all conjugates and at the 10 mg/kg dose for the MMAD conjugate. There were no clinical observations or body weight changes in the surviving groups.

The target organs of the conjugates identified by microscopic examination in the surviving dose groups were as follows. The conjugate at 10 mg/kg had debris in the lumen of the epididymis (5/5, minimal to mild), inflammation at the base of the heart (1/5 rats, minimal) and increased mitosis in the cornea (1/5 rats, minimal). There were no histological findings for the conjugate at 3 m/kg. For the MMAD conjugate in the surviving dose group at 3 mg/kg, there were changes in and related to the bone marrow and in the testis and epididymidis. For the MMAE conjugate at 10 mg/kg, there were changes in the bone marrow, kidney, liver and epididymis. At the 3 mg/kg dose for this conjugate, there were kidney changes and increased mitosis in the liver. Thus, in studies of similar design and in the surviving groups, the conjugate did not have the bone marrow findings seen with the comparator conjugates and also did not have the liver or kidney findings seen with one of the comparators.

In summary, the maximum tolerated dose (MTD) of the conjugate and the MMAE conjugate was 10 mg/kg and the MTD of the MMAD conjugate was 3 mg/kg. The no observed adverse effect level (NOAEL) of the conjugate was 3 mg/kg whereas the NOAEL of the comparator linker-payload conjugates was less than 3 mg/kg. This study demonstrates how the toxicological profile for #D54 compares to certain compounds described in the art.

Anti-IL-13Rα2 ADC In Vitro and In Vivo Studies

Anti-IL-13Rα2 Antibodies and ADCs

The humanized antibody hu08 specifically binds to the IL-13Rα2 receptor. The amino acid and the nucleotide sequences for hu08 are shown in Table 3. Kabat CDRs are underlined.

TABLE 3

Amino acid and nucleotide sequences of humanized antibody hu08.

| SEQ ID NO | DESCRIPTION | SEQUENCE |
| --- | --- | --- |
| 9 | hu08 heavy chain variable region amino acid sequence (CDRs underlined). | EVQLVESGGGLVQPGGSLRLSCAASGFTF<u>SRNGMS</u>WVR QAPGKGLEWVA<u>TVSSGGSYIYYADSVKG</u>RFTISRDNAK NSLYLQMNSLRAEDTAVYYCAR<u>QGTTALATRFFDV</u>WG QGTLVTVSS |
| 10 | hu08 light chain variable region amino acid sequence (CDRs underlined). | DIQMTQSPSSLSASVGDRVTITC<u>KASQDVGTAVAW</u>YQQ KPGKAPKWY<u>SASYRST</u>GVPSRFSGSGSGTDFTLTISSLQ PEDFATYYC<u>QHHYSAPWT</u>FGGGTKVEIK |
| 11 | hu08 heavy chain amino acid sequence (CDRs underlined). | EVQLVESGGGLVQPGGSLRLSCAASGFTF<u>SRNGMS</u>WVR QAPGKGLEWVA<u>TVSSGGSYIYYADSVKG</u>RFTISRDNAK NSLYLQMNSLRAEDTAVYYCAR<u>QGTTALATRFFDV</u>WG QGTLVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKKVEPKSCDKTHT CPPCPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKAK GQPREPQVYTLPPSREEMTKNQVSLTCLVKGFYPSDIAV EWESNGQPENNYKTTPPVLDSDGSFFLYSKLTVDKSRW QQGNVFSCSVMHEALHNHYTQKSLSCSPGK |
| 12 | hu08 light chain amino acid sequence (CDRs underlined). | DIQMTQSPSSLSASVGDRVTITC<u>KASQDVGTAVAW</u>YQQ KPGKAPKLLI<u>YSASYRST</u>GVPSRFSGSGSGTDFTLTISSLQ PEDFATYYC<u>QHHYSAPWT</u>FGGGTKVEIK TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| 13 | hu08-heavy chain nucleotide sequence | GAGGTGCAGCTGGTGGAGTCTGGCGGCGGACTGGTGC AGCCTGGCGGCTCTCTGAGACTGTCTTGTGCCGCCTCC GGCTTCACCTTCAGTAGGAATGGCATGTCTTGGGTGA GGCAGGCCCCTGGCAAGGGCCTGGAGTGGGTGGCCA CCGTTAGTAGTGGTGGTAGTTACATCTACTATGCAGA CAGTGTGAAGGGGCGGTTCACCATCTCCAGGGACAAC GCCAAGAACTCCCTGTACCTCCAGATGAACTCCCTGA GGGCCGAGGATACCGCCGTGTACTACTGTGCCAGACA AGGGACTACGGCCACTAGCTACGAGGTTCTTCGATGTC TGGGGCCAGGGCACCCTGGTGACCGTGTCCTCTGCGT CGACCAAGGGCCCATCGGTCTTCCCCCTGGCACCCTC CTCCAAGAGCACCTCTGGGGGCACAGCGGCCCTGGGC TGCCTGGTCAAGGACTACTTCCCCGAACCGGTGACGG TGTCGTGGAACTCAGGCGCCCTGACCAGCGGCGTGCA CACCTTCCCGGCTGTCCTACAGTCCTCAGGACTCTACT |

TABLE 3 -continued

Amino acid and nucleotide sequences of humanized antibody hu08.

| SEQ ID NO | DESCRIPTION | SEQUENCE |
|---|---|---|
| | | CCCTCAGCAGCGTGGTGACCGTGCCCTCCAGCAGCTT |
| | | GGGCACCCAGACCTACATCTGCAACGTGAATCACAAG |
| | | CCCAGCAACACCAAGGTGGACAAGAAAGTTGAGCCC |
| | | AAATCTTGTGACAAAACTCACACATGCCCACCGTGCC |
| | | CAGCACCTGAACTCCTGGGGGGACCGTCAGTCTTCCT |
| | | CTTCCCCCCAAAACCCAAGGACACCCTCATGATCTCC |
| | | CGGACCCCTGAGGTCACATGCGTGGTGGTGGACGTGA |
| | | GCCACGAAGACCCTGAGGTCAAGTTCAACTGGTACGT |
| | | GGACGGCGTGGAGGTGCATAATGCCAAGACAAAGCC |
| | | GCGGGAGGAGCAGTACAACAGCACGTACCGTGTGGT |
| | | CAGCGTCCTCACCGTCCTGCACCAGGACTGGCTGAAT |
| | | GGCAAGGAGTACAAGTGCAAGGTCTCCAACAAAGCC |
| | | CTCCCAGCCCCCATCGAGAAAACCATCTCCAAAGCCA |
| | | AAGGGCAGCCCCGAGAACCACAGGTGTACACCCTGC |
| | | CCCCATCCCGGGAGGAGATGACCAAGAACCAGGTCA |
| | | GCCTGACCTGCCTGGTCAAAGGCTTCTATCCCAGCGA |
| | | CATCGCCGTGGAGTGGGAGAGCAATGGGCAGCCGGA |
| | | GAACAACTACAAGACCACGCCTCCCGTGCTGGACTCC |
| | | GACGGCTCCTTCTTCCTCTATAGCAAGCTCACCGTGG |
| | | ACAAGAGCAGGTGGCAGCAGGGGAACGTCTTCTCAT |
| | | GCTCCGTGATGCATGAGGCTCTGCACAACCACTACAC |
| | | GCAGAAGAGCCTCTCCCTGTCCCCGGGTAAA |
| 14 | hu08-light chain nucleotide sequence | GACATCCAGATGACCCAGTCCCCCTCTTCTCTGTCTGC |
| | | CTCTGTGGGCGACAGAGTGACCATCACCTGTAAGGCC |
| | | AGTCAGGATGTAGGTACTGCTGTAGCCTGGTATCAGC |
| | | AGAAGCCTGGCAAGGCTCCCAAGCTGCTGATCTACTC |
| | | GGCATCCTACCGGTCCACTGGCGTGCCTTCCAGATTCT |
| | | CCGGCTCTGGCTCTGGCACCGATTTCACCCTGACCATC |
| | | TCCTCCCTCCAGCCTGAGGATTTCGCCACCTACTACTG |
| | | CCAGCACCATTATAGTGCTCCGTGGACGTTTGGCGGC |
| | | GGAACAAAGGTGGAGATCAAGACTGTGGCTGCACCA |
| | | TCTGTCTTCATCTTCCCGCCATCTGATGAGCAGTTGAA |
| | | ATCTGGAACTGCCTCTGTTGTGTGCCTGCTGAATAACT |
| | | TCTATCCCAGAGAGGCCAAAGTACAGTGGAAGGTGG |
| | | ATAACGCCCTCCAATCGGGTAACTCCCAGGAGAGTGT |
| | | CACAGAGCAGGACAGCAAGGACAGCACCTACAGCCT |
| | | CAGCAGCACCCTGACGCTGAGCAAAGCAGACTACGA |
| | | GAAACACAAAGTCTACGCCTGCGAAGTCACCCATCAG |
| | | GGCCTGAGCTCGCCCGTCACAAAGAGCTTCAACAGGG |
| | | GAGAGTGT |

Humanized anti-IL-13Rα2 antibody hu08 was conjugated to various linker-payload combinations of the present invention, as provided in Table 4. The antibody drug conjugates were prepared according to the methods of the present invention.

TABLE 4 anti-IL-13Rα2 ADCs.

| ADC Linker-Payload # | Corresponding ADC Nomenclature |
|---|---|
| IL13Ra2-AB08-v1010-hG1-(C)_mcValCitPABC-#54 | hu08-vc-0101 |
| IL13Ra2-AB08-v1010-hG1-(C)_mc-#115 | hu08-mc-3377 |
| IL13Ra2-AB08-v1010-hG1-(C)_mc-0#118 | hu08-mc-0131 |
| IL13Ra2-AB08-v1010-hG1-(C)_MalPeg6C2-#117 | hu08-Malpeg-6121 |
| IL13Ra2-AB08-v1010-hG1-(C)_Mal(H2O)Peg6C2-0#118 | hu08-Malpeg-0131 |
| IL13Ra2-AB08-v1010-hG1-(C)_mc-#117 | hu08-mc-6121 |
| IL13Ra2-AB08-v1010-hG1-(C)_mcValCitPABC-#226 | hu08-vc-3906 |
| IL13Ra2-AB08-v1010-hG1-(C)_mcValCitPABC-#112 | hu08-vc-6780 |
| IL13Ra2-AB08-v1010-hG1-(C)_mc-#69 | hu08-mc-8261 |
| IL13Ra2-AB08-v1010-hG1-(C)_mc-#226 | hu08-mc-3906 |
| IL13Ra2-AB08-v1010-hG1-(C)_MalPeg6C2-#69 | hu08-MalPeg-8261 |
| huIgG8.84-mcValCitPABC-#54 | huIgG8.84-vc0101 |
| huIgG8.84-mc-#115 | huIgG8.84-mc3377 |

In Vitro Cytotoxicity Assay with Anti-IL-13Rα2ADCs

Cell lines expressing the IL-13Rα2 antigen and a negative control cell line, were cultured with increasing concentrations of anti-IL-13Rα2ADCs comprising the hu08 antibody conjugated to various linker payloads of the present invention. After four days, viability of each culture was assessed. $IC_{50}$ values were calculated by logistic non-linear regression and are presented as ng Ab/mL.

The data demonstrates that the anti-IL-13Rα2 antibody huO8v1.0/1.0 conjugated to six different auristatin payloads is effective against both of the IL-13Rα2 positive cell lines tested (PC3mM2), having an $IC_{50}$ ranging from 1.1 to 4.9 ng Ab/mL or 7.3-32.7 µM (Table 5). All ADCs were not active against the IL-13Rα2 negative cell line, H460, and the non-IL-13Rα2 binding control ADCs, huIgG8.84-vc0101 and huIgG8.84-mc3377, were not active against any of the cell lines tested.

TABLE 5

$IC_{50}$ (ng Ab/mL) values of humanized anti-IL-13Rα2 ADCs.

| | | $IC_{50}$ (ng Ab/mL) | | |
|---|---|---|---|---|
| ADC | DAR | PC3MM2 | A375 | H460 |
| hu08-vc0101 | 3.2 | 2.5 | 3.8 | >400000 |
| hu08-mc3377 | 4.3 | 1.2 | 2.2 | >400000 |

TABLE 5-continued

IC$_{50}$ (ng Ab/mL) values of humanized anti-IL-13Rα2 ADCs.

| ADC | DAR | IC$_{50}$ (ng Ab/mL) | | |
|---|---|---|---|---|
| | | PC3MM2 | A375 | H460 |
| hu08-mc-0131 | 3.2 | 1.3 | 2.1 | >400000 |
| hu08-Malpeg-6121 | 3.3 | 3.5 | 3.4 | >400000 |
| hu08-Malpeg-0131 | 2.9 | 2.9 | 4.9 | >400000 |
| hu08-mc-6121 | 3.3 | 1.1 | 2.4 | >400000 |
| hu08-vc-3906 | 3 | 1.5 | 2.9 | >400000 |
| hu08 vc-6780 | 4 | 1.2 | 2.2 | >400000 |
| huIgG8.84-vc0101 | 3.7 | >400000 | >400000 | >400000 |
| huIgG8.84-mc3377 | 4.3 | >400000 | >400000 | >400000 |

In Vivo Subcutaneous Xenograft Models with Anti-IL13Rα2 ADCs

The humanized antibody hu08 specifically binds to the IL-13Rα2 receptor. hu08 ADCs with eleven different linker-payload combinations were tested in an in vivo xenograft model. Female, athymic (nude) mice were injected subcutaneous with PC3mM2. Mice with staged tumors, approximately 0.1 to 0.3 g (n=8 to 10 mice/treatment group), were administered intravenously q4d×4 with normal saline (vehicle), huO8v1.0/1.0 ADCs with linker-payloads vc-0101, vc-6780, vc-3906, mc-8261, mc-0131, mc-6121, mc-3377, MalPeg-8261, MalPeg-0131, MalPeg-6121, or MalPeg-3906, and a non-binding Ab (huIgG8.84) conjugated with vc-0101 or mc-3377, at a dose of 2 or 3 mg Ab/kg. The ADCs were dosed based on Ab content. Tumors were measured at least once a week and their size is calculated as mm$^3$=0.5× (tumor width)×(tumor length).

The in vivo efficacy results listed in Table 6 show a range of anti-tumor activity with the various ADCs tested. The relative order of potency is hu08-vc-0101>hu08-vc-6780>hu08-mc-0131>hu08-mc-6121>hu08-mc-3906>hu08-MalPeg-0131>hu08-MalPeg-6121>hu08-MalPeg-3906>>hu08-mc-8261. At the 3 mg/kg dose level, both hu08-vc-0101 and hu08-mc-3377 demonstrated antitumor activity, whereas the non-binding Ab (huIgG8.84) conjugated with vc-0101 or mc-3377 had no activity and were similar to the vehicle control.

TABLE 6

Efficacy of anti-IL-13Rα2 ADCs in PC3MM2 xenografts.

| ADC | Dose (mg/kg) Q4dx4 | PC3MM2 xenograft, tumor volume (mm$^3$ +/− SEM) | | | | | | | |
|---|---|---|---|---|---|---|---|---|---|
| | | Day −1 | Day 3 | Day 8 | Day 16 | Day 20 | Day 30 | Day 42 | Day 52 |
| Vehicle | 0 | 638 ± 27 | 1149 ± 82 | 1707 ± 133 | GT | GT | GT | GT | GT |
| hu08-MalPeg-3906 | 2 | 642 ± 36 | 1036 ± 60 | 1176 ± 51 | GT | GT | GT | GT | GT |
| hu08-mc-8261 | 2 | 642 ± 51 | 1088 ± 121 | 1429 ± 158 | GT | GT | GT | GT | GT |
| hu08-mc-0131 | 2 | 637 ± 44 | 1004 ± 73 | 778 ± 83 | GT | GT | GT | GT | GT |
| hu08-MalPeg-6121 | 2 | 638 ± 36 | 947 ± 85 | 1000 ± 126 | GT | GT | GT | GT | GT |
| hu08-MalPeg-0131 | 2 | 649 ± 39 | 1085 ± 54 | 1040 ± 88 | GT | GT | GT | GT | GT |
| hu08-vc-0101 | 2 | 646 ± 36 | 899 ± 54 | 557 ± 49 | 243 ± 28 | 201 ± 20 | 113 ± 17 | 207 ± 49 | 532 ± 151 |
| hu08-vc-6780 | 2 | 641 ± 28 | 850 ± 100 | 652 ± 54 | 279 ± 55 | 217 ± 45 | 230 ± 133 | GT | GT |
| hu08-mc-6121 | 2 | 636 ± 37 | 909 ± 63 | 821 ± 93 | GT | GT | GT | GT | GT |
| hu08-mc-3906 | 2 | 637 ± 26 | 875 ± 48 | 806 ± 70 | GT | GT | GT | GT | GT |
| hu08-MalPeg-8261 | 2 | 645 ± 34 | 991 ± 71 | 1220 ± 115 | GT | GT | GT | GT | GT |
| hu08-vc0101 | 3 | 339 ± 18 | 433 ± 45 | 38 ± 14 | 6 ± 6 | 110 ± 110 | 230 ± 230 | GT | GT |
| hu08-mc3377 | 3 | 337 ± 21 | 385 ± 36 | 41 ± 12 | 0 ± 0 | 78 ± 36 | 346 ± 147 | 616 ± 243 | 902 ± 364 |
| huIgG8.84-vc0101 | 3 | 365 ± 22 | 581 ± 47 | 1017 ± 168 | GT | GT | GT | GT | GT |
| huIgG8.84-mc3377 | 10 | 328 ± 27 | 459 ± 63 | 295 ± 121 | 544 ± 258 | GT | GT | GT | GT |

GT = group terminated due to large tumor size

Anti-Notch ADC In Vitro and In Vivo Studies

Anti-Notch Antibodies and ADCs

Humanized antibodies, hu28 and hu75, and rat-human chimeric antibodies, ch28 and ch75, specifically bind to the Notch receptor. The amino acid and nucleotide sequences for hu28 and hu75 are provided in Table 7. Kabat CDRs are underlined.

TABLE 7

Amino acid and nucleotide sequences of humanized anti-Notch antibodies.

| SEQ ID NO. | DESCRIPTION | SEQUENCES |
|---|---|---|
| 15 | hu28 Heavy Chain Variable Region amino acid sequence (CDRs underlined). | EVQLVESGGGLVQPGGSLRLSCAASGFTFR<u>DYGMT</u>WVRQAPGKGL EWVA<u>YISSGSNYIYYAEAVKG</u>RFTISRDNAKNSLYLQMNSLRAEDT AVYYCAR<u>RGPFVLDA</u>WGQGTLVTVSS |
| 16 | hu28 Heavy Chain amino acid sequence (CDRs underlined). Human IgG1 Constant Region | EVQLVESGGGLVQPGGSLRLSCAASGFTFR<u>DYGMT</u>WVRQAPGKGL EWVA<u>YISSGSNYIYYAEAVKG</u>RFTISRDNAKNSLYLQMNSLRAEDT AVYYCAR<u>RGPFVLDA</u>WGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 17 | hu28 Heavy Chain nucleotide sequence | GAGGTGCAGCTGGTGGAGTCTGGGGGAGGCTTGGTCCAGCCTGG GGGGTCCCTGAGACTCTCCTGTGCAGCCTCTGGATTCACTTTCAG GGACTATGGAATGACCTGGGTCCGCCAGGCTCCAGGGAAGGGGC TGGAGTGGGTGGCCTATATTAGTAGTGGTAGCAATTACATCTATT ATGCAGAAGCGGTGAAGGGCCGATTCACCATCTCCAGAGACAAC GCCAAGAACTCACTGTATCTGCAAATGAACAGCCTGAGAGCCGA GGACACGGCTGTGTATTACTGTGCGAGACGAGGCCCGTTTGTTTT GGATGCCTGGGGCCAGGGAACCCTGGTCACCGTCTCCTCAGCGTC GACCAAGGGCCCATCGGTCTTCCCCCTGGCACCCTCCTCCAAGAG CACCTCTGGGGGCACAGCGGCCCTGGGCTGCCTGGTCAAGGACT ACTTCCCCGAACCGGTGACGGTGTCGTGGAACTCAGGCGCCCTGA CCAGCGGCGTGCACACCTTCCCGGCTGTCCTACAGTCCTCAGGAC TCTACTCCCTCAGCAGCGTGGTGACCGTGCCCTCCAGCAGCTTGG GCACCCAGACCTACATCTGCAACGTGAATCACAAGCCCAGCAAC ACCAAGGTGGACAAGAAAGTTGAGCCCAAATCTTGTGACAAAAC TCACACATGCCCACCGTGCCCAGCACCTGAACTCCTGGGGGGACC GTCAGTCTTCCTCTTCCCCCCAAAACCCAAGGACACCCTCATGAT CTCCCGGACCCCTGAGGTCACATGCGTGGTGGTGGACGTGAGCC ACGAAGACCCTGAGGTCAAGTTCAACTGGTACGTGGACGGCGTG GAGGTGCATAATGCCAAGACAAAGCCGCGGGAGGAGCAGTACA ACAGCACGTACCGTGTGGTCAGCGTCCTCACCGTCCTGCACCAGG ACTGGCTGAATGGCAAGGAGTACAAGTGCAAGGTCTCCAACAAA GCCCTCCCAGCCCCCATCGAGAAAACCATCTCCAAAGCCAAAGG GCAGCCCCGAGAACCACAGGTGTACACCCTGCCCCCATCCCGGG AGGAGATGACCAAGAACCAGGTCAGCCTGACCTGCCTGGTCAAA GGCTTCTATCCCAGCGACATCGCCGTGGAGTGGGAGAGCAATGG GCAGCCGGAGAACAACTACAAGACCACGCCTCCCGTGCTGGACT CCGACGGCTCCTTCTTCCTCTATAGCAAGCTCACCGTGGACAAGA GCAGGTGGCAGCAGGGGAACGTCTTCTCATGCTCCGTGATGCATG AGGCTCTGCACAACCACTACACGCAGAAGAGCCTCTCCCTGTCCC CGGGT |
| 18 | hu28 Light Chain Variable Region amino acid sequence (CDRs underlined). | DIQMTQSPSSLSASVGDRVTITC<u>KASQSINRYLH</u>WYQQKPGKAPKLL IY<u>NANGLQT</u>GVPSRFSGSGSGTDFTLTISSLQPEDFATYYC<u>LQHNTWP DT</u>FGGGTKVEIK |
| 19 | hu28 Light Chain amino acid sequence (CDRs underlined). Human kappa Constant Region | DIQMTQSPSSLSASVGDRVTITC<u>KASQSINRYLH</u>WYQQKPGKAPKLL IY<u>NANGLQT</u>GVPSRFSGSGSGTDFTLTISSLQPEDFATYYC<u>LQHNTWP DT</u>FGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 20 | hu28 Light Chain nucleotide sequence | GACATCCAGATGACCCAGTCTCCATCCTCCCTGTCTGCATCTGTA GGAGACAGAGTCACCATCACTTGCAAAGCAAGTCAGAGTATTAA CAGGTACTTACACTGGTATCAGCAGAAACCAGGGAAAGCCCCTA AGCTCCTGATCTATAATGCAAACGGTTTGCAAACGGGGGTCCCAT CAAGGTTCAGTGGCAGTGGATCTGGGACAGATTTCACTCTCACCA TCAGCAGTCTGCAACCTGAAGATTTTGCAACTTACTACTGTTTGC AGCATAATACGTGGCCGGACACGTTTGGCGGAGGGACCAAGGTG GAGATCAAACGGACCGTGGCCGCTCCTTCCGTGTTCATCTTCCCC CCTTCCGACGAGCAGCTGAAGTCTGGCACCGCCTCTGTGGTGTGT CTGCTGAACAACTTCTACCCCGGGAGGCCAAGGTGCAGTGGAA GGTGGACAACGCTCTGCAGTCCGGCAACTCCCAGGAGTCTGTGA CCGAGCAGGACTCCAAGGACAGCACCTACTCCCTGTCCTCTACCC TGACCCTGTCCAAGGCCGACTACGAGAAGCACAAGGTGTACGCC TGTGAGGTGACCCACCAGGGCCTGTCCTCTCCTGTGACCAAGTCC TTCAACCGGGGCGAGTGC |

TABLE 7 -continued

Amino acid and nucleotide sequences of humanized anti-Notch antibodies.

| SEQ ID NO. | DESCRIPTION | SEQUENCES |
|---|---|---|
| 21 | hu75 Heavy Chain Variable Region amino acid sequence (CDRs underlined). | EVQLVESGGGLVQPGGSLRLSCAASGYAFT<u>DYWMT</u>WVRQAPGKGL EWVA<u>EISPNSGGTNFNEKFKG</u>RFTISVDNAKNSLYLQMNSLRAEDT AVYYCAR<u>GEIRYNWFAY</u>WGQGTLVTVSS |
| 22 | hu75 Heavy Chain amino acid sequence (CDRs underlined). Human IgG1 Constant region | EVQLVESGGGLVQPGGSLRLSCAASGYAFT<u>DYWMT</u>WVRQAPGKGL EWVA<u>EISPNSGGTNFNEKFKG</u>RFTISVDNAKNSLYLQMNSLRAEDT AVYYCAR<u>GEIRYNWFAY</u>WGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVDK SRWQQGNVFSCSVMHEALHNHYTQKSLSLSPG |
| 23 | hu75 Heavy Chain nucleotide sequence | GAGGTGCAGCTGGTGGAGTCTGGGGGAGGCTTGGTCCAGCCTGG GGGGTCCCTGAGACTCTCCTGTGCAGCCTCTGGTTATGCATTCAC TGACTACTGGATGACCTGGGTCCGCCAGGCTCCAGGGAAGGGGC TGGAGTGGGTGGCCGAAATTTCTCCTAACAGTGGTGGTACTAACT TCAATGAAAAGTTCAAGGGCCGATTCACCATCTCCGTTGACAACG CCAAGAACTCACTGTATCTGCAAATGAACAGCCTGAGAGCCGAG GACACGGCTGTGTATTACTGTGCGAGAGGGGAAATCCGTTACAA TTGGTTTGCTTACTGGGGCCAGGGAACCCTGGTCACCGTCTCCTC AGCGTCGACCAAGGGCCCATCGGTCTTCCCCCTGGCACCCTCCTC CAAGAGCACCTCTGGGGGCACAGCGGCCCTGGGCTGCCTGGTCA AGGACTACTTCCCCGAACCGGTGACGGTGTCGTGGAACTCAGGC GCCCTGACCAGCGGCGTGCACACCTTCCCGGCTGTCCTACAGTCC TCAGGACTCTACTCCCTCAGCAGCGTGGTGACCGTGCCCTCCAGC AGCTTGGGCACCCAGACCTACATCTGCAACGTGAATCACAAGCC CAGCAACACCAAGGTGGACAAGAAAGTTGAGCCCAAATCTTGTG ACAAAACTCACACATGCCCACCGTGCCCAGCACCTGAACTCCTGG GGGGACCGTCAGTCTTCCTCTTCCCCCCAAAACCCAAGGACACCC TCATGATCTCCCGGACCCCTGAGGTCACATGCGTGGTGGTGGACG TGAGCCACGAAGACCCTGAGGTCAAGTTCAACTGGTACGTGGAC GGCGTGGAGGTGCATAATGCCAAGACAAAGCCGCGGGAGGAGC AGTACAACAGCACGTACCGTGTGGTCAGCGTCCTCACCGTCCTGC ACCAGGACTGGCTGAATGGCAAGGAGTACAAGTGCAAGGTCTCC AACAAAGCCCTCCCAGCCCCCATCGAGAAAACCATCTCCAAAGC CAAAGGGCAGCCCCGAGAACCACAGGTGTACACCCTGCCCCCAT CCCGGGAGGAGATGACCAAGAACCAGGTCAGCCTGACCTGCCTG GTCAAAGGCTTCTATCCCAGCGACATCGCCGTGGAGTGGGAGAG CAATGGGCAGCCGGAGAACAACTACAAGACCACGCCTCCCGTGC TGGACTCCGACGGCTCCTTCTTCCTCTATAGCAAGCTCACCGTGG ACAAGAGCAGGTGGCAGCAGGGGAACGTCTTCTCATGCTCCGTG ATGCATGAGGCTCTGCACAACCACTACACGCAGAAGAGCCTCTC CCTGTCCCCGGGT |
| 24 | hu75 Light Chain Variable Region amino acid sequence (CDRs underlined). | DIQMTQSPSSLSASVGDRVTITC<u>KASQNVGNNIA</u>WYQQKPGKAPKL LIY<u>YASNRYT</u>GVPSRFSGSGYGTDFTLTISSLQPEDFATYYC<u>QRLYNS PFT</u>FGGGTKVEIK |
| 25 | hu75 Light Chain amino acid sequence (CDRs underlined). Human kappa Constant Region | DIQMTQSPSSLSASVGDRVTITC<u>KASQNVGNNIA</u>WYQQKPGKAPKL LIY<u>YASNRYT</u>GVPSRFSGSGYGTDFTLTISSLQPEDFATYYC<u>QRLYNS PFT</u>FGGGTKVEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 26 | hu75 Light Chain nucleotide sequence | GACATCCAGATGACCCAGTCTCCATCCTCCCTGTCTGCATCTGTA GGAGACAGAGTCACCATCACTTGCAAGGCCAGTCAGAATGTGGG TAATAATATAGCCTGGTATCAGCAGAAACCAGGGAAAGCCCCTA AGCTCCTGATCTATTATGCATCTAACCGGTACACTGGGGTCCCAT CAAGGTTCAGTGGCAGTGGATATGGGACAGATTTCACTCTCACCA TCAGCAGTCTGCAACCTGAAGATTTTGCAACTTACTACTGTCAGC GTCTTTACAATTCTCCATTCACGTTCGGCGGAGGGACCAAGGTGG AGATCAAACGGACCGTGGCCGCTCCTTCCGTGTTCATCTTCCCCC CTTCCGACGAGCAGCTGAAGTCTGGCACCGCCTCTGTGGTGTGTC TGCTGAACAACTTCTACCCCCGGGAGGCCAAGGTGCAGTGGAAG GTGGACAACGCTCTGCAGTCCGGCAACTCCCAGGAGTCTGTGACC GAGCAGGACTCCAAGGACAGCACCTACTCCCTGTCCTCTACCCTG ACCCTGTCCAAGGCCGACTACGAGAAGCACAAGGTGTACGCCTG TGAGGTGACCCACCAGGGCCTGTCCTCTCCTGTGACCAAGTCCTT CAACCGGGGCGAGTGC |

Humanized anti-Notch antibodies, hu28 and hu75, and rat-human chimeric anti-Notch antibodies, ch28 and ch75, were conjugated to various linker-payload combinations of the present invention, as provided in Table 8. The antibody drug conjugates were prepared according to the methods of the present invention.

TABLE 8

Anti-Notch ADCs.

| ADC Linker-Payload # | Corresponding ADC Nomenclature |
|---|---|
| Notch-28-v1010-hG1-(C)_mcValCitPABC-#54 | hu28-vc0101 |
| Notch-28-v1010-hG1-(C)_mcValCitPABC-#112 | hu28-vc6780 |
| Notch-75-v1913-hG1-(C)_mcValCitPABC-#54 | hu75-vc0101 |
| Notch-75-v1913-hG1-(C)_mcValCitPABC-#112 | hu75-vc6780 |
| Notch-28-cG1-(C)_mcValCitPABC-#54 | ch28-vc0101 |
| Notch-28-cG1-(C)_mcValCitPABC-#112 | ch28-vc6780 |
| Notch-28-cG1-(C)_mc-#54 | ch28-mc0101 |
| Notch-28-cG1-(C)_mc-0#118 | ch28-mc0131 |
| Notch-28-cG1-(C)_mc-#115 | ch28-mc3377 |
| Notch-28-cG1-(C)_mc-#69 | ch28-mc8261 |
| Notch-28-cG1-(C)_MalPeg6C2-0#118 | ch28-MalPeg6C2-0131 |
| Notch-28-cG1-(C)_MalPeg6C2-#69 | ch28-MalPeg6C2-8261 |
| Notch-28-cG1-(C)_me-0#118 | ch28-me0131 |
| Notch-28-cG1-(C)_m(H2O)c-0#118 | ch28-m(H2O)c-0131 |
| Notch-75-cG1-(C)_mcValCitPABC-#54 | ch75-vc0101 |
| Notch-75-cG1-(C)_mcValCitPABC-#112 | ch75-vc6780 |
| Notch-75-cG1-(C)_mc-0#118 | ch75-mc0131 |
| Notch-75-cG1-(C)_mc-#115 | ch75-mc3377 |
| Notch-75-cG1-(C)_MalPeg6C2-0#118 | ch75-MalPegC2-0131 |
| Notch-75-cG1-(C)_MalPeg6C2-#69 | ch75-MalPeg6C2-8261 |
| Notch-75-cG1-(C)_me-0#118 | ch75-me0131 |
| Notch-75-cG1-(C)_m(H2O)c-0#118 | ch75-m(H2O)c-0131 |
| huNeg8.8-(C)_mcValCitPABC-#54 | huNeg8.8-vc0101 |
| huNeg8.8-(C)_mcValCitPABC-#112 | huNeg8.8-vc6780 |
| huNeg8.8-(C)_mc-0#118 | huNeg8.8-mc0131 |
| huNeg8.8-(C)_mc-#115 | huNeg8.8-mc3377 |
| huNeg8.8-(C)_me-0#118 | huNeg8.8-me0131 |
| huNeg8.8-(C)_MalPeg6C2-#69 | huNeg8.8-MalPeg6C2-8261 |
| ch2H6-(C)_mc-#69 | ch2H6-mc8261 |

In Vitro Cytotoxicity Assays with Anti-Notch ADCs

The effects of anti-Notch ADCs were assessed on 1) cell lines endogenously expressing Notch protein: HCC2429 (lung cancer), OVCAR3 (ovarian cancer) and MDA-MB-468 (breast cancer), 2) cell lines engineered to over-express Notch protein: MDA-MB-468/hNotch and U2OS/hNotch, and 3) a negative control cell line (SW900) using an MTS cellular viability indicator (Promega, Madison, Wis.). These cell lines were cultured with increasing concentrations of anti-Notch ADCs comprising humanized anti-Notch antibodies, hu28 and hu75, and rat-human chimeric anti-Notch antibodies, ch28 and ch75, conjugated to various linker-payload combinations of the present invention. As a specificity control for the anti-Notch-ADCs, non-targeted control-ADCs (huNeg8.8-ADCs or ch2H6-ADCs) were also tested on the same cell lines. After four days, viability of each culture was assessed. $IC_{50}$ values were calculated by logistic non-linear regression and presented as ng Ab/mL. The drug antibody ratio (DAR) is also provided.

Table 9 shows $IC_{50}$ (ng Ab/mL) values of the humanized anti-Notch ADC treatments. HCC2429 and MDA-MB-468/hNotch cell lines had two individual repeats. The data demonstrates that the humanized anti-Notch ADCs with various linker-payloads were active and induced cell death in the Notch expressing and over-expressing cancer cell lines HCC2429, OVCAR3, MDA-MB-468, MDA-MB-468/hNotch, U2OS/hNotch, but not in the negative control cell line SW900 lacking Notch expression. The non-targeted control-ADCs either lacked potency (LP) and therefore $IC_{50}$ values were not generated as indicated, or were minimally active at the highest doses tested. Anti-Notch ADCs having $IC_{50}$ values equal to or higher than $IC_{50}$ values for control-ADCs were considered to lack potency in vitro and indicted as LP.

TABLE 9

$IC_{50}$ (ng Ab/mL) values of humanized anti-Notch ADCs.

$IC_{50}$ (ng Ab/mL) ± S.E.M.

| ADC | DAR | HCC2429 | OVCAR3 | MDA-MB-468 | MDA-MB-468/hNotch | U2OS/hNotch | SW900 |
|---|---|---|---|---|---|---|---|
| hu28-vc0101 | 3.9 | 473 | 2940 | 306 | 6545 | 3.2 | 3 | 1330 | LP |
| hu75-vc0101 | 3.8 | 611 | 3295 | 515 | 7001 | 37 | 36 | 523 | LP |
| huNeg8.8-vc0101 | 3.7 | 18417 | 23978 | 3770 | LP | 5122 | LP | LP | 23379 |
| hu28-vc6780 | 3.9 | 148 | 2050 | 17 | LP | 1.3 | 3 | LP | LP |
| hu75-vc6780 | 4.2 | 214 | 630 | 254 | LP | 26 | 25 | LP | LP |
| huNeg8.8-vc6780 | 4.2 | LP | LP | 9238 | LP | LP | LP | LP | LP |

Table 10 shows $IC_{50}$ (ng Ab/mL) values of the rat-human chimeric anti-Notch ADC treatments. For experiments with 2-4 individual repeats, average $IC_{50}$ values were calculated along with standard error of the mean (S.E.M.). The data demonstrates that the rat-human chimeric anti-Notch ADCs with various linker-payloads were active and induced cell death in the Notch expressing and over-expressing cancer cell lines HCC2429, OVCAR$^3$, MDA-MB-468, MDA-MB-468/hNotch, U2OS/hNotch. The non-targeted control-ADCs either lacked potency (LP) and therefore $IC_{50}$ values were not generated as indicated, or were minimally active at the highest doses tested. Anti-Notch ADCs having $IC_{50}$ values equal to or higher than $IC_{50}$ values for control-ADCs were considered to lack potency in vitro and indicted as LP.

TABLE 10

IC$_{50}$ (ng Ab/mL) values of rat-human chimeric anti-Notch ADCs (nd = not determined).

| | | IC$_{50}$ (ng Ab/mL) ± S.E.M. | | | | |
|---|---|---|---|---|---|---|
| ADC | DAR | HCC2429 | OVCAR3 | MDA-MB-468 | MDA-MB-468/ hNotch | U2OS/ hNotch |
| ch28-mc8261 | 3.7 | LP | nd | 12147 ± 4806.4 | nd | nd |
| ch2H6-mc8261 | 4.1 | LP | nd | LP | nd | nd |
| ch28-MalPeg6C2-8261 | 4.3 | LP | nd | 83 ± 35.5 | nd | nd |
| ch75-MalPeg6C2-8261 | 3.8 | LP | nd | 4255 ± 2375 | nd | nd |
| huNeg8.8-MalPeg6C2-8261 | 4.1 | LP | nd | LP | nd | nd |
| ch28-mc0131 | 3.4 | 251 ± 77.5 | 6 ± 1.0 | 35 ± 18.5 | nd | 3 ± 0.5 |
| ch75-mc0131 | 3.3 | 671 ± 406.5 | 289 | 8202 ± 2773.0 | nd | 19 |
| huNeg8.8-mc0131 | 3.9 | Nd | LP | LP | nd | LP |
| ch28-me0131 | 3.9 | 30 | 8 ± 2.0 | 24 ± 14.0 | nd | 3 ± 1.15 |
| ch75-me0131 | 3.5 | Nd | nd | 259 | nd | nd |
| huNeg8.8-me0131 | 3.7 | Nd | LP | LP | nd | LP |
| ch28-mc3377 | 3.7 | LP | 14 ± 5.5 | 27 ± 11.3 | nd | 3 ± 0.5 |
| ch75-mc3377 | 3.7 | Nd | nd | 560 | nd | nd |
| huNeg8.8-mc3377 | 3.6 | Nd | LP | LP | nd | LP |
| ch28-MalPeg6C2-0131 | 4.1 | LP | 10 ± 2.0 | 10 ± 1.0 | nd | 3 ± 0.85 |
| ch28-vc0101 | 3.8 | 3230 ± 1116.5 | 635 | 5443 ± 2630.9 | 4 ± 0.5 | 95 ± 18.2 |
| ch75-vc0101 | 2.7 | 2112 ± 826.0 | LP | 4064 ± 1793.9 | 24 ± 4.0 | LP |
| huNeg8.8-vc0101 | 3.7 | 15341 | LP | 4523 ± 2789.5 | 8833 | LP |
| ch28-vc6780 | 4.1 | 324 ± 78.9 | 90 ± 48.5 | 4407 ± 2128.2 | 3 ± 0.5 | LP |
| ch75-vc6780 | 2.8 | 1004 ± 177.0 | 922 | 6873 ± 4230.0 | 21 ± 3.5 | LP |
| huNeg8.8-vc6780 | 4.1 | LP | LP | LP | LP | LP |

In vivo Human Tumor Xenograft Models with Anti-Notch ADCs

Humanized anti-Notch antibodies, hu28 and hu75, and rat-human chimeric anti-Notch antibodies, ch28 and ch75, were conjugated to various linker-payload combinations and tested in 37622A1 non-small cell lung cancer (NSCLC), HCC2429 lung cancer, MDA-MB-468 breast cancer and N87 gastric cancer xenograft models. For each model described below the first dose was given on Day 0. The tumors were measured at least once a week and their volume was calculated with the formula: tumor volume (mm$^3$)=0.5×(tumor width$^2$)(tumor length). The mean tumor volumes (±S.E.M.) for each treatment group were calculated having a maximum of 10 animals and a minimum of 6 animals to be included.

A. 37622A1 NSCLC Xenografts

The effects of anti-Notch ADCs were examined in immunodeficient mice on the in vivo growth of human tumor xenografts that were established from fragments of freshly resected 37622A1 NSCLC tumors obtained in accordance with appropriate consent procedures (Asterand). The 37622A1 NSCLC patient-derived xenografts were subcutaneously passaged in vivo as fragments from animal to animal in nude (Nu/Nu) female mice. When the tumors reached a volume of 150 to 300 mm$^3$, they were staged to ensure uniformity of the tumor size among various treatment groups. The 37622A1 NSCLC model was dosed intravenously four times every four days (Q4dx4) with PBS vehicle, humanized anti-Notch ADCs, control huNeg-8.8 ADCs and cisplatin at the doses provided in Table 11.

Cisplatin is a platinum-based anti-cancer agent used in the treatment of cancer and considered a standard-of-care therapy. Cisplatin cross-links DNA thereby inducing apoptosis and cell growth inhibition. The data demonstrates that anti-Notch ADCs hu28-vc0101, hu28-vc6780, hu75-vc0101 and hu75-vc6780 inhibited growth of 37622A1 NSCLC xenografts. Further, the data shows that anti-Notch ADCs inhibited tumor growth more potently than control huNeg8.8-ADCs. Furthermore, the data shows that anti-Notch ADCs inhibited tumor growth more potently than cisplatin indicating a greater potency than a platinum-based standard-of-care chemotherapeutic drug.

TABLE 11

Efficacy of anti-Notch ADCs in 37622A1 NSCLC xenografts.

| | 37622A1 NSCLC xenografts, tumor volume (mm$^3$ ± SEM) | | | | | | | |
|---|---|---|---|---|---|---|---|---|
| | PBS | hu28-vc0101 | hu28-vc6780 | hu75-vc0101 | hu75-vc6780 | huNeg-8.8-vc0101 | huNeg-8.8-vc6780 | Cisplatin |
| | | | | Dose mg/kg | | | | |
| | 0 | 3 | 10 | 3 | 10 | 3 | 10 | 5 |
| DAY −1 | 187 ± 10 | 186 ± 13 | 182 ± 16 | 185 ± 17 | 183 ± 17 | 184 ± 18 | 182 ± 17 | 185 ± 11 |
| DAY 4 | 227 ± 19 | 202 ± 16 | 176 ± 13 | 200 ± 16 | 205 ± 23 | 225 ± 17 | 226 ± 26 | 226 ± 15 |
| DAY 7 | 279 ± 24 | 202 ± 15 | 176 ± 19 | 227 ± 16 | 195 ± 22 | 274 ± 18 | 265 ± 28 | 280 ± 29 |
| DAY 11 | 371 ± 42 | 130 ± 11 | 122 ± 10 | 175 ± 20 | 147 ± 23 | 309 ± 26 | 246 ± 30 | 301 ± 34 |
| DAY 14 | 419 ± 49 | 119 ± 11 | 95 ± 7 | 156 ± 19 | 118 ± 18 | 303 ± 26 | 277 ± 41 | 345 ± 47 |
| DAY 18 | 516 ± 63 | 71 ± 6 | 65 ± 6 | 112 ± 16 | 93 ± 14 | 298 ± 28 | 219 ± 31 | 309 ± 37 |
| DAY 21 | 562 ± 65 | 55 ± 6 | 56 ± 6 | 122 ± 27 | 98 ± 20 | 320 ± 41 | 218 ± 42 | 373 ± 50 |
| DAY 25 | 610 ± 78 | 49 ± 6 | 51 ± 6 | 137 ± 33 | 93 ± 24 | 315 ± 52 | 264 ± 52 | 401 ± 58 |
| DAY 28 | 624 ± 94 | 41 ± 7 | 51 ± 8 | 161 ± 53 | 99 ± 26 | 358 ± 61 | 246 ± 51 | 446 ± 64 |
| DAY 32 | 817 ± 99 | 42 ± 13 | 72 ± 15 | 175 ± 52 | 165 ± 45 | 398 ± 64 | 332 ± 77 | 482 ± 62 |

TABLE 11-continued

Efficacy of anti-Notch ADCs in 37622A1 NSCLC xenografts.

37622A1 NSCLC xenografts, tumor volume (mm³ ± SEM)

| | PBS | hu28-vc0101 | hu28-vc6780 | hu75-vc0101 | hu75-vc6780 | huNeg-8.8-vc0101 | huNeg-8.8-vc6780 | Cisplatin |
|---|---|---|---|---|---|---|---|---|
| | | | | Dose mg/kg | | | | |
| | 0 | 3 | 10 | 3 | 10 | 3 | 10 | 5 |
| DAY 35 | 900 ± 104 | 42 ± 11 | 92 ± 21 | 271 ± 79 | 229 ± 59 | 487 ± 79 | 384 ± 94 | 587 ± 80 |
| DAY 39 | 960 ± 117 | 62 ± 26 | 120 ± 31 | 319 ± 103 | 294 ± 78 | 569 ± 102 | 431 ± 114 | 591 ± 83 |
| DAY 42 | 931 ± 108 | 75 ± 34 | 151 ± 37 | 357 ± 113 | 318 ± 71 | 590 ± 101 | 495 ± 128 | 612 ± 92 |
| DAY 46 | 1037 102 | 92 ± 44 | 172 ± 47 | 431 ± 137 | 412 ± 106 | 743 ± 133 | 610 ± 165 | 723 ± 119 |
| DAY 49 | 1119 ± 120 | 120 ± 63 | 248 ± 62 | 519 ± 135 | 521 ± 132 | 810 ± 121 | 718 ± 202 | 853 ± 139 |
| DAY 53 | 1345 ± 158 | 144 ± 67 | 339 ± 93 | 678 ± 195 | 629 ± 162 | 989 ± 146 | 848 ± 251 | 970 ± 193 |
| DAY 56 | 1485 ± 185 | 126 ± 51 | 376 ± 100 | 818 ± 251 | 808 ± 196 | 1149 ± 191 | 776 ± 184 | 1215 ± 231 |
| DAY 60 | 1691 ± 220 | 180 ± 85 | 503 ± 138 | 710 ± 162 | 917 ± 209 | 1287 ± 194 | 964 ± 232 | 1428 ± 273 |
| DAY 63 | 1736 ± 193 | 223 ± 111 | 604 ± 160 | 824 ± 191 | 917 ± 147 | 1503 ± 227 | 1097 ± 254 | — |
| DAY 67 | — | 296 ± 152 | 888 ± 272 | 938 ± 202 | 1116 ± 173 | 1600 ± 251 | 1167 ± 260 | — |
| DAY 70 | — | 312 ± 162 | 773 ± 235 | 953 ± 209 | 1181 ± 203 | — | 1352 ± 305 | — |
| DAY 74 | — | 331 ± 160 | 881 ± 264 | — | — | — | — | — |
| DAY 77 | — | 422 ± 210 | 1029 ± 325 | — | — | — | — | — |
| DAY 81 | — | 510 ± 248 | — | — | — | — | — | — |
| DAY 84 | — | 622 ± 322 | — | — | — | — | — | — |

B. HCC2429 Lung Xenografts

Similar in vivo experiments were performed with the HCC2429 lung cancer cell line as described above. To generate xenografts, nude (Nu/Nu) female mice were implanted subcutaneously with 3.5×10⁶ HCC2429 cells in 50% Matrigel (BD Biosciences). When the tumors reached a volume of 200 to 400 mm³, the tumors were staged to ensure uniformity of the tumor mass among various treatment groups. The HCC2429 lung model was dosed intraveneously Q4dx4 with PBS vehicle, humanized anti-Notch ADCs and control huNeg-8.8 ADCs at the doses provided in Tables 12 and 13.

The data demonstrates that anti-Notch ADCs hu28-vc0101, hu28-vc6780, hu75-vc0101 and hu75-vc6780 inhibited growth of HCC2429 lung xenografts in a dose-dependent manner. Further, the data shows that anti-Notch ADCs inhibited tumor growth more potently than control huNeg8.8-ADCs at the 1 and 3 mg/kg doses for anti-Notch ADCs with vc0101 linker-payloads and at the 3 and 10 mg/kg doses for anti-Notch ADCs with vc6780 linker-payloads. Furthermore, the data demonstrates that a 3 mg/kg dose of hu28-vc0101 was more potent than a 10 mg/kg dose of hu28-vc6780.

TABLE 12

Efficacy of anti-Notch-vc0101 ADCs in HCC2429 lung xenografts.

HCC2429 Lung xenografts, tumor volume (mm³ +/− SEM)

| | PBS | hu28-vc0101 | | | hu75-vc0101 | | | huNeg-8.8-vc0101 | | |
|---|---|---|---|---|---|---|---|---|---|---|
| | | | | | Dose mg/kg | | | | | |
| | 0 | 3 | 1 | 0.3 | 3 | 1 | 0.3 | 3 | 1 | 0.3 |
| DAY −1 | 245 ± 24 | 245 ± 23 | 246 ± 26 | 246 ± 30 | 245 ± 28 | 246 ± 23 | 247 ± 29 | 244 ± 30 | 245 ± 33 | 246 ± 27 |
| DAY 1 | 529 ± 52 | 548 ± 52 | 532 ± 36 | 528 ± 50 | 498 ± 39 | 548 ± 37 | 524 ± 66 | 482 ± 59 | 519 ± 72 | 514 ± 50 |
| DAY 3 | 742 ± 73 | 606 ± 78 | 757 ± 68 | 733 ± 78 | 498 ± 44 | 753 ± 93 | 713 ± 74 | 695 ± 91 | 756 ± 97 | 724 ± 73 |
| DAY 6 | 1205 ± 120 | 723 ± 101 | 1095 ± 119 | 1112 ± 132 | 469 ± 70 | 1096 ± 146 | 1078 ± 74 | 1075 ± 132 | 1144 ± 100 | 1207 ± 100 |
| DAY 8 | 1720 ± 181 | 696 ± 100 | 1324 ± 173 | 1617 ± 172 | 407 ± 71 | 1428 ± 200 | 1499 ± 115 | 1404 ± 183 | 1598 ± 133 | 1683 ± 165 |
| DAY 10 | 2312 ± 197 | 620 ± 90 | 1606 ± 250 | 2027 ± 233 | 370 ± 81 | 1611 ± 189 | 1830 ± 120 | 1735 ± 253 | 1974 ± 185 | 2163 ± 260 |
| DAY 13 | 3235 ± 120 | 543 ± 92 | 1717 ± 223 | 2642 ± 297 | 273 ± 69 | 1803 ± 208 | 2408 ± 226 | 2162 ± 376 | 2676 ± 346 | 2589 ± 287 |
| DAY 15 | — | 512 ± 111 | 1865 ± 263 | — | 298 ± 88 | 1871 ± 232 | — | — | — | — |
| DAY 17 | — | 442 ± 114 | 2228 ± 333 | — | 250 ± 77 | 1948 ± 228 | — | — | — | — |
| DAY 20 | — | 428 ± 144 | — | — | 177 ± 44 | — | — | — | — | — |
| DAY 23 | — | 405 ± 149 | — | — | 160 ± 35 | — | — | — | — | — |
| DAY 27 | — | 422 ± 164 | — | — | 174 ± 51 | — | — | — | — | — |
| DAY 30 | — | 394 ± 182 | — | — | 196 ± 72 | — | — | — | — | — |
| DAY 34 | — | 505 ± 236 | — | — | 295 ± 121 | — | — | — | — | — |
| DAY 37 | — | 606 ± 283 | — | — | 433 ± 179 | — | — | — | — | — |
| DAY 41 | — | 750 ± 361 | — | — | 606 ± 259 | — | — | — | — | — |
| DAY 45 | — | 872 ± 415 | — | — | 836 ± 359 | — | — | — | — | — |
| DAY 49 | — | 558 ± 303 | — | — | 732 ± 350 | — | — | — | — | — |
| DAY 52 | — | 571 ± 310 | — | — | — | — | — | — | — | — |
| DAY 56 | — | 704 ± 399 | — | — | — | — | — | — | — | — |

TABLE 13

Efficacy of anti-Notch-vc6780 ADCs in HCC2429 lung xenografts.

| | | | | HCC2429 Lung xenografts, tumor volume (mm³ ± SEM) | | | | | |
|---|---|---|---|---|---|---|---|---|---|
| PBS | hu28-vc6780 | | | hu75-vc6780 | | | huNeg-8.8-vc6780 | | |
| | | | | Dose mg/kg | | | | | |
| 0 | 10 | 3 | 1 | 10 | 3 | 1 | 10 | 3 | 1 |
| DAY −1 | | | | | | | | | |
| 245 ± 28 | 244 ± 22 | 245 ± 24 | 245 ± 27 | 244 ± 19 | 246 ± 30 | 245 ± 16 | 244 ± 22 | 244 ± 26 | 245 ± 20 |
| DAY 1 | | | | | | | | | |
| 398 ± 50 | 369 ± 31 | 379 ± 45 | 400 ± 66 | 407 ± 43 | 403 ± 51 | 418 ± 34 | 429 ± 56 | 427 ± 49 | 402 ± 53 |
| DAY 3 | | | | | | | | | |
| 701 ± 102 | 318 ± 31 | 493 ± 65 | 579 ± 113 | 339 ± 36 | 526 ± 74 | 629 ± 65 | 619 ± 62 | 689 ± 83 | 655 ± 97 |
| DAY 5 | | | | | | | | | |
| 949 ± 140 | 228 ± 28 | 609 ± 82 | 826 ± 191 | 251 ± 33 | 615 ± 98 | 916 ± 97 | 808 ± 101 | 965 ± 114 | 837 ± 117 |
| DAY 7 | | | | | | | | | |
| 1345 ± 200 | 172 ± 22 | 638 ± 86 | 1023 ± 259 | 225 ± 24 | 615 ± 115 | 1164 ± 131 | 1072 ± 154 | 1380 ± 136 | 1099 ± 172 |
| DAY 10 | | | | | | | | | |
| 2045 ± 356 | 143 ± 22 | 784 ± 115 | 1439 ± 398 | 198 ± 24 | 717 ± 129 | 1705 ± 184 | 1452 ± 210 | 2082 ± 192 | 1722 ± 363 |
| DAY 12 | | | | | | | | | |
| — | 134 ± 20 | 883 ± 132 | 1442 ± 487 | 166 ± 22 | 807 ± 130 | 2029 ± 270 | 1673 ± 290 | 2701 ± 228 | 1586 ± 337 |
| DAY 14 | | | | | | | | | |
| — | 115 ± 16 | 895 ± 175 | — | 150 ± 22 | 831 ± 145 | 2294 ± 287 | 1809 ± 314 | — | — |
| DAY 17 | | | | | | | | | |
| — | 127 ± 18 | 1105 ± 253 | — | 158 ± 32 | 1017 ± 178 | — | — | — | — |
| DAY 20 | | | | | | | | | |
| — | 149 ± 27 | 1219 ± 311 | — | 164 ± 48 | 1297 ± 231 | — | — | — | — |
| DAY 24 | | | | | | | | | |
| — | 206 ± 60 | 1618 ± 468 | — | 261 ± 89 | 1813 ± 343 | — | — | — | — |
| DAY 27 | | | | | | | | | |
| — | 290 ± 100 | — | — | 316 ± 135 | 1970 ± 462 | — | — | — | — |
| DAY 31 | | | | | | | | | |
| — | 378 ± 150 | — | — | 438 ± 201 | — | — | — | — | — |
| DAY 34 | | | | | | | | | |
| — | 551 ± 244 | — | — | 423 ± 177 | — | — | — | — | — |
| DAY 38 | | | | | | | | | |
| — | 718 ± 332 | — | — | 504 ± 203 | — | — | — | — | — |
| DAY 42 | | | | | | | | | |
| — | 1011 ± 504 | — | — | 655 ± 266 | — | — | — | — | — |
| DAY 46 | | | | | | | | | |
| — | — | — | — | 793 ± 320 | — | — | — | — | — |
| DAY 49 | | | | | | | | | |
| — | — | — | — | 901 ± 351 | — | — | — | — | — |
| DAY 53 | | | | | | | | | |
| — | — | — | — | 1228 ± 472 | — | — | — | — | — |

The HCC2429 lung model was also dosed intravenously Q4dx4 with PBS vehicle, rat-human chimeric anti-Notch ADCs and control huNeg-8.8 ADCs, at a dose of 5 mg/kg as provided in FIG. 8A. The data demonstrates that anti-Notch ADCs with non-cleavable (mc) and cleavable (vc) linkers and various payload combinations inhibited growth of HCC2429 lung xenografts. Further, the data shows that rat-human chimeric anti-Notch ADCs inhibited tumor growth more potently than control huNeg8.8-ADCs. Furthermore, the data demonstrates that rat-human chimeric anti-Notch ADCs with vc0101 linker-payloads were more potent than the other anti-Notch ADCs tested.

C. MDA-MB-468 Breast Xenografts

Similar in vivo experiments were performed with the MDA-MB-468 breast cancer cell line as described above. MDA-MB-468 cells are classified as a triple-negative breast cancer (TNBC) basal-like subtype since they lack expression of the estrogen receptor, progesterone receptor and human epidermal growth factor receptor 2 (HER$^2$) (Lehmann, B D, et al, J Clin Invest. 2011; 121(7):2750-2767). To generate xenografts, female SCID Hairless Outbred (SHO) mice were orthotopically implanted with 10×10$^6$ MDA-MB-468 cells containing 50% Matrigel (BD Biosciences) in the mammary fat pad. When the tumors reached a volume of 250 to 450 mm³, the tumors were staged to ensure uniformity of the tumor mass among various treatment groups. The MDA-MB-468 breast model was dosed intravenously Q4dx4 with PBS vehicle, humanized anti-Notch ADCs and control huNeg-8.8 ADCs at the doses provided in Tables 14 and 15. The data demonstrates that anti-Notch ADCs hu28-vc0101, hu28-vc6780, hu75-vc0101 and hu75-vc6780 inhibited growth of MDA-MB-468 breast xenografts in a dose-dependent manner. Further, the data shows that anti-Notch ADCs inhibited tumor growth more potently than control huNeg8.8-ADCs at the 1 and 3 mg/kg doses for ADCs with vc0101 linker-payloads and 1, 3 and 10 mg/kg doses for ADC with vc6780 linker-payloads. Furthermore, the data demonstrates that a 1 mg/kg dose of anti-Notch ADCs with vc0101 linker-payloads were more potent than a 3 mg/kg dose of anti-Notch ADCs with vc6780 linker-payloads.

TABLE 14

Efficacy of anti-Notch-vc0101 ADCs in MDA-MB-468 breast xenografts.

MDA-MB-468 Breast xenografts, tumor volume (mm³ ± SEM)

| | PBS | hu28-vc0101 | | | hu75-vc0101 | | | huNeg-8.8-vc0101 | | |
|---|---|---|---|---|---|---|---|---|---|---|
| | | | | | Dose mg/kg | | | | | |
| | 0 | 3 | 1 | 0.3 | 3 | 1 | 0.3 | 3 | 1 | 0.3 |
| DAY 0 | 343 ± 12 | 347 ± 15 | 348 ± 22 | 336 ± 19 | 347 ± 20 | 347 ± 22 | 348 ± 21 | 334 ± 23 | 346 ± 16 | 344 ± 19 |
| DAY 4 | 441 ± 24 | 359 ± 24 | 439 ± 21 | 403 ± 28 | 444 ± 28 | 410 ± 32 | 439 ± 31 | 424 ± 29 | 447 ± 32 | 442 ± 19 |
| DAY 7 | 469 ± 32 | 326 ± 27 | 415 ± 25 | 395 ± 38 | 338 ± 20 | 383 ± 33 | 435 ± 27 | 411 ± 26 | 449 ± 20 | 438 ± 23 |
| DAY 11 | 495 ± 28 | 227 ± 27 | 372 ± 34 | 412 ± 42 | 277 ± 22 | 373 ± 33 | 504 ± 38 | 439 ± 36 | 538 ± 23 | 496 ± 37 |
| DAY 14 | 581 ± 35 | 147 ± 20 | 314 ± 27 | 488 ± 45 | 181 ± 19 | 350 ± 40 | 507 ± 30 | 445 ± 29 | 592 ± 47 | 560 ± 36 |
| DAY 18 | 639 ± 43 | 77 ± 10 | 261 ± 33 | 497 ± 55 | 90 ± 12 | 296 ± 33 | 587 ± 44 | 479 ± 42 | 619 ± 42 | 578 ± 36 |
| DAY 21 | 638 ± 46 | 16 ± 8 | 219 ± 41 | 509 ± 60 | 60 ± 9 | 260 ± 49 | 590 ± 55 | 481 ± 34 | 676 ± 46 | 627 ± 30 |
| DAY 26 | 707 ± 41 | 0 ± 0 | 253 ± 61 | 590 ± 66 | 16 ± 10 | 267 ± 59 | 652 ± 64 | 548 ± 41 | 793 ± 54 | 671 ± 56 |
| DAY 29 | 749 ± 59 | 0 ± 0 | 238 ± 64 | — | 8 ± 8 | 261 ± 62 | 675 ± 63 | — | 819 ± 73 | 669 ± 37 |
| DAY 32 | 812 ± 80 | 0 ± 0 | 266 ± 67 | — | 7 ± 7 | 264 ± 67 | 738 ± 70 | — | 913 ± 72 | 758 ± 44 |
| DAY 35 | 891 ± 79 | 0 ± 0 | 271 ± 73 | — | 0 ± 0 | 326 ± 86 | 821 ± 69 | — | 1023 ± 96 | 848 ± 58 |
| DAY 39 | 892 ± 84 | 0 ± 0 | 310 ± 88 | — | 0 ± 0 | 324 ± 81 | 864 ± 74 | — | — | 884 ± 64 |
| DAY 42 | 1037 ± 104 | 0 ± 0 | 349 ± 95 | — | 0 ± 0 | 381 ± 94 | 997 ± 84 | — | — | 1002 ± 55 |
| DAY 47 | 1173 ± 134 | 0 ± 0 | 394 ± 123 | — | 0 ± 0 | 442 ± 69 | — | — | — | 1145 ± 78 |
| DAY 50 | — | 0 ± 0 | 377 ± 118 | — | 0 ± 0 | 484 ± 89 | — | — | — | 1120 ± 67 |
| DAY 53 | — | 0 ± 0 | 414 ± 127 | — | 0 ± 0 | 452 ± 78 | — | — | — | 1229 ± 100 |
| DAY 56 | — | 0 ± 0 | 470 ± 128 | — | 0 ± 0 | 535 ± 93 | — | — | — | 1314 ± 120 |
| DAY 60 | — | 0 ± 0 | 532 ± 140 | — | 0 ± 0 | 603 ± 98 | — | — | — | — |
| DAY 63 | — | 0 ± 0 | 509 ± 117 | — | 0 ± 0 | — | — | — | — | — |
| DAY 67 | — | 0 ± 0 | 611 ± 148 | — | 0 ± 0 | — | — | — | — | — |
| DAY 70 | — | 0 ± 0 | — | — | 0 ± 0 | — | — | — | — | — |

TABLE 15

Efficacy of anti-Notch-vc6780 ADCs in MDA-MB-468 breast xenografts.

MDA-MB-468 Breast xenografts, tumor volume (mm³ ± SEM)

| | PBS | hu28-vc6780 | | | hu75-vc6780 | | | huNeg-8.8-vc6780 | | |
|---|---|---|---|---|---|---|---|---|---|---|
| | | | | | Dose mg/kg | | | | | |
| | 0 | 10 | 3 | 1 | 10 | 3 | 1 | 10 | 3 | 1 |
| DAY 0 | 342 ± 9 | 335 ± 9 | 342 ± 18 | 342 ± 16 | 343 ± 10 | 344 ± 11 | 340 ± 14 | 339 ± 18 | 341 ± 12 | 346 ± 16 |
| DAY 4 | 466 ± 20 | 395 ± 19 | 394 ± 33 | 462 ± 22 | 418 ± 15 | 406 ± 22 | 423 ± 27 | 432 ± 45 | 457 ± 23 | 466 ± 29 |
| DAY 7 | 481 ± 17 | 350 ± 19 | 399 ± 24 | 452 ± 30 | 370 ± 18 | 378 ± 21 | 434 ± 29 | 449 ± 45 | 529 ± 24 | 528 ± 25 |
| DAY 11 | 611 ± 44 | 248 ± 26 | 380 ± 25 | 512 ± 35 | 302 ± 21 | 403 ± 21 | 471 ± 39 | 504 ± 38 | 599 ± 23 | 621 ± 43 |
| DAY 14 | 610 ± 19 | 154 ± 23 | 401 ± 30 | 507 ± 38 | 228 ± 19 | 370 ± 28 | 470 ± 44 | 503 ± 64 | 622 ± 31 | 639 ± 48 |
| DAY 19 | 707 ± 34 | 65 ± 17 | 438 ± 39 | 538 ± 47 | 112 ± 23 | 339 ± 19 | 536 ± 49 | 437 ± 54 | 697 ± 36 | 713 ± 48 |
| DAY 22 | — | 25 ± 16 | 414 ± 41 | 551 ± 48 | 52 ± 21 | 360 ± 17 | 552 ± 44 | 415 ± 54 | — | — |
| DAY 25 | — | 26 ± 19 | 491 ± 37 | 575 ± 55 | 63 ± 25 | 381 ± 23 | 597 ± 48 | 421 ± 76 | — | — |
| DAY 28 | — | 15 ± 15 | 497 ± 68 | 654 ± 74 | 64 ± 26 | 443 ± 33 | 660 ± 53 | 451 ± 84 | — | — |
| DAY 32 | — | 0 ± 0 | 524 ± 69 | 653 ± 82 | 71 ± 31 | 437 ± 28 | 634 ± 74 | 456 ± 94 | | |
| DAY 35 | — | 0 ± 0 | — | 734 ± 89 | 85 ± 38 | 495 ± 33 | 742 ± 80 | 541 ± 108 | — | — |
| DAY 40 | — | 0 ± 0 | — | 761 ± 99 | 125 ± 44 | 535 ± 41 | 794 ± 87 | 563 ± 109 | — | — |
| DAY 43 | — | 0 ± 0 | — | 816 ± 122 | 134 ± 42 | 619 ± 47 | 878 ± 78 | 581 ± 120 | — | — |
| DAY 46 | — | 0 ± 0 | — | 859 ± 126 | 143 ± 42 | 636 ± 38 | 868 ± 99 | 617 ± 116 | — | — |
| DAY 49 | — | 0 ± 0 | — | 948 ± 178 | 159 ± 44 | 723 ± 71 | 996 ± 109 | 733 ± 129 | — | — |
| DAY 53 | — | 0 ± 0 | — | 1008 ± 192 | 201 ± 63 | 795 ± 67 | — | 758 ± 163 | — | — |
| DAY 56 | — | 0 ± 0 | — | — | 211 ± 63 | 819 ± 77 | — | — | — | — |
| DAY 60 | — | 0 ± 0 | — | — | 240 ± 63 | 976 ± 115 | — | — | — | — |
| DAY 63 | — | 0 ± 0 | — | — | 201 ± 57 | — | — | — | — | — |

The MDA-MB-468 breast model was also dosed intravenously Q4dx4 with PBS vehicle, rat-human chimeric anti-Notch ADCs and control huNeg-8.8 ADCs, at a dose of 5 mg/kg as provided in FIGS. 8B and 8C. The data demonstrates that rat-human chimeric anti-Notch ADCs with non-cleavable (mc) and cleavable (vc) linkers and various payload combinations inhibited growth of MDA-MB-468 breast xenografts. Further, the data shows that rat-human chimeric anti-Notch ADCs inhibited tumor growth more potently than control huNeg8.8-ADCs. Furthermore, the data demonstrates that rat-human chimeric anti-Notch ADCs with vc0101 linker-payloads were more potent than the other rat-human chimeric anti-Notch ADCs tested.

D. N87 Gastric Xenografts

Similar in vivo experiments were performed with the N87 gastric cancer cell line as described above. To generate xenografts, nude (Nu/Nu) female mice were implanted subcutaneously with 7.5×10⁶ N87 cells in 50% Matrigel (BD Biosciences). When the tumors reached a volume of 250 to 450 mm³, the tumors were staged to ensure uniformity of the tumor mass among various treatment groups. The N87 gastric model was dosed intraveneously Q4dx4 with PBS vehicle, humanized anti-Notch ADCs, control huNeg-8.8 ADCs and cisplatin at the doses provided in Tables 16 and 17. The data demonstrates that anti-Notch ADCs hu28-vc0101, hu28-vc6780, hu75-vc0101 and hu75-vc6780 inhibited growth of N87 gastric xenografts in a dose-dependent manner. Further, the data shows that anti-Notch ADCs inhibited tumor growth more potently than control huNeg8.8-ADCs at the 1, 3, 5 mg/kg doses for ADCs with vc0101 linker-payloads and 3 and 10 mg/kg doses for ADCs with vc6780 linker-payloads. Furthermore, the data demonstrates that ADCs with vc0101 linker-payloads were in general more potent than cisplatin standard-of-care therapy and ADCs with vc6780 linker-payloads.

TABLE 16

Efficacy of anti-Notch-vc0101 ADCs in N87 gastric xenografts.

N87 Gastric xenografts, tumor volume (mm³ ± SEM)

| | PBS | hu28-vc0101 | | | hu75-vc0101 | | | huNeg-8.8-vc0101 | | | Cisplatin |
|---|---|---|---|---|---|---|---|---|---|---|---|
| | | | | | Dose mg/kg | | | | | | |
| | 0 | 1 | 3 | 5 | 1 | 3 | 5 | 1 | 3 | 5 | 5 |
| DAY 0 | 327 ± 11 | 321 ± 21 | 326 ± 13 | 321 ± 8 | 321 ± 9 | 324 ± 19 | 320 ± 11 | 327 ± 18 | 324 ± 11 | 321 ± 16 | 328 ± 20 |
| DAY 4 | 526 ± 19 | 369 ± 18 | 339 ± 11 | 344 ± 14 | 392 ± 15 | 362 ± 35 | 315 ± 15 | 437 ± 34 | 478 ± 19 | 423 ± 32 | 414 ± 27 |
| DAY 7 | 706 ± 27 | 429 ± 43 | 302 ± 10 | 272 ± 7 | 417 ± 25 | 303 ± 21 | 246 ± 12 | 584 ± 54 | 625 ± 34 | 512 ± 34 | 520 ± 26 |
| DAY 11 | 854 ± 36 | 304 ± 30 | 182 ± 14 | 152 ± 13 | 331 ± 21 | 174 ± 14 | 156 ± 10 | 702 ± 60 | 716 ± 53 | 501 ± 38 | 501 ± 29 |
| DAY 14 | 887 ± 45 | 282 ± 25 | 191 ± 5 | 155 ± 13 | 305 ± 17 | 172 ± 10 | 151 ± 7 | 822 ± 65 | 823 ± 42 | 549 ± 37 | 637 ± 31 |
| DAY 18 | 1045 ± 68 | 263 ± 24 | 161 ± 7 | 138 ± 11 | 267 ± 17 | 151 ± 10 | 128 ± 6 | 823 ± 73 | 789 ± 33 | 491 ± 51 | — |
| DAY 21 | 1072 ± 76 | 227 ± 23 | 123 ± 15 | 110 ± 9 | 218 ± 23 | 130 ± 5 | 115 ± 7 | 857 ± 78 | 785 ± 35 | 413 ± 50 | — |
| DAY 26 | 1303 ± 140 | 205 ± 32 | 108 ± 16 | 69 ± 16 | 185 ± 24 | 92 ± 14 | 82 ± 10 | 895 ± 126 | 825 ± 62 | 343 ± 63 | — |
| DAY 29 | 1276 ± 139 | 180 ± 30 | 99 ± 14 | 50 ± 13 | 211 ± 37 | 104 ± 16 | 75 ± 12 | 957 ± 126 | 879 ± 72 | 411 ± 89 | — |
| DAY 33 | 1480 ± 183 | 211 ± 43 | 106 ± 17 | 43 ± 14 | 251 ± 53 | 91 ± 18 | 73 ± 12 | 988 ± 180 | 966 ± 98 | 411 ± 89 | — |
| DAY 36 | — | 215 ± 42 | 122 ± 22 | 52 ± 16 | 272 ± 59 | 86 ± 18 | 85 ± 9 | 884 ± 143 | 1023 ± 106 | 481 ± 86 | — |
| DAY 39 | — | 261 ± 54 | 128 ± 23 | 45 ± 14 | 304 ± 72 | 59 ± 16 | 72 ± 13 | 937 ± 167 | 1142 ± 121 | 535 ± 128 | — |
| DAY 42 | — | 283 ± 52 | 149 ± 25 | 34 ± 15 | 314 ± 73 | 81 ± 22 | 74 ± 13 | 1008 ± 179 | 1240 ± 143 | 596 ± 119 | — |
| DAY 47 | — | 262 ± 64 | 105 ± 19 | 25 ± 14 | 334 ± 95 | 80 ± 25 | 36 ± 8 | 1061 ± 210 | 1380 ± 153 | 621 ± 137 | — |
| DAY 53 | — | 302 ± 75 | 104 ± 30 | 29 ± 16 | 393 ± 115 | 86 ± 24 | 69 ± 13 | — | — | 757 ± 189 | — |
| DAY 62 | — | 415 ± 111 | 116 ± 47 | 33 ± 18 | 463 ± 155 | 106 ± 35 | 50 ± 15 | — | — | 690 ± 122 | — |
| DAY 70 | — | 521 ± 135 | 139 ± 54 | 58 ± 30 | 658 ± 241 | 148 ± 54 | 76 ± 22 | — | — | 852 ± 150 | — |

TABLE 17

Efficacy of anti-Notch-vc6780 ADCs in N87 gastric xenografts.

N87 Gastric xenografts, tumor volume (mm³ ± SEM)

| | PBS | hu28-vc6780 | | | hu75-vc6780 | | | huNeg8.8-vc6780 | | |
|---|---|---|---|---|---|---|---|---|---|---|
| | | | | | Dose mg/kg | | | | | |
| | 0 | 10 | 3 | 1 | 10 | 3 | 1 | 10 | 3 | |
| DAY 0 | 345 ± 14 | 350 ± 14 | 349 ± 10 | 348 ± 13 | 349 ± 8 | 351 ± 20 | 359 ± 16 | 356 ± 20 | 344 ± 14 | |
| DAY 4 | 600 ± 16 | 434 ± 24 | 552 ± 24 | 560 ± 26 | 468 ± 18 | 545 ± 37 | 552 ± 40 | 581 ± 60 | 537 ± 36 | |
| DAY 8 | 675 ± 20 | 379 ± 12 | 545 ± 37 | 592 ± 44 | 351 ± 24 | 511 ± 31 | 568 ± 62 | 605 ± 67 | 670 ± 45 | |
| DAY 11 | 763 ± 54 | 315 ± 18 | 511 ± 25 | 617 ± 48 | 316 ± 25 | 544 ± 43 | 591 ± 63 | 636 ± 79 | 706 ± 38 | |
| DAY 14 | 886 ± 72 | 292 ± 24 | 564 ± 29 | 782 ± 60 | 269 ± 27 | 558 ± 36 | 666 ± 77 | 775 ± 117 | 917 ± 36 | |
| DAY 18 | 997 ± 93 | 199 ± 18 | 479 ± 29 | 797 ± 88 | 224 ± 26 | 494 ± 41 | 642 ± 90 | 665 ± 112 | 958 ± 57 | |
| DAY 21 | 1041 ± 107 | 194 ± 20 | 499 ± 34 | 839 ± 93 | 192 ± 19 | 534 ± 41 | 710 ± 117 | 637 ± 119 | 1002 ± 59 | |
| DAY 25 | 1151 ± 144 | 181 ± 21 | 588 ± 40 | 878 ± 105 | 227 ± 32 | 628 ± 58 | 748 ± 138 | 647 ± 134 | 1075 ± 82 | |
| DAY 28 | 1200 ± 155 | 204 ± 16 | 672 ± 48 | 904 ± 123 | 244 ± 35 | 645 ± 57 | 763 ± 145 | 674 ± 146 | 1148 ± 77 | |
| DAY 33 | 1481 ± 206 | 196 ± 27 | 786 ± 65 | 1043 ± 152 | 267 ± 52 | 730 ± 66 | 991 ± 239 | 733 ± 195 | 1290 ± 128 | |
| DAY 36 | — | 189 ± 37 | 827 ± 69 | 1108 ± 185 | 300 ± 64 | 850 ± 74 | — | 817 ± 222 | 1265 ± 111 | |
| DAY 39 | — | 228 ± 44 | 847 ± 77 | 1204 ± 209 | 323 ± 69 | 881 ± 88 | — | 880 ± 247 | 1429 ± 121 | |
| DAY 42 | — | 257 ± 60 | 959 ± 81 | — | 350 ± 78 | 1020 ± 99 | — | 797 ± 244 | — | |
| DAY 46 | — | 253 ± 59 | 1018 ± 94 | — | 380 ± 78 | 1097 ± 129 | — | 874 ± 267 | — | |
| DAY 50 | — | 253 ± 67 | 1111 ± 95 | — | 415 ± 77 | 1162 ± 134 | — | — | — | |
| DAY 56 | — | 298 ± 85 | 1279 ± 108 | — | 504 ± 111 | 1331 ± 187 | — | — | — | |
| DAY 63 | — | 345 ± 93 | 1368 ± 133 | — | 581 ± 121 | — | — | — | — | |
| DAY 70 | — | 376 ± 117 | 1483 ± 154 | — | 726 ± 163 | — | — | — | — | |
| DAY 77 | — | 388 ± 123 | — | — | 797 ± 184 | — | — | — | — | |

The N87 gastric model was also dosed intraveneously Q4dx4 with PBS vehicle, rat-human chimeric anti-Notch ADCs and control huNeg-8.8 ADCs, at a dose of 5 mg/kg as provided in FIG. 8D. The data demonstrates that rat-human chimeric anti-Notch ADCs with non-cleavable (mc) and cleavable (vc) linkers and various payload combinations inhibited growth of N87 gastric xenografts. Further, the data shows that rat-human chimeric anti-Notch ADCs inhibited tumor growth more potently than control huNeg8.8-ADCs. Furthermore, the data demonstrates that rat-human chimeric anti-Notch ADCs with vc0101 linker-payloads were more potent than the other anti-Notch ADCs tested.

The N87 gastric model was also dosed intravenously Q4dx4 with PBS vehicle and rat-human chimeric anti-Notch ADCs ch28-mc0131, ch75-mc0131, ch28-m(H2O)c-0131 and ch75-m(H2O)c-0131 at a dose of 5 mg/kg as provided in FIG. 8E. The data demonstrates that rat-human chimeric anti-Notch ADCs having mc0131 and m(H2O)c-0131 linker-payloads inhibited growth of N87 gastric xenografts. Further, the data demonstrates that rat-human chimeric anti-Notch ADCs having m(H2O)c-0131 linker-payloads were more potent than rat-human chimeric anti-Notch ADCs having mc0131 linker-payloads.

TABLE 18A

Selected compounds (cytotoxic peptides with linkers) of the invention

| Linker-Payload # | Preparation method | Purification method | Quantity in mg (Yield) |
|---|---|---|---|
| mcValCitPABC-#34 | General procedure E | Method D | 4.7 (12%) |
| MalPeg3C2-#41 | General procedure D | Method C | 36 (28%) |
| MalPeg6C2-#42 | General procedure D | Method C | 125 (88%) |
| mc-#44 | General procedure D | Method C | 5.9 (25%) |
| MalPeg3C2-#44 | General procedure D | Method C | 10 (28%) |
| MalPeg6C2-#44 | General procedure D | Method C | 1.8 (6%) |
| MalValCitPABC-#44 | General procedure E | Method F | 4 (10%) |
| mc-#45 | General procedure D | Method C | 12.8 (53%) |
| MalPeg3C2-#45 | General procedure D | Method C | 7.5 (28%) |
| MalPeg6C2-#45 | General procedure D | Method E1* | 13.6 (45%) |
| mcValCitPABC-#45 | General procedure E | Method C & Method E1 | 5.8 (15%) |
| mcValCitPABC-#54 | General procedure E | Method D | 33 (36%) |
| mc-#69 | General procedure D | Method C | 30.2 (24%) |
| MalPeg6C2-#69 | General procedure D | Method C | 3.6 (13%) |
| mcValCitPABC-#69 | General procedure E | Method I | 51 (9%) |
| mcValCitPABC-#70 | General procedure E | Method D | 6.9 (12%) |
| mcValCitPABC-#75 | General procedure E | Method H | 5.3 (14%) |
| mc-#79 | General procedure D | Method E | 5.6 (19%) |
| mcValCitPABC-#79 | General procedure E | Method D | 5.5 (10%) |
| mcValCitPABC-#92 | General procedure E | Method E | 9.5 (26%) |
| mcValCitPABC-#112 | General procedure E | Method C | 11.8 (21%) |
| mv-#115 | General procedure D | Method J | 1.4 (3.3%) |
| mc-#115 | — | Method L | 124 (11%) |
| mb-#115 | General procedure D | — | — |
| me-#115 | General procedure D | — | — |
| mcValCitPABC-#115 | General procedure E | Method K | 4.9 (12%) |
| mc-#51 | General procedure D | Method E1 | 5.5 (42%) |
| mc-#47 | General procedure D | Method E1 | 8.4 (46%) |
| mc-#54 | General procedure D | Method E1 | 12.9 (65%) |

TABLE 18A-continued

Selected compounds (cytotoxic peptides with linkers) of the invention

| Linker-Payload # | Preparation method | Purification method | Quantity in mg (Yield) |
|---|---|---|---|
| mcValCitPABC-#47 | General procedure E | Method E1 | 3.3 (20%) |
| mcValCitPABC-#26 | General procedure E | Method E1 | 2.3 (20%) |
| mc-#26 | General procedure D | Method E1 | 5.4 (10%) |
| mcValCitPABC-#42 | General procedure E | Method E1 | 10.8 (38%) |
| mcValCitPABC-#36 | General procedure E | Method E1 | 12.6 (32%) |
| mc-#42 | General procedure D | Method E1 | 7.1 (83%) |
| AmPeg6C2-#54 | General procedure N | Method J | 44 (67%) |
| MalPeg3C2-#54 | General procedure D | Method J | 19 (69%) |
| mcValCitPABCAmPeg6C2-#54 | General procedure O | Method J | 12 (42%) |
| mcValCitPABCAmPeg3C2-#54 | General procedure O | Method J | 12.4 (30%) |
| MalPeg3C2-#47 | General procedure D | Method J* | 19 (62%) |
| AmPeg6C2-#47 | General procedure N | Method J | 50 (77%) |
| mcValCitPABCAmPeg3C2-#47 | General procedure O | Method J | 6.4 (18%) |
| mcValCitPABCAmPeg6C2-#47 | General procedure O | Method J | 18 (50%) |
| MalPeg3C2-#42 | General procedure D | Method J | 22 (70%) |
| AmPeg6C2-#42 | General procedure N | Method J | 53 (75%) |
| mcValCitPABCAmPeg6C2-#42 | General procedure O | Method J | 15.4 (43%) |
| mcValCitPABCAmPeg3C2-#42 | General procedure O | Method J* | 12 (26%) |
| MalPeg3C2-#26 | General procedure D | Method J* | 13.8 (51%) |
| mc-#41 | General procedure D | Method J* | 9.6 (38%) |
| AmPeg6C2-#26 | General procedure N | Method J | 59 (87%) |
| mcValCitPABCAmPeg3C2-#26 | General procedure O | Method J | 23.4 (45%) |
| MalPeg3C2Val1CitPABC-#26 | General procedure P | Method J | 16 (42%) |
| mcValCitPABCAmPeg6C2-#26 | General procedure O | Method J | 15 (38%) |
| mc-#36 | General procedure D | Method J* | 26 (80%) |
| MalPeg6C2-#54 | General procedure D | Method J | 27 (67%) |
| MalPeg3C2Val1CitPABC-#47 | General procedure P | Method J | 17 (49%) |
| MalPeg3C2-#36 | General procedure D | Method J* | 9.2 (33%) |
| MalPeg6C2-#47 | General procedure D | Method J* | 24 (78%) |
| MalPeg6C2-#26 | General procedure D | Method J* | 29 (75%) |
| MalPeg6C2-#36 | General procedure D | Method J | 18 (58%) |
| mcValCitPABCAmPeg3C2-#36 | General procedure O | Method J | 16 (51%) |
| AmPeg6C2-#36 | General procedure N | Method J | 51 (78%) |
| mcValCitPABC-#60 | General procedure E | Method J | 1.9 (4.3%) |
| mcValCitPABCAmPeg6C2-#36 | General procedure O | Method J | 11.6 (35%) |
| mcValCitPABCAmPeg3C2-#41 | General procedure O | Method J | 5.7 (26%) |
| MalPeg6C2-#60 | General procedure D | Method J | 24 (75%) |

TABLE 18A-continued

Selected compounds (cytotoxic peptides with linkers) of the invention

| Linker-Payload # | Preparation method | Purification method | Quantity in mg (Yield) |
|---|---|---|---|
| AmPeg6C2-#60 | General procedure N | Method J | 31 (80%) |
| MalPeg3C2-#60 | General procedure D | Method J | 17.3 (58%) |
| MalPeg6C2-#41 | General procedure D | Method J with AcOH as modifier | 11 (28%) |
| AmPeg6C2-#66 | General procedure N | Method J | 5 (10%) |
| mcValCitPABCAmPeg6C2-#60 | General procedure O | Method J | 12 (34%) |
| mc-#70 | General procedure D | Method J* | 11.2 (46%) |
| 2AcAmPeg6C2-#66 | General procedure Q | Method J | 8 (60%) |
| mc-#66 | General procedure D | Method J with AcOH as modifier | 8.2 (32%) |
| mcValCitPABC-#88 | General procedure E | Method J | 7.9 (45%) |
| mcValCitPABC-#88 | General procedure E | Method J | 7.5 (39%) |
| mc-#92 | General procedure D | Method F | 15 (66%) |
| mcValCitPABC-#44 | General procedure E | Method F | 1.6 (4%) |
| mc-#108 | General procedure D | Method H without modifier | 8.8 (37%) |
| mcValCitPABC-#108 | General procedure E | Method F | 6.1 (14%) |
| NHSCOPeg2C2ValCitPABC-#66 | General procedure X2 | Method F* | 6.8 (32%) |
| mcValCitPABC-#98 | General procedure E | Method J* | 4.8 (11%) |
| mcValCitPABC-#95 | General procedure E | Method J* | 13 (28%) |
| MalPeg3C2-#69 | General procedure D | Method K | 12.8 (35%) |
| AmPeg6C2-#69 | General procedure N | Method J* | 71 (69%) |
| mcValCitPABC-#84 | General procedure E | Method J* | 4.9 (11%) |
| AmCapValCitPABC-#54 | General procedure R | Method K* | 97 (53%) |
| mcValCitPABC-#226 | General procedure E | Method J* | 7.1 (16%) |
| mcValCitPABC-#117 | General procedure E | Method J* | 15.8 (36%) |
| MalPeg6C2-#98 | General procedure D | Method I* | 7.4 (22%) |
| mcValCitPABC-#118 | General procedure E | Method J* | 11.7 (29%) |
| mcValCitPABC-#80 | General procedure E | Method J* | 3.8 (12%) |
| MalPeg6C2-#118 | General procedure D | Method J* | 11 (4.5%) |
| MalPeg6C2-#230 | General procedure D | Method H | 2.8 (8%) |
| mcValCitPABC-#232 | General procedure E | Method J* | 13.6 (29%) |
| mc-#117 | General procedure D | Method J* | 9.5 (40%) |
| MalPeg6C2-#117 | General procedure D | Method K* | 2.3 (8%) |
| mv-#69 | General procedure D | Method J* | 22 (49%) |
| mb-#69 | General procedure D | Method J* | 12 (28%) |
| AmPeg6C2-#234 | General procedure N | Method J* | 16 (52%) |
| AmPeg6C2-#235 | General procedure N | Method J* | 16.5 (70%) |
| mc-#118 | General procedure D | Method J* | 41 (38%) |
| MalPeg6C2-#123 | General procedure D | Method J* | 85 (40%) |

TABLE 18A-continued

Selected compounds (cytotoxic peptides with linkers) of the invention

| Linker-Payload # | Preparation method | Purification method | Quantity in mg (Yield) |
|---|---|---|---|
| mc-#226 | General procedure D | silica chromatography | 290 (40%) |
| mc-#118 | General procedure D | Method J* | 16.2 (42%) |
| mc-#131 | General procedure D | Method J* | 16.3 (51%) |
| mb-#118 | General procedure D | Method J* | 7.9 (23%) |
| mcValCitPABC-#134 | General procedure E | Method J* | 17 (33%) |
| mc-#145 | General procedure D | Method K | 6 (20%) |
| MalPeg6C2-#126 | General procedure D | Method J* | 16.4 (26%) |
| mc-#126 | General procedure D | Method K* | 16.3 (32%) |
| mv-#118 | General procedure D | Method J* | 11.7 (34%) |
| mc-#172 | General procedure D | Method J* | 10 (56%) |
| MalPeg6C2-#226 | General procedure D | Method K* | 15 (10%) |
| MalPeg6C2-#145 | General procedure D | Method K | 1.8 (3.7%) |
| mc-#162 | General procedure D | Method H* without modifier | 1.2 (3.1%) |
| mc-#163 | General procedure D | Method K* | 9.9 (26%) |
| mcValCitPABC-#231 | General procedure E | Method J* | 0.2 (4%) |
| MalPeg6C2-#238 | General procedure D | silica chromatography | 240 (77%) |
| MalPeg6C2-#239 | General procedure D | medium pressure C18 chromatography | 104 (39%) |
| mc-#123 | General procedure D | silica chromatography | 345 (quant.) |
| MalC6-#54 | General procedure S | Method J* | 16.3 (30%) |
| mc-#231 | General procedure D | Method J* | 10 (60%) |
| MalC6-#118 | General procedure S | Method J* | 5.3 (10%) |
| mcValCitPABC-#123 | General procedure E | silica chromatography | 179 (60%) |
| mc-#237 | General procedure D | Method J* | 12.6 (47%) |
| mc-#158 | General procedure D | Method J* | 7.1 (28%) |
| MalC6Am-#151 | General procedure D | Method J* | 18.4 (86%) |
| PFPCOPeg2C2 ValCitPABC-#54 | General procedure X3 | Method J* AcOH as modifier | 70 (68%) |
| mcValCitPABC-#154 | General procedure E | medium pressure C18 chromatography | 10 (19%) |
| MalC6Am-#153 | General procedure D | Method K* | 18.7 (47%) |
| PFPCOPeg2C2AmPeg2C2-#69 | General procedure X4 | Method R* | 40 (64%) |
| mcValCitPABC-#246 | General procedure E | medium pressure C18 chromatography | 21 (45%) |
| PFPCOPeg2C2AlaAlaAsnPABC-#54 | General procedure X1 | Method R* | 16.8 (54%) |
| PFPCOPeg2C2-#54 | General procedure V | Method R* | 4.1 (56%) |
| PFPCOPeg2C2AmPeg2C2PABC-#54 | General procedure W | Method R* | 1.1 (39%) |
| AmPeg6C2-#115 | General procedure N | Method J* | 100 (48%) |
| PFPCOPeg5C2-#115 | General procedure V | Method J* | 29 (26%) |
| mcGly-#201 | — | silica chromatography | 25 (16.2%) |
| AzCOC2Ph4AmCOPeg2C2-#54 | General procedure T | Method R* | 3.5 (52%) |

TABLE 18A-continued

Selected compounds (cytotoxic peptides with linkers) of the invention

| Linker-Payload # | Preparation method | Purification method | Quantity in mg (Yield) |
|---|---|---|---|
| AzCOC2Ph4AmPeg1C1ValCitPABC-#54 | General procedure U | Method R* | 93 (43%) |
| AzCOC2Ph4AmPeg1C1ValCitPABC-#30 | General procedure U | Method R* | 1.7 (42%) |
| AzCOC2Ph4AmCOPeg2C2-#69 | General procedure T | Method R* | 88 (62%) |
| AzCOC2Ph4AmCOPeg2C2-#115 | General procedure T | Method R* | 75 (82%) |
| AcLysValCitPABC-#54 | General procedure X5 | Method J* | 86 (40%) |

TABLE 18B

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| mcValCitPABC-#34 | HPLC (Protocol M): 1380.6 [M + Na$^+$], (12.899 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide |
| MalPeg3C2-#41 | LC-MS: 1031.7 [M + H$^+$], 1054.8 [M + Na$^+$] (0.88 minutes); HPLC (Protocol D): 10.559 minutes | N-[3-(2-{2-[2-(2,5-dioxo-2,5-dihydro-1H-pyrrol-1-yl)ethoxy]ethoxy}ethoxy)propanoyl]-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide |
| MalPeg6C2-#42 | LC-MS: 1178.2 [M + H$^+$], 1197.4 [M + Na$^+$] (3.50 minutes); HPLC (Protocol Q): 25.235 minutes | N-[1-(2,5-dioxo-2,5-dihydro-1H-pyrrol-1-yl)-21-oxo-3,6,9,12,15,18-hexaoxahenicosan-21-yl]-N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| mc-#44 | LC-MS: 913.7 [M + H$^+$] (0.85 minutes); HRMS: Calc: 913.5103 [M + H$^+$], Obsd: 913.5103. | N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidiN-1-yl}-3-methoxy-5-methyl-1-oxoheptaN-4-yl]-N-methyl-L-valinamide |
| MalPeg3C2-#44 | LC-MS: 1003.8 [M + H$^+$] (0.82 minutes); HPLC (Protocol A): 1003.5 [M + H$^+$], 1026.4 [M + Na$^+$] (9.095 minutes) | N-[3-(2-{2-[2-(2,5-dioxo-2,5-dihydro-1H-pyrrol-1-yl)ethoxy]ethoxy}ethoxy)propanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide |
| MalPeg6C2-#44 | LC-MS: 1135.8 [M + H$^+$] (0.83 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide |
| MalValCitPABC-#44 | LC-MS: 1318.9 [M + H$^+$] (0.89 minutes); HPLC (Protocol A): 1319.6 [M + H$^+$], 1342.6 [M + Na$^+$] (9.132 minutes) | N-[6-(2,5-dioxo-2,5-dihydro-1H-pyrrol-1-yl)hexanoyl]-L-valyl-N-{4-[(8S,11S,12R)-11-[(2S)-butaN-2-yl]-12-(2-{(2S)-2-[(1R,2R)-3-{[(1S)-1-carboxy-2-phenylethyl]amino}-1-methoxy-2-methyl-3-thioxopropyl]pyrrolidiN-1-yl}-2-oxoethyl)-5,5,10-trimethyl-3,6,9-trioxo-8-(propaN-2-yl)-2,13-dioxa-4,7,10-triazatetradec-1-yl]phenyl}-N$^5$-carbamoyl-L-ornithinamide |
| mc-#45 | LC-MS: 927.7 [M + H$^+$] (0.92 minutes); | N-[6-(2,5-dioxo-2,5-dihydro-1H-pyrrol-1-yl)hexanoyl]-2-methylalanyl-N-[(3R,4S,5S)-3-methoxy-1-{(2S)-2-[(1R,2R)-1-methoxy-3-{[(2S)-1-methoxy-1-oxo-3- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| | HRMS: Calc: 927.5260 [M + H⁺], Obsd: 927.5259. | phenylpropaN-2-yl]amino}-2-methyl-3-thioxopropyl]pyrrolidiN-1-yl}-5-methyl-1-oxoheptaN-4-yl]-N-methyl-L-valinamide |
| MalPeg3C2-#45 | LC-MS: 1017.8 [M + H⁺] (0.90 minutes); | N-[3-(2-{2-[2-(2,5-dioxo-2,5-dihydro-1H-pyrrol-1-yl)ethoxy]ethoxy}ethoxy)propanoyl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| MalPeg6C2-#45 | LC-MS: 1149.9 [M + H⁺] (0.90 minutes); HPLC (Protocol A at 45° C.): 1150.5 [M + H⁺], 1171.5 [M + Na⁺] (9.788 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| mcValCitPABC-#45 | LC-MS: 1332.8 [M + H⁺] (1.86 minutes); HPLC (Protocol A at 45° C.): 1333.6 [M + H⁺] (9.737 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide |
| mcValCitPABC-#54 | HPLC (Protocol A at 45° C.): 1342.6 [M + H⁺] (9.114 minutes). | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide |
| mc-#69 | LC-MS: 897.7 [M + H⁺], 919.7 (0.81 minutes); HPLC (Protocol A at 45° C.): 897.5 [M + H⁺] (9.058 minutes) | N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| MalPeg6C2-#69 | HPLC (Protocol A at 45° C.): 1120.6 [M + H⁺], 1142.5 (9.076 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#69 | HPLC (ProtocolM): 1326.6 [M + Na⁺] (11.962 minutes) | N-[3-(2-{2-[2-(2,5-dioxo-2,5-dihydro-1H-pyrrol-1-yl)ethoxy]ethoxy}ethoxy)propanoyl]-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidiN-1-yl}-3-methoxy-5-methyl-1-oxoheptaN-4-yl]-N-methyl-L-valinamide |
| mcValCitPABC-#70 | HPLC (Protocol A at 45° C.): 1317.6 [M + H⁺] (9.282 minutes) | N-[6-(2,5-dioxo-2,5-dihydro-1H-pyrrol-1-yl)hexanoyl]-L-valyl-N-{4-[(8S,11S,12R)-11-[(2S)-butaN-2-yl]-12-(2-{(2S)-2-[(1R,2R)-1-methoxy-3-{[(2S)-1-methoxy-1-oxo-3-phenylpropaN-2-yl]amino}-2-methyl-3-oxopropyl]pyrrolidiN-1-yl}-2-oxoethyl)-5,5,10-trimethyl-3,6,9-trioxo-8-(propaN-2-yl)-2,13-dioxa-4,7,10-triazatetradec-1-yl]phenyl}-N⁵-carbamoyl-L-ornithinamide |
| mcValCitPABC-#75 | LC-MS: 1273.9 [M + H⁺] (0.82 minutes); HPLC (Protocol A at 45° C.): 1273.6 [M + H⁺], (8.814 minutes) | N-[6-(2,5-dioxo-2,5-dihydro-1H-pyrrol-1-yl)hexanoyl]-L-valyl-N⁵-carbamoyl-N-{4-[({[3-({(2S)-1-[{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}(methyl)amino]-3-methyl-1-oxobutan-2-yl}carbamoyl)oxetan-3-yl]carbamoyl}oxy)methyl]phenyl}-L-ornithinamide |
| mc-#79 | HPLC (Protocol A at 45° C.): 941.5 [M + H⁺], 963.4 [M + Na⁺] (10.444 | N-[6-(2,5-dioxo-2,5-dihydro-1H-pyrrol-1-yl)hexanoyl]-N,2-dimethylalanyl-N-[(3R,4S,5S)-3-methoxy-1-{(2S)-2-[(1R,2R)-1-methoxy-3-{[(2S)-1-methoxy-1-oxo-3-phenylpropaN-2-yl]amino}-2-methyl-3- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| | minutes) | thioxopropyl]pyrrolidiN-1-yl}-5-methyl-1-oxoheptaN-4-yl]-N-methyl-L-valinamide |
| mcValCitPABC-#79 | HPLC (Protocol A): 1346.6 [M + H$^+$], (9.807 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N$^5$-carbamoyl-L-ornithinamide |
| mcValCitPABC-#92 | LC-MS: 1282.6 [M + H$^+$] (0.79 minutes); HPLC (Protocol A at 45° C.): 1282.6 [M + H$^+$] (7.953 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-(quinolin-6-ylamino)propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide |
| mcValCitPABC-#112 | HPLC (Protocol M): 1288.6 [M + H$^+$], 1310.6 [M + Na$^+$] (11.757 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-3-{[(1S)-1-carboxy-2-phenylethyl]amino}-1-methoxy-2-methyl-3-oxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide |
| mv-#115 | HPLC (Protocol A at 45° C.): m/z 897.5 [M + H$^+$], (9.149 minutes) | N-[5-(2,5-dioxo-2,5-dihydro-1H-pyrrol-1-yl)pentanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide |
| mc-#115 | HPLC (Protocol A at 45° C.;) m/z 911.5 [M + H$^+$], (9.676 minutes) | N-[6-(2,5-dioxo-2,5-dihydro-1H-pyrrol-1-yl)hexanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide |
| mb-#115 | — | N-[4-(2,5-dioxo-2,5-dihydro-1H-pyrrol-1-yl)butanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide |
| me-#115 | — | N-[7-(2,5-dioxo-2,5-dihydro-1H-pyrrol-1-yl)heptanoyl]-N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide |
| mcValCitPABC-#115 | HPLC (Protocol M): m/z 1317.7 [M + H$^+$] (12.261 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-3-{[(1S)-1-carboxy-2-phenylethyl]amino}-1-methoxy-2-methyl-3-oxopropyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N~5~-carbamoyl-L-ornithinamide |
| mc-#51 | HPLC (Protocol M): m/z 934.5 [M + H$^+$] (11.94 minutes) | N~2~-[(1-{[6-(2,5-dioxo-2,5-dihydro-1H-pyrrol-1-yl)hexanoyl]amino}cyclopropyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| mc-#47 | HPLC (Protocol M): m/z 962.5 [M + H$^+$] (13.014 minutes) | N~2~-[(1-{[6-(2,5-dioxo-2,5-dihydro-1H-pyrrol-1-yl)hexanoyl]amino}cyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
| --- | --- | --- |
| mc-#54 | HPLC (Protocol M): m/z 936.5 [M + H$^+$] (9.22 minutes) | N-[6-(2,5-dioxo-2,5-dihydro-1H-pyrrol-1-yl)hexanoyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| mcValCitPABC-#47 | HPLC (Protocol M): m/z 1368.6 [M + H$^+$] (13.157 minutes) | N-[6-(2,5-dioxo-2,5-dihydro-1H-pyrrol-1-yl)hexanoyl]-L-valyl-N~5~-carbamoyl-N-[4-({[(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}cyclopentyl)carbamoyl]oxy}methyl)phenyl]-L-ornithinamide |
| mcValCitPABC-#26 | HPLC (Protocol M): m/z 1386.6 [M + H$^+$] (16.21 minutes) | N-[6-(2,5-dioxo-2,5-dihydro-1H-pyrrol-1-yl)hexanoyl]-L-valyl-N-{4-[(5S,8S,11S,12R)-11-[(2S)-butan-2-yl]-12-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-4,10-dimethyl-3,6,9-trioxo-5,8-di(propan-2-yl)-2,13-dioxa-4,7,10-triazatetradec-1-yl]phenyl}-N~5~-carbamoyl-L-ornithinamide |
| mc-#26 | HPLC (Protocol A*): m/z 980.5 [M + H$^+$] (10.628 minutes) | N-[6-(2,5-dioxo-2,5-dihydro-1H-pyrrol-1-yl)hexanoyl]-N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide |
| mcValCitPABC-#42 | HPLC (Protocol A*): m/z 1361.7 [M + H$^+$] (9.831 minutes) | N-[6-(2,5-dioxo-2,5-dihydro-1H-pyrrol-1-yl)hexanoyl]-L-valyl-N-{4-[(5S,8S,11S,12R)-11-[(2S)-butan-2-yl]-12-(2-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-2-oxoethyl)-4,10-dimethyl-3,6,9-trioxo-5,8-di(propan-2-yl)-2,13-dioxa-4,7,10-triazatetradec-1-yl]phenyl}-N~5~-carbamoyl-L-ornithinamide |
| mcValCitPABC-#36 | HPLC (Protocol A*): m/z 1324.6 [M + Na$^{+23}$] (9.987 minutes) | N-[6-(2,5-dioxo-2,5-dihydro-1H-pyrrol-1-yl)hexanoyl]-L-valyl-N-{4-[(5S,8S,11S,12R)-11-[(2S)-butan-2-yl]-12-{2-[(2S)-2-{(1R,2R)-1-methoxy-2-methyl-3-[(2-phenylethyl)amino]-3-thioxopropyl}pyrrolidin-1-yl]-2-oxoethyl}-4,10-dimethyl-3,6,9-trioxo-5,8-di(propan-2-yl)-2,13-dioxa-4,7,10-triazatetradec-1-yl]phenyl}-N~5~-carbamoyl-L-ornithinamide |
| mc-#42 | HPLC (Protocol A*): m/z 955.5 [M + H$^+$] (10.679 minutes) | N-[6-(2,5-dioxo-2,5-dihydro-1H-pyrrol-1-yl)hexanoyl]-N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| AmPeg6C2-#54 | LC-MS (Protocol H): m/z 1078.7 [M + H$^+$] (2.56 minutes) | N-(21-amino-4,7,10,13,16,19-hexaoxahenicosan-1-oyl)-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| MalPeg3C2-#54 | LC-MS (Protocol H): m/z 1026.6 [M + H$^+$] (3.54 minutes) | N-[3-(2-{2-[2-(2,5-dioxo-2,5-dihydro-1H-pyrrol-1-yl)ethoxy]ethoxy}ethoxy)propanoyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| mcValCitPABCAmPeg6C2-#54 | LC-MS (Protocol H): m/z 1677.9 [M + H$^+$] (3.48 minutes) | N-[6-(2,5-dioxo-2,5-dihydro-1H-pyrrol-1-yl)hexanoyl]-L-valyl-N-{4-[(30S,33S,34R)-33-[(2S)-butan-2-yl]-34-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-27,27,32-trimethyl-3,25,28,31-tetraoxo-30-(propan-2-yl)-2,7,10,13,16,19,22,35-octaoxa-4,26,29,32- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| mcValCitPABCAmPeg3C2-#54 | LC-MS (Protocol H): m/z 1545.8 [M + H⁺] (3.48 minutes) | tetraazahexatriacont-1-yl]phenyl}-N~5~-carbamoyl-L-ornithinamide<br>N-[6-(2,5-dioxo-2,5-dihydro-1H-pyrrol-1-yl)hexanoyl]-L-valyl-N-{4-[(21S,24S,25R)-24-[(2S)-butan-2-yl]-25-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-18,18,23-trimethyl-3,16,19,22-tetraoxo-21-(propan-2-yl)-2,7,10,13,26-pentaoxa-4,17,20,23-tetraazaheptacos-1-yl]phenyl}-N~5~-carbamoyl-L-ornithinamide |
| MalPeg3C2-#47 | LC-MS (Protocol Q1): m/z 1052.7 [M + H⁺] (0.88 minutes) | N~2~-[(1-{[3-(2-{2-[2-(2,5-dioxo-2,5-dihydro-1H-pyrrol-1-yl]ethoxy]ethoxy)propanoyl]amino}cyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| AmPeg6C2-#47 | LC-MS (Protocol H): m/z 1104.88 [M + H⁺] (2.65 minutes) | 1-amino-N-(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]prrolidin-1-yl}-5-methyl-1-oxoheptan-4-yl}(methyl)amino}-3-methyl-1-oxobutan-2-yl]carbamoyl}cyclopentyl)-3,6,9,12,15,18-hexaoxahenicosan-21-amide |
| mcValCitPABCAmPeg3C2-#47 | LC-MS (Protocol H): m/z 1571.8 [M + H⁺] (3.56 minutes) | N-[6-(2,5-dioxo-2,5-dihydro-1H-pyrrol-1-yl)hexanoyl]-L-valyl-N~5~-carbamoyl-N-(4-{16-[(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]prrolidin-1-yl}-5-methyl-1-oxoheptan-4-yl](methyl)amino}-3-methyl-1-oxobutan-2-yl]carbamoyl}cyclopentyl)amino]-3,16-dioxo-2,7,10,13-tetraoxa-4-azahexadec-1-yl}phenyl)-L-ornithinamide |
| mcValCitPABCAmPeg6C2-#47 | HPLC (Protocol H): m/z 1703.8 [M + H⁺] (3.57 minutes) | N-[6-(2,5-dioxo-2,5-dihydro-1H-pyrrol-1-yl)hexanoyl]-L-valyl-N~5~-carbamoyl-N-(4-{25-[(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]prrolidin-1-yl}-5-methyl-1-oxoheptan-4-yl](methyl)amino}-3-methyl-1-oxobutan-2-yl]carbamoyl}cyclopentyl)amino]-3,25-dioxo-2,7,10,13,16,19,22-heptaoxa-4-azapentacos-1-yl}phenyl)-L-ornithinamide |
| MalPeg3C2-#42 | LC-MS (Protocol H): m/z 1045.7 [M + H⁺] (3.92 minutes) | N-[3-(2-{2-[2-(2,5-dioxo-2,5-dihydro-1H-pyrrol-1-yl)ethoxy]ethoxy}ethoxy)propanoyl]-N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| AmPeg6C2-#42 | LC-MS (Protocol H): m/z 1097.7 [M + H⁺] (2.80 minutes) | N-(21-amino-4,7,10,13,16,19-hexaoxahenicosan-1-oyl)-N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-5-methyl-1-oxoheptan-4-yl]-N-methyl-L-valinamide |
| mcValCitPABCAmPeg6C2-#42 | LC-MS (Protocol H): m/z 1696.8 [M + H⁺] (3.73 minutes) | N-[6-(2,5-dioxo-2,5-dihydro-1H-pyrrol-1-yl)hexanoyl]-L-valyl-N-{4-[(27S,30S,33S,34R)-33-[(2S)-butan-2-yl]-34-(2-{(2S)-2-[(1R,2R)-1-methoxy-3-{[(2S)-1-methoxy-1-oxo-3-phenylpropan-2-yl]amino}-2-methyl-3-thioxopropyl]pyrrolidin-1-yl}-2-oxoethyl)-26,32-dimethyl-3,25,28,31-tetraoxo-27,30-di(propan-2-yl)-2,7,10,13,16,19,22,35-octaoxa-4,26,29,32-tetraazahexatriacont-1-yl]phenyl}-N~5~-carbamoyl-L-ornithinamide |
| mcValCitPABCAmPeg3C2-#42 | LC-MS (Protocol H): m/z 1564.8 [M + H⁺] (3.70 minutes) | N-[6-(2,5-dioxo-2,5-dihydro-1H-pyrrol-1-yl)hexanoyl]-L-valyl-N-{4-[(18S,21S,24S,25R)-24-[(2S)-butan-2-yl]-25-(2-{(2S)-2-[(1R,2R)-1-methoxy-3-{[(2S)-1-methoxy-1-oxo-3-phenylpropan-2-yl]amino}-2-methyl- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| MalPeg3C2-#26 | LC-MS (Protocol H): m/z 1070.6 [M + H⁺] (3.94 minutes) | 3-thioxopropyl]pyrrolidin-1-yl}-2-oxoethyl)-17,23-dimethyl-3,16,19,22-tetraoxo-18,21-di(propan-2-yl)-2,7,10,13,26-pentaoxa-4,17,20,23-tetraazaheptacos-1-yl]phenyl}-N~5~-carbamoyl-L-ornithinamide<br>N-[3-(2-{2-[2-(2,5-dioxo-2,5-dihydro-1H-pyrrol-1-yl)ethoxy]ethoxy}ethoxy)propanoyl]-N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide |
| mc-PLC | (Protocol N-[6-(2,5-dioxo-2,5-dihydro-1H-pyrrol-1-yl)hexanoyl]-A): m/z 941.5 [M + H⁺] (9.883 minutes) | N-methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide |
| AmPeg6C2-#26 | LC-MS (Protocol H): m/z 1122.6 [M + H⁺] (2.76 minutes) | N-(21-amino-4,7,10,13,16,19-hexaoxahenicosan-1-oyl)-N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide |
| mcValCitPABCAmPeg3C2-#26 | LC-MS (Protocol H): m/z 1588.0 [M + H⁺] (3.74 minutes) | N-[6-(2,5-dioxo-2,5-dihydro-1H-pyrrol-1-yl)hexanoyl]-L-valyl-N-{4-[(18S,21S,24S,25R)-24-[(2S)-butan-2-yl]-25-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-17,23-dimethyl-3,16,19,22-tetraoxo-18,21-di(propan-2-yl)-2,7,10,13,26-pentaoxa-4,17,20,23-tetraazaheptacos-1-yl]phenyl}-N~5~-carbamoyl-L-ornithinamide |
| MalPeg3C2ValCitPABC-#26 | LC-MS (Protocol H): m/z 1476.8 [M + H⁺] (3.81 minutes) | N-[3-(2-{2-[2-(2,5-dioxo-2,5-dihydro-1H-pyrrol-1-yl)ethoxy]ethoxy}ethoxy)propanoyl]-L-valyl-N-{4-[(5S,8S,11S,12R)-11-[(2S)-butan-2-yl]-12-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-4,10-dimethyl-3,6,9-trioxo-5,8-di(propan-2-yl)-2,13-dioxa-4,7,10-triazatetradec-1-yl]phenyl}-N~5~-carbamoyl-L-ornithinamide |
| mcValCitPABCAmPeg6C2-#26 | LC-MS (Protocol H): m/z 1721.9 [M + H⁺] (3.75 minutes) | N-[6-(2,5-dioxo-2,5-dihydro-1H-pyrrol-1-yl)hexanoyl]-L-valyl-N-{4-[(27S,30S,33S,34R)-33-[(2S)-butan-2-yl]-34-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-26,32-dimethyl-3,25,28,31-tetraoxo-27,30-di(propan-2-yl)-2,7,10,13,16,19,22,35-octaoxa-4,26,29,32-tetraazahexatriacont-1-yl]phenyl}-N~5~-carbamoyl-L-ornithinamide |
| mc-#36 | LC-MS (Protocol Q1): m/z 897.7 [M + H⁺] (1.00 minutes) | N-[6-(2,5-dioxo-2,5-dihydro-1H-pyrrol-1-yl)hexanoyl]-N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide |
| MalPeg6C2-#54 | LC-MS (Protocol H): m/z 1158.7 [M + H⁺] (3.55 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| MalPeg3C2ValCitPABC-#47 | LC-MS (Protocol H): m/z 1458.7 [M + H⁺] (3.56 minutes) | N-[3-(2-{2-[2-(2,5-dioxo-2,5-dihydro-1H-pyrrol-1-yl)ethoxy]ethoxy}ethoxy)propanoyl]-L-valyl-N~5~-carbamoyl-N-[4-({[(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}cyclopentyl)carbamoyl]oxy}methyl)phenyl]-L-ornithinamide |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| MalPeg3C2-#36 | LC-MS (Protocol H): m/z 987.7 [M + H$^+$] (3.97 minutes) | N-[3-(2-{2-[2-(2,5-dioxo-2,5-dihydro-1H-pyrrol-1-yl)ethoxy]ethoxy}ethoxy)propanoyl]-N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide |
| MalPeg6C2-#47 | LC-MS (Protocol H): m/z 1184.7 [M + H$^+$] (3.67 minutes) | 1-(2,5-dioxo-2,5-dihydro-1H-pyrrol-1-yl)-N-(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}cyclopentyl)-3,6,9,12,15,18-hexaoxahenicosan-21-amide |
| MalPeg6C2-#26 | LC-MS (Protocol H): m/z 1202.7 [M + H$^+$] (3.93 minutes) | N-[1-(2,5-dioxo-2,5-dihydro-1H-pyrrol-1-yl)-21-oxo-3,6,9,12,15,18-hexaoxahenicosan-21-yl]-N-methyl-L-valyl-N-[(3R,4S,5S)-3-methoxy-1-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-5-methyl-1-oxoheptan-4-yl]-N-methyl-L-valinamide |
| MalPeg6C2-#36 | LC-MS (Protocol H): m/z 1118.8 [M – H] (3.96 minutes) | N-[1-(2,5-dioxo-2,5-dihydro-1H-pyrrol-1-yl)-21-oxo-3,6,9,12,15,18-hexaoxahenicosan-21-yl]-N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide |
| mcValCitPABCAmPeg3C2-#36 | LC-MS (Protocol H): m/z 1506.8 [M + H$^+$] (3.76 minutes) | N-[6-(2,5-dioxo-2,5-dihydro-1H-pyrrol-1-yl)hexanoyl]-L-valyl-N-{4-[(18S,21S,24S,25R)-24-[(2S)-butan-2-yl]-25-{2-[(2S)-2-{(1R,2R)-1-methoxy-2-methyl-3-[(2-phenylethyl)amino]-3-thioxopropyl}pyrrolidin-1-yl]-2-oxoethyl}-17,23-dimethyl-3,16,19,22-tetraoxo-18,21-di(propan-2-yl)-2,7,10,13,26-pentaoxa-4,17,20,23-tetraazaheptacos-1-yl]phenyl}-N~5~-carbamoyl-L-ornithinamide |
| AmPeg6C2-#36 | LC-MS (Protocol H): m/z 1039.7 [M + H$^+$] (2.68 minutes) | N-(21-amino-4,7,10,13,16,19-hexaoxahenicosan-1-oyl)-N-methyl-L-valyl-N-{(3R,4S,5S)-3-methoxy-1-[(2S)-2-{(1R,2R)-1-methoxy-2-methyl-3-[(2-phenylethyl)amino]-3-thioxopropyl}pyrrolidin-1-yl]-5-methyl-1-oxoheptan-4-yl}-N-methyl-L-valinamide |
| mcValCitPABC-#60 | HPLC (Protocol M): m/z 1307.6 [M + H$^+$] (12.696 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-{(2S)-2-[(1R,2R)-1-methoxy-2-methyl-3-oxo-3-{[(1-phenylcyclopropyl)methyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mcValCitPABCAmPeg6C2-#36 | LC-MS (Protocol H): m/z 1638.0 [M + H$^+$] (3.77 minutes) | N-[6-(2,5-dioxo-2,5-dihydro-1H-pyrrol-1-yl)hexanoyl]-L-valyl-N-{4-[(27S,30S,33S,34R)-33-[(2S)-butan-2-yl]-34-{2-[(2S)-2-{(1R,2R)-1-methoxy-2-methyl-3-[(2-phenylethyl)amino]-3-thioxopropyl}pyrrolidin-1-yl]-2-oxoethyl}-26,32-dimethyl-3,25,28,31-tetraoxo-27,30-di(propan-2-yl)-2,7,10,13,16,19,22,35-octaoxa-4,26,29,32-tetraazahexatriacont-1-yl]phenyl}-N~5~-carbamoyl-L-ornithinamide |
| mcValCitPABCAmPeg3C2-#41 | LC-MS (Protocol H): m/z 1550.9 [M + H$^+$] (3.53 minutes) | N-[6-(2,5-dioxo-2,5-dihydro-1H-pyrrol-1-yl)hexanoyl]-L-valyl-N-{4-[(18S,21S,24S,25R)-24-[(2S)-butan-2-yl]-25-(2-{(2S)-2-{(1R,2R)-3-{[(1S)-1-carboxy-2-phenylethyl]amino}-1-methoxy-2-methyl-3-thioxopropyl]pyrrolidin-1-yl}-2-oxoethyl)-17,23-dimethyl-3,16,19,22-tetraoxo-18,21-di(propan-2-yl)-2,7,10,13,26-pentaoxa-4,17,20,23-tetraazaheptacos-1-yl]phenyl}-N~5~-carbamoyl-L-ornithinamide |
| MalPeg6C2-#60 | LC-MS (Protocol H): m/z 1101.8 [M + H$^+$] (3.66 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide |
| AmPeg6C2-#60 | LC-MS (Protocol H): m/z | N-(21-amino-4,7,10,13,16,19-hexaoxahenicosan-1-oyl)-2-methylalanyl-N-[(3R,4S,5S)-3-methoxy-1-{(2S)-2- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| | 1021.7 [M + H$^+$] (2.57 minutes) | [(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide |
| MalPeg3C2-#60 | LC-MS (Protocol H): m/z 969.7 [M + H$^+$] (3.65 minutes) | N-[3-(2-{2-[2-(2,5-dioxo-2,5-dihydro-1H-pyrrol-1-yl)ethoxy]ethoxy}ethoxy)propanoyl]-2-methylalanyl-N-[(3R,4S,5S)-3-methoxy-1-{(2S)-2-[(1R,2R)-1-methoxy-2-methyl-3-oxo-3-{[(1-phenylcyclopropyl)methyl]amino}propyl]pyrrolidin-1-yl}-5-methyl-1-oxoheptan-4-yl]-N-methyl-L-valinamide |
| MalPeg6C2-#41 | LC-MS (Protocol H): m/z 1163.0 [M − H] (3.70 minutes) | N-[1-(2,5-dioxo-2,5-dihydro-1H-pyrrol-1-yl)-21-oxo-3,6,9,12,15,18-hexaoxahenicosan-21-yl]-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-thioxopropyl]pyrrolidin-1-yl}-3-methoxy-5-methyl-1-oxoheptan-4-yl]-N-methyl-L-valinamide |
| AmPeg6C2-#66 | LC-MS (Protocol Q1): m/z 1009.8 [M + H$^+$] (0.72 minutes) | N-(21-amino-4,7,10,13,16,19-hexaoxahenicosan-1-oyl)-2-methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABCAmPeg6C2-#60 | LC-MS (Protocol H): m/z 1621.0 [M + H$^+$] (3.55 minutes) | N-[6-(2,5-dioxo-2,5-dihydro-1H-pyrrol-1-yl)hexanoyl]-L-valyl-N-{4-[(30S,33S,34R)-33-[(2S)-butan-2-yl]-34-(2-{(2S)-2-[(1R,2R)-1-methoxy-2-methyl-3-oxo-3-{[(1-phenylcyclopropyl)methyl]amino}propyl]pyrrolidin-1-yl}-2-oxoethyl)-27,27,32-trimethyl-3,25,28,31-tetraoxo-30-(propan-2-yl)-2,7,10,13,16,19,22,35-octaoxa-4,26,29,32-tetraazahexatriacont-1-yl]phenyl}-N~5~-carbamoyl-L-ornithinamide |
| mc-#70 | HPLC (Protocol M): m/z 911.5 [M + H$^+$] (11.847 minutes) | N-[6-(2,5-dioxo-2,5-dihydro-1H-pyrrol-1-yl)hexanoyl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| 2AcAmPeg6C2-#66 | LC-MS (Protocol Q1): m/z 1129.8 [M + H$^+$] (0.85 minutes) | N-(24-bromo-23-oxo-4,7,10,13,16,19-hexaoxa-22-azatetracosan-1-oyl)-2-methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide |
| mc-#66 | LC-MS (Protocol Q1): m/z 867.7 [M + H$^+$] (0.90 minutes) | N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#88 | LC-MS (Protocol Q1): m/z 1355.9 [M + H$^+$] (0.87 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N~5~-carbamoyl-L-ornithinamide |
| mcValCitPABC-#88 | LC-MS (Protocol Q1): m/z 1314.9 [M + H$^+$] (0.91 minutes) | N-{6-[(bromoacetyl)amino]hexanoyl}-L-valyl-N-{4-[(8S,11S,12R)-11-[(2S)-butan-2-yl]-12-(2-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mc-#92 | LC-MS (Protocol Q1): m/z 876.7 [M + H$^+$] (0.75 minutes) | N-[6-(2,5-dioxo-2,5-dihydro-1H-pyrrol-1-yl)hexanoyl]-2-methylalanyl-N-[(3R,4S,5S)-3-methoxy-1-{(2S)-2-[(1R,2R)-1-methoxy-2-methyl-3-oxo-3-(quinolin-6-ylamino)propyl]pyrrolidin-1-yl}-5-methyl-1-oxoheptan-4-yl]-N-methyl-L-valinamide |

TABLE 18B-continued

_Selected compounds (cytotoxic peptides with linkers) of the invention_

| linker with payload # | Mass spectrum: LC-MS or HPLC observed m/z and retention time in minutes: ESI-MS | IUPAC Name |
|---|---|---|
| mcValCitPABC-#44 | HPLC (Protocol A): m/z 1318.6 [M + H$^+$] (9.174 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-3-{[(1S)-1-carboxy-2-phenylethyl]amino}-1-methoxy-2-methyl-3-thioxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mc-#108 | HPLC (Protocol A): m/z 909.5 [M + H$^+$] (9.063 minutes) | N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(R)-(7S)-bicyclo[4.2.0]octa-1,3,5-trien-7-yl(carboxy)methyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#108 | HPLC (Protocol M): m/z 1315.7 [M + H$^+$] (11.89 minutes) | N-[6-(2,5-dioxo-2,5-dihydro-1H-pyrrol-1-yl)hexanoyl]-L-valyl-N-{4-[(8S,11S,12R)-12-(2-{(2S)-2-[(1R,2R)-3-{[(R)-(7S)-bicyclo[4.2.0]octa-1,3,5-trien-7-yl(carboxy)methyl]amino}-1-methoxy-2-methyl-3-oxopropyl]pyrrolidin-1-yl}-2-oxoethyl)-11-[(2S)-butan-2-yl]-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| NHSCOPeg2C2ValCitPABC-#66 | HPLC (Protocol M): m/z 683.3 [M + $^{+2}$] (10.03 minutes) | N-[3-(2-{3-[(2,5-dioxopyrrolidin-1-yl)oxy]-3-oxopropoxy}ethoxy)propanoyl]-L-valyl-N-{4-[(8S,11S,12R)-11-[(2S)-butan-2-yl]-12-(2-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mcValCitPABC-#98 | HPLC (Protocol M): m/z 1368.6 [M + H$^+$] (12.504 minutes) | N-[6-(2,5-dioxo-2,5-dihydro-1H-pyrrol-1-yl)hexanoyl]-L-valyl-N~5~-carbamoyl-N-{4-[({[(2S)-2-{[(2S)-1-{(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}-2-methylpyrrolidin-1-yl]carbonyl}oxy)methyl]phenyl}-L-ornithinamide |
| mcValCitPABC-#95 | LC-MS (Protocol Q): m/z 1356.5 [M + H$^+$] (1.79 minutes) | N-[6-(2,5-dioxo-2,5-dihydro-1H-pyrrol-1-yl)hexanoyl]-L-valyl-N-{4-[(9S,12S,13R)-12-[(2S)-butan-2-yl]-13-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-6,6,11-trimethyl-3,7,10-trioxo-9-(propan-2-yl)-2,14-dioxa-4,8,11-triazapentadec-1-yl]phenyl}-N~5~-carbamoyl-L-ornithinamide |
| MalPeg3C2-#69 | HPLC (Protocol M): m/z 987.5 [M + H$^+$] (10.702 minutes) | N-[3-(2-{2-[2-(2,5-dioxo-2,5-dihydro-1H-pyrrol-1-yl)ethoxy]ethoxy}ethoxy)propanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| AmPeg6C2-#69 | LC-MS (Protocol H): m/z 1040.1 [M + H$^+$] (2.12 minutes) | N-(21-amino-4,7,10,13,16,19-hexaoxahenicosan-1-oyl)-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#84 | LC-MS (Protocol Q): m/z 1371.4 [M + H$^+$] (1.89 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-2-methyl-3-{[(1S)-2-phenyl-1-(1,3-thiazol-2-yl)ethyl]amino}-3-thioxopropyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N~5~-carbamoyl-L-ornithinamide |
| AmCapValCitPABC-#54 | LC-MS (Protocol H): m/z | N-(6-aminohexanoyl)-L-valyl-N-{4-[(8S,11S,12R)-11-[(2S)-butan-2-yl]-12-(2-{(2S)-2-[(1R,2R)-1-methoxy-2- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| | 1262.3 [M + H⁺] (2.35 minutes) | methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mcValCitPABC-#226 | LC-MS (Protocol Q): m/z 1330.9 [M + H⁺] (1.77 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N~5~-carbamoyl-L-ornithinamide |
| mcValCitPABC-#117 | LC-MS (Protocol Q): m/z 1342.6 [M + H⁺] (1.80 minutes) | N-[6-(2,5-dioxo-2,5-dihydro-1H-pyrrol-1-yl)hexanoyl]-L-valyl-N~5~-carbamoyl-N-{4-[({[(2S)-2-{[(2S)-1-{[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl](methyl)amino}-3-methyl-1-oxobutan-2-yl]carbamoyl}-2-methylpyrrolidin-1-yl]carbonyl}oxy)methyl]phenyl}-L-ornithinamide |
| MalPeg6C2-#98 | HPLC (Protocol M): m/z 1185.6 [M + H⁺] (11.985 minutes) | 1-[1-(2,5-dioxo-2,5-dihydro-1H-pyrrol-1-yl)-21-oxo-3,6,9,12,15,18-hexaoxahenicosan-21-yl]-2-methyl-L-prolyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| mcValCitPABC-#118 | LC-MS (Protocol Q): m/z 1328.6 [M + H⁺] (1.68 minutes) | N-[6-(2,5-dioxo-2,5-dihydro-1H-pyrrol-1-yl)hexanoyl]-L-valyl-N~5~-carbamoyl-N-{4-[({[(2S)-2-{[(2S)-1-{[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]carbamoyl}-2-methylpyrrolidin-1-yl]carbonyl}oxy)methyl]phenyl}-L-ornithinamide |
| mcValCitPABC-#80 | HPLC (Protocol M): m/z 1353.6 [M + Na⁺] (12.751 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-3-{[(1S)-1-carboxy-2-phenylethyl]amino}-1-methoxy-2-methyl-3-thioxopropyl]pyrrolidin-1-yl}-2-oxoethyl)-4,5,5,10-tetramethyl-3,6,9-trioxo-8-(propan-2-yl)-2,13-dioxa-4,7,10-triazatetradec-1-yl]phenyl}-N~5~-carbamoyl-L-ornithinamide |
| MalPeg6C2-#118 | LC-MS (Protocol Q): m/z 1145.6 [M + H⁺] (1.66 minutes) | 1-[1-(2,5-dioxo-2,5-dihydro-1H-pyrrol-1-yl)-21-oxo-3,6,9,12,15,18-hexaoxahenicosan-21-yl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| MalPeg6C2-#230 | HPLC (Protocol M): m/z 1146.6 [M + H⁺] (12.071 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-1-{(2S)-2-[(1R,2R)-3-{[(R)-carboxy(1-phenylcyclopropyl)methyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#232 | LC-MS (Protocol Q): m/z 1367.3 [M + H⁺] (1.81 minutes) | N-[6-(2,5-dioxo-2,5-dihydro-1H-pyrrol-1-yl)hexanoyl]-L-valyl-N~5~-carbamoyl-N-{4-[({[(2R)-2-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}-2-methylpyrrolidin-1-yl]carbonyl}oxy)methyl]phenyl}-L-ornithinamide |
| mc-#117 | LC-MS (Protocol Q): m/z 937.4 [M + H⁺] (1.91 minutes) | 1-[6-(2,5-dioxo-2,5-dihydro-1H-pyrrol-1-yl)hexanoyl]-2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| MalPeg6C2-#117 | HPLC (Protocol M): m/z 1161.6 [M + H$^+$] (12.115 minutes) | 1-[1-(2,5-dioxo-2,5-dihydro-1H-pyrrol-1-yl)-21-oxo-3,6,9,12,15,18-hexaoxahenicosan-21-yl]-2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| mv-#69 | LC-MS (Protocol Q): m/z 883.3 [M + H$^+$] (1.57 minutes) | N-[5-(2,5-dioxo-2,5-dihydro-1H-pyrrol-1-yl)pentanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mb-#69 | HPLC (Protocol M): m/z 869.5 [M + H$^+$] (10.874 minutes) | N-[4-(2,5-dioxo-2,5-dihydro-1H-pyrrol-1-yl)butanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| AmPeg6C2-#234 | LC-MS (Protocol Q1): m/z 1514.3 [M + H$^+$] (0.76 minutes) | N-(21-amino-4,7,10,13,16,19-hexaoxahenicosan-1-oyl)-2-methylalanyl-N-{(3R,4S,5S)-1-[(2S)-2-{(3R,4R,7S,12S)-7-benzyl-14-[3-chloro-4-(propan-2-yloxy)phenyl]-4-methyl-12-[4-(8-methylimidazo[1,2-a]pyridin-2-yl)benzyl]-5,8,14-trioxo-2,9-dioxa-6,13-diazatetradecan-3-yl}pyrrolidin-1-yl]-3-methoxy-5-methyl-1-oxoheptan-4-yl}-N-methyl-L-valinamide |
| AmPeg6C2-#235 | LC-MS (Protocol Q1): m/z 1280.2 [M + H$^+$] (0.87 minutes) | N-(21-amino-4,7,10,13,16,19-hexaoxahenicosan-1-oyl)-2-methylalanyl-N-[(3R,4S,5S)-1-{(2S)-2-[(1R,2R)-3-{[(2S)-1-{[4-(5-fluoro-1,3-benzothiazol-2-yl)-2-methylphenyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| mc-#118 | LC-MS (Protocol Q): m/z 923.3 [M + H$^+$] (1.73 minutes) | 1-[6-(2,5-dioxo-2,5-dihydro-1H-pyrrol-1-yl)hexanoyl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| MalPeg6C2-#123 | LC-MS (Protocol Q1): m/z 1175.3 [M + H$^+$] (0.99 minutes) | N-[1-(2,5-dioxo-2,5-dihydro-1H-pyrrol-1-yl)-21-oxo-3,6,9,12,15,18-hexaoxahenicosan-21-yl]-2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| mc-#226 | LC-MS (Protocol Q): m/z 925.7 [M + H$^+$] (1.85 minutes) | N-[6-(2,5-dioxo-2,5-dihydro-1H-pyrrol-1-yl)hexanoyl]-N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| me-#118 | LC-MS (Protocol Q): m/z 937.7 [M + H$^+$] (1.80 minutes) | 1-[7-(2,5-dioxo-2,5-dihydro-1H-pyrrol-1-yl)heptanoyl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mc-#131 | LC-MS (Protocol Q): m/z 937.3 [M + H$^+$] (1.88 minutes) | 1-[6-(2,5-dioxo-2,5-dihydro-1H-pyrrol-1-yl)hexanoyl]-2-methyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| mb-#118 | LC-MS (Protocol Q): m/z 895.3 [M + H$^+$] (1.63 minutes) | 1-[4-(2,5-dioxo-2,5-dihydro-1H-pyrrol-1-yl)butanoyl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#134 | LC-MS (Protocol Q): m/z 1314.3 [M + H$^+$] (1.67 minutes) | N-[6-(2,5-dioxo-2,5-dihydro-1H-pyrrol-1-yl)hexanoyl]-L-valyl-N~5~-carbamoyl-N-{4-[({[(2S)-2-{[(2S)-1-{[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| mc-#145 | LC-MS (Protocol Q1): m/z 897.34 [M + H⁺] (0.90 minutes) | 2-yl]carbamoyl}-2-methylpyrrolidin-1-yl]carbamoyl}oxy)methyl]phenyl]-L-ornithinamide N-[6-(2,5-dioxo-2,5-dihydro-1H-pyrrol-1-yl)hexanoyl]-N,2-dimethylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| MalPeg6C2-#126 | HPLC (Protocol M): m/z 1169.6 [M + Na⁺] (12.583 minutes) | methyl N-{(2R,3R)-3-[(2S)-1-{(3R,4S,5S)-4-[{N-[1-(2,5-dioxo-2,5-dihydro-1H-pyrrol-1-yl)-24,24-dimethyl-21,25-dioxo-3,6,9,12,15,18-hexaoxa-22-azapentacosan-25-yl]-L-valyl}(methyl)amino]-3-methoxy-5-methylheptanoyl]pyrrolidin-2-yl]-3-methoxy-2-methylpropanoyl}-L-phenylalaninate |
| mc-#126 | HPLC (Protocol M): m/z 925.5 [M + H⁺] (12.994 minutes) | methyl N-[(2R,3R)-3-{(2S)-1-[(3R,4S,5S)-4-{[N-(3-{[6-(2,5-dioxo-2,5-dihydro-1H-pyrrol-1-yl)hexanoyl]amino}-2,2-dimethylpropanoyl)-L-valyl](methyl)amino}-3-methoxy-5-methylheptanoyl]pyrrolidin-2-yl}-3-methoxy-2-methylpropanoyl]-L-phenylalaninate |
| mv-#118 | LC-MS (Protocol Q): m/z 909.2 [M + H⁺] (1.68 minutes) | 1-[5-(2,5-dioxo-2,5-dihydro-1H-pyrrol-1-yl)pentanoyl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mc-#172 | LC-MS (Protocol Q1): m/z 941.3 [M + H⁺] (0.96 minutes) | methyl N-[(2R,3R)-3-{(2S)-1-[(3R,4S,5S)-4-{[N-({(3S)-1-[6-(2,5-dioxo-2,5-dihydro-1H-pyrrol-1-yl)hexanoyl]-3-fluoropyrrolidin-3-yl}carbonyl)-L-valyl](methyl)amino}-3-methoxy-5-methylheptanoyl]pyrrolidin-2-yl}-3-methoxy-2-methylpropanoyl]-L-phenylalaninate |
| MalPeg6C2-#226 | LC-MS (Protocol Q): m/z 1147.3 [M + H⁺] (1.76 minutes) | N-[1-(2,5-dioxo-2,5-dihydro-1H-pyrrol-1-yl)-21-oxo-3,6,9,12,15,18-hexaoxahenicosan-21-yl]-N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| MalPeg6C2-#145 | LC-MS (Protocol Q1): m/z 1141.3 [M + Na⁺] (0.87 minutes) | N-[1-(2,5-dioxo-2,5-dihydro-1H-pyrrol-1-yl)-21-oxo-3,6,9,12,15,18-hexaoxahenicosan-21-yl]-N,2-dimethylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| mc-#162 | LC-MS (Protocol Q): m/z 937.3 [M + H⁺] (1.50 minutes) | N-[(2R,3R)-3-{(2S)-1-[(3R,4S,5S)-4-{[N-({(2S)-1-[6-(2,5-dioxo-2,5-dihydro-1H-pyrrol-1-yl)hexanoyl]-2-methylpiperidin-2-yl}carbonyl)-L-valyl](methyl)amino}-3-methoxy-5-methylheptanoyl]pyrrolidin-2-yl}-3-methoxy-2-methylpropanoyl]-L-phenylalanine |
| mc-#163 | HPLC (Protocol A): m/z 937.5 [M + H⁺] (7.855 minutes) | N-[(2R,3R)-3-{(2S)-1-[(3R,4S,5S)-4-{[N-({(2R)-1-[6-(2,5-dioxo-2,5-dihydro-1H-pyrrol-1-yl)hexanoyl]-2-methylpiperidin-2-yl}carbonyl)-L-valyl](methyl)amino}-3-methoxy-5-methylheptanoyl]pyrrolidin-2-yl}-3-methoxy-2-methylpropanoyl]-L-phenylalanine |
| mcValCitPABC-#231 | LC-MS (Protocol Q1): m/z 1640.4 [M + Na⁺²³] (0.94 minutes) | (N-[6-(2,5-dioxo-2,5-dihydro-1H-pyrrol-1-yl)hexanoyl]-L-valyl-N-{4-[(8S,11S,12R)-12-(2-{(2S)-2-[(3R,4R,7S)-7-benzyl-15-{2-[(3,5-dimethyl-1H-pyrrol-2-yl-kappaN)methylidene]-2H-pyrrol-5-yl-kappaN}-4-methyl-5,8,13-trioxo-2-oxa-6,9,12-triazapentadecan-3-yl]pyrrolidin-1-yl}-2-oxoethyl)-11-[(2S)-butan-2-yl]-5,5,10-trimethyl-3,6,9-trioxo-8-(propan-2-yl)-2,13-dioxa-4,7,10-triazatetradec-1-yl]phenyl}-N~5~-carbamoyl-L-ornithinamidato)(difluoro)boron |
| MalPeg6C2-#238 | LC-MS (Protocol Q1): m/z 1173.3 [M + H⁺] (0.96 minutes) | N-[1-(2,5-dioxo-2,5-dihydro-1H-pyrrol-1-yl)-21-oxo-3,6,9,12,15,18-hexaoxahenicosan-21-yl]-N,2-dimethylalanyl-N-[(3R,4S,5S)-3-methoxy-1-{(2S)-2-[(1R,2R)-1-methoxy-2-methyl-3-oxo-3-{[(2S)-1-oxo-3- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| MalPeg6C2-#239 | LC-MS (Protocol Q): m/z 1201.3 [M + H$^+$] (2.02 minutes) | phenyl-1-(prop-2-en-1-yloxy)propan-2-yl]amino}propyl]pyrrolidin-1-yl}-5-methyl-1-oxoheptan-4-yl]-N-methyl-L-valinamide 1-[1-(2,5-dioxo-2,5-dihydro-1H-pyrrol-1-yl)-21-oxo-3,6,9,12,15,18-hexaoxahenicosan-21-yl]-2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| mc-#123 | LC-MS (Protocol Q1): m/z 953.3 [M + H$^+$] (1.04 minutes) | N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| MalC6-#54 | LC-MS (Protocol Q): m/z 922.3 [M + H$^+$] (1.50 minutes) | N-[6-(2,5-dioxo-2,5-dihydro-1H-pyrrol-1-yl)hexyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| mc-#231 | LC-MS (Protocol Q1): m/z 1213.3 [M + H$^+$] (0.98 minutes) | {N-[6-(2,5-dioxo-2,5-dihydro-1H-pyrrol-1-yl)hexanoyl]-2-methylalanyl-N-[(3R,4S,5S)-1-{(2S)-2-[(3R,4R,7S)-7-benzyl-15-{2-[(3,5-dimethyl-1H-pyrrol-2-yl-kappaN)methylidene]-2H-pyrrol-5-yl-kappaN]-4-methyl-5,8,13-trioxo-2-oxa-6,9,12-triazapentadecan-3-yl]pyrrolidin-1-yl}-3-methoxy-5-methyl-1-oxoheptan-4-yl]-N-methyl-L-valinamidato}(difluoro)boron |
| MalC6-#118 | LC-MS (Protocol Q1): m/z 909.3 [M + H$^+$] (0.76 minutes) | 1-[6-(2,5-dioxo-2,5-dihydro-1H-pyrrol-1-yl)hexyl]-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#123 | LC-MS (Protocol Q1): m/z 1358.3 [M + H$^+$] (0.97 minutes) | N-[6-(2,5-dioxo-2,5-dihydro-1H-pyrrol-1-yl)hexanoyl]-L-valyl-N-{4-[(8S,11S,12R)-11-[(2S)-butan-2-yl]-12-(2-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| mc-#237 | LC-MS (Protocol Q1): m/z 964.4 [M + H$^+$] (0.96 minutes) | N-[6-(2,5-dioxo-2,5-dihydro-1H-pyrrol-1-yl)hexanoyl]-N,2-dimethylalanyl-N-[(3R,4S,5S)-1-{(2S)-2-[(1R,2R)-3-{[(2S)-3-(1H-indol-3-yl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| mc-#158 | HPLC (Protocol M): m/z 951.4 [M + H$^+$] (12.839 minutes) | methyl N-[(2R,3R)-3-{(2S)-1-[(3R,4S,5S)-4-{[N-({(2S)-1-[6-(2,5-dioxo-2,5-dihydro-1H-pyrrol-1-yl)hexanoyl]-2-methylpiperidin-2-yl}carbonyl)-L-valyl](methyl)amino}-3-methoxy-5-methylheptanoyl]pyrrolidin-2-yl}-3-methoxy-2-methylpropanoyl]-L-phenylalaninate |
| MalC6Am-#151 | LC-MS (Protocol Q): m/z 922.3 [M + H$^+$] (1.43 minutes) | 1,2-dimethyl-L-prolyl-N-[(3R,4S,5S)-1-{(2S)-2-[(1R,2R)-3-{[(2S)-1-{[6-(2,5-dioxo-2,5-dihydro-1H-pyrrol-1-yl)hexyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| PFPCOPeg2C2ValCitPABC-#54 | LC-MS (Protocol Q): m/z 1502.8 [M + H$^+$] (1.98 minutes) | N-(3-{2-[3-oxo-3-(pentafluorophenoxy)propoxy]ethoxy}propanoyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| | | 4,7,10-triazatetradec-1-yl]phenyl}-N~5~-carbamoyl-L-ornithinamide |
| mcValCitPABC-#154 | LC-MS (Protocol Q1): m/z 1370.2 [M + H$^+$] (0.93 minutes) | N-[6-(2,5-dioxo-2,5-dihydro-1H-pyrrol-1-yl)hexanoyl]-L-valyl-N-{4-[(9S,12S,13R)-12-[(2S)-butan-2-yl]-13-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-4,6,6,11-tetramethyl-3,7,10-trioxo-9-(propan-2-yl)-2,14-dioxa-4,8,11-triazapentadec-1-yl]phenyl}-N~5~-carbamoyl-L-ornithinamide |
| MalC6Am-#153 | HPLC (Protocol A): m/z 922.5 [M + H$^+$] (7.352 minutes) | 1,2-dimethyl-D-prolyl-N-[(3R,4S,5S)-1-{(2S)-2-[(1R,2R)-3-{[(2S)-1-{[6-(2,5-dioxo-2,5-dihydro-1H-pyrrol-1-yl)hexyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| PFPCOPeg2C2AmPeg2C2-#69 | HPLC (Protocol BB): m/z 1217.6 [M + H$^+$] (12.936 minutes) | N-[11,20-dioxo-20-(pentafluorophenoxy)-4,7,14,17-tetraoxa-10-azaicosan-1-oyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcValCitPABC-#246 | LC-MS (Protocol Q): m/z 1327.9 [M + H$^+$] (1.36 minutes) | N-[6-(2,5-dioxo-2,5-dihydro-1H-pyrrol-1-yl)hexanoyl]-L-valyl-N-(4-{(6S,9R,10R)-6-benzyl-10-[(2S)-1-{(3R,4S,5S)-4-[(1,2-dimethyl-L-prolyl-L-valyl)(methyl)amino]-3-methoxy-5-methylheptanoyl}pyrrolidin-2-yl]-9-methyl-3,8-dioxo-2,11-dioxa-4,7-diazadodec-1-yl}phenyl)-N~5~-carbamoyl-L-ornithinamide |
| PFPCOPeg2C2AlaAlaAsnPABC-#54 | HPLC (Protocol AB): m/z 1503.6 [M + H$^+$] (8.06 minutes) | N-(3-{2-[3-oxo-3-(pentafluorophenoxy)propoxy]ethoxy}propanoyl)-L-alanyl-L-alanyl-N~1~-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-L-aspartamide |
| PFPCOPeg2C2-#54 | HPLC (Protocol AB): m/z 1098.4 [M + H$^+$] (8.44 minutes) | 2-methyl-N-(3-{2-[3-oxo-3-(pentafluorophenoxy)propoxy]ethoxy}propanoyl)alanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| PFPCOPeg2C2AmPeg2C2PABC-#54 | HPLC (Protocol AB): m/z 1428.2 [M + Na$^+$] (10.32 minutes) | N-{[(4-{[11,20-dioxo-20-(pentafluorophenoxy)-4,7,14,17-tetraoxa-10-azaicosan-1-oyl]amino}benzyl)oxy]carbonyl}-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| AmPeg6C2-#115 | HPLC (Protocol A): m/z 1053.5 [M + H$^+$] (7.35 minutes) | N-(21-amino-4,7,10,13,16,19-hexaoxahenicosan-1-oyl)-N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| PFPCOPeg5C2-#115 | LC-MS (Protocol Q): m/z 1205.1 [M + H$^+$] (1.99 minutes) | N,2-dimethyl-N-[19-oxo-19-(pentafluorophenoxy)-4,7,10,13,16-pentaoxanonadecan-1-oyl]alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| mcGly-#201 | HPLC (Protocol EB): (4.0 minutes): ESI-MS m/z 1023.59 [M + H$^+$] | 1,2-dimethyl-D-prolyl-N-[(3R,4S,5S)-1-{(2S)-2-[(1R,2R)-3-({(2S)-3-[4-({N-[6-(2,5-dioxo-2,5-dihydro-1H-pyrrol-1-yl)hexanoyl]glycyl}amino)phenyl]-1-methoxy-1-oxopropan-2-yl}amino)-1-methoxy-2-methyl-3-oxopropyl]pyrrolidin- |

TABLE 18B-continued

Selected compounds (cytotoxic peptides with linkers) of the invention

| linker with payload # | Mass spectrum: LC-MS or HPLC observed m/z and retention time in minutes: ESI-MS | IUPAC Name |
|---|---|---|
| AzCOC2Ph4AmCOPeg2C2-#54 | HPLC (Protocol FB): m/z 1132.4 [M + H$^+$] (10.18 minutes) | 1-yl}-3-methoxy-5-methyl-1-oxoheptan-4-yl]-N-methyl-L-valinamide 2-methyl-N-(3-{2-[3-oxo-3-({4-[3-oxo-3-(2-oxoazetidin-1-yl)propyl]phenyl}amino)propoxy]ethoxy}propanoyl)alanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| AzCOC2Ph4AmPeg1C1ValCit PABC-#54 | HPLC (Protocol FB): m/z 1465.8 [M + H$^+$] (10.97 minutes) | N-{[2-oxo-2-({4-[3-oxo-3-(2-oxoazetidin-1-yl)propyl]phenyl}amino)ethoxy]acetyl}-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide |
| AzCOC2Ph4AmPeg1C1ValCit PABC-#30 | HPLC (Protocol FB): m/z 1491.8 [M + H$^+$] (10.56 minutes) | N-{[2-oxo-2-({4-[3-oxo-3-(2-oxoazetidin-1-yl)propyl]phenyl}amino)ethoxy]acetyl}-L-valyl-N~5~-carbamoyl-N-[4-({[(1-{[(2S)-1-{[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl](methyl)amino}-3-methyl-1-oxobutan-2-yl]carbamoyl}cyclopentyl)carbamoyl]oxy}methyl)phenyl]-L-ornithinamide |
| AzCOC2Ph4AmCOPeg2C2-#69 | HPLC (Protocol AB): m/z 1065.3 [M + H$^+$] (12.02 minutes) | 2-methyl-N-(3-{2-[3-oxo-3-({4-[3-oxo-3-(2-oxoazetidin-1-yl)propyl]phenyl}amino)propoxy]ethoxy}propanoyl)alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| AzCOC2Ph4AmCOPeg2C2-#115 | HPLC (Protocol AA): m/z 1078.6 [M + H$^+$] (12.02 minutes) | N,2-dimethyl-N-(3-{2-[3-oxo-3-({4-[3-oxo-3-(2-oxoazetidin-1-yl)propyl]phenyl}amino)propoxy]ethoxy}propanoyl)alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| AcLysValCitPABC-#54 | LC-MS (Protocol Q): m/z 1319.3 [M + H$^{+2}$] (1.34 minutes) | N~2~-acetyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide, trifluoroacetic acid salt |

TABLE 19A

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-(C)_MalPeg3C2-#41 | General procedure F | 2.3/7.5 | 1031 |
| H-(C)_MalPeg6C2-#42 | General procedure F | 2.3/7.5 | 1177 |
| H-(C)_mc-#44 | General procedure F | 2.3/7.5 | 913 |
| H-(C)_MalPeg3C2-#44 | General procedure F | 2.2/7 | 1003 |
| H-(C)_MalPeg6C2-#44 | General procedure F | 2.0/7 | 1135 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
| --- | --- | --- | --- |
| H-(C)__mcValCitPABC-#44 | General procedure F | 2.5/7.5 | 1319 |
| H-(C)__Mal-PEG3C2-#45 | General procedure F | 2.3/7.5 | 1017 |
| H-(C)__Mal-PEG6C2-#45 | General procedure F | 2.05/10 | 1149 |
| H-(C)__mcValCitPABC-#45 | General procedure F | 2.5/10 | 1342 |
| H-(C)__mc-#54 | General procedure F | 2.2/7.5 | 897 |
| H-(C)__Mal-PEG6C2-#69 | General procedure F | 2.1/7.5 | 1119 |
| H-(C)__mcValCitPABC-#69 | General procedure F | 2.5/7.5 | 1303 |
| H-(C)__mcValCitPABC-#70 | General procedure F | 2.0/7 | 1317 |
| H-(C)__mc-#79 | General procedure F | 2.0/7 | 941 |
| H-(C)__mcValCitPABC-#79 | General procedure F | 2.3/7.5 | 1345 |
| H-(C)__mc-#115 | General procedure F | 2.2/6.5 | 911 |
| H-A114C-(C114)__mc-#51 | General procedure G | NA | 934.21 |
| H-A114C-(C114)__mc-#47 | General procedure G | NA | 962.27 |
| H-A114C-(C114)__mc-#54 | General procedure G | NA | 936.2 |
| H-A114C-(C114)__mcValCitPABC-#47 | General procedure H | 50/10 | 1367.72 |
| H-A114C-(C114)__mcValCitPABC-#54 | General procedure H | 100/10 | 1341.68 |
| H-A114C-(C114)__mcValCitPABC-#26 | General procedure H | 50/10 | 1385.8 |
| H-A114C-(C114)__mc-#26 | General procedure H | 50/10 | 980.35 |
| H-A114C-(C114)__mcValCitPABC-#36 | General procedure H | 50/10 | 1302.69 |
| H-A114C-(C114)__mcValCitPABC-#42 | General procedure H | 100/7 | 1360.73 |
| H-A114C-(C114)__mc-#42 | General procedure H | 50/10 | 955.27 |
| H-(C)-mcValCitPABC-#54 | General procedure F | 2.5/10 | 1342 |
| H-(C)__mcValCitPABCAmPeg3C2-#54 | General procedure F | 2.5/9 | 1544 |
| H-(C)__mcValCitPABCAmPeg6C2-#54 | General procedure F | 2.6/10 | 1677 |
| H-(C)__mc-#47 | General procedure F | 1.9/10 | 962.27 |
| H-(C)__MalPeg3C2-#54 | General procedure F | 1.9/10 | 1026 |
| H-(C)__mc-#54 | General procedure F | 2.07/10 | 936.2 |
| H-(C)__mcValCitPABCAmPeg3C2-#47 | General procedure F | 2.3/7.5 | 1569.96 |
| H-(C)__MalPeg3C2-#47 | General procedure F | 2.3/7.5 | 1052 |
| H-(C)__mcValCitPABCAmPeg3C2-#42 | General procedure F | 2.5/7.5 | 1562.87 |
| H-(C)__mc-#41 | General procedure F | 2.5/10 | 941.24 |
| H-(C)__mcValCitPABCAmPeg3C2-#26 | General procedure F | 2.5/10 | 1589.04 |
| H-(C)__mcValCitPABCAmPeg6C2-#47 | General procedure F | 2.4/7 | 1701.9 |
| H-(C)__MalPeg3C2-#42 | General procedure F | 2.3/7 | 1044.58 |
| H-(C)__mcValCitPABCAmPeg6C2-#26 | General procedure F | 2.5/7.5 | 1719.9 |
| H-(C)__mcValCitPABCAmPeg6C2-#42 | General procedure F | 2.3/7.5 | 1696.1 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-(C)__MalPeg6C2-#54 | General procedure F | 2.3/7.5 | 1158.5 |
| H-(C)__MalPeg6C2-#47 | General procedure F | 2.3/7.5 | 1184.5 |
| H-(C)__MalPeg6C2-#26 | General procedure F | 2.3/7.5 | 1202.6 |
| H-(C)-MalPeg6C2-#42 | General procedure F | 2.3/7.5 | 1177 |
| H-(C)__mc-#36 | General procedure F | 2.3/7.5 | 896 |
| H-(C)__mcValCitPABC-#60 | General procedure F | 3.0/7 | 1284.61 |
| H-(C)__MalPeg3C2-#26 | General procedure F | 2.5/10 | 1070.42 |
| H-(C)__mcValCitPABCAmPeg3C2-#36 | General procedure F | 3.0/10 | 1505.93 |
| H-A114C-(C114)__mcValCitPABCAmPeg3C2-#36 | General procedure H | 50/10 | 1505.93 |
| H-A114C-(C114)__MalPeg6C2-#54 | General procedure H | 50/10 | 1158.5 |
| H-(C)__MalPeg3C2-#60 | General procedure F | 2.3/7.5 | 969.23 |
| H-(C)__MalPeg6C2-#60 | General procedure F | 2.3/7.5 | 1101.4 |
| H-(C)__MalPeg6C2-#41 | General procedure F | 2.3/7.5 | 1163.5 |
| H-(C)-mc-#69 | General procedure F | 2.2/7.5 | 897 |
| H-(C)__MalPeg3C2-#36 | General procedure F | 2.15/10 | 987.31 |
| H-(C)__mcValCitPABCAmPeg6C2-#36 | General procedure F | 2.25/10 | 1636 |
| H-(C)__MalPeg6C2-#36 | General procedure F | 2.15/10 | 1119.5 |
| H-(C)__mcValCitPABCAmPeg3C2-#41 | General procedure F | 2.5/10 | 1549.94 |
| H-(C)-MalPeg3C2-#41 | General procedure F | 2.3/7.5 | 1031 |
| H-(C)__mcValCitPABCAmPeg6C2-#60 | General procedure F | 2.5/10 | 1620 |
| H-A114C-(C114)__mc-#66 | General procedure H | 50/7 | 866.5 |
| H-L398C + L443C-(C398 + C443)__mcValCitPABC-#54 | General procedure H | 50/7 | 1341.68 |
| H-K392C + L443C-(C392 + C443)__mcValCitPABC-#54 | General procedure H | 100/10 | 1341 |
| H-L443C-(C443)__mcValCitPABC-#54 | General procedure H | 100/10 | 1341 |
| H-L398C + V422C-(C398 + C422)__mcValCitPABC-#54 | General procedure H | 50/7 | 1341.68 |
| H-(C)-mc-#44 | General procedure F | 2.3/7.5 | 913 |
| H-(C)-Mal-PEG3C2-#45 | General procedure F | 2.3/7.5 | 1017 |
| H-(C)__2AcAmPeg6C2-#66 | General procedure F | 2.4/10 | 1049.6 |
| H-(C)-Mal-PEG6C2-#45 | General procedure F | 2.05/10 | 1149 |
| H-(C)-mc-#79 | General procedure F | 2.0/7 | 941 |
| H-(C)-MalPeg3C2-#44 | General procedure F | 2.2/7 | 1003 |
| H-(C)-mcValCitPABC-#70 | General procedure F | 2.0/7 | 1317 |
| H-(C)-MalPeg6C2-#44 | General procedure F | 2.0/7 | 1135 |
| H-A114C-(C114)__mcValCitPABC-#69 | General procedure H | 100/8.25 | 1302 |
| H-(C)-mcValCitPABC-#79 | General procedure F | 2.3/7.5 | 1345 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-A114C-(C114)__mcValCitPABC-#79 | General procedure H | 100/7.5 | 1346 |
| H-(C)-mcValCitPABC-#44 | General procedure F | 2.5/7.5 | 1319 |
| H-A114C-(C114)__mcValCitPABC-#88 | General procedure H | 100/7.5 | 1355 |
| H-(C)-mcValCitPABC-#69 | General procedure F | 2.5/7.5 | 1303 |
| H-(C)__2AcAmCapValCitPABC-#66 | General procedure F | 2.2/10 | 1313.49 |
| H-A114C-(C114)__mcValCitPABC-#45 | General procedure H | 100/7.5 | 1331.7 |
| H-A114C-(C114)__mcValCitPABC-#34 | General procedure H | 100/10 | 1357 |
| H-A114C-(C114)__mc-#45 | General procedure H | 100/10 | 926 |
| H-A114C-(C114)__mc-#70 | General procedure H | 100/10 | 911.15 |
| H-(C)__mcValCitPABC-#112 | General procedure F | 2.3/7.5 | 1288 |
| H-(C)-Mal-PEG6C2-#69 | General procedure F | 2.1/7.5 | 1119 |
| H-Q347C-(C347)__mcValCitPABC-#69 | General procedure H | 100/10 | 1302 |
| H-Y373C-(C373)__mcValCitPABC-#69 | General procedure H | 100/10 | 1302 |
| H-E388C-(C388)__mcValCitPABC-#69 | General procedure H | 100/10 | 1302 |
| H-N421C-(C421)__mcValCitPABC-#69 | General procedure H | 100/10 | 1302 |
| H-L443C-(C443)__mcValCitPABC-#69 | General procedure H | 100/10 | 1302 |
| H-L443C-(C443)__mcValCitPABC-#79 | General procedure H | 100/10 | 1346 |
| H-A114C-(C114)__mcValCitPABC-#95 | General procedure H | 100/10 | 1354 |
| H-A114C-(C114)__mcValCitPABC-#98 | General procedure H | 100/10 | 1367 |
| H-A114C-(C114)__MalPeg3C2-#69 | General procedure H | 100/10 | 987.2 |
| H-N297Q-(Q)__AmPeg6C2-#42 | General procedure K | NA | 1080 |
| H-N297Q-(Q)__AmPeg6C2-#54 | General procedure K | NA | 1061 |
| H-N297Q-(Q)__AmPeg6C2-#47 | General procedure K | NA | 1087 |
| H-N297Q-(Q)__AmPeg6C2-#36 | General procedure K | NA | 1022 |
| H-N297Q-(Q)__AmPeg6C2-#26 | General procedure K | NA | 1105 |
| H-N297Q-(Q)__AmPeg6C2-#66 | General procedure K | NA | 992 |
| H-L443C-(C443)__MalPeg6C2-#69 | General procedure H | 100/10 | 1119 |
| H-Q347C-(C347)__MalPeg6C2-#69 | General procedure H | 100/10 | 1119 |
| H-E388C-(C388)__MalPeg6C2-#69 | General procedure H | 100/10 | 1119 |
| H-N421C-(C421)__MalPeg6C2-#69 | General procedure H | 100/10 | 1119 |
| H-E380C-(C380)__MalPeg6C2-#69 | General procedure H | 100/10 | 1119 |
| H-L398C + L443C-(C398 + C443)__MalPeg6C2-#69 | General procedure H | 100/10 | 1119 |
| H-K392C + L443C-(C392 + C443)__MalPeg6C2-#69 | General procedure H | 100/10 | 1119 |
| H-kA111C-(kC111)__MalPeg6C2-#69 | General procedure H | 100/10 | 1119 |
| H-kK183C-(kC183)__MalPeg6C2-#69 | General procedure H | 100/10 | 1119 |
| H-kK207C-(kC207)__MalPeg6C2-#69 | General procedure H | 100/10 | 1119 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-A114C-(C114)__mcValCitPABC-#108 | General procedure H | 100/10 | 1314.59 |
| H-A114C-(C114)__mcValCitPABC-#84 | General procedure H | 100/10 | 1371 |
| H-A114C-(C114)__mcValCitPABC-#226 | General procedure H | 100/10 | 1330 |
| H-A114C-(C114)__mc-#108 | General procedure H | 100/10 | 909.12 |
| H-A114C-(C114)__mcValCitPABC-#117 | General procedure H | 100/10 | 1342 |
| H-A114C-(C114)__mcValCitPABC-#115 | General procedure H | 100/10 | 1316 |
| H-A114C-(C114)__MalPeg6C2-#98 | General procedure H | 100/10 | 1184 |
| IL13Ra2-AB08-v1010-hG1-(C)__mcValCitPABC-#54 | General procedure F | 2.2/7 | 1341.68 |
| IL13Ra2-AB08-v1010-hG1-(C)__mc-#69 | General procedure F | 2.3/7 | 897.12 |
| IL13Ra2-AB08-v1010-hG1-(C)__MalPeg6C2-#69 | General procedure F | 2.3/8 | 1119 |
| IL13Ra2-AB08-v1010-hG1-(C)__mcValCitPABC-#69 | General procedure F | 2.5/8 | 1302 |
| H-A114C-(C114)__MalPeg6C2-0#118 | General procedure H | 100/15 | 1145 |
| H-A114C-(C114)__mcValCitPABC-0#118 | General procedure H | 100/15 | 1328 |
| H-A114C-(C114)__mcValCitPABC-#80 | General procedure H | 100/15 | 1332 |
| H-A114C-(C114)__mc-#117 | General procedure H | 100/15 | 937 |
| H-A114C-(C114)__mcValCitPABC-#232 | General procedure H | 100/15 | 1366 |
| H-A114C-(C114)__MalPeg6C2-#230 | General procedure H | 100/15 | 1145 |
| H-A114C-(C114)__MalPeg6C2-#117 | General procedure H | 100/15 | 1159 |
| H-A114C-(C114)__mc-#115 | General procedure H | 100/10 | 911 |
| H-A114C-(C114)__mv-#115 | General procedure H | 100/10 | 897 |
| H-A114C-(C114)__mb-#69 | General procedure H | 100/15 | 869 |
| H-A114C-(C114)__mv-#69 | General procedure H | 100/15 | 883 |
| H-A114C-(C114)__mc-0#118 | General procedure H | 100/15 | 923 |
| H-(C)__mc-#117 | General procedure F | 2.0/6.5 | 937 |
| H-(C)__MalPeg6C2-#117 | General procedure F | 2.05/6.5 | 1159 |
| H-(C)__mc-0#118 | General procedure F | 2.1/7 | 923 |
| H-(C)__MalPeg6C2-0#118 | General procedure F | 2.2/7.5 | 1145 |
| IL13Ra2-AB08-v1010-hG1-(C)__mc-0#118 | General procedure F | 2.35/7 | 923 |
| IL13Ra2-AB08-v1010-hG1-(C)__mc-#226 | General procedure F | 3.0/10 | 925 |
| IL13Ra2-AB08-v1010-hG1-(C)__mc-#117 | General procedure F | 3.0/10 | 937 |
| IL13Ra2-AB08-v1010-hG1-(C)__MalPeg6C2-#117 | General procedure F | 3.0/10 | 1159 |
| IL13Ra2-AB08-v1010-hG1-(C)__MalPeg6C2-0#118 | General procedure F | 3.0/10 | 1145 |
| H-A114C-(C114)__MalPeg6C2-#226 | General procedure H | 100/10 | 1147 |
| H-A114C-(C114)__mc-#172 | General procedure H | 100/15 | 940.53 |
| H-A114C-(C114)__mb-0#118 | General procedure H | 100/15 | 895 |
| H-A114C-(C114)__me-0#118 | General procedure H | 100/15 | 937 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-A114C-(C114)__mcValCitPABC-#134 | General procedure H | 100/15 | 1314 |
| H-A114C-(C114)__mc-#131 | General procedure H | 100/15 | 937 |
| H-A114C-(C114)__MalPeg6C2-#126 | General procedure H | 100/15 | 1147 |
| H-A114C-(C114)__MalPeg6C2-#123 | General procedure H | 100/15 | 1174 |
| H-A114C-(C114)__mc-#126 | General procedure H | 100/15 | 925 |
| H-A114C-(C114)__mv-0#118 | General procedure H | 100/15 | 909 |
| H-(C)__MalPeg6C2-#226 | General procedure F | 2.4/7 | 1147 |
| H-(C)__mc-#226 | General procedure F | 2.4/7 | 925 |
| IL13Ra2-AB08-v1010-hG1-(C)__MalPeg6C2-#226 | General procedure F | 3.0/10 | 1147 |
| Notch-28-cG1-(C)__mc-0#118 | General procedure F | 2.5/7 | 923 |
| Notch-28-cG1-(C)__mc-#115 | General procedure F | 2.35/7 | 911 |
| Notch-28-cG1-(C)__MalPeg6C2-0#118 | General procedure F | 2.35/7 | 1145 |
| Notch-28-cG1-(C)__me-0#118 | General procedure F | 2.4/7 | 937 |
| Notch-75-cG1-(C)__mc-0#118 | General procedure F | 2.5/7 | 923 |
| IL13Ra2-19F9-cG1-(C)__mcValCitPABC-#54 | General procedure F | 2.5/8 | 1341.68 |
| IL13Ra2-19F9-cG1-(C)__mcValCitPABC-#112 | General procedure F | 2.5/7 | 1288 |
| Notch-28-cG1-(C)__mcValCitPABC-#112 | General procedure F | 2.3/7 | 1288 |
| Notch-28-cG1-(C)__MalPeg6C2-#69 | General procedure F | 2.4/7 | 1119 |
| Notch-75-cG1-(C)__MalPeg6C2-#69 | General procedure F | 2.4/7 | 1119 |
| H-(C)__m(H2O)c-0#118 | General procedure I | 2.35/7 | 941 |
| H-(C)__Mal(H2O)Peg6C2-0#118 | General procedure I | 2.35/7 | 1163 |
| H-(C)__Mal(H2O)Peg6C2-#69 | General procedure I | 2.1/7 | 1137 |
| H-(C)__m(H2O)c-#69 | General procedure I | 2.4/7 | 915 |
| H-(C)__me-0#118 | General procedure F | 2.2/7 | 937 |
| H-(C)__mv-0#118 | General procedure F | 2.2/7 | 909 |
| H-(C)__mb-0#118 | General procedure F | 2.1/7 | 895 |
| H-A114C-(C114)__MalC6-#54 | General procedure H | 100/5 | 922.22 |
| H-A114C-(C114)__mc-#231 | General procedure H | 100/5 | 1213 |
| H-A114C-(C114)__MalC6-0#118 | General procedure H | 100/5 | 909.18 |
| H-(C)__Mal(H2O)Peg6C2-#115 | General procedure I | 2.4/7 | 1151 |
| H-A114C-(C114)__mc-#158 | General procedure H | 100/10 | 951 |
| H-A114C-(C114)__mcValCitPABC-#231 | General procedure H | 100/10 | 1617 |
| H-(C)__m(H2O)c-#115 | General procedure I | 2.4/7 | 929 |
| Notch-75-cG1-(C)__mc-#115 | General procedure F | 3.0/7.0 | 911.15 |
| Notch-75-cG1-(C)__me-0#118 | General procedure F | 3.0/7.0 | 937 |
| Notch-75-cG1-(C)__MalPeg6C2-0#118 | General procedure F | 3.0/7.0 | 1144 |

TABLE 19A-continued

Selected conjugates of the invention

| ADC-Linker-Payload # | Prep. Method | Amount of 2,2',2''-phosphanetriyltripropanoic acid/Linker-Payload or TCEP/PL (x/y) | Theoretical Δ mass or payload/linker molecular weight |
|---|---|---|---|
| H-A114C-(C114)__mc-#237 | General procedure H | 100/10 | 963 |
| H-A114C-(C114)__mc-#145 | General procedure H | 100/10 | 897 |
| H-A114C-(C114)__MalPeg6C2-#145 | General procedure H | 100/10 | 1119 |
| H-A114C-(C114)__mc-#162 | General procedure H | 100/10 | 937 |
| H-A114C-(C114)__MalC6Am-#151 | General procedure H | 100/10 | 905 |
| Notch-28-cG1-(C)__m(H2O)c-0#118 | General procedure I | 2.2/7 | 941 |
| Notch-75-cG1-(C)__m(H2O)c-0#118 | General procedure I | 2.2/7 | 941 |
| H-(kK188)__COPeg2C2ValCitPABC-#54 | General procedure J | — | 1318 |
| IL13Ra2-AB08-v1010-hG1-(C)__Mal(H2O)Peg6C2-0#118 | General procedure F | 2.3/7 | 1163 |
| IL13Ra2-AB08-v1010-hG1-(C)__Mal(H2O)Peg6C2-#115 | General procedure F | 2.3/7 | 1151 |
| IL13Ra2-AB08-v1010-hG1-(C)__mc-#115 | General procedure F | 2.35/7 | 911 |
| IL13Ra2-AB08-v1010-hG1-(C)__m(H2O)c-0#118 | General procedure F | 2.8/7 | 941 |
| H-(C)__mcValCitPABC-0#118 | General procedure F | 2.2/7 | 1328 |
| IL13Ra2-AB08-v1010-hG1-(C)__m(H2O)c-#115 | General procedure F | 2.35/7 | 929 |
| H-A114C-(C114)__mcValCitPABC-#154 | General procedure H | 100/5 | 1369 |
| H-A114C-(C114)__MalC6Am-#153 | General procedure H | 100/10 | 921 |
| IL13Ra2-AB08-v1010-Q347C + kK183C-hG1-(C347 + kC183)__mcValCitPABC-#54 | General procedure H | 100/10 | 1341.68 |
| IL13Ra2-AB08-v1010-Q347C-hG1-(C347)__mcValCitPABC-#54 | General procedure H | 100/10 | 1341.68 |
| IL13Ra2-AB08-v1010-hG1-(kK188)__COPeg2C2AmPeg2C2-#69 | General procedure J | — | 1032 |
| IL13Ra2-AB08-v1010-hG1-(kK188)__COPeg2C2ValCitPABC-#54 | General procedure J | — | 1318 |
| IL13Ra2-AB08-v1010-L443C-hG1-(C443)__mcValCitPABC-#54 | General procedure H | 100/10 | 1341.68 |
| IL13Ra2-AB08-v1010-K392C + L443C-hG1-(C392 + C443)__mcValCitPABC-#54 | General procedure H | 100/10 | 1341.68 |
| IL13Ra2-AB08-v1010-L443C + kK183C-hG1-(C443 + kC183)__mcValCitPABC-#54 | General procedure H | 100/10 | 1341.68 |
| H-(C)__mcValCitPABC-#98 | General procedure F | 2.2/7 | 1367 |
| H-A114C-(C114)__mcValCitPABC-#246 | General procedure H | 100/10 | 1327 |
| H-H435A-(C)__mcValCitPABC-#54 | General procedure F | 2.2/8 | 1341.7 |
| H-M428L + N434S-(C)__mcValCitPABC-#70 | General procedure F | 2.2/8 | 1316 |
| H-M428L + N434S-(C)__mcValCitPABC-#54 | General procedure F | 2.2/8 | 1341.7 |
| H-E388C + N421C-(C388 + C421)__mcValCitPABC-#54 | General procedure H | 100/10 | 1341 |
| H-Q347C + K392C-(C347 + C392)__mcValCitPABC-#54 | General procedure H | 100/10 | 1341 |
| H-L443C + kK183C-(C443 + kC183)__mcValCitPABC-#54 | General procedure H | 100/10 | 1341 |
| H-Q347C + kK183C-(C347 + kC183)__mcValCitPABC-#54 | General procedure H | 100/10 | 1341 |
| H-Q347C-(C347)__mcValCitPABC-#54 | General procedure H | 100/10 | 1341 |
| H-K392C + L443C-(C392 + C443)__mc-#115 | General procedure H | 100/10 | 911 |

TABLE 19A-continued

Selected conjugates of the invention

| ADC-Linker-Payload # | Prep. Method | Amount of 2,2',2"-phosphanetriyltripropanoic acid/Linker-Payload or TCEP/PL (x/y) | Theoretical Δ mass or payload/linker molecular weight |
|---|---|---|---|
| H-E388C + N421C-(C388 + C421)__mc-#115 | General procedure H | 100/10 | 911 |
| H-Q347C + K392C-(C347 + C392)__mc-#115 | General procedure H | 100/10 | 911 |
| H-L443C + kK183C-(C443 + kC183)__mc-#115 | General procedure H | 100/10 | 911 |
| H-Q347C + kK183C-(C347 + kC183)__mc-#115 | General procedure H | 100/10 | 911 |
| H-Q347C-(C347)__mc-#115 | General procedure H | 100/10 | 911 |
| H-kK183C-(kC183)__mcValCitPABC-#54 | General procedure H | 100/10 | 1341 |
| H-E388C-(C388)__mcValCitPABC-#54 | General procedure H | 100/10 | 1341 |
| H-kK183C-(kC183)__mc-#115 | General procedure H | 100/10 | 911 |
| H-E388C-(C388)__mc-#115 | General procedure H | 100/10 | 911 |
| H-L443C-(C443)__mc-#115 | General procedure H | 100/10 | 911 |
| H-N421C-(C421)__mcValCitPABC-#54 | General procedure H | 100/10 | 1341 |
| H-N421C-(C421)__mc-#115 | General procedure H | 100/10 | 911 |
| H-A114C-(C114)__mcGly-#201 | General procedure G | 100/10 | 1023 |

TABLE 19B

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-(C)__MalPeg3C2-#41 | SEC (Protocol O): 7.317 minutes; HPLC (Protocol P): HC Δ mass = 1032 | 4.3 |
| H-(C)__MalPeg6C2-#42 | SEC (Protocol O): 7.177 minutes; HPLC (Protocol P): HC Δ mass = 1180 | 3.9 |
| H-(C)__mc-#44 | SEC (Protocol O): 7.195 minutes; HPLC (Protocol P): HC Δ mass = 915 | 4.4 |
| H-(C)__MalPeg3C2-#44 | SEC (Protocol O): 7.247 minutes; HPLC (Protocol P): HC Δ mass = 1005 | 3.4 |
| H-(C)__MalPeg6C2-#44 | SEC (Protocol O): 7.237 minutes; HPLC (Protocol P): HC Δ mass = 1135 | 3.4 |
| H-(C)__mcValCitPABC-#44 | SEC (Protocol O): 7.351 minutes; HPLC (Protocol P): HC Δ mass = 1321 | 4.2 |
| H-(C)__Mal-PEG3C2-#45 | SEC (Protocol O): 7.364 minutes; HPLC (Protocol P): HC Δ mass = 1017 | 4.3 |
| H-(C)__Mal-PEG6C2-#45 | SEC (Protocol O): 7.419 minutes; HPLC (Protocol P): HC Δ mass = 1154 | 3.9 |
| H-(C)__mcValCitPABC-#45 | SEC (Protocol O): 7.159 minutes; HPLC (Protocol P): HC Δ mass = 1343 | 4.1 |
| H-(C)__mc-#54 | SEC (Protocol O): 7.192 minutes; HPLC (Protocol P): HC Δ mass = 899 | 4.5 |
| H-(C)__Mal-PEG6C2-#69 | SEC (Protocol O): 7.350 minutes; HPLC (Protocol P): HC Δ mass = 1122 | 3.4 |
| H-(C)__mcValCitPABC-#69 | SEC (Protocol O): 7.254 minutes; HPLC (Protocol P): HC Δ mass = 1305 | 4.5 |
| H-(C)__mcValCitPABC-#70 | SEC (Protocol O): 7.466 minutes; HPLC (Protocol P): HC Δ mass = 1318 | 3.7 |
| H-(C)__mc-#79 | SEC (Protocol O): 7.478 minutes; HPLC (Protocol P): HC Δ mass = 946 | 4 |
| H-(C)__mcValCitPABC-#79 | SEC (Protocol O): 7.635 minutes; HPLC (Protocol P): HC Δ mass = 1349 | 3.7 |
| H-(C)__mc-#115 | SEC (Protocol O): 7.510 minutes; HPLC (Protocol P): HC Δ mass = 912 | 3.54 |

TABLE 19B-continued

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-A114C-(C114)__mc-#51 | — | 2.4 |
| H-A114C-(C114)__mc-#47 | — | 2.3 |
| H-A114C-(C114)__mc-#54 | — | 2.3 |
| H-A114C-(C114)__mcValCitPABC-#47 | — | 2 |
| H-A114C-(C114)__mcValCitPABC-#54 | — | 1.9 |
| H-A114C-(C114)__mcValCitPABC-#26 | — | 2 |
| H-A114C-(C114)__mc-#26 | — | 1.9 |
| H-A114C-(C114)__mcValCitPABC-#36 | — | 2 |
| H-A114C-(C114)__mcValCitPABC-#42 | SEC (Protocol P): 7.681 minutes; HPLC (Protocol O): HC Δ mass = 1378 | 1.95 |
| H-A114C-(C114)__mc-#42 | — | 2 |
| H-(C)-mcValCitPABC-#54 | SEC (Protocol P): 7.159 minutes; HPLC (Protocol O): HC Δ mass = 1343 | 4.1 |
| H-(C)__mcValCitPABCAmPeg3C2-#54 | — | 4.6 |
| H-(C)__mcValCitPABCAmPeg6C2-#54 | — | 4.5 |
| H-(C)__mc-#47 | — | 4.2 |
| H-(C)__MalPeg3C2-#54 | SEC (Protocol P): 7.179 minutes; HPLC (Protocol O): HC Δ mass = 1028 | 3.7 |
| H-(C)__mc-#54 | — | 4 |
| H-(C)__mcValCitPABCAmPeg3C2-#47 | — | 3.7 |
| H-(C)__MalPeg3C2-#47 | — | 4.3 |
| H-(C)__mcValCitPABCAmPeg3C2-#42 | — | 4.3 |
| H-(C)__mc-#41 | — | 3.1 |
| H-(C)__mcValCitPABCAmPeg3C2-#26 | — | 3 |
| H-(C)__mcValCitPABCAmPeg6C2-#47 | — | 4.2 |
| H-(C)__MalPeg3C2-#42 | SEC (Protocol P): 7.142 minutes; HPLC (Protocol O): HC Δ mass = 1050 | 4.3 |
| H-(C)__mcValCitPABCAmPeg6C2-#26 | — | 4.2 |
| H-(C)__mcValCitPABCAmPeg6C2-#42 | — | 4.1 |
| H-(C)__MalPeg6C2-#54 | SEC (Protocol P): 7.254 minutes; HPLC (Protocol O): HC Δ mass = 1161 | 4.4 |
| H-(C)__MalPeg6C2-#47 | SEC (Protocol P): 7.303 minutes; HPLC (Protocol O): HC Δ mass = 1182 | 4.4 |
| H-(C)__MalPeg6C2-#26 | — | 4.1 |
| H-(C)-MalPeg6C2-#42 | SEC (Protocol P): 7.177 minutes; HPLC (Protocol O): HC Δ mass = 1180 | 3.9 |
| H-(C)__mc-#36 | — | 4.2 |
| H-(C)__mcValCitPABC-#60 | — | 3.8 |
| H-(C)__MalPeg3C2-#26 | — | 3.8 |
| H-(C)__mcValCitPABCAmPeg3C2-#36 | — | 3.5 |
| H-A114C-(C114)__mcValCitPABCAmPeg3C2-#36 | — | 1.9 |
| H-A114C-(C114)__MalPeg6C2-#54 | — | 2 |
| H-(C)__MalPeg3C2-#60 | — | 4.2 |
| H-(C)__MalPeg6C2-#60 | — | 4.1 |
| H-(C)__MalPeg6C2-#41 | — | 4 |
| H-(C)-mc-#69 | SEC (Protocol P): 7.192 minutes; HPLC (Protocol O): HC Δ mass = 899 | 4.5 |
| H-(C)__MalPeg3C2-#36 | — | 5.2 |
| H-(C)__mcValCitPABCAmPeg3C2-#36 | — | 4.2 |
| H-(C)__MalPeg6C2-#36 | — | 5 |
| H-(C)__mcValCitPABCAmPeg3C2-#41 | — | 4.4 |
| H-(C)-MalPeg3C2-#41 | SEC (Protocol P): 7.317 minutes; HPLC (Protocol O): HC Δ mass = 1032 | 4.3 |
| H-(C)__mcValCitPABCAmPeg6C2-#60 | — | 4.1 |
| H-A114C-(C114)__mc-#66 | — | 1.8 |
| H-L398C + L443C-(C398 + C443)__mcValCitPABC-#54 | — | 3.8 |
| H-K392C + L443C-(C392 + C443)__mcValCitPABC-#54 | — | 3.8 |
| H-L443C-(C443)__mcValCitPABC-#54 | SEC (Protocol P): 8.827 minutes; HPLC (Protocol O): HC Δ mass = 1344 | 2 |
| H-L398C + V422C-(C398 + C422)__mcValCitPABC-#54 | — | 3.4 |
| H-(C)-mc-#44 | SEC (Protocol P): 7.195 minutes; HPLC (Protocol O): HC Δ mass = 915 | 4.4 |
| H-(C)-Mal-PEG3C2-#45 | SEC (Protocol P): 7.364 minutes; HPLC (Protocol O): HC Δ mass = 1017 | 4.3 |
| H-(C)__2AcAmPeg6C2-#66 | — | 4 |
| H-(C)-Mal-PEG6C2-#45 | SEC (Protocol P): 7.419 minutes; HPLC (Protocol O): HC Δ mass = 1154 | 3.9 |

TABLE 19B-continued

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-(C)-mc-#79 | SEC (Protocol P): 7.478 minutes; HPLC (Protocol O): HC Δ mass = 946 | 4 |
| H-(C)-MalPeg3C2-#44 | SEC (Protocol P): 7.247 minutes; HPLC (Protocol O): HC Δ mass = 1005 | 3.4 |
| H-(C)-mcValCitPABC-#70 | SEC (Protocol P): 7.466 minutes; HPLC (Protocol O): HC Δ mass = 1318 | 3.7 |
| H-(C)-MalPeg6C2-#44 | SEC (Protocol P): 7.237 minutes; HPLC (Protocol O): HC Δ mass = 1135 | 3.4 |
| H-A114C-(C114)__mcValCitPABC-#69 | — | 2 |
| H-(C)-mcValCitPABC-#79 | SEC (Protocol P): 7.635 minutes; HPLC (Protocol O): HC Δ mass = 1349 | 3.7 |
| H-A114C-(C114)__mcValCitPABC-#79 | — | 1.84 |
| H-(C)-mcValCitPABC-#44 | SEC (Protocol P): 7.351 minutes; HPLC (Protocol O): HC Δ mass = 1321 | 4.2 |
| H-A114C-(C114)__mcValCitPABC-#88 | — | 1.93 |
| H-(C)-mcValCitPABC-#69 | SEC (Protocol P): 7.254 minutes; HPLC (Protocol O): HC Δ mass = 1305 | 4.5 |
| H-(C)__2AcAmCapValCitPABC-#66 | — | 3.3 |
| H-A114C-(C114)__mcValCitPABC-#45 | — | 1.92 |
| H-A114C-(C114)__mcValCitPABC-#34 | — | 2 |
| H-A114C-(C114)__mc-#45 | — | 1.95 |
| H-A114C-(C114)__mc-#70 | — | 2 |
| H-(C)__mcValCitPABC-#112 | SEC (Protocol P): 7.083 minutes; HPLC (Protocol O): HC Δ mass = 1291 | 4.4 |
| H-(C)-Mal-PEG6C2-#69 | SEC (Protocol P): 7.350 minutes; HPLC (Protocol O): HC Δ mass = 1122 | 3.4 |
| H-Q347C-(C347)__mcValCitPABC-#69 | — | 2 |
| H-Y373C-(C373)__mcValCitPABC-#69 | — | 1.6 |
| H-E388C-(C388)__mcValCitPABC-#69 | — | 2 |
| H-N421C-(C421)__mcValCitPABC-#69 | — | 1.95 |
| H-L443C-(C443)__mcValCitPABC-#69 | — | 2 |
| H-L443C-(C443)__mcValCitPABC-#79 | — | 2 |
| H-A114C-(C114)__mcValCitPABC-#95 | — | 2 |
| H-A114C-(C114)__mcValCitPABC-#98 | — | 2 |
| H-A114C-(C114)__MalPeg3C2-#69 | — | 2 |
| H-N297Q-(Q)__AmPeg6C2-#42 | — | 3.2 |
| H-N297Q-(Q)__AmPeg6C2-#54 | — | 3.04 |
| H-N297Q-(Q)__AmPeg6C2-#47 | — | 3.16 |
| H-N297Q-(Q)__AmPeg6C2-#36 | — | 3.36 |
| H-N297Q-(Q)__AmPeg6C2-#26 | — | 3.4 |
| H-N297Q-(Q)__AmPeg6C2-#66 | — | 2.8 |
| H-L443C-(C443)__MalPeg6C2-#69 | SEC (Protocol P): 7.012 minutes; HPLC (Protocol O): HC Δ mass = 1120 | 2 |
| H-Q347C-(C347)__MalPeg6C2-#69 | — | 1.9 |
| H-E388C-(C388)__MalPeg6C2-#69 | — | 1.8 |
| H-N421C-(C421)__MalPeg6C2-#69 | — | 1.8 |
| H-E380C-(C380)__MalPeg6C2-#69 | — | 1.8 |
| H-L398C + L443C-(C398 + C443)__MalPeg6C2-#69 | — | 3.9 |
| H-K392C + L443C-(C392 + C443)__MalPeg6C2-#69 | — | 3.5 |
| H-kA111C-(kC111)__MalPeg6C2-#69 | — | 3.7 |
| H-kK183C-(kC183)__MalPeg6C2-#69 | — | 2.1 |
| H-kK207C-(kC207)__MalPeg6C2-#69 | — | 2.3 |
| H-A114C-(C114)__mcValCitPABC-#108 | — | 2 |
| H-A114C-(C114)__mcValCitPABC-#84 | — | 1.9 |
| H-A114C-(C114)__mcValCitPABC-#226 | — | 1.8 |
| H-A114C-(C114)__mc-#108 | — | 1.9 |
| H-A114C-(C114)__mcValCitPABC-#117 | — | 1.8 |
| H-A114C-(C114)__mcValCitPABC-#115 | — | 1.9 |
| H-A114C-(C114)__MalPeg6C2-#98 | — | 1.9 |
| IL13Ra2-AB08-v1010-hG1-(C)__mcValCitPABC-#54 | — | 3.9 |
| IL13Ra2-AB08-v1010-hG1-(C)__mc-#69 | — | 3.5 |
| IL13Ra2-AB08-v1010-hG1-(C)__MalPeg6C2-#69 | — | 3.5 |
| IL13Ra2-AB08-v1010-hG1-(C)__mcValCitPABC-#69 | — | 4.4 |
| H-A114C-(C114)__MalPeg6C2-0#118 | — | 1.9 |
| H-A114C-(C114)__mcValCitPABC-0#118 | — | 1.8 |
| H-A114C-(C114)__mcValCitPABC-#80 | — | 1.8 |

TABLE 19B-continued

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-A114C-(C114)__mc-#117 | — | 1.9 |
| H-A114C-(C114)__mcValCitPABC-#232 | — | 1.8 |
| H-A114C-(C114)__MalPeg6C2-#230 | — | 1.9 |
| H-A114C-(C114)__MalPeg6C2-#117 | — | 1.9 |
| H-A114C-(C114)__mc-#115 | — | 2 |
| H-A114C-(C114)__mv-#115 | — | 2 |
| H-A114C-(C114)__mb-#69 | — | 2 |
| H-A114C-(C114)__mv-#69 | — | 2 |
| H-A114C-(C114)__mc-0#118 | — | 2 |
| H-(C)__mc-#117 | SEC (Protocol P): 7.797 minutes; HPLC (Protocol O): HC Δ mass = 937 | 3.5 |
| H-(C)__MalPeg6C2-#117 | SEC (Protocol P): 8.005 minutes; HPLC (Protocol O): HC Δ mass = 1163 | 3.56 |
| H-(C)__mc-0#118 | — | 4.1 |
| H-(C)__MalPeg6C2-0#118 | SEC (Protocol P): NA; HPLC (Protocol O): HC Δ mass = 1148 | 3.9 |
| IL13Ra2-AB08-v1010-hG1-(C)__mc-0#118 | — | 4 |
| IL13Ra2-AB08-v1010-hG1-(C)__mc-#226 | — | 4.6 |
| IL13Ra2-AB08-v1010-hG1-(C)__mc-#117 | — | 3.3 |
| IL13Ra2-AB08-v1010-hG1-(C)__MalPeg6C2-#117 | — | 3.3 |
| IL13Ra2-AB08-v1010-hG1-(C)__MalPeg6C2-0#118 | — | 2.9 |
| H-A114C-(C114)__MalPeg6C2-#226 | — | 1.9 |
| H-A114C-(C114)__mc-#172 | — | 1.9 |
| H-A114C-(C114)__mb-0#118 | — | 1.9 |
| H-A114C-(C114)__me-0#118 | — | 2 |
| H-A114C-(C114)__mcValCitPABC-#134 | — | 1.9 |
| H-A114C-(C114)__mc-#131 | — | 2 |
| H-A114C-(C114)__MalPeg6C2-#126 | — | 1.9 |
| H-A114C-(C114)__MalPeg6C2-#123 | — | 1.7 |
| H-A114C-(C114)__mc-#126 | — | 2 |
| H-A114C-(C114)__mv-0#118 | — | 2 |
| H-(C)__MalPeg6C2-#226 | SEC (Protocol P): 7.501 minutes; HPLC (Protocol O): HC Δ mass = 1150 | 4.5 |
| H-(C)__mc-#226 | SEC (Protocol P): 7.418 minutes; HPLC (Protocol O): HC Δ mass = 927 | 4.5 |
| IL13Ra2-AB08-v1010-hG1-(C)__MalPeg6C2-#226 | — | 4.2 |
| Notch-28-cG1-(C)__mc-0#118 | — | 4.6 |
| Notch-28-cG1-(C)__mc-#115 | SEC (Protocol P): 7.015 minutes; HPLC (Protocol O): HC Δ mass = 911 | 3.7 |
| Notch-28-cG1-(C)__MalPeg6C2-0#118 | — | 4.1 |
| Notch-28-cG1-(C)__me-0#118 | SEC (Protocol P): 7.182 minutes; HPLC (Protocol O): HC Δ mass = 937 | 3.9 |
| Notch-75-cG1-(C)__mc-0#118 | — | 3.3 |
| IL13Ra2-19F9-cG1-(C)__mcValCitPABC-#54 | — | 4.1 |
| IL13Ra2-19F9-cG1-(C)__mcValCitPABC-#112 | — | 4.2 |
| Notch-28-cG1-(C)__mcValCitPABC-#112 | — | 4.1 |
| Notch-28-cG1-(C)__MalPeg6C2-#69 | — | 4.3 |
| Notch-75-cG1-(C)__MalPeg6C2-#69 | — | 3.8 |
| H-(C)__m(H2O)c-0#118 | SEC (Protocol P): 7.010 minutes; HPLC (Protocol O): HC Δ mass = 942 | 4.1 |
| H-(C)__Mal(H2O)Peg6C2-0#118 | SEC (Protocol P): 6.964 minutes; HPLC (Protocol O): HC Δ mass = 1166 | 4 |
| H-(C)__Mal(H2O)Peg6C2-#69 | — | 2.8 |
| H-(C)__m(H2O)c-#69 | — | 3.6 |
| H-(C)__me-0#118 | — | 4.4 |
| H-(C)__mv-0#118 | — | 4.4 |
| H-(C)__mb-0#118 | SEC (Protocol P): 7.032 minutes; HPLC (Protocol O): HC Δ mass = 896 | 4.1 |
| H-A114C-(C114)__MalC6-#54 | — | 1.9 |
| H-A114C-(C114)__mc-#231 | — | 1.7 |
| H-A114C-(C114)__MalC6-0#118 | — | 2 |
| H-(C)__Mal(H2O)Peg6C2-#115 | SEC (Protocol P): 6.936 minutes; HPLC (Protocol O): HC Δ mass = 1152 | 4.1 |

TABLE 19B-continued

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-A114C-(C114)__mc-#158 | — | 2 |
| H-A114C-(C114)__mcValCitPABC-#231 | — | 1.7 |
| H-(C)__m(H2O)c-#115 | SEC (Protocol P): 6.928 minutes; HPLC (Protocol O): HC Δ mass = 930 | 3.7 |
| Notch-75-cG1-(C)__mc-#115 | — | 3.7 |
| Notch-75-cG1-(C)__mc-0#118 | — | 3.5 |
| Notch-75-cG1-(C)__MalPeg6C2-0#118 | — | 3.8 |
| H-A114C-(C114)__mc-#237 | — | 2 |
| H-A114C-(C114)__mc-#145 | — | 2 |
| H-A114C-(C114)__MalPeg6C2-#145 | — | 2 |
| H-A114C-(C114)__mc-#162 | — | 1.9 |
| H-A114C-(C114)__MalC6Am-#151 | — | 1.9 |
| Notch-28-cG1-(C)__m(H2O)c-0#118 | — | 3.7 |
| Notch-75-cG1-(C)__m(H2O)c-0#118 | — | 3 |
| H-(kK188)__COPeg2C2ValCitPABC-#54 | — | 2 |
| IL13Ra2-AB08-v1010-hG1-(C)__Mal(H2O)Peg6C2-0#118 | SEC (Protocol P): 7.766 minutes; HPLC (Protocol O): HC Δ mass = 1164 | 3.5 |
| IL13Ra2-AB08-v1010-hG1-(C)__Mal(H2O)Peg6C2-#115 | — | 3.9 |
| IL13Ra2-AB08-v1010-hG1-(C)__mc-#115 | SEC (Protocol P): 7.813 minutes; HPLC (Protocol O): HC Δ mass = 911 | 4.3 |
| IL13Ra2-AB08-v1010-hG1-(C)__m(H2O)c-0#118 | — | 3.3 |
| H-(C)__mcValCitPABC-0#118 | — | 4.5 |
| IL13Ra2-AB08-v1010-hG1-(C)__m(H2O)c-#115 | SEC (Protocol P): 7.783 minutes; HPLC (Protocol O): HC Δ mass = 930 | 3.8 |
| H-A114C-(C114)__mcValCitPABC-#154 | — | 1.9 |
| H-A114C-(C114)__MalC6Am-#153 | — | 2 |
| IL13Ra2-AB08-v1010-Q347C + kK183C-hG1-(C347 + kC183)__mcValCitPABC-#54 | — | 4.3 |
| IL13Ra2-AB08-v1010-Q347C-hG1-(C347)__mcValCitPABC-#54 | — | 2.1 |
| IL13Ra2-AB08-v1010-hG1-(kK188)__COPeg2C2AmPeg2C2-#69 | — | 2 |
| IL13Ra2-AB08-v1010-hG1-(kK188)__COPeg2C2ValCitPABC-#54 | — | 1.9 |
| IL13Ra2-AB08-v1010-L443C-hG1-(C443)__mcValCitPABC-#54 | — | 2.1 |
| IL13Ra2-AB08-v1010-K392C + L443C-hG1-(C392 + C443)__mcValCitPABC-#54 | — | 3.7 |
| IL13Ra2-AB08-v1010-L443C + kK183C-hG1-(C443 + kC183)__mcValCitPABC-#54 | — | 4 |
| H-(C)__mcValCitPABC-#98 | SEC (Protocol P): 7.232 minutes; HPLC (Protocol O): HC Δ mass = 1371 | 4.2 |
| H-A114C-(C114)__mcValCitPABC-#246 | — | 1.9 |
| H-H435A-(C)__mcValCitPABC-#54 | — | 4 |
| H-M428L + N434S-(C)__mcValCitPABC-#70 | — | 4.2 |
| H-M428L + N434S-(C)__mcValCitPABC-#54 | — | 4 |
| H-E388C + N421C-(C388 + C421)__mcValCitPABC-#54 | — | 3.6 |
| H-Q347C + K392-(C347 + C392)__mcValCitPABC-#54 | — | 3.9 |
| H-L443C + kK183C-(C443 + kC183)__mcValCitPABC-#54 | — | 3.7 |
| H-Q347C + kK183C-(C347 + kC183)__mcValCitPABC-#54 | SEC (Protocol P): 8.278 minutes; HPLC (Protocol O): HC Δ mass = 1339 | 3.7 |
| H-Q347C-(C347)__mcValCitPABC-#54 | — | 1.9 |
| H-K392C + L443C-(C392 + C443)__mc-#115 | — | 4 |
| H-E388C + N421C-(C388 + C421)__mc-#115 | — | 3.8 |
| H-Q347C + K392C-(C347 + C392)__mc-#115 | — | 4 |
| H-L443C + kK183C-(C443 + kC183)__mc-#115 | — | 3.8 |
| H-Q347C + kK183C-(C347 + kC183)__mc-#115 | — | 3.8 |

TABLE 19B-continued

Selected conjugates of the invention

| ADC-Linker-Payload # | Mass spectra: HPLC-SEC retention time and HPLC Δ mass for the Heavy Chain (HC) portion (up to 6 Da difference with theoretical Δ mass) | Loading or Drug per Antibody ratio (DAR) |
|---|---|---|
| H-Q347C-(C347)__mc-#115 | — | 2 |
| H-kK183C-(kC183)__mcValCitPABC-#54 | — | 1.9 |
| H-E388C-(C388)__mcValCitPABC-#54 | — | 2 |
| H-kK183C-(kC183)__mc-#115 | — | 1.8 |
| H-E388C-(C388)__mc-#115 | SEC (Protocol P): 7.364 minutes; HPLC (Protocol O): HC Δ mass = 914 | 2 |
| H-L443C-(C443)__mc-#115 | — | 2 |
| H-N421C-(C421)__mcValCitPABC-#54 | — | 2 |
| H-N421C-(C421)__mc-#115 | — | 2 |
| H-A114C-(C114)__mcGly-#201 | — | 1.9 |

TABLE 20

$IC_{50}$ values for selected compounds (cytotoxic peptides) of the invention

| Example # | BT474 GMEAN $IC_{50}$ (nM) | N87 GMEAN $IC_{50}$ (nM) | MDA-MB-361-DYT2 GMEAN $IC_{50}$ (nM) |
|---|---|---|---|
| #26 | 0.368 | 0.543 | 1.045 |
| #30 | 0.682 | 6.709 | 1.853 |
| #34 | 0.211 | 1.95 | 1.119 |
| #36 | 0.499 | 1.205 | 1.111 |
| #41 | 29.666 | 33.21 | 51.784 |
| #42 | 0.125 | 0.327 | 0.195 |
| #44 | 7.119 | 14.61 | >16.401 |
| #45 | 0.15 | 0.385 | 0.415 |
| #47 | <0.244 | <0.256 | 0.317 |
| #51 | <0.599 | 3.658 | — |
| #54 | <0.133 | <0.221 | 0.206 |
| #56 | 0.316 | 1.256 | 0.766 |
| #60 | 0.524 | 1.245 | 0.957 |
| #66 | 0.244 | 0.463 | 0.334 |
| #69 | 80.191 | 65.979 | 40.988 |
| #70 | 0.179 | 0.327 | 0.225 |
| #75 | >100.000 | >100.000 | >100.000 |
| #79 | 0.079 | 0.137 | 0.129 |
| #80 | 20.346 | 28.204 | 32.846 |
| #84 | 0.246 | 0.426 | 0.686 |
| #115 | 31.493 | 50.302 | 19.870 |
| #117 | 0.096 | 0.103 | 0.118 |
| #118 | 100.000 | 100.000 | 100.000 |
| #123 | 0.125 | 0.089 | 0.129 |
| #126 | 0.315 | 0.375 | 0.454 |
| #130 | 0.050 | 0.076 | 0.039 |
| #131 | 0.072 | 0.185 | 0.081 |
| #134 | 0.108 | 0.115 | 0.134 |
| #140 | — | — | — |
| #141 | 3.367 | 3.018 | — |
| #142 | 0.279 | 0.259 | — |
| #143 | — | — | — |
| #144 | 0.172 | 0.182 | 0.174 |
| #145 | 0.185 | 0.167 | 0.229 |
| #146 | 0.435 | 0.195 | 0.387 |
| #147 | 0.456 | 0.144 | 0.421 |
| #148 | 0.429 | 0.219 | 0.502 |
| #149 | 0.417 | 0.250 | 0.428 |
| #151 | 84.867 | 61.953 | 84.599 |
| #153 | 98.160 | 47.274 | 91.350 |
| #154 | 0.193 | 0.572 | 0.198 |
| #155 | 0.323 | 0.875 | 0.318 |
| #158 | 0.082 | 0.115 | 0.100 |
| #159 | 0.070 | 0.075 | 0.074 |
| #162 | 31.448 | 21.610 | 27.824 |
| #163 | 100.000 | 72.703 | 99.433 |
| #172 | 0.057 | 0.144 | 0.086 |
| #173 | 0.088 | 0.099 | 0.067 |
| #178 | 0.968 | 1.262 | 0.911 |
| #180 | 0.159 | 0.117 | 0.113 |
| #182 | 0.153 | 0.148 | 0.122 |
| #184 | 2.478 | 5.098 | 3.427 |
| #186 | — | — | — |
| #188 | 0.250 | 0.283 | 0.404 |
| #190 | 0.134 | 0.066 | 0.095 |
| #192 | 0.262 | 0.360 | 0.408 |
| #194 | 0.134 | 0.212 | 0.198 |
| #200 | 0.048 | 0.029 | 0.017 |
| #201 | 0.144 | 0.150 | 0.121 |
| #207 | 0.219 | 0.626 | 0.260 |
| #208 | 0.418 | 0.379 | 0.336 |
| #209 | 0.067 | 0.067 | 0.058 |
| #217 | — | — | — |
| #219 | — | — | — |
| #220 | 35.163 | 100.000 | 100.000 |
| #221 | 32.402 | 87.857 | 65.401 |
| #222 | 0.158 | 0.352 | 0.272 |
| #223 | 7.589 | 13.026 | 10.863 |
| #224 | 0.383 | 1.563 | 0.998 |
| #225 | 3.449 | 10.524 | 7.575 |
| #226 | 0.118 | 0.478 | 0.106 |
| #227 | 11.008 | 18.975 | 12.899 |
| #228 | 0.105 | 0.090 | 0.078 |
| #229 | 18.372 | 16.566 | 10.218 |
| #230 | 100.000 | 89.133 | 70.236 |
| #231 | 3.706 | 15.127 | 22.855 |
| #232 | 0.071 | 0.194 | 0.095 |
| #233 | 1.074 | 8.413 | 5.042 |
| #234 | 0.684 | 0.756 | 2.004 |
| #235 | 0.852 | 1.320 | 1.278 |
| #236 | 0.020 | 0.023 | 0.010 |
| #237 | 0.162 | 0.217 | 0.278 |
| #238 | 0.139 | 0.077 | 0.084 |
| #239 | — | — | — |
| #240 | 11.710 | 19.930 | 23.480 |
| #241 | 0.364 | 0.388 | 0.494 |
| #242 | 32.330 | 41.329 | 34.529 |
| #243 | 1.252 | 1.301 | 1.284 |
| #244 | 73.123 | 100.000 | 100.000 |
| #245 | 11.793 | 33.037 | 31.856 |
| #246 | 3.159 | 10.828 | 5.430 |
| #247 | 1.007 | 2.061 | 1.334 |
| #257 | — | — | — |

TABLE 21A

| | \multicolumn{6}{c|}{IC$_{50}$ values for selected conjugates of the invention} |
|---|---|---|---|---|---|---|
| | BT474 | | HCC1954 | | N87 | |
| ADC-Linker-Payload # | IC$_{50}$ (nM) | IC50 of Antibody (ng/mL) | IC$_{50}$ (nM) | IC50 of Antibody (ng/mL) | IC$_{50}$ (nM) | IC50 of Antibody (ng/mL) |
| H-(C)__MalPeg3C2-#41 | 0.725 | 25.592 | 0.465 | 16.617 | 4.02 | 175.448 |
| H-(C)__MalPeg6C2-#42 | 0.502 | 19.855 | 0.604 | 24.783 | >14.090 | >6681.150 |
| H-(C)__mc-#44 | 3.553 | 121.414 | 14.464 | 493.077 | >841.360 | >29495.311 |
| H-(C)__MalPeg3C2-#44 | 2.603 | 114.847 | 5.113 | 225.594 | >440.881 | >26346.532 |
| H-(C)__MalPeg6C2-#44 | 1.318 | 58.155 | 1.466 | 64.663 | 98.174 | 4873.851 |
| H-(C)__mcValCitPABC-#44 | 0.188 | 6.717 | 0.155 | 5.329 | 0.781 | 28.146 |
| H-(C)__Mal-PEG3C2-#45 | 2.886 | 103.762 | 1.513 | 52.791 | >740.001 | >27967.742 |
| H-(C)__Mal-PEG6C2-#45 | 1.274 | 49.903 | 1.423 | 54.715 | 111.434 | 9072.131 |
| H-(C)__mcValCitPABC-#45 | 0.258 | 9.997 | 0.204 | 7.988 | 0.417 | 16.737 |
| H-(C)__mc-#54 | 0.436 | 19.821 | 0.992 | 45.072 | 2.45 | 138.026 |
| H-(C)__Mal-PEG6C2-#69 | 1.938 | 5147.54 | 0.356 | 12.995 | 5.743 | 2427.639 |
| H-(C)__mcValCitPABC-#69 | 0.18 | 7.17 | 0.073 | 2.878 | <0.185 | <8.946 |
| H-(C)__mcValCitPABC-#70 | 0.133 | 4.522 | 0.078 | 2.61 | 0.249 | 8.722 |
| H-(C)__mc-#79 | 0.483 | 18.097 | 0.654 | 24.543 | 7.576 | 297.254 |
| H-(C)__mcValCitPABC-#79 | 0.152 | 6.634 | 0.127 | 5.682 | 0.469 | 21.134 |
| H-(C)__mc-#115 | 0.272 | — | 0.109 | — | 0.841 | — |
| H-A114C-(C114)__mc-#51 | 41.768 | — | | — | 17.297 | — |
| H-A114C-(C114)__mc-#47 | 3.269 | — | | — | 8.216 | — |
| H-A114C-(C114)__mc-#54 | 4.294 | — | | — | 7.195 | — |
| H-A114C-(C114)__mcValCitPABC-#47 | 0.493 | — | 0.31 | — | 0.696 | — |
| H-A114C-(C114)__mcValCitPABC-#54 | 0.174 | — | 0.17 | — | 0.189 | — |
| H-A114C-(C114)__mcValCitPABC-#26 | 2.548 | — | 28.2 | — | 4.314 | — |
| H-A114C-(C114)__mc-#26 | >60.648 | — | >1000.00 | — | >980.026 | — |
| H-A114C-(C114)__mcValCitPABC-#36 | 2.007 | — | 26.18 | — | 13.579 | — |
| H-A114C-(C114)__mcValCitPABC-#42 | 0.283 | — | 0.16 | — | 0.524 | — |
| H-A114C-(C114)__mc-#42 | 0.81 | — | 1.54 | — | 44.164 | — |
| H-(C)-mcValCitPABC-#54 | 0.292 | — | 0.27 | — | 0.345 | — |
| H-(C)__mcValCitPABCAmPeg3C2-#54 | 15.134 | — | 14.33 | — | 41.016 | — |
| H-(C)__mcValCitPABCAmPeg6C2-#54 | 1.898 | — | 1.4 | — | 11.71 | — |
| H-(C)__mc-#47 | 4.429 | — | 3.52 | — | 20.007 | — |
| H-(C)__MalPeg3C2-#54 | 2.181 | — | 1.54 | — | >41.711 | — |
| H-(C)__mc-#54 | 3.565 | — | 6.28 | — | 48.566 | — |
| H-(C)__mcValCitPABCAmPeg3C2-#47 | 5.228 | — | >1000.00 | — | >543.852 | — |
| H-(C)__MalPeg3C2-#47 | 1.467 | — | 1.29 | — | 16.856 | — |
| H-(C)__mcValCitPABCAmPeg3C2-#42 | 1.587 | — | 4.95 | — | >1000.000 | — |
| H-(C)__mc-#41 | 0.506 | — | 0.68 | — | 7.543 | — |
| H-(C)__mcValCitPABCAmPeg3C2-#26 | 11.211 | — | >1000.00 | — | >1000.000 | — |
| H-(C)__mcValCitPABCAmPeg6C2-#47 | 0.935 | — | 2.46 | — | 14.283 | — |
| H-(C)__MalPeg3C2-#42 | 0.517 | — | 0.51 | — | 5.479 | — |
| H-(C)__mcValCitPABCAmPeg6C2-#26 | 10.992 | — | >1000.00 | — | >1000.000 | — |
| H-(C)__mcValCitPABCAmPeg6C2-#42 | 1.819 | — | 1.97 | — | 75.643 | — |
| H-(C)__MalPeg6C2-#54 | 2.108 | — | 1.02 | — | >56.928 | — |
| H-(C)__MalPeg6C2-#47 | 1.637 | — | 1.42 | — | 31.762 | — |
| H-(C)__MalPeg6C2-#26 | 6.385 | — | 9.55 | — | >817.859 | — |
| H-(C)-MalPeg6C2-#42 | 0.518 | — | 0.55 | — | >7.993 | — |
| H-(C)__mc-#36 | >1000.000 | — | >1000.00 | — | >1000.000 | — |
| H-(C)__mcValCitPABC-#60 | 0.835 | — | 6.45 | — | 14.917 | — |
| H-(C)__MalPeg3C2-#26 | 11.506 | — | 9.43 | — | >1000.000 | — |
| H-(C)__mcValCitPABCAmPeg3C2-#36 | >1000.000 | — | >1000.00 | — | >1000.000 | — |

TABLE 21A-continued

IC$_{50}$ values for selected conjugates of the invention

| ADC-Linker-Payload # | BT474 IC$_{50}$ (nM) | BT474 IC50 of Antibody (ng/mL) | HCC1954 IC$_{50}$ (nM) | HCC1954 IC50 of Antibody (ng/mL) | N87 IC$_{50}$ (nM) | N87 IC50 of Antibody (ng/mL) |
|---|---|---|---|---|---|---|
| H-A114C-(C114)__mcValCitPABCAmPeg3C2-#36 | >1000.000 | — | >1000.00 | — | >325.714 | — |
| H-A114C-(C114)__MalPeg6C2-#54 | 1.228 | — | 2.01 | — | 133.426 | — |
| H-(C)__MalPeg3C2-#60 | >1000.000 | — | >1000.00 | — | >1000.000 | — |
| H-(C)__MalPeg6C2-#60 | >1000.000 | — | >1000.00 | — | >1000.000 | — |
| H-(C)__MalPeg6C2-#41 | 1.166 | — | 0.36 | — | 5.882 | — |
| H-(C)-mc-#69 | 0.427 | — | 0.47 | — | 3.05 | — |
| H-(C)__MalPeg3C2-#36 | 720.826 | — | >1000.00 | — | >1000.000 | — |
| H-(C)__mcValCitPABCAmPeg6C2-#36 | >1000.000 | — | >1000.00 | — | >1000.000 | — |
| H-(C)__MalPeg6C2-#36 | 878.903 | — | 159.1 | — | >1000.000 | — |
| H-(C)__mcValCitPABCAmPeg3C2-#41 | 2.363 | — | 2.28 | — | 18.728 | — |
| H-(C)-MalPeg3C2-#41 | 0.725 | — | 0.54 | — | 4.004 | — |
| H-(C)__mcValCitPABCAmPeg6C2-#60 | 979.982 | — | >1000.00 | — | 392.905 | — |
| H-A114C-(C114)__mc-#66 | 17.235 | — | >1000.00 | — | >1000.000 | — |
| H-L398C + L443C-(C398 + C443)__mcValCitPABC-#54 | 0.249 | — | 0.27 | — | 0.678 | — |
| H-K392C + L443C-(C392 + C443)__mcValCitPABC-#54 | <0.195 | — | 0.42 | — | <0.254 | — |
| H-L443C-(C443)__mcValCitPABC-#54 | <0.130 | — | 0.32 | — | <0.267 | — |
| H-L398C + V422C-(C398 + C422)__mcValCitPABC-#54 | 0.387 | — | 0.27 | — | 0.504 | — |
| H-(C)-mc-#44 | 3.553 | — | >507.23 | — | >878.489 | — |
| H-(C)-Mal-PEG3C2-#45 | 2.886 | — | 68.41 | — | >834.717 | — |
| H-(C)__2AcAmPeg6C2-#66 | 703.419 | — | >1000.00 | — | >1000.000 | — |
| H-(C)-Mal-PEG6C2-#45 | 1.274 | — | 2.74 | — | >268.047 | — |
| H-(C)-mc-#79 | 0.483 | — | 0.65 | — | 7.576 | — |
| H-(C)-MalPeg3C2-#44 | 2.603 | — | 5.11 | — | >440.881 | — |
| H-(C)-mcValCitPABC-#70 | 0.188 | — | 0.09 | — | <0.179 | — |
| H-(C)-MalPeg6C2-#44 | 1.318 | — | 1.47 | — | 98.174 | — |
| H-A114C-(C114)__mcValCitPABC-#69 | 0.174 | — | 0.06 | — | 0.207 | — |
| H-(C)-mcValCitPABC-#79 | 0.152 | — | 0.15 | — | 0.469 | — |
| H-A114C-(C114)__mcValCitPABC-#79 | 0.124 | — | 0.12 | — | 0.386 | — |
| H-(C)-mcValCitPABC-#44 | 0.252 | — | 0.18 | — | 0.732 | — |
| H-A114C-(C114)__mcValCitPABC-#88 | 8.127 | — | >1000.00 | — | 62.825 | — |
| H-(C)-mcValCitPABC-#69 | 0.133 | — | 0.1 | — | 0.249 | — |
| H-(C)__2AcAmCapValCitPABC-#66 | 0.436 | — | 0.99 | — | 2.45 | — |
| H-A114C-(C114)__mcValCitPABC-#45 | 0.217 | — | 0.2 | — | 0.496 | — |
| H-A114C-(C114)__mcValCitPABC-#34 | 3.724 | — | >1000.00 | — | 18.422 | — |
| H-A114C-(C114)__mc-#45 | 6.431 | — | >1000.00 | — | 148.852 | — |
| H-A114C-(C114)__mc-#70 | 0.349 | — | 0.62 | — | 7.208 | — |
| H-(C)__mcValCitPABC-#112 | 0.226 | — | 0.24 | — | 0.469 | — |
| H-(C)-Mal-PEG6C2-#69 | 0.453 | — | 0.54 | — | 1.8 | — |
| H-Q347C-(C347)__mcValCitPABC-#69 | 0.368 | — | 0.06 | — | 0.22 | — |
| H-Y373C-(C373)__mcValCitPABC-#69 | 0.359 | — | 0.06 | — | 0.295 | — |
| H-E388C-(C388)__mcValCitPABC-#69 | 0.427 | — | 0.06 | — | 0.314 | — |
| H-N421C-(C421)__mcValCitPABC-#69 | 0.434 | — | 0.09 | — | 0.244 | — |
| H-L443C-(C443)__mcValCitPABC-#69 | 0.239 | — | 0.05 | — | 0.272 | — |
| H-L443C-(C443)__mcValCitPABC-#79 | 0.3 | — | 0.15 | — | 0.412 | — |

TABLE 21A-continued

IC$_{50}$ values for selected conjugates of the invention

| ADC-Linker-Payload # | BT474 IC$_{50}$ (nM) | BT474 IC50 of Antibody (ng/mL) | HCC1954 IC$_{50}$ (nM) | HCC1954 IC50 of Antibody (ng/mL) | N87 IC$_{50}$ (nM) | N87 IC50 of Antibody (ng/mL) |
|---|---|---|---|---|---|---|
| H-A114C-(C114)__mcValCitPABC-#95 | 0.381 | — | 0.36 | — | 0.852 | — |
| H-A114C-(C114)__mcValCitPABC-#98 | 0.171 | — | 0.24 | — | 0.258 | — |
| H-A114C-(C114)__MalPeg3C2-#69 | 0.221 | — | 0.58 | — | 1.589 | — |
| H-N297Q-(Q)__AmPeg6C2-#42 | 0.466 | — | 0.36 | — | 5.42 | — |
| H-N297Q-(Q)__AmPeg6C2-#54 | 0.557 | — | 0.37 | — | 6.899 | — |
| H-N297Q-(Q)__AmPeg6C2-#47 | 0.346 | — | 0.43 | — | 4.337 | — |
| H-N297Q-(Q)__AmPeg6C2-#36 | 3.003 | — | >1000.00 | — | 284.267 | — |
| H-N297Q-(Q)__AmPeg6C2-#26 | 0.991 | — | 1.07 | — | 35.331 | — |
| H-N297Q-(Q)__AmPeg6C2-#66 | 13.812 | — | >1000.00 | — | >1000.000 | — |
| H-L443C-(C443)__MalPeg6C2-#69 | 0.251 | — | 0.25 | — | 1.989 | — |
| H-Q347C-(C347)__MalPeg6C2-#69 | 0.267 | — | 0.3 | — | 0.887 | — |
| H-E388C-(C388)__MalPeg6C2-#69 | 0.382 | — | 0.46 | — | 3.035 | — |
| H-N421C-(C421)__MalPeg6C2-#69 | 0.35 | — | 0.45 | — | 1.329 | — |
| H-E380C-(C380)__MalPeg6C2-#69 | 0.482 | — | 0.49 | — | 5.588 | — |
| H-L398C + L443C-(C398 + C443)__MalPeg6C2-#69 | 0.226 | — | 0.3 | — | 1.346 | — |
| H-K392C + L443C-(C392 + C443)__MalPeg6C2-#69 | 0.268 | — | 0.31 | — | 1.63 | — |
| H-kA111C-(kC111)__MalPeg6C2-#69 | 0.297 | — | 0.34 | — | 1.635 | — |
| H-kK183C-(kC183)__MalPeg6C2-#69 | 0.257 | — | 0.5 | — | 2.23 | — |
| H-kK207C-(kC207)__MalPeg6C2-#69 | 0.252 | — | 0.41 | — | 1.744 | — |
| H-A114C-(C114)__mcValCitPABC-#108 | 0.212 | — | 0.12 | — | 0.777 | — |
| H-A114C-(C114)__mcValCitPABC-#84 | 0.627 | — | 12.2 | — | 1.733 | — |
| H-A114C-(C114)__mcValCitPABC-#226 | 0.2 | — | 0.1 | — | 0.239 | — |
| H-A114C-(C114)__mc-#108 | >1000.000 | — | >1000.00 | — | 113.889 | — |
| H-A114C-(C114)__mcValCitPABC-#117 | 0.242 | — | 0.17 | — | 0.239 | — |
| H-A114C-(C114)__mcValCitPABC-#115 | 0.202 | — | 0.2 | — | 0.211 | — |
| H-A114C-(C114)__MalPeg6C2-#98 | 0.576 | — | 0.47 | — | 1.46 | — |
| H-A114C-(C114)__MalPeg6C2-0#118 | 0.257 | — | 0.17 | — | 0.505 | — |
| H-A114C-(C114)__mcValCitPABC-0#118 | 0.251 | — | 0.24 | — | 0.398 | — |
| H-A114C-(C114)__mcValCitPABC-#80 | 0.341 | — | 0.31 | — | 0.887 | — |
| H-A114C-(C114)__mc-#117 | 0.197 | — | 0.14 | — | 0.465 | — |
| H-A114C-(C114)__mcValCitPABC-#232 | 0.376 | — | 1.31 | — | 1.367 | — |
| H-A114C-(C114)__MalPeg6C2-#230 | 0.504 | — | 0.85 | — | 3.179 | — |
| H-A114C-(C114)__MalPeg6C2-#117 | 0.335 | — | 0.21 | — | 0.792 | — |
| H-A114C-(C114)__mc-#115 | 0.243 | — | 0.23 | — | 0.45 | — |
| H-A114C-(C114)__mv-#115 | 0.21 | — | 0.15 | — | 0.65 | — |
| H-A114C-(C114)__mb-#69 | 0.256 | — | 0.43 | — | 2.137 | — |
| H-A114C-(C114)__mv-#69 | 0.215 | — | 0.27 | — | 1.043 | — |
| H-A114C-(C114)__mc-0#118 | 0.151 | — | 0.1 | — | 0.342 | — |
| H-(C)__mc-#117 | 0.162 | — | 0.06 | — | 0.314 | — |
| H-(C)__MalPeg6C2-#117 | 0.283 | — | 0.07 | — | 0.515 | — |
| H-(C)__mc-0#118 | 0.18 | — | <0.10 | — | 0.303 | — |
| H-(C)__MalPeg6C2-0#118 | 0.269 | — | 0.15 | — | 0.499 | — |
| H-A114C-(C114)__MalPeg6C2-#226 | 0.28 | — | 0.22 | — | 0.685 | — |
| H-A114C-(C114)__mc-#172 | 0.296 | — | 0.41 | — | 0.694 | — |
| H-A114C-(C114)__mb-0#118 | 0.318 | — | 0.33 | — | 0.709 | — |
| H-A114C-(C114)__me-0#118 | 0.256 | — | 0.33 | — | 0.64 | — |

TABLE 21A-continued

IC$_{50}$ values for selected conjugates of the invention

| ADC-Linker-Payload # | BT474 IC$_{50}$ (nM) | BT474 IC50 of Antibody (ng/mL) | HCC1954 IC$_{50}$ (nM) | HCC1954 IC50 of Antibody (ng/mL) | N87 IC$_{50}$ (nM) | N87 IC50 of Antibody (ng/mL) |
|---|---|---|---|---|---|---|
| H-A114C-(C114)__mcValCitPABC-#134 | 0.301 | — | 0.34 | — | 0.501 | — |
| H-A114C-(C114)__mc-#131 | 0.357 | — | 0.76 | — | 1.614 | — |
| H-A114C-(C114)__MalPeg6C2-#126 | 0.284 | — | 0.36 | — | 1.377 | — |
| H-A114C-(C114)__MalPeg6C2-#123 | 0.362 | — | 0.34 | — | 1.867 | — |
| H-A114C-(C114)__mc-#126 | 0.319 | — | 0.49 | — | 3.294 | — |
| H-A114C-(C114)__mv-0#118 | 0.209 | — | 0.25 | — | 0.719 | — |
| H-(C)__MalPeg6C2-#226 | 0.575 | — | 0.22 | — | 1.126 | — |
| H-(C)__mc-#226 | 0.359 | — | 0.18 | — | 0.69 | — |
| H-(C)__m(H2O)c-0#118 | 0.26 | — | 0.11 | — | 0.448 | — |
| H-(C)__Mal(H2O)Peg6C2-0#118 | 0.482 | — | 0.19 | — | 0.9 | — |
| H-(C)__Mal(H2O)Peg6C2-#69 | 0.832 | — | 0.51 | — | 5.769 | — |
| H-(C)__m(H2O)c-#69 | 0.418 | — | 0.28 | — | 1.529 | — |
| H-(C)__me-0#118 | 0.186 | — | 0.11 | — | 0.218 | — |
| H-(C)__mv-0#118 | 0.201 | — | 0.14 | — | 0.265 | — |
| H-(C)__mb-0#118 | 0.222 | — | 0.13 | — | 0.267 | — |
| H-A114C-(C114)__MalC6-#54 | 0.662 | — | 5.11 | — | 8.003 | — |
| H-A114C-(C114)__mc-#231 | >1000.000 | — | >1000.00 | — | >1000 | — |
| H-A114C-(C114)__MalC6-0#118 | 0.976 | — | 113 | — | 15.407 | — |
| H-(C)__Mal(H2O)Peg6C2-#115 | 1.06 | — | 0.28 | — | 3.439 | — |
| H-A114C-(C114)__mc-#158 | 0.247 | — | 0.35 | — | 0.739 | — |
| H-A114C-(C114)__mcValCitPABC-#231 | 1.178 | — | 24.41 | — | 13.447 | — |
| H-(C)__m(H2O)c-#115 | 0.393 | — | 0.17 | — | 0.498 | — |
| H-A114C-(C114)__mc-#237 | 0.97 | — | 0.68 | — | 27.907 | — |
| H-A114C-(C114)__mc-#145 | 4.681 | — | 585.59 | — | 643.391 | — |
| H-A114C-(C114)__MalPeg6C2-#145 | 12.856 | — | 190.59 | — | 89.125 | — |
| H-A114C-(C114)__mc-#162 | 0.377 | — | 0.15 | — | 1.144 | — |
| H-A114C-(C114)__MalC6Am-#151 | 0.42 | — | 0.1 | — | 0.694 | — |
| H-(kK188)__COPeg2C2ValCitPABC-#54 | — | — | — | — | — | — |
| H-(C)__mcValCitPABC-0#118 | 0.227 | — | 0.14 | — | 0.182 | — |
| H-A114C-(C114)__mcValCitPABC-#154 | 0.323 | — | 0.32 | — | 0.363 | — |
| H-A114C-(C114)__MalC6Am-#153 | 0.377 | — | 0.27 | — | 0.34 | — |
| H-(C)__mcValCitPABC-#98 | 0.211 | — | 0.14 | — | 0.162 | — |
| H-A114C-(C114)__mcValCitPABC-#246 | 0.357 | — | 0.65 | — | 3.197 | — |
| H-H435A-(C)__mcValCitPABC-#54 | 0.358 | — | 0.17 | — | 0.237 | — |
| H-M428L + N434S-(C)__mcValCitPABC-#70 | 0.322 | — | 0.1 | — | 0.114 | — |
| H-M428L + N434S-(C)__mcValCitPABC-#54 | 0.354 | — | — | — | 0.217 | — |
| H-E388C + N421C-(C388 + C421)__mcValCitPABC-#54 | 1.38 | — | 0.99 | — | 0.855 | — |
| H-Q347C + K392C-(C347 + C392)__mcValCitPABC-#54 | 0.276 | — | 0.29 | — | 0.147 | — |
| H-L443C + kK183C-(C443 + kC183)__mcValCitPABC-#54 | <0.129 | — | 0.37 | — | <0.111 | — |
| H-Q347C + kK183C-(C347 + kC183)__mcValCitPABC-#54 | 0.146 | — | 0.25 | — | 0.08 | — |
| H-Q347C-(C347)__mcValCitPABC-#54 | 0.153 | — | 0.33 | — | 0.111 | — |
| H-K392C + L443C-(C392 + C443)__mc-#115 | 0.323 | — | 0.1 | — | 0.304 | — |
| H-E388C + N421C-(C388 + C421)__mc-#115 | 1.251 | — | 0.42 | — | 0.997 | — |
| H-Q347C + K392C-(C347 + C392)__mc-#115 | 0.342 | — | 0.1 | — | 0.219 | — |
| H-L443C + kK183C-(C443 + kC183)__mc-#115 | 0.319 | — | 0.1 | — | 0.268 | — |

TABLE 21A-continued

IC50 values for selected conjugates of the invention

| ADC-Linker-Payload # | BT474 IC$_{50}$ (nM) | BT474 IC50 of Antibody (ng/mL) | HCC1954 IC$_{50}$ (nM) | HCC1954 IC50 of Antibody (ng/mL) | N87 IC$_{50}$ (nM) | N87 IC50 of Antibody (ng/mL) |
|---|---|---|---|---|---|---|
| H-Q347C + kK183C-(C347 + kC183)__mc-#115 | 0.347 | — | 0.1 | — | 0.403 | — |
| H-Q347C-(C347)__mc-#115 | 0.272 | — | 0.18 | — | 0.278 | — |
| H-kK183C-(kC183)__mcValCitPABC-#54 | 0.287 | — | 0.34 | — | 0.194 | — |
| H-E388C-(C388)__mcValCitPABC-#54 | 0.098 | — | 0.38 | — | 0.084 | — |
| H-kK183C-(kC183)__mc-#115 | 0.28 | — | 0.27 | — | 0.269 | — |
| H-E388C-(C388)__mc-#115 | 0.302 | — | 0.15 | — | 0.301 | — |
| H-L443C-(C443)__mc-#115 | 0.222 | — | 0.1 | — | 0.259 | — |
| H-N421C-(C421)__mcValCitPABC-#54 | <0.051 | — | 0.42 | — | <0.051 | — |
| H-N421C-(C421)__mc-#115 | 0.312 | — | 0.23 | — | 0.306 | — |
| H-A114C-(C114)__mcGly-#201 | 0.321 | — | — | — | — | — |

TABLE 21B

IC$_{50}$ values for selected conjugates of the invention

| ADC-Linker-Payload # | DYT2 IC$_{50}$ (nM) | DYT2 IC50 of Antibody (ng/mL) | MDA-MB-468 IC$_{50}$ (nM) | MDA-MB-468 IC50 of Antibody (ng/mL) |
|---|---|---|---|---|
| H-(C)__MalPeg3C2-#41 | >69.685 | >17528.581 | — | >35714.286 |
| H-(C)__MalPeg6C2-#42 | 33.396 | 5455.61 | >629.281 | >25857.971 |
| H-(C)__mc-#44 | >1000.000 | >34090.909 | >1000.000 | >34090.909 |
| H-(C)__MalPeg3C2-#44 | >1000.000 | >44117.647 | >1000.000 | >44117.647 |
| H-(C)__MalPeg6C2-#44 | >1000.000 | >44117.647 | >1000.000 | >44117.647 |
| H-(C)__mcValCitPABC-#44 | 0.203 | 7.246 | >1000.000 | >35714.286 |
| H-(C)__Mal-PEG3C2-#45 | >1000.000 | >34883.721 | >1000.000 | >34883.721 |
| H-(C)__Mal-PEG6C2-#45 | >1000.000 | >38461.538 | >1000.000 | >38461.538 |
| H-(C)__mcValCitPABC-#45 | 0.371 | 14.304 | 613.294 | 24435.914 |
| H-(C)__mc-#54 | >1000.000 | >45454.545 | >1000.000 | >45454.545 |
| H-(C)__Mal-PEG6C2-#69 | >467.163 | >29849.279 | >1000.000 | >35714.286 |
| H-(C)__mcValCitPABC-#69 | 0.156 | 7.54 | 547.953 | 21860.354 |
| H-(C)__mcValCitPABC-#70 | 0.098 | 3.332 | >1000.000 | >33333.333 |
| H-(C)__mc-#79 | >1000.000 | >37500.000 | 978.508 | 36694.065 |
| H-(C)__mcValCitPABC-#79 | 0.212 | 9.528 | 351.392 | 15383.462 |
| H-(C)__mc-#115 | 0.21 | — | — | — |
| H-A114C-(C114)__mc-#51 | >1000.000 | — | >1000.000 | — |
| H-A114C-(C114)__mc-#47 | >1000.000 | — | >1000.000 | — |
| H-A114C-(C114)__mc-#54 | >1000.000 | — | >1000.000 | — |
| H-A114C-(C114)__mcValCitPABC-#47 | 383.667 | — | 445.014 | — |
| H-A114C-(C114)__mcValCitPABC-#54 | 0.372 | — | 362.213 | — |
| H-A114C-(C114)__mcValCitPABC-#26 | >1000.000 | — | >930.555 | — |
| H-A114C-(C114)__mc-#26 | >1000.000 | — | >1000.000 | — |
| H-A114C-(C114)__mcValCitPABC-#36 | >927.422 | — | >1000.000 | — |
| H-A114C-(C114)__mcValCitPABC-#42 | 0.436 | — | 530.596 | — |
| H-A114C-(C114)__mc-#42 | >727.245 | — | 567.735 | — |
| H-(C)-mcValCitPABC-#54 | 0.275 | — | 471.905 | — |
| H-(C)__mcValCitPABCAmPeg3C2-#54 | >1000.000 | — | >1000.000 | — |
| H-(C)__mcValCitPABCAmPeg6C2-#54 | >1000.000 | — | >1000.000 | — |
| H-(C)__mc-#47 | >1000.000 | — | >1000.000 | — |
| H-(C)__MalPeg3C2-#54 | >1651.007 | — | >1651.007 | — |
| H-(C)__mc-#54 | >1000.000 | — | >1000.000 | — |
| H-(C)__mcValCitPABCAmPeg3C2-#47 | >1000.000 | — | >1000.000 | — |
| H-(C)__MalPeg3C2-#47 | >1000.000 | — | >1000.000 | — |
| H-(C)__mcValCitPABCAmPeg3C2-#42 | >1000.000 | — | >1000.000 | — |
| H-(C)__mc-#41 | >1000.000 | — | >1000.000 | — |
| H-(C)__mcValCitPABCAmPeg3C2-#26 | >1000.000 | — | >1000.000 | — |
| H-(C)__mcValCitPABCAmPeg6C2-#47 | >1000.000 | — | >1000.000 | — |
| H-(C)__MalPeg3C2-#42 | 9.675 | — | 358.435 | — |
| H-(C)__mcValCitPABCAmPeg6C2-#26 | >1000.000 | — | >1000.000 | — |
| H-(C)__mcValCitPABCAmPeg6C2-#42 | >1000.000 | — | >1000.000 | — |
| H-(C)__MalPeg6C2-#54 | >1731.544 | — | >1731.544 | — |
| H-(C)__MalPeg6C2-#47 | >1651.007 | — | >1651.007 | — |
| H-(C)__MalPeg6C2-#26 | >1000.000 | — | >1000.000 | — |

TABLE 21B-continued

IC₅₀ values for selected conjugates of the invention

| | DYT2 | | MDA-MB-468 | |
|---|---|---|---|---|
| ADC-Linker-Payload # | IC$_{50}$ (nM) | IC50 of Antibody (ng/mL) | IC$_{50}$ (nM) | IC50 of Antibody (ng/mL) |
| H-(C)-MalPeg6C2-#42 | 5.705 | — | >642.029 | — |
| H-(C)__mc-#36 | >1000.000 | — | >1000.000 | — |
| H-(C)__mcValCitPABC-#60 | >699.241 | — | >544.495 | — |
| H-(C)__MalPeg3C2-#26 | >1000.000 | — | >1000.000 | — |
| H-(C)__mcValCitPABCAmPeg3C2-#36 | >1000.000 | — | >1000.000 | — |
| H-A114C-(C114)__mcValCitPABCAmPeg3C2-#36 | >1000.000 | — | >1000.000 | — |
| H-A114C-(C114)__MalPeg6C2-#54 | >1000.000 | — | >1000.000 | — |
| H-(C)__MalPeg3C2-#60 | >1000.000 | — | >1000.000 | — |
| H-(C)__MalPeg6C2-#60 | >1000.000 | — | >1000.000 | — |
| H-(C)__MalPeg6C2-#41 | >1000.000 | — | >1000.000 | — |
| H-(C)-mc-#69 | >71.831 | — | >899.249 | — |
| H-(C)__MalPeg3C2-#36 | >1000.000 | — | >1000.000 | — |
| H-(C)__mcValCitPABCAmPeg6C2-#36 | >1000.000 | — | >1000.000 | — |
| H-(C)__MalPeg6C2-#36 | >1000.000 | — | >1000.000 | — |
| H-(C)__mcValCitPABCAmPeg3C2-#41 | >1000.000 | — | >1000.000 | — |
| H-(C)__MalPeg3C2-#41 | >69.685 | — | >1000.000 | — |
| H-(C)__mcValCitPABCAmPeg6C2-#60 | >1000.000 | — | >1000.000 | — |
| H-A114C-(C114)__mc-#66 | >1000.000 | — | >1000.000 | — |
| H-L398C + L443C-(C398 + C443)__mcValCitPABC-#54 | 0.463 | — | 801.354 | — |
| H-K392C + L443C-(C392 + C443)__mcValCitPABC-#54 | <0.171 | — | 565.01 | — |
| H-L443C-(C443)__mcValCitPABC-#54 | 0.371 | — | 500.958 | — |
| H-L398C + V422C-(C398 + C422)__mcValCitPABC-#54 | 0.48 | — | 610.884 | — |
| H-(C)-mc-#44 | >1000.000 | — | >1000.000 | — |
| H-(C)-Mal-PEG3C2-#45 | >1000.000 | — | >1000.000 | — |
| H-(C)__2AcAmPeg6C2-#66 | >1000.000 | — | >1000.000 | — |
| H-(C)-Mal-PEG6C2-#45 | >1000.000 | — | >1000.000 | — |
| H-(C)-mc-#79 | >1000.000 | — | 978.508 | — |
| H-(C)-MalPeg3C2-#44 | >1000.000 | — | >1000.000 | — |
| H-(C)-mcValCitPABC-#70 | 0.116 | — | 547.953 | — |
| H-(C)-MalPeg6C2-#44 | >1000.000 | — | >1000.000 | — |
| H-A114C-(C114)__mcValCitPABC-#69 | 0.083 | — | >1000.000 | — |
| H-(C)-mcValCitPABC-#79 | 0.212 | — | 351.392 | — |
| H-A114C-(C114)__mcValCitPABC-#79 | 0.199 | — | 472.593 | — |
| H-(C)-mcValCitPABC-#44 | 0.248 | — | >1000.000 | — |
| H-A114C-(C114)__mcValCitPABC-#88 | >1000.000 | — | >1000.000 | — |
| H-(C)-mcValCitPABC-#69 | 0.098 | — | >1000.000 | — |
| H-(C)__2AcAmCapValCitPABC-#66 | >1000.000 | — | >1000.000 | — |
| H-A114C-(C114)__mcValCitPABC-#45 | 2.37 | — | >968.025 | — |
| H-A114C-(C114)__mcValCitPABC-#34 | >1000.000 | — | >1000.000 | — |
| H-A114C-(C114)__mc-#45 | >1000.000 | — | >1000.000 | — |
| H-A114C-(C114)__mc-#70 | >1000.000 | — | >1000.000 | — |
| H-(C)__mcValCitPABC-#112 | 0.185 | — | >563.999 | — |
| H-(C)-Mal-PEG6C2-#69 | 0.963 | — | 748.275 | — |
| H-Q347C-(C347)__mcValCitPABC-#69 | 0.094 | — | >1000.000 | — |
| H-Y373C-(C373)__mcValCitPABC-#69 | 0.156 | — | >1000.000 | — |
| H-E388C-(C388)__mcValCitPABC-#69 | 0.117 | — | >1000.000 | — |
| H-N421C-(C421)__mcValCitPABC-#69 | 0.162 | — | >1000.000 | — |
| H-L443C-(C443)__mcValCitPABC-#69 | 0.1 | — | >1000.000 | — |
| H-L443C-(C443)__mcValCitPABC-#79 | 0.303 | — | 370.53 | — |
| H-A114C-(C114)__mcValCitPABC-#95 | 61.8 | — | >1000.000 | — |
| H-A114C-(C114)__mcValCitPABC-#98 | 0.218 | — | 609.904 | — |
| H-A114C-(C114)__MalPeg3C2-#69 | >1000.000 | — | >1000.000 | — |
| H-N297Q-(Q)__AmPeg6C2-#42 | >1000.000 | — | >1000.000 | — |
| H-N297Q-(Q)__AmPeg6C2-#54 | >1000.000 | — | >1000.000 | — |
| H-N297Q-(Q)__AmPeg6C2-#47 | >1000.000 | — | >1000.000 | — |
| H-N297Q-(Q)__AmPeg6C2-#36 | >1000.000 | — | >1000.000 | — |
| H-N297Q-(Q)__AmPeg6C2-#26 | >1000.000 | — | >1000.000 | — |
| H-N297Q-(Q)__AmPeg6C2-#66 | >1000.000 | — | >1000.000 | — |
| H-L443C-(C443)__MalPeg6C2-#69 | >1000.000 | — | 758.157 | — |
| H-Q347C-(C347)__MalPeg6C2-#69 | 1.752 | — | 832.08 | — |
| H-E388C-(C388)__MalPeg6C2-#69 | 6.883 | — | >973.529 | — |
| H-N421C-(C421)__MalPeg6C2-#69 | 1.027 | — | 472.466 | — |
| H-E380C-(C380)__MalPeg6C2-#69 | >65.641 | — | 873.254 | — |
| H-L398C + L443C-(C398 + C443)__MalPeg6C2-#69 | 0.827 | — | 846.418 | — |
| H-K392C + L443C-(C392 + C443)__MalPeg6C2-#69 | >32.438 | — | 804.407 | — |
| H-kA111C-(kC111)__MalPeg6C2-#69 | 0.423 | — | 740.791 | — |

TABLE 21B-continued

IC50 values for selected conjugates of the invention

| ADC-Linker-Payload # | DYT2 IC$_{50}$ (nM) | DYT2 IC50 of Antibody (ng/mL) | MDA-MB-468 IC$_{50}$ (nM) | MDA-MB-468 IC50 of Antibody (ng/mL) |
|---|---|---|---|---|
| H-kK183C-(kC183)__MalPeg6C2-#69 | >1000.000 | — | 749.154 | — |
| H-kK207C-(kC207)__MalPeg6C2-#69 | >138.618 | — | 586.857 | — |
| H-A114C-(C114)__mcValCitPABC-#108 | >1000.000 | — | 873.831 | — |
| H-A114C-(C114)__mcValCitPABC-#84 | 976.796 | — | >1000.000 | — |
| H-A114C-(C114)__mcValCitPABC-#226 | 0.101 | — | 385.851 | — |
| H-A114C-(C114)__mc-#108 | >1000.000 | — | >1000.000 | — |
| H-A114C-(C114)__mcValCitPABC-#117 | 0.107 | — | 469.882 | — |
| H-A114C-(C114)__mcValCitPABC-#115 | 0.142 | — | 989.147 | — |
| H-A114C-(C114)__MalPeg6C2-#98 | 355.331 | — | >1000.000 | — |
| H-A114C-(C114)__MalPeg6C2-0#118 | 0.126 | — | >865.455 | — |
| H-A114C-(C114)__mcValCitPABC-0#118 | 0.215 | — | >1000.000 | — |
| H-A114C-(C114)__mcValCitPABC-#80 | 0.432 | — | >1000.000 | — |
| H-A114C-(C114)__mc-#117 | 0.107 | — | >414.892 | — |
| H-A114C-(C114)__mcValCitPABC-#232 | 38.422 | — | 959.259 | — |
| H-A114C-(C114)__MalPeg6C2-#230 | >1000.000 | — | >1000.000 | — |
| H-A114C-(C114)__MalPeg6C2-#117 | 0.179 | — | >1000.000 | — |
| H-A114C-(C114)__mc-#115 | 0.238 | — | >699.755 | — |
| H-A114C-(C114)__mv-#115 | 0.322 | — | >668.891 | — |
| H-A114C-(C114)__mb-#69 | >1000.000 | — | >1000.000 | — |
| H-A114C-(C114)__mv-#69 | >1000.000 | — | >1000.000 | — |
| H-A114C-(C114)__mc-0#118 | 0.098 | — | 432.816 | — |
| H-(C)__mc-#117 | <0.093 | — | 194.684 | — |
| H-(C)__MalPeg6C2-#117 | <0.080 | — | 361.061 | — |
| H-(C)__mc-0#118 | <0.073 | — | 541.542 | — |
| H-(C)__MalPeg6C2-0#118 | 0.074 | — | 465.455 | — |
| H-A114C-(C114)__MalPeg6C2-#226 | 0.513 | — | 574.794 | — |
| H-A114C-(C114)__mc-#172 | 1.48 | — | 500.864 | — |
| H-A114C-(C114)__mb-0#118 | 0.208 | — | 506.604 | — |
| H-A114C-(C114)__me-0#118 | 0.236 | — | 903.571 | — |
| H-A114C-(C114)__mcValCitPABC-#134 | 1.434 | — | 648.066 | — |
| H-A114C-(C114)__mc-#131 | >1000.000 | — | 480.901 | — |
| H-A114C-(C114)__MalPeg6C2-#126 | 54.268 | — | 656.645 | — |
| H-A114C-(C114)__MalPeg6C2-#123 | >1000.000 | — | 543.693 | — |
| H-A114C-(C114)__mc-#126 | >1000.000 | — | 749.49 | — |
| H-A114C-(C114)__mv-0#118 | 0.147 | — | 490.276 | — |
| H-(C)__MalPeg6C2-#226 | 0.206 | — | 582.309 | — |
| H-(C)__mc-#226 | 0.219 | — | 477.622 | — |
| H-(C)__m(H2O)c-0#118 | 0.071 | — | 306.626 | — |
| H-(C)__Mal(H2O)Peg6C2-0#118 | <0.059 | — | 441.766 | — |
| H-(C)__Mal(H2O)Peg6C2-#69 | 0.203 | — | 459.502 | — |
| H-(C)__m(H2O)c-#69 | 0.315 | — | 740.334 | — |
| H-(C)__me-0#118 | <0.061 | — | 455.314 | — |
| H-(C)__mv-0#118 | 0.084 | — | 531.617 | — |
| H-(C)__mb-0#118 | 0.076 | — | 584.327 | — |
| H-A114C-(C114)__MalC6-#54 | 52.056 | — | 65.721 | — |
| H-A114C-(C114)__mc-#231 | >1000.000 | — | >1000.000 | — |
| H-A114C-(C114)__MalC6-0#118 | >1000.000 | — | >1000.000 | — |
| H-(C)__Mal(H2O)Peg6C2-#115 | 0.095 | — | 698.101 | — |
| H-A114C-(C114)__mc-#158 | 0.164 | — | 329.554 | — |
| H-A114C-(C114)__mcValCitPABC-#231 | >1000.000 | — | >1000.000 | — |
| H-(C)__m(H2O)c-#115 | <0.069 | — | 534.743 | — |
| H-A114C-(C114)__mc-#237 | >1000.000 | — | 646.464 | — |
| H-A114C-(C114)__mc-#145 | >1000.000 | — | >1000.000 | — |
| H-A114C-(C114)__MalPeg6C2-#145 | >1000.000 | — | >1000.000 | — |
| H-A114C-(C114)__mc-#162 | 0.201 | — | 676.764 | — |
| H-A114C-(C114)__MalC6Am-#151 | 0.469 | — | 75.696 | — |
| H-(kK188)__COPeg2C2ValCitPABC-#54 | — | — | — | — |
| H-(C)__mcValCitPABC-0#118 | 0.081 | — | >1000.000 | — |
| H-A114C-(C114)__mcValCitPABC-#154 | 1.708 | — | 566.056 | — |
| H-A114C-(C114)__MalC6Am-#153 | 0.114 | — | 69.259 | — |
| H-(C)__mcValCitPABC-#98 | 0.23 | — | 270.019 | — |
| H-A114C-(C114)__mcValCitPABC-#246 | >1000.000 | — | >1000.000 | — |
| H-H435A-(C)__mcValCitPABC-#54 | 0.208 | — | 339.77 | — |
| H-M428L + N434S-(C)__mcValCitPABC-#70 | 0.069 | — | 380.393 | — |
| H-M428L + N434S-(C)__mcValCitPABC-#54 | 0.178 | — | — | — |
| H-E388C + N421C-(C388 + C421)__mcValCitPABC-#54 | 1.033 | — | 826.243 | — |
| H-Q347C + K392C-(C347 + C392)__mcValCitPABC-#54 | 0.103 | — | 390.7 | — |
| H-L443C + kK183C-(C443 + kC183)__mcValCitPABC-#54 | <0.103 | — | 395.707 | — |

TABLE 21B-continued

IC$_{50}$ values for selected conjugates of the invention

| ADC-Linker-Payload # | DYT2 IC$_{50}$ (nM) | DYT2 IC50 of Antibody (ng/mL) | MDA-MB-468 IC$_{50}$ (nM) | MDA-MB-468 IC50 of Antibody (ng/mL) |
|---|---|---|---|---|
| H-Q347C + kK183C-(C347 + kC183)__mcValCitPABC-#54 | <0.051 | — | 384.028 | — |
| H-Q347C-(C347)__mcValCitPABC-#54 | 2.89 | — | 393.412 | — |
| H-K392C + L443C-(C392 + C443)__mc-#115 | 0.07 | — | 542.081 | — |
| H-E388C + N421C-(C388 + C421)__mc-#115 | 0.227 | — | >1000.000 | — |
| H-Q347C + K392C-(C347 + C392)__mc-#115 | 0.068 | — | 934.867 | — |
| H-L443C + kK183C-(C443 + kC183)__mc-#115 | 0.071 | — | 757.604 | — |
| H-Q347C + kK183C-(C347 + kC183)__mc-#115 | 0.073 | — | 741.434 | — |
| H-Q347C-(C347)__mc-#115 | 0.098 | — | 888.128 | — |
| H-kK183C-(kC183)__mcValCitPABC-#54 | 1.329 | — | 160.012 | — |
| H-E388C-(C388)__mcValCitPABC-#54 | 0.658 | — | 287.88 | — |
| H-kK183C-(kC183)__mc-#115 | 0.179 | — | 775.698 | — |
| H-E388C-(C388)__mc-#115 | 0.124 | — | 958.96 | — |
| H-L443C-(C443)__mc-#115 | 0.108 | — | 451.857 | — |
| H-N421C-(C421)__mcValCitPABC-#54 | 0.601 | — | 263.107 | — |
| H-N421C-(C421)__mc-#115 | 0.108 | — | 668.857 | — |
| H-A114C-(C114)__mcGly-#201 | 0.073 | — | — | — |

TABLE 22

Selected pharmacokinetic values in rats for conjugates of the invention and selected pharmacokinetic values in rats for conjugates comprising MMAD, MMAE or MMAF. AUCs were calculated at a 0-last of 0-336 h except where noted.

| ADC | Dose | AUC (0-last) (µg * Hours/mL) ADC | AUC (0-last) (µg * Hours/mL) Ab | ADC/Ab Ratio |
|---|---|---|---|---|
| H(C)-#D54 | 3 | 3390[1] | 4560[1] | 74 |
|  | 10 | 13200[1] | 16400[1] | 80 |
|  | 30 | 37800[2] | 41700[1] | 91 |
| H(C)-#A69 | 10 | 14140 | 20840 | 68 |
|  | 30 | 44040 | 63480 | 69 |
|  | 100 | 146000 | 212000 | 69 |
| H(C)-MalPEG6C2-MMAD | 10 | 13300 | 15780 | 84 |
|  | 30 | 56180 | 60280 | 93 |
|  | 100 | 134400 | 146800 | 92 |
| H(C)-mc-MMAD | 10 | 7650 | 14500 | 53 |
|  | 30 | 20700 | 43800 | 47 |
|  | 100 | 58000 | 121000 | 48 |
| H(C)-vc-MMAE | 3 | 1080[3] | 2950[3] | 37 |
|  | 10 | 3930[3] | 10600[3] | 37 |
|  | 30 | 13400[3] | 18400[3] | — |
| H(C)-mc-MMAF | 10 | 10700 | 24500 | 44 |
|  | 30 | 32000 | 71500 | 45 |
|  | 100 | 83600 | 176000 | 48 |
| H(K)-MCC-DM1 | 3 | 3800 | 5200 | 73 |
|  | 10 | 12800 | 16200 | 79 |
|  | 30 | 39100 | 49600 | 79 |

[1]denotes a 0-last of 0-312 hours
[2]denotes a 0-last of 0-168 hours
[3]denotes a 0-last of 0-96 hours

TABLE 23

Selected pharmacokinetic values in mice for conjugates of the invention and for conjugates comprising MMAD, MMAE or MMAF. AUCs were calculated at a 0-last of 0-336 h except where noted.

| ADC | Dose | AUC (0-last) (µg * Hours/mL) ADC | AUC (0-last) (µg * Hours/mL) Ab | ADC/Ab Ratio |
|---|---|---|---|---|
| H(C)-#D44 | 3 | 1070[1] | 2720[1] | 39 |
| H(C)-#D70 | 3 | 2240 | 4890 | 46 |
| H(C)-#D69 | 3 | 2490 | 4770 | 52 |
| H(C)-#A69 | 3 | 3594 | 5722 | 63 |
| H(C)-MalPEG6C2-MMAD | 3 | 2641 | 5415 | 49 |
| H(C)-mc-MMAD | 3 | 3580 | 4970 | 72 |
| H(C)-vc-MMAE | 3 | 1600 | 3290 | 49 |
| H(C)-mc-MMAF | 3 | 3080 | 4800 | 64 |

[1]denotes a 0-last of 0-168 hours

TABLE 24

Data showing stability of conjugates prepared using ring-opened versus ring closed succinimide-based linkers.

| Herceptin ADC | | GSH stability (6 d) (% loading remaining on day 6) | Mouse ADC AUC (ug * h/mL) | Mouse PK ADC/Ab |
|---|---|---|---|---|
| mc-#118 | ring-closed | 65% | 2160 | 55% |
|  | ring-opened | 87% | 3490 | 65% |
| MalPeg6C2-#118 | ring-closed | 82% | 2010 | 70% |
|  | ring-opened | 100% | 3000 | 77% |
| mc-#8261 | ring-closed | 51% | 3590 | 52% |
|  | ring-opened | 96% | 4470 | 73% |
| MalPeg6C2-#8261 | ring-closed | 61% | 2950 | 72% |
|  | ring-opened | 104% | — | — |
| mc-#115 | ring-closed | — | 1930 | 58% |
|  | ring-opened | — | 2330 | 68% |

TABLE 25A

Selected payloads and their methods of synthesis

| Example | Prepared in the Same Manner as or Preparation Method | Purification Method | Quantity in mg (Yield) |
|---|---|---|---|
| #220 | example #107 | Method M | 10.5 mg (43%) |
| #221 | example #107 | Method M | 15.2 mg (76%) |
| #222 | General procedure L | Method J* | 14 mg (39%) |
| #223 | General procedure L | Method J* | 16.6 mg (42%) |
| #224 | General procedure L | Method J* | 18.8 mg (68%) |
| #225 | General procedure L | Method J* | 17.3 mg (64%) |
| #226 | example #146 | silica chromatography | 354 mg (78%) |
| #227 | General procedure L | Method J* | 19.4 mg (77%) |
| #228 | example #131 | Method E1* | 30 mg (51%) |
| #229 | example #151 | Method J* | 16 mg (61%) |
| #230 | General procedure L | Method J* | 69 mg (42%) |
| #231 | General procedure L* | Method J* | 4.2 mg (44%) |
| #232 | example #98 | Method J* | 113 mg (50%) |
| #233 | example #146 | silica chromatography | 88 mg (82%) |
| #234 | General procedure L | Method J* | 8.5 mg (78%) |
| #235 | General procedure L* | Method J* | 27 mg (77%) |
| #236 | example #131 | achiral | 3.7 mg (14%) |
| #237 | example #145 | silica chromatography | 38.6 mg (93%) |
| #238 | example #145 | silica chromatography | 419 mg (81%) |
| #239 | example #130 | silica chromatography | 315 mg (48%) |
| #240 | example #142 | Method E1* | 6 mg (20%) |
| #241 | example #142 | Method E1* | 6 mg (20%) |
| #242 | example #145 | Method J* | 8 mg (10%) |
| #243 | example #145 | Method J* | 12 mg (22%) |
| #244 | example #145 | Method J* | 9.6 mg (20%) |
| #245 | General procedure M | medium pressue C18 | 38 mg (55%) |
| #246 | example #130 | medium pressue C18 | 78 mg (80%) |
| #247 | example #178 | Method M* | 10.5 mg (57%) |

TABLE 25B

Selected payloads and their IUPAC name and characterization data

| Example | IUPACNAME | Mass spectrum: LC-MS or HPLC observed m/z and retention time in minutes: $^1$H NMR (400 MHz, DMSO-$d_6$) unless indicated otherwise |
|---|---|---|
| #220 | 2-methylalanyl-N-[(3R,4S,5S)-1-{(2S)-2-[(1R,2R)-3-{[(2R,4S)-4-carboxy-1-phenylpentan-2-yl]amino}-1-methoxy-2-methyl-3-oxopropyl]pyrrolidin-1-yl}-3-methoxy-5-methyl-1-oxoheptan-4-yl]-N-methyl-1-valinamide | HPLC (Protocol CB): m/z 746.51 [M + H$^+$] (1.57 minutes) |
| #221 | 2-methylalanyl-N-[(3R,4S,5S)-1-{(2S)-2-[(1R,2R)-3-(bicyclo[1.1.1]pent-1-ylamino)-1-methoxy-2-methyl-3-oxopropyl]pyrrolidin-1-yl}-3-methoxy-5-methyl-1-oxoheptan-4-yl]-N-methyl-L-valinamide | HPLC (Protocol DB): m/z 622.42 [M + H$^+$] (1.57 minutes) |
| #222 | 2-methylalanyl-N-[(3R,4S,5S)-3-methoxy-1-{(2S)-2-[(1R,2R)-1-methoxy-3-{[(1R)-2-methoxy-2-oxo-1-(1-phenylcyclopropyl)ethyl]amino}-2-methyl-3-oxopropyl]pyrrolidin-1-yl}-5-methyl-1-oxoheptan-4-yl]-N-methyl-L-valinamide | LC-MS (Protocol H): m/z 744.9 [M + H$^+$] (2.19 minutes). $^1$H NMR (400 MHz, CDCl$_3$) δ 7.16-7.22 (m), 6.99-7.08 (m), 6.42-6.51 (m), 6.10-6.17 (m), 4.87-4.96 (m), 4.65-4.79 (m), 4.27-4.36 (m), 4.04-4.27 (m), 3.95-4.02 (m), 3.87-3.93 (m), 3.64-3.84 (m), 3.44-3.57 (m), 3.22-3.42 (m), 3.08-3.17 (m), 2.98-3.07 (m), 2.90-2.93 (m), 2.85-2.89 (m), 2.53-2.57 (m), 2.35-2.51 (m), 2.19-2.27 (m), 2.02-2.16 (m), 1.93-2.00 (m), 1.77-1.90 (m), 1.57-1.70 (m), 1.35-1.52 (m), 1.26-1.33 (m), 1.19-1.25 (m), 1.11-1.16 (m), 1.03-1.11 (m), 0.83-1.02 (m), 0.79-0.88 (m). |
| #223 | 2-methylalanyl-N-[(3R,4S,5S)-3-methoxy-1-{(2S)-2-[(1R,2R)-1-methoxy-3-{[(1S)-2-methoxy-2-oxo-1-(1-phenylcyclopropyl)ethyl]amino}-2-methyl-3-oxopropyl]pyrrolidin-1-yl}-5-methyl-1-oxoheptan-4-yl]-N-methyl-L-valinamide | LC-MS (Protocol H): m/z 744.4 [M + H$^+$] (2.17 minutes). $^1$H NMR (400 MHz, CD$_3$OD) δ 8.19-8.24 (m), 7.87-7.92 (m), 7.20-7.38 (m), 4.71-5.04 (m), 4.61-4.71 (m), 4.47-4.52 (m), 4.38-4.44 (m), 4.05-4.13 (m), 3.99-4.04 (m), 3.90-3.98 (m), 3.64-3.73 (m), 3.52-3.60 (m), 3.46-3.52 (m), 3.37-3.46 (m), 3.35-3.37 (m), 3.29-3.35 (m), 3.24-3.28 (m), 3.15-3.19 (m), 3.08-3.14 (m), 3.01-3.06 (m), 2.84-2.87 (m), 2.43-2.63 (m), 1.96-2.20 (m), 1.68-1.95 (m), 1.60-1.66 (m), 1.52-1.57 (m), 1.33-1.44 (m), 1.27-1.32 (m), 1.23-1.27 (m), 1.12-1.17 (m), 1.04-1.10 (m), 0.96-1.03 (m), 0.90-0.96 (m), 0.82-0.90 (m). |
| #224 | 2-methylalanyl-N-[(3R,4S,5S)-1-{(2S)-2-[(1R,2R)-3-({(1R)-1-[(7R)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan- | LC-MS (Protocol H): m/z 730.8 [M + H$^+$] (2.15 minutes). $^1$H NMR (400 MHz, CD$_3$OD) δ 7.09-7.18 (m), 6.95-7.08 (m), 4.88-4.93 (m), 4.75-4.85 (m), 4.72-4.74 (m), 4.62-4.70 (m), 4.50-4.59 (m), 4.09-4.16 (m), 3.96-4.06 (m), 3.82-3.90 (m), 3.67-3.76 (m), 3.58-3.67 (m), 3.58-3.67 (m), 3.45-3.54 (m), 3.33-3.44 (m), 3.33-3.44 (m), 3.28-3.33 (m), 3.10-3.27 (m), 3.00-3.10 (m), |

TABLE 25B-continued

Selected payloads and their IUPAC name and characterization data

| Example | IUPACNAME | Mass spectrum: LC-MS or HPLC observed m/z and retention time in minutes: $^1$H NMR (400 MHz, DMSO-d$_6$) unless indicated otherwise |
|---|---|---|
| | 4-yl]-N-methyl-L-valinamide | 2.93-3.00 (m), 2.75-2.78 (m), 2.56-2.65 (m), 2.36-2.45 (m), 2.17-2.35 (m), 1.94-2.16 (m), 1.67-1.94 (m), 1.48-1.67 (m), 1.27-1.33 (m), 1.23-1.27 (m), 1.17-1.26 (m), 1.08-1.17 (m), 0.98-1.07 (m), 0.86-0.98 (m), 0.77-0.84 (m). |
| #225 | 2-methylalanyl-N-[(3R,4S,5S)-1-{(2S)-2-[(1R,2R)-3-({(1S)-1-[(7S)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan-4-yl]-N-methyl-L-valinamide | LC-MS (Protocol H): m/z 730.9 [M + H$^+$] (2.19 minutes) |
| #226 | N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide | LC-MS (Protocol Q): m/z 732.4 [M + H$^+$] (1.24 minutes). $^1$H NMR δ 8.47-8.53 (m), 8.24-8.29 (m), 7.81-7.91 (m), 7.14-7.27 (m), 4.54-4.75 (m), 4.44-4.54 (m), 3.94-4.02 (m), 3.72-3.78 (m), 3.61-3.69 (m), 3.28-3.36 (m), 3.14-3.28 (m), 2.99-3.08 (m), 2.81-2.97 (m), 2.29-2.57 (m), 2.16-2.29 (m), 1.91-2.16 (m), 1.60-1.87 (m), 1.35-1.53 (m), 0.99-1.33 (m), 0.80-0.99 (m), 0.71-0.80 (m). |
| #227 | 2-methylalanyl-N-[(3R,4S,5S)-1-{(2S)-2-[(1R,2R)-3-({(1S)-1-[(7R)-bicyclo[4.2.0]octa-1,3,5-trien-7-yl]-2-methoxy-2-oxoethyl}amino)-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q): m/z 730.4 [M + H$^+$] (1.29 minutes) |
| #228 | N,N,2-trimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide | HPLC (Protocol A*): m/z 746.5 [M + H$^+$] (7.103 minutes) |
| #229 | N,N,2-trimethylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 732.3 [M + H$^+$] (0.70 minutes) |
| #230 | 2-methylalanyl-N-[(3R,4S,5S)-1-{(2S)-2-[(1R,2R)-3-{[(R)-carboxy(1-phenylcyclopropyl)methyl]amino}-1-methoxy-2-methyl-3-oxopropyl]pyrrolidin-1-yl}-3-methoxy-5-methyl-1-oxoheptan-4-yl]-N-methyl-L-valinamide | HPLC (Protocol G): m/z 730.4 [M + H$^+$] (1.25 minutes) |
| #231 | difluoro{2-methylalanyl-N-[(3R,4S,5S)-1-{(2S)-2-[(3R,4R,7S)-7-benzyl-15-{2-[(3,5-dimethyl-1H-pyrrol-2-yl-kappaN)methylidene]-2H-pyrrol-5-yl-kappaN}-4-methyl-5,8,13-trioxo-2-oxa-6,9,12-triazapentadecan-3-yl]pyrrolidin-1-yl}-3-methoxy-5-methyl-1-oxoheptan-4-yl]-N-methyl-L-valinamidato}boron | LC-MS (Protocol Q1): m/z 1020.6 [M + H$^+$] (0.83 minutes). $^1$H NMR (400 MHz, CD$_3$OD) δ 8.19-8.23 (m), 7.99-8.07 (m), 7.93-7.98 (m), 7.41-7.45 (m), 7.23-7.31 (m), 7.17-7.22 (m), 7.00-7.04 (m), 6.32-6.37 (m), 6.20-6.24 (m), 4.72-4.93 (m), 4.61-4.69 (m), 4.05-4.17 (m), 3.88-3.93 (m), 3.72-3.81 (m), 3.63-3.70 (m), 3.56-3.62 (m), 3.48-3.56 (m), 3.25-3.44 (m), 3.16-3.25 (m), 3.09-3.14 (m), 2.98-3.09 (m), 2.81-2.90 (m), 2.54-2.67 (m), 2.39-2.53 (m), 2.09-2.32 (m), 1.75-1.97 (m), 1.60-1.69 (m), 1.52-1.59 (m), 1.32-1.44 (m), 1.28-1.32 (m), 1.16-1.21 (m), 0.98-1.09 (m), 0.86-0.98 (m), 0.79-0.90 (m). |
| #232 | 2-methyl-D-prolyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide | LC-MS (Protocol Q): m/z 769.3 [M + H$^+$] (1.34 minutes). $^1$H NMR δ 9.04-9.17 (m), 8.88-8.94 (m), 8.70-8.86 (m), 8.62-8.67 (m), 7.79-7.84 (m), 7.76-7.79 (m), 7.65-7.69 (m), 7.61-7.64 (m), 7.20-7.31 (m), 7.12-7.20 (m), 5.44-5.52 (m), 5.34-5.46 (m), 4.70-4.78 (m), 4.56-4.67 (m), 4.47-4.54 (m), 3.94-4.04 (m), 3.76-3.83 (m), 3.52-3.61 (m), 3.36-3.52 (m), 3.28-3.35 (m), 3.10-3.27 (m), 2.93-3.08 (m), 2.77-2.80 (m), 2.64-2.70 (m), |

TABLE 25B-continued

Selected payloads and their IUPAC name and characterization data

| Example | IUPACNAME | Mass spectrum: LC-MS or HPLC observed m/z and retention time in minutes: $^1$H NMR (400 MHz, DMSO-$d_6$) unless indicated otherwise |
|---|---|---|
| | | 2.35-2.54 (m), 2.09-2.34 (m), 1.96-2.09 (m), 1.54-1.88 (m), 1.38-1.52 (m), 1.18-1.36 (m), 1.03-1.13 (m), 0.81-1.01 (m), 0.68-0.81 (m). |
| #233 | methyl N-{(2R,3R)-3-[(2S)-1-{(3R,4S,5S)-4-[{N-[(3-aminooxetan-3-yl)carbonyl]-L-valyl}(methyl)amino]-3-methoxy-5-methylheptanoyl}pyrrolidin-2-yl]-3-methoxy-2-methylpropanoyl}-L-phenylalaninate | LC-MS (Protocol Q): m/z 732.2 [M + H$^+$] (1.28 minutes). $^1$H NMR δ 8.48-8.53 (m), 8.22-8.28 (m), 7.80-7.92 (m), 7.14-7.28 (m), 4.74-4.79 (m), 4.54-4.72 (m), 4.43-4.52 (m), 4.24-4.35 (m), 4.07-4.12 (m), 3.94-4.02 (m), 3.72-3.78 (m), 3.61-3.69 (m), 3.48-3.58 (m), 3.40-3.48 (m), 3.11-3.35 (m), 2.98-3.11 (m), 2.75-2.97 (m), 2.64-2.69 (m), 2.30-2.55 (m), 2.17-2.28 (m), 2.03-2.14 (m), 1.92-2.02 (m), 1.59-1.87 (m), 1.35-1.54 (m), 1.21-1.33 (m), 1.112-1.20 (m), 1.00-1.09 (m), 0.70-0.98 (m). |
| #234 | 2-methylalanyl-N-{(3R,4S,5S)-1-[(2S)-2-{(3R,4R,7S,12S)-7-benzyl-14-[3-chloro-4-(propan-2-yloxy)phenyl]-4-methyl-12-[4-(8-methylimidazo[1,2-a]pyridin-2-yl)benzyl]-5,8,14-trioxo-2,9-dioxa-6,13-diazatetradecan-3-yl}pyrrolidin-1-yl]-3-methoxy-5-methyl-1-oxoheptan-4-yl}-N-methyl-L-valinamide | LC-MS (Protocol H): m/z 589.9 [M + H$^{+2}$] (2.29 minutes). $^1$H NMR (400 MHz, CD$_3$OD) δ 8.55-8.61 (m), 8.40-8.45 (m), 8.34-8.39 (m), 8.23-8.28 (m), 8.14-8.19 (m), 7.84-7.95 (m), 7.79-7.84 (m), 7.71-7.77 (m), 7.61-7.68 (m), 7.46-7.52 (m), 7.34-7.40 (m), 7.09-7.27 (m), 7.03-7.09 (m), 4.77-4.90 (m), 4.58-4.77 (m), 4.43-4.55 (m), 4.17-4.33 (m), 4.07-4.16 (m), 4.00-4.07 (m), 3.79-3.85 (m), 3.58-3.70 (m), 3.44-3.52 (m), 3.12-3.40 (m), 2.80-3.12 (m), 2.64-2.71 (m), 2.62-2.64 (m), 2.38-2.47 (m), 2.00-2.33 (m), 1.66-2.00 (m), 1.46-1.63 (m), 1.29-1.44 (m), 1.07-1.16 (m), 0.91-1.07 (m), 0.79-0.87 (m). |
| #235 | 2-methylalanyl-N-[(3R,4S,5S)-1-{(2S)-2-[(1R,2R)-3-{[(2S)-1-{[4-(5-fluoro-1,3-benzothiazol-2-yl)-2-methylphenyl]amino}-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 944.3 [M + H$^+$] (0.84 minutes). $^1$NMR (400 MHz, CD$_3$OD) δ 8.54-8.59 (m), 8.29-8.33 (m), 7.87-8.02 (m), 7.80-7.87 (m), 7.68-7.74 (m), 7.62-7.67 (m), 7.20-7.38 (m), 4.98-5.06 (m), 4.84-4.97 (m), 4.66-4.79 (m), 4.61-4.66 (m), 4.13-4.19 (m), 3.98-4.04 (m), 3.91-3.96 (m), 3.79-3.85 (m), 3.64-3.73 (m), 3.38-3.56 (m), 3.34-3.38 (m), 3.28-3.34 (m), 3.17-3.27 (m), 3.12-3.16 (m), 3.03-3.11 (m), 2.99-3.03 (m), 2.86-2.87 (m), 2.80-2.82 (m), 2.69-2.71 (m), 2.31-2.54 (m), 2.27-2.31 (m), 2.06-2.27 (m), 1.88-2.00 (m), 1.74-1.88 (m), 1.64-1.74 (m), 1.59-1.64 (m), 1.50-1.59 (m), 1.27-1.48 (m), 1.19-1.26 (m), 1.11-1.16 (m), 1.06-1.11 (m), 0.96-1.05 (m), 0.86-0.94 (m), 0.77-0.83 (m). |
| #236 | 1,2-dimethyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide | LC-MS (Protocol Q1): m/z 758.3 [M + H$^+$] (0.74 minutes) |
| #237 | N,2-dimethylalanyl-N-[(3R,4S,5S)-1-{(2S)-2-[(1R,2R)-3-{[(2S)-3-(1H-indol-3-yl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 771.2 [M + H$^+$] (0.67 minutes). $^1$H NMR (400 MHz, CD$_3$OD) δ 7.95-7.96 (m), 7.48-7.55 (m), 7.45-7.48 (m), 7.26-7.31 (m), 6.94-7.18 (m), 5.45-5.49 (m), 5.19-5.22 (m), 5.11-5.17 (m), 4.97-5.00 (m), 4.78-4.87 (m), 4.68-4.77 (m), 4.59-4.64 (m), 4.27-4.34 (m), 3.99-4.16 (m), 3.84-3.92 (m), 3.78-3.82 (m), 3.62-3.78 (m), 3.49-3.59 (m), 3.41-3.49 (m), 3.20-3.41 (m), 2.99-3.20 (m), 2.95-2.98 (m), 2.82-2.86 (m), 2.77-2.79 (m), 2.62-2.68 (m), 2.28-2.49 (m), 2.19-2.27 (m), 1.98-2.16 (m), 1.56-1.91 (m), 1.31-1.49 (m), 1.19-1.30 (m), 1.15-1.19 (m), 1.06-1.13 (m), 0.88-1.03 (m), 0.79-0.87 (m). |
| #238 | N,2-dimethylalanyl-N-[(3R,4S,5S)-3-methoxy-1-{(2S)-2-[(1R,2R)-1-methoxy-2-methyl-3-oxo-3-{[(2S)-1-oxo-3-phenyl-1-(prop-2-en-1-yloxy)propan-2-yl]amino}propyl]pyrrolidin-1-yl}-5-methyl-1-oxoheptan-4-yl]-N-methyl-L-valinamide | LC-MS (Protocol Q1): m/z 758.84 [M + H$^+$] (0.71 minutes). $^1$H NMR (400 MHz, CD$_3$OD) δ 7.15-7.32 (m), 5.86-6.00 (m), 5.28-5.40 (m), 5.17-5.27 (m), 4.97-5.04 (m), 4.69-4.91 (m), 4.57-4.69 (m), 4.05-4.21 (m), 3.91-3.96 (m), 3.79-3.88 (m), 3.71-3.78 (m), 3.62-3.70 (m), 3.25-3.56 (m), 3.15-3.24 (m), 3.08-3.14 (m), 2.90-3.02 (m), 2.79-2.87 (m), 2.42-2.52 (m), 2.20-2.38 (m), 2.12-2.20 (m), 2.03-2.12 (m), 2.00-2.03 (m), 1.71-2.1.96 (m), 1.33-1.70 (m), 1.23-1.32 (m), 1.17-1.23 (m), 1.12-1.17 (m), 1.05-1.10 (m), 0.94-1.05 (m), 0.82-0.89 (m). |
| #239 | 2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4- | LC-MS (Protocol Q): m/z 786.6 [M + H$^+$] (1.46 minutes). $^1$NMR δ 8.35-8.42 (m), 8.21-8.31 (m), 8.14-8.20 (m), 7.15-7.29 (m), 4.66-4.76 (m), 4.53-4.65 (m), 4.46-4.53 (m), 4.32-4.42 (m), 4.07-4.15 (m), 3.96-4.04 (m), 3.76-3.82 (m), 3.41-3.61 (m), 3.30-3.38 (m), 3.16-3.30 (m), 3.08-3.15 (m) 2.99-3.08 (m), 2.92-2.96 (m), |

TABLE 25B-continued

Selected payloads and their IUPAC name and characterization data

| Example | IUPACNAME | Mass spectrum: LC-MS or HPLC observed m/z and retention time in minutes: $^1$H NMR (400 MHz, DMSO-d$_6$) unless indicated otherwise |
|---|---|---|
| | yl]-N-methyl-L-valinamide | 2.78-2.90 (m), 2.63-2.78 (m), 2.37-2.58 (m), 2.18-2.36 (m), 2.03-2.13 (m), 1.89-2.01 (m), 1.64-1.88 (m), 1.35-1.62 (m), 1.31-1.35 (m), 1.17-1.31 (m), 1.03-1.14 (m), 0.70-1.01 (m). |
| #240 | N,2-dimethylalanyl-N-[(3R,4S,5S)-3-methoxy-1-{(2S)-2-[(1R,2R)-1-methoxy-2-methyl-3-oxo-3-({(2S)-1-oxo-3-phenyl-1-[(1H-1,2,3-triazol-4-ylmethyl)amino]propan-2-yl}amino)propyl]pyrrolidin-1-yl}-5-methyl-1-oxoheptan-4-yl]-N-methyl-L-valinamide | LC-MS (Protocol Q1): m/z 798.2 [M + H$^+$] (0.66 minutes). $^1$H NMR (400 MHz, CD$_3$OD) δ 8.43-8.49 (m), 7.50-7.53 (m), 7.42-7.48 (m), 7.06-7.20 (m), 4.21-4.83 (m), 3.95-4.13 (m), 3.76-3.88 (m), 3.53-3.67 (m), 3.16-3.47 (m), 3.08-3.15 (m) 3.00-3.16 (m), 2.77-2.90 (m), 2.70-2.73 (m), 2.62-2.69 (m), 2.45-2.58 (m), 2.34-2.41 (m), 2.21-2.29 (m), 2.12-2.21 (m), 1.55-2.09 (m), 1.39-1.54 (m), 1.16-1.36 (m), 1.04-1.14 (m), 0.85-0.99 (m), 0.73-0.80 (m), 0.00-0.02 (m). |
| #241 | N,2-dimethylalanyl-N-[(3R,4S,5S)-3-methoxy-1-{(2S)-2-[(1R,2R)-1-methoxy-2-methyl-3-oxo-3-{[(2S)-1-oxo-3-phenyl-1-(prop-2-yn-1-ylamino)propan-2-yl]amino}propyl]pyrrolidin-1-yl}-5-methyl-1-oxoheptan-4-yl]-N-methyl-L-valinamide | LC-MS (Protocol Q1): m/z 755.1 [M + H$^+$] (0.69 minutes). $^1$H NMR (400 MHz, CD$_3$OD) δ 8.36-8.67 (m), 7.26-7.50 (m), 7.10-7.26 (m), 5.13-5.17 (m), 4.95-4.99 (m), 4.67-4.84 (m), 4.61-4.66 (m), 4.50-4.60 (m), 3.77-4.12 (m), 3.69-3.75 (m), 3.56-3.66 (m), 3.44-3.54 (m), 3.19-3.44 (m) 3.12-3.19 (m), 3.03-3.12 (m), 2.74-2.94 (m), 2.37-2.60 (m), 2.14-2.36 (m), 1.60-2.13 (m), 1.47-1.59 (m), 1.19-1.40 (m), 1.11-1.16 (m), 0.88-1.11 (m), 0.75-0.84 (m), 0.02-0.06 (m). |
| #242 | N,2-dimethylalanyl-N-[(3R,4S,5S)-1-{(2S)-2-[(1R,2R)-3-{[(2S)-3-(1H-imidazol-4-yl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 722.95 [M + H$^+$] (0.52 minutes) $^1$H NMR (400 MHz, CD$_3$OD) δ 8.78-8.86 (m), 8.71-8.73 (m), 7.96-8.00 (m), 7.34-7.40 (m), 4.74-4.91 (m), 4.67-4.71 (m), 4.55-4.63 (m), 4.13-4.22 (m), 4.04-4.10 (m), 3.97-4.01 (m), 3.84-3.92 (m), 3.66-3.82 (m), 3.42-3.64 (m), 3.26-3.42 (m) 3.11-3.21 (m), 2.90-2.92 (m), 2.83-2.84 (m), 2.59-2.64 (m), 2.48-2.56 (m), 2.32-2.41 (m), 2.09-2.24 (m), 1.99-2.08 (m), 1.68-1.95 (m), 1.59-1.66 (m), 1.51-1.58 (m), 1.35-1.45 (m), 1.22-1.26 (m), 1.17-1.21 (m). 0.95-1.12 (m), 0.83-0.89 (m). |
| #243 | N,2-dimethylalanyl-N-[(3R,4S,5S)-1-{(2S)-2-[(1R,2R)-3-{[(2S)-3-(4-hydroxyphenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 748.2 [M + H$^+$] (0.52 minutes) $^1$H NMR (400 MHz, CD$_3$OD), δ 8.91-8.99 (m), 8.42-8.46 (m), 8.15-8.20 (m), 7.92-8.01 (m), 7.00-7.10 (m), 6.64-6.74 (m), 5.22-5.26 (m), 5.06-5.09 (m), 4.79-4.95 (m), 4.65-4.79 (m), 4.59-4.65 (m), 4.12-4.21 (m), 4.05-4.12 (m), 3.91-3.99 (m), 3.84-3.90 (m), 3.67-3.79 (m), 3.60-3.66 (m), 3.39-3.57 (m), 3.34-3.39 (m) 3.29-3.34 (m), 3.12-3.27 (m), 2.98-3.00 (m), 2.78-2.88 (m), 2.61-2.65 (m), 2.55-2.57 (m), 2.46-2.53 (m), 2.10-2.36 (m), 1.68-1.96 (m), 1.61-1.68 (m), 1.55-1.60 (m), 1.35-1.53 (m), 1.19-1.24 (m), 1.14-1.18 (m), 1.08-1.13 (m), 0.98-1.08 (m), 0.84-0.92 (m). |
| #244 | N,2-dimethylalanyl-N-[(3R,4S,5S)-1-{(2S)-2-[(1R,2R)-3-{[(1R)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q1): m/z 718.4 [M + H$^+$] (0.66 minutes) $^1$H NMR (400 MHz, CD$_3$OD), δ 7.87-7.92 (m), 7.71-7.76 (m), 7.46-7.53 (m), 7.40-7.46 (m), 7.19-7.33 (m), 4.81-4.96 (m), 4.68-4.77 (m), 4.60-4.65 (m), 4.47-4.53 (m), 4.01-4.17 (m), 3.94-3.98 (m), 3.81-3.86 (m), 3.68-3.76 (m), 3.56-3.64 (m), 3.40-3.50 (m), 3.36-3.40 (m) 3.26-3.35 (m), 3.23-3.26 (m), 3.16-3.22 (m), 3.12-3.16 (m), 2.94-3.06 (m), 2.91-2.93 (m), 2.86-2.88 (m), 2.41-2.66 (m), 2.32-2.41 (m), 1.97-2.23 (m), 1.85-1.97 (m), 1.71-1.85 (m), 1.62-1.68 (m), 1.50-1.61 (m), 1.37-1.46 (m), 0.98-1.14 (m), 0.85-0.92 (m). |
| #245 | 1,2-dimethyl-L-prolyl-N-[(3R,4S,5S)-3-methoxy-1-{(2S)-2-[(1R,2R)-1-methoxy-2-methyl-3-oxo-3-{[(2S)-1-oxo-3-phenyl-1-(piperazin-1-yl)propan-2-yl]amino}propyl]pyrrolidin-1-yl}-5-methyl-1-oxoheptan-4-yl]-N-methyl-L-valinamide | LC-MS (Protocol Q): m/z 835.0 [M + Na$^+$] (0.87 minutes) $^1$H NMR δ 9.58-9.69 (m), 8.84-9.16 (m), 8.69-8.77 (m), 8.54-8.60 (m), 8.44-8.50 (m), 8.32-8.42 (m), 8.25-8.30 (m), 7.13-7.31 (m), 7.00-7.01 (m), 4.97-5.06 (m), 4.88-4.97 (m), 4.57-4.75 (m), 4.45-4.57 (m), 3.84-4.45 (m), 3.62-3.84 (m), 3.40-3.62 (m), 3.13-3.33 (m), 2.77-3.10 (m), 2.67-2.75 (m), 2.47-2.57 (m), 2.38-2.45 (m), 1.92-2.35 (m), 1.58-1.88 (m), 1.37-1.55 (m), 1.22-1.32 (m), 0.97-1.06 (m), 0.84-0.97 (m), 0.73-0.81 (m). |
| #246 | 1,2-dimethyl-L-prolyl-N-[(3R,4S,5S)-1-{(2S)-2-[(1R,2R)-3-{[(2S)-1-amino-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide | LC-MS (Protocol Q): m/z 366.2 [M + H$^{+2}$] (0.91 minutes) $^1$H NMR δ 9.56-9.65 (m), 8.70-8.76 (m), 8.05-8.09 (m), 7.77-7.92 (m), 7.14-7.30 (m), 4.60-4.72 (m), 4.46-4.57 (m), 3.61-4.39 (m), 3.41-3.61 (m), 3.11-3.33 (m), 2.97-3.09 (m), 2.79-2.94 (m), 2.63-2.74 (m), 2.38-2.56 (m), 2.13-2.37 (m), 1.93-2.13 (m), 1.45-1.89 (m), 1.21-1.32 (m), 1.09-1.14 (m), 1.03-1.08 (m), 0.84-095 (m), 0.73-0.80 (m). |

TABLE 25B-continued

Selected payloads and their IUPAC name and characterization data

| Example | IUPAC NAME | Mass spectrum: LC-MS or HPLC observed m/z and retention time in minutes: $^1$H NMR (400 MHz, DMSO-$d_6$) unless indicated otherwise |
|---|---|---|
| #247 | 2-methyl-D-prolyl-N-[(3R,4S,5S)-1-{(2S)-2-[(1R,2R)-3-{[2-(cyclohepta-2,4,6-trien-1-yl)ethyl]amino}-1-methoxy-2-methyl-3-oxopropyl]pyrrolidin-1-yl}-3-methoxy-5-methyl-1-oxoheptan-4-yl]-N-methyl-L-valinamide | HPLC (Protocol DB): m/z 700.51 [M + H$^+$] (2.56 minutes) |

We claim:
1. A compound of formula I:

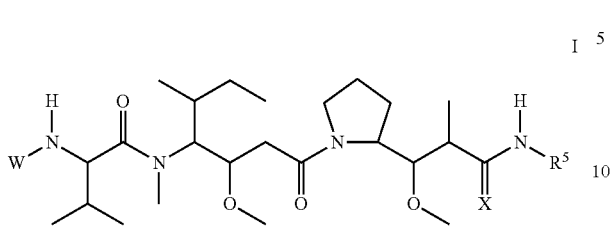

or a pharmaceutically acceptable salt or solvate thereof, wherein, independently for each occurrence, W is

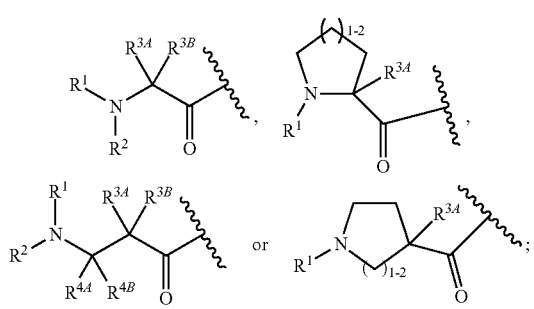

$R^1$ is hydrogen, $C_1$-$C_8$ alkyl or $C_1$-$C_8$ haloalkyl;

$R^2$ is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

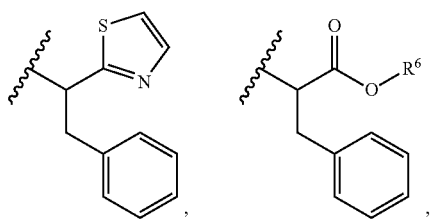

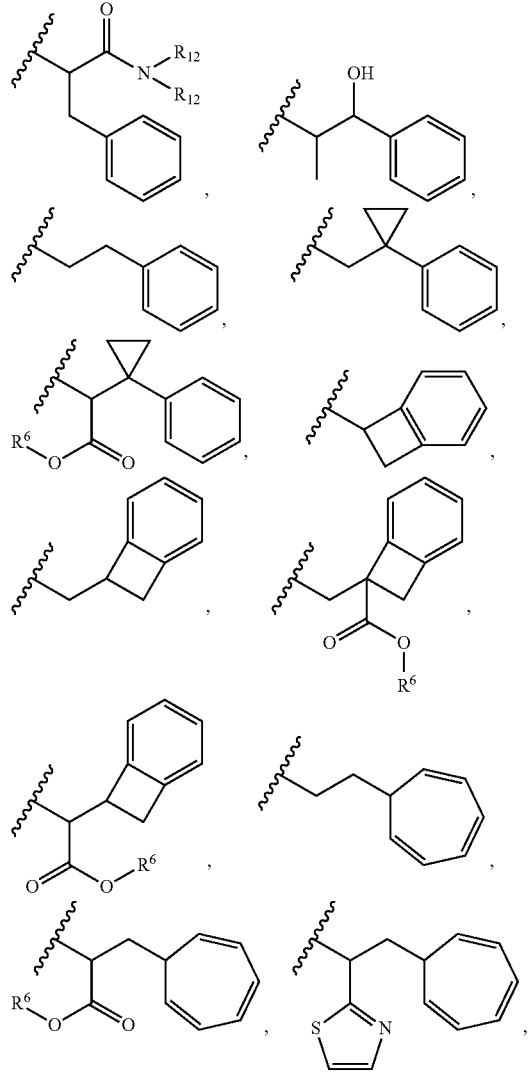

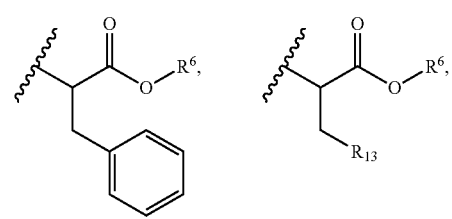

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

-continued

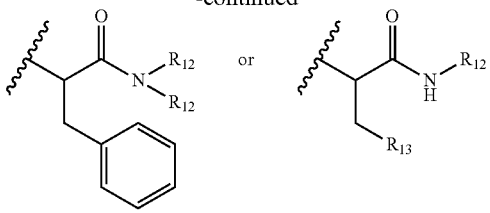

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O or S;

provided that when $R^{3A}$ is hydrogen X is S.

2. A compound of formula IIa:

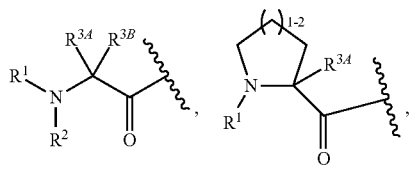

IIa or a pharmaceutically acceptable salt or solvate thereof, wherein, independently for each occurrence, W is

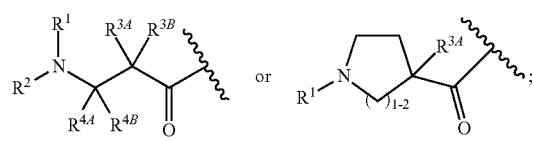

$R^1$ is

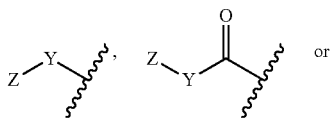

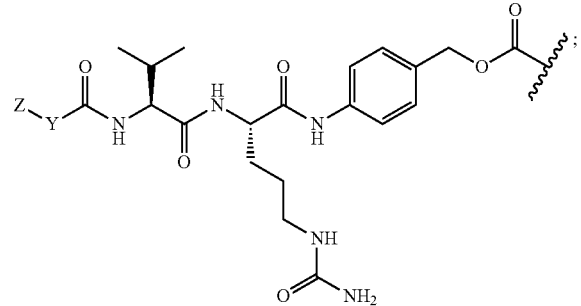

Y is —$C_2$-$C_{20}$ alkylene-, —$C_2$-$C_{20}$ heteroalkylene-; —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)- or —$C_3$-$C_8$ heterocyclo)-$C_1$-$C_{10}$alkylene-;

Z is

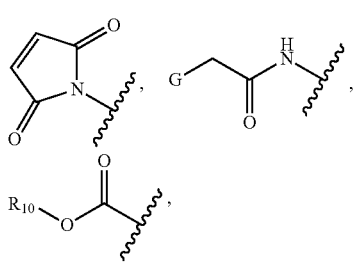

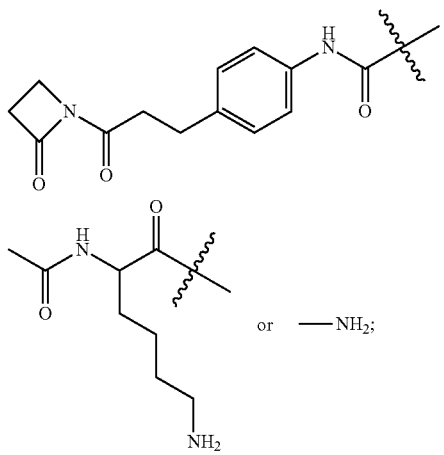

G is halogen, —OH, —SH or —S—$C_1$-$C_6$ alkyl;

$R^2$ is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl or halogen; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

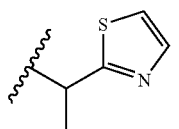 , 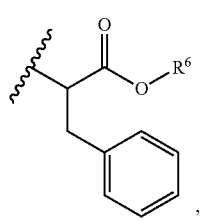 ,

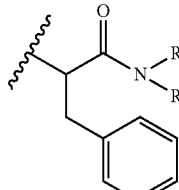 , 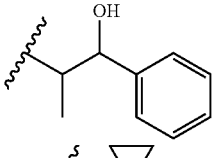 ,

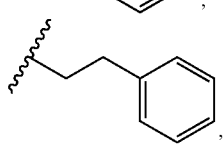 ,

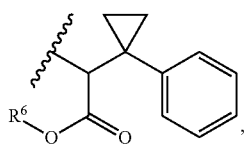 , 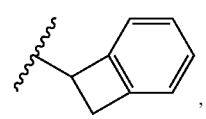 ,

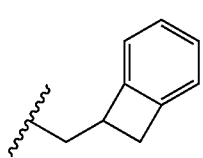 , 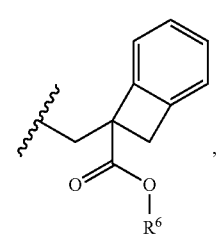 ,

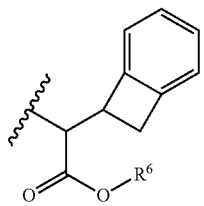 , 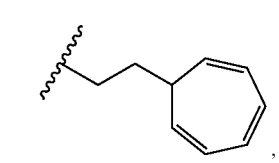 ,

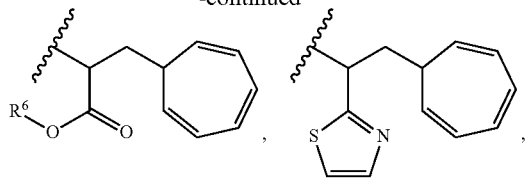

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

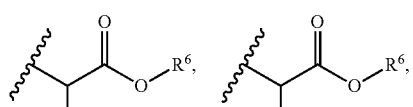 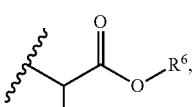

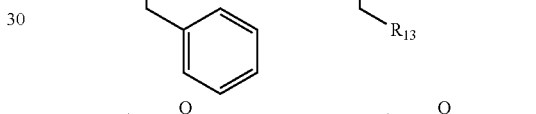

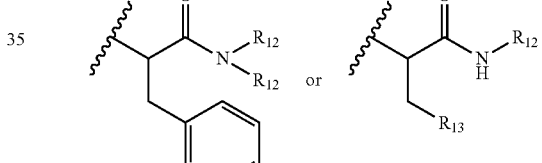

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —O(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and $R^7$ is independently selected for each occurrence from the group consisting of F, Cl, I, Br, NO$_2$, CN and CF$_3$;

$R^{10}$ is hydrogen, —$C_1$-$C_{10}$alkyl, —$C_3$-$C_8$-carbocyclyl, -aryl, —$C_1$-$C_{10}$heteroalkyl, —$C_3$-$C_8$heterocyclo, —$C_1$-$C_{10}$alkylene-aryl, -arylene—$C_1$-$C_{10}$alkyl, —$C_1$-$C_{10}$alkylene-($C_3$-$C_8$-carbocyclo), —($C_3$-$C_8$ carbocyclo)-$C_1$-$C_{10}$alkyl, —$C_1$-$C_{10}$alkylene-($C_3$-$C_8$heterocyclo), and —($C_3$-$C_8$ heterocyclo)-$C_1$-

$C_{10}$ alkyl, where aryl on $R_{10}$ comprising aryl is optionally substituted with $[R_7]_h$;
h is 1, 2, 3, 4 or 5; and
X is O or S;
provided that when $R^{3A}$ is hydrogen X is S.

3. A compound of formula IIIa:

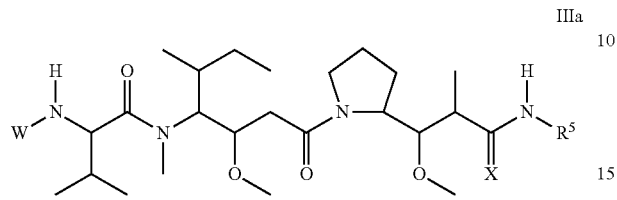

IIIa or a pharmaceutically acceptable salt or solvate thereof, wherein, independently for each occurrence,
W is

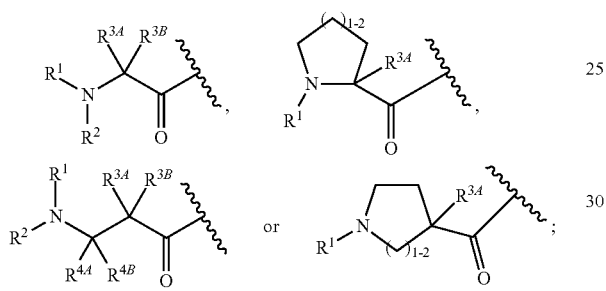

$R^1$ is hydrogen, $C_1$-$C_8$ alkyl or $C_1$-$C_8$ haloalkyl;
$R^2$ is hydrogen, $C_1$-$C_8$ alkyl or $C_1$-$C_8$ haloalkyl;
$R^{3A}$ and $R^{3B}$ are either of the following:
(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or
(ii) $R^{3A}$ and $R^{3B}$ taken together are $C_2$-$C_8$ alkylene or $C_1$-$C_8$ heteroalkylene;
$R^{4A}$ and $R^{4B}$ are either of the following:
(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(ii) $R^{4A}$ and $R^{4B}$ taken together are $C_2$-$C_8$ alkylene or $C_1$-$C_8$ heteroalkylene;
$R^5$ is

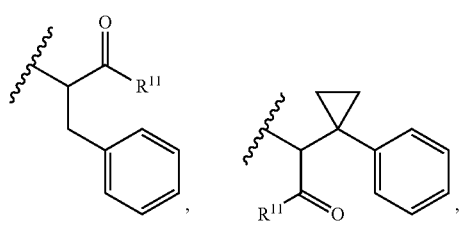

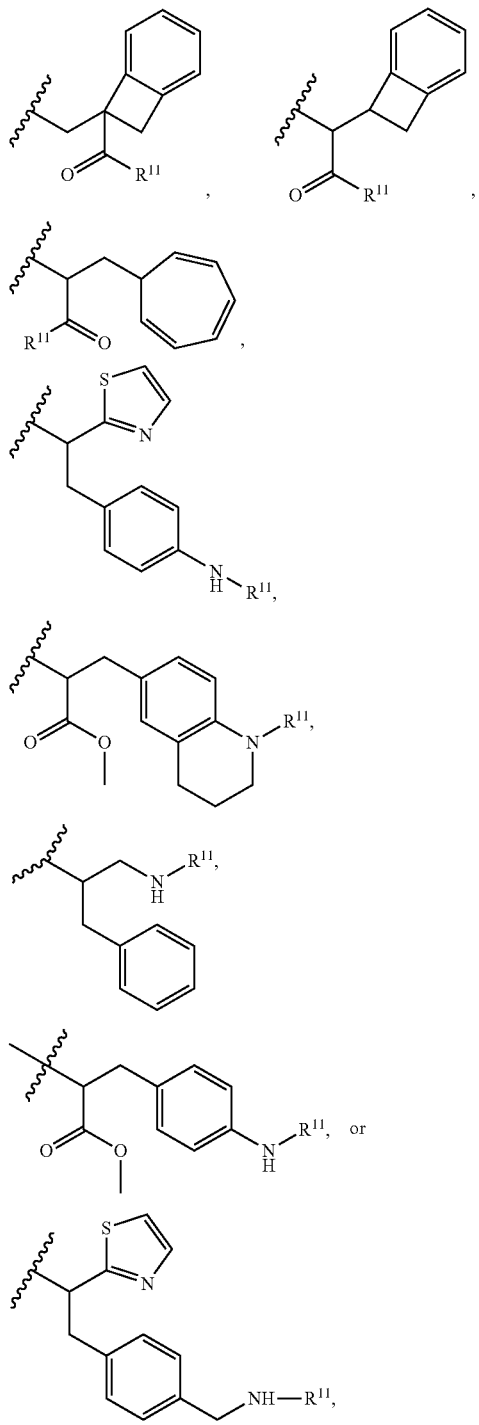

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

$R^{11}$ is

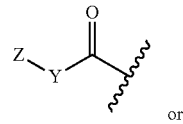

or

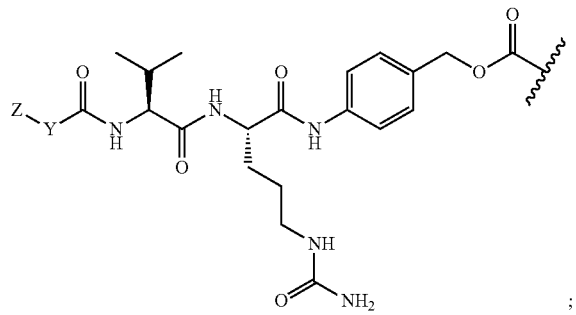

Y is —$C_2$-$C_{20}$ alkylene-, —$C_2$-$C_{20}$ heteroalkylene-, —$C_3$-$C_8$ carbocyclo-, -arylene-, —$C_3$-$C_8$ heterocyclo-, —$C_1$-$C_{10}$alkylene-arylene-, -arylene-$C_1$-$C_{10}$alkylene-, —$C_1$-$C_1$alkylene-($C_3$-$C_{10}$-carbocyclo)-, —($C_3$-$C_8$-carbocyclo)-$C_1$-$C_{10}$alkylene-, —$C_1$-$C_{10}$alkylene-($C_3$-$C_{10}$heterocyclo)-, or -($C_3$-$C_8$ heterocyclo)-$C_1$-$C_{10}$alkylene-;

Z is

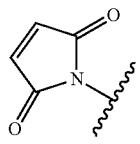 , 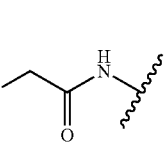 , 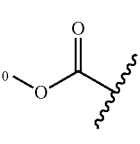

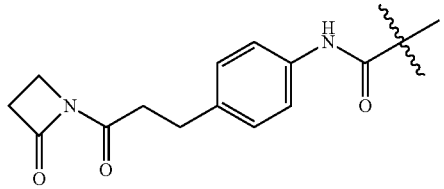

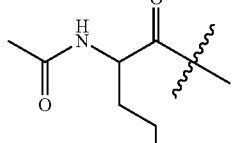 or —$NH_2$;

$R^7$ is independently selected for each occurrence from the group consisting of F, Cl, I, Br, $NO_2$, CN and $CF_3$;

$R^{10}$ is hydrogen, —$C_1$-$C_{10}$alkyl, —$C_3$-$C_8$-carbocycle, aryl, —$C_1$-$C_{10}$ heteroalkyl, —$C_3$-$C_8$heterocyclo, —$C_1$-$C_{10}$alkylene-aryl, -arylene-$C_1$-$C_{10}$alkyl, —$C_1$-$C_{10}$alkylene-($C_3$-$C_{10}$-carbocyclo), —($C_3$-$C_{10}$ carbocyclo)-$C_1$-$C_{10}$alkyl, —$C_1$-$C_{10}$alkylene-($C_3$-$C_{10}$heterocyclo), and -($C_3$-$C_{10}$ heterocyclo)-$C_1$-$C_{10}$alkyl, where aryl on $R_{10}$ comprising aryl is optionally substituted with $[R_7]_h$;

X is O or S $R^6$ is hydrogen, $C_1$-$C_8$ alkyl or $C_1$-$C_8$ haloalkyl; and h is 1, 2, 3, 4 or 5.

4. A compound of formula IIb:

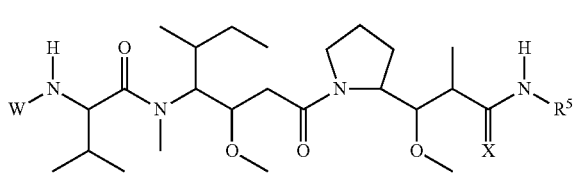

IIb or a pharmaceutically acceptable salt or solvate thereof, wherein, independently for each occurrence, W is

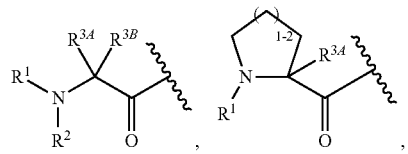

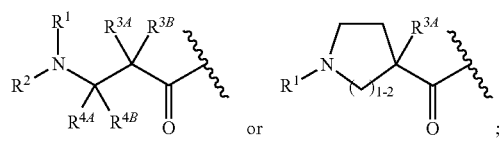

or

;

$R^1$ is

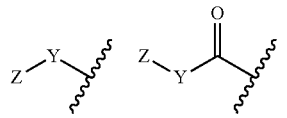

,

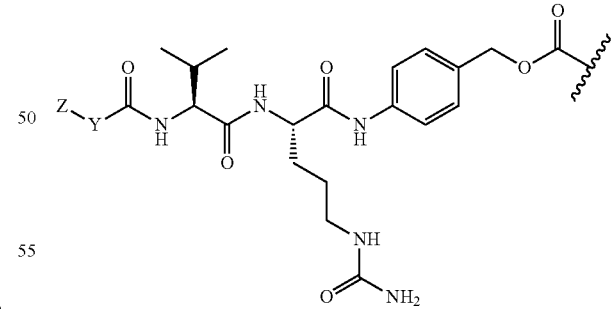

;

Y is —$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z is

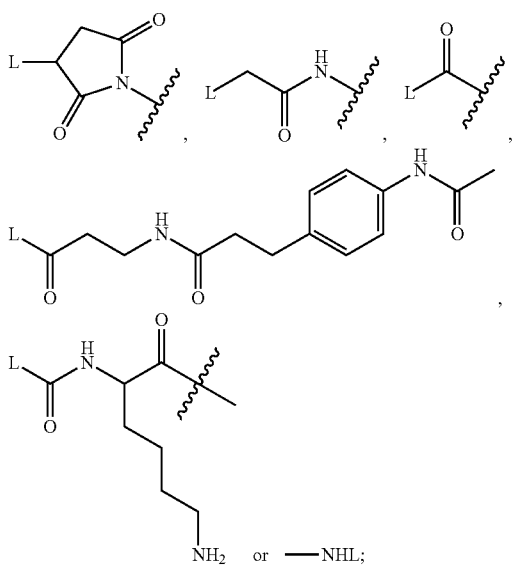

L is an antibody;
$R^2$ is hydrogen, $C_1$-$C_8$ alkyl or $C_1$-$C_8$ haloalkyl;
$R^{3A}$ and $R^{3B}$ are either of the following:
(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or
(ii) $R^{3A}$ and $R^{3B}$ taken together are $C_2$-$C_8$ alkylene or $C_1$-$C_8$ heteroalkylene;
$R^{4A}$ and $R^{4B}$ are either of the following:
(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B}$ is hydrogen, $C_1$-$C_8$ alkyl, $C_1$-$C_8$ haloalkyl, $C_3$-$C_8$ carbocyclyl, $C_1$-$O_{10}$ heterocyclyl, aryl, heteroaralkyl or aralkyl; or
(ii) $R^{4A}$ and $R^{4B}$ taken together are $C_2$-$C_8$ alkylene or $C_1$-$C_8$ heteroalkylene;
$R^5$ is

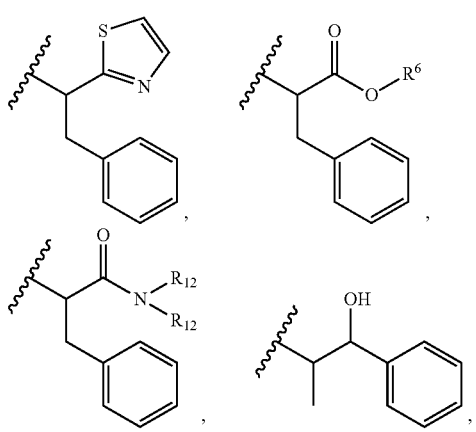

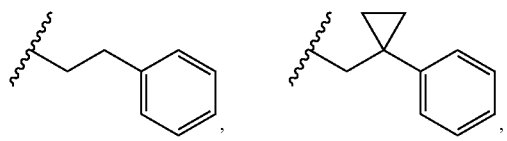

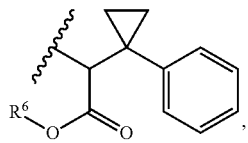

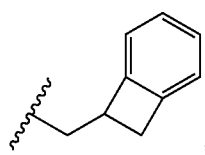

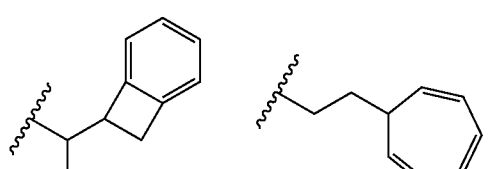

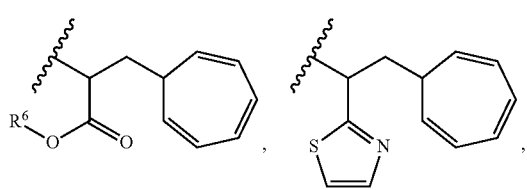

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;
or $R^5$ is

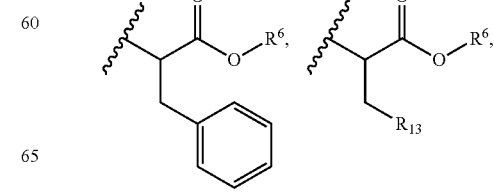

-continued

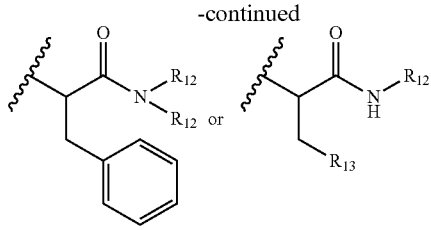

optionally substituted with 1, 2, 3, 4 or 5 groups independently selected from the group consisting of $C_1$-$C_8$ alkyl, —$C_1$-$C_8$ alkyl-$N(R')_2$, —$C_1$-$C_8$ alkyl-$C(O)R'$, —$C_1$-$C_8$ alkyl-$C(O)OR'$, —O—($C_1$-$C_8$ alkyl), —$C(O)R'$, —$OC(O)R'$, —$C(O)OR'$, —$C(O)N(R)_2$, —$NHC(O)R'$, —$S(O)_2R'$, —$S(O)R'$, —OH, halogen, —$N_3$, —$N(R')_2$, —CN, —NHC(=NH)$NH_2$, —$NHCONH_2$, —$S(=O)_2R'$, —$SR'$ and arylene-R', wherein each R' is independently selected from the group consisting of hydrogen, $C_1$-$C_8$ alkyl, $C_1$-$C_8$heterocyclyl, $C_1$-$C_{10}$ alkylene—$C_3$-$C_8$heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O or S;

provided that when $R^{3A}$ is hydrogen X is S.

5. A compound of formula IIIb:

IIIb

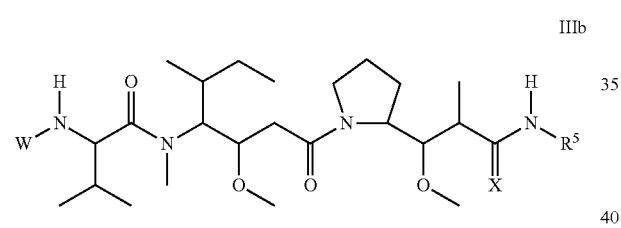

or a pharmaceutically acceptable salt or solvate thereof, wherein, independently for each occurrence, W is $R^1$ is hydrogen, $C_1$-$C_8$ alkyl or $C_1$-$C_8$ haloalkyl;

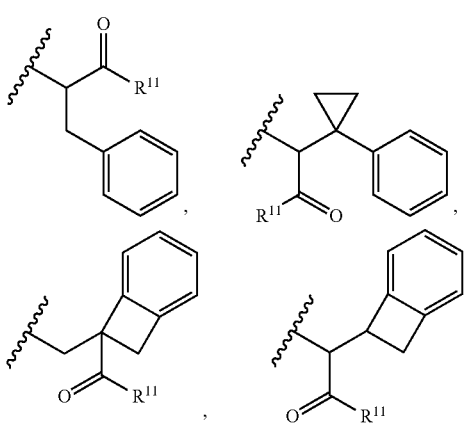

$R^2$ is hydrogen, $C_1$-$C_8$ alkyl or $C_1$-$C_8$ haloalkyl;
$R^{3A}$ and $R^{3B}$ are either of the following:
(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or
(ii) $R^{3A}$ and $R^{3B}$ taken together are $C_2$-$C_8$ alkylene or $C_1$-$C_8$ heteroalkylene;

$R^{4A}$ and $R^{4B}$ are either of the following:
(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(ii) $R^{4A}$ and $R^{4B}$ taken together are $C_2$-$C_8$ alkylene or $C_1$-$C_8$ heteroalkylene;

$R^5$ is

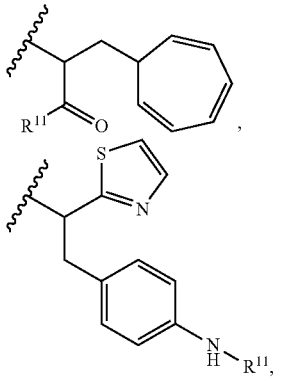

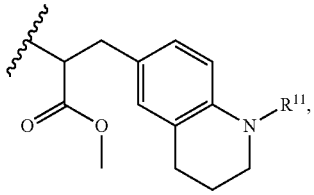

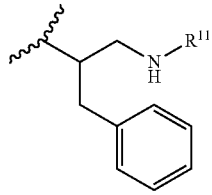

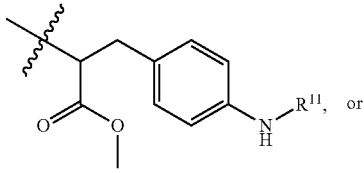

489

-continued

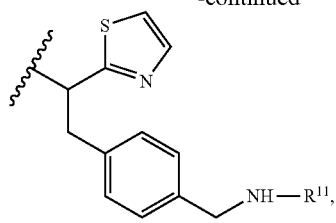

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R)$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

R$^{11}$ is

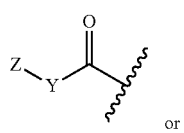

or

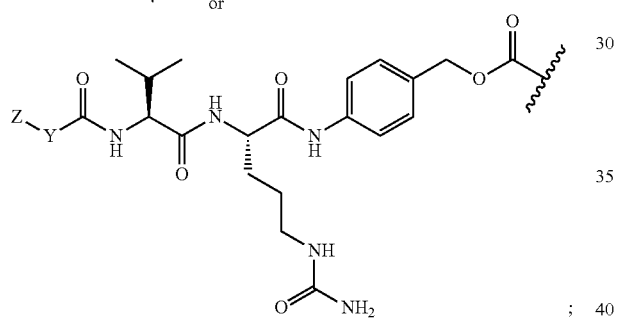

490

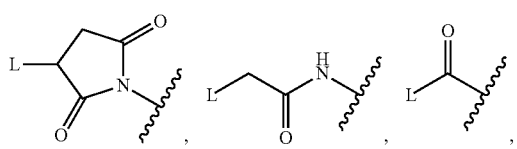

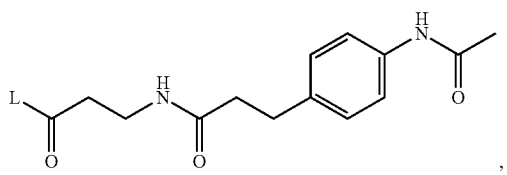

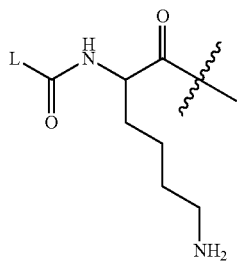

L is an antibody;
X is O or S.

6. A compound of formula IIc:

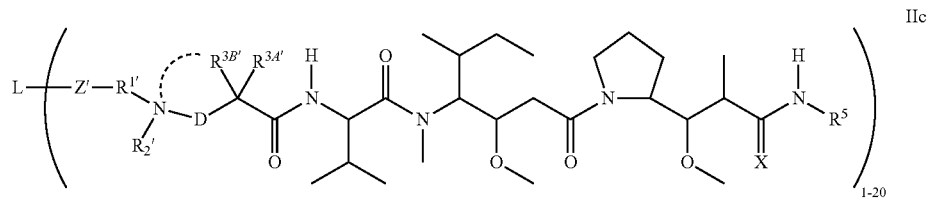

or a pharmaceutically acceptable salt or solvate thereof, wherein, independently for each occurrence, R$^{1'}$ is

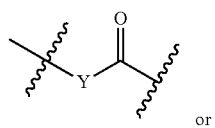

or

Y is —$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z is

-continued

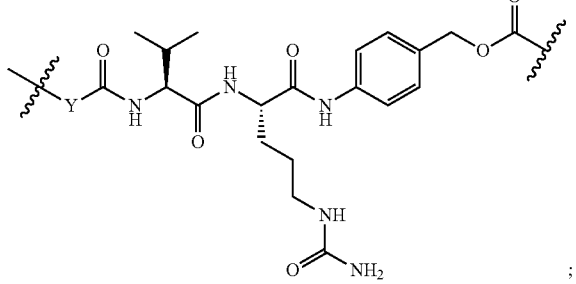

Y is —$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z' is

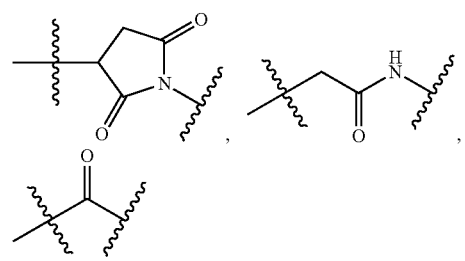

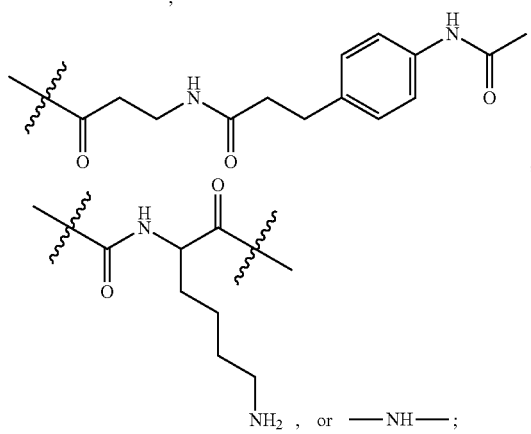

L is an antibody;
D is —$C(R^{4A'})(R^{4B'})$— or is absent;
$R^{2'}$ is hydrogen, $C_1$-$C_8$ alkyl, $C_1$-$C_8$ haloalkyl, or is absent if ⁀⁀⁀ is present;
$R^{3A'}$ and $R^{3B'}$ are either of the following:
(i) $R^{3A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{3B'}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl, or $R^{3B'}$ is $C_2$-$C_4$ alkylene and forms 5-7 member ring as indicated by ⁀⁀⁀; or
(ii) $R^{3A'}$ and $R^{3B'}$ taken together are $C_2$-$C_8$ alkylene or $C_1$-$C_8$ heteroalkylene;
$R^{4A'}$ and $R^{4B'}$ are either of the following:

(i) $R^{4A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{4B'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(ii) $R^{4A'}$ and $R^{4B'}$ taken together are $C_2$-$C_8$ alkylene or $C_1$-$C_8$ heteroalkylene;
$R^5$ is

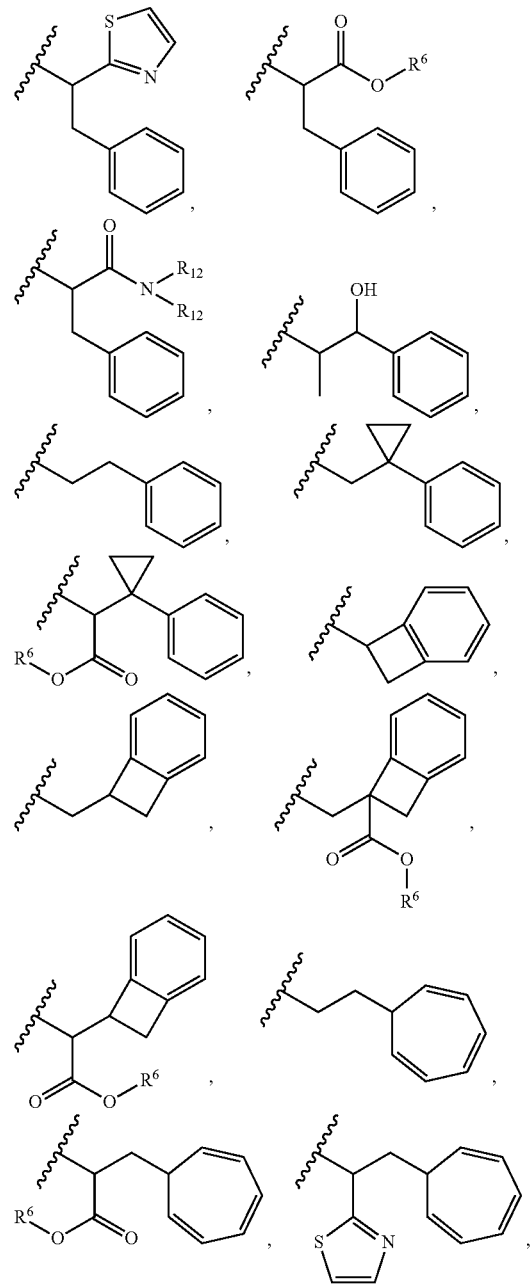

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N₃, —N(R')₂, —CN, —NHC(=NH)NH₂, —NHCONH₂, —S(=O)₂R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

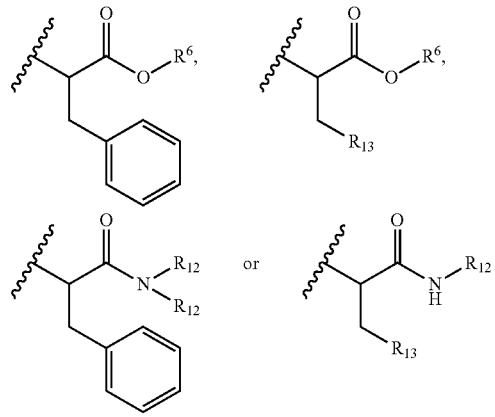

optionally substituted with 1, 2, 3, 4 or 5 groups independently selected from the group consisting of $C_1$-$C_8$ alkyl, —$C_1$-$C_8$ alkyl-N(R')₂, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')₂, —NHC(O)R', —S(O)₂R', —S(O)R', —OH, halogen, —N₃, —N(R')₂, —CN, —NHC(=NH)NH₂, —NHCONH₂, —S(=O)₂R', —SR' and arylene-R', wherein each R' is independently selected from the group consisting of hydrogen, $C_1$-$C_8$ alkyl, $C_1$-$C_8$ heterocyclyl, $C_1$-$C_{10}$ alkylene-$C_3$-$C_8$ heterocyclyl and aryl, or two R' can, together with the nitrogen to which they are attached, form a $C_1$-$C_{10}$ heterocyclyl;

$R^6$ is hydrogen, —$C_1$-$C_8$ alkyl, —$C_2$-$C_8$ alkenyl, —$C_2$-$C_8$ alkynyl or —$C_1$-$C_8$ haloalkyl;

$R^{12}$ is hydrogen, $C_1$-$C_4$ alkyl, $C_1$-$C_{10}$ heterocyclyl or $C_6$-$C_{14}$ aryl;

$R^{13}$ is $C_1$-$C_{10}$ heterocyclyl; and

X is O or S;

provided that when $R^{3A}$ is hydrogen X is S.

7. A compound of formula IIIc:

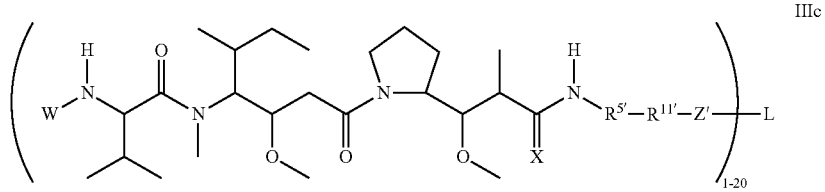

IIIc or a pharmaceutically acceptable salt or solvate thereof, wherein, independently for each occurrence,

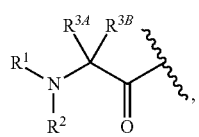 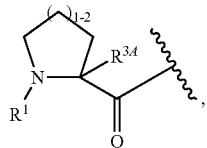

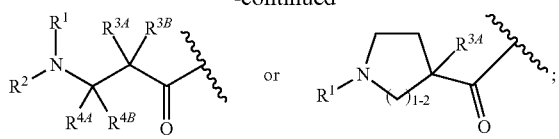

W is $R^1$ is hydrogen, $C_1$-$C_8$ alkyl or $C_1$-$C_8$ haloalkyl;

$R^2$ is hydrogen, $C_1$-$C_8$ alkyl or $C_1$-$C_8$ haloalkyl;

$R^{3A}$ and $R^{3B}$ are either of the following:

(i) $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or (ii) $R^{3A}$ and $R^{3B}$ taken together are $C_2$-$C_8$ alkylene or $C_1$-$C_8$ heteroalkylene;

$R^{4A}$ and $R^{4B}$ are either of the following:

(i) $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A}$ and $R^{4B}$ taken together are $C_2$-$C_8$ alkylene or $C_1$-$C_8$ heteroalkylene;

$R^5$ is

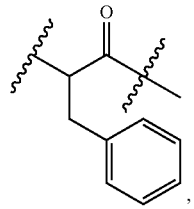 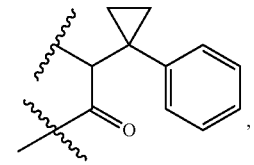

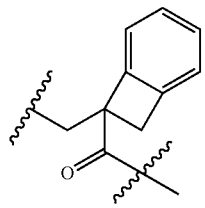 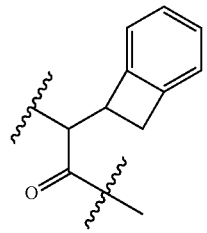

-continued

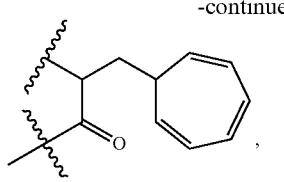

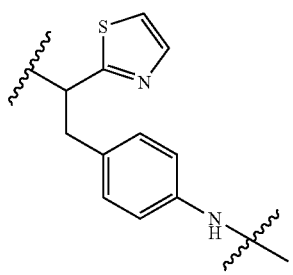

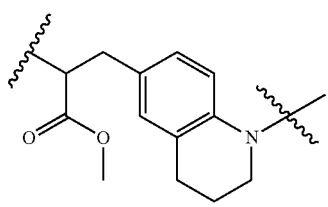

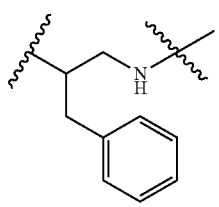

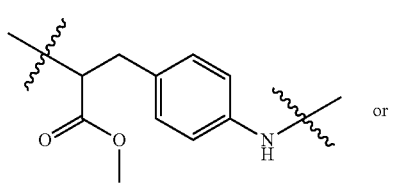 or

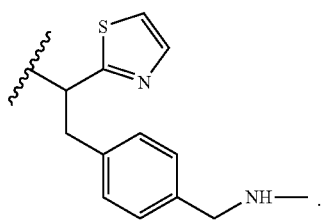 [SMILES: *C(Cc1ccc(CNC)cc1)c1nccs1]

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;

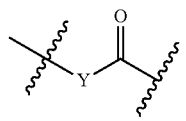 or

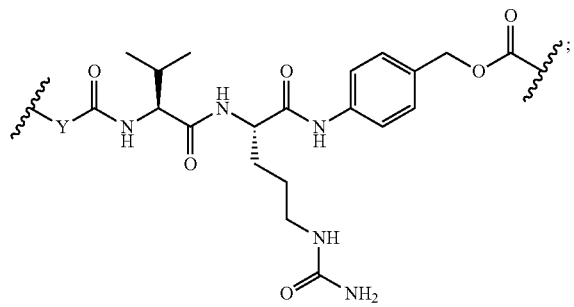;

Y is is —$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-;

Z' is

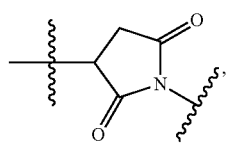, 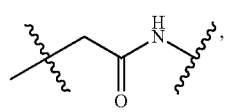,

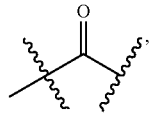,

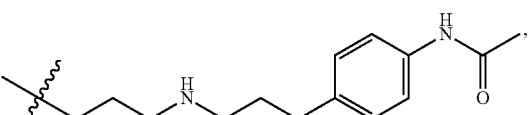

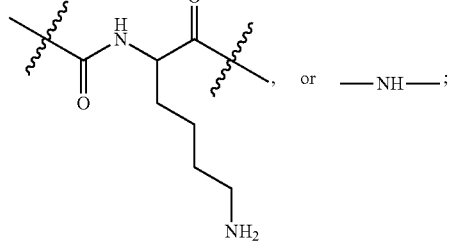, or —NH—;

L is an antibody;

X is O or S.

8. A compound of formula IId:

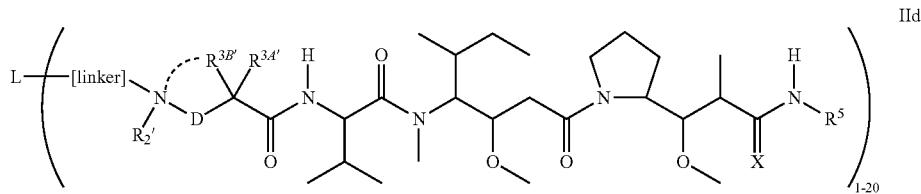

or a pharmaceutically acceptable salt or solvate thereof, wherein, independently for each occurrence, L is an antibody;

[linker] is a divalent linker;

D is —C($R^{4A'}$)($R^{4B'}$)— or is absent;

$R^{2'}$ is hydrogen, $C_1$-$C_8$ alkyl, $C_1$-$C_8$ haloalkyl, or is absent if ⁀⁀⁀ is present;

$R^{3A'}$ and $R^{B'}$ are either of the following:

(i) $R^{3A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and $R^{3B'}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl, or $R^{3B'}$ is $C_2$-$C_4$ alkylene and forms 5-7 member ring as indicated by ⁀⁀⁀ ; or (ii) $R^{3A'}$ and $R^{3B'}$ taken together are $C_2$-$C_8$ alkylene or $C_1$-$C_8$ heteroalkylene;

$R^{4A'}$ and $R^{4B'}$ are either of the following:

(i) $R^{4A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) $R^{4A'}$ and $R^{4B'}$ taken together are $C_2$-$C_8$ alkylene or $C_1$-$C_8$ heteroalkylene;

$R^5$ is

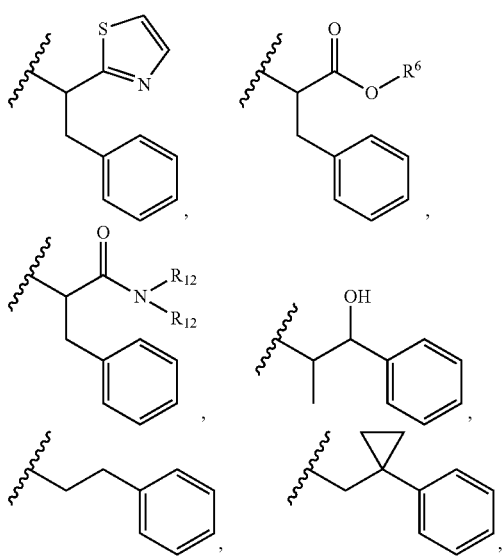

-continued

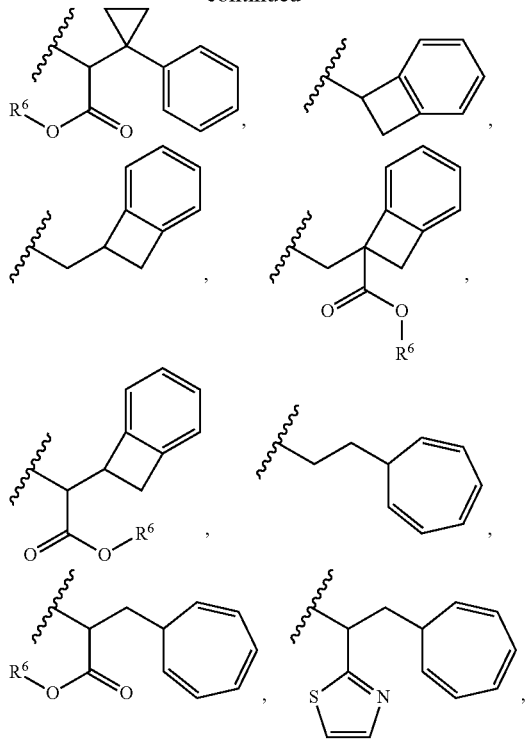

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;

or $R^5$ is

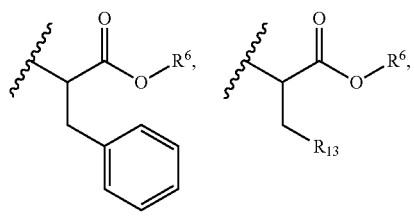

-continued

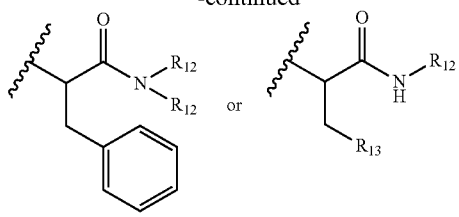

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

R$^6$ is hydrogen, —$C_1$-$C_8$ alkyl, —$C_2$-$C_8$ alkenyl, —$C_2$-$C_8$ alkynyl or —$C_1$-$C_8$ haloalkyl;

R$^{12}$ is hydrogen, $C_1$-$C_4$ alkyl, $C_1$-$C_{10}$ heterocyclyl or $C_6$-$C_{14}$ aryl;

R$^{13}$ is $C_1$-$C_{10}$ heterocyclyl; and

X is O or S;

provided that when R$^{3A}$ is hydrogen X is S.

9. A compound of formula IIId:

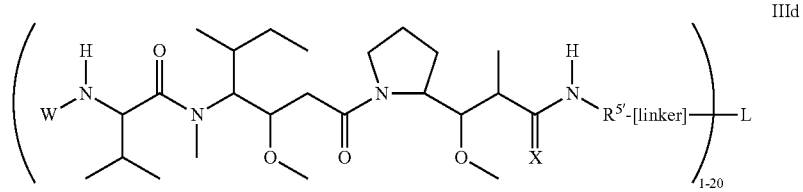

IIId or a pharmaceutically acceptable salt or solvate thereof, wherein, independently for each occurrence, W is

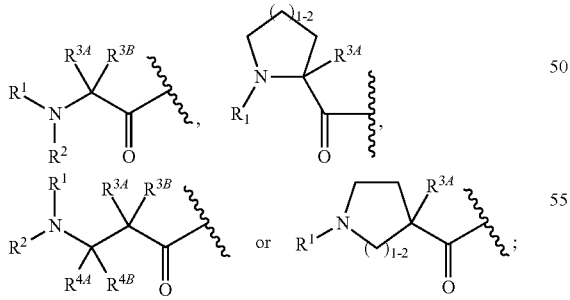

R$^1$ is hydrogen, $C_1$-$C_8$ alkyl or $C_1$-$C_8$ haloalkyl;

R$^2$ is hydrogen, $C_1$-$C_8$ alkyl or $C_1$-$C_8$ haloalkyl;

R$^{3A}$ and R$^{3B}$ are either of the following:

(i) R$^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and R$^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl; or (ii) R$^{3A}$ and R$^{3B}$ taken together are $C_2$-$C_8$ alkylene or $C_1$-$C_8$ heteroalkylene;

R$^{4A}$ and R$^{4B}$ are either of the following:

(i) R$^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and R$^{4B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or (ii) R$^{4A}$ and R$^{4B}$ taken together are $C_2$-$C_8$ alkylene or $C_1$-$C_8$ heteroalkylene;

R$^5$ is

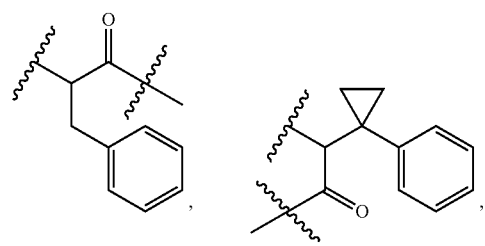

-continued

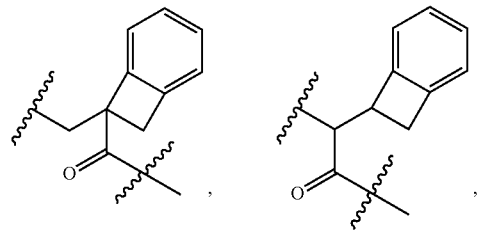

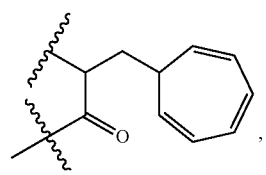

-continued

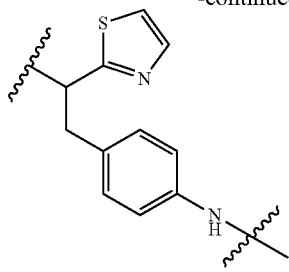

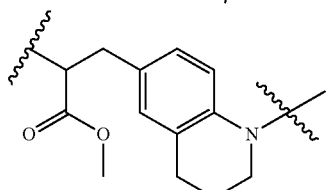

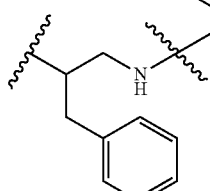

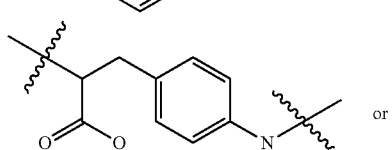 or

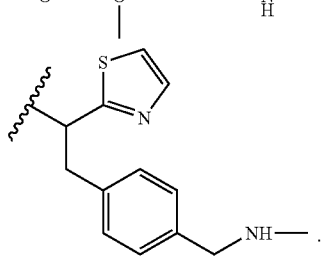

optionally substituted with 1, 2, 3, 4 or 5 groups independently selected from the group consisting of $C_1$-$C_8$ alkyl, —O—($C_1$-$C_8$ alkyl), —C(O)R', —OC(O)R', —C(O)OR', —C(O)NH$_2$, —C(O)NHR', —C(O)N(R)$_2$, —NHC(O)R', —S(O)$_2$R', —S(O)R', —OH, halogen, —N$_3$, —NH$_2$, —NH(R'), —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl;
[linker] is a divalent linker;
L is an antibody;
X is O or S.

10. The compound, salt or solvate of claim 1, wherein W is

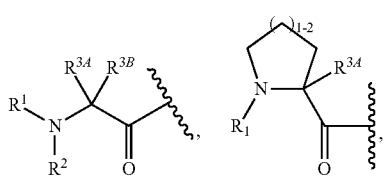

-continued

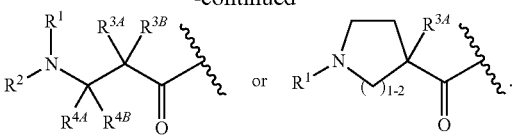 or

11. The compound, salt or solvate of claim 1, wherein $R^1$ is hydrogen, $C_1$-$C_8$ alkyl or $C_1$-$C_8$ haloalkyl.

12. The compound, salt or solvate of claim 2, wherein $R^1$ is

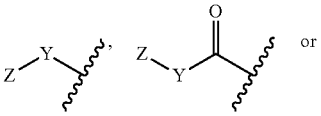 or

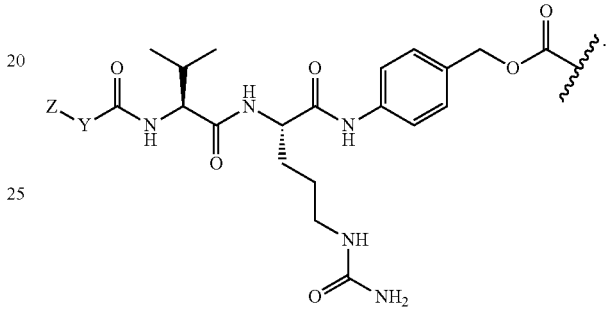

13. The compound, salt or solvate of claim 4 wherein $R^1$ is

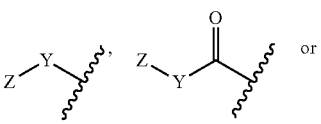 or

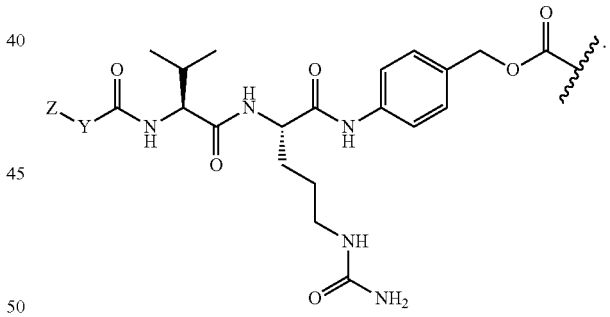

14. The compound, salt or solvate of claim 1, wherein $R^{3A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{3B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen.

15. The compound, salt or solvate of claim 1, wherein $R^{3A}$ and $R^{3B}$ taken together are $C_2$-$C_8$ alkylene or $C_1$-$C_8$ heteroalkylene.

16. The compound, salt or solvate of claim 1, wherein $R^{4A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and $R^{4B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or $R^{4A}$ and $R^{4B}$ taken together are $C_2$-$C_8$ alkylene or $C_1$-$C_8$ heteroalkylene.

17. The compound, salt or solvate of claim 6, wherein $R^{3A'}$ and $R^{3B'}$ are defined as either of the following:
  (i) $R^{3A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
  $R^{3B'}$ $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen or aralkyl, or $R^{3B'}$ is $C_2$-$C_4$ alkylene and forms 5-7 member ring as indicated by ⌒; or
  (ii) $R^{3A'}$ and $R^{3B'}$ taken together are $C_2$-$C_8$ alkylene or $C_1$-$C_8$ heteroalkylene.

18. The compound, salt or solvate of claim 6, wherein $R^{4A'}$ and $R^{4B'}$ are defined as either of the following:
  (i) $R^{4A'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
  $R^{4B'}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
  (ii) $R^{4A'}$ and $R^{4B'}$ taken together are $C_2$-$C_8$ alkylene or $C_1$-$C_8$ heteroalkylene.

19. The compound, salt or solvate of claim 1, wherein $R^5$ is

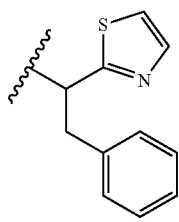 , 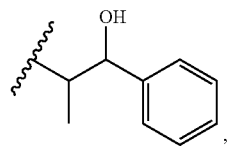 ,

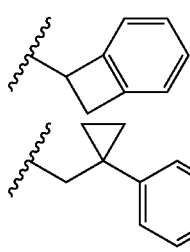 , 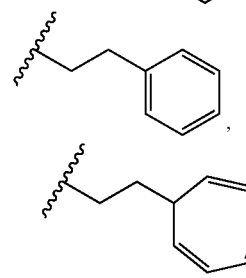 ,

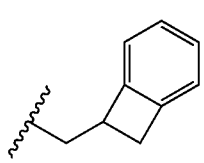 , 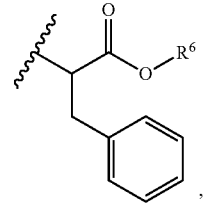 ,

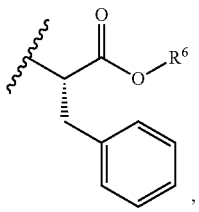 , 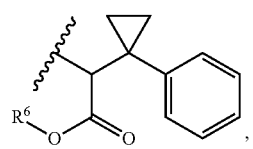 ,

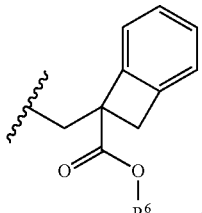 , 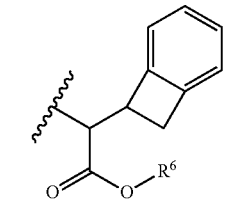 ,

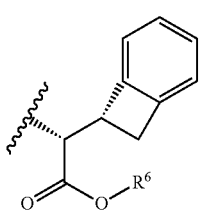 or 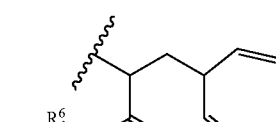 .

20. The compound, salt or solvate of claim 2, wherein Y is
—$C_2$-$C_{20}$ alkylene-, —$C_2$-$C_{20}$ heteroalkylene-, —$C_3$-$C_8$ carbocyclo-, -arylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$heterocyclo)-, or —($C_3$-$C_8$ heterocyclo)-$C_1$-$C_{10}$alkylene-.

21. The compound, salt or solvate of claim 5, wherein antibody is selected from trastuzumab, oregovomab, edrecolomab, cetuximab, a humanized monoclonal antibody to the vitronectin receptor ($\alpha_v\beta_3$); alemtuzumab; a humanized anti-HLA-DR antibody for the treatment of non-Hodgkin's lymphoma; 131I Lym-1; a murine anti-HLA-Dr10 antibody for the treatment of non-Hodgkin's lymphoma; a humanized anti-CD2 mAb for the treatment of Hodgkin's Disease or non-Hodgkin's lymphoma; labetuzumab; bevacizumab; ibritumomab tiuxetan; ofatumumab; panitumumab; rituximab; tositumomab; ipilimumab; gemtuzumab; an anti-IL13 antibody; and an anti-Notch antibody.

22. A compound, or a pharmaceutically acceptable salt or solvate thereof, selected from:

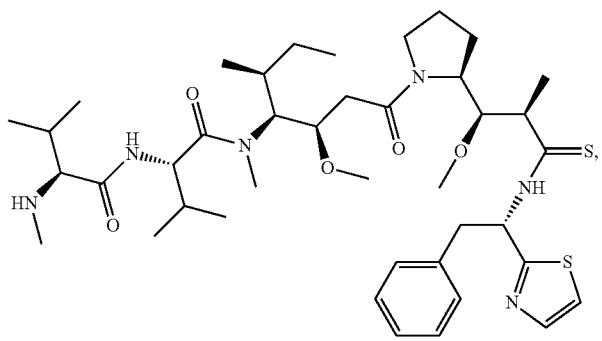

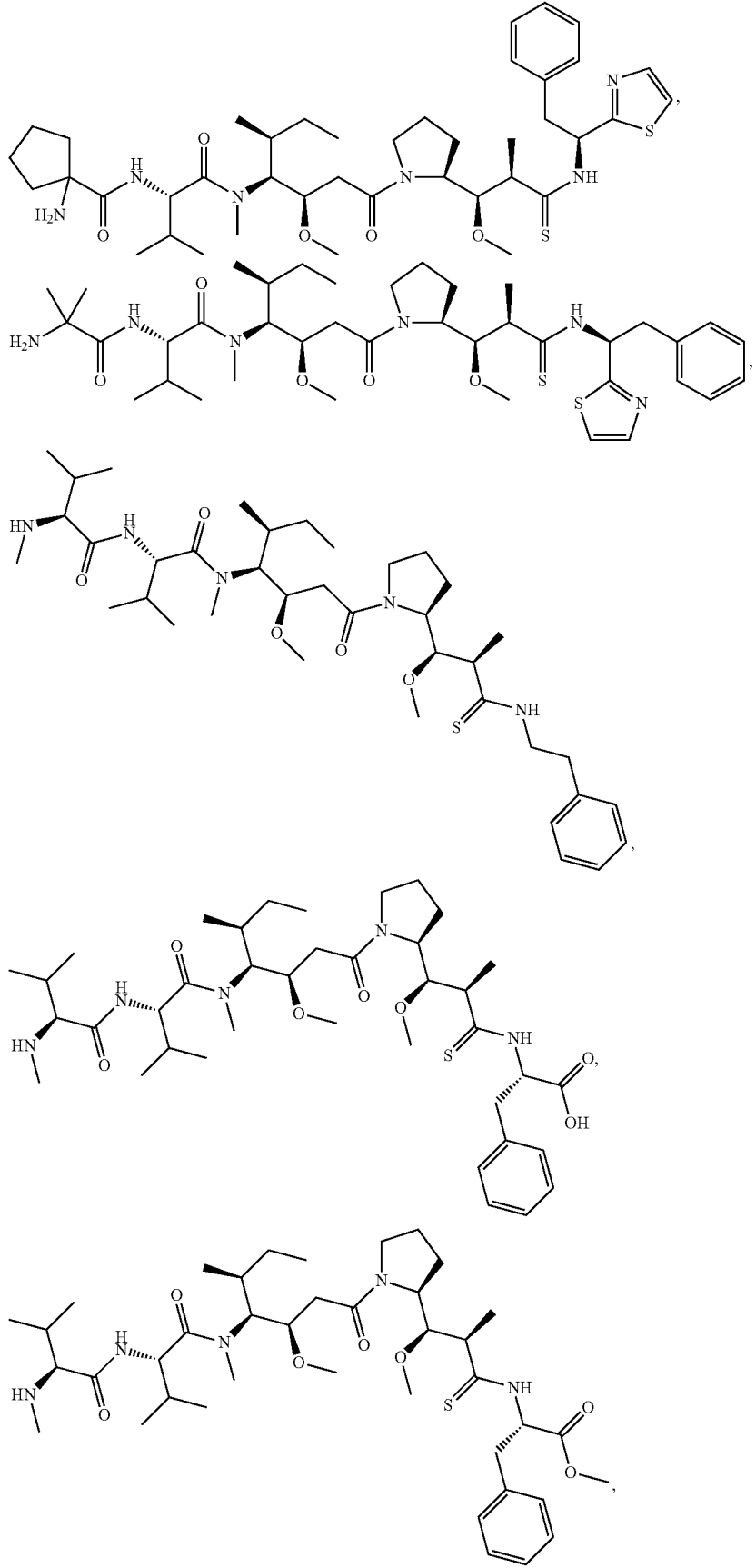

-continued
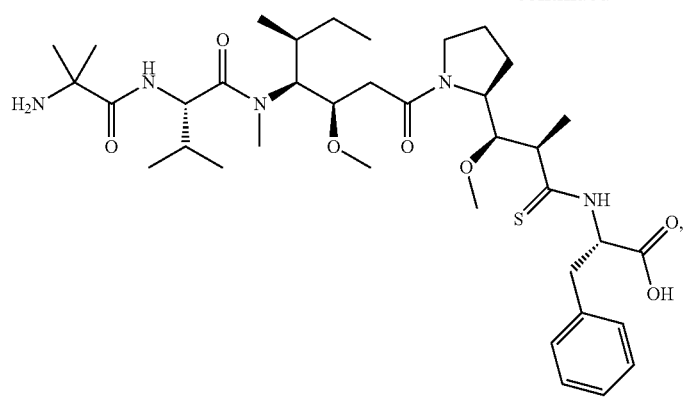
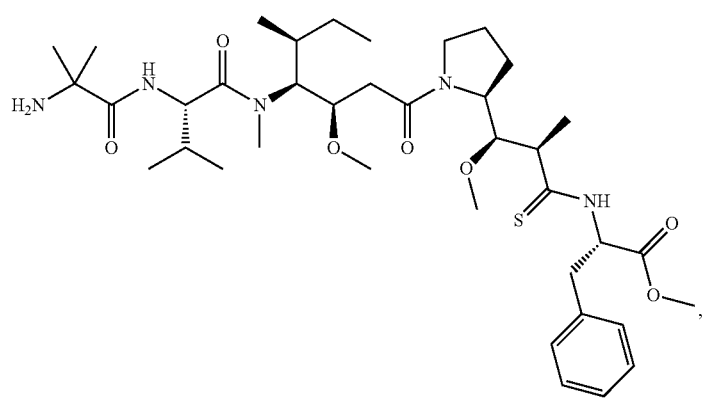
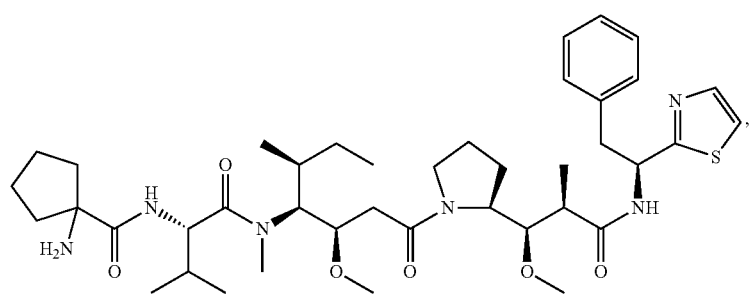
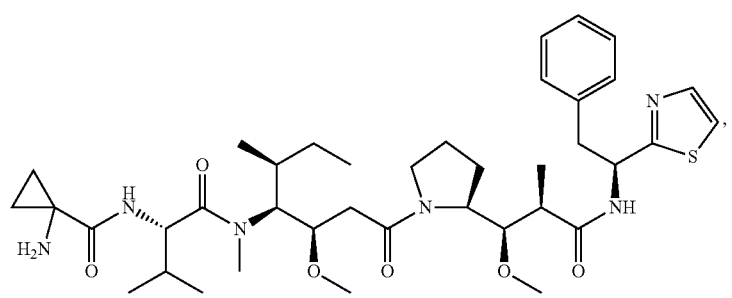
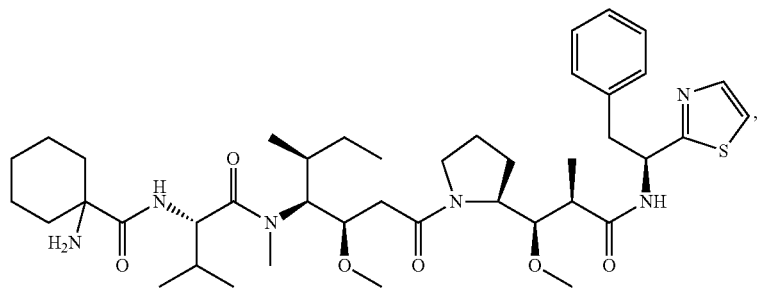

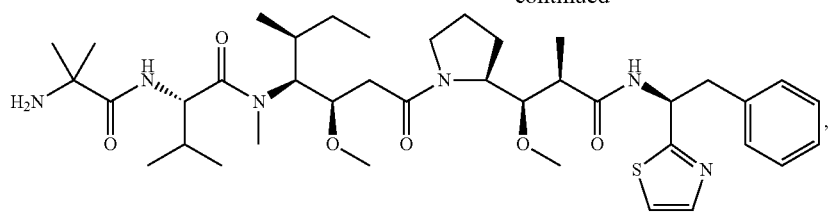
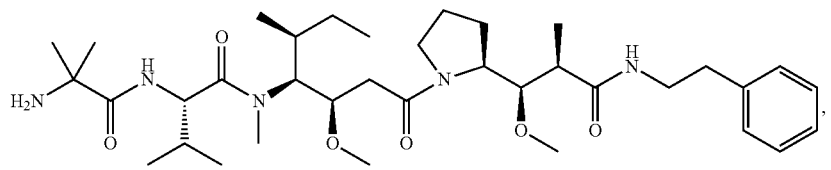
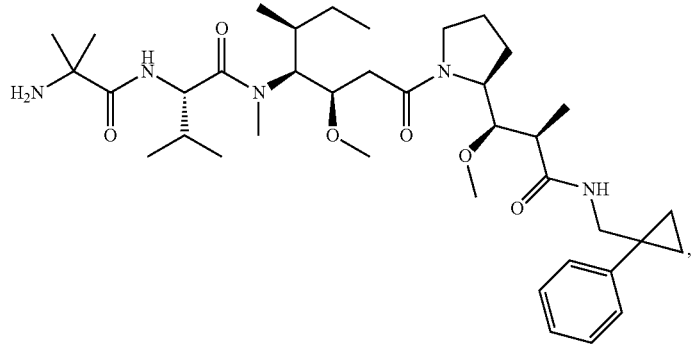
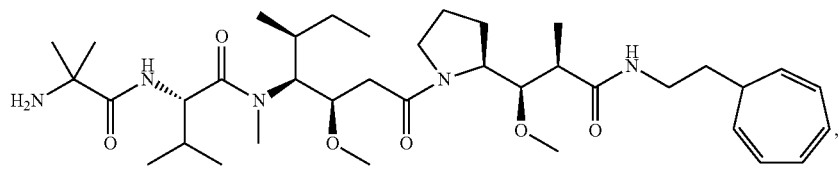
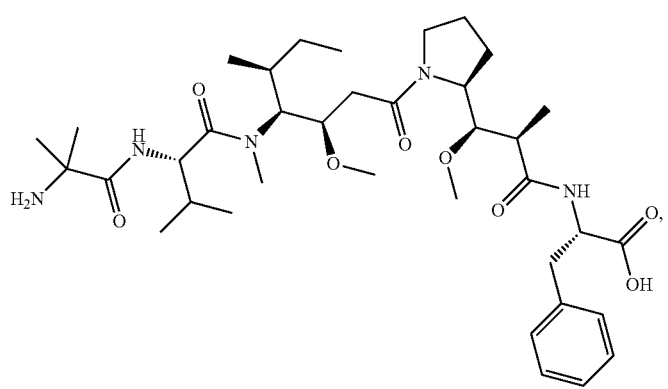
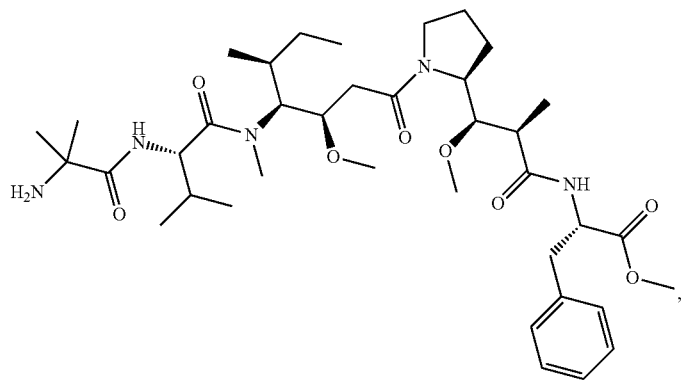

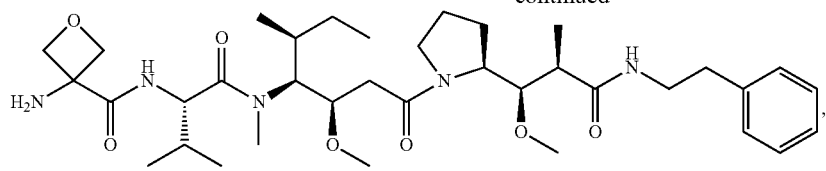
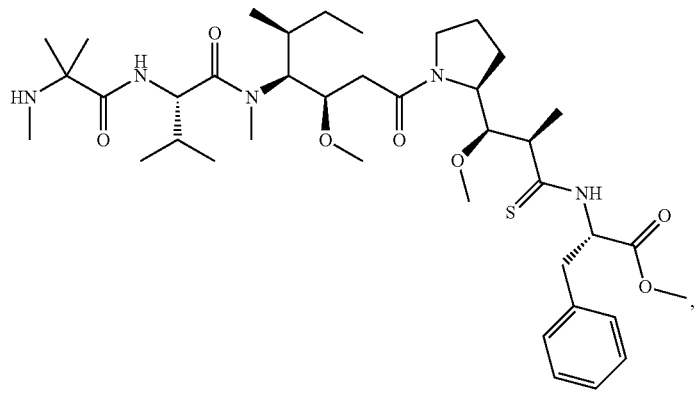
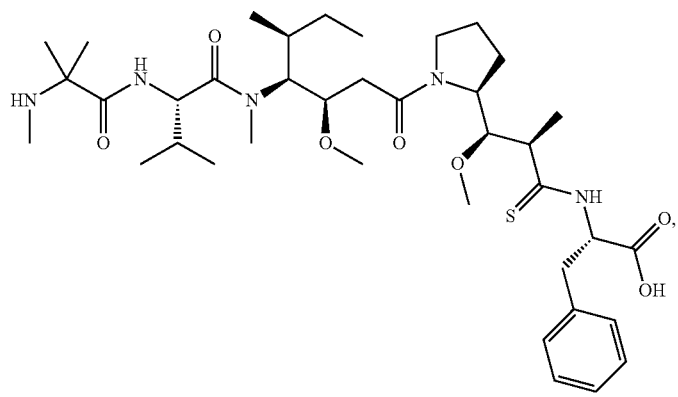
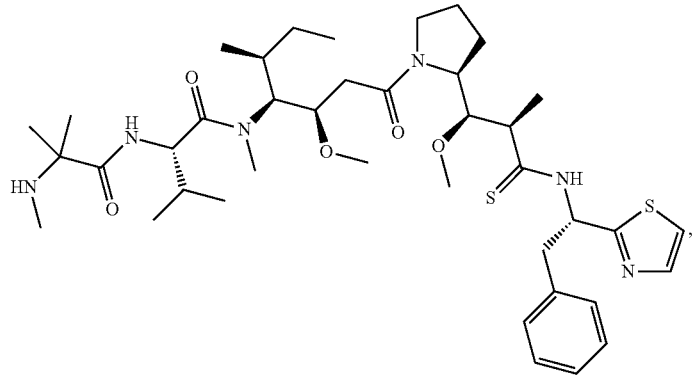
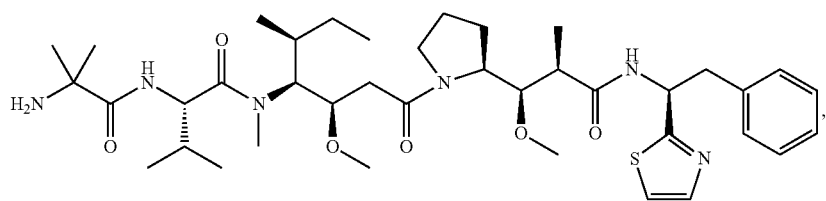

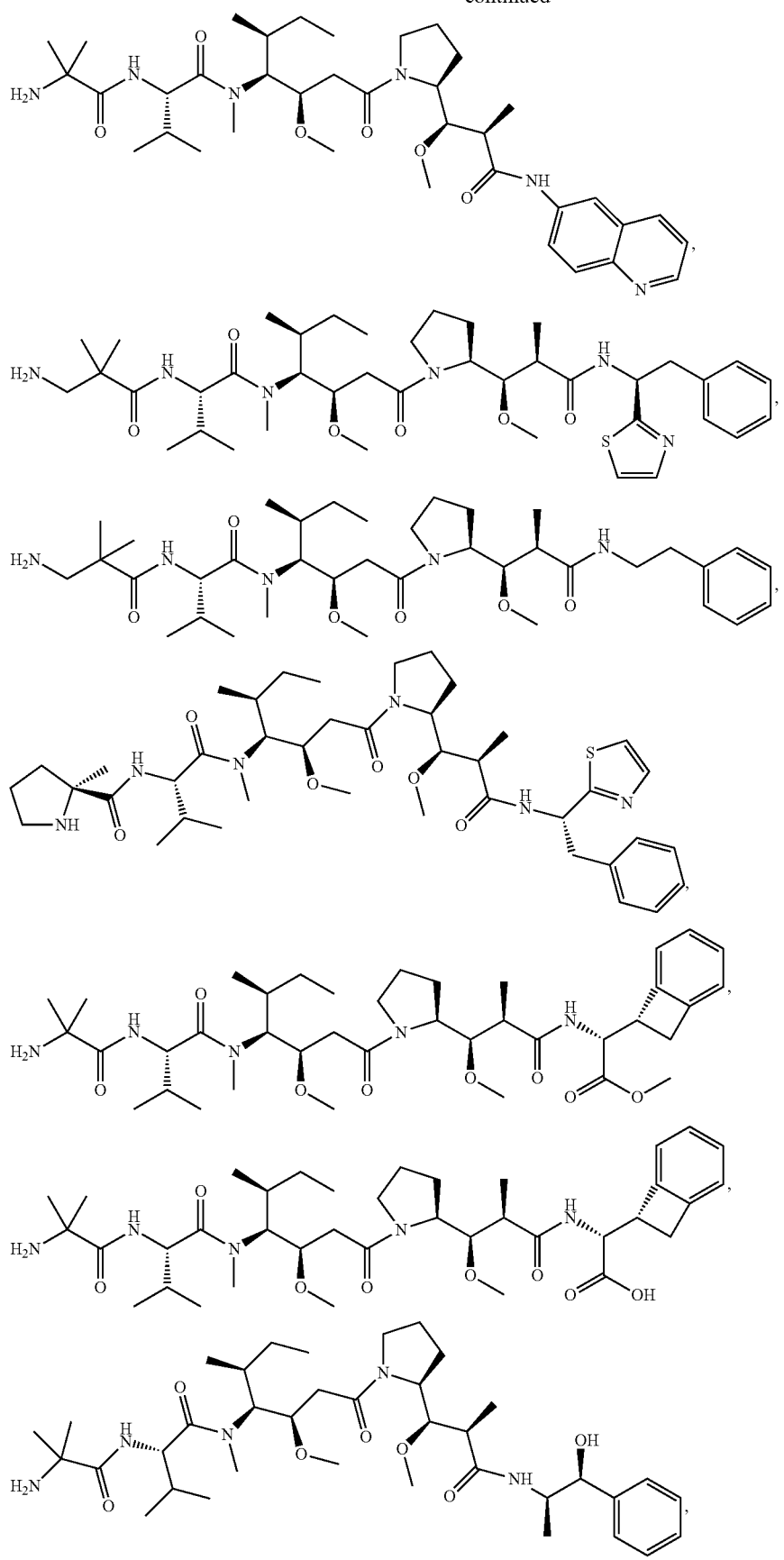

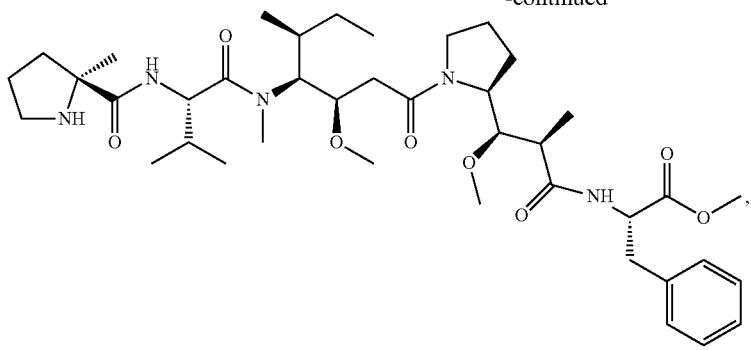
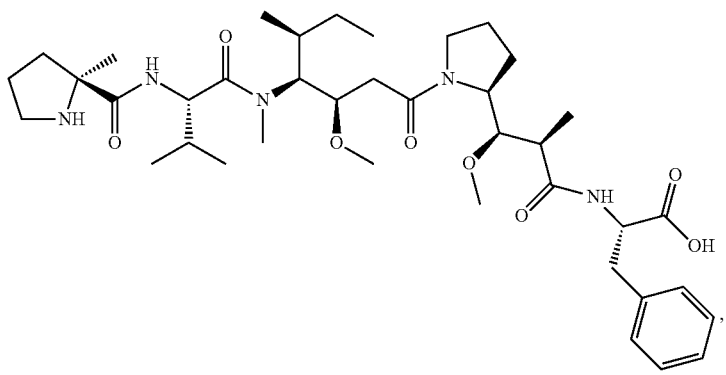
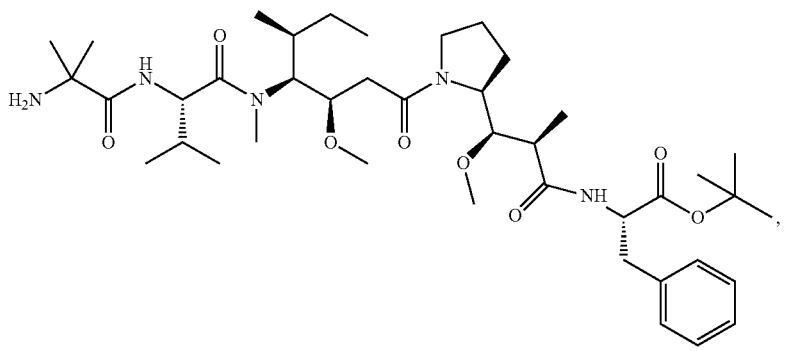
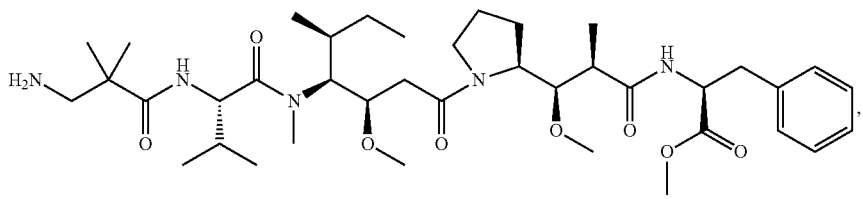
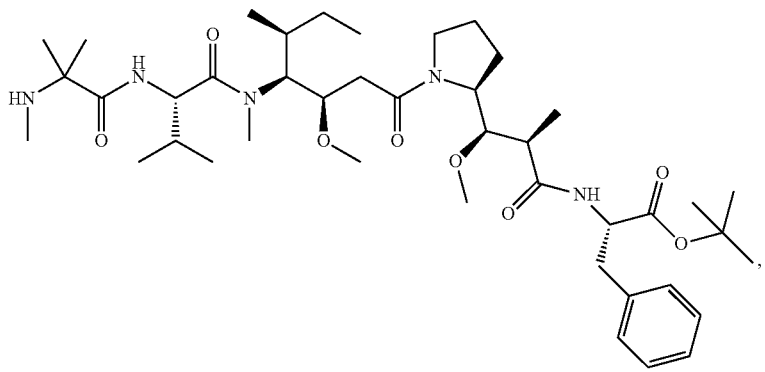

-continued
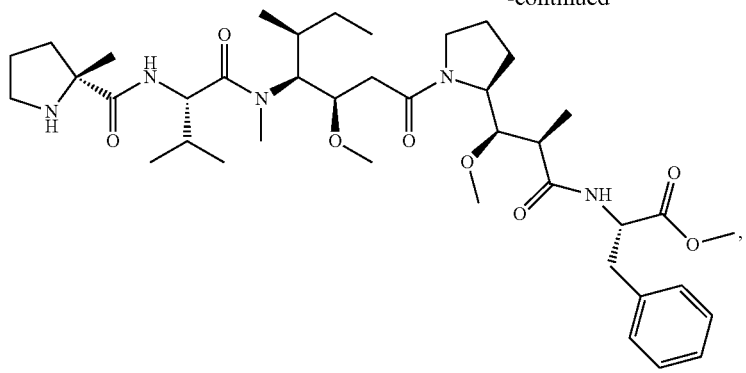
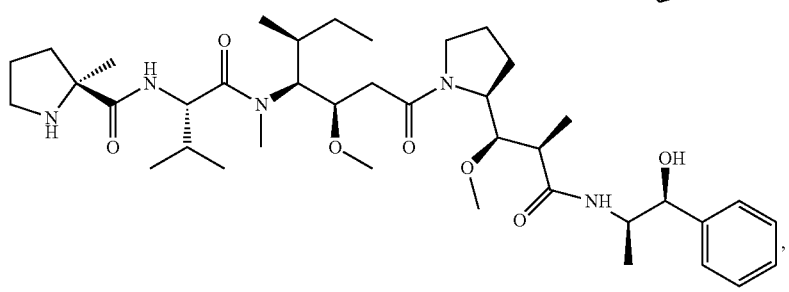
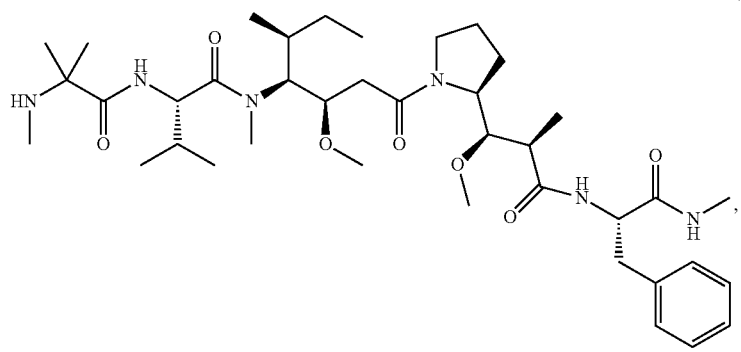
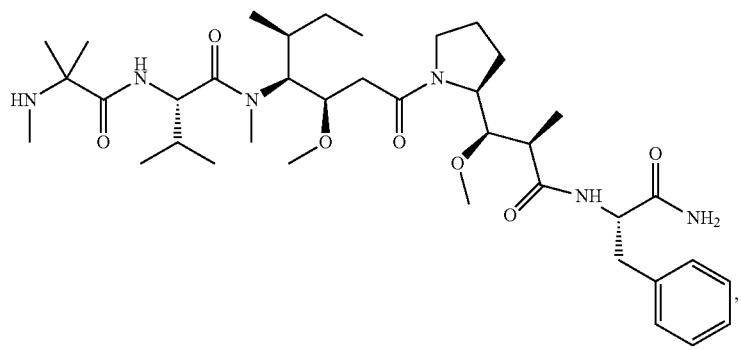
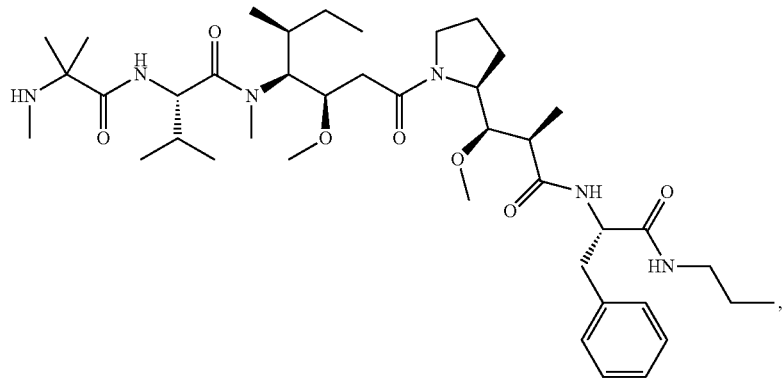

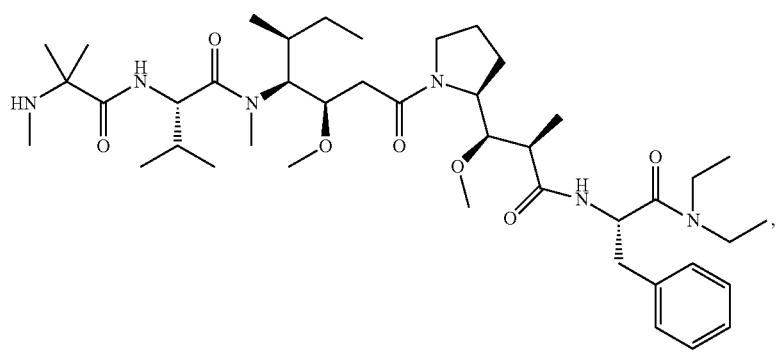
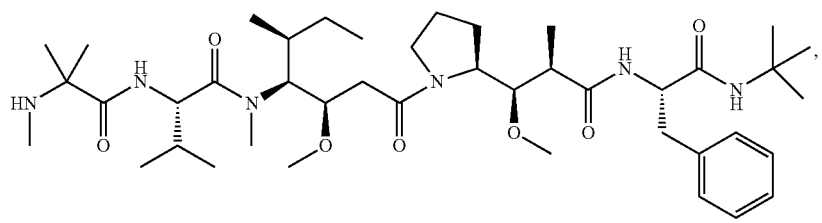
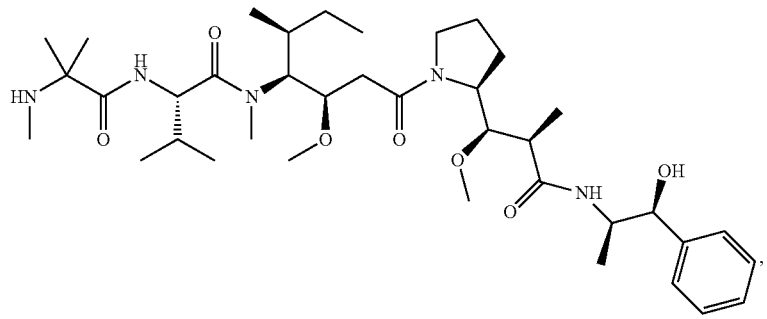
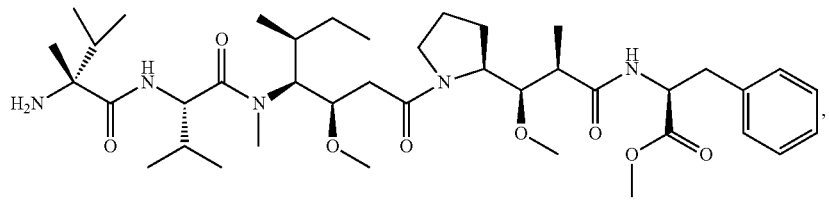
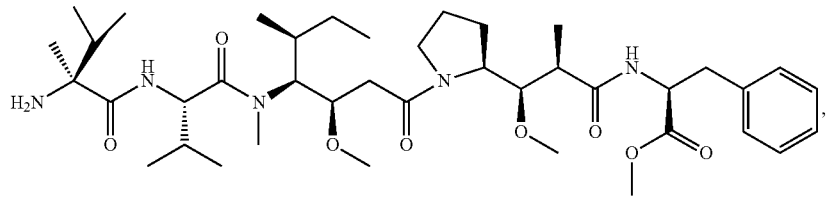
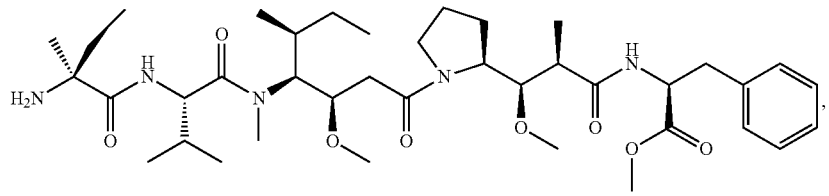
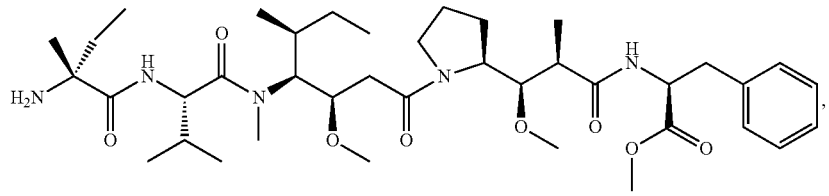

-continued
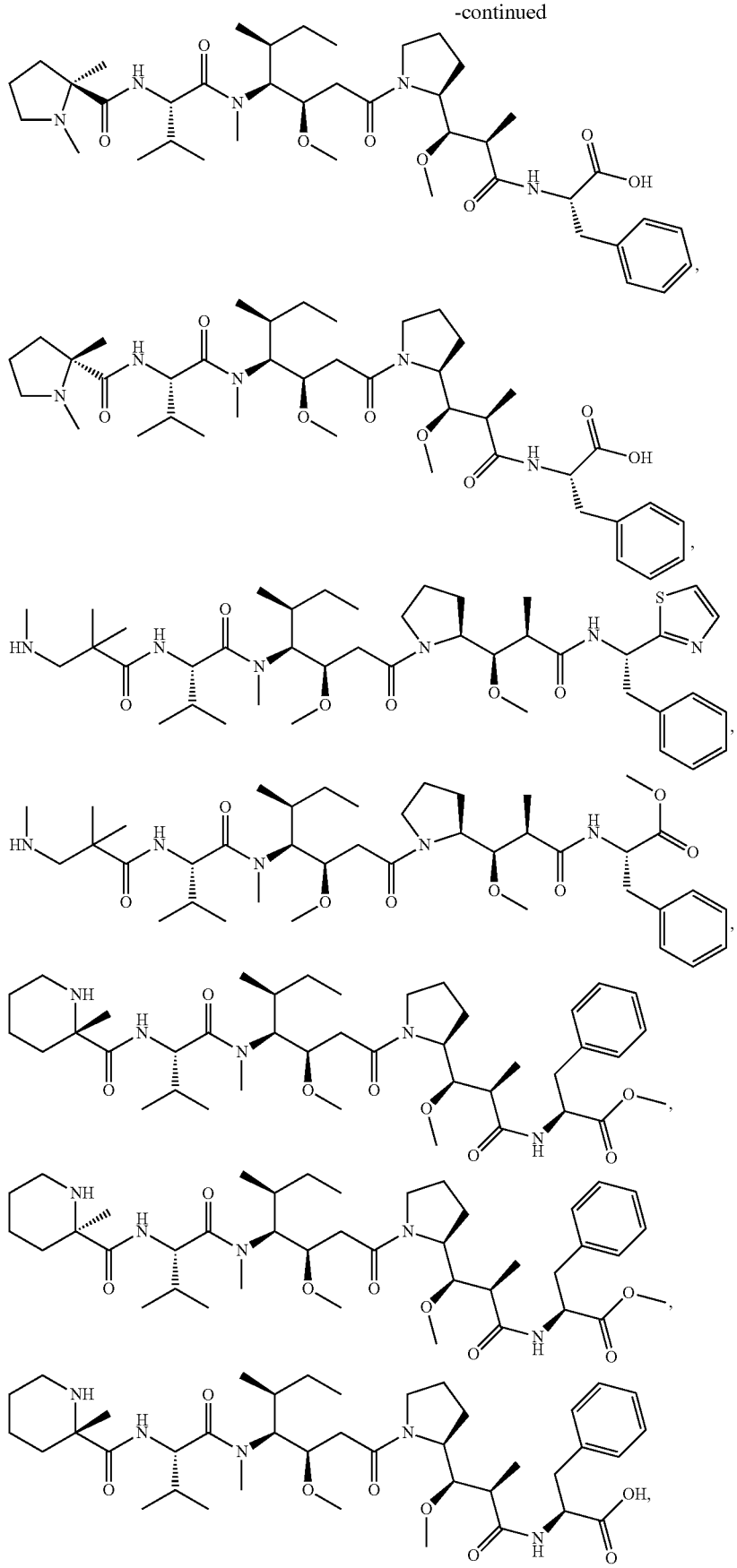

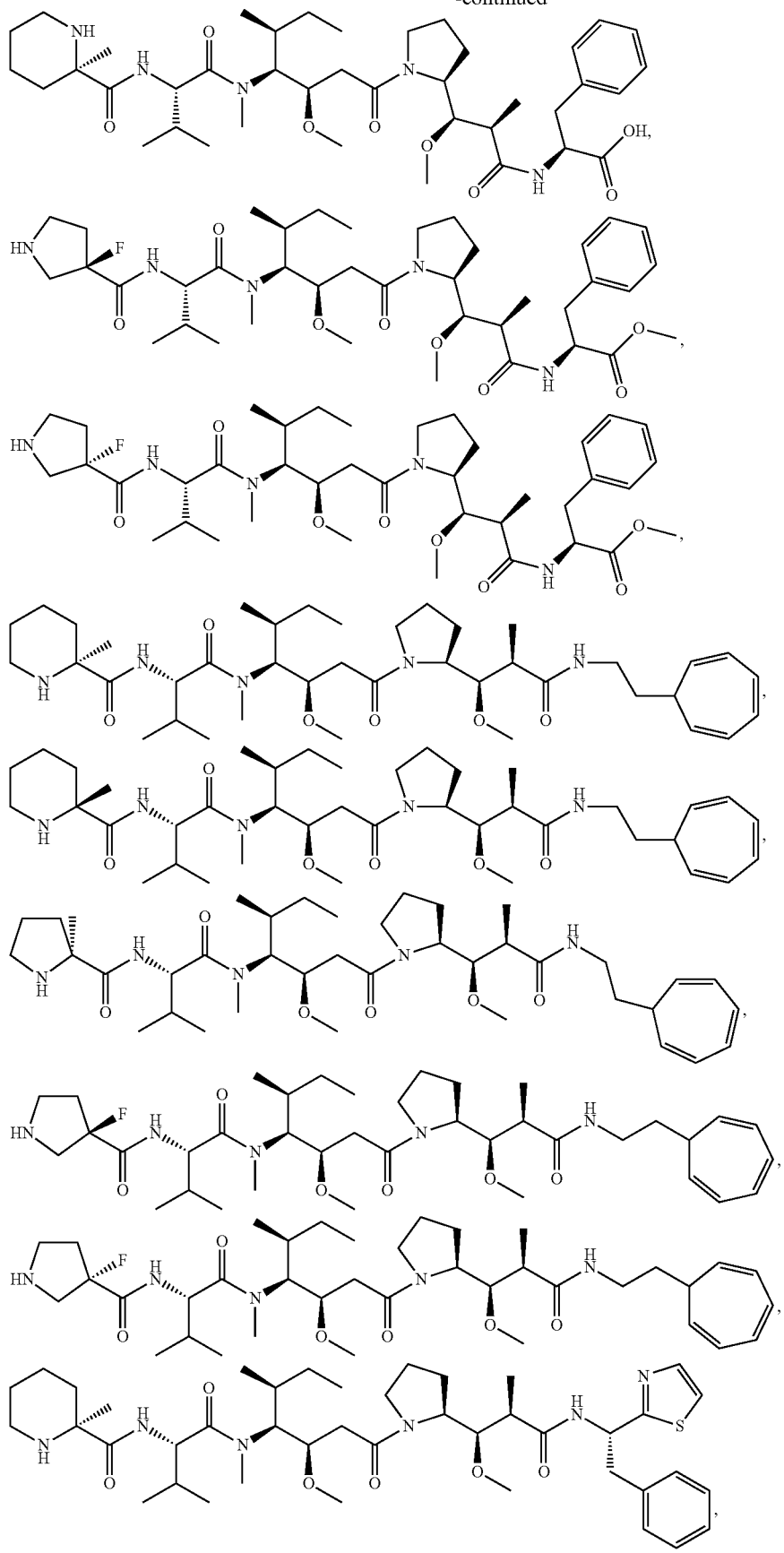

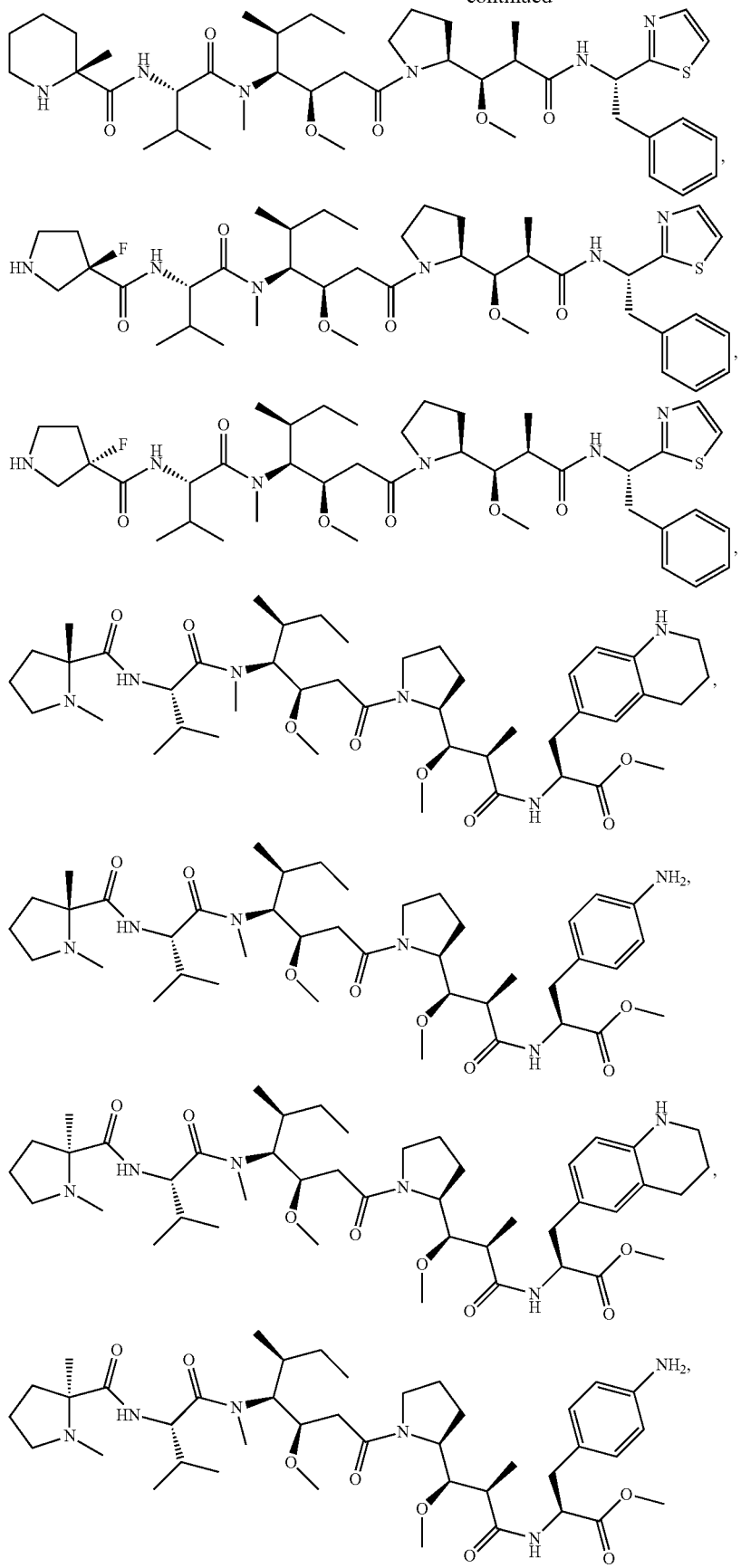

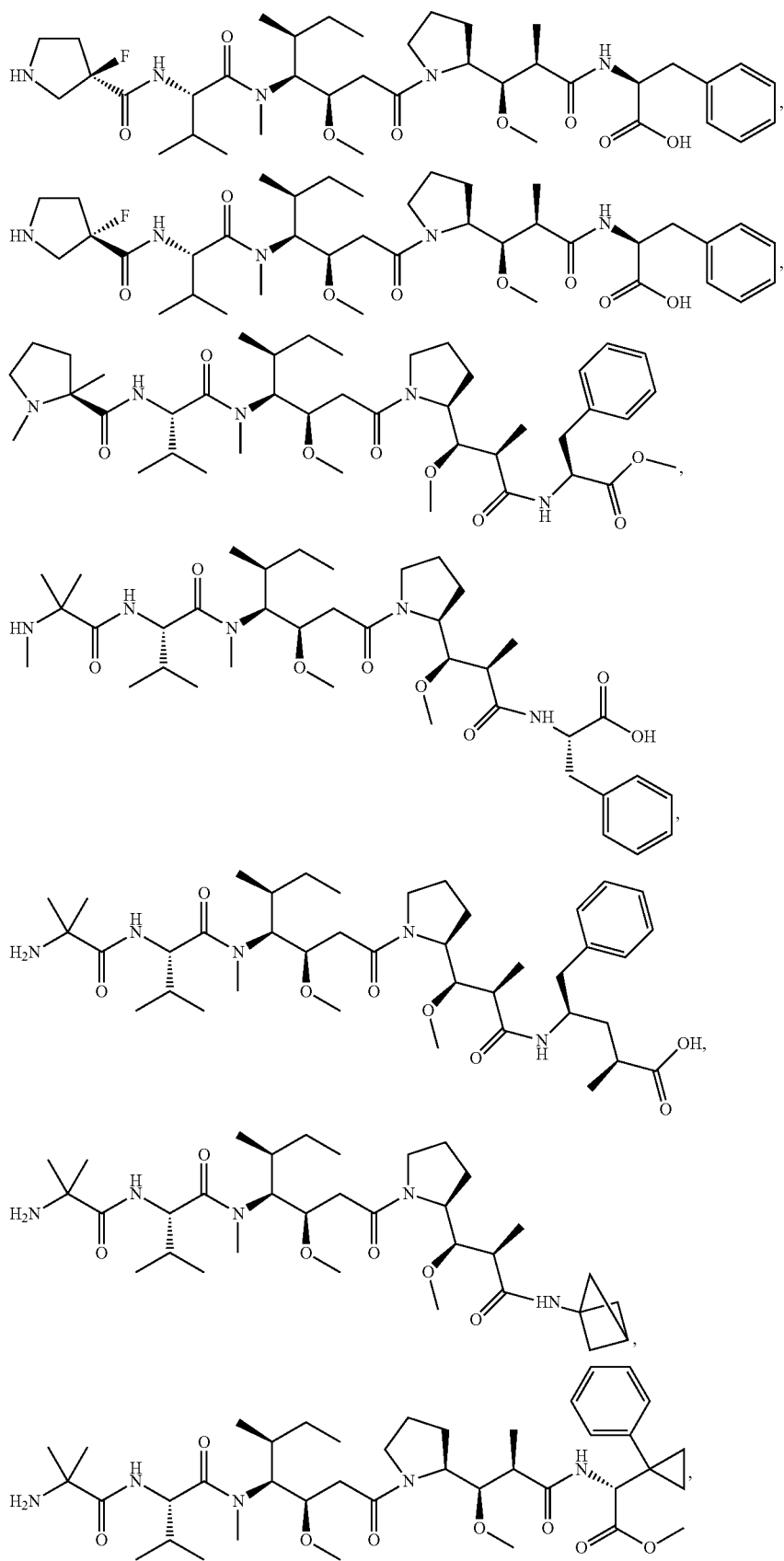

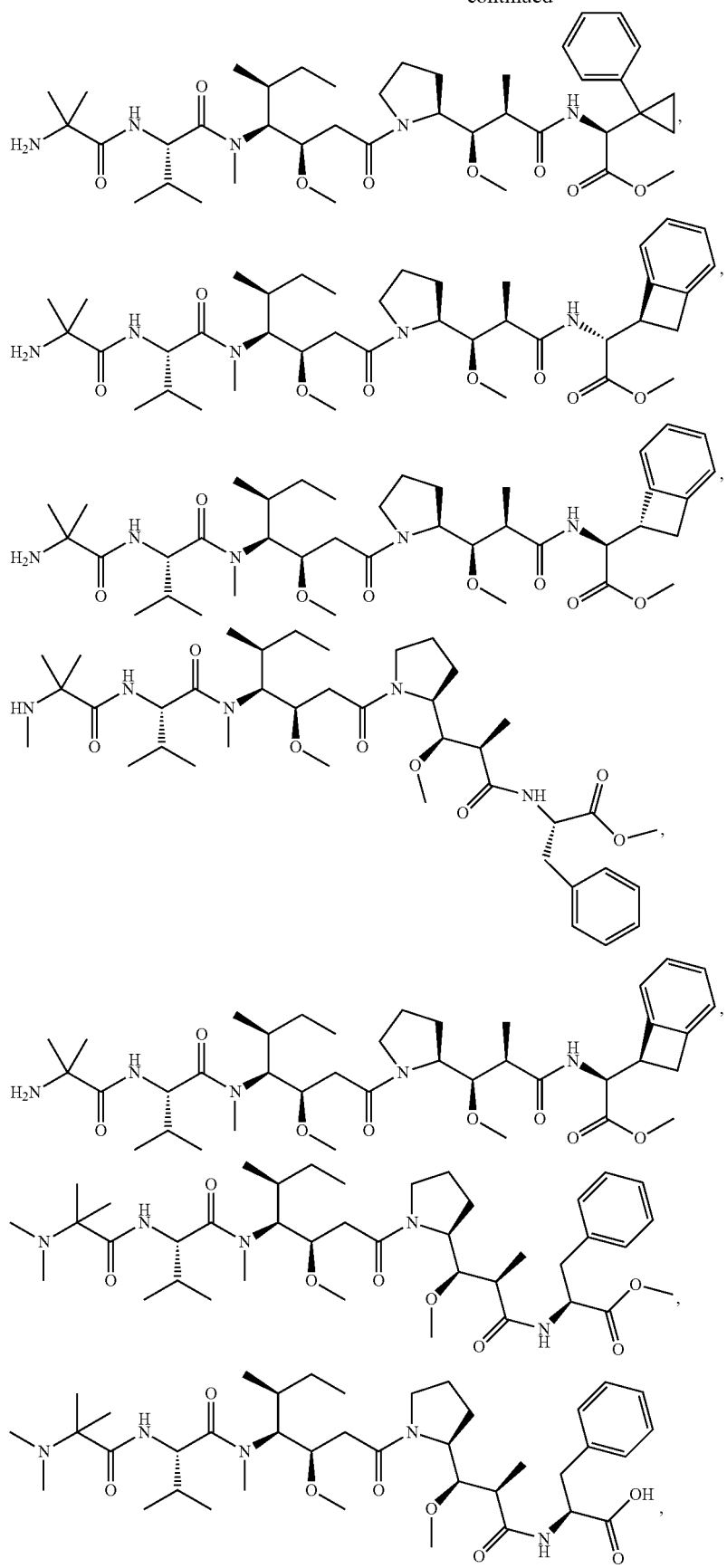

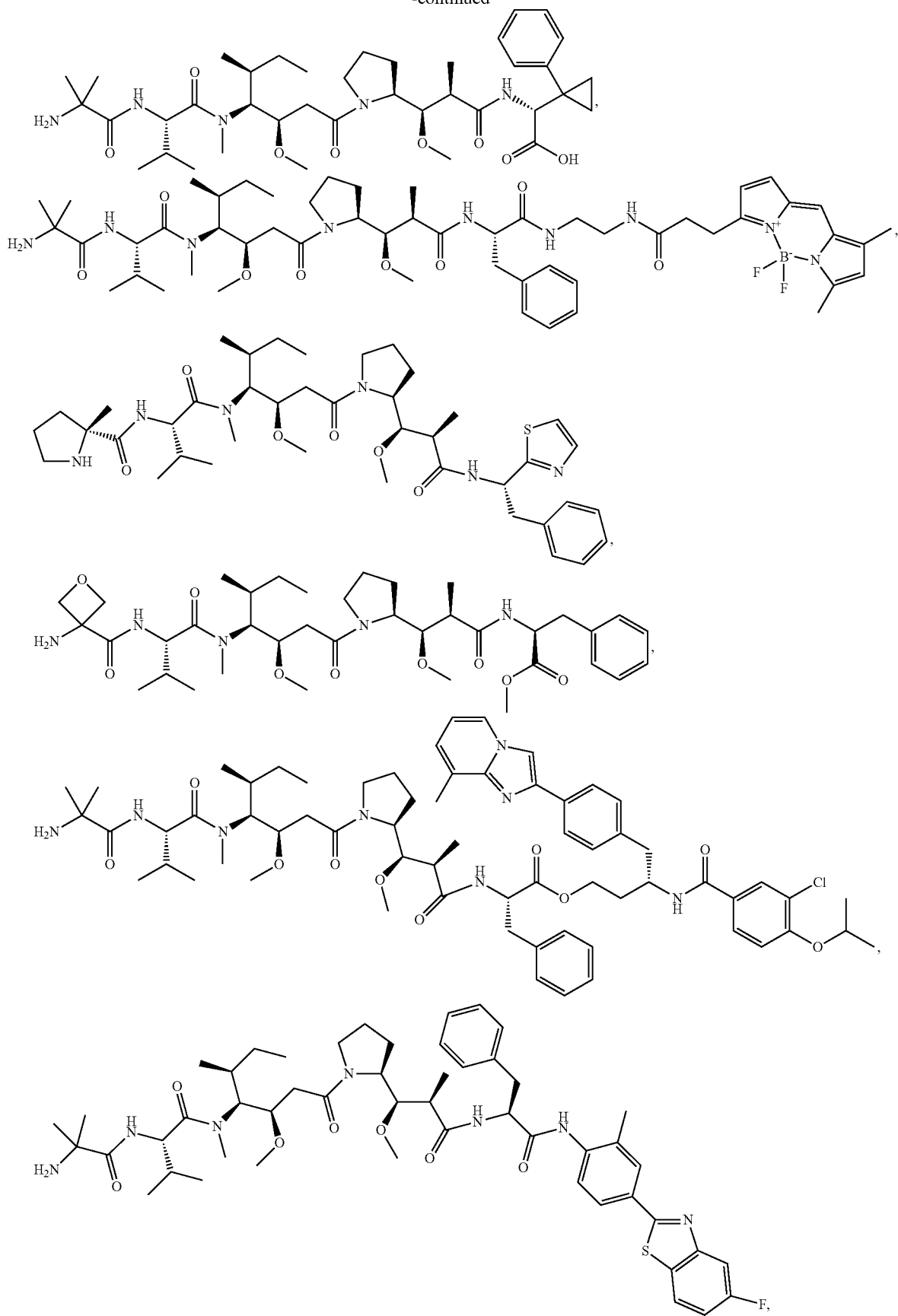

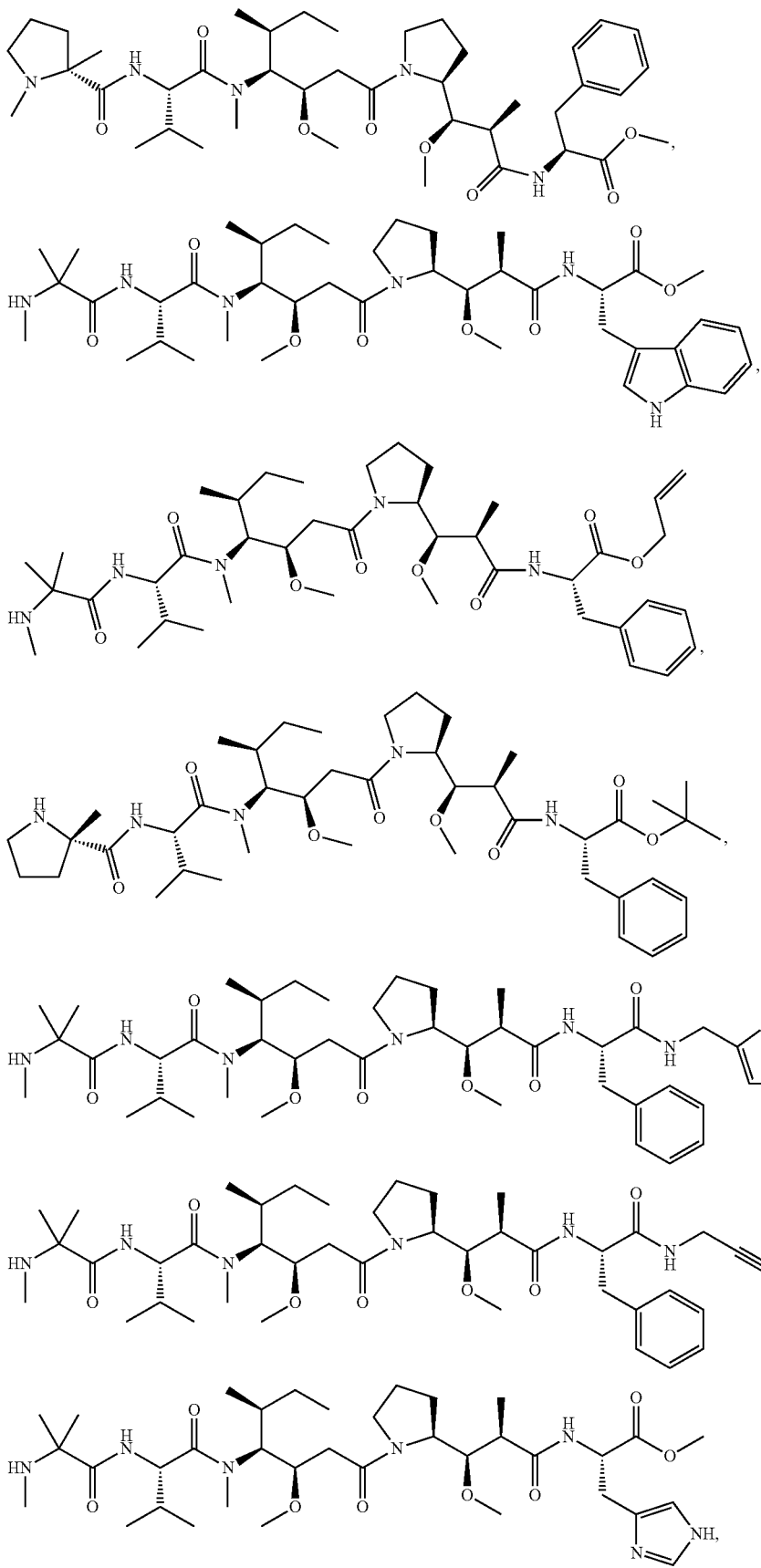

-continued
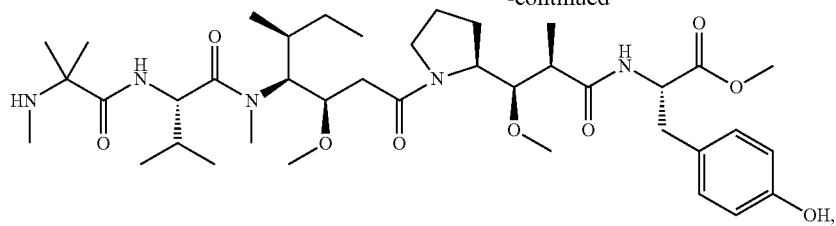
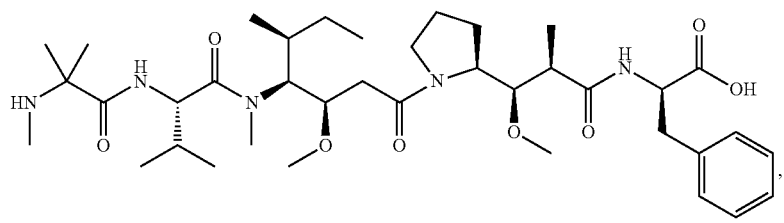
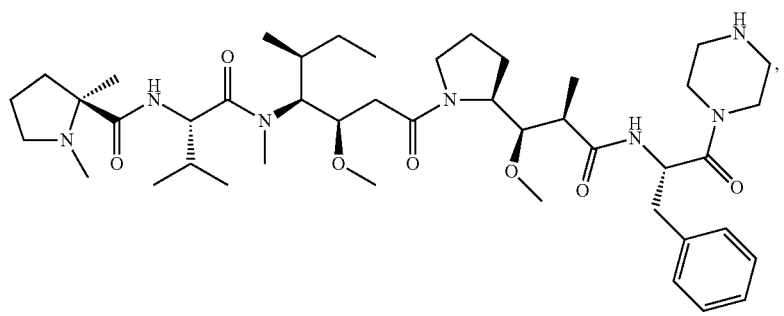 [SMILES: CCC(C)C(C(CC(=O)N1CCCC1C(OC)C(C)C(=O)NC(Cc1ccccc1)C(=O)N1CCNCC1)OC)N(C)C(=O)C(NC(=O)C1(C)CCCN1C)C(C)C]
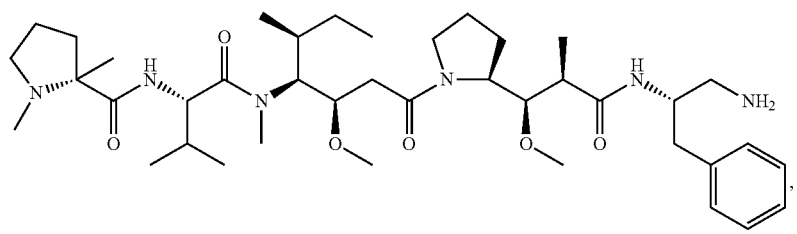
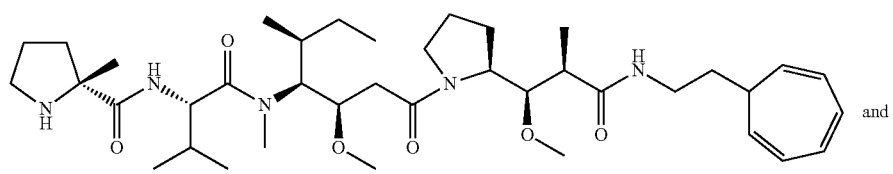 and
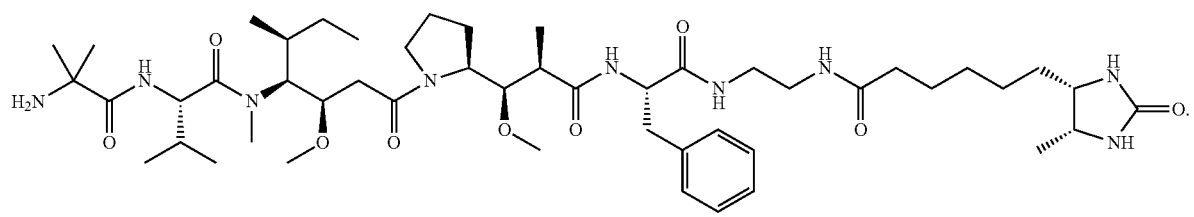

23. A compound, or a pharmaceutically acceptable salt or solvate thereof, selected from:
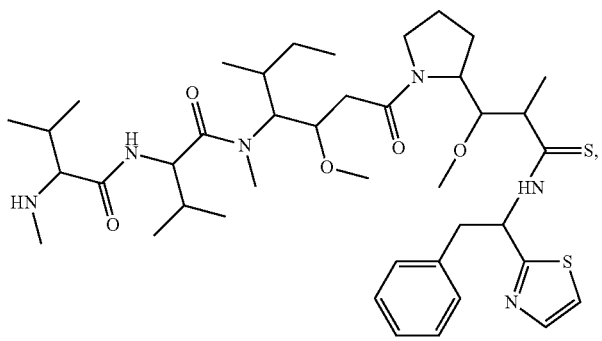
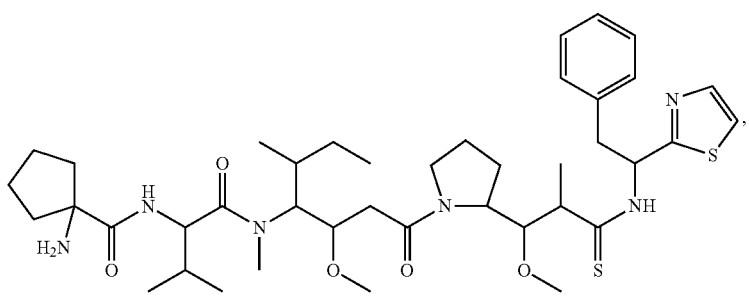
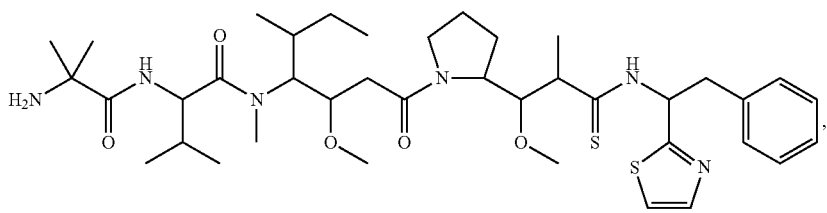
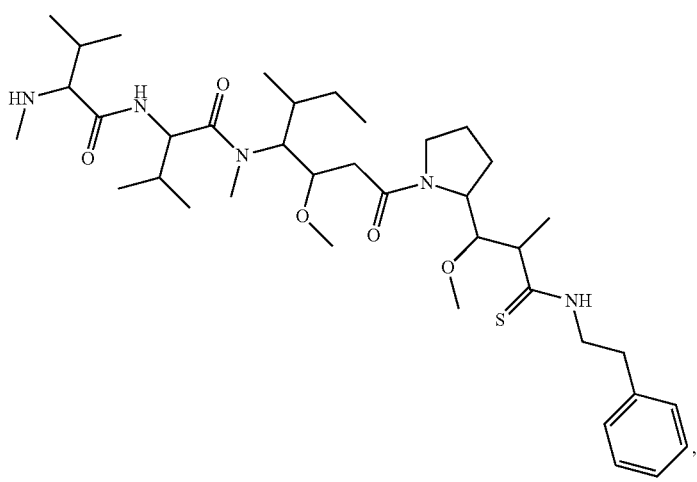

-continued
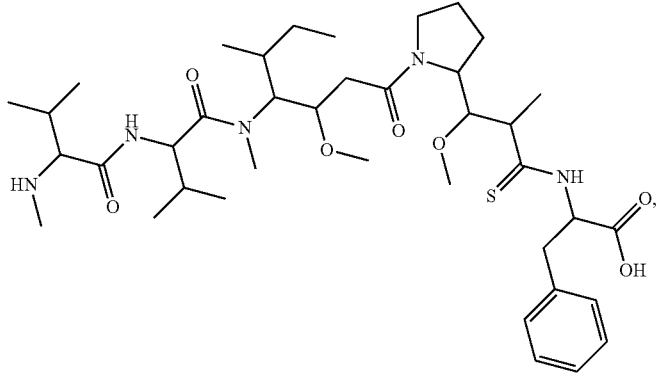
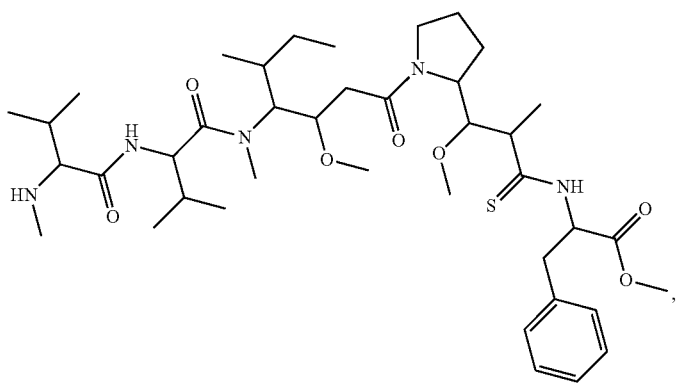
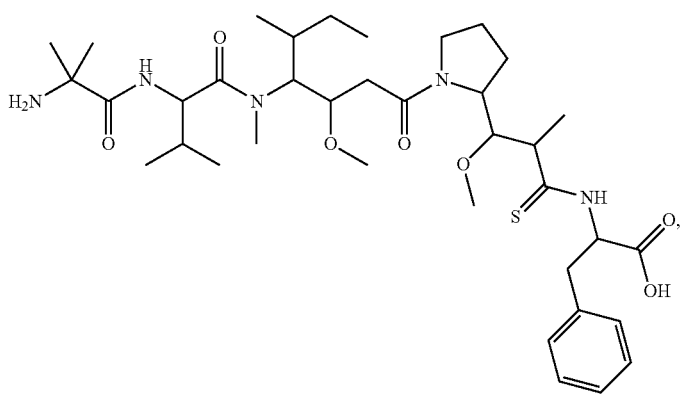
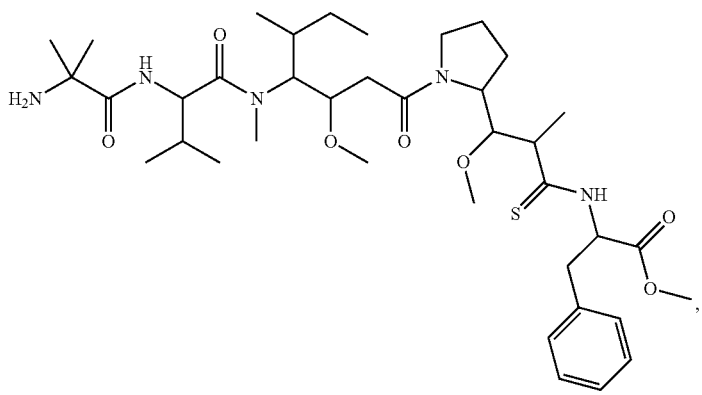

-continued
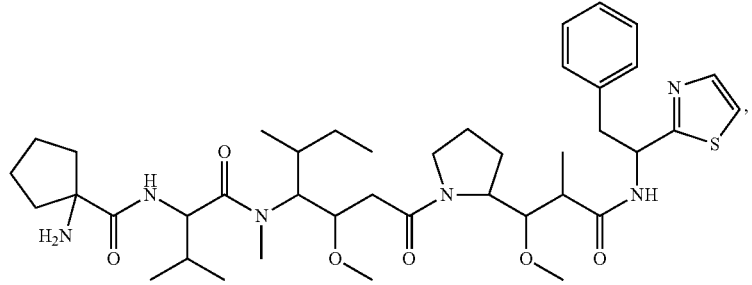
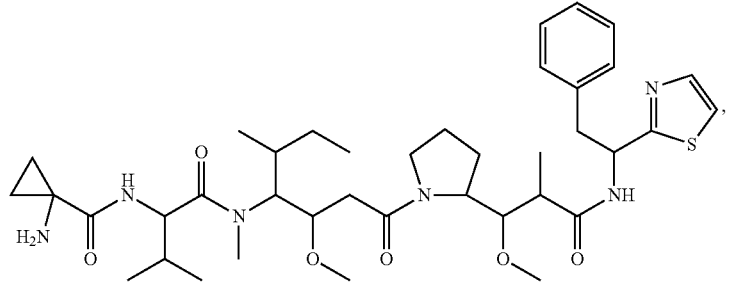
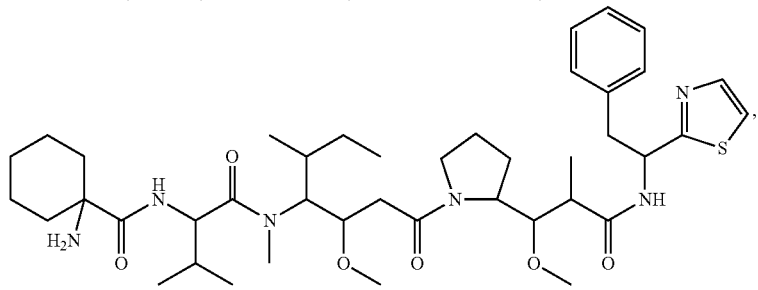
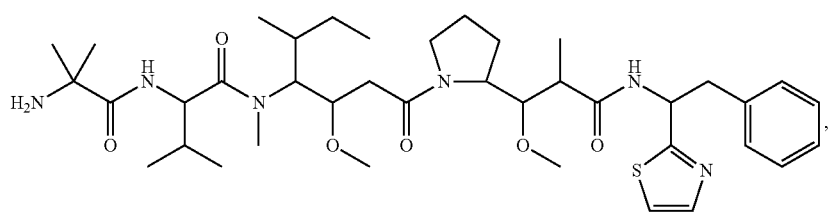
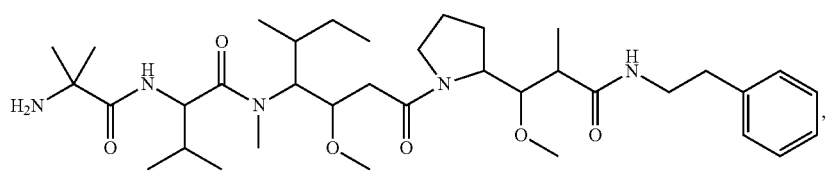
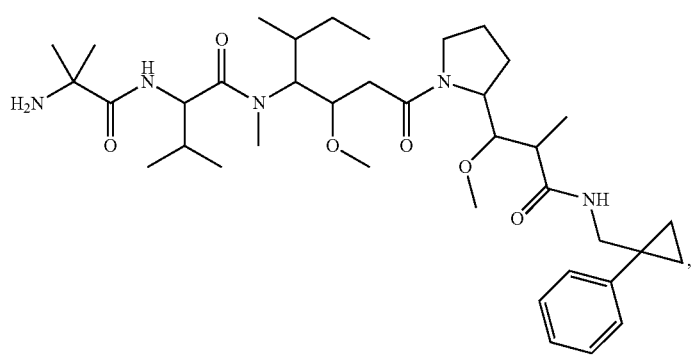

-continued
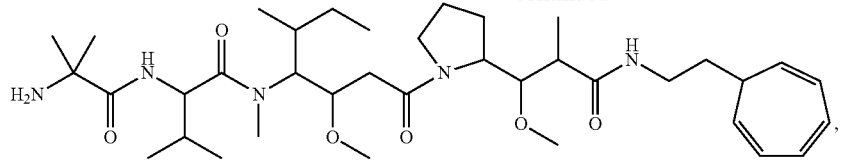
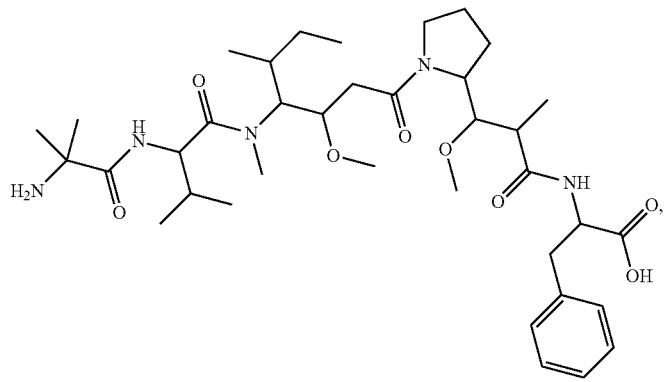
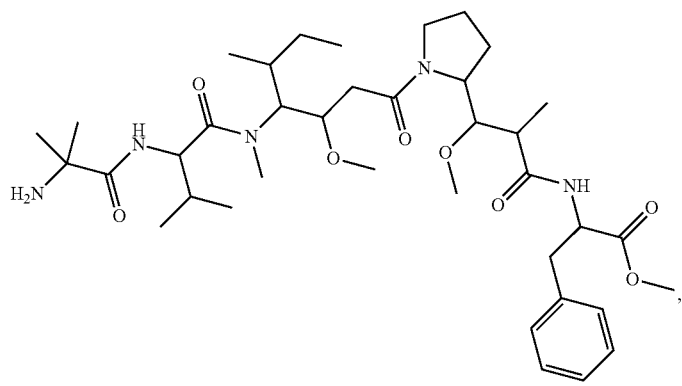
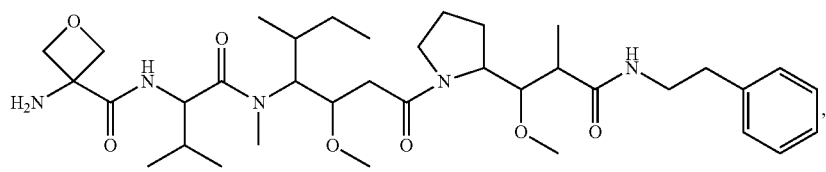
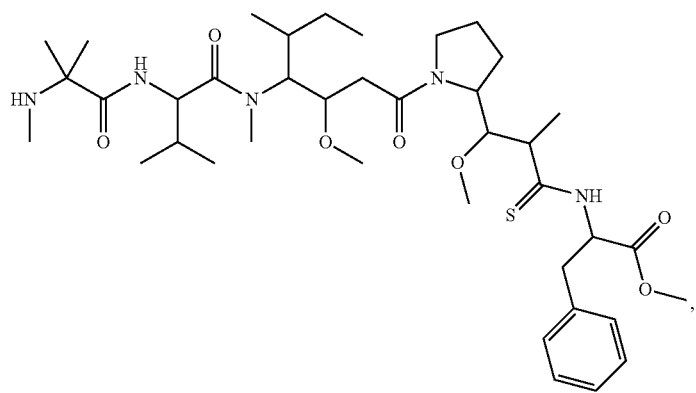

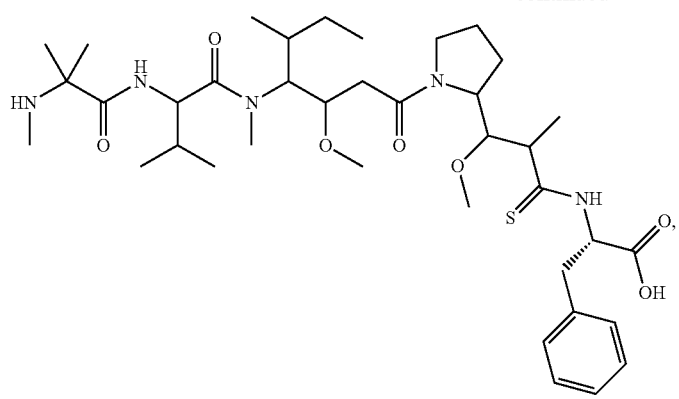
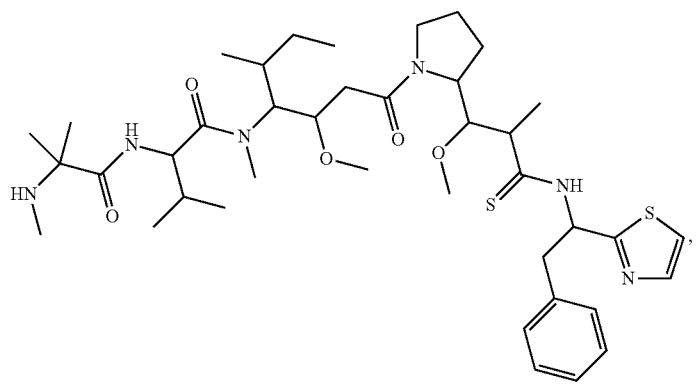
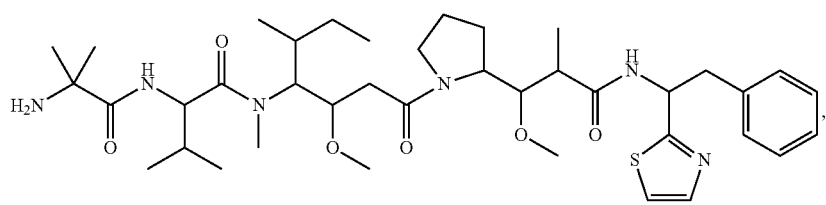
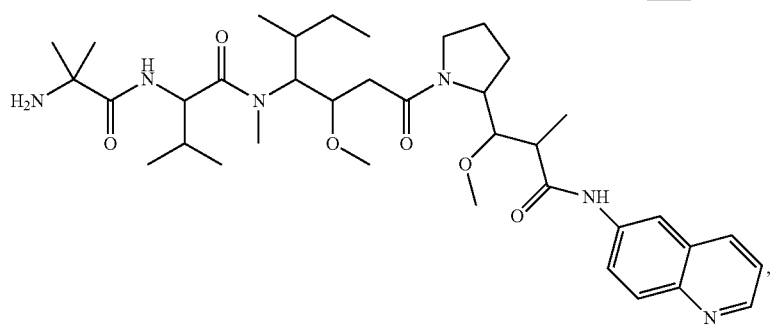
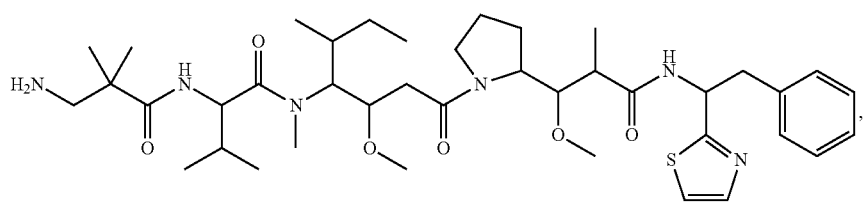
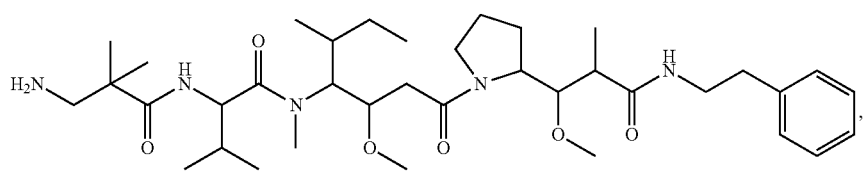

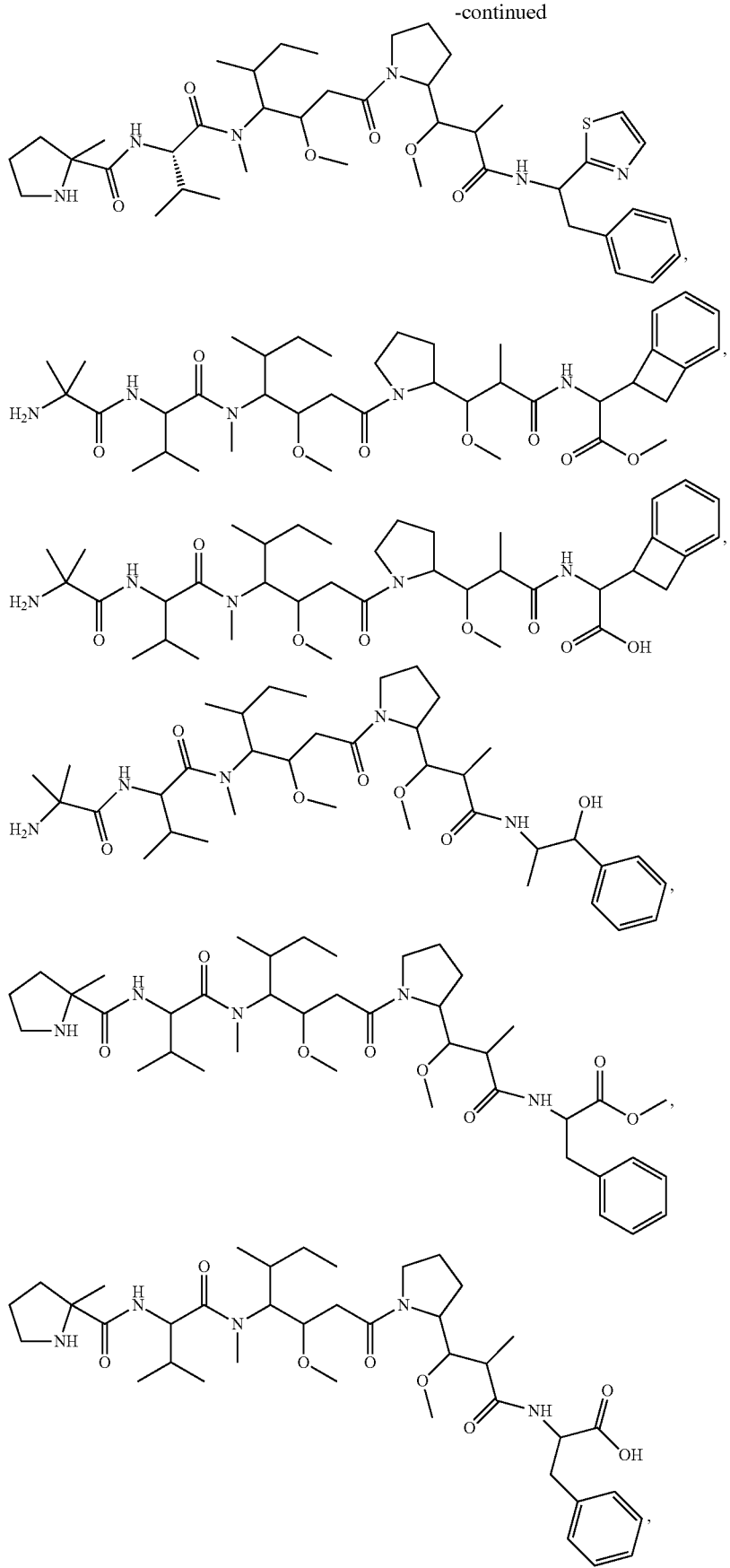

-continued
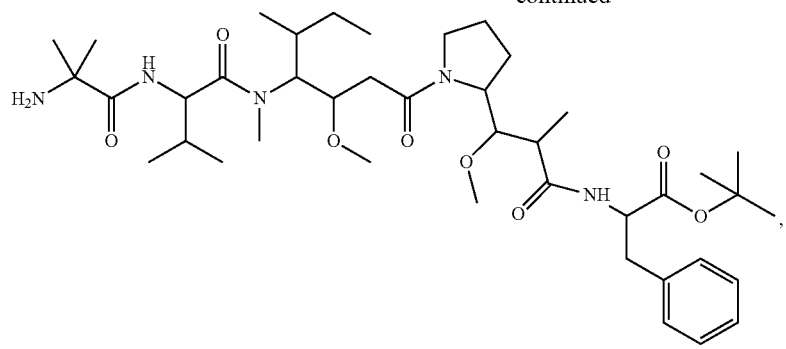
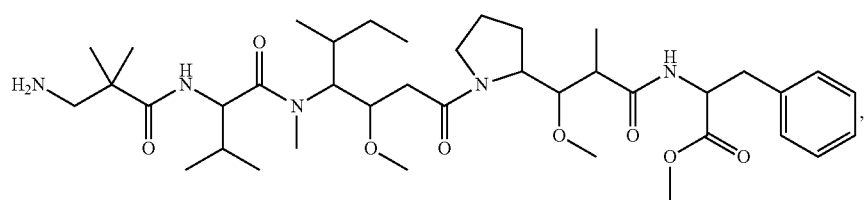
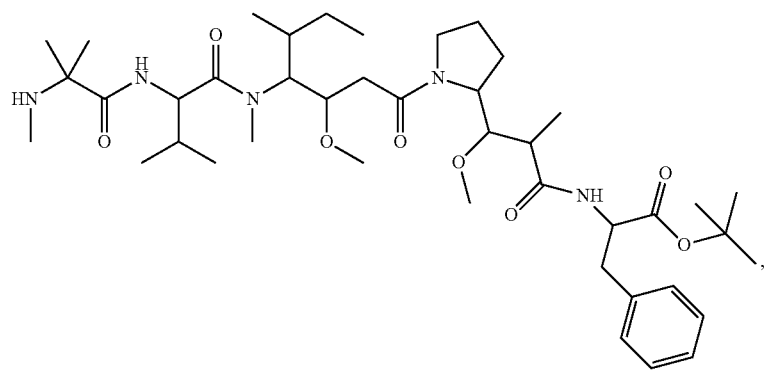
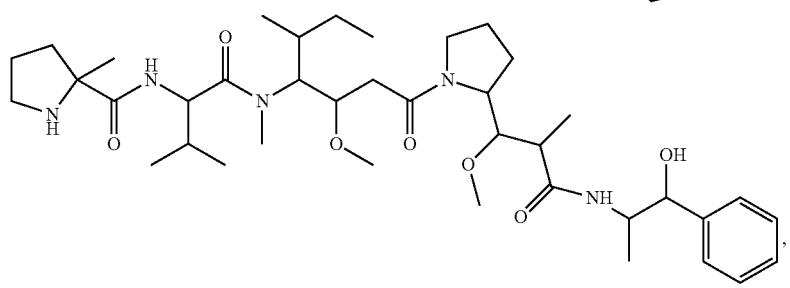
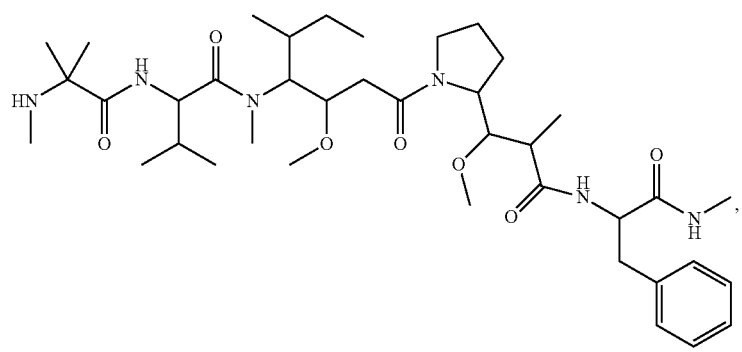

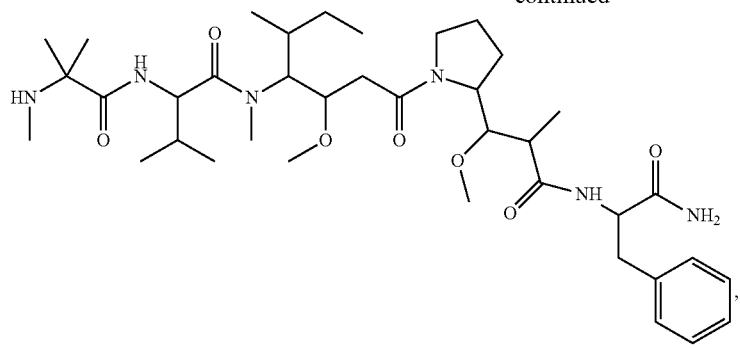
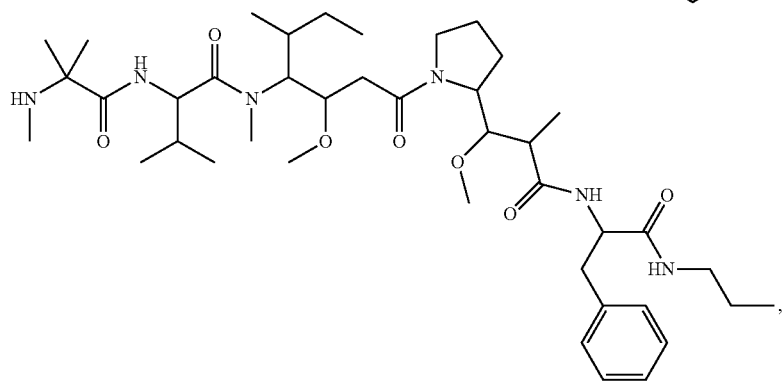
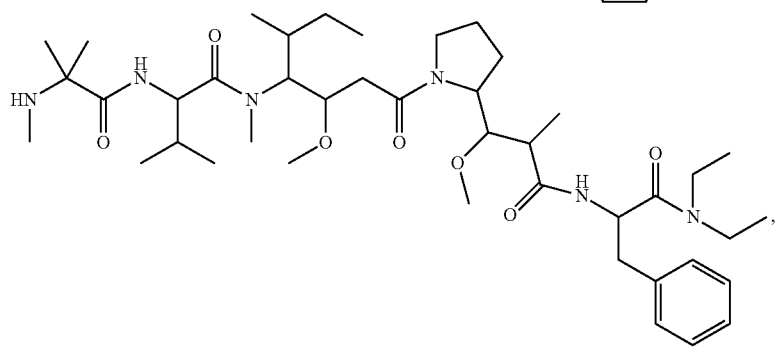
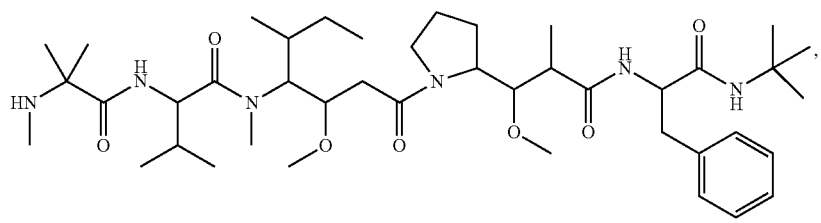
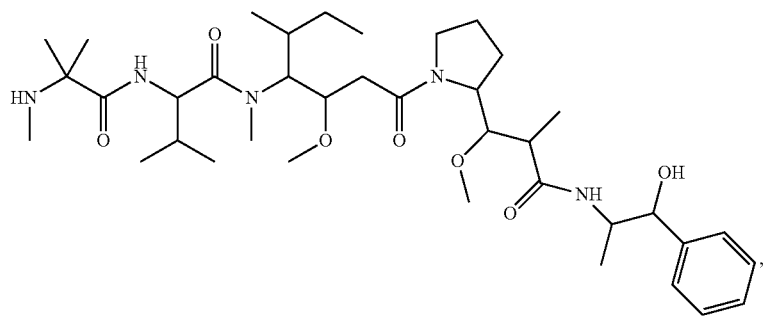

-continued
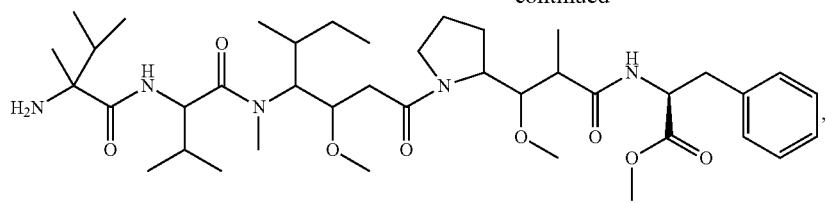
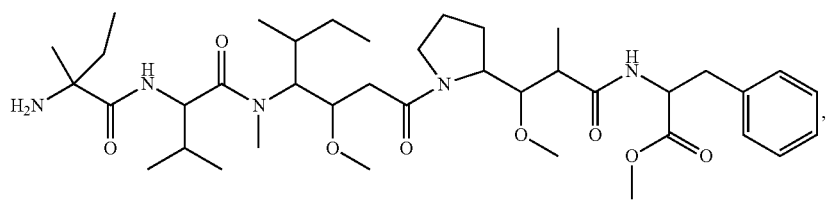
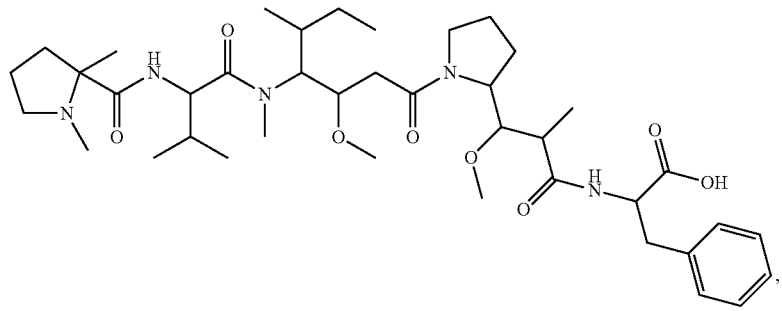
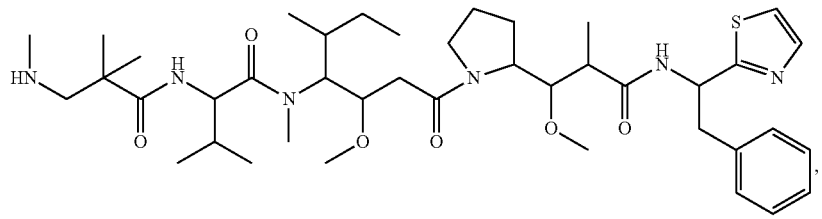
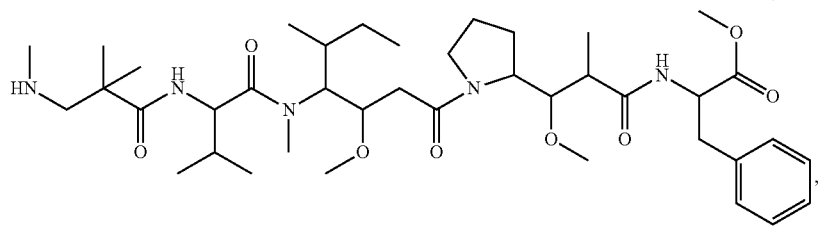
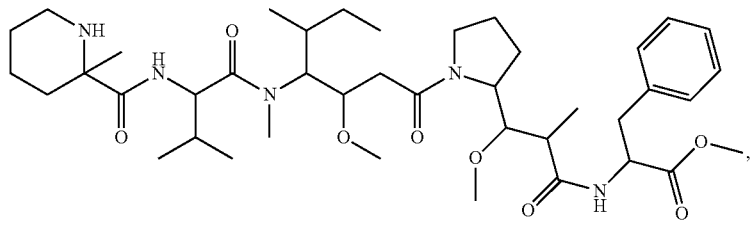
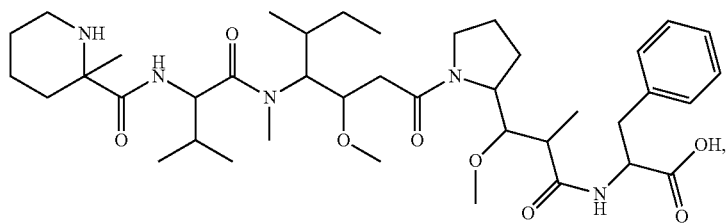

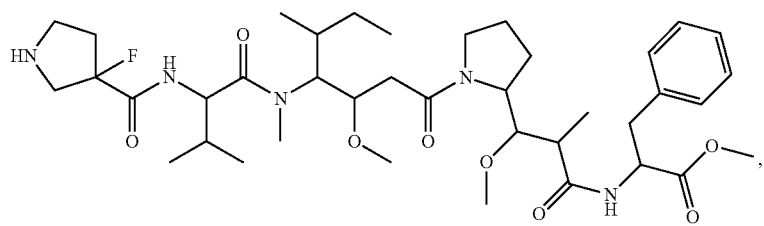
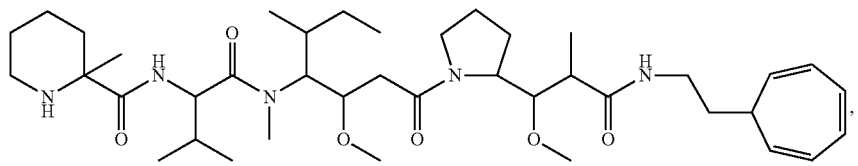
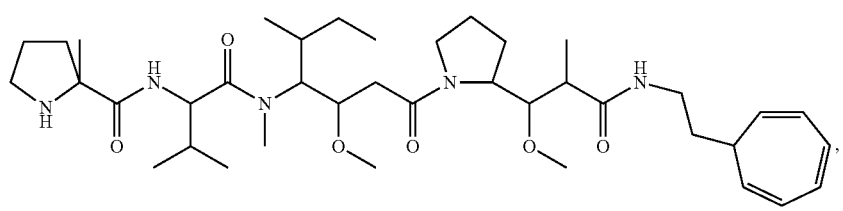
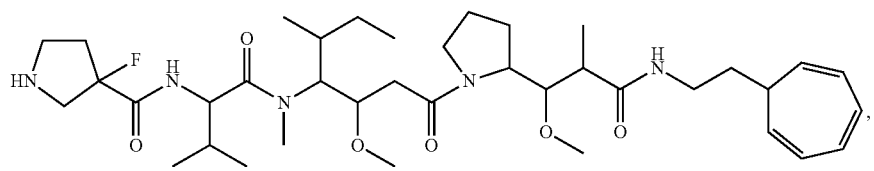
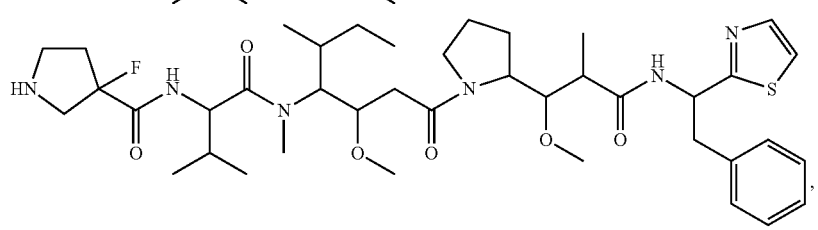
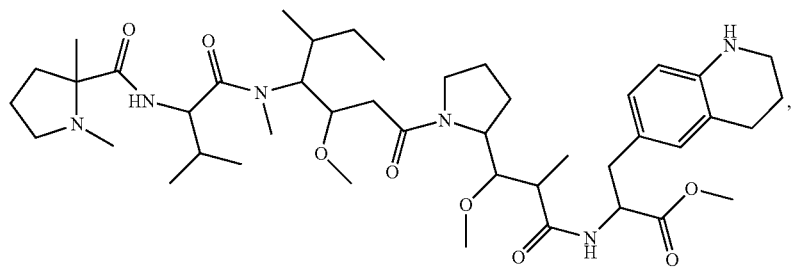
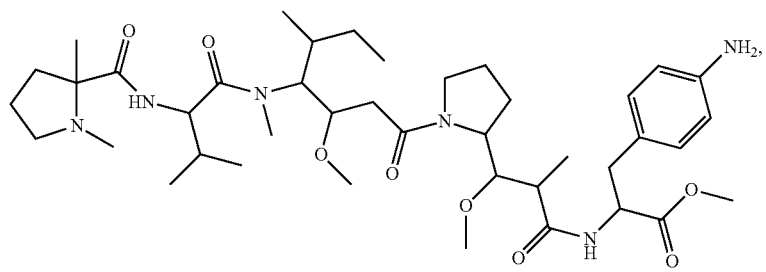
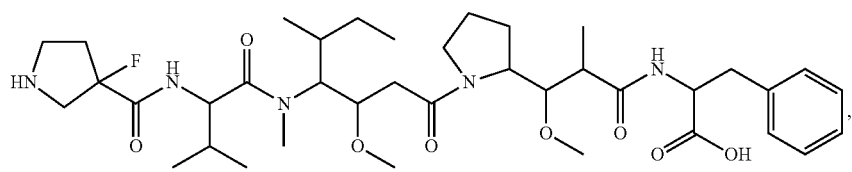

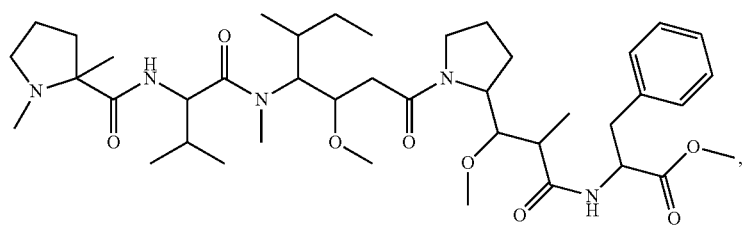
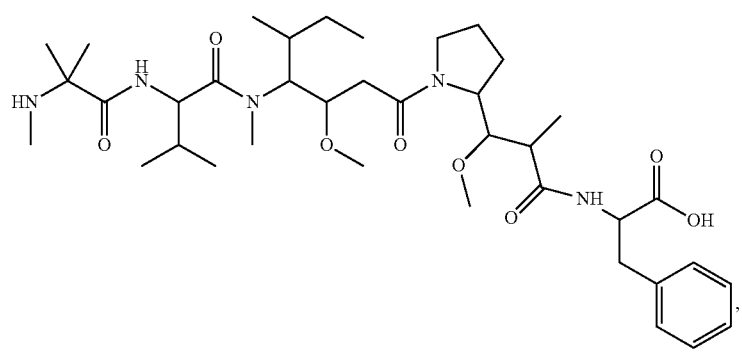
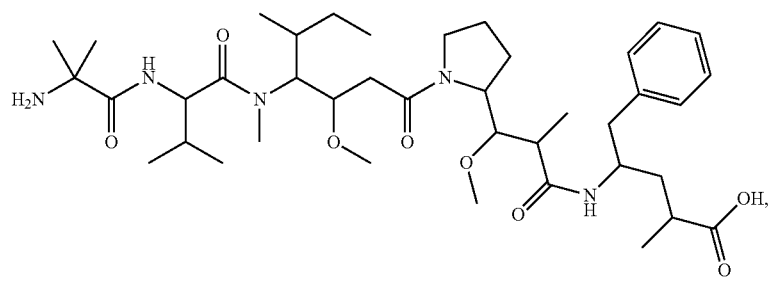
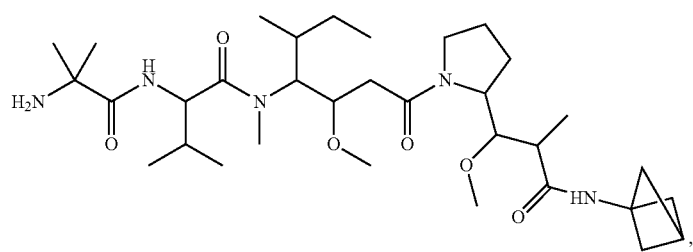
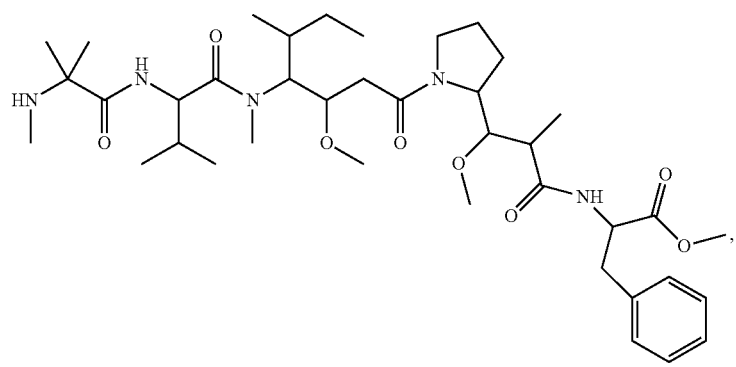
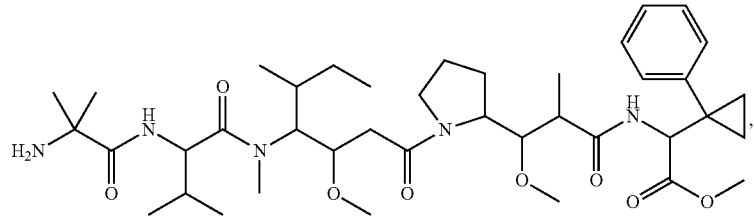

-continued
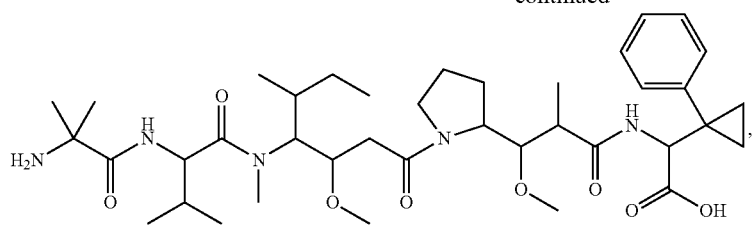
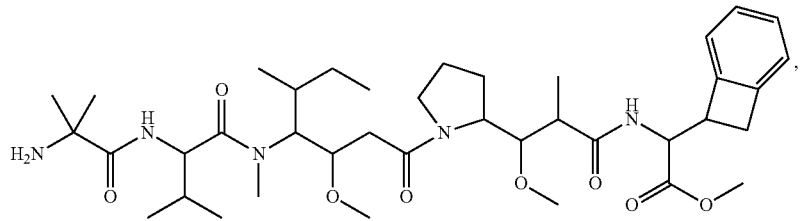
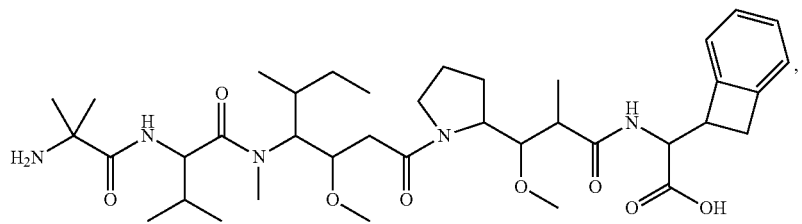
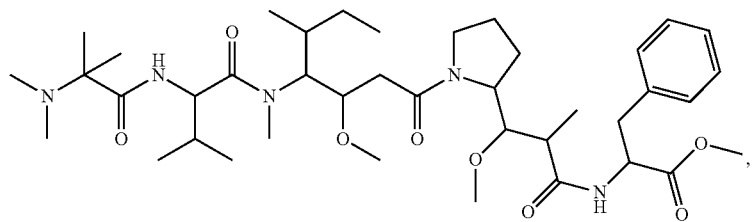
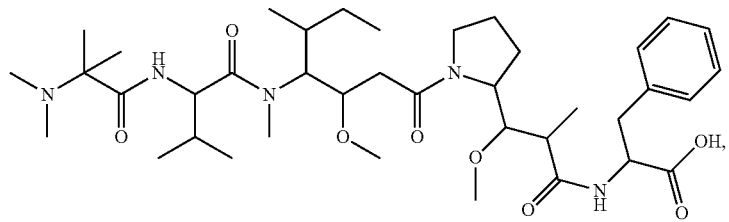
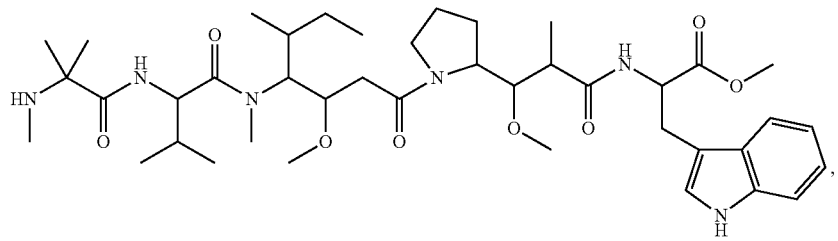
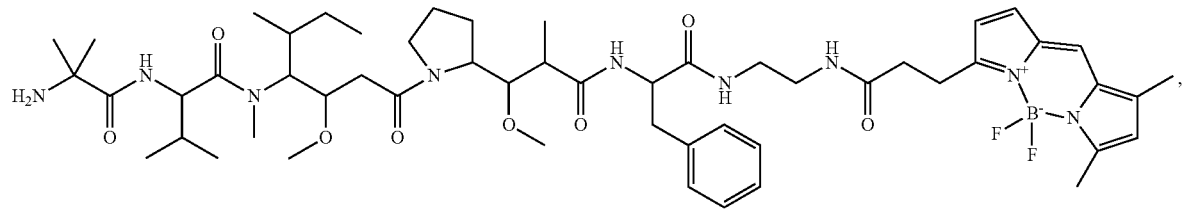

-continued
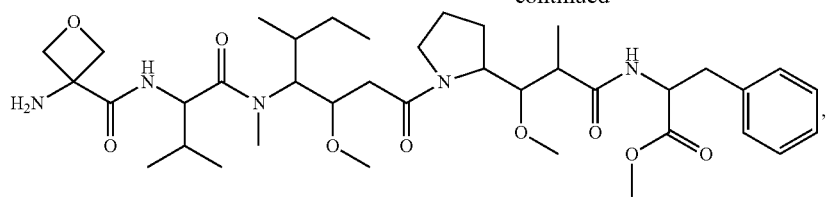
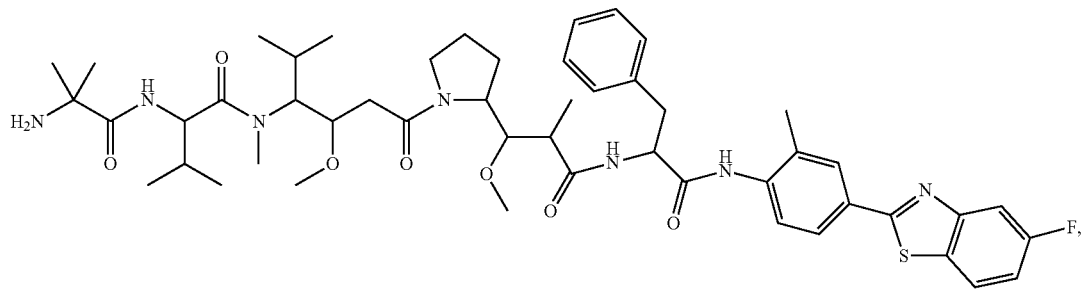
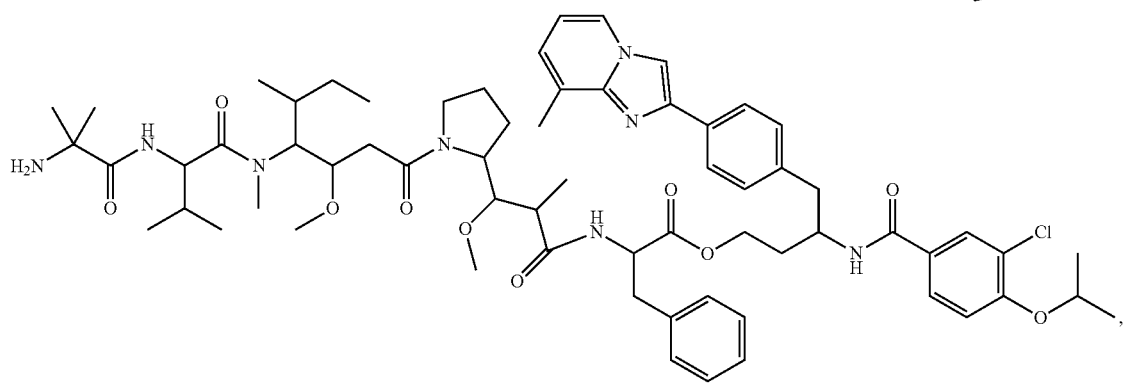
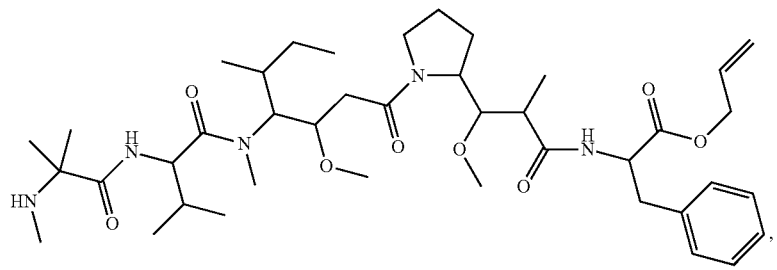
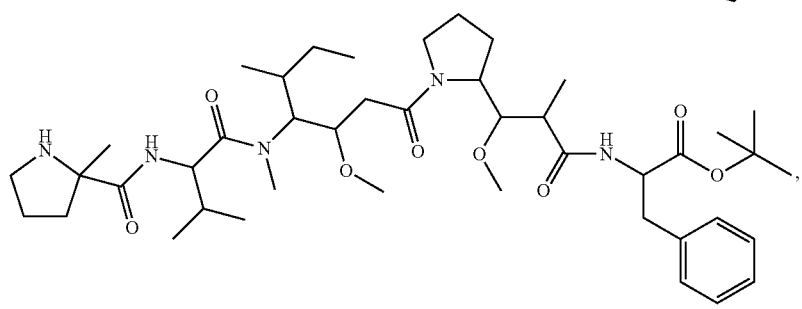
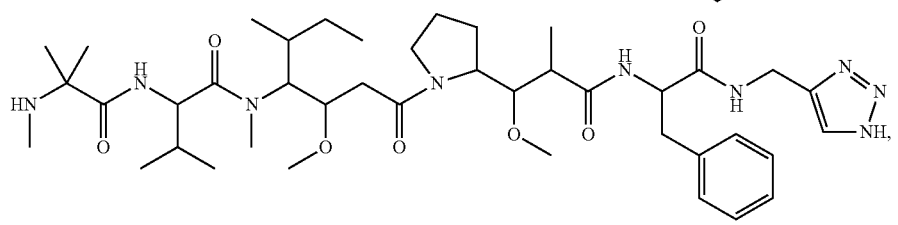

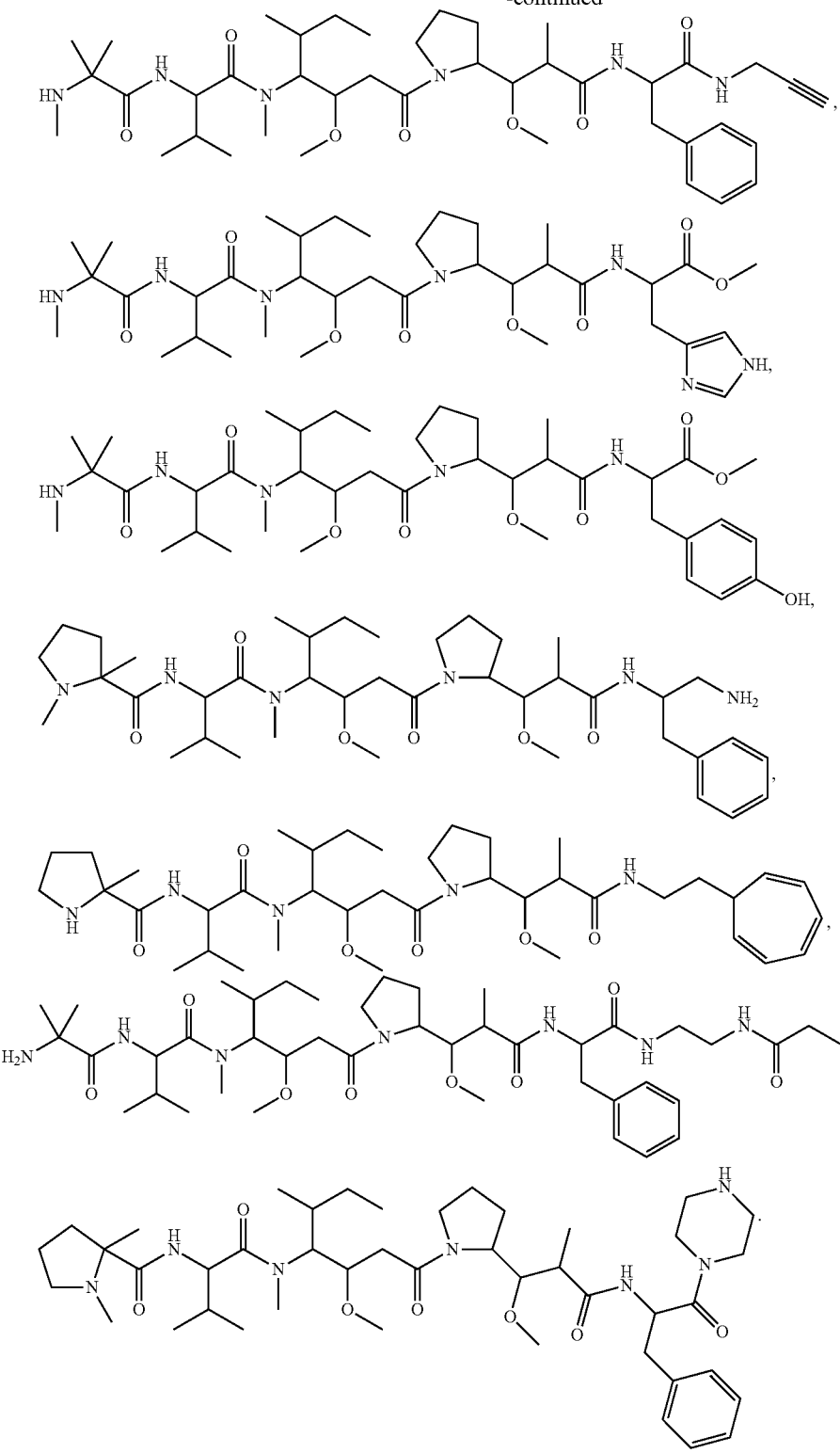
24. A payload-linker comprising a radical of a compound of claim 22 or 23.
25. An antibody drug conjugate comprising a radical of a compound of any of claims 1, 2, or 3.
26. A compound, or a pharmaceutically acceptable salt or solvate thereof, selected from:

565  566
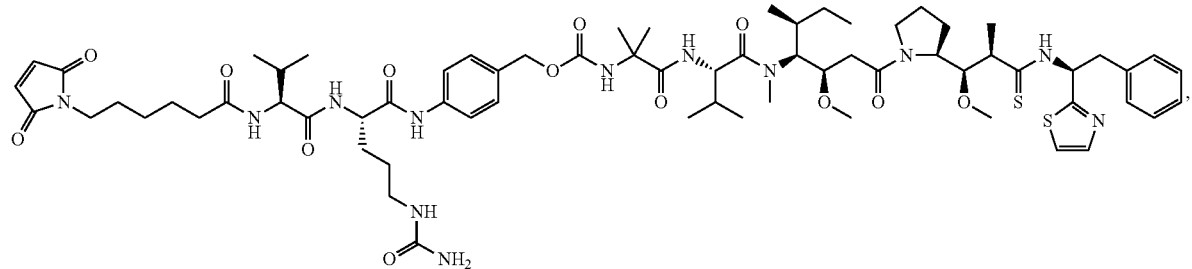
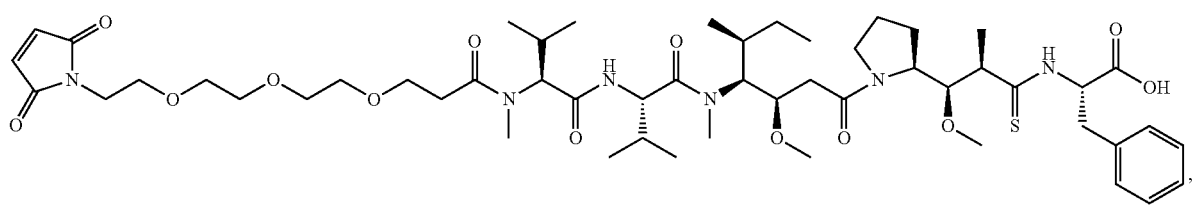
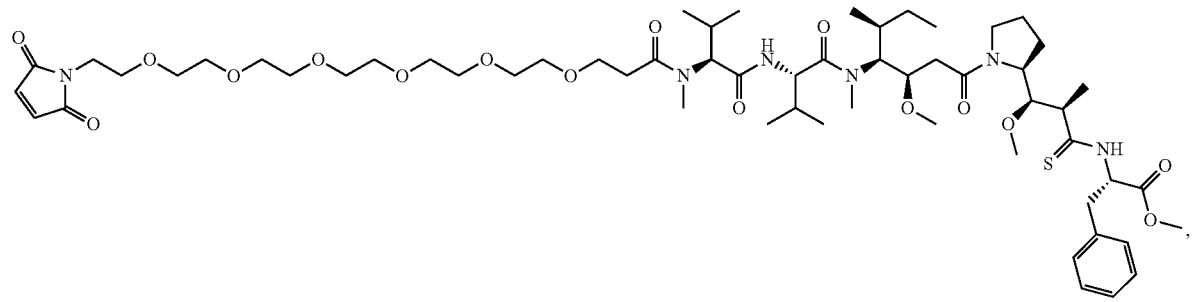
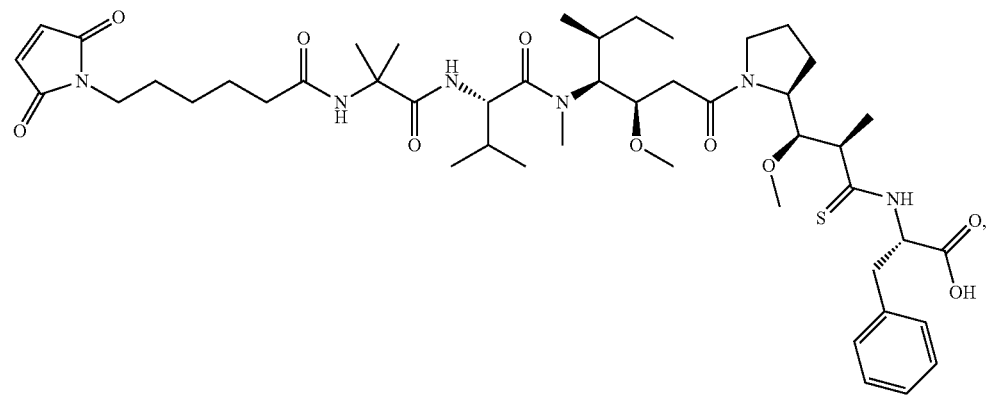
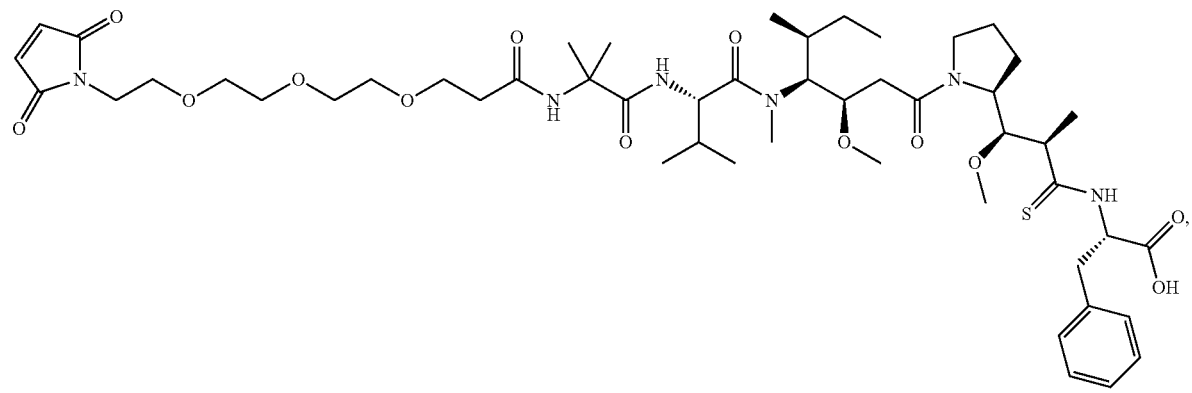

567  568
-continued
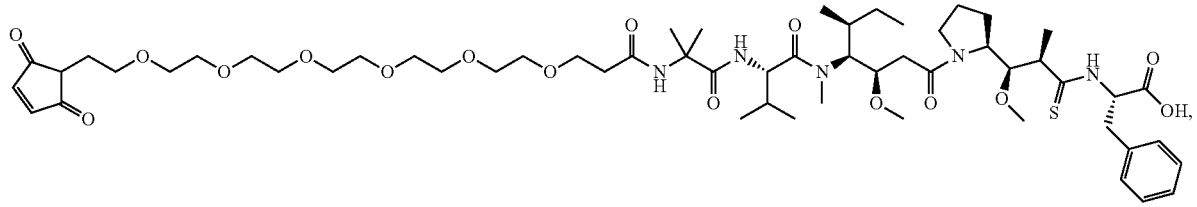
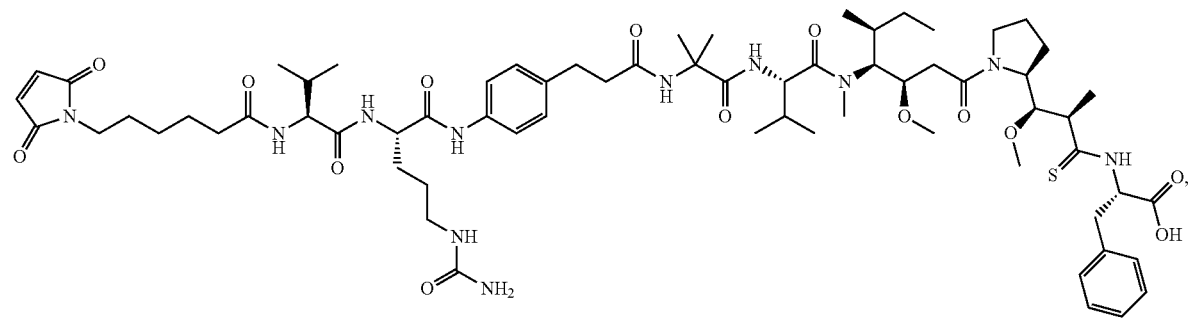
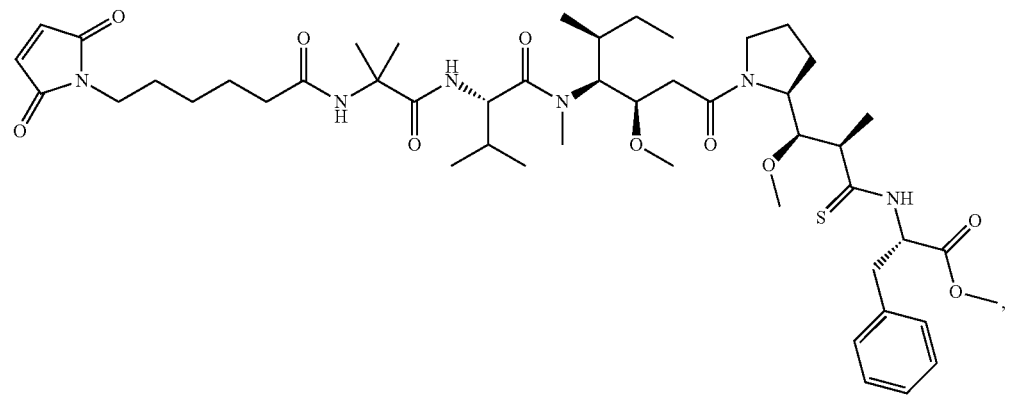
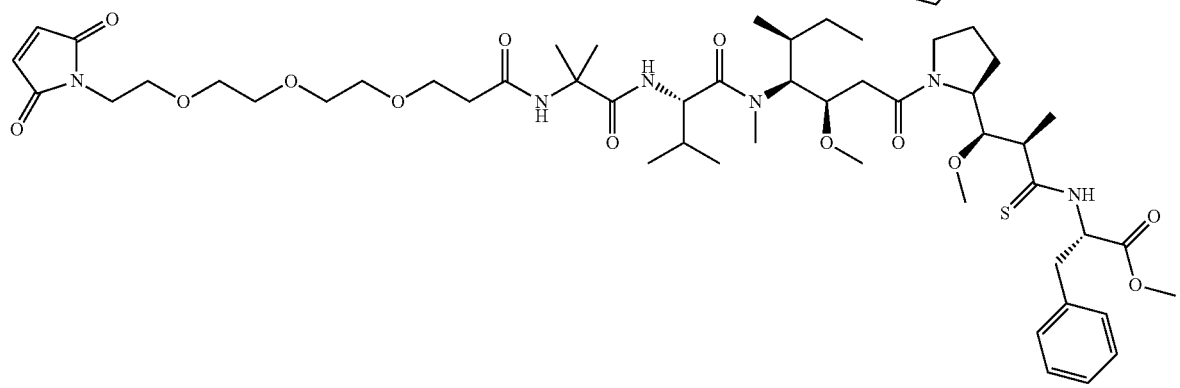
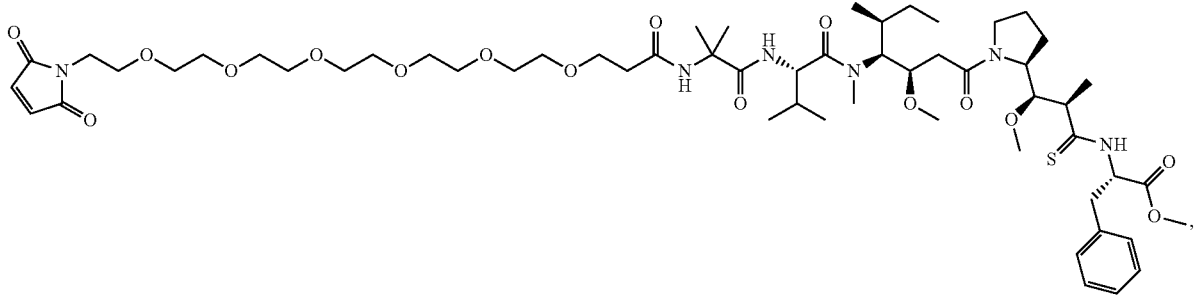

-continued
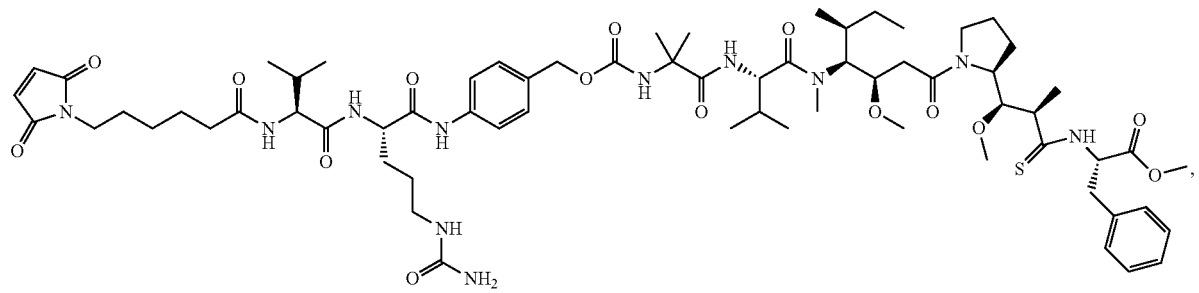
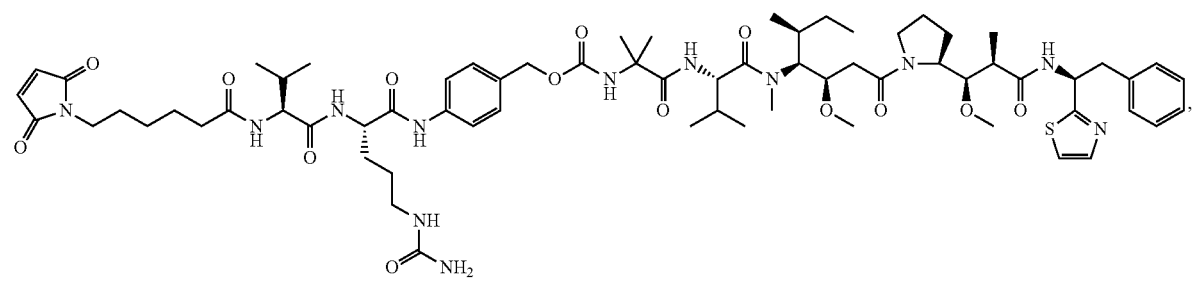
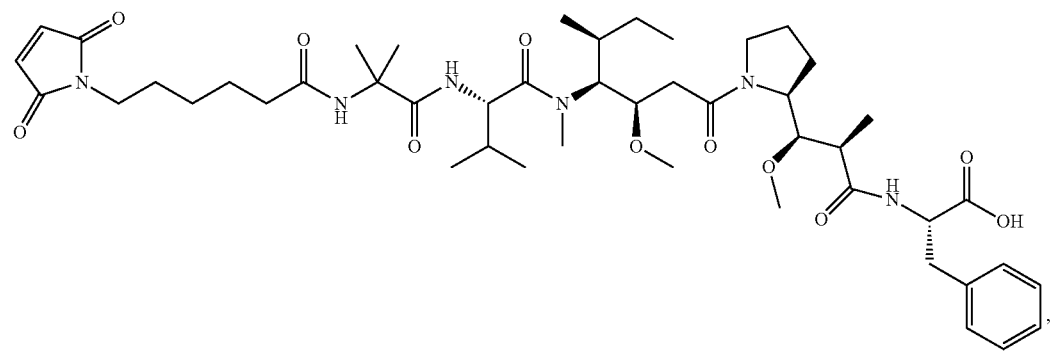
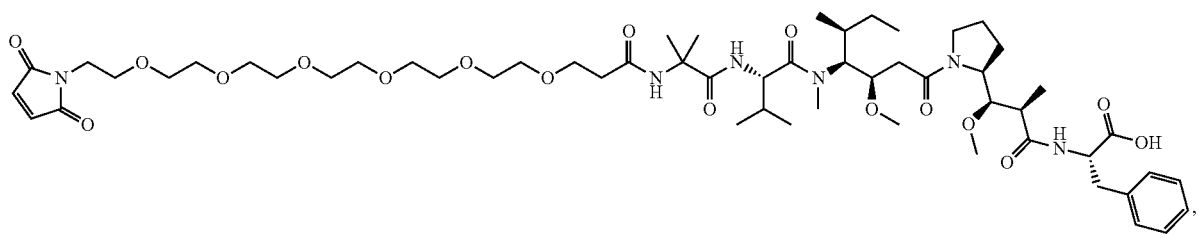
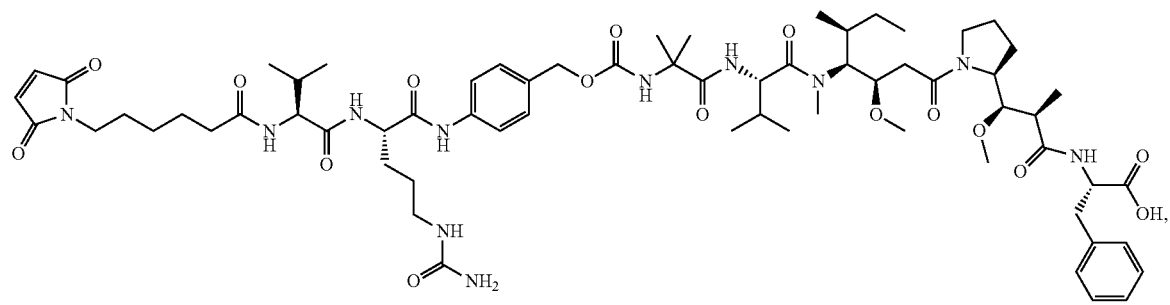

571
-continued
572
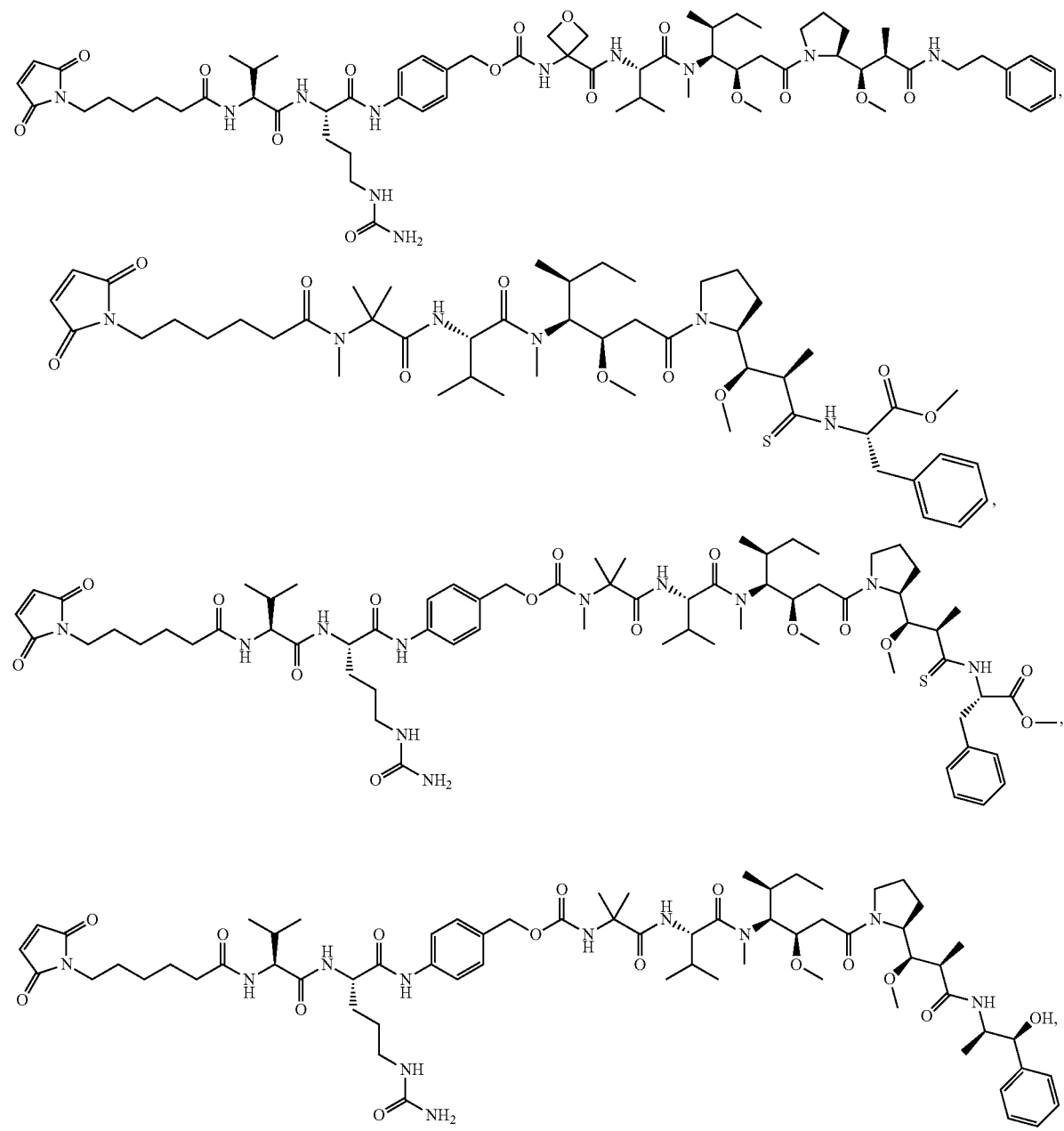

-continued
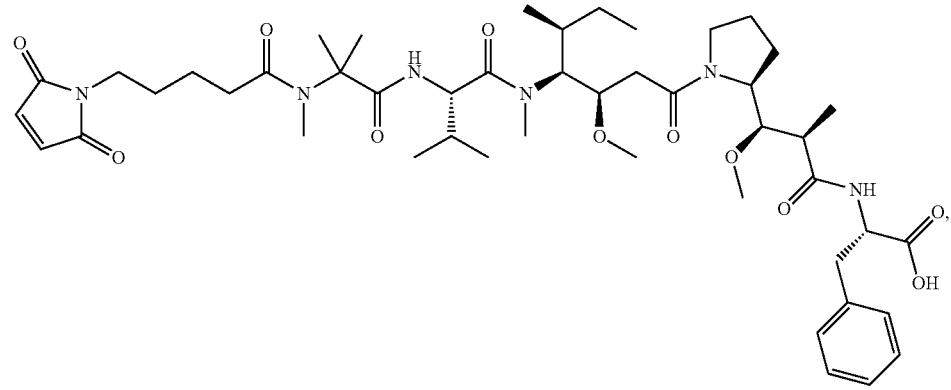
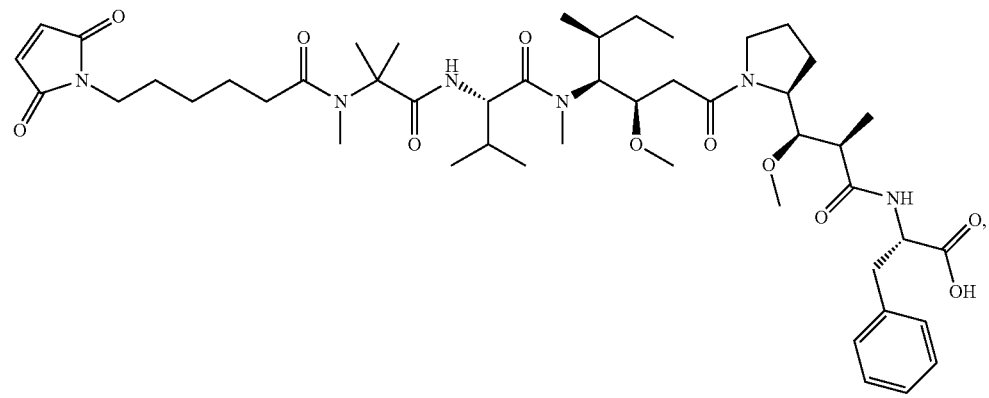
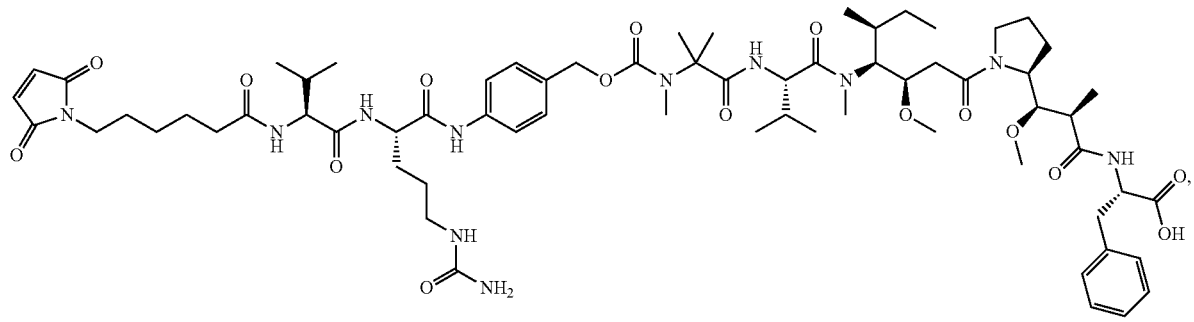
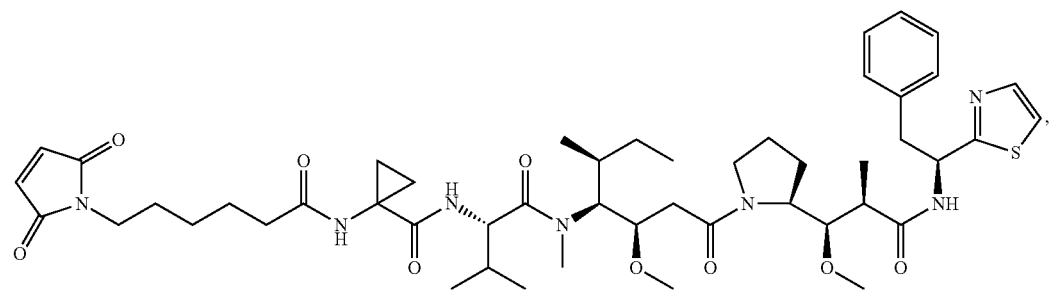
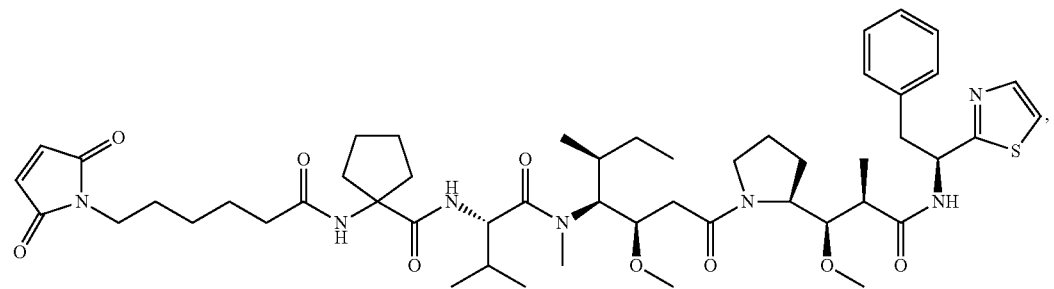

575
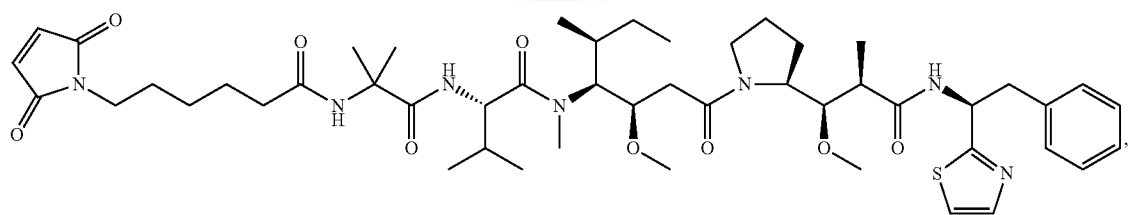
-continued
576
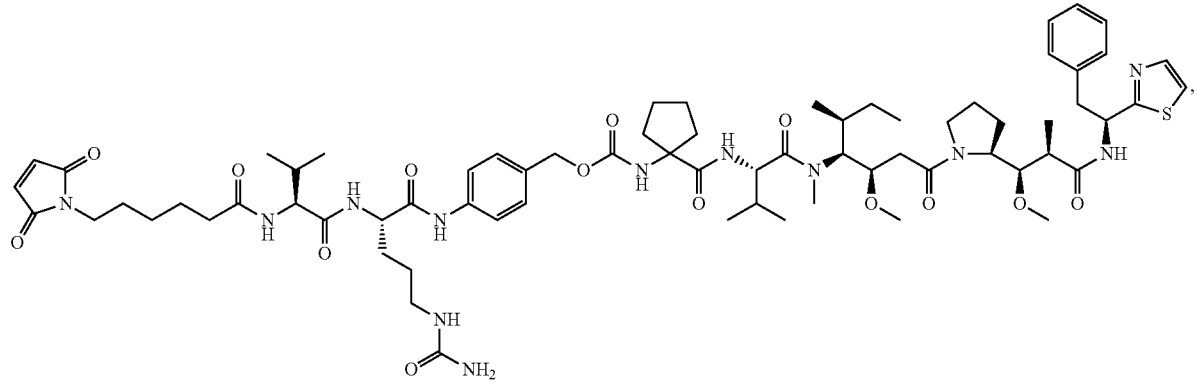
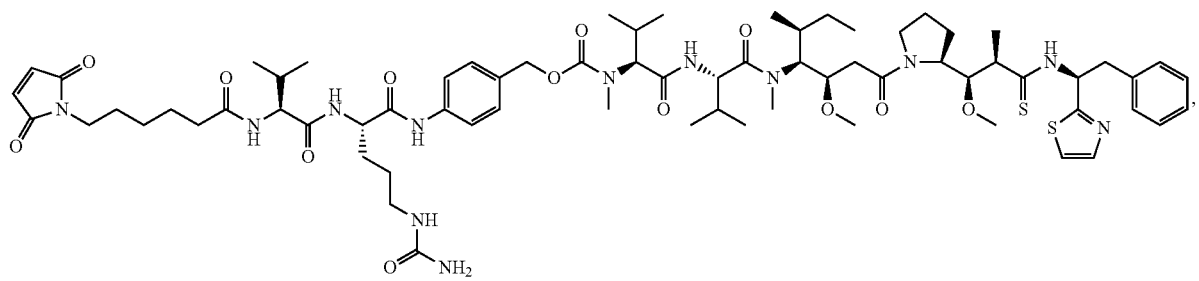
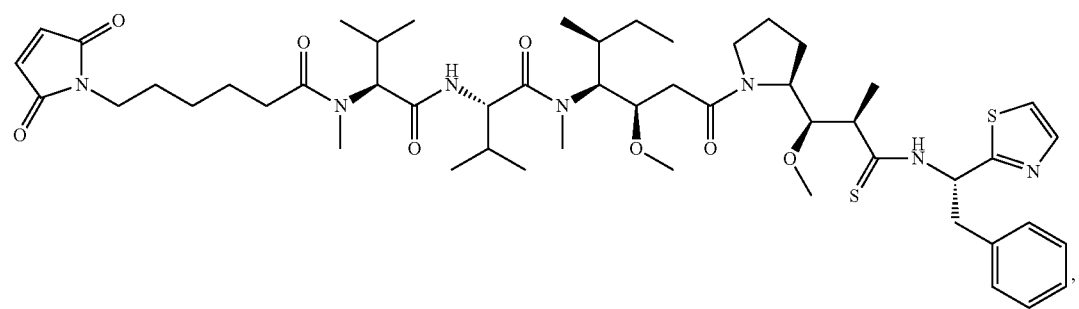
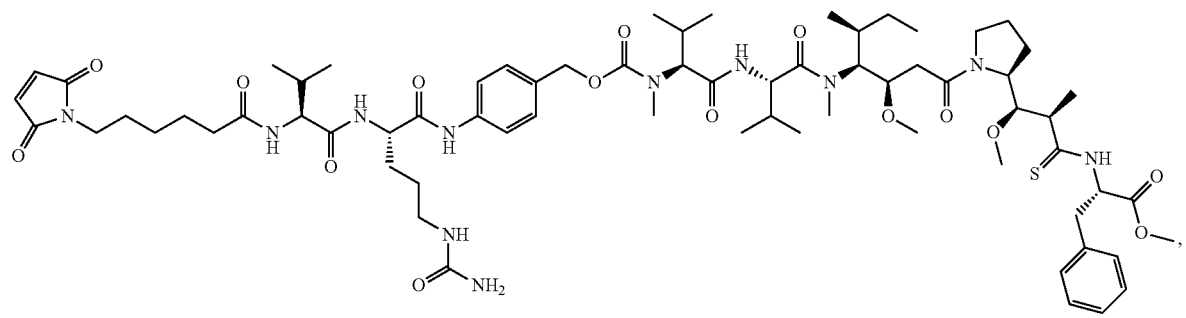

577 578
-continued
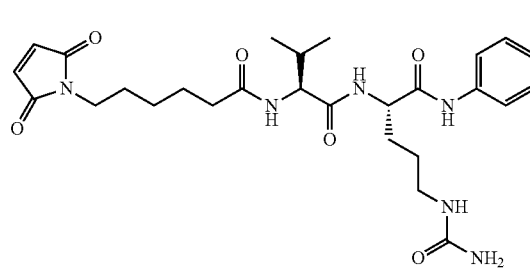
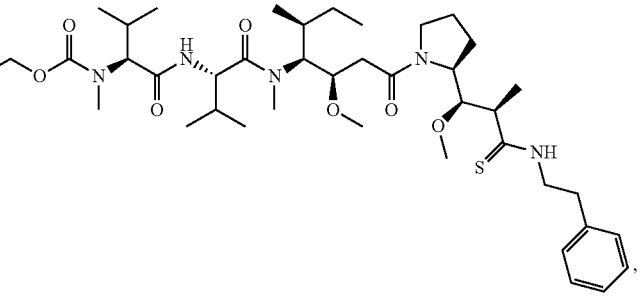
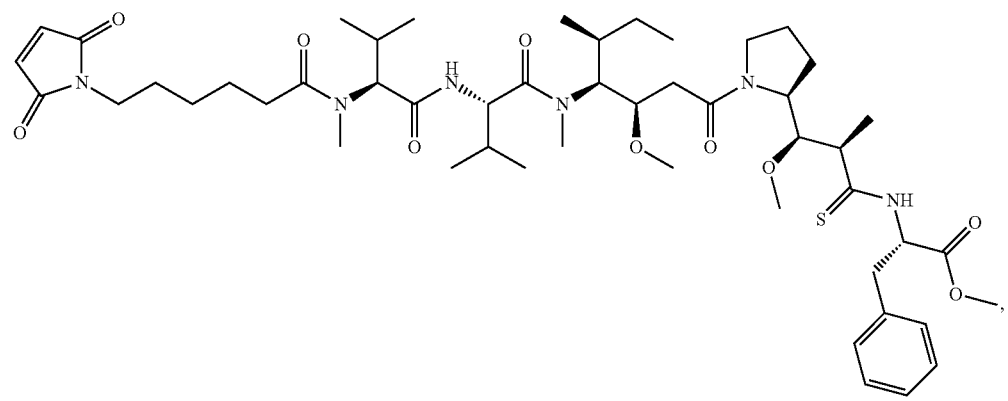
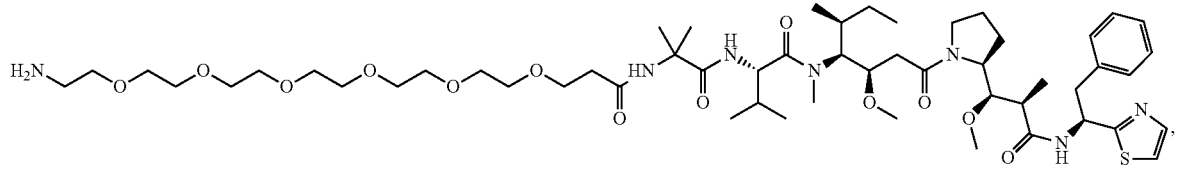
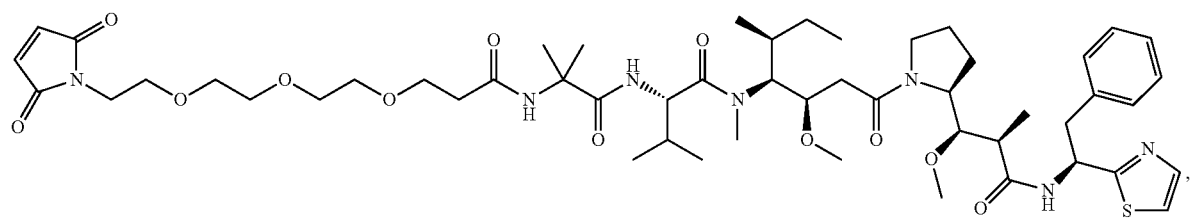
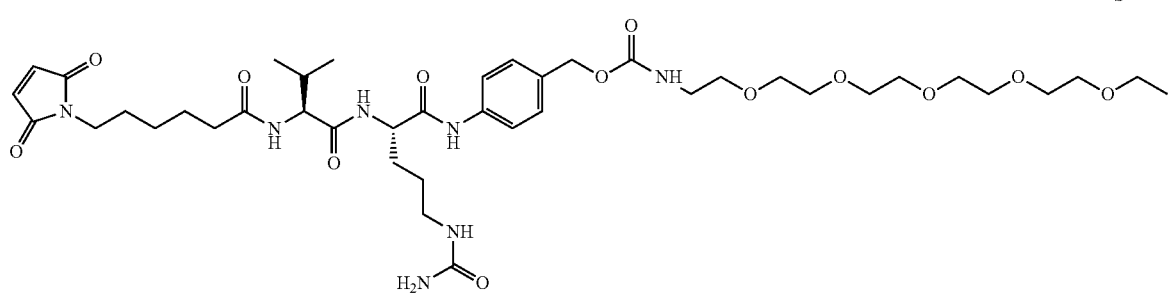
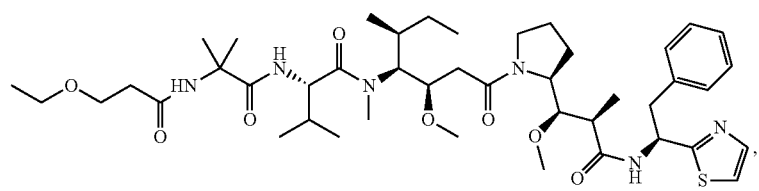

579
-continued
580
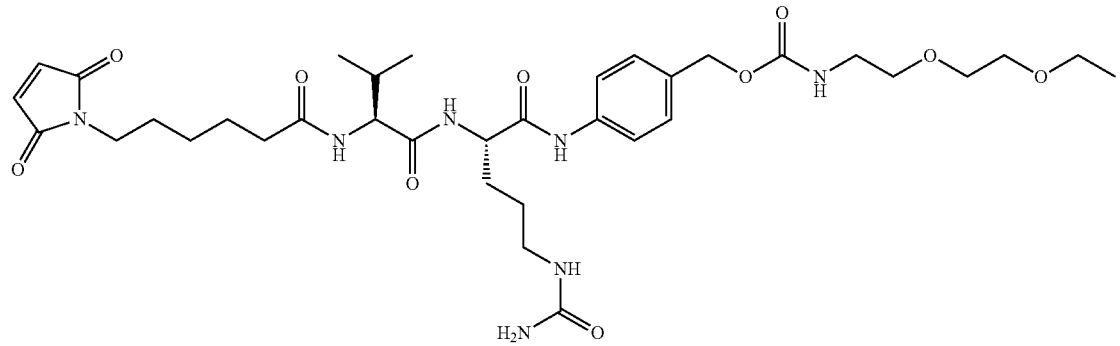
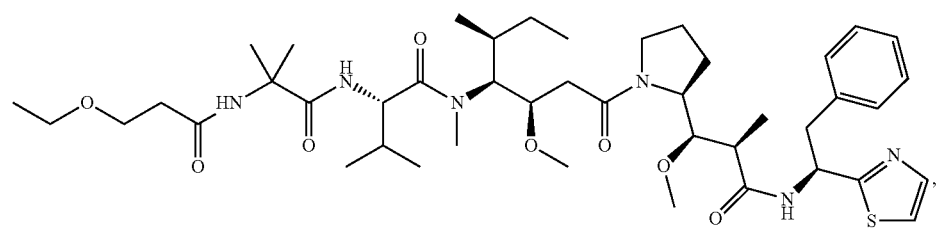
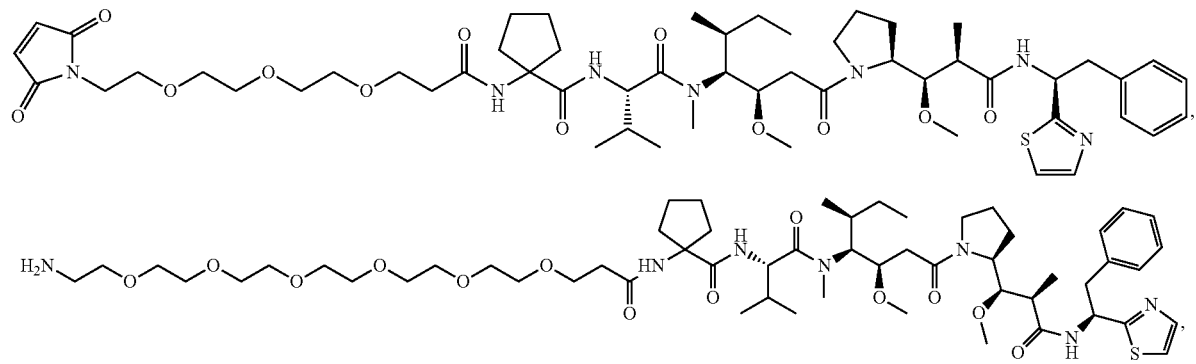
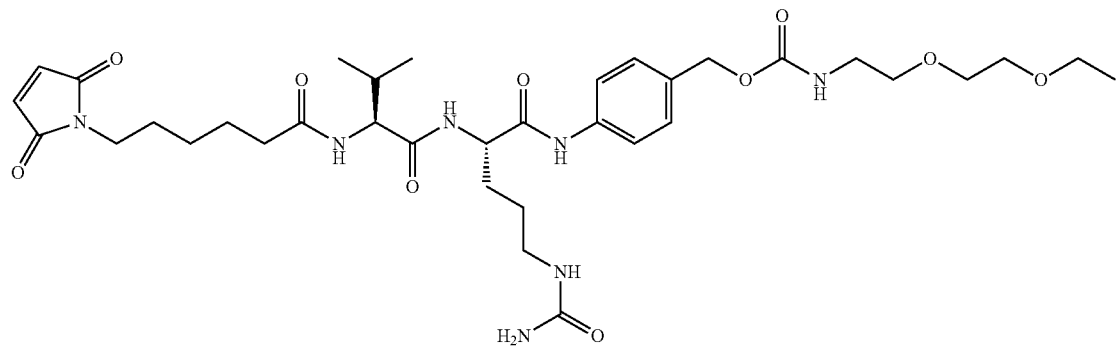
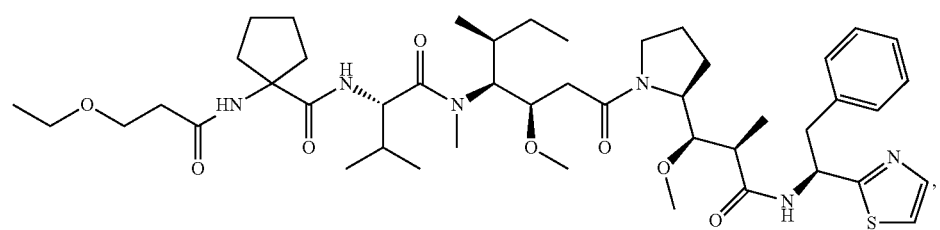

-continued
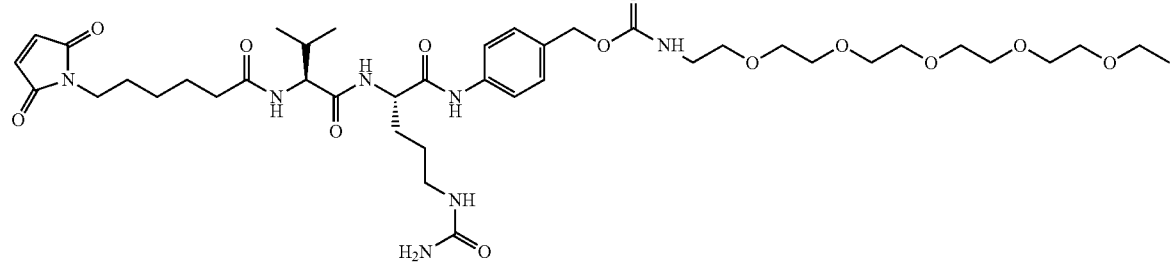
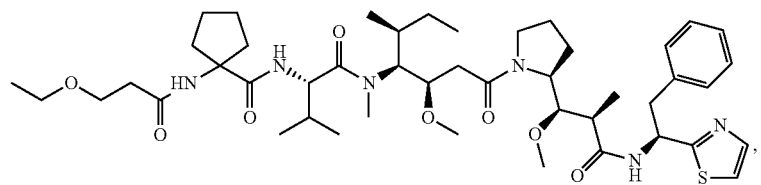
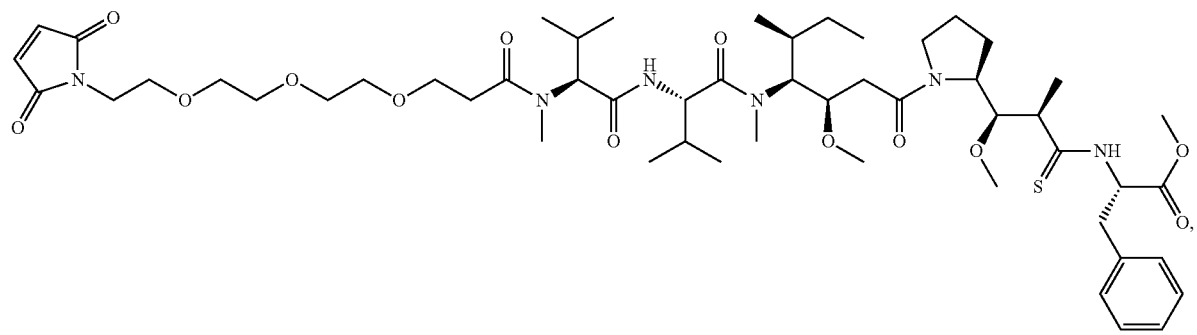
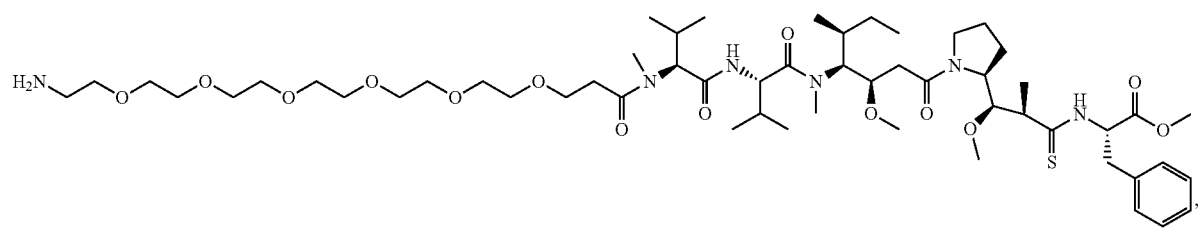
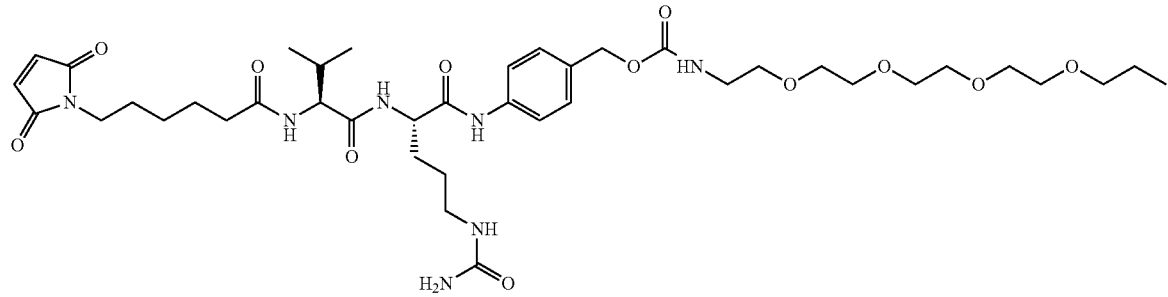
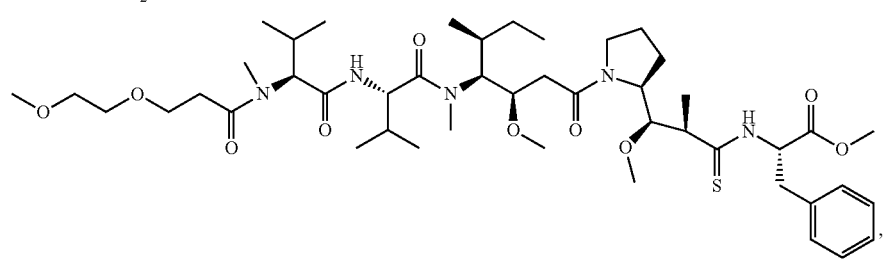

-continued
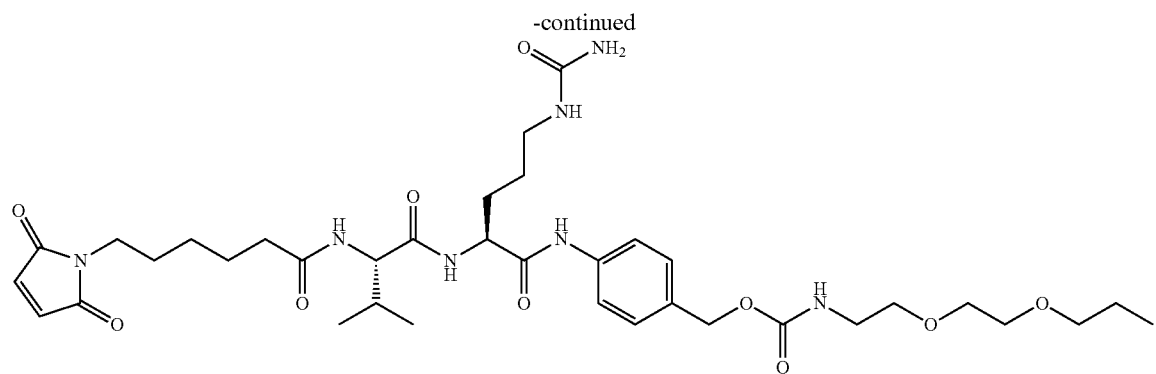
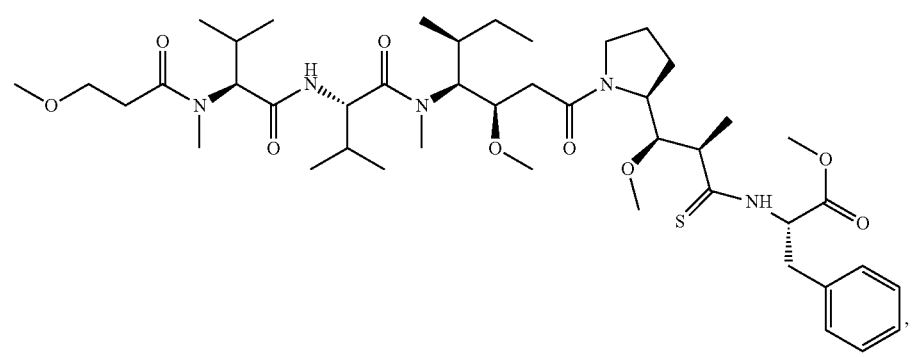
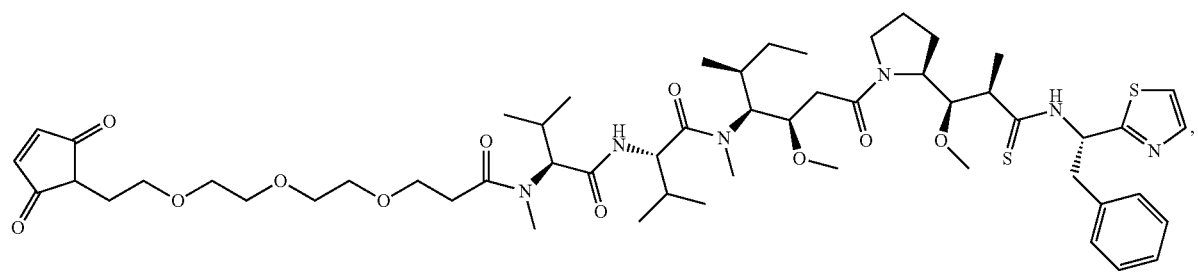
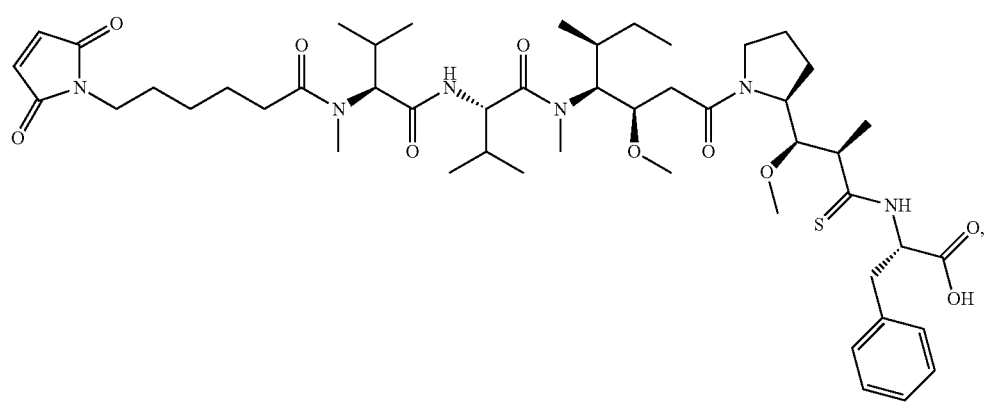
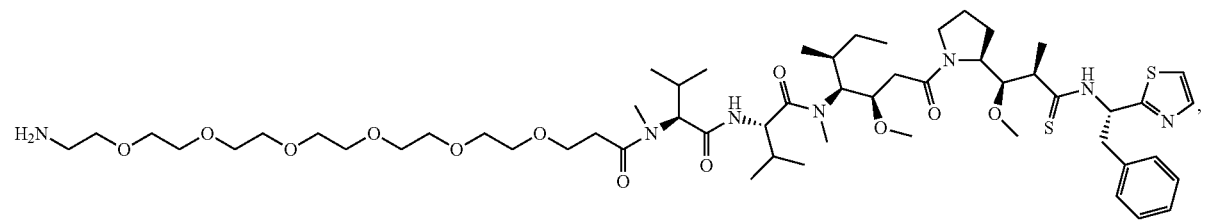

585
586
-continued
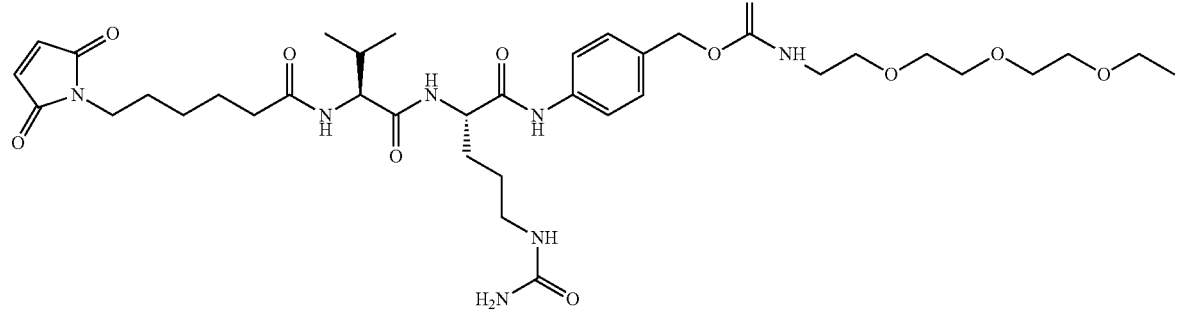
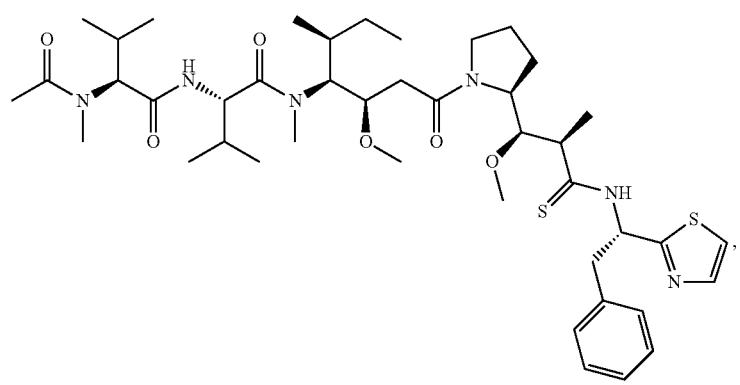
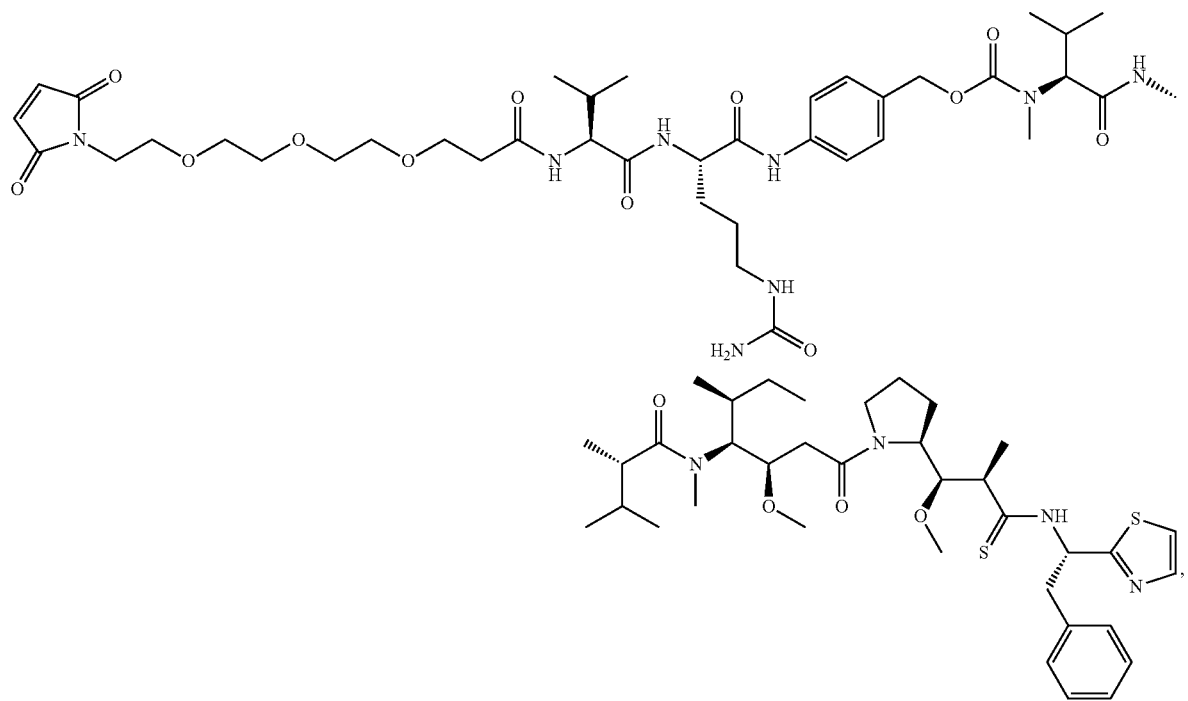

-continued
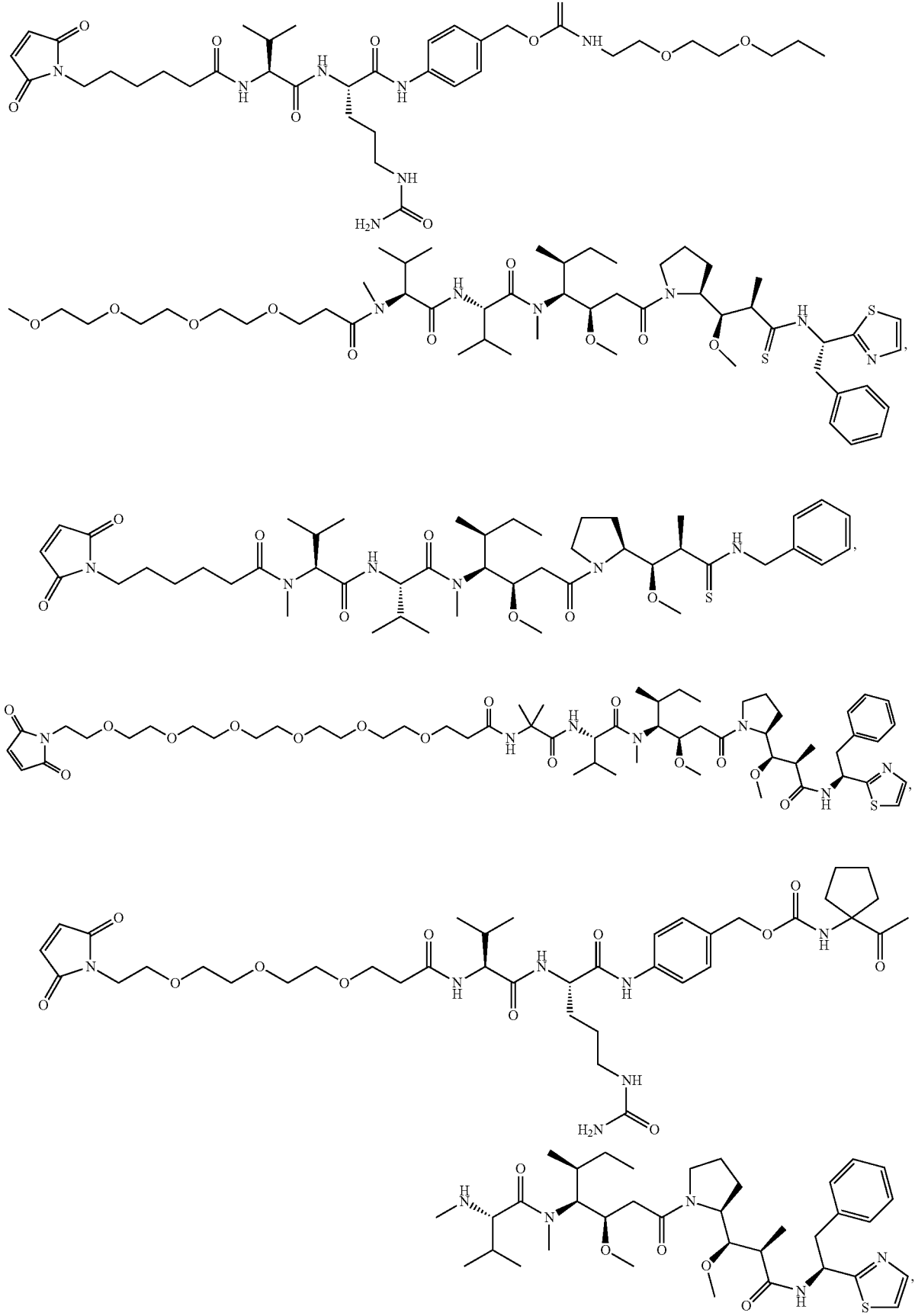

-continued
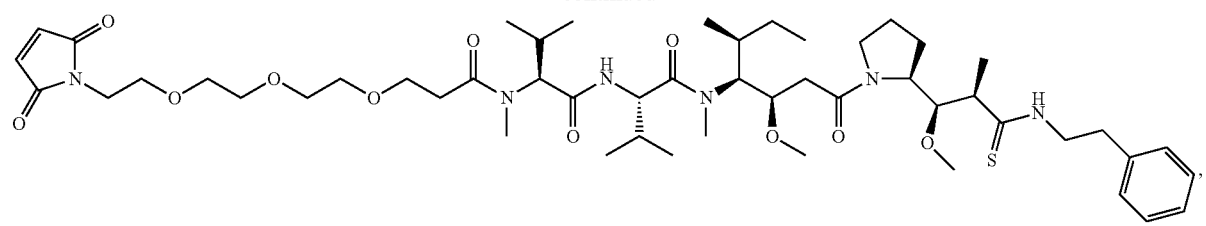
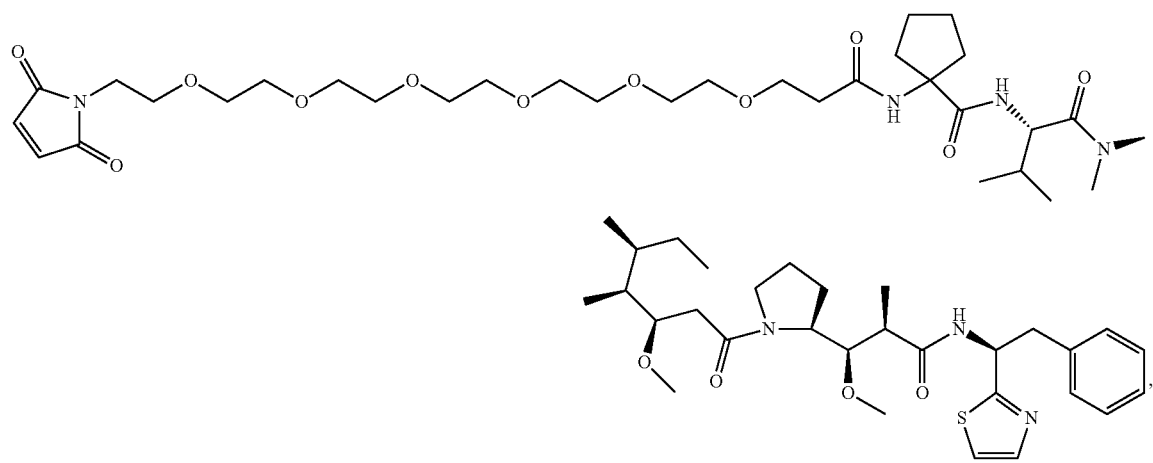
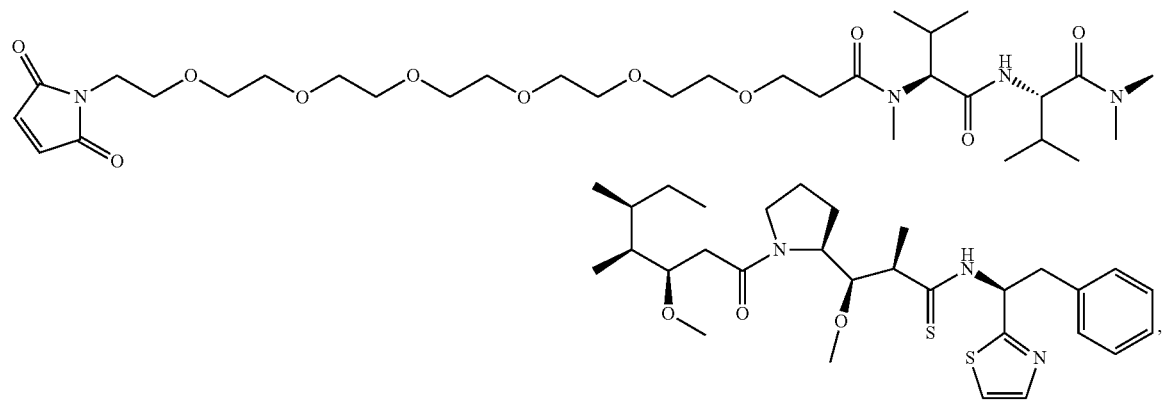
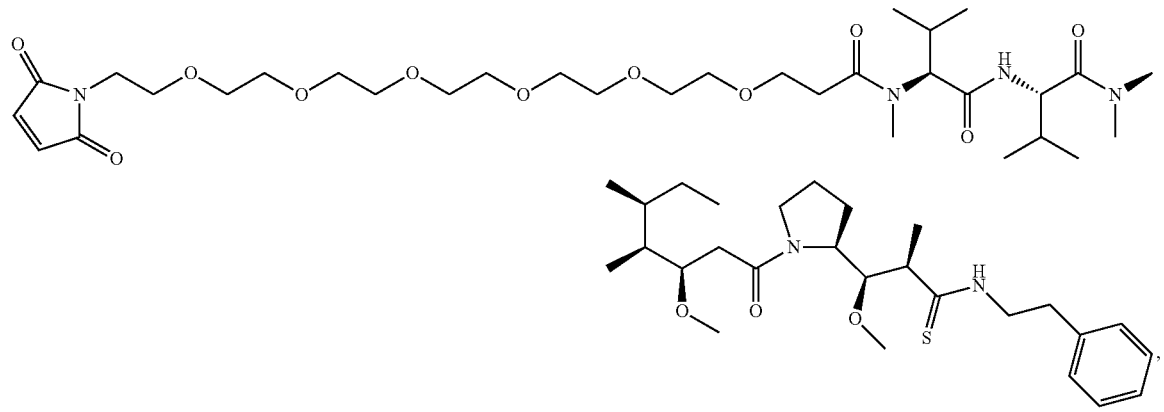

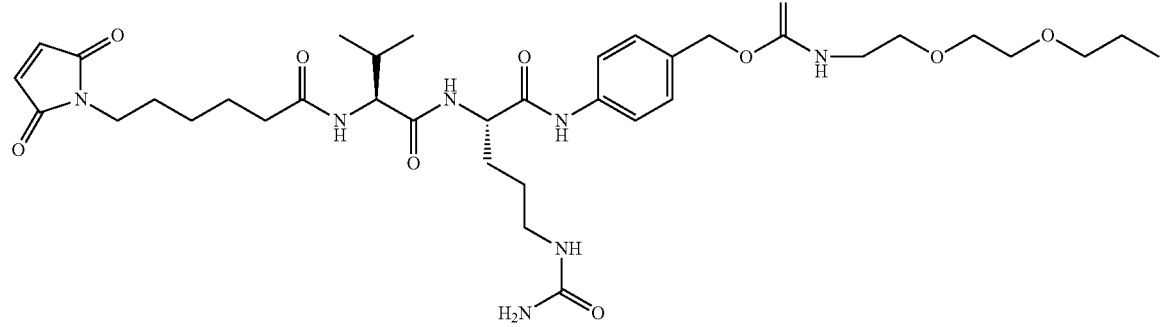
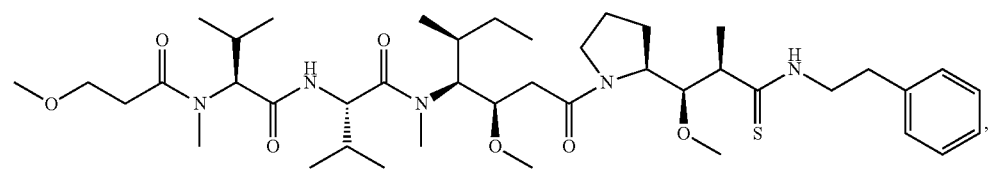
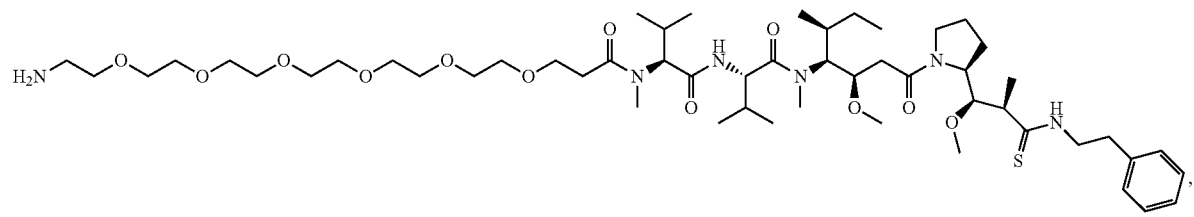
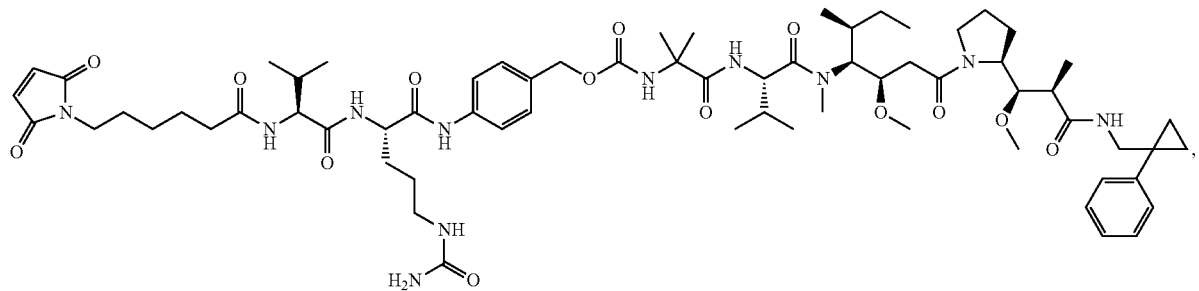
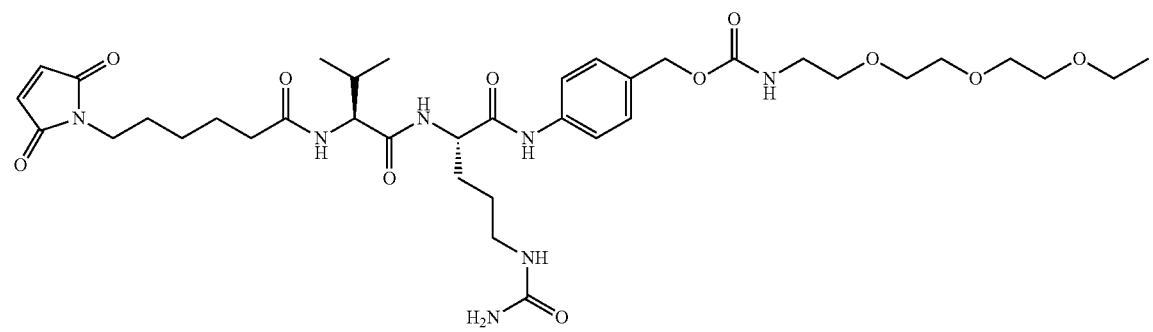
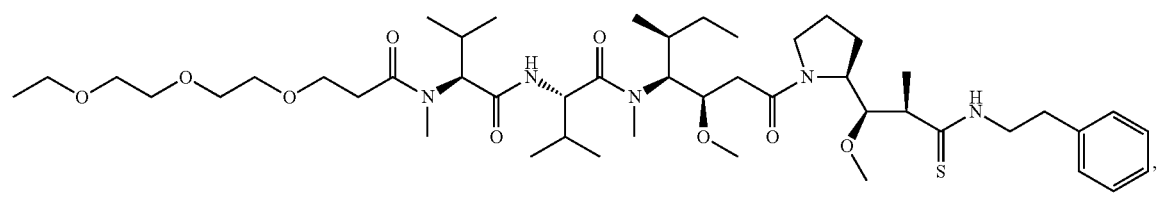

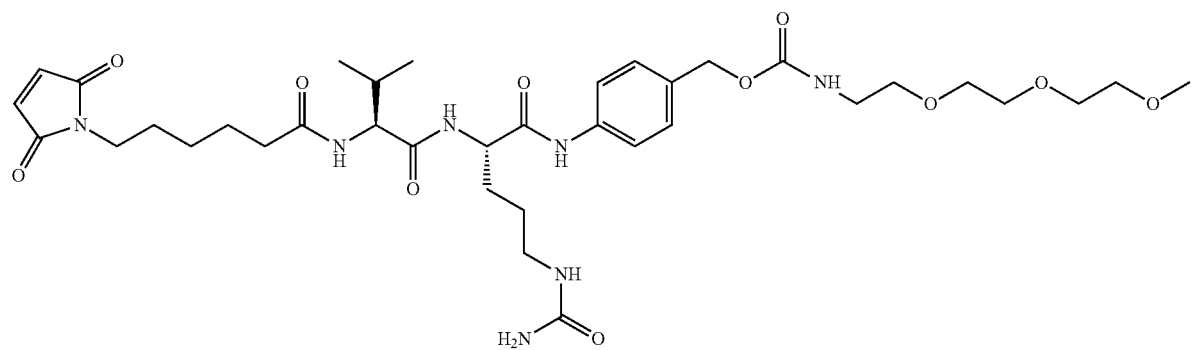
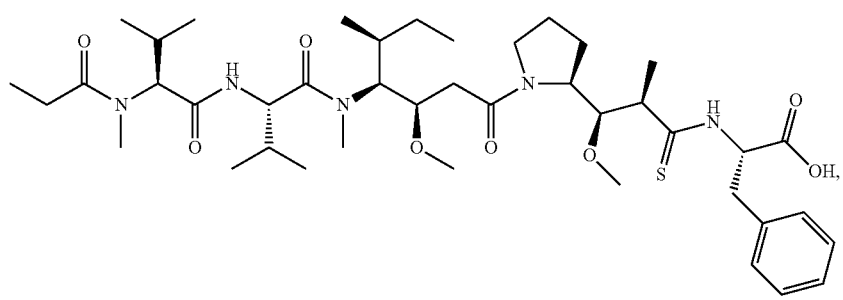
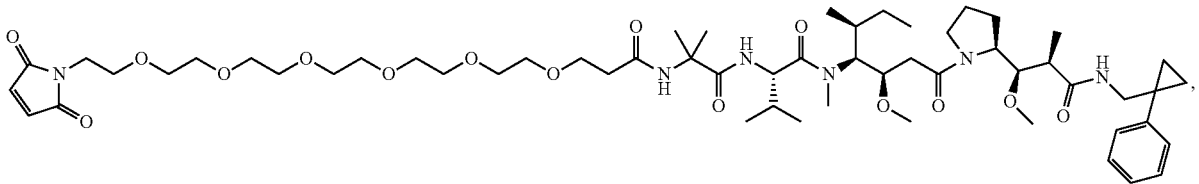
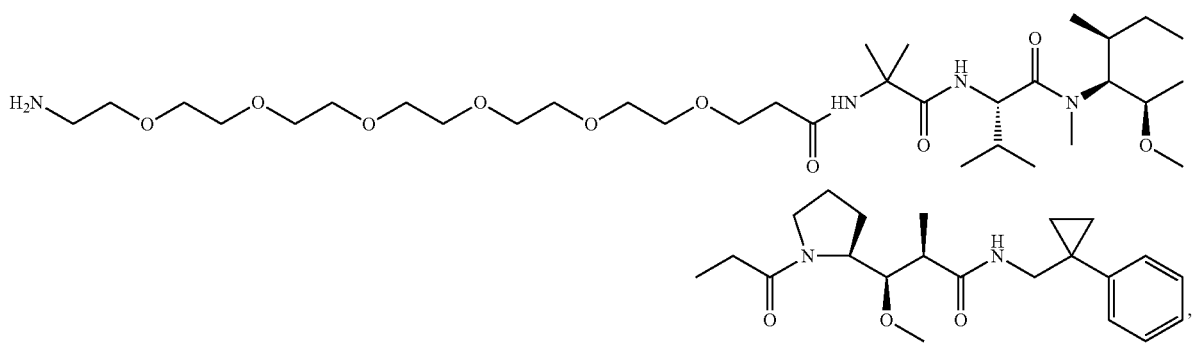
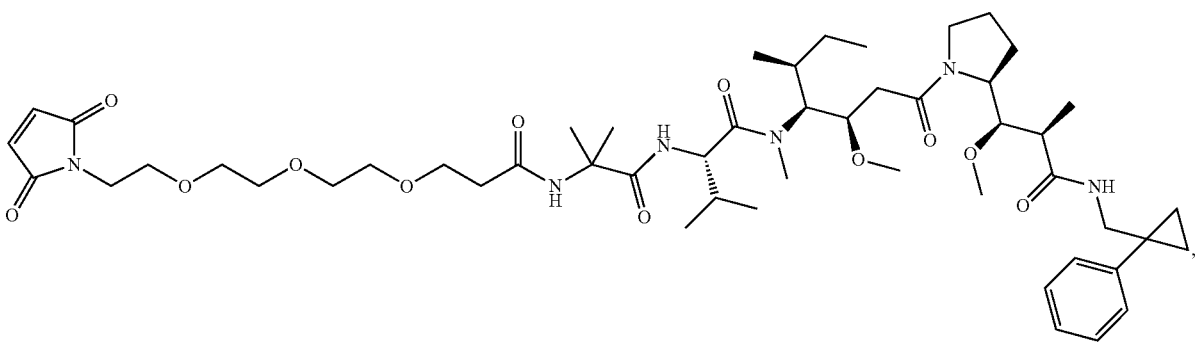

595
596
-continued
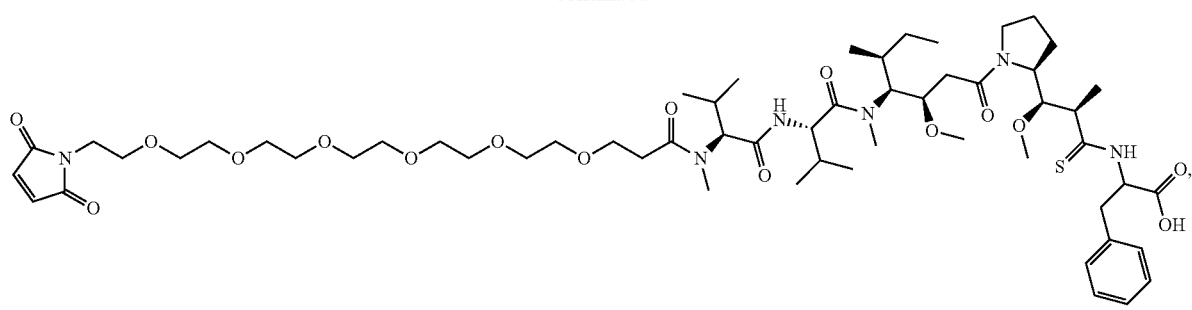
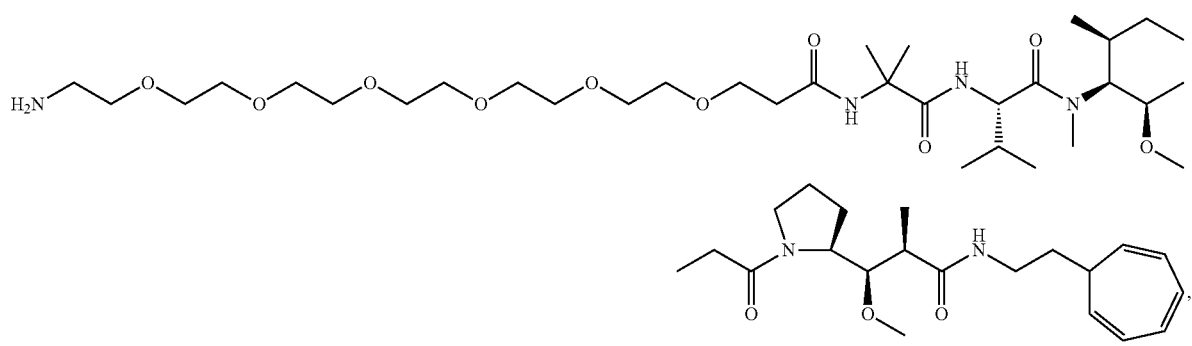
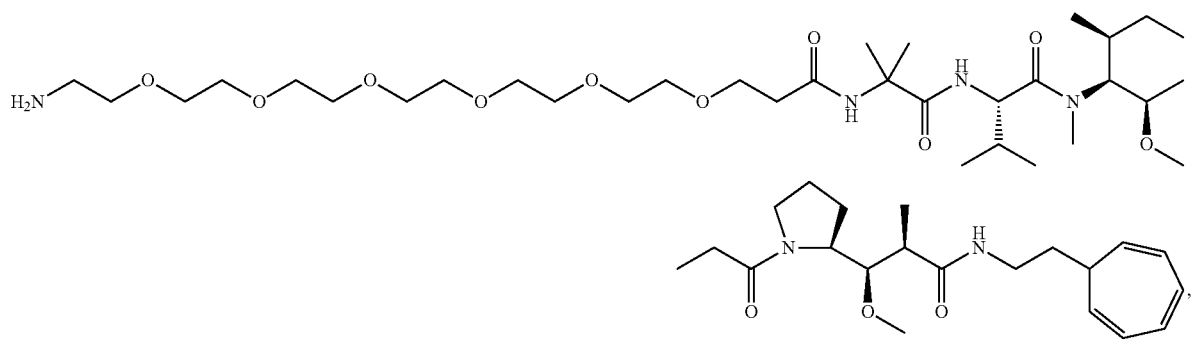
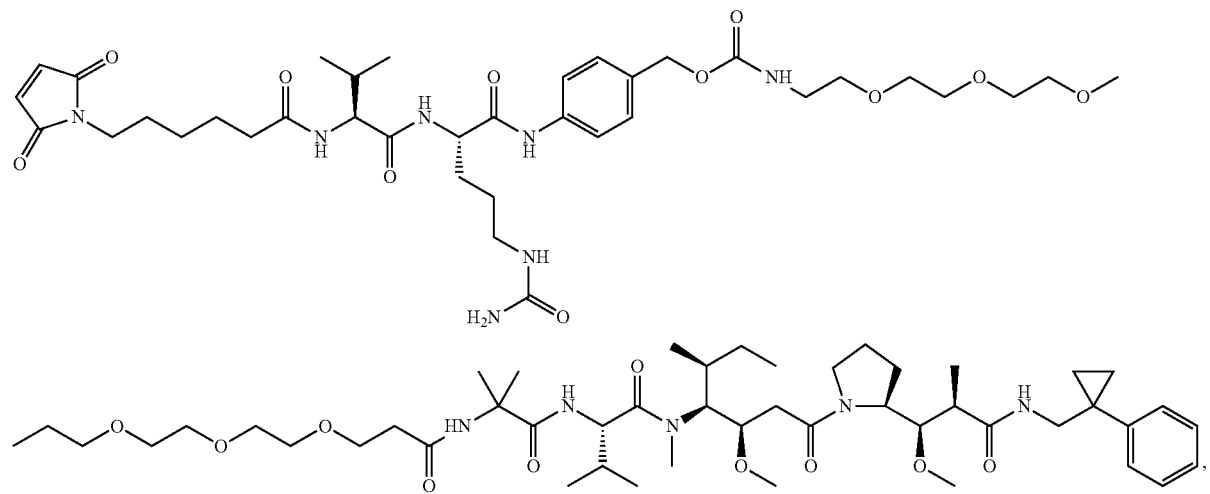

-continued
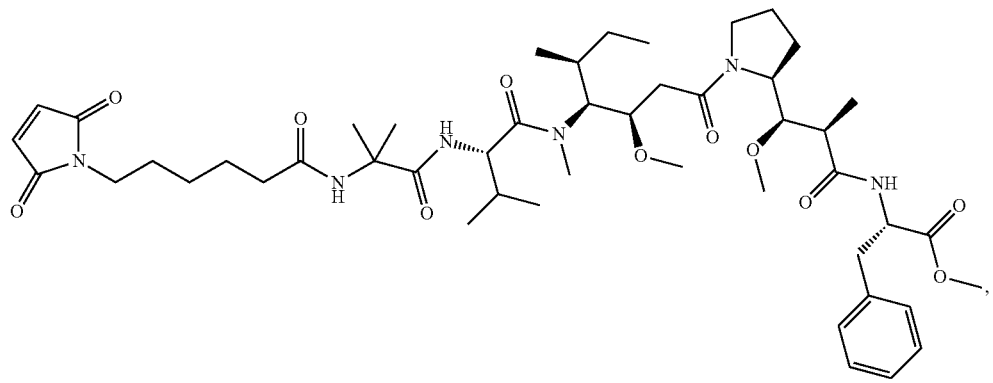
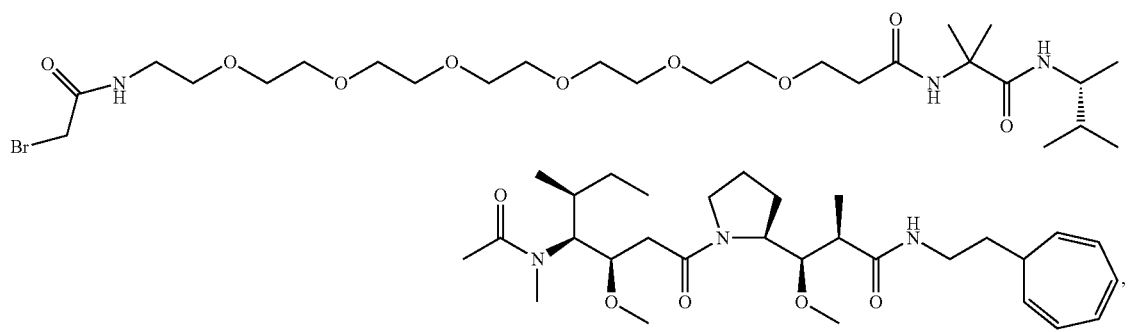
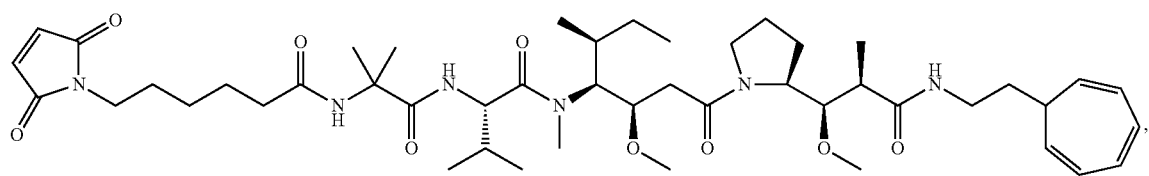
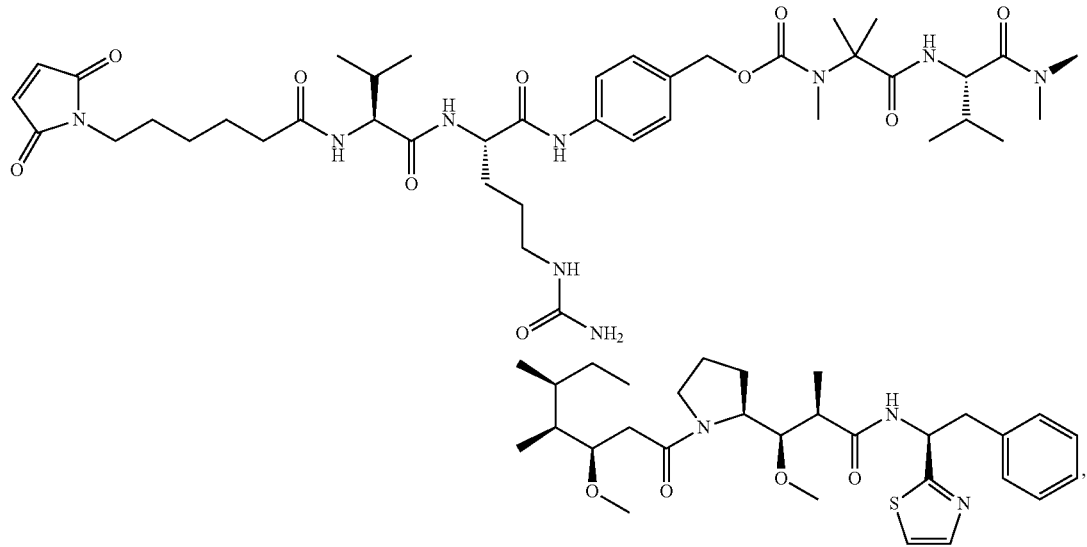

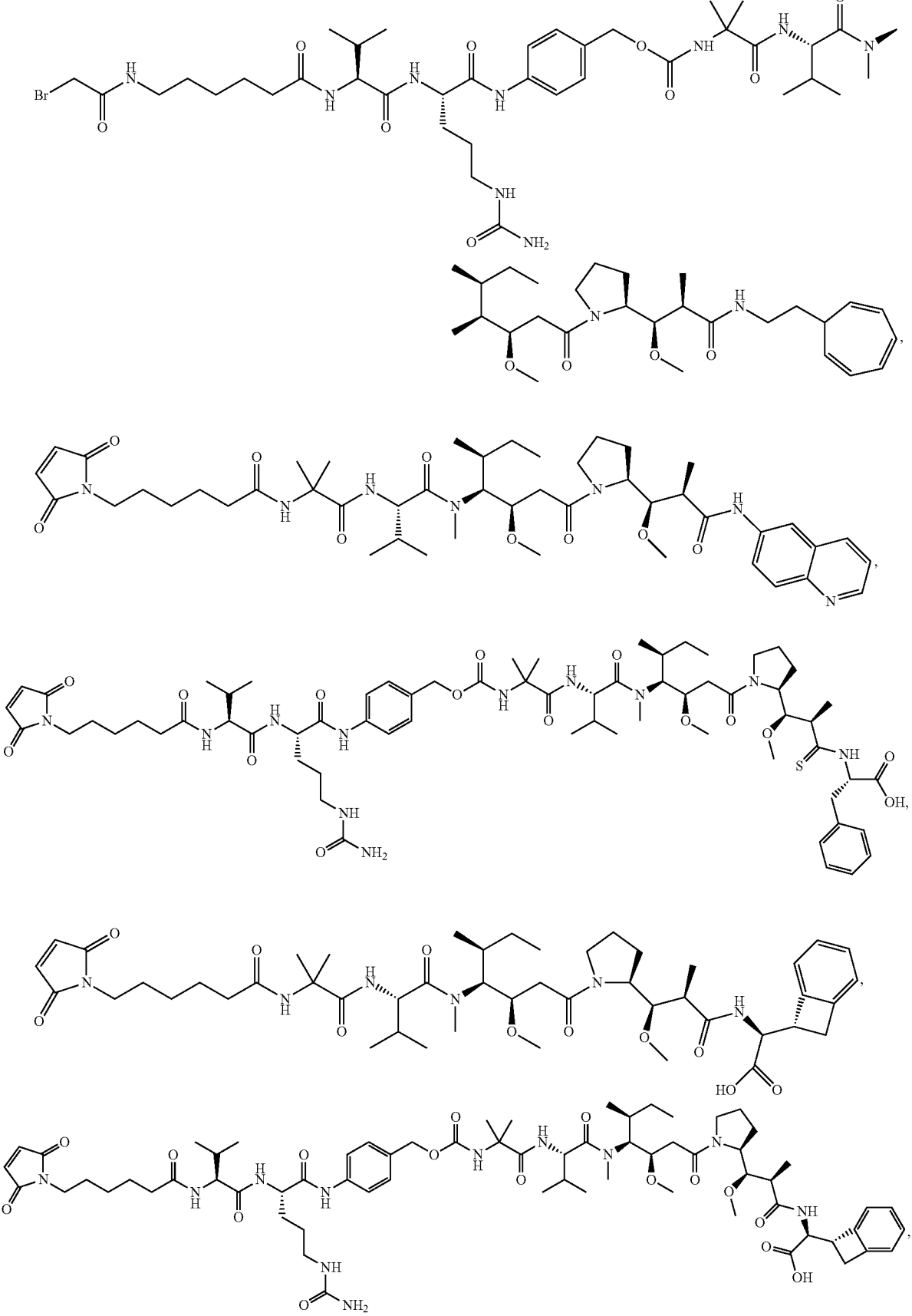

601              602
-continued
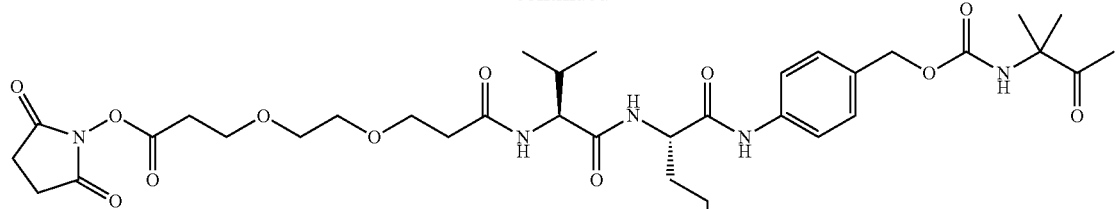
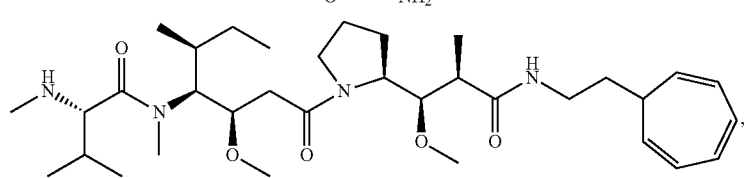
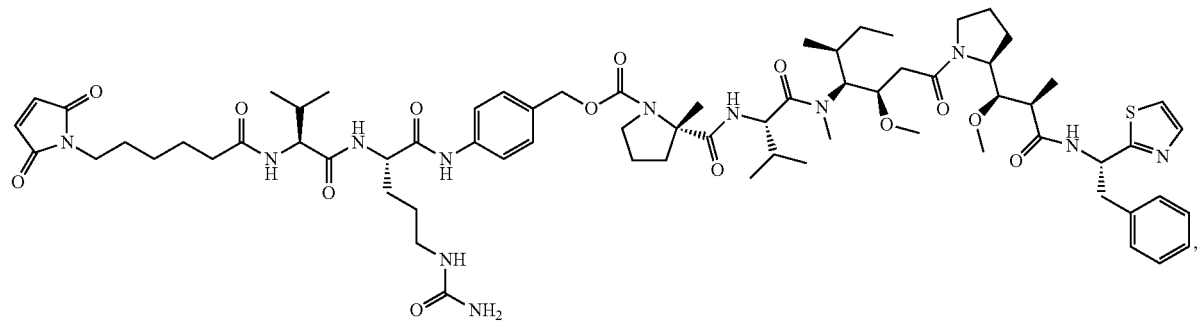
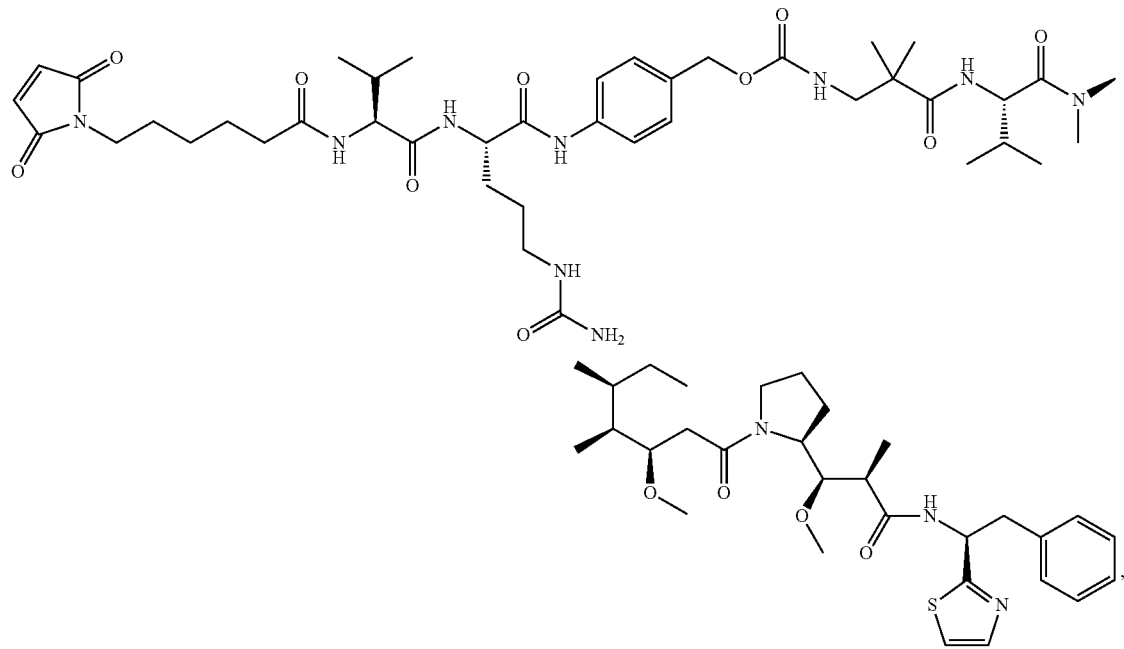

603 604
-continued
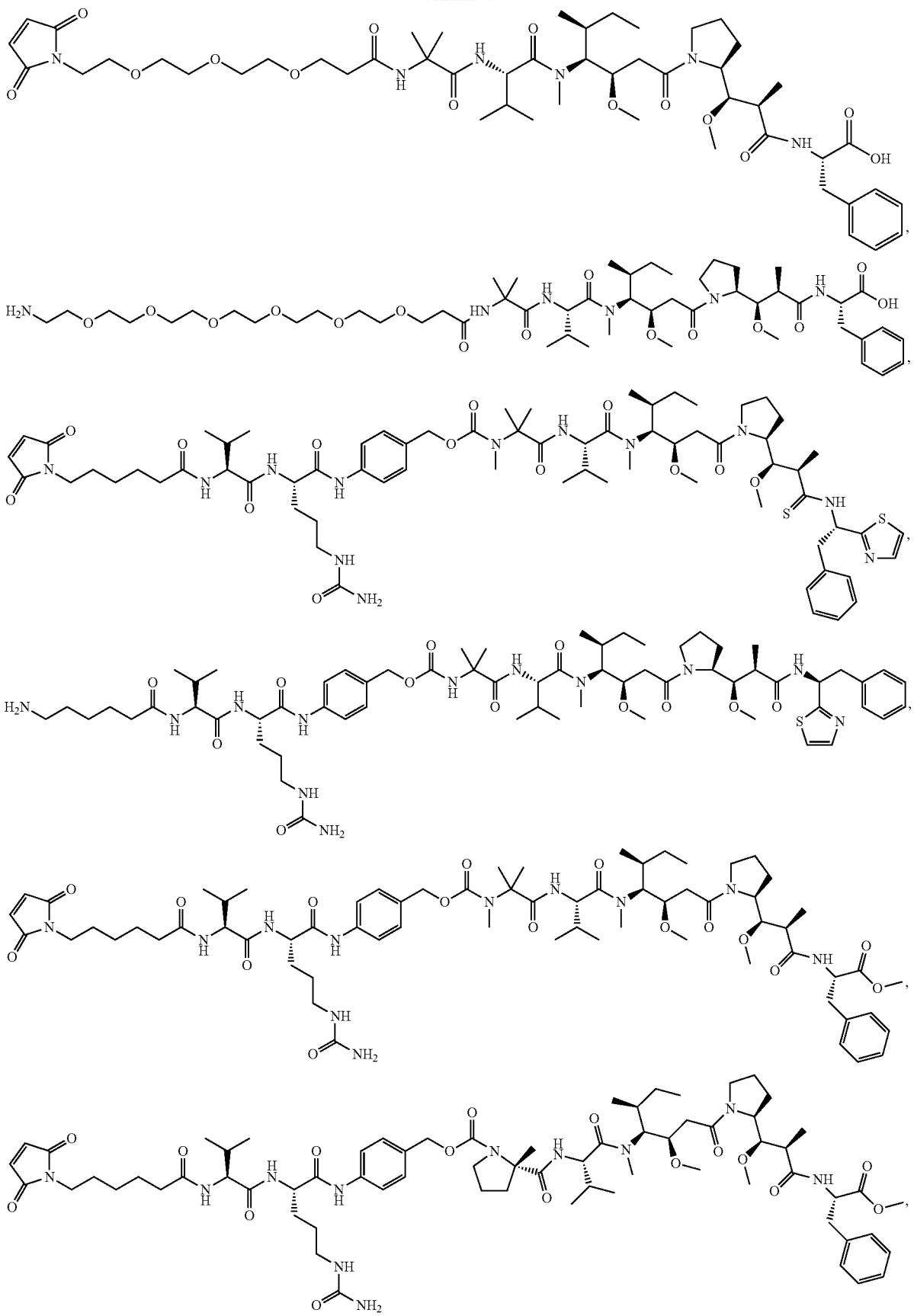

605 606
-continued
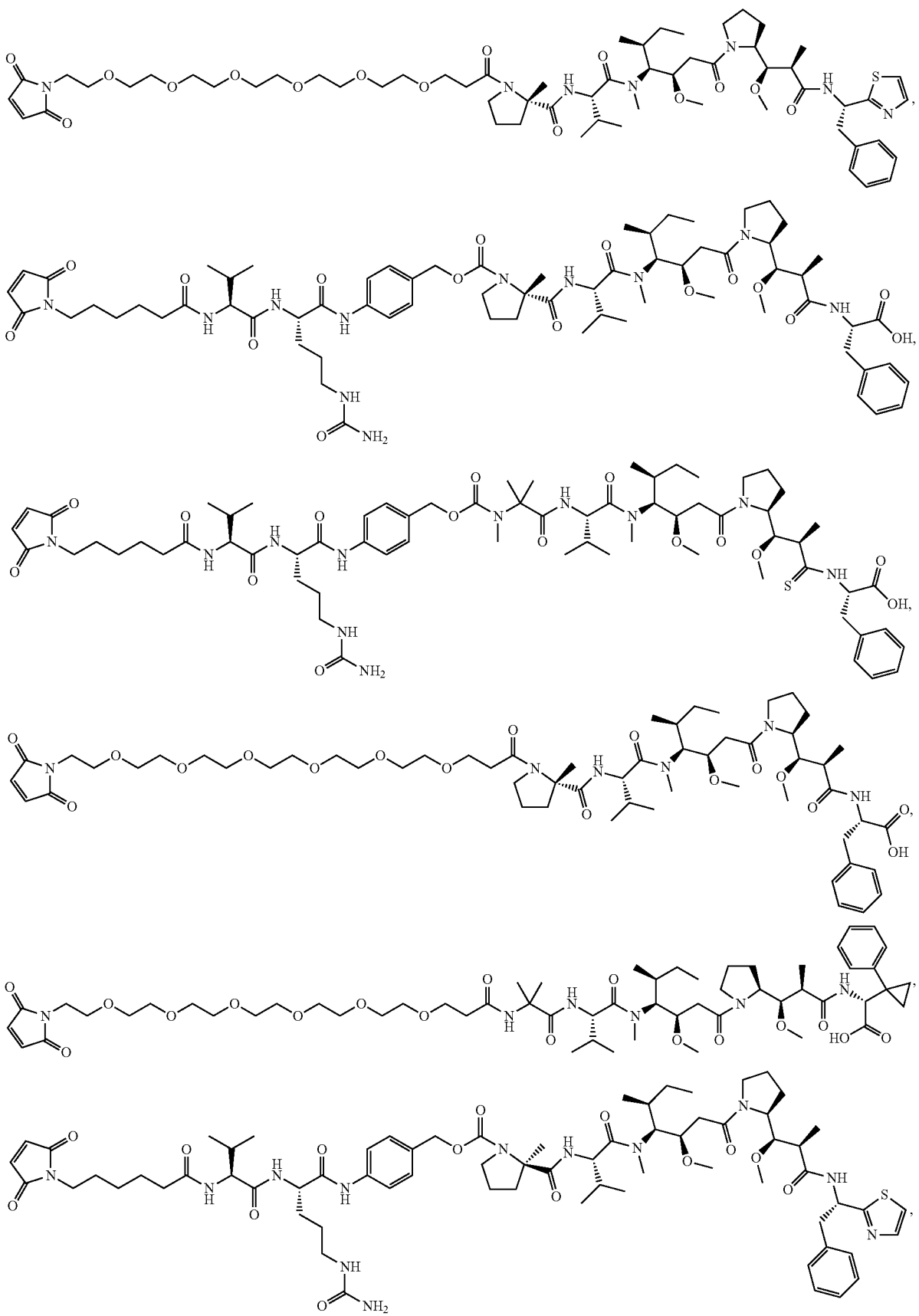

607 608
-continued
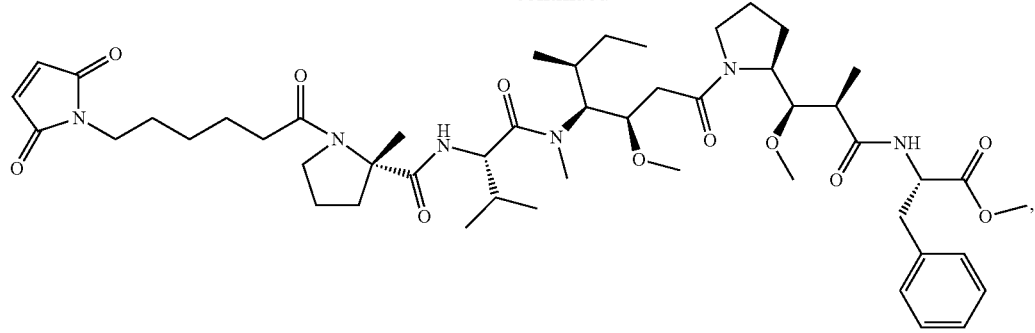
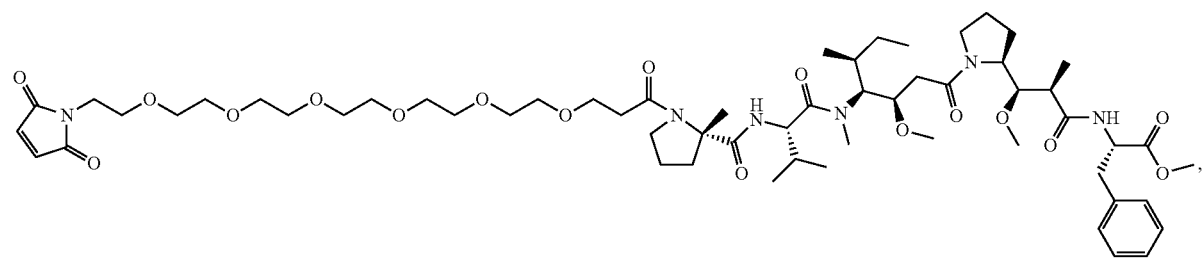
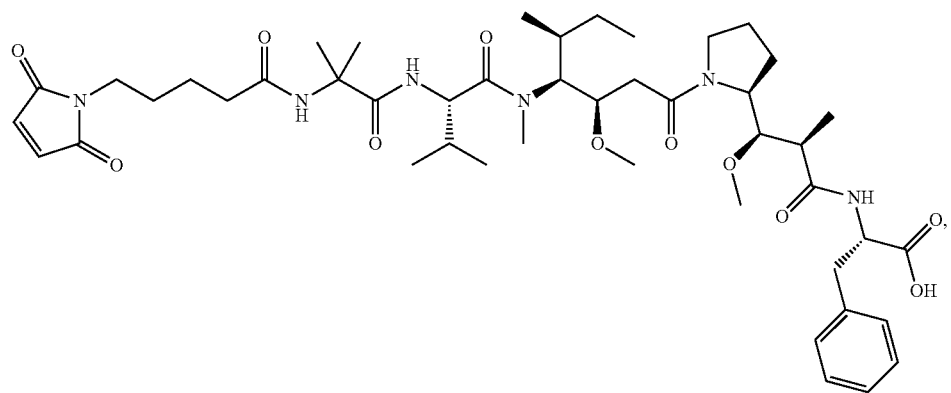
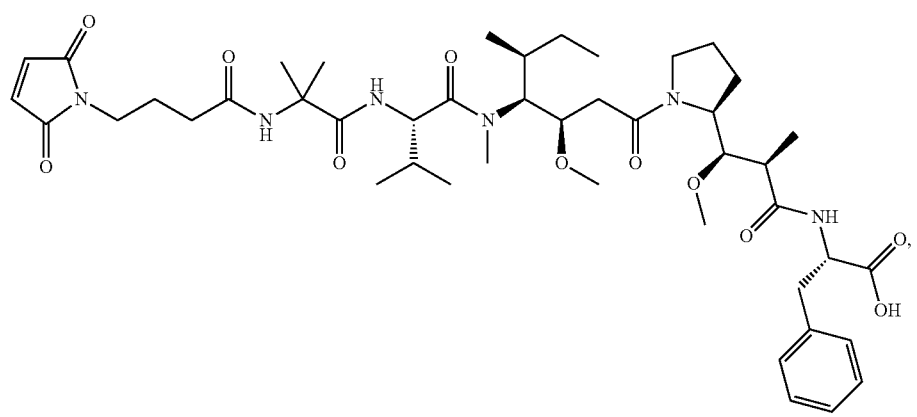

609
610
-continued
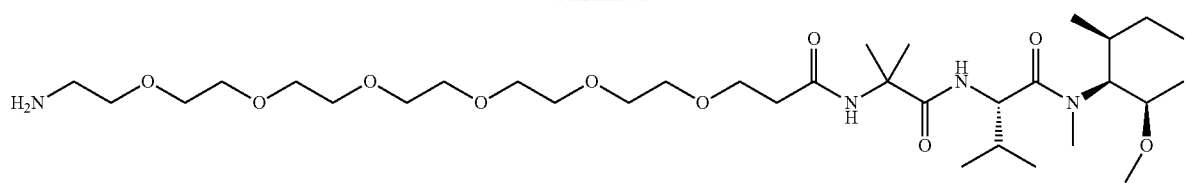
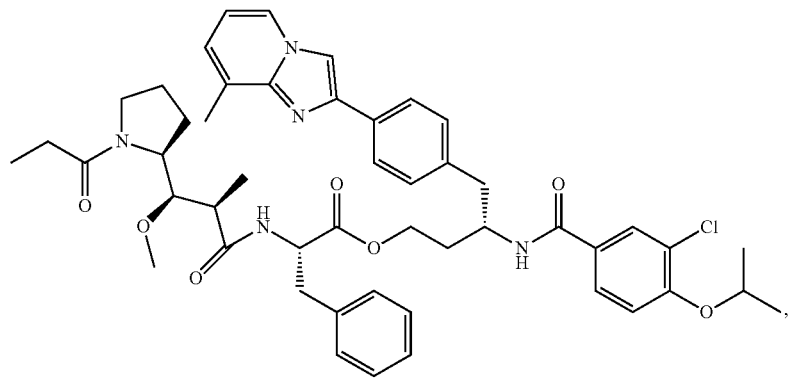
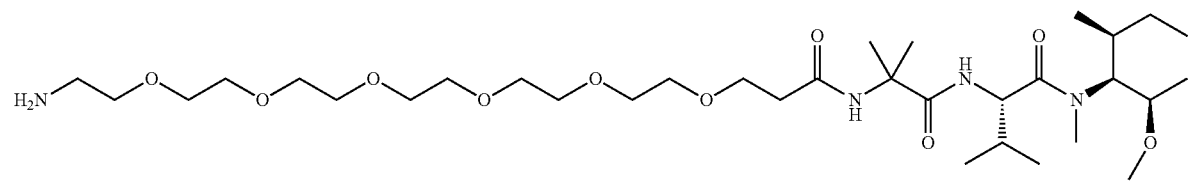
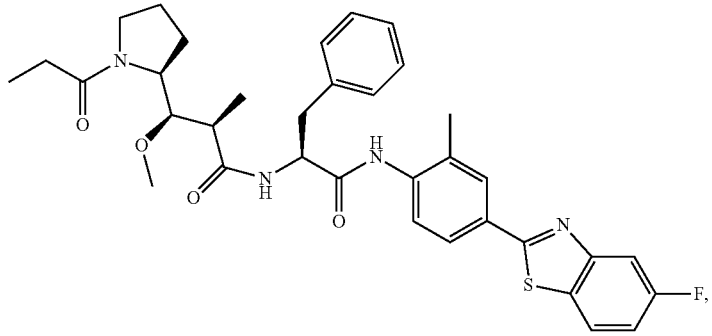
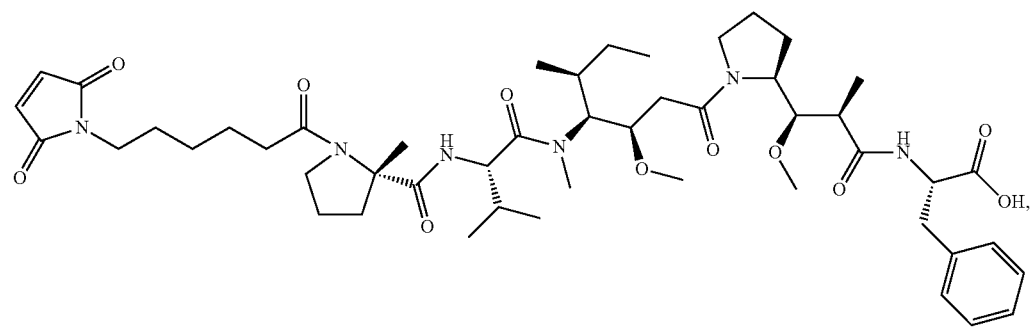

611 612
-continued
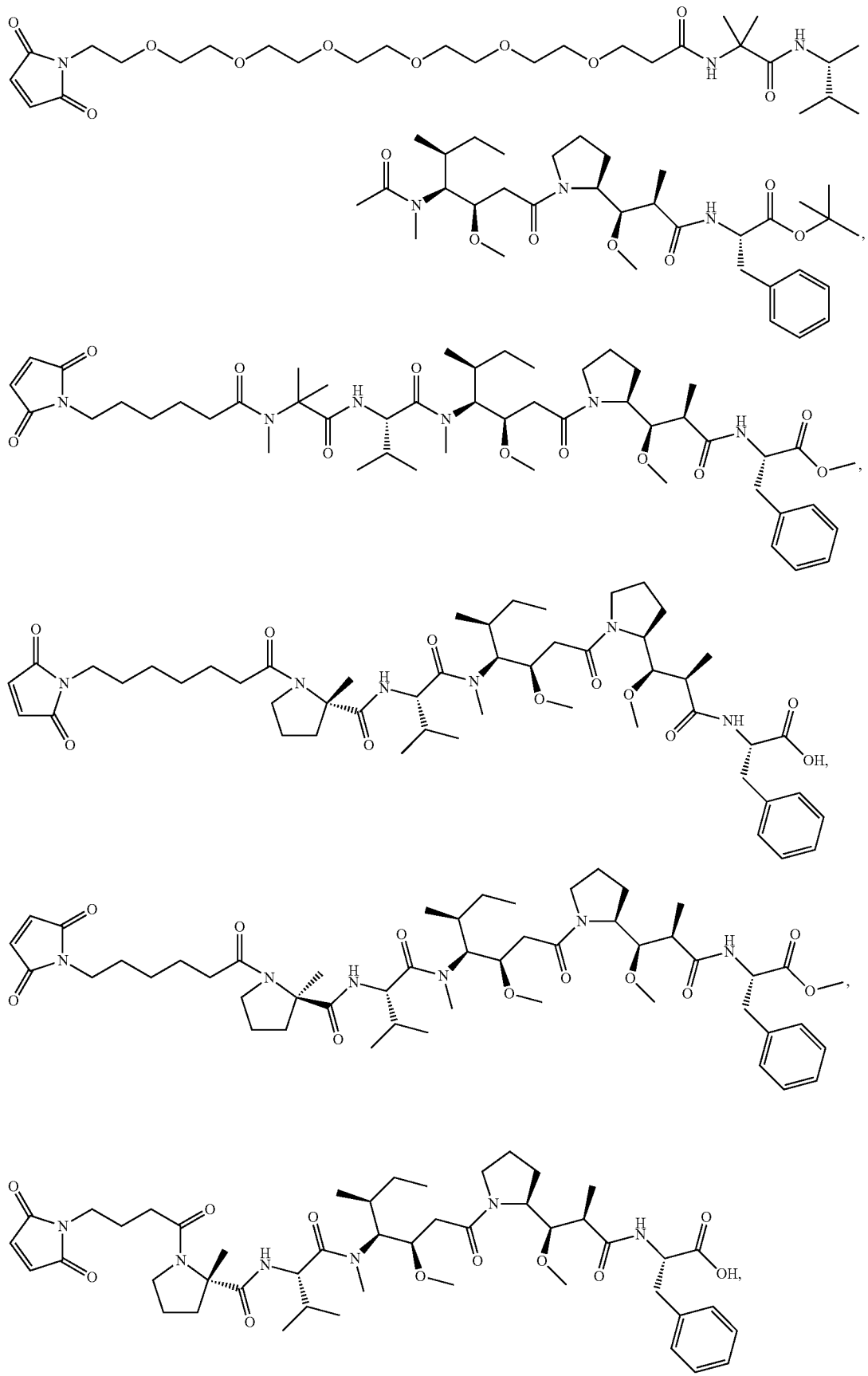

613 614
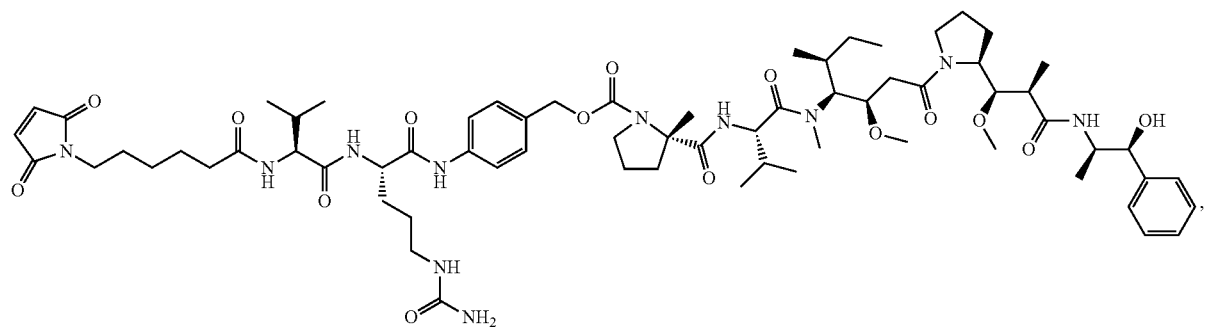
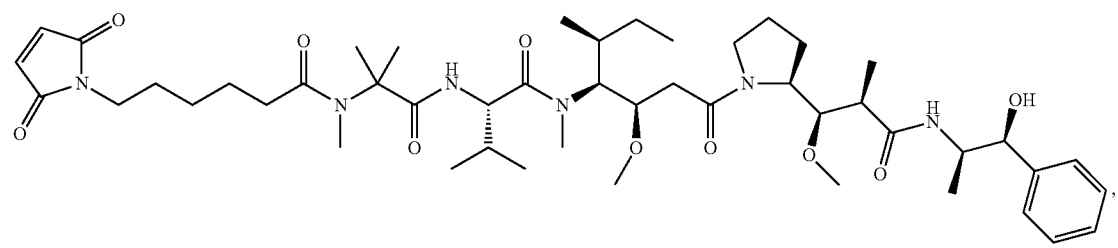
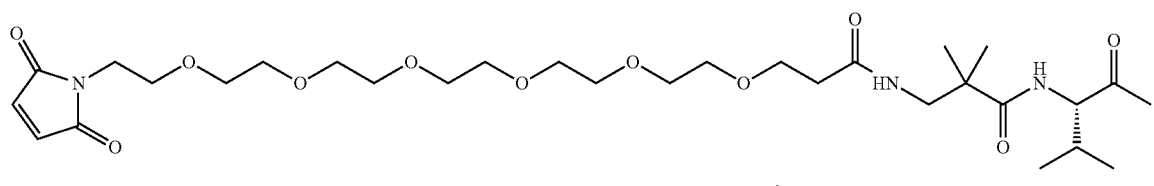
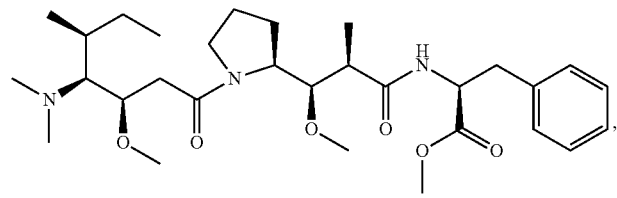
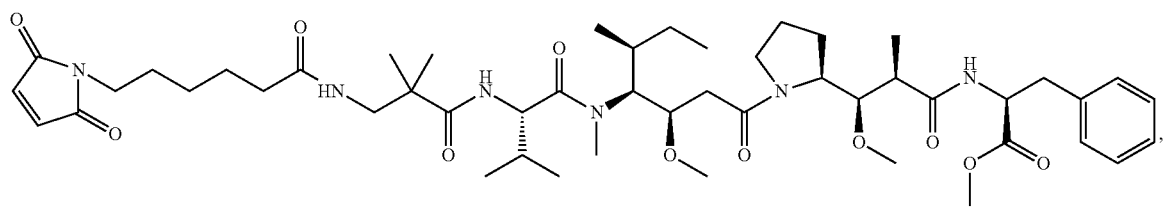
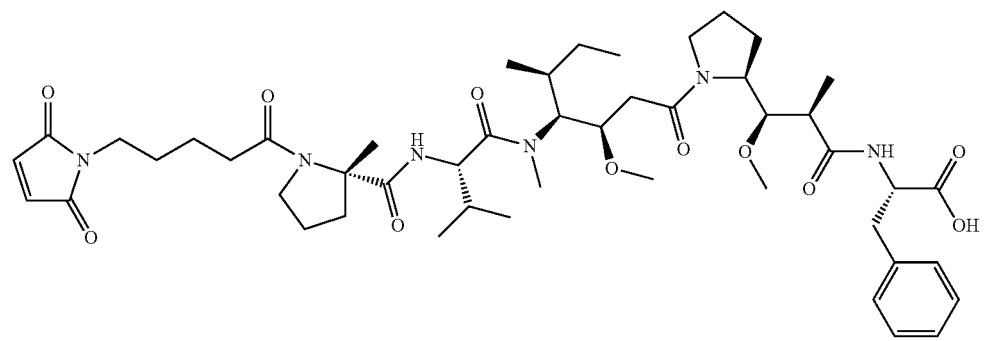

615 616
-continued
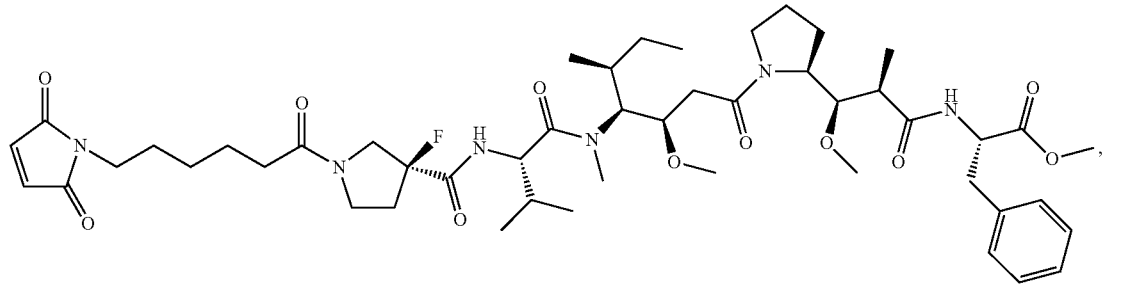
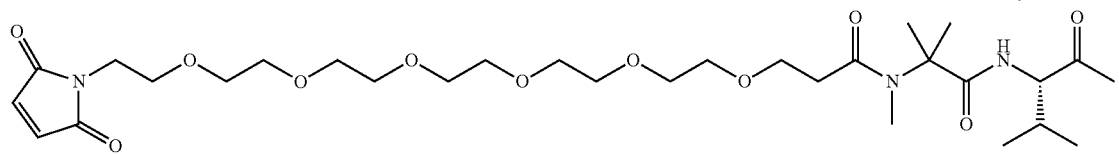
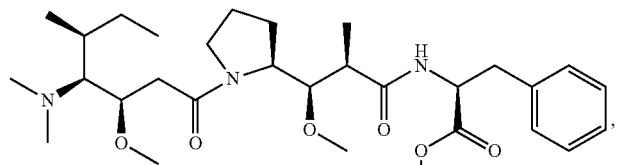
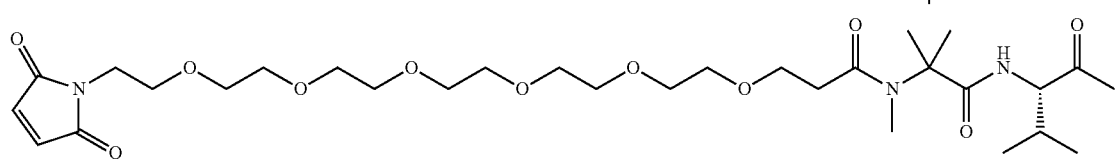
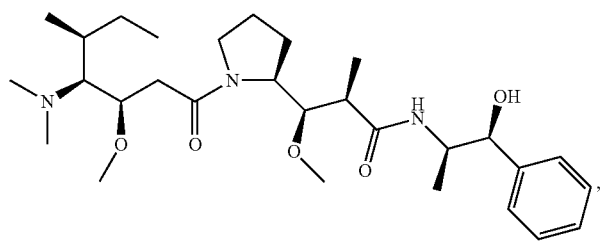
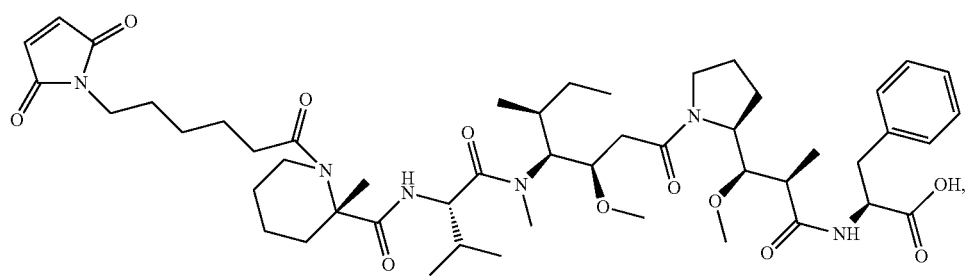
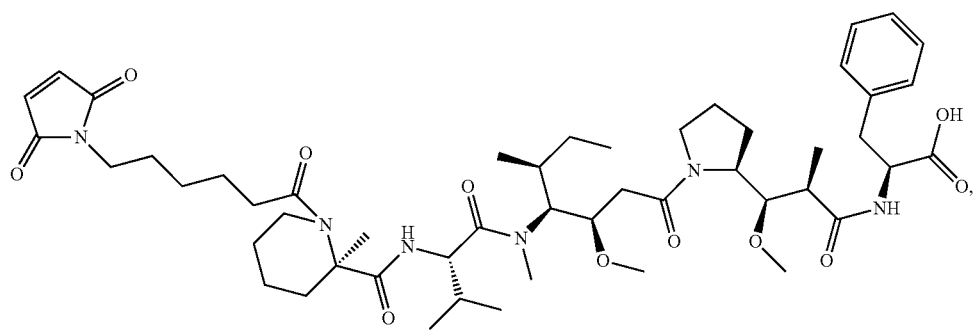

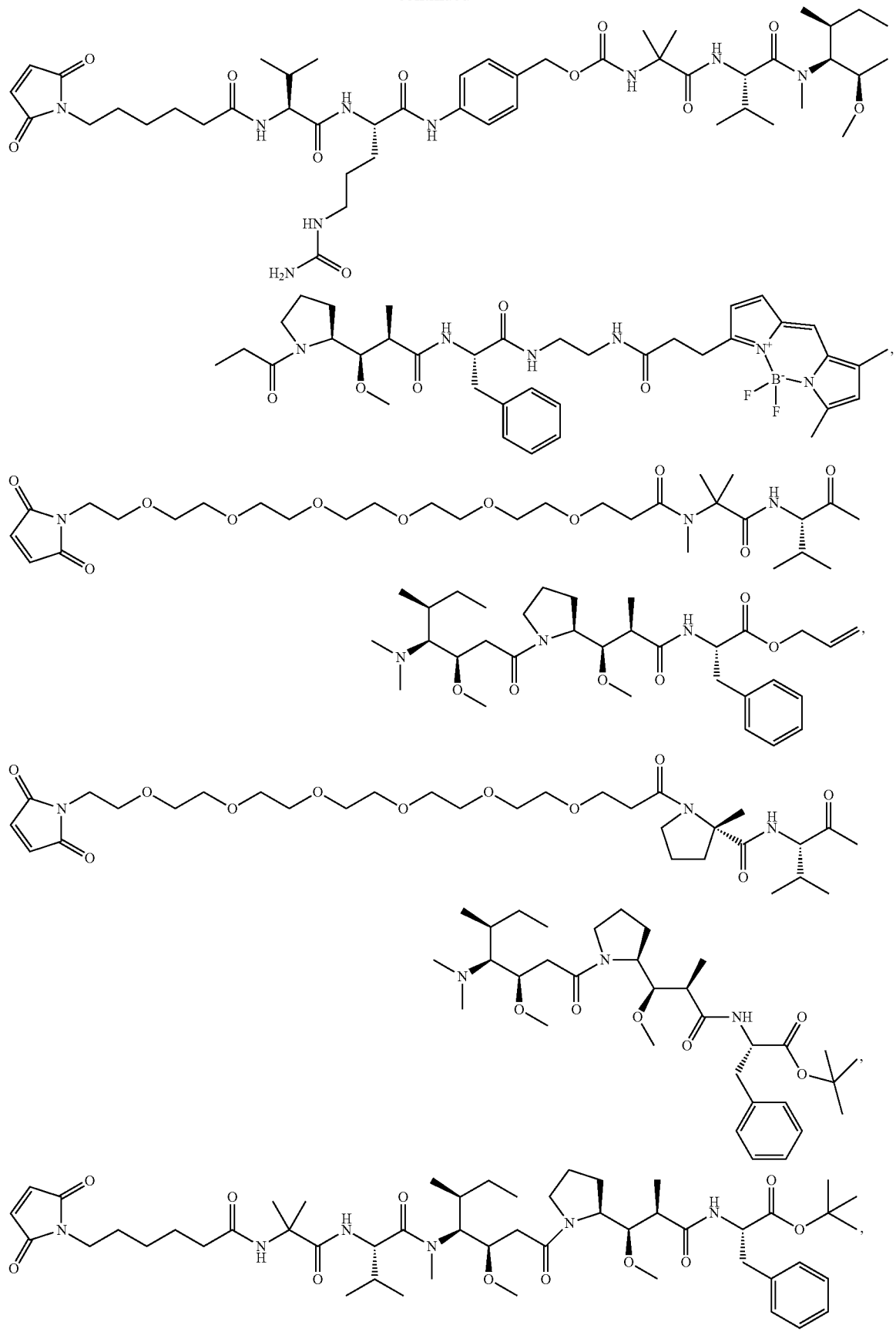

619
-continued
620
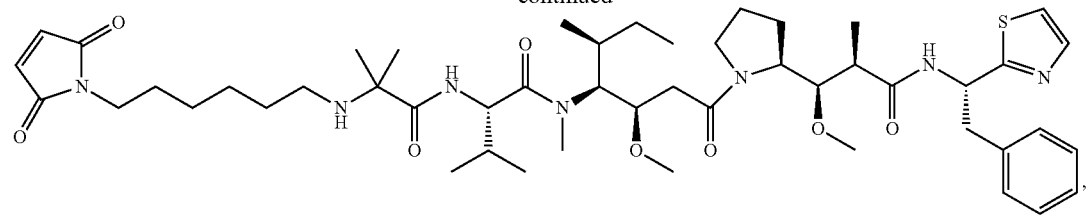
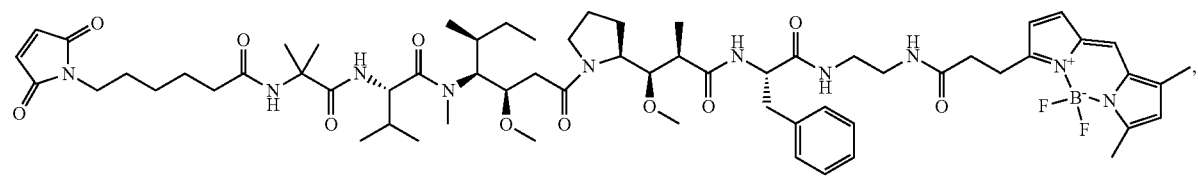
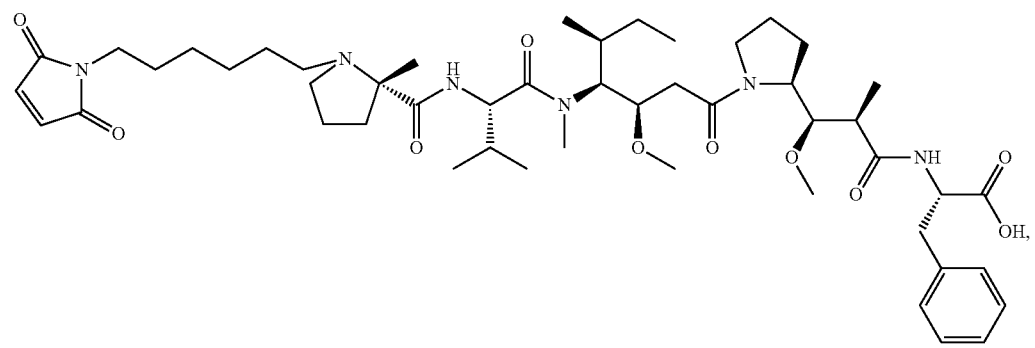
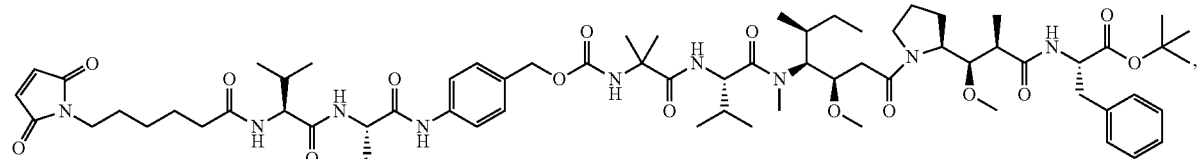
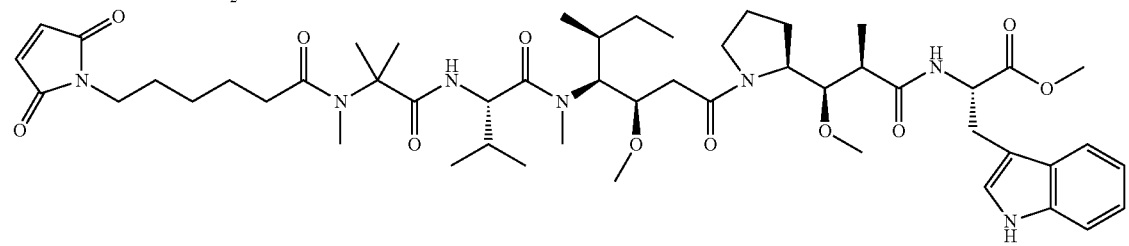
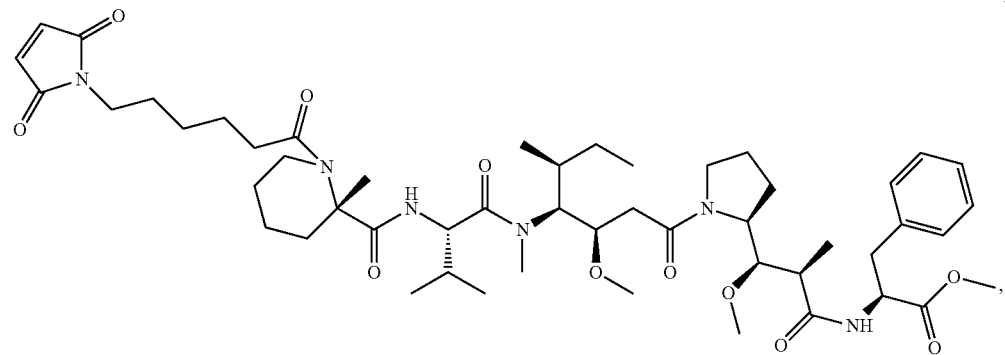

621 -continued 622
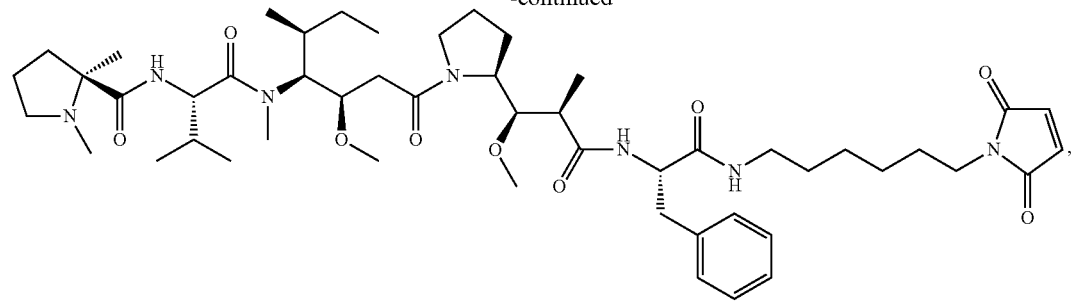
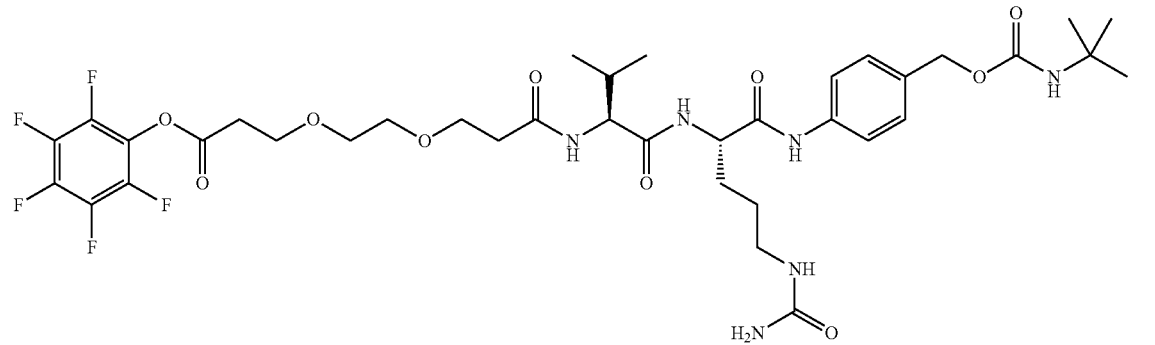
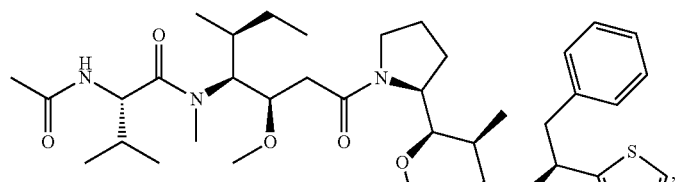
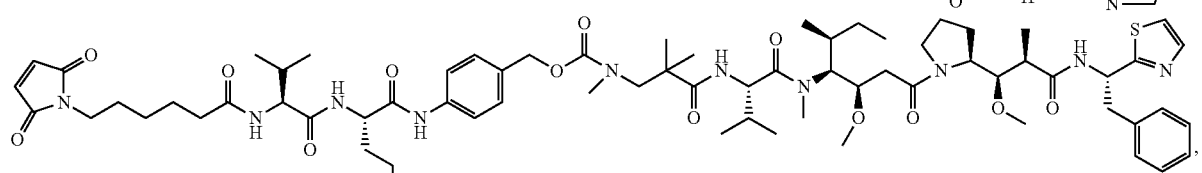
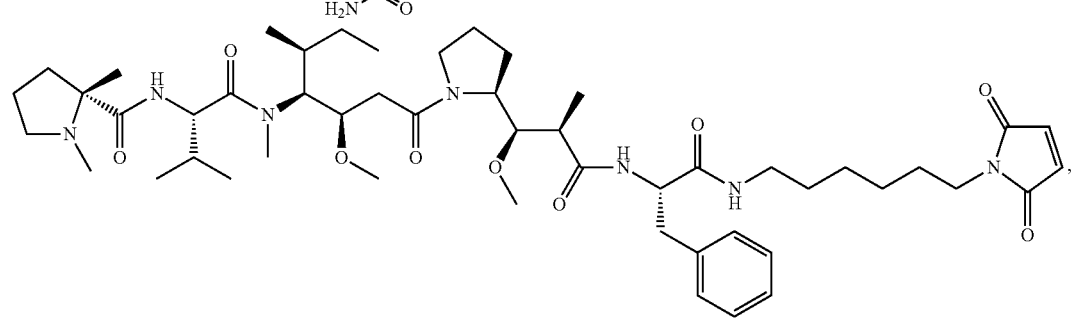
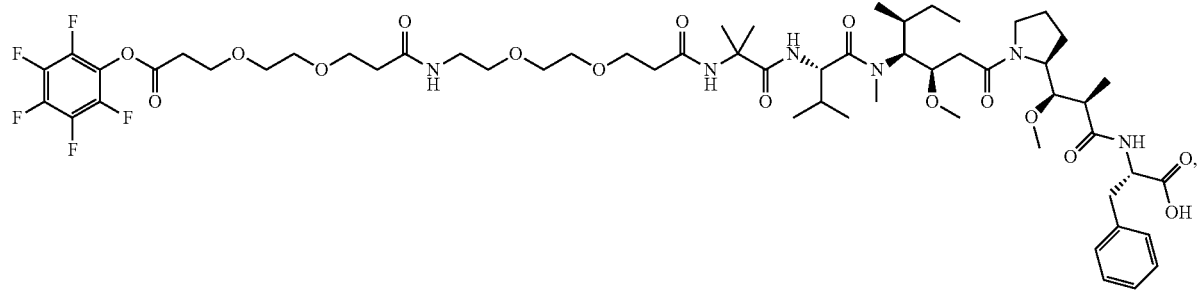

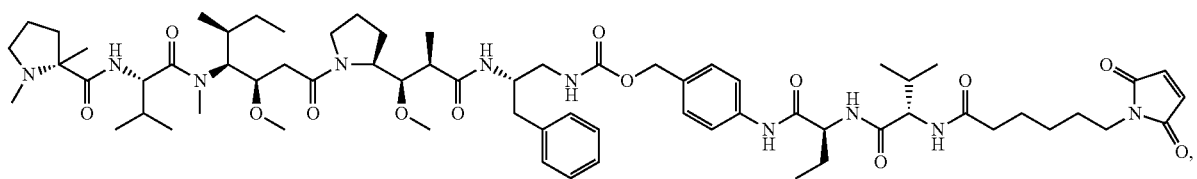
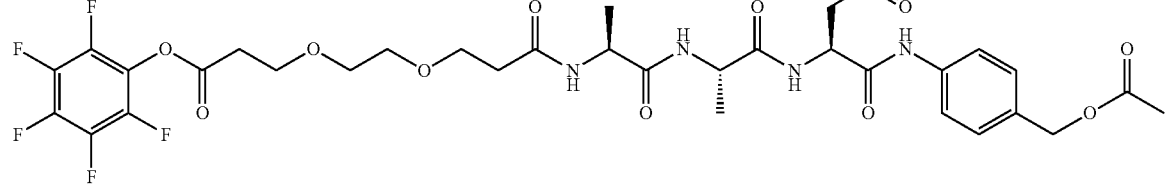
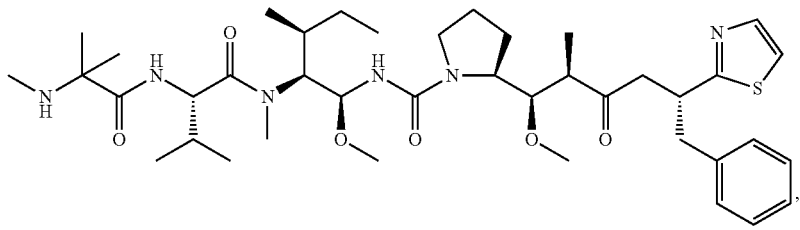
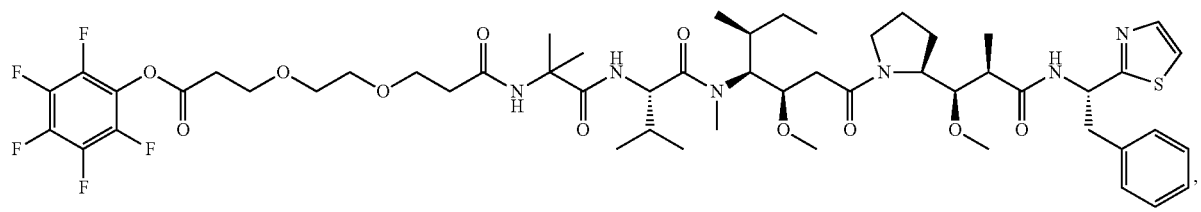
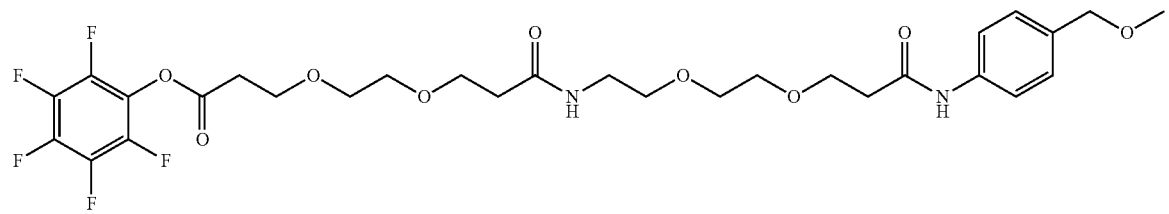
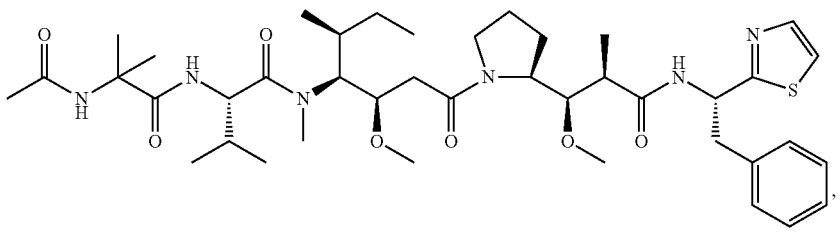
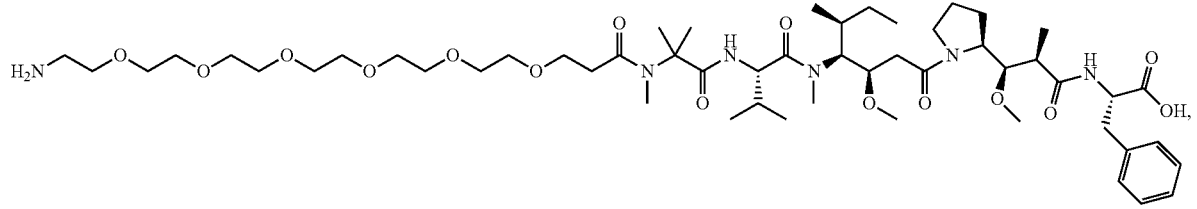

625 626
-continued
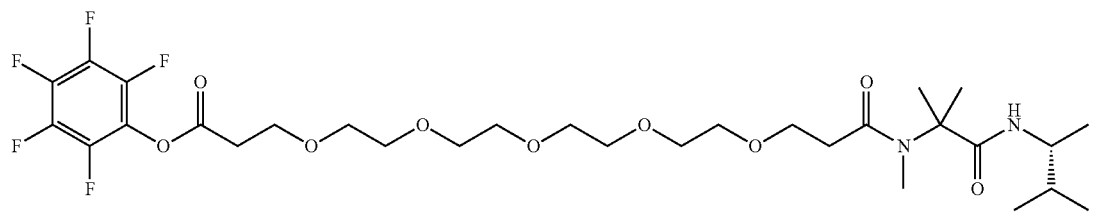
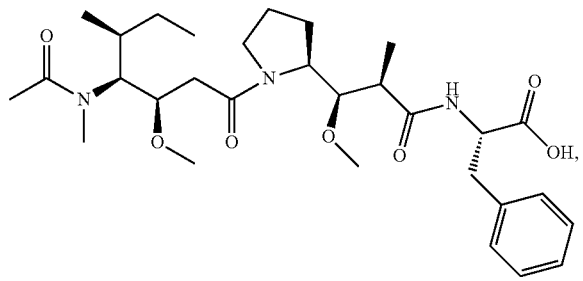
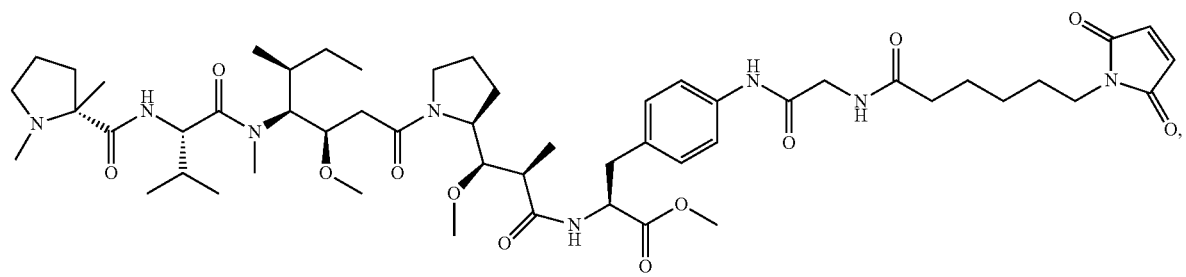
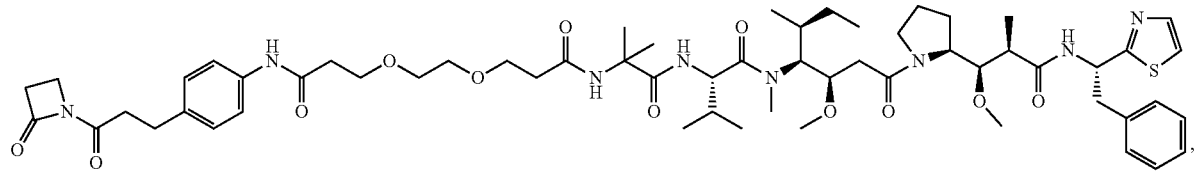
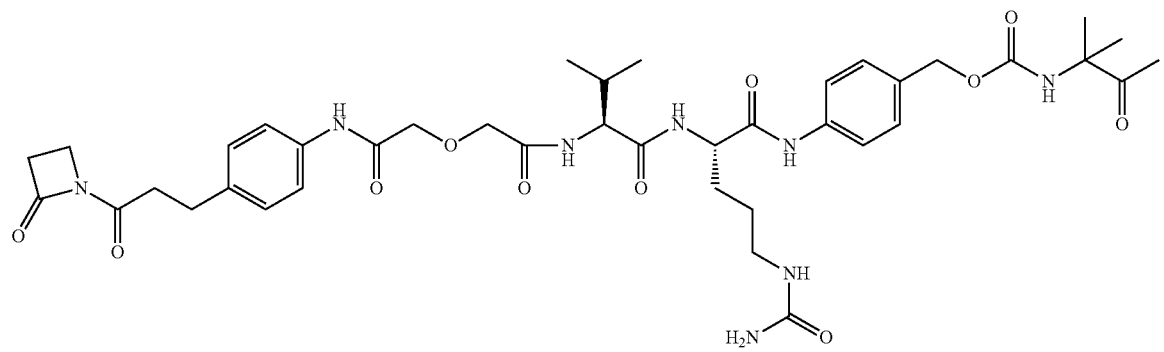
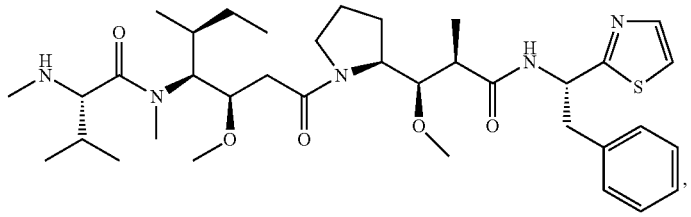

-continued

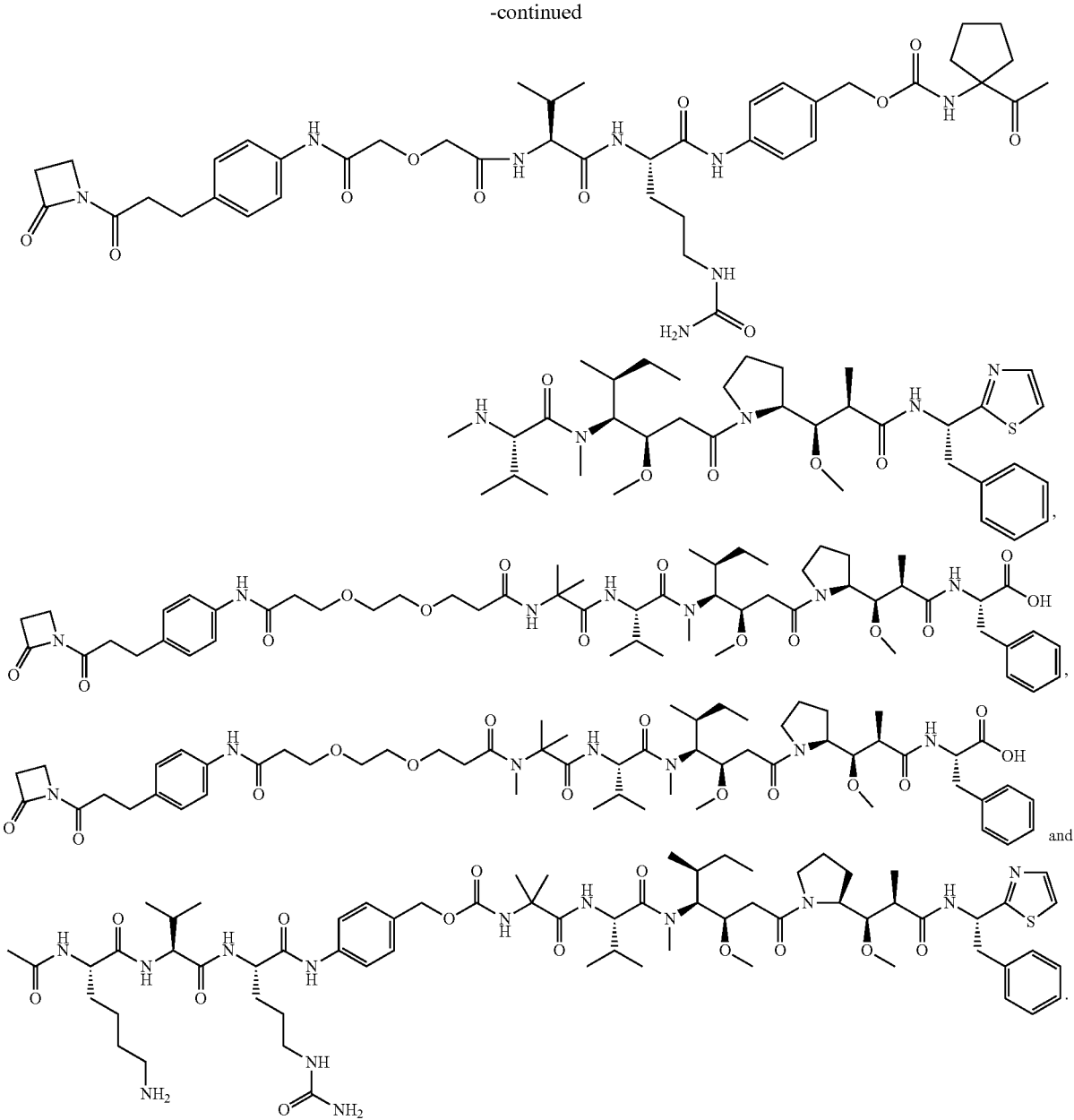

27. An antibody-drug-conjugate comprising a radical of a compound of any one of claims 22, 23, 24, 25, or 26.

28. A pharmaceutical composition comprising a compound of claim 1, or a pharmaceutically acceptable salt or solvate thereof, and pharmaceutically acceptable excipient.

29. A method of treating cancer comprising administering to a patient in need thereof a therapeutically effective amount of a compound of claim 4.

30. The compound:

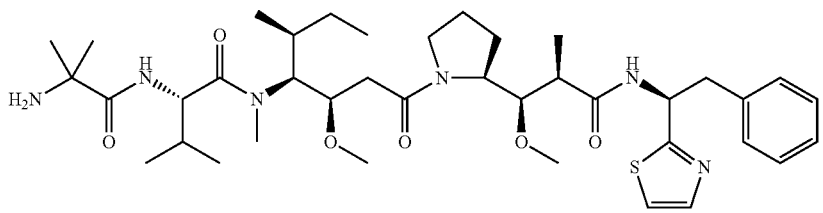 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

or a pharmaceutically acceptable salt or solvate thereof.

31. The compound:

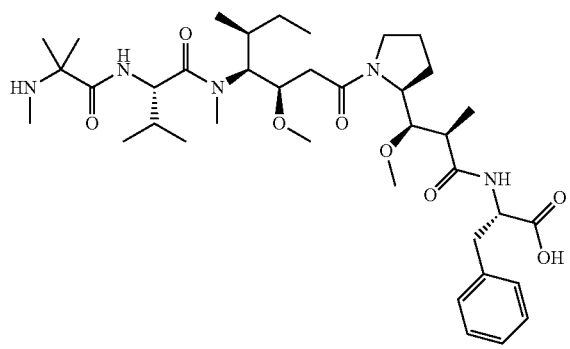 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

or a pharmaceutically acceptable salt or solvate thereof.

32. The compound:

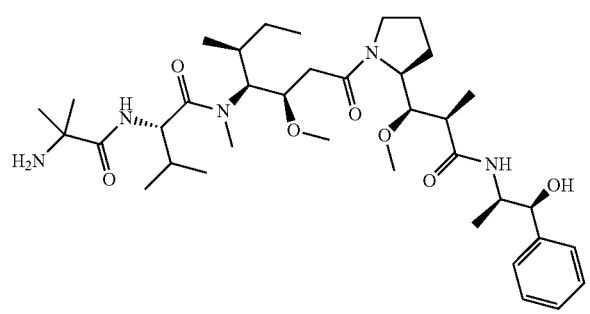 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)N)C(C)C]

or a pharmaceutically acceptable salt or solvate thereof.

33. The compound:

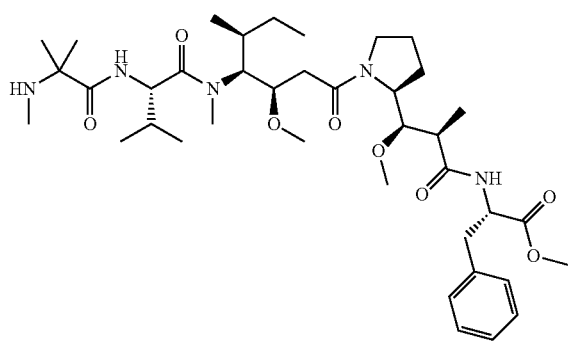 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)C(C)(C)NC)C(C)C]

or a pharmaceutically acceptable salt or solvate thereof.

34. The compound:

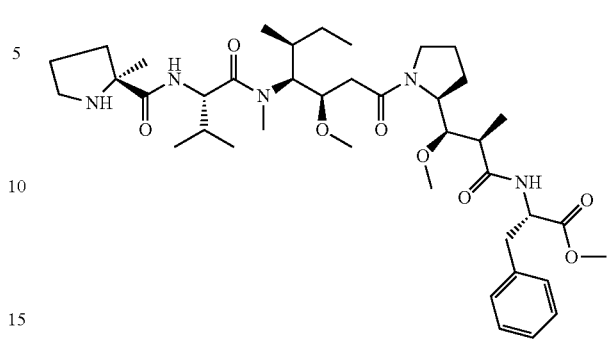

or a pharmaceutically acceptable salt or solvate thereof.

35. The compound:

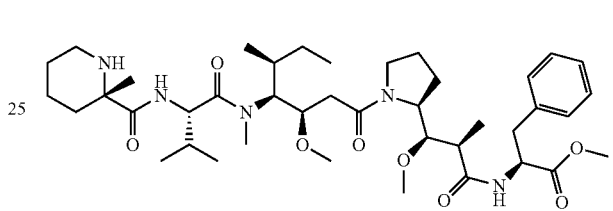

or a pharmaceutically acceptable salt or solvate thereof.

36. The compound:

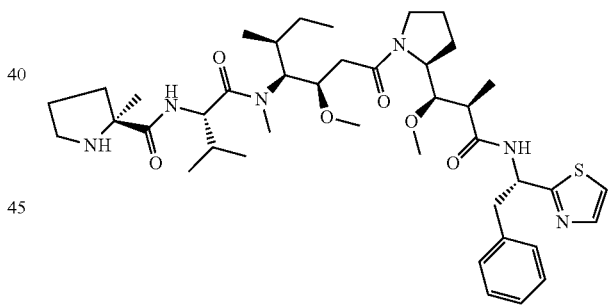

or a pharmaceutically acceptable salt or solvate thereof.

* * * * *

UNITED STATES PATENT AND TRADEMARK OFFICE
CERTIFICATE OF CORRECTION

PATENT NO. : 8,828,401 B2  
APPLICATION NO. : 13/670612  
DATED : September 9, 2014  
INVENTOR(S) : Matthew David Doroski et al.

Page 1 of 1

It is certified that error appears in the above-identified patent and that said Letters Patent is hereby corrected as shown below:

In the Claims

--On column 493 of the patent, lines 47-57, claim 7, the variable $R^{5\dagger}$ in the related structure should be $R^5$.--

--On column 496 of the patent, after line 3, claim 7, the language "$R^{11'}$ is" should be added.--

--On column 499 of the patent, structure on lines 31-42, claim 9, the variable $R^{5'}$ in the recited structures should be $R^5$.--

Signed and Sealed this
Eighteenth Day of August, 2015

Michelle K. Lee  
*Director of the United States Patent and Trademark Office*

```
                         SEQUENCE LISTING

<160> NUMBER OF SEQ ID NOS: 26

<210> SEQ ID NO 1
<211> LENGTH: 106
<212> TYPE: PRT
<213> ORGANISM: Homo sapiens
<220> FEATURE:
<221> NAME/KEY: MISC_FEATURE
<222> LOCATION: (45)..(45)
<223> OTHER INFORMATION: xaa at position 45 is Ala or Val
<220> FEATURE:
<221> NAME/KEY: MISC_FEATURE
<222> LOCATION: (83)..(83)
<223> OTHER INFORMATION: xaa at position 83 is Leu or Val

<400> SEQUENCE: 1

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 2
<211> LENGTH: 106
<212> TYPE: PRT
<213> ORGANISM: Homo sapiens

<400> SEQUENCE: 2

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Val Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
```

-continued

```
                65                  70                  75                  80
His Lys Leu Tyr Ala Cys Glu Val Thr His Gln Gly Leu Ser Ser Pro
                    85                  90                  95

Val Thr Lys Ser Phe Asn Arg Gly Glu Cys
                100                 105

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 5
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 5

Glu Leu Gln Met Thr Gln Ser Pro Ser Ser Leu Ser Ala Ser Val Gly
1               5                   10                  15
```

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
        115

<210> SEQ ID NO 7
<211> LENGTH: 219
<212> TYPE: PRT
<213> ORGANISM: Artificial Sequence
<220> FEATURE:
<223> OTHER INFORMATION: Synthetic peptide sequence

<400> SEQUENCE: 7

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 8
<211> LENGTH: 448
<212> TYPE: PRT
<213> ORGANISM: Artificial Sequence
<220> FEATURE:
<223> OTHER INFORMATION: Synthetic peptide sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

```
Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 9
<211> LENGTH: 122
<212> TYPE: PRT
<213> ORGANISM: Artificial Sequence
<220> FEATURE:
<223> OTHER INFORMATION: Synthetic peptide sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
        115                 120

<210> SEQ ID NO 10
<211> LENGTH: 107
<212> TYPE: PRT
<213> ORGANISM: Artificial Sequence
```

<220> FEATURE:
<223> OTHER INFORMATION: Synthetic peptide sequence

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105
```

<210> SEQ ID NO 11
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
```

```
                 225                 230                 235                 240
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Cys
        435                 440                 445

Ser Pro Gly Lys
    450

<210> SEQ ID NO 12
<211> LENGTH: 213
<212> TYPE: PRT
<213> ORGANISM: Artificial Sequence
<220> FEATURE:
<223> OTHER INFORMATION: Synthetic peptide sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 13
<211> LENGTH: 1356
<212> TYPE: DNA
<213> ORGANISM: Artificial Sequence
<220> FEATURE:
<223> OTHER INFORMATION: Synthetic nucleotide sequence

<400> SEQUENCE: 13
gaggtgcagc tggtggagtc tggcggcgga ctggtgcagc ctggcggctc tctgagactg      60
tcttgtgccg cctccggctt caccttcagt aggaatggca tgtcttgggt gaggcaggcc     120
cctggcaagg gcctggagtg ggtggccacc gttagtagtg gtggtagtta catctactat     180
gcagacagtg tgaaggggcg gttcaccatc tccagggaca cgccaagaa ctccctgtac      240
ctccagatga actccctgag ggccgaggat accgccgtgt actactgtgc agacaagggg     300
actacggcac tagctacgag gttcttcgat gtctggggcc agggcaccct ggtgaccgtg     360
tcctctgcgt cgaccaaggg cccatcggtc ttccccctgg cacctctc caagagcacc       420
tctgggggca gcggccct gggctgcctg gtcaaggact acttccccga accggtgacg        480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg      780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagccccat cgagaaaacc     1020
atctccaaag ccaaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcctctc cctgtccccg ggtaaa                              1356

<210> SEQ ID NO 14
<211> LENGTH: 639
<212> TYPE: DNA
<213> ORGANISM: Artificial Sequence
<220> FEATURE:

-continued

<223> OTHER INFORMATION: Synthetic nucleotide sequence

<400> SEQUENCE: 14

```
gacatccaga tgacccagtc ccctcttct ctgtctgcct ctgtgggcga cagagtgacc      60
atcacctgta aggccagtca ggatgtaggt actgctgtag cctggtatca gcagaagcct    120
ggcaaggctc ccaagctgct gatctactcg gcatcctacc ggtccactgg cgtgccttcc    180
agattctccg gctctggctc tggcaccgat ttcaccctga ccatctcctc cctcagcct    240
gaggatttcg ccacctacta ctgccagcac cattatagtg ctccgtggac gtttggcggc    300
ggaacaaagg tggagatcaa gactgtggct gcaccatctg tcttcatctt cccgccatct    360
gatgagcagt tgaaatctgg aactgcctct gttgtgtgcc tgctgaataa cttctatccc    420
agagaggcca agtacagtg aaggtggat aacgccctcc aatcgggtaa ctcccaggag      480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639
```

<210> SEQ ID NO 15
<211> LENGTH: 117
<212> TYPE: PRT
<213> ORGANISM: Artificial Sequence
<220> FEATURE:
<223> OTHER INFORMATION: Synthetic peptide sequence

<400> SEQUENCE: 15

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Asp Tyr
            20                  25                  30
Gly Met Thr Trp Val Arg Gln Ala Pro Gly Lys Gly Leu Glu Trp Val
        35                  40                  45
Ala Tyr Ile Ser Ser Gly Ser Asn Tyr Ile Tyr Tyr Ala Glu Ala Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Gly Pro Phe Val Leu Asp Ala Trp Gly Gln Gly Thr Leu
            100                 105                 110
Val Thr Val Ser Ser
        115

<210> SEQ ID NO 16
<211> LENGTH: 446
<212> TYPE: PRT
<213> ORGANISM: Artificial Sequence
<220> FEATURE:
<223> OTHER INFORMATION: Synthetic peptide sequence

<400> SEQUENCE: 16

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Asp Tyr
            20                  25                  30
Gly Met Thr Trp Val Arg Gln Ala Pro Gly Lys Gly Leu Glu Trp Val
        35                  40                  45

```
Ala Tyr Ile Ser Ser Gly Ser Asn Tyr Ile Tyr Tyr Ala Glu Ala Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Arg Gly Pro Phe Val Leu Asp Ala Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 17
<211> LENGTH: 1338
<212> TYPE: DNA
```

<213> ORGANISM: Artificial Sequence
<220> FEATURE:
<223> OTHER INFORMATION: Synthetic nucleotide sequence

<400> SEQUENCE: 17

```
gaggtgcagc tggtggagtc tgggggaggc ttggtccagc ctgggggtc cctgagactc      60
tcctgtgcag cctctggatt cactttcagg gactatggaa tgacctgggt ccgccaggct     120
ccagggaagg gctggagtg gtggcctat attagtagtg gtagcaatta catctattat      180
gcagaagcgg tgaagggccg attcaccatc tccagagaca cgccaagaa ctcactgtat     240
ctgcaaatga acagcctgag agccgaggac acggctgtgt attactgtgc gagacgaggc    300
ccgtttgttt tggatgcctg gggccaggga accctggtca ccgtctcctc agcgtcgacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaccatctc caaagccaaa     1020
gggcagcccc gagaaccaca ggtgtacacc ctgcccccat cccgggagga tgaccaag     1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggt                                                  1338
```

<210> SEQ ID NO 18
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Asn Arg Tyr
            20                  25                  30

Leu His Trp Tyr Gln Gln Lys Pro Gly Lys Ala Pro Lys Leu Leu Ile
        35                  40                  45

Tyr Asn Ala Asn Gly Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Thr Trp Pro Asp
                85                  90                  95
```

```
Thr Phe Gly Gly Gly Thr Lys Val Glu Ile Lys
            100                 105

<210> SEQ ID NO 19
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Asn Arg Tyr
            20                  25                  30

Leu His Trp Tyr Gln Gln Lys Pro Gly Lys Ala Pro Lys Leu Leu Ile
        35                  40                  45

Tyr Asn Ala Asn Gly Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Thr Trp Pro Asp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 20
gacatccaga tgacccagtc tccatcctcc ctgtctgcat ctgtaggaga cagagtcacc      60
atcacttgca aagcaagtca gagtattaac aggtacttac actggtatca gcagaaacca    120
gggaaagccc ctaagctcct gatctataat gcaaacggtt tgcaaacggg ggtcccatca    180
aggttcagtg gcagtggatc tgggacagat ttcactctca ccatcagcag tctgcaacct    240
gaagattttg caacttacta ctgtttgcag cataatacgt ggccggacac gtttggcgga    300
gggaccaagg tggagatcaa acggaccgtg gccgctcctt ccgtgttcat cttcccccct    360
tccgacgagc agctgaagtc tggcaccgcc tctgtggtgt gtctgctgaa caacttctac    420
```

```
cccgggagg ccaaggtgca gtggaaggtg gacaacgctc tgcagtccgg caactcccag    480
gagtctgtga ccgagcagga ctccaaggac agcacctact ccctgtcctc taccctgacc    540
ctgtccaagg ccgactacga gaagcacaag gtgtacgcct gtgaggtgac ccaccagggc    600
ctgtcctctc ctgtgaccaa gtccttcaac cggggcgagt gc                      642
```

```
<210> SEQ ID NO 21
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 21
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asp Tyr
            20                  25                  30

Trp Met Thr Trp Val Arg Gln Ala Pro Gly Lys Gly Leu Glu Trp Val
        35                  40                  45

Ala Glu Ile Ser Pro Asn Ser Gly Gly Thr Asn Phe Asn Glu Lys Phe
    50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Ile Arg Tyr Asn Trp Phe Ala Tyr Trp Gly Gln Gly
            100                 105                 110

Thr Leu Val Thr Val Ser Ser
        115

```
<210> SEQ ID NO 22
<211> LENGTH: 448
<212> TYPE: PRT
<213> ORGANISM: Artificial Sequence
<220> FEATURE:
<223> OTHER INFORMATION: Synthetic peptide sequence

<400> SEQUENCE: 22
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asp Tyr
            20                  25                  30

Trp Met Thr Trp Val Arg Gln Ala Pro Gly Lys Gly Leu Glu Trp Val
        35                  40                  45

Ala Glu Ile Ser Pro Asn Ser Gly Gly Thr Asn Phe Asn Glu Lys Phe
    50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Ile Arg Tyr Asn Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 23
<211> LENGTH: 1344
<212> TYPE: DNA
<213> ORGANISM: Artificial Sequence
<220> FEATURE:
<223> OTHER INFORMATION: Synthetic nucleotide sequence

<400> SEQUENCE: 23
gaggtgcagc tggtggagtc tgggggaggc ttggtccagc ctggggggtc cctgagactc      60
tcctgtgcag cctctggtta tgcattcact gactactgga tgacctgggt ccgccaggct     120
ccagggaagg ggctggagtg ggtggccgaa atttctccta cagtggtgg tactaacttc      180 aatgaaaagt tcaagggccg attcaccatc tccgttgaca cgccaagaa ctcactgtat      240 ctgcaaatga acagcctgag agccgaggac acggctgtgt attactgtgc gagggggaa      300 atccgttaca attggtttgc ttactggggc cagggaaccc tggtcaccgt ctcctcagcg     360

-continued

```
tcgaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggaggagatg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctatagc aagctcaccg tggacaagag caggtggcag     1260
caggggaacg tcttctcatg ctccgtgatg catgaggctc tgcacaacca ctacacgcag     1320
aagagcctct ccctgtcccc gggt                                            1344
```

<210> SEQ ID NO 24
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Ile Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Arg Leu Tyr Asn Ser Pro Phe
                85                  90                  95

Thr Phe Gly Gly Gly Thr Lys Val Glu Ile Lys
            100                 105
```

<210> SEQ ID NO 25
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 25

```
Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asn Val Gly Asn Asn
            20                  25                  30

Ile Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Arg Leu Tyr Asn Ser Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 26
gacatccaga tgacccagtc tccatcctcc ctgtctgcat ctgtaggaga cagagtcacc      60
atcacttgca aggccagtca gaatgtgggt aataatatag cctggtatca gcagaaacca     120
gggaaagccc ctaagctcct gatctattat gcatctaacc ggtacactgg ggtcccatca     180
aggttcagtg gcagtggata tgggacagat ttcactctca ccatcagcag tctgcaacct     240
gaagattttg caacttacta ctgtcagcgt ctttacaatt ctccattcac gttcggcgga     300
gggaccaagg tggagatcaa acggaccgtg gccgctcctt ccgtgttcat cttccccct      360 tccgacgagc agctgaagtc tggcaccgcc tctgtggtgt gtctgctgaa caacttctac     420 cccgggagg ccaaggtgca gtggaaggtg gacaacgctc tgcagtccgg caactcccag     480
gagtctgtga ccgagcagga ctccaaggac agcacctact ccctgtcctc taccctgacc     540
ctgtccaagg ccgactacga gaagcacaag gtgtacgcct gtgaggtgac ccaccagggc     600
ctgtcctctc ctgtgaccaa gtccttcaac cggggcgagt gc                        642